(12) United States Patent
Friedman et al.

(10) Patent No.: US 11,806,711 B1
(45) Date of Patent: Nov. 7, 2023

(54) SYSTEMS, DEVICES, AND METHODS FOR FLUIDIC PROCESSING OF BIOLOGICAL OR CHEMICAL SAMPLES USING FLEXIBLE FLUIDIC CIRCUITS

(71) Applicant: Hound Labs, Inc., Oakland, CA (US)

(72) Inventors: Daniel H. Friedman, Mountain View, CA (US); Michael V. D'Ambrosio, Berkeley, CA (US); William Welch, Sunnyvale, CA (US); Thu M. Nguyen, Mountain View, CA (US)

(73) Assignee: Hound Labs, Inc., Oakland, CA (US)

( * ) Notice: Subject to any disclaimer, the term of this patent is extended or adjusted under 35 U.S.C. 154(b) by 0 days.

(21) Appl. No.: 17/647,807

(22) Filed: Jan. 12, 2022

Related U.S. Application Data

(60) Provisional application No. 63/228,023, filed on Jul. 31, 2021, provisional application No. 63/203,820, filed on Jul. 30, 2021, provisional application No. 63/201,062, filed on Apr. 9, 2021, provisional application No. 63/199,696, filed on Jan. 18, 2021, provisional application No. 63/199,610, filed on Jan. 12, 2021.

(51) Int. Cl.
*B01L 3/00* (2006.01)
(52) U.S. Cl.
CPC ..... *B01L 3/502738* (2013.01); *B01L 3/50273* (2013.01); *B01L 2400/0688* (2013.01)
(58) Field of Classification Search
CPC ........... B01L 3/502738; B01L 3/50273; B01L 2400/0688
See application file for complete search history.

(56) References Cited

U.S. PATENT DOCUMENTS

| | | | |
|---|---|---|---|
| 3,086,833 | A | 4/1963 | Streck |
| 3,393,108 | A | 7/1968 | Jones |
| 3,676,072 | A | 7/1972 | Krivis |
| 4,133,202 | A | 1/1979 | Marple |

(Continued)

FOREIGN PATENT DOCUMENTS

| | | |
|---|---|---|
| EP | 0132313 B1 | 9/1991 |
| EP | 2498093 A1 | 9/2012 |

(Continued)

OTHER PUBLICATIONS

"Pexa—The importance of early diagnosis", downloaded on Mar. 25, 2019 from http://pexa.se/en/respiratory-research/the-importance-of-early-diagnosis/.

(Continued)

*Primary Examiner* — Jennifer Wecker
*Assistant Examiner* — Oyeleye Alexander Alabi
(74) *Attorney, Agent, or Firm* — Mahamedi IP Law LLP

(57) ABSTRACT

Various fluidic structures are described that may be implemented between two portions of material, at least one of which may be made of a flexible but inelastic material, such as Mylar. Such fluidic circuits may be configured such that applying a clamping pressure zone to such fluidic circuits and then moving the clamping pressure zone along the fluidic circuit and along a particular axis may cause the fluidic circuit to operate in a particular manner, thereby driving fluids contained within the fluidic circuit around the fluidic circuit according to a desired flow sequence.

7 Claims, 137 Drawing Sheets

(56) References Cited

U.S. PATENT DOCUMENTS

| | | |
|---|---|---|
| 4,232,667 A | 11/1980 | Chalon et al. |
| 4,288,344 A | 9/1981 | Reiss |
| 4,771,005 A | 9/1988 | Spiro |
| 4,796,475 A | 1/1989 | Marple |
| 4,926,679 A | 5/1990 | Dewhurst |
| 5,026,027 A | 6/1991 | Hamilton |
| 5,103,857 A | 4/1992 | Kuhn et al. |
| 5,140,993 A | 8/1992 | Opekun, Jr. et al. |
| 5,196,306 A | 3/1993 | Bobrow et al. |
| 5,230,866 A | 7/1993 | Shartle et al. |
| 5,361,771 A | 11/1994 | Craine et al. |
| 5,438,980 A | 8/1995 | Phillips |
| 5,583,001 A | 12/1996 | Bobrow et al. |
| 5,589,346 A | 12/1996 | Kanan et al. |
| 5,731,158 A | 3/1998 | Bobrow et al. |
| 5,922,610 A | 7/1999 | Alving et al. |
| 6,040,191 A | 3/2000 | Grow |
| 6,067,983 A | 5/2000 | Stenzler |
| 6,326,159 B1 | 12/2001 | Ullman et al. |
| 6,460,539 B1 | 10/2002 | Japuntich et al. |
| 6,537,823 B1 | 3/2003 | Smith |
| 6,582,376 B2 | 6/2003 | Baghdassarian |
| 6,605,444 B1 | 8/2003 | Klein et al. |
| 6,727,067 B2 | 4/2004 | Russman et al. |
| 6,780,617 B2 | 8/2004 | Chen |
| 6,964,862 B2 | 11/2005 | Chen |
| 7,059,349 B2 | 6/2006 | Breda |
| 7,337,072 B2 | 2/2008 | Chen |
| 7,364,553 B2 | 4/2008 | Paz et al. |
| 7,547,285 B2 | 6/2009 | Kline |
| 7,718,421 B2 | 5/2010 | Chen et al. |
| 7,799,521 B2 | 9/2010 | Chen |
| 7,833,489 B2 | 11/2010 | Chen |
| 7,935,504 B2 | 5/2011 | Chen |
| 8,148,116 B2 | 4/2012 | Chen |
| 8,237,118 B2 | 8/2012 | Prox et al. |
| 8,586,932 B2 | 11/2013 | Rousso et al. |
| 8,705,029 B2 | 4/2014 | Palmskog et al. |
| 8,707,758 B2 | 4/2014 | Keays |
| 8,936,933 B2 | 1/2015 | Chen et al. |
| 8,955,366 B2 | 2/2015 | Abraham-Fuchs et al. |
| 9,239,323 B2 | 1/2016 | Keays |
| 9,429,564 B2 | 8/2016 | Beck |
| 9,617,582 B2 | 4/2017 | Milton et al. |
| 9,662,652 B2 | 5/2017 | Chen |
| 9,708,599 B2 | 7/2017 | Chen et al. |
| 9,709,581 B1 | 7/2017 | Gordon et al. |
| 9,709,582 B1 | 7/2017 | Gordon et al. |
| 9,726,684 B1 | 8/2017 | Gordon et al. |
| 9,921,234 B1 | 3/2018 | Lynn et al. |
| 9,933,445 B1 | 4/2018 | Lynn et al. |
| 9,945,878 B1 | 4/2018 | Gordon et al. |
| 9,970,950 B1 | 5/2018 | Lynn et al. |
| 9,976,944 B1 | 5/2018 | Olin et al. |
| 10,226,201 B2 | 3/2019 | Ahmad et al. |
| 10,247,742 B1 | 4/2019 | Lynn et al. |
| 10,408,850 B1 | 9/2019 | Gordon et al. |
| 10,443,050 B2 | 10/2019 | Chen et al. |
| 10,557,563 B2 | 2/2020 | Thurau |
| 10,641,783 B2 | 5/2020 | Lynn et al. |
| 10,955,428 B2 | 3/2021 | Lynn et al. |
| 11,026,596 B1 | 6/2021 | Lynn et al. |
| 11,187,711 B1 | 11/2021 | Lynn et al. |
| 11,426,097 B1 | 8/2022 | Lynn et al. |
| 2002/0177232 A1 | 11/2002 | Melker et al. |
| 2003/0153844 A1 | 8/2003 | Smith et al. |
| 2003/0190259 A1 | 10/2003 | Alley |
| 2004/0043479 A1 | 3/2004 | Briscoe et al. |
| 2005/0105077 A1 | 5/2005 | Padmanabhan et al. |
| 2005/0137491 A1 | 6/2005 | Paz et al. |
| 2005/0279181 A1 | 12/2005 | Trakumas et al. |
| 2006/0094123 A1 | 5/2006 | Day et al. |
| 2006/0195040 A1 | 8/2006 | Nason et al. |
| 2006/0257941 A1 | 11/2006 | McDevitt et al. |
| 2007/0031283 A1 | 2/2007 | Davis et al. |
| 2007/0077660 A1 | 4/2007 | Glas |
| 2007/0258894 A1 | 11/2007 | Melker et al. |
| 2008/0004542 A1 | 1/2008 | Allen et al. |
| 2008/0038154 A1 | 2/2008 | Longbottom et al. |
| 2008/0045825 A1 | 2/2008 | Melker et al. |
| 2008/0050839 A1 | 2/2008 | Suslick et al. |
| 2009/0017555 A1 | 1/2009 | Jehanli et al. |
| 2010/0297635 A1 | 11/2010 | Olin et al. |
| 2011/0020945 A1 | 1/2011 | Day et al. |
| 2011/0086364 A1 | 4/2011 | Takkinen et al. |
| 2011/0167932 A1 | 7/2011 | Thornburg et al. |
| 2012/0302907 A1 | 11/2012 | Palmskog et al. |
| 2012/0329142 A1* | 12/2012 | Battrell .............. C12Q 1/686 435/287.2 |
| 2013/0006068 A1 | 1/2013 | Gemer et al. |
| 2013/0011859 A1 | 1/2013 | Putnam et al. |
| 2013/0021153 A1 | 1/2013 | Keays |
| 2013/0102018 A1 | 4/2013 | Schentag et al. |
| 2013/0165806 A1 | 6/2013 | Wondka et al. |
| 2013/0319239 A1 | 12/2013 | Takenaka et al. |
| 2014/0004534 A1 | 1/2014 | Hill et al. |
| 2014/0094391 A1 | 4/2014 | McDevitt et al. |
| 2014/0120633 A1 | 5/2014 | Gandini et al. |
| 2014/0276100 A1 | 9/2014 | Satterfield et al. |
| 2014/0288454 A1 | 9/2014 | Paz et al. |
| 2014/0296089 A1 | 10/2014 | Holmes et al. |
| 2014/0311215 A1 | 10/2014 | Keays et al. |
| 2014/0366609 A1 | 12/2014 | Beck et al. |
| 2015/0024957 A1 | 1/2015 | Cameron et al. |
| 2015/0025407 A1 | 1/2015 | Eichler et al. |
| 2015/0033824 A1 | 2/2015 | Hammarlund et al. |
| 2015/0065901 A1 | 3/2015 | Bhatnagar et al. |
| 2015/0265184 A1 | 9/2015 | Wondka et al. |
| 2015/0305651 A1 | 10/2015 | Attariwala et al. |
| 2015/0313608 A1 | 11/2015 | Baudenbacher et al. |
| 2015/0369830 A1 | 12/2015 | Crichlow |
| 2016/0000358 A1 | 1/2016 | Lundin et al. |
| 2016/0032798 A1 | 2/2016 | Herman et al. |
| 2016/0055359 A1 | 2/2016 | Jensen et al. |
| 2016/0069810 A1 | 3/2016 | Walavalkar et al. |
| 2016/0069919 A1 | 3/2016 | Holmes et al. |
| 2016/0256656 A1 | 9/2016 | Glenn et al. |
| 2016/0299125 A1 | 10/2016 | Cristoni et al. |
| 2017/0023546 A1 | 1/2017 | Holmes et al. |
| 2017/0122851 A1 | 5/2017 | Thatcher et al. |
| 2017/0128692 A1 | 5/2017 | Christopher et al. |
| 2017/0184609 A1 | 6/2017 | Milton et al. |
| 2017/0197213 A1 | 7/2017 | Nielsen et al. |
| 2017/0303822 A1 | 10/2017 | Allsworth et al. |
| 2017/0303823 A1 | 10/2017 | Allsworth et al. |
| 2018/0038798 A1 | 2/2018 | Zhang et al. |
| 2018/0120278 A1 | 5/2018 | Hoorfar et al. |
| 2018/0224471 A1 | 8/2018 | Lynn et al. |
| 2018/0238916 A1 | 8/2018 | Lynn et al. |
| 2018/0243523 A1 | 8/2018 | Nason et al. |
| 2018/0257069 A1 | 9/2018 | Bercovici et al. |
| 2018/0306775 A1 | 10/2018 | Beck et al. |
| 2019/0039069 A1 | 2/2019 | Marshall et al. |
| 2019/0160460 A1 | 5/2019 | Keatch et al. |
| 2019/0317115 A1 | 10/2019 | MacLean et al. |
| 2020/0124625 A1 | 4/2020 | Dunlop et al. |
| 2020/0147333 A1 | 5/2020 | Stoll et al. |
| 2020/0182892 A1 | 6/2020 | Lynn et al. |
| 2020/0245898 A1 | 8/2020 | Heanue et al. |
| 2020/0245899 A1 | 8/2020 | Heanue et al. |
| 2020/0278275 A1 | 9/2020 | Turgul et al. |
| 2020/0300876 A1 | 9/2020 | Lynn et al. |
| 2020/0397340 A1 | 12/2020 | Dweik |
| 2021/0330516 A1 | 10/2021 | Letourneau et al. |

FOREIGN PATENT DOCUMENTS

| | | |
|---|---|---|
| EP | 2762880 A1 | 8/2014 |
| EP | 2781917 A1 | 9/2014 |
| WO | 9014043 A1 | 11/1990 |
| WO | 2006083269 A2 | 8/2006 |
| WO | 2011029889 A1 | 3/2011 |
| WO | 2016065300 A1 | 4/2016 |
| WO | 2018076099 A1 | 5/2018 |

(56) References Cited

FOREIGN PATENT DOCUMENTS

| WO | 2018185164 A1 | 10/2018 |
|---|---|---|
| WO | 2018211280 A1 | 11/2018 |
| WO | 2019011750 A1 | 1/2019 |

OTHER PUBLICATIONS

"Pexa—The search for new biomarkers", downloaded on Mar. 25, 2019 from http://pexa.se/en/respiratory-research/the-search-for-new-biomarkers/.

Piao, Wen et al., "Development of azo-based fluorescent probes to detect different levels of hypoxia," Angew. Chem. Int. Ed. 2013, 52, 13028-13032.

Prodromidis, M.I., "Impedimetric immunosensors—A review", Electrochimica Acta, (May 30, 2010), 55(14):4227-33.

Quintela, Oscar et al., "Recovery of drugs of abuse from the immunalysis quantisal oral fluid collection device," Journal of Analytical Toxicology, vol. 30, Oct. 2006.

Rahim S.A. et al., "Colorimetric determination of ethanol in the presence of methanol and other species in aqueous solution," Taianta. Nov. 1992;39(11):1489-91, PubMed abstract 18965558.

Rohrich, J. et al., "Concentrations of delta9-tetrahydrocannabinol and 11-nor-9-carboxytetrahydrocannabinol in blood and urine after passive exposure to cannabis smoke in a coffee shop," Journal of Analytical Toxicology, vol. 34, May 2010.

Russo, E. et al., "A tale of two cannabinoids: the therapeutic rational for combining tetrahydrocannabinol and cannabidiol," Med Hypotheses. 2006;66(2):234-46, PubMed abstract 16209908.

Saalberg, Yannick and Marcus Wolff, "VOC breath biomarkers in lung cancer", Clinica Chimica Acta, (Aug. 1, 2016), 459:5-9.

Samitas, K., et al., "Exhaled cysteinyl-leukotrienes and 8-isoprostane in patients with asthma and their relation to clinical severity", Respiratory medicine, (May 1, 2009), 103(5):750-6.

Samyn N. et al., "On-site testing of saliva and sweat with Drugwipe and determination of concentrations of drugs of abuse in saliva, plasma and urine of suspected users," Int J Legal Med. 2000;113(3):150-4, PubMed abstract 10876986.

Sarafian, Theodor et al., "Inhaled marijuana smoke disrupts mitochondrial energetics in pulmonary epithelial cells in vivo," Am J Physiol Lung Cell Mol Physiol, 2006, 290. L1202-L1209. (Year:2006).

Scheuplein, Robert J., "Mechanism of percutaneous absorption. II. Transient diffusion and the relative importance of various routes of skin penetration," J. Invest. Dermatol 1967;48:79.

Schwartz, Richard H. et al., "Laboratory detection of marijuana use, Experience with a photometric immunoassay to measure urinary cannabinoids," Aj J Dis Child. 1985;139(11): 1093-1096, abstract.

Schwilke, Eugene W. et al., "Delta9-tetrahydrocannabinol (THC), 11-hydroxy-THC, and 11-nor-9-carboxy-THC plasma pharmacokinetics during and after continuous high-dose oral THC," Clinical Chemistry 55:12 2180-2189 (2009).

Shaw, Leslie M. et al., "Ultrasensitive measurement of delta-9-tetrahydrocannabinol with a high energy dynode detector and electron-capture negative chemical-ionization mass spectrometry," Clin. Chem. 37/12, 2062-2068 (1991).

Sigma, "How Proximity Ligation Assays (PLA) Work".

Sivashanmugan K, Squire K, Tan A, Zhao Y, Kraai JA, Rorrer GL, Wang AX. Trace detection of tetrahydrocannabinol in body fluid via surface-enhanced Raman scattering and principal component analysis. ACS sensors. Mar. 25, 2019;4(4):1109-17.

Skopp, G. et al., "Partition coefficient, blood to plasma ratio, protein binding and short-term stability of 11-nor-Delta(9)-carboxy tetra-hydrocannabinol glucuronide," Forensic Sci Int. Mar. 28, 2002;126(1):17-23, PubMed abstract 11955826.

Soares, J.R. et al., "Significant developments in radioimmune methods applied to delta9-THC and its 9-substituted metabolites," Analysis of Cannabinoids Research Monograph 42, NIDA 1982.

"Drug detection, health monitoring etc.", SensAbues AB—Innovation, downloaded on Mar. 25, 2019 from http://sensabues.com/innovation.

"Exhaled breath sampling company", SensAbues AB—About, downloaded on Mar. 25, 2019 from http://sensabues.com/about.

Stevenson H, Bacon A, Joseph KM, Gwandaru WR, Bhide A, Sankhala D, Dhamu VN, Prasad S. A rapid response electrochemical biosensor for detecting THC in saliva. Scientific reports. Sep. 3, 2019; 9(1):1-11. (11 pages) //9:12701 https://doi.org/10.1038/s41598-019-49185-y.

Stiles PL, Dieringer JA, Shah NC, Van Duyne RP. Surface-enhanced Raman spectroscopy. Annu. Rev. Anal. Chem . . . Jul. 19, 2008;1:601-26.

Stinchcomb, A.L. et al., "Human skin permeation of Delta8-tetrahydrocannabinol, cannabidiol and cannbinol,"J Pharm Pharmacol. Mar. 2004;56(3):291-7, PubMed abstract 15025853.

Strano-Rossi, Sabina et al., "Analysis of stimulants in oral fluid and urine by gas chromatography-mass spectrometry II: Pseudophedrine," Journal of Analytical Toxicology, vol. 34, May 2010.

Switz, N. A., et al., "Low-Cost Mobile Phone Microscopy with a Reversed Mobile Phone Camera Lens", PloS one, (May 22, 2014), 9(5):e95330. 7 pages.

Tan, Chongxiao et al., "Direct detection of delta9-tetrahydrocannabinol in aqueous samples using a homogeneous increasing fluorescence immunoassay (HiFi)," Anal Bioaanal Chem, 2010. 8 pgs.

Teshima, N. et al., "Determination of acetone in breath", Analytica Chimica Acta, 2005, 535, pp. 189-199.

"The Chemistry of Phenols," Zvi Rappoport, editor, © 2003 John Wiley & Sons, Ltd. ISBN: 0-471-49737-1.

Toennes, Stefan W et al., "Pharmacokinetic properties of delta9-tetrahydrocannabinol in oral fluid of occasional and chronic users," Journal of Analytical Toxicology, vol. 34, May 2010.

Townsend, Doug, Ian Eustis, Mark Lewis, Steven Rodgers, Kevin Smith, Ariel Bohman, C. T. Shelton, and C. A. Sacramento. "The Determination of Total THC and CBD Content in Cannabis Flower by Fourier Transform Near Infrared Spectroscopy." (2018); Document No. 014329_01, 5 pages, accessed at perkinelmer.com/lab-solutions/resources/docs/app_determination_of_thc_and_cbd_cannabisflower.pdf.

Turner, Carton E. et al., "Constituents of cannabis sativa I. XVII. A review of the natural constituents," J. Nat. Prod. 1980;43:169.

Ullman EF, Kirakossian H, Switchenko AC, Ishkanian J, Ericson M, Wartchow CA, Pirio M, Pease J, Irvin BR, Singh S, Singh R. Luminescent oxygen channeling assay (LOCI): sensitive, broadly applicable homogeneous immunoassay method. Clinical chemistry. Sep. 1, 1996;42(9):1518-26.

Vahimaa P et al., "Surface-Enhanced Raman Spectroscopy (SERS)," Institute of Photonics at the University of Eastern Finland, accessible at sway.com/s/XtgAoh8F5QewSEFL/embed.

Valiveti, S. et al., "In vitro/in vivo correlation studies for transdermal delta 8-THC development," J Pharm Sci. May 2004;93(5):1154-64, PubMed abstract 15067692.

Van der Kooy, F. et al., "Cannabis smoke condensate I: The effect of different preparation methods on tetrahydrocannabinol levels," Inhalation Toxicology, 20:801-804, 2008.

Vinciguerra, V. et al., "Inhalation marijuana as an antiemetic for cancer chemotherapy," NY State J Med. Oct. 1988;88(10):525-7.

"Volatile Organic Compounds (VOC) as non-invasive biomarkers for a range of diseases", downloaded on Mar. 25, 2019 from https://www.owlstonemedical.com/science-technology/voc-biomarkers/.

Wall, M.E. et al., "Metabolism, disposition, and kinetics of delta-9-tetrahydrocannabinol in men and women," Clin Pharmacol Ther. Sep. 1983;34(3):352-63, PubMed abstract 6309462.

Wall, M.E. et al., "The metabolism of delta 9-tetrahydrocannabinol and related cannabinoids in man," J Clin Pharmacol. Aug.-Sep. 1981;21 (8-9 Suppl):178S-189S, PubMed abstract 6271823.

Walsh, J. Michael et al., "An evaluation of rapid point-of-collection oral fluid drug-testing devices," Journal of Analytical Toxicology, vol. 27, Oct. 2003.

Wan, G.H., et al., "Cysteinyl leukotriene levels correlate with 8-isoprostane levels in exhaled breath condensates of atopic and healthy children", Pediatric research (Nov. 2013), 74(5):584.

Wang, AX, Kong X. Review of recent progress of plasmonic materials and nano-structures for surface-enhanced Raman scattering. Materials. Jun. 2015;8(6):3024-52.

(56) References Cited

OTHER PUBLICATIONS

Watanabe, K. et al., "Brain microsomal oxidation of delta 8- and delta 9- tetrahydrocannabinol," Biochem Biophys Res Commun. Nov. 30, 1988;157(1):75-80, PubMed abstract 2848522.

Widman, M. et al., "Metabolism of delta 1-tetrahydrocannabinol by the isolated perfused dog lung. Comparison with in vitro liver matabolism." J Phar Pharmacol. Nov. 1975;27(11):842-8, PubMed abstract 1493.

Wiegand, D.M. et al., "Evaluation of police officers exposure to secondhand cannabis smoke at open-air stadium events", NIOSH health hazard evaluation report; HHE 2017-0174-335, (Mar. 2019), https://www.cdc.gov/niosh/hhe/reports/pdfs/2017-0174-3335.pdf.

Williams, P.L. et al., "Identification in human urine of delta 9-tetrahydrocannabinol-11-oic acid glucuronide: a tetrahydrocannabinol metabolite," J Pharm Pharmacol. Jul. 1980;32(7):445-8, PubMed abstract 6105177.

Wingert, William E., "Lowering cutoffs for initial and confirmation testing for cocaine and marijuana: large-scale study of effects on the rates of drug-positive results," Clinical Chemistry 43:1 100-103 (1997).

Written Opinion of the Searching Authority dated Apr. 6, 2020, for International Patent Application No. PCT/US2020/13553, 7 pages.

Mikuriya, Tod H., "Cannabis as a substitute for alcohol: a harm-reduction approach," Journal of Cannabis Therapeutics, vol. 4(1) 2004.

Milman, Garry et al., "Simultaneous quantification of cannabinoids and metabolites in oral fluid by two-dimensional gas chromatography mass spectrometry," J Chromatogr A. Feb. 26, 2010; 1217(9): 1513-1521.

Moeller, M.R et al., "Simultaneous quantitation of delta-9-tetrahydrocannabinol (THC) and 11-nor-9-carboxy-delta-9-tetrahydrocannabinol (THC-COOH) in serum by GC/MS using deuterated internal standards and its application to a smoking study and forensic cases," J Forensic Sci. Jul. 1992;37(4):969-83, PubMed abstract 1324293.

Moldoveanu, Serban C. et al., "Differences in the chemical composition of the particulate phase of inhaled and exhaled cigarette mainstream smoke," Contributions to Tobacco Research 22(4), 290 (2007).

Moore, Christine et al., "Analytical procedure for the determination of the marijuana metabolite 11-nor-delta9-tetrahydrocannabinol-9-carboxylic acid in oral fluid specimens," Journal of Analytical Toxicology, vol. 30, Sep. 2006.

Moore, Christine et al., "Application of two-dimensional gas chromatography with electron capture chemical ionization mass spectrometry to the detection of 11-nor-delta9-tetrahydrocannabinol-9-carboxylic acid (THC-COOH) in hair," Journal of Analytical Toxicology, vol. 30, Apr. 2006.

Moore, Christine et al., "Detection of the marijuana metabolite 11-nor-delta9-tetrahydrocannabinol-9-carboxylic acid in oral fluid specimens and its contribution to positive results in screening assays," Journal of Analytical Toxicology, vol. 30, Sep. 2006.

Moore, Christine et al., "The determination of 11-nor-delta9-tetrahydrocannabinol-9-carboxylic acid (THC-COOH) in hair using negative ion gas chromatography-mass spectrometry and high-volume injection," Journal of Analytical Toxicology, vol. 25, Oct. 2001.

Morland, J. et al., "Cannabinoids in blood and urine after passive inhalation of cannabis smoke," J Forensic Sci. 1985 0ct;30(4):997-1002, PubMed abstract 2999292.

Mule, S.J. et al., "Active and realistic passive marijuana exposure tested by three immunoassays and GC/MS in urine," Journal of Analytical Toxicology, vol. 12, May/Jun. 1988.

Mura, P. et al., "Evaluation of six rapid tests for screening of cannabis in sweat, saliva and tears," Acta Clin Belg. 1999;53 Suppl 1:35-8, PubMed abstract 10216980.

Mura, P. et al., "THC can be detected in brain while absent in blood," Letter to the Editor, Journal of Analytical Toxicology, vol. 29, Nov./Dec. 2005.

Nadulski T. et al., "Simultaneous and sensitive analysis of THC, 11-OH-THC, THC-COOH, CBD, and CBN by GC-MS in plasma after oral application of small doses of THC and cannabis extract," Journal of Analytical Toxicology, vol. 29, Nov./Dec. 2005.

Nadulski T. et al., "Randomized, double-blind, placebo-controlled study about the effects of cannabidiol (CBD) on the pharmacokinetics of Delat9-tetrahydrocannabinol (THC) after oral application of THC verses standardized cannabis extract," Ther Drug Monit. Dec. 2005;27(6):799-810.

Nahas, Gabriel G. et al., "Pharmacokinetics of THC in brain and testis, male gametotoxicity and premature apoptosis of spermatozoa," Human Psycopharmacology: Clinical and Experimental, vol. 17, Issue 2, pp. 103-113, Mar. 2002, abstract.

Niedbala, R. Sam et al., "Detection of marijuana use by oral fluid and urine analysis following single-dose administration of smoked and oral marijuana," Journal of Analytical Toxicology, vol. 25, Jul./Aug. 2001.

Niedbala, R. Sam et al., "Passive cannabis smoke exposure and oral fluid testing. II. Two studies of extreme cannabis smoke exposure in a motor vehicle," Journal of Analytical Toxicology, vol. 29, Oct. 2005.

"N.S. woman who tested positive for pot when she wasnt high to challenge roadside testing laws," CBC Radio, posted Apr. 3, 2019. 6 pages.

Oguma, T., et al., "Clinical contributions of exhaled volatile organic compounds in the diagnosis of lung cancer", PloS one, (Apr. 6, 2017), 12(4):e0174802.

Ohlsson, A. et al., "Plasma delta-9 tetrahydrocannabinol concentrations and clinical effects after oral and intravenous administration and smoking," Clin Pharmacol Ther. Sep. 1980;28(3):409-16, PubMed abstract 6250760.

Ohlsson, Agneta et al., "Single dose kinetics of deuterium labelled delta1-tetrahydrocnnabinol in heavy and light cannabis users," Biological Mass Spectrometry, vol. 9, Issue 1, pp. 6-10, Jan. 1982, abstract.

Olmon RL, Slovick B, Johnson TW, Shelton D, Oh SH, Boreman GD, Raschke MB. "Optical dielectric function of gold", Physical Review B. Dec. 28, 2012;86(23):235147.

Owens, S. Michael et al., I Radioimmunoassay of delta-9-tetrahydrocannabinol in blood and plasma with a solid-phase second-antibody separation method, Clin. Chem. 27/4, 619-624 (1981).

"Owlstone—About", downloaded on Mar. 25, 2019 from https://www.owlstonemedical.com/about/.

"Owlstone—EVOC Probes", downloaded on Mar. 25, 2019 from https://www.owlstonemedical.com/science-technology/evoc-probes/.

"Owlstone—FAIMS technology", downloaded on Mar. 25, 2019 from https://www.owlstonemedical.com/science-technology/faims-technology/.

"Owlstone—Research case studies", downloaded on Mar. 25, 2019 from https://www.owlstonemedical.com/science-technology/research-case-studies/.

"Owlstone Medical—Active Clinical Pipeline", downloaded on Mar. 25, 2019 from https://www.owlstonemedical.com/clinical-pipeline/.

"Owlstone Medical—Products", downloaded on Mar. 21, 2019 from https://www.owlstonemedical.com/products/.

"Owlstone Medical—The Home of Breath Biopsy: A Breathalyzer for Disease", downloaded on Mar. 25, 2019 from https://www.owlstonemedical.com/#.

"Owlstone Medical—The Home of Breath Biopsy: Breath Biopsy—VOC Biomarkers", downloaded on Mar. 25, 2019 from https://www.owlstonemedical.com/#.

Pardon, G, et al., "Aerosol sampling using an electrostatic precipitator integrated with a microfluidic interface", Sensors and Actuators B: Chemical. Feb. 2015, vol. 212, pp. 344-352.

Peel, H.W. et al., "Detection of drugs in saliva of impaired drivers," J Forensic Sci. Jan. 1984;29(1):185-9, PubMed abstract 6366113.

Perez-Reyes, M. et al., "Comparison of effects of marihuana cigarettes to three different potencies," Clin Pharmacol Ther. May 1982;31(5):617-24, PubMed abstract 6280918.

(56) References Cited

OTHER PUBLICATIONS

Perez-Reyes, M. et al., "Intravenous injection in man of 9-tetrahydrocannabinol and 11-OH-9-tetrahydrocannabinol," Science. Aug. 18, 1972;177(4049):633-5, PubMed abstract 4558903.
Perez-Reyes, M. et al., "The clinical pharmacology and dynamics of marihuana cigarette smoking," J Clin Pharmacol. Aug.-Sep. 1981;21(8-9 Suppl):201S-207S, PubMed abstract 6271825.
Perez-Reyes, Mario, "Marijuana smoking: factors that influence the bioavailability of tetrahydrocannabinol," NIDA Monograph 1990;99:42.
PerkinElmer Inc., "TSA Signal Amplification (TSA) Systems," Document No. 007703_01, 16 pages, accessed at perkinelmer.com/lab-solutions/resources/docs/BRO_tsasignalamplification systems.pdf.
"Pexa—About PExA", downloaded on Mar. 25, 2019 from http://pexa.se/en/about-pexa/.
"Pexa—Analysis", downloaded on Mar. 25, 2019 from http://pexa.se/en/product-services/analysis/.
"Pexa—Business Concept & Vision", downloaded on Mar. 25, 2019 from http://pexa.se/en/about-pexa/business-concept-vision/.
"Pexa—History", downloaded on Mar. 25, 2019 from http://pexa.se/en/about-pexa/history/.
"Pexa—How PExA works", downloaded on Mar. 25, 2019 from http://pexa.se/en/product-services/how-pexa-works/.
"Pexa—Particles in Exhaled Air", downloaded on Mar. 25, 2019 from http://pexa.se/en/.
"Pexa—PExA 2.0", downloaded on Mar. 25, 2019 from http://pexa.se/en/product-services/pexa-2-0/.
"Pexa—Product Services", downloaded on Mar. 25, 2019 from http://pexa.se/en/product-services/.
"Pexa—Product-Sheet", Sep. 2016.
"Pexa—Research & Development", downloaded on Mar. 25, 2019 from http://pexa.se/en/product-services/research-development/.
"Pexa—Research areas", downloaded on Mar. 25, 2019 from http://pexa.se/en/respiratory-research/research-areas/.
"Pexa—Respiratory Research Needs", downloaded on Mar. 25, 2019 from http://pexa.se/en/respiratory-research/.
Sean I. Hwang, "Tetrahydrocannabinol Detection Using Semiconductor-Enriched Single-Walled Carbon Nanotube Chemiresistors", 2019 hereafter Hwang (Year: 2019).
Sarah Milliken, "Self-assembled vertically aligned Au nanorod arrays for surface-enhanced Raman scattering (SERS) detection of Cannabinol", Jan. 12, 2018 (Year: 2018).
Sezin Yuksel, "Trace detection of tetrahydrocannabinol (THC) with a SERS-based capillary platform prepared by the in situ microwave synthesis of AgNPs", May 24, 2016 (Year: 2016).
Massachusetts Probation Service, "Probation"s Plan to Strengthen Drug Testing", Apr. 15, 2016 (Year: 2016).
Adams, I.B. et al., "Cannabis: pharmacology and toxicology in animals and humans," Addiction, Nov. 1996;91 (11):1585-614, PubMed abstract 8972919.
Coucke et al., "Tetrahydrocannabinol concentrations in exhaled breath and physiological effects following cannabis intake—A pilot study using illicit cannabis", Clinical Biochemistry, 2016, pp. 1072-1077.
Al-Asmari, Ahmed et al., "Method for the quantification of diamorphine and its metabolites in pediatric plasma samples by liquid chromatography-tandem mass spectrometry," Journal of Analytical Toxicology, vol. 34, May 2010.
Alexander, Brentan R., "Design of a microbreather for two-phase microchannel devices", Dissertation submitted to Massachusetts Institute of Technology. Dept. of Mechanical Engineering, (Jun. 2008), 59 pages.
Aliberti, S, et al., "Serum and exhaled breath condensate inflammatory cytokines in community-acquired pneumonia: a prospective cohort study", Pneumonia (Nathan), (Jun. 23, 2016), 8:8. doi: 10.1186/s41479-016-0009-7. eCollection 2016.
Andrews, Travis M., "Breathalyzers of the Future Today," The Atlantic, Jun. 27, 2013. Downloaded from the Internet on Feb. 4, 2019, http://www.theatlantic.com/health/archive/2013/06/breathalyzers-of-the-future-today/277249/.

Atkinson, H.C. et al., "Drugs in human milk. Clinical pharmacokinetic considerations." Clin Pharmacokinet. Apr. 1988;14 (4):217-40, PubMed abstract 3292101.
Azorlosa, J.L. et al., "Marijuana smoking: effect of varying delta 9-tetrahydrocannabinol content and number of puffs," J. Pharmacol. Exper. Ther 1992;261:114, abstract.
Bailey, J.R. et al., "Fetal disposition of delta 9-tetrahydrocannabinol (THC) during late pegnancy in the rhesus monkey," Toxicol Appl Pharmacol. Sep. 15, 1987;90(2):315-21, abstract.
Bajaj, P., and F.T. Ishmael, "Exhaled breath condensates as a source for biomarkers for characterization of inflammatory lung diseases", Journal of Analytical Sciences, Methods and Instrumentation, (Mar. 20, 2013), 3(01):17.
Baker, D. et al., "Cannabinoids control spasticity and tremor in a multiple sclerosis model," Nature, Mar. 2, 2000;404(6773):84-7, abstract.
Balabanova, S. et al., "Detection of drugs in sweat," Belt Gerichtl Med. 1990;48:45-9, abstract.
Bashir, W. et al., "Spectrophotometric Determination of Acetone in Acetic Acid", Microchemical Journal, 1983, 28, pp. 77-81.
Beaudet L, Rodriguez-Suarez R, Venne MH, Caron M, Bedard J, Brechler V, Parent S, Bielefeld-Sevigny M. "AlphaLISA immunoassays: the no-wash alternative to ELISAs for research and drug discovery", Nature Methods, (Dec. 2008), 5(12):an8-9.
Beck, O., et al., "Detection of drugs of abuse in exhaled breath using a device for rapid collection: comparison with plasma, urine and self-re porting in 47 drug users" Journal of breath research, (Apr. 25, 2013), 7(2):026006.
Beck, Olof et al., "Detection of Delta9-tetrahydrocannabinol in exhaled breath collected from cannabis users," Journal of Analytical Toxicology, vol. 35, Oct. 2011.
Benowitz, Neal L. et al., "Metabolic and psychophysiologic studies of cannabidiol-hexobarbital interaction," Clinical Pharmacology and Therapeutics (1980) 28, 115-120, abstract.
Blanc, Jennifer A. et al., "Adsorption losses from urine-based cannabinoid calibrators during routine use," Clin. Chem. 39/8, 1705-1712 (1993).
Bloom, A.S., Effect of delta9-tetrahydrocannabinol on the synthesis of dopamine and norepinephrine in mouse brain synaptosomes, J Pharmacol Exp Ther. Apr. 1982;221(1):97-103.
Bornheim, Lester M. et al., "Characterization of cytochrome P450 3A inactivation by cannabidiol: possible involvement of cannabidiol-hydroxyquinone as a P450 inactivator," Chem. Res. Toxicol., 1998, 11 (10), pp. 1209-0450.
Bornheim, L.M. et al., "Human hepatic microsomal metabolism of delta 1-tetrahydrocannabinol," Drug Metab Dispos. Mar.-Apr. 1992;20(2):241-6, PubMed abstract 1352216.
Brenneisen, R. et al., "The effect of orally and rectally administered delta 9-tetrahydrocannabinol on spaticity: a pilot study with 2 patients," Int J Clin Pharmcol Ther. Oct. 1996;34(10):446-52.
Brunet, B. et al., "Validation of large white pig as an animal model for the study of cannabinoids metabolism: application to the study of THC distribution in issues," Forensic Sci Int. Sep. 12, 2006;161(2-3):169-74, PubMed abstract 16859848.
Burstein, S. et al., "Isolation and characterization of two major urinary metabolites of 1-tetrahydrocannabinol," Science, Apr. 28, 1972;176(4033):422-3, PubMed abstract 5026162.
Cami, J. et al., "Effect of subject expectancy on the THC intoxication and disposition from smoked hashish cigarettes," Pharmacology Biochemistry and Behavior, vol. 40, Issue 1, Sep. 1991, pp. 115-119.
Carpenter, C.T., Price PV, Christman BW. Exhaled breath condensate isoprostanes are elevated in patients with acute lung injury or ARDS. Chest. Dec. 1, 1998;114(6):1653-9.
Cecinato, A., Balducci C, Perilli M., "Illicit psychotropic substances in the air: The state-of-art", Sci Total Environ, (Jan. 1, 2016), 539:1-6. doi: 10.1016/j.scitotenv.2015.08.051. Epub Sep. 8, 2015. PMID: 26360454.
Challapalli, P.V. et al., "In vitro experiment optimization for measuring tetrahydrocannabinol skin permeation," Int J Pharm. Jul. 25, 2002;241(2):329-39, PubMed abstract 12100860.
Chaturvedi, Arvind K., "Postmortem aviation forensic toxicology: an overview," Journal of Analytical Toxicology, vol. 34, May 2010.

(56) References Cited

OTHER PUBLICATIONS

Chiang, C. Nora et al., "Prenatal drug exposure: kinetics and dynamics," NIDA Research Monograph 60, 1985.
Christophersen, Asbjorg Solberg et al., "Tetrahydrocannabinol stability in whole blood: plastic versus glass containers," Journal of Analytical Toxicology, vol. 10, Jul./Aug. 1986.
Chuah K, Wu Y, Vivekchand SR, Gaus K, Reece PJ, Micolich AP, Gooding JJ. "Nanopore blockade sensors for ultrasensitive detection of proteins in complex biological samples", Nature communications, (May 8, 2019), 10(1):1-9. (9 pages).
Cirimele, V. et al., "Testing human hair for cannabis. III. Rapid screening procedure for the simultaneous identification of delta9-tetrahydrocannabinol, cannabinol, and cannabidiol," Journal of Analytical Toxicology, vol. 20, Jan./Feb. 1996.
Cone, Edward J. et al., "In vivo adulteration: excess fluid ingestion causes false-negative marijuana and cocaine urine test results," Journal of Analytical Toxicology, vol. 22, Oct. 1998.
Cone, Edward J. et al., "Marijuana-laced brownies: behavioral effects, physiologic effects, and urinalysis in humans following ingestion," Journal of Analytical Toxicology, vol. 12, Jul./Aug. 1988.
Cone, EJ, Johnson RE, Darwin WD, Yousefnejad D, Mell LD, Paul BD, Mitchell J., "Passive inhalation of marijuana smoke: urinalysis and room air levels of delta-9-tetrahydrocannabinol", J Anal Toxicol. (May-Jun 1987), 11 (3):89-96. doi: 10.1093/jat/11.3.89. PMID: 3037193.
Crouch, Dennis J. et al., "An evaluation of selected oral fluid point-of-collection drug-testing devices," Journal of Analytical Toxicology, vol. 29, May/Jun. 2005.
Crouch, D.J., "Oral fluid collection: the neglected variable in oral fluid testing," Forensic Sci Int. Jun. 10, 2005;150(2-3):165-73, PubMed abstract 15899565.
D'Ambrosio, M. et al., "Point-of-care quantification of blood-borne filarial parasites with a mobile phone microscope", Science Translational Medicine (May 6, 2015), vol. 7, Issue 286, p. 286re4. 10 pages.
Day, David et al., "Detection of THCA in oral fluid by GC-MS-MS," Journal of Analytical Toxicology, vol. 30, Nov./Dec. 2006.
Doran, GS, Deans R, De Filippis C, Kostakis C, Howitt JA., "Work place drug testing of police officers after THC exposure during large volume cannabis seizures", Forensic Sci Int. (Jun. 2017), 275:224-233. doi: 10.1016/j.forsciint.2017.03.023. Epub Apr. 2, 2017. PMID: 28412574.
D'Souza, Deepak Cyril et al., "The psychotomimetic effects of intravenous delta-9-tetrahydrocannabinol in healthy individuals: implications for psychosis," Neuropsychopharmacology (2004) 29, 1558-1572.
Dunk, et al., "Development of a Portable Marijuana Breathalyzer", (Mar. 2018), URL=http://https://houndlabs.com/wp-content/uploads/2018/03/Hound-TRT-Pittcon-Poster.pdf.
Ellis, George M. Jr. et al. "Excretion patterns of cannabinoid metabilites after last use," 420 Magazine, Oct. 4, 2011, downloaded from https://www.420magazine.com/forums/drug-testing-urine/153724.
Ellis, G.M. Jr. et al., "Excretion patterns of cannabiniod metabolites after last use in a group of chronic users," Clin Pharmacol Ther. Nov. 1985;38(5):572-8, PubMed abstract 3902318.
ElSohly, M. et al., "Potency trends of Delta9-THC and other cannabinoids in confiscated marijuana from 1980-1997," Journal of Forensic Sciences, vol. 45, No. 1, 2000, pp. 24-30.
Written Opinion of the Searching Authority dated Jan. 23, 2020, for International Patent Application No. PCT/US2019/060342, 9 pages.
Yang HU, DArchangel J, Sundheimer ML, Tucker E, Boreman GD, Raschke MB. "Optical dielectric function of silver", Physical Review B. Jun. 22, 2015;91(23):235137.
Zajicek, J. et al., "Cannabinoids for treatment of spasticity and other symptoms related to multiple sclerosis (CAMS study): multicentre randomised placebo-controlled trial," Lancet. Nov. 8, 2003;362(9395):1517-26, abstract.
Zanconato, S., et al., "Leukotrienes and 8-isoprostane in exhaled breath condensate of children with stable and unstable asthma", Journal of Allergy and Clinical Immunology, (Feb. 1, 2004), 113(2):257-63.
Zhou, J., "Review of recent developments in determining volatile organic compounds in exhaled breath as biomarkers for lung cancer diagnosis", Analytica chimica acta, (Dec. 15, 2017), 996:1-9.
Zhu, H.J., Wang JS, Markowitz JS, Donovan JL, Gibson BB, Gefroh HA, DeVane CL., "Characterization of P-glycoprotein inhibition by major cannabinoids from marijuana", Journal of Pharmacology and Experimental Therapeutics. May 1, 2006;317(2):850-7.
Zias, Joe et al., "Early medical use of cannabis," Nature; May 20, 1993; 363,6426; Research Library Core p. 215.
Zuardi, A.W. et al., "Action of cannabidiol on the anxiety and other effects produced by delta 9-THC in normal subjects," Psychopharmacology (Berl). 1982;76(3):245-50, PubMed abstract 6285406.
Emelyanov, A., et al., "Elevated concentrations of exhaled hydrogen peroxide in asthmatic patients", Chest, (Oct. 1, 2001), 120(4):1136-9.
"SensAbues AB—Next generation drug detection and health monitoring", SensAbues AB—Home, downloaded on Mar. 25, 2019 from http://sensabues.com/home.
"Exhaled breath biological sample matrix. EB", SensAbues AB—Product, downloaded on Mar. 25, 2019 from http://sensabues.com/product.
"FAIMS Breathalyzer Device", downloaded on Mar. 25, 2019 from https://algernonpharmaceuticals.com/faims-breathalyzer-device/.
Feng, Shixia et al., "Simultaneous analysis of Delta9-THC and its major metabolites in urine, plasma, and meconium by GC-MS using an immunoaffinity extraction procedure," Journal of Analytical Toxicology, vol. 24, Sep. 2000.
Fraser, A.D. et al., "Monitoring urinary excretion of cannabinoids by fluorescence-polarization immunoassay: a cannabiniod-to-creatinine ratio study," Ther Drug Monit. Dec. 2002;24(6):746-50, PubMed abstract 12451292.
Fraser, A.D. et al., "Urinary excretion profiles of 11-nor9-carboxy-delta9-tetrahydrocannabinol and 11-hydroxy-delta9-THC: cannabinoid metabolites to creatinine ratio study IV," Forensic Sci Int. Jul. 16, 2004;143(2-3):147-52, PubMed abstract 15240035.
Fraser, A.D. et al., "Urinary excretion profiles of 11-nor-9-carboxy-Delta9-tetrahydrocannabinol. Study III. A Delta9-THC-COOH to creatinine ratio study," Forensic Sci Int. Nov. 26, 2003;137(2-3):196-202, PubMed abstract 14609657.
Garrett, Edward R. et al., "Physicochemical properties, solubility, and protein binding of Delta9-tetrahydrocannabinol," J Pharm Sci. Jul. 1974;63(7):1056-64, abstract.
Garrett, E.R. et al., "Pharmacokinetics of delta9-tetrahydrocannabinol in dogs," J Pharm Sci. Mar. 1977;66(3):395-407, PubMed abstract 845807.
Gjerde, H. et al., "Incidence of alcohol and drugs in fatally injured car drivers in Norway," Accid Anal Prev. Aug. 1993;25(4):479-83, PubMed abstract 8357462.
Gjerde, Hallvard et al., "Comparison of drug concentrations in blood and oral fluid collected with the Intercept® sampling device," Journal of Analytical Toxicology, vol. 34, May 2010.
Goodwin, R.S. et al., "Delta(9)-tetrahydrocannabinol, 11-hydroxy-delta(9)-tetrahydrocannabinol and 11-nor-9-carboxy-delta(9)-tetrahydrocannabinol in human plasma after controlled oral administration of cannabinoids," Ther Drug Monit. Aug. 2006;28(4):545-51, PubMed abstract 16885723.
Gramse G, Dols-Perez A, Edwards MA, Fumagalli L, Gomila G. Nanoscale measurement of the dielectric constant of supported lipid bilayers in aqueous solutions with electrostatic force microscopy. Biophysical journal. Mar. 19, 2013;104(6):1257-62.
Green, Mitchell D. et al., "Glucuronidation of opioids, carboxylic acid-containing drugs, and hydroxylated xenobiotics catalyzed by expressed monkey UDP-glucuronosyltransferase 2B9 protein," Drug Metabolism and Disposition, vol. 25, No. 12, (1997).
Grob NM, Aytekin M, Dweik RA. "Biomarkers in exhaled breath condensate: a review of collection, processing and analysis", Journal of breath research, (Sep. 8, 2008), 2(3):037004.

(56) References Cited

OTHER PUBLICATIONS

Gross, Stanley J. et al., "Detection of recent cannabis use by saliva Delta9-THC radioimmunoassay," Journal of Analytical Toxicology, vol. 9, Jan./Feb. 1985.
Grotenhermen, F., "Pharmacokinetics and pharmacodynamics of cannabinids," Clin Pharmacokinet. 2003;42(4):327-60, PubMed abstract 12648025.
Gustafson, R.A. et al., "Validated method for the simultaneous determination of Delta 9-tetrahydrocannabinol (THC), 11-hydroxy-THC and 11-nor-9-carboxy-THC in human plasma using solid phase extraction and gas chromatography-mass spectrometry with positive chemical ionization," J. Chromatogr B Analyt Technol Biomed Life Sci, Dec. 5, 2003;798(1):145-54, PubMed abstract 14630369.
Gustafson, Richard A. et al., "Urinary cannabinoid detection times after controlled oral administration of Delta9-tetrahydrocannabinol to humans," Clinical Chemistry 49:7, 1114-1124 (2003).
Gustafson, Richard A. et al., "Urinary pharmacokinetics of 11-Nor-9-carboxy-delta9-tetrahydrocannabinol after controlled oral delat9-tetrahydrocannabinol administration," Journal of Analytical Toxicology, vol. 28, Apr. 2004.
Guy, G.W. et al., "A phase I, double blind, three-way crossover study to assess the pharmacokinetic profile of cannabis based medicine extract (CBME) administered sublingually in variant cannabinoid ratios in normal healthy male volunteers (GWPK0215)," Journal of Cannabis Therapeutics, vol. 3, No. 4, 2003, pp. 121-152.
Hall, B.J. et al., "Determination of cannabinoids in water and human saliva by solid-phase microextraction and quadrupole ion trap gas chromatography/mass spectrometry," Anal chem. May 1, 1998;70(9):1788-96, PubMed abstract 9599579.
Halldin, M.M. et al., "Identification of in vitro metabolites of delta 1-tetrahydrocannabinol formed by human livers," Drug Metab Dispos. Jul.-Aug. 1982;10(4):297-301, PubMed abstract 6126323.
Hampson, A.J. et al., "Cannabidiol and (-)delta9-tetrahydrocannabinol are neuroprotective antioxidants," Proc Natl Acad Sci U.S.A. Jul. 7, 1998; 95(14): 8268-8273.
Hanson, V.W. et al., "Comparison of 3H- and 125I-radioimmunoassay and gas chromatography/mass spectrometry for the determination of delta9-tetrahydrocannabinol and cannabinoids in blood and serum," Journal of Analytical Toxicology, vol. 7, Mar./Apr. 1983.
Harder, S. et al., "Concentration-effect relationship of delta-9-tetrahydrocannabiol and prediction of psychotropic effects after smoking marijuana," Int J Clin Pharmacol Ther. Apr. 1997;35(4):155-9, PubMed abstract 9112136.
Harvey, D.J. et al., "Metabolites of cannabidiol identified in human urine," Xenobiotic, Mar. 1990;20(3):303-20, PubMed abstract 2336840.
Hasan, R.A., et al., "Lipoxin A4 and 8-isoprostane in the exhaled breath condensate of children hospitalized for status asthmaticus", Pediatric critical care medicine: a journal of the Society of Critical Care Medicine and the World Federation of Pediatric Intensive and Critical Care Societies, (Mar. 2012), 13(2):141.
Hawks, Richard L., "The Analysis of Cannabinoids in Biological Fluids," NIDA Research Monograph 42, 1982.
Hazekamp, Arno et al., "Cannabis; extracting the medicine," thesis/dissertation 2007.
Heishman, Stephen J. et al., "Effects of tetrahydrocannabinol content on marijuana smoking behavior, subjective reports, and performance," Pharmacology Biochemistry and Behavior, vol. 34, Issue 1, Sep. 1989, pp. 173-179, abstract.
Himes, Sarah K. et al., "Cannabinoids in exhaled breath following controlled administration of smoked cannabis," Clinical chemistry 59:12 1780-1789 (2013).
Huang, Wei et al., "Simultaneous determination of delta9-tetrahydrocannabinol and 11-nor-9-carboxy-delta9-tetrahydrocannabinol in human plasma by solid-phase extraction and gas chromatography-negative ion chemical ionization-mass spectrometry," Journal of Analytical Toxicology, vol. 25, Oct. 2001.
Huestis, M.A. et al., "Characterization of the absorption phase of marijuana smoking," Clin Pharmacol Ther. Jul. 1992;52(1):31-41, PubMed abstract 1320536.
Huestis, Marilyn A. et al., "Alternative testing matrices," chapter 11 of the Drug Abuse Handbook, 1998 CRC Press LLC, ISBN 0-8493-2637-0.
Huestis, Marilyn A. et al., "Blood cannabinoids. I. Absorption of THC and formation of 11-OH-THC and THCCOOH during and after smoking marijuana," Journal of Analytical Toxicology, vol. 16, Sep./Oct. 1992.
Huestis, Marilyn A. et al., "Blood cannabinoids. II. Models for the prediction of time of marijuana exposure from plasma concentraitons of delta9-tetrahydrocannabinol (THC) and 11-nor-9-carboxy-delta9-tetrahydrocannabinol (THCCOOH)," Journal of Analytical Toxicology, vol. 16, Sep./Oct. 1992.
Huestis, Marilyn A. et al., "Cannabinoid concentrations in hair from documented cannabis users," Forensic Sci Int. Jul. 4, 2007; 169(2-3): 129-136.
Huestis, Marilyn A. et al., "Detection times of marijuana metabolites in urine by immunoassay and GC-MS," Journal of Analytical Toxicology, vol. 19, Oct. 1995.
Huestis, Marilyn A. et al., "Differentiating new marijuana use from residual drug excretion in occasional marijuana users," Journal of Analytical Toxicology, vol. 22, Oct. 1998.
Huestis, Marilyn A. et al., "Estimating the time of last cannabis use from plasma delta9-tetrahydrocannabinol and 11-nor-9-carboxy-delta9-tetrahydrocannabinol concentrations," Clinical Chemistry 51:12 2289-2295 (2005).
Huestis, Marilyn A. et al., "Relationship of delta9-tetrahydrocannabinol concentrations in oral fluid and plasma after controlled administration of smoked cannabis," Journal of Analytical Toxicology, vol. 28, Sep. 2004.
Huestis, Marilyn A. et al., "Urinary excretion profiles of 11-nor-9-carboxy-delta9-tetrahydrocannabinol in humans after single smoked doses of marijuana," Journal of Analytical Toxicology, vol. 20, Oct. 1996.
Huestis, Marilyn A., "Human cannabinoid pharmacokinetics," Chem Biodivers. Aug. 2007; 4(8): 1770-1804.
Hunt, C.A. et al., "Evidence that cannabidiol does not significantly alter the pharmacokinetics of tetrahydrocannabinol in man," J Pharmacokinet Biopharm. Jun. 1981;9(3):245-60, PubMed abstract 6270295.
Hunt, C.A. et al., "Tolerance and disposition of tetrahydrocannabinol in man," J Pharmacol Exp Ther. Oct. 1980;215(1):35-44, PubMed abstract 6256518.
"Information for health care professionals: cannabis (marihuana, marijuana) and the cannabinoids," Health Canada, Feb. 2013.
International Preliminary Report on Patentability dated Jul. 27, 2021, for International Patent Application No. PCT/US2020/13553, 8 pages.
International Preliminary Report on Patentability dated May 11, 2021, for International Patent Application No. PCT/US2019/060342, 9 pages.
International Search Report dated Apr. 6, 2020, for International Patent Application No. PCT/US2020/13553, 2 pages.
International Search Report dated Jan. 23, 2020, for International Patent Application No. PCT/US2019/060342, 2 pages.
Iribarne, C. et al., "Involvement of cytochrome P450 3A4 enzyme in the N-demethylation of methadone in human liver microsomes," Chem Res Toxicol. Mar. 1996;9(2):365-73, PubMed abstract 8839037.
Jehanli, A. et al., "Blind trials of an onsite saliva drug test for marijuana and opiates," J Forensic Sci. Sep. 2001;46(5):1214-20, PubMed 11569567.
Joern, William A., "Surface adsorption of the urinary marijuana carboxy metabolite: the problem and a partial solution," Letter to the Editor, Journal of Analytical Toxicology, vol. 16, Nov./Dec. 1992.
Johannson, E. et al., "Terminal elimination plasma half-life of delta 1-tetrahydrocannabinol (delta 1-THC) in heavy users of marijuana," Eur J Clin Pharmacol. 1989;37(3):273-7, PubMed abstract 2558889.
Johansson, E. et al., "Determination of delta 1-tetrahydrocannabinol in human fat biopsies from marihuana users by gas chromatography-mass spectrometry," Biomed Chromatogr. Jan. 1989;3(1):35-8, PubMed abstract 2539872.

(56) References Cited

OTHER PUBLICATIONS

Johansson, E. et al., "Prolonged apparent half-life of delta 1-tetrahydrocannabinol in plasma of chronic marijuana users," J Pharm Pharmacol. May 1988;40(5):374-5, PubMed abstract 2899638.

Johansson, Eva et al., "Urinary excretion half-life of delta1-tetrahydrocannabinol-7-oic acid in heavy marijuana users after smoking," Journal of Analytical Toxicology, vol. 13, Jul./Aug. 1989.

Jokerst JV, Chen Z, Xu L, NoIley R, Chang E, Mitchell B, Brooks JD, Gambhir SS. A magnetic bead-based sensor for the quantification of multiple prostate cancer biomarkers. PloS One. (Sep. 30, 2015), 10(9):e0139484. (15 pages).

Kadehijian, Leo, "Syva has been a leading developer and manufacturer of drugs-of-abuse tests for more than 30 years," Cannabinoid Issues: Passive inhalation, excretion patterns, and retention times, test result interpretation, Siemens Healthcare Diagnostics Inc., 2009.

Karst, Matthias et al., "Analgesic effect of the synthetic cannabinoid CT-3 on chronic neuropathic pain," JAMA. 2003;290(13):1757-1762.

Kelly, Peggy et al., "Metabolism of tetrahydrocannabinol in frequent and infrequent marijuana users," Journal of Analytical Toxicology, vol. 16, Jul./Aug. 1992.

Kemp, Philip M. et al., "Cannabinoids in Humans. I. Analysis of delta9-tetrahydrocannabinol and six metabolites in plasma and urine using GC-MS," Journal of Analytical Toxicology, vol. 19, Sep. 1995.

Kemp, Philip M. et al., "Cannabinoids in Humans. II. The influence of three methods of hydrolysis on the concentration of THC and two metabolites in urine," Journal of Analytical Toxicology, vol. 19, Sep. 1995.

Kidwell, David A. et al., "Testing for drugs of abuse in saliva and sweat," Journal of Chromatography B: Biomedical Sciences and Applications, vol. 713, Issue 1, Aug. 21, 1998, pp. 111-135, abstract.

Kintz, P. et al., "Testing human hair for cannabis. II. Identification of TCD-COOH by GC-MS-NCI as a unique proof," J Forensic Sci. Jul. 1995;40(4):619-22, PubMed abstract 7595299.

Kintz, Pascal et al., "Detection of cannabis in oral fluid (saliva) and forehead wipes (sweat) from impaired drivers," Journal of Analytical Toxicology, vol. 24, Oct. 2000.

Kintz, Pascal et al., "Sweat testing for heroin and metabolites in a heroin maintenance program," Clinical Chemistry 43:5, 736-739 (1997).

Klejnowski, K et al. "Number Size Distribution of Ambient Particles in a Typical Urban Site: The First Polish Assessment Based on Long-Term (9 Months) Measurements", The Scientific World Journal, (Oct. 2013), 2013(1):539568.

Kodavanti, U.P. "Respiratory toxicity biomarkers", In Biomarkers in Toxicology, (Jan. 1, 2014) (pp. 217-239). Academic Press.

Kovatsi, Leda et al., "Development and validation of a high-performance liquid chromatography method for the evaluation of niflumic acid cross-reactivity of two commercial immunoassays for cannabinoids in urine," Journal of Analytical Toxicology, vol. 34, May 2010.

Krenke, K. et al., "Inflammatory cytokines in exhaled breath condensate in children with inflammatory bowel diseases", Pediatric pulmonology, (Dec. 2014), 49(12):1190-5.

Kreuz, D.S. et al., "Delta-9-tetrahydrocannabinol: localization in body fat," Science, Jan. 26, 1973;179(4071):391-3, PubMed abstract 4682965.

Krishna, D.R. et al., "Extrahepatic metabolism of drugs in humans," Clin Pharmacokinet. Feb. 1994;26(2):144-60, PubMed abstract 8162658.

Lafolie, P. et al., "Importance of creatinine analyses of urine when screening for abused drugs," Clin. Chem. 37/11, 1927-1931 (1991).

Laloup, M. et al., "Correlation of delta9-tetrahydrocannabinol concentrations determined by LC-MS-MS in oral fluid and plasma from impaired drivers and evaluation of the on-site Drager Drug Test," Forensic Sci Int. 2006 Srp 12;161(2-3):175-9, PubMed abstract 16842950.

Law, B. et al., "Forensic aspects of the metabolism and excretion of cannabinoids following oral ingestion of cannabis resin," J Pharm Pharmacol. May 1984;36(5):289-94, PubMed abstract 6145762.

Le Ru EC, Blackie E, Meyer M, Etchegoin PG. Surface enhanced Raman scattering enhancement factors: a comprehensive study. The Journal of Physical Chemistry C. Sep. 20, 2007;111(37):13794-803.

Lee, Sooyeun et al., "Estimation of the measurement uncertainty by the bottom-up approach for the determination of methamphetamine and amphetamine in urine," Journal of Analytical Toxicology, vol. 34, May 2010.

Lemberger, L. et al., "11-hydroxy-9-tetrahydrocannabinol: pharmacology, disposition, and metabolism of a major metabolite of marihuana in man," Science. Jul. 7, 1972;177(4043):62-4, PubMed abstract 5041775.

Lemberger, L. et al., "Delta-9-tetrahydrocannabinol: metabolism and disposition in long-term marihuana smokers," Science. Jul. 2, 1971;173(3991):72-4, PubMed abstract 5087483.

Lemberger, L. et al., "Marihuana: studies on the disposition and metabolism of delta-9-tetrahydrocannabinol in man," Science. Dec. 18, 1970;170(3964):1320-2, PubMed abstract 5479011.

Lindgren, J.E. et al., "Clinical effects and plasma levels of delta 9-tetrahydrocannabinol (delta 9-THC) in heavy and light users of cannabis," Psychopharmacology (Berl). 1981;74(3):208-12, PubMed 6267648.

"Low cost, non-invasive and non-intrusi", SensAbues AB—Benefits, downloaded on Mar. 25, 2019 from http://sensabues.com/benefits.

Malfait, A.M. "The nonpsychoactive cannabis constituent cannabidiol is an oral anti-arthritic therapeutic in murine collagen-induced arthritis," Proc Natl Acad Sci USA Aug. 15, 2000;97(17):9561-9566.

Manno, Joseph E. et al., "Temporal indication of marijuana use can be estimated from plasma and urine concentrations of delta9-tetrahydrocannabinol, 11-hydroxy-delta9-tetrahydrocannabinol, and 11-nor-delta9-tetrahydrocannabinol-9-carboxylic acid," Journal of Analytical Toxicology, vol. 25, Oct. 2001.

Manolis, Antony et al., "The detection of delta9-tetrahydrocannabinol in the breath of human subjects," Clinical Biochem. 16,229 (1983).

"Marihuana 84," Proceedings of the Oxford Symposium on Cannabis, D.J. Harvy, editor, IRL Press, Oxford 1984.

Martin, B.R. et al., "3H-delta9-tetrahydrocannabinol distribution in pregnant dogs and their fetuses," Res Commun Chem Pathol Pharmacol. Jul. 1977;17(3):457-70, PubMed abstract 897339.

Mason, A.P. et al., "Cannabis: pharmacology and interpretation of effects," J Forensic Sci. Jul. 1985;30(3):615-31, PubMed abstract 2993473.

Mason, A.P. et al., "Ethanol, marijuana, and other drug use in 600 drivers killed in single-vehicle crashes in North Carolina, 1978-1981," J Forensic Sci. Oct. 1984;29(4):987-1026, PubMed abstract 6502125.

Matsunaga, T. et al., "Metabolism of delta 9-tetrahydrocannabinol by cytochrome P450 isozymes purified from hepatic microsomes of monkeys," Life Sci. 1995;56(23-24):2089-95, PubMed abstract 7776836.

Mattes, R.D. et al., "Bypassing the first-pass effect for the therapeutic use of cannabinoids," Pharmacol Biochem Behav. Mar. 1993;44(3):745-7, PubMed abstract 8383856.

Mattes, R.D. et al., "Cannabinoids and appetite stimulation," Pharmacol Biochem Behav. Sep. 1994;49(1):187-95, PubMed abstract 7816872.

McBurney, L.J. et al., "GC/MS and EMIT analyses for delta9-tetrahydrocannabinol metabolites in plasma and urine of human subjects," Journal of Analytical Toxicology, vol. 10, Mar./Apr. 1986.

Mechoulam, Raphael et al., "Cannabidiol: an overview of some chemical and pharmacological aspects. Part I: chemical aspects," Chemistry and Physics of Lipids 121 (2002) 35-43.

Mechoulam, Raphael, "Plant cannabinoids: a neglected pharmacological treasure trove," Br J Pharmacol. Dec. 2005; 146(7): 913-915.

Meier, H. et al., "Cannabis poisoning after eating salad," Schweiz Med Wochenschr. Feb. 8, 1997;127(6):214-8, PubMed abstract 9157527.

(56) References Cited

OTHER PUBLICATIONS

Menkes, D.B. et al., "Salivary THC following cannabis smoking correlates with subjective intoxication and heart rate," Psychopharmacology (Berl). 1991;103(2):277-9, PubMed abstract 1851311.

* cited by examiner

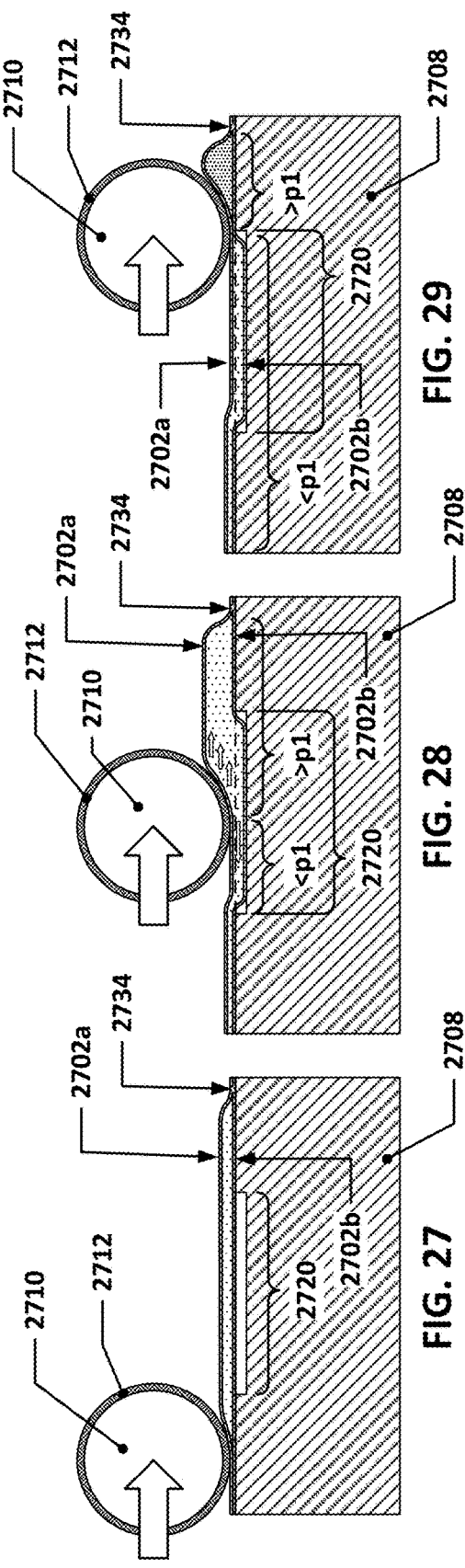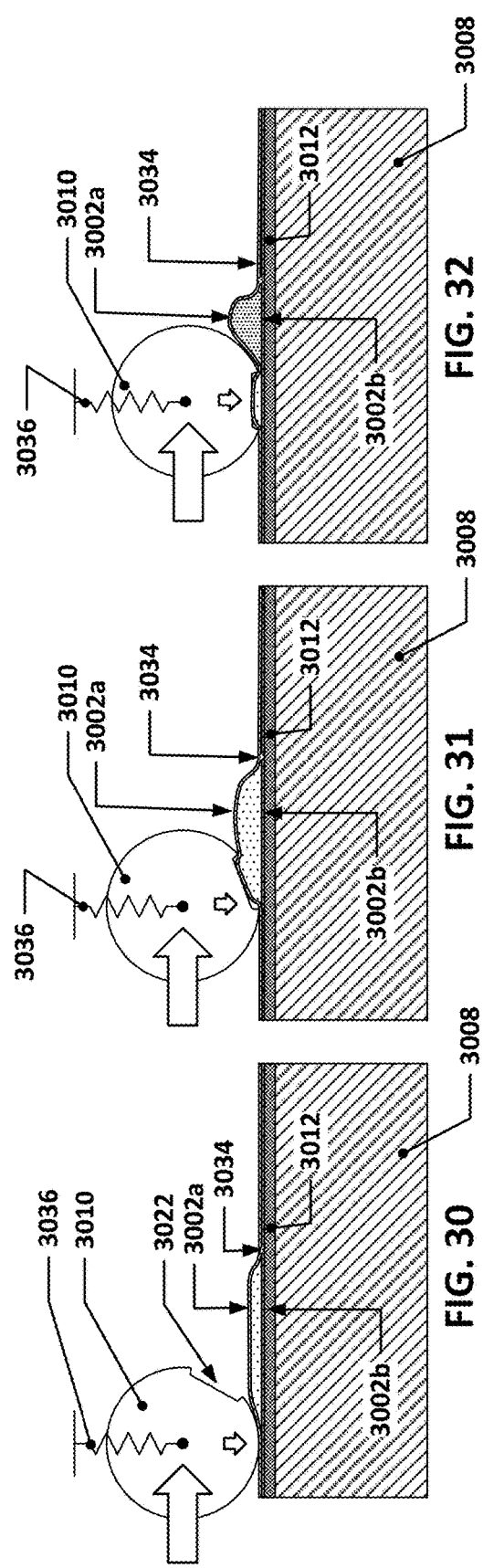

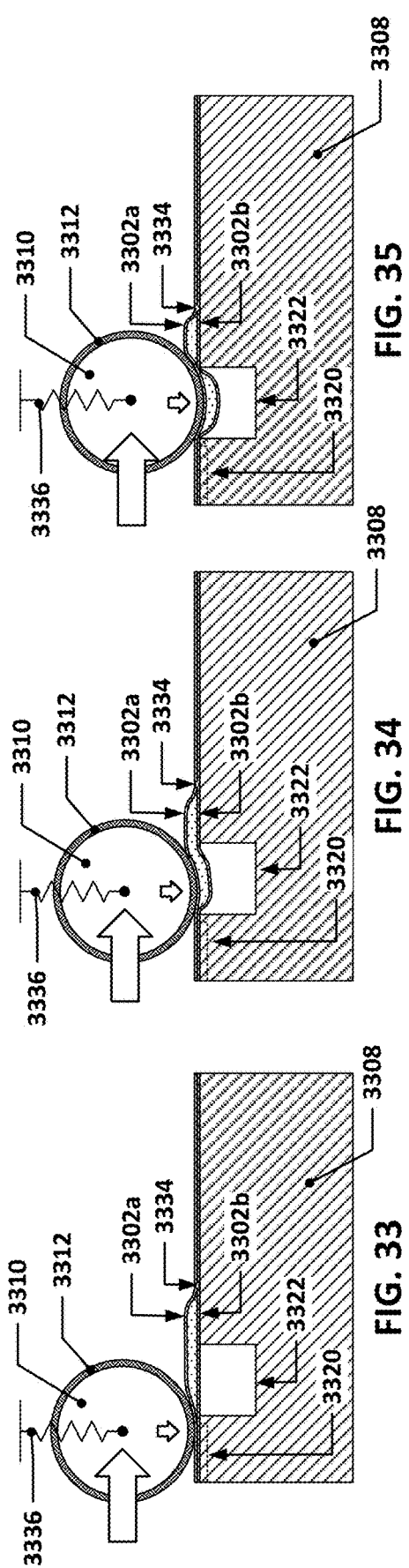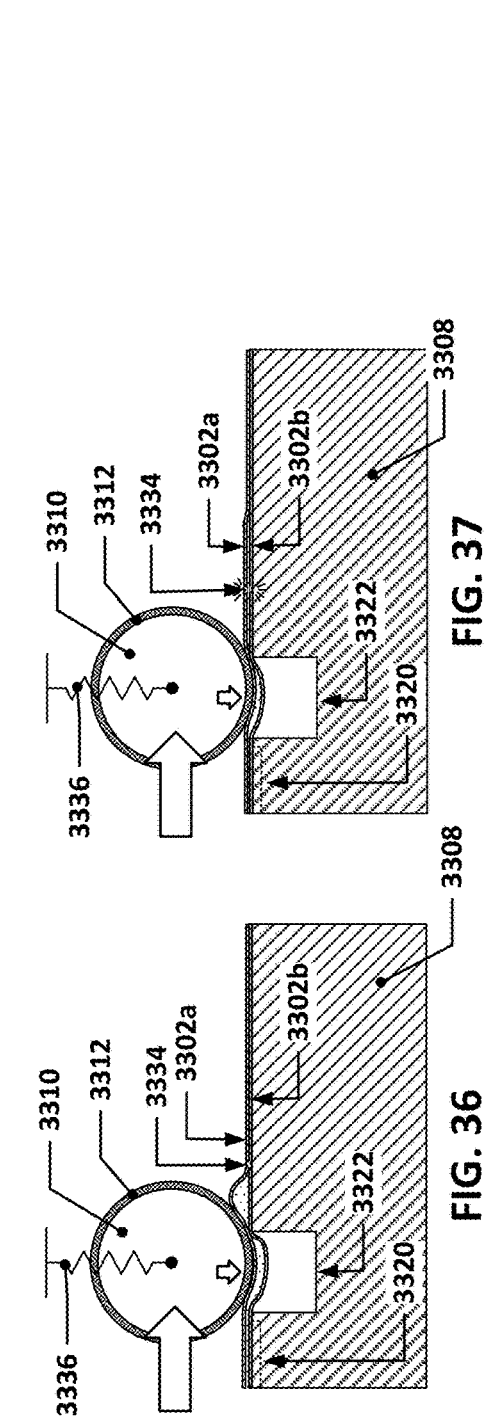

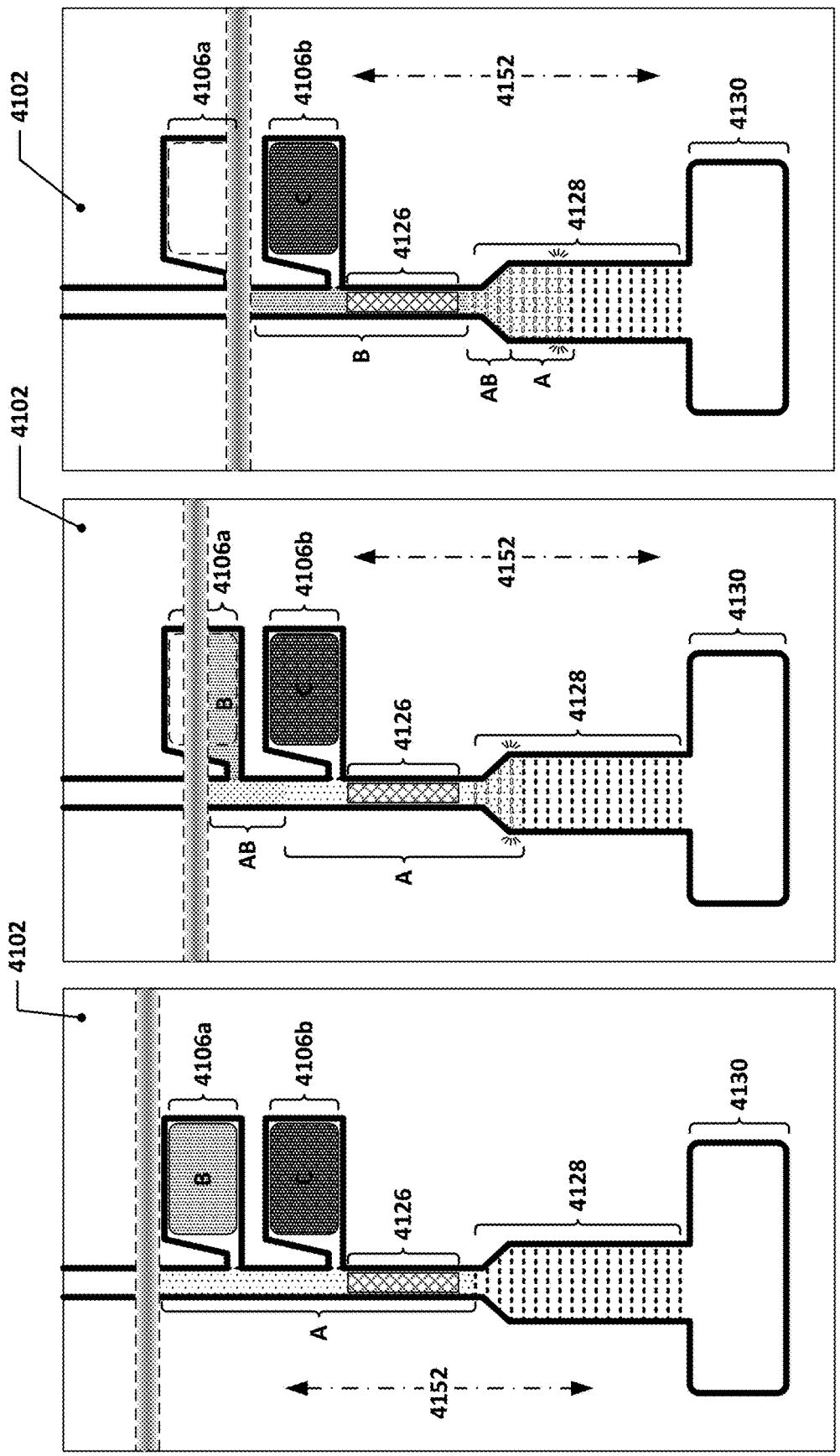

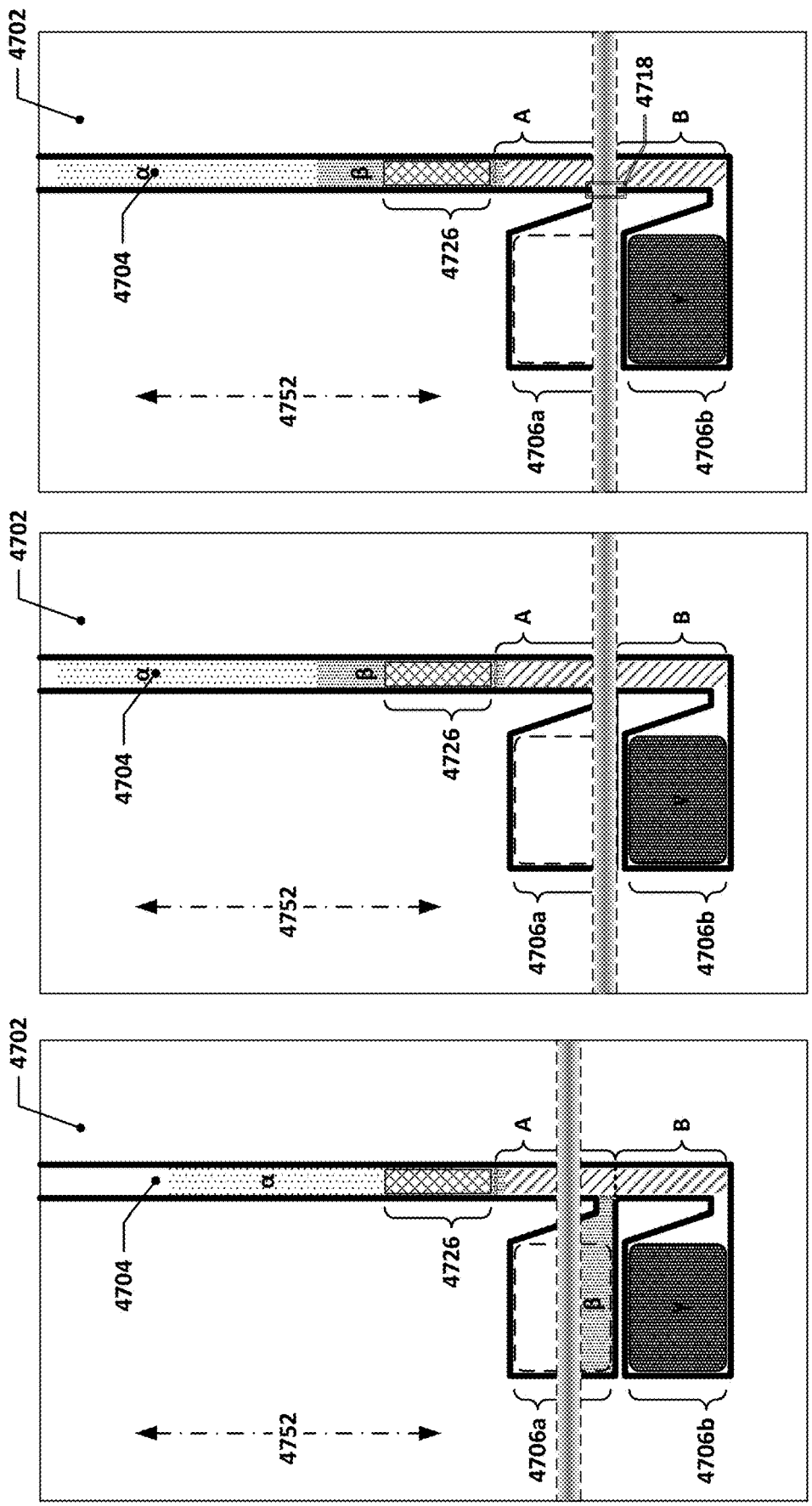

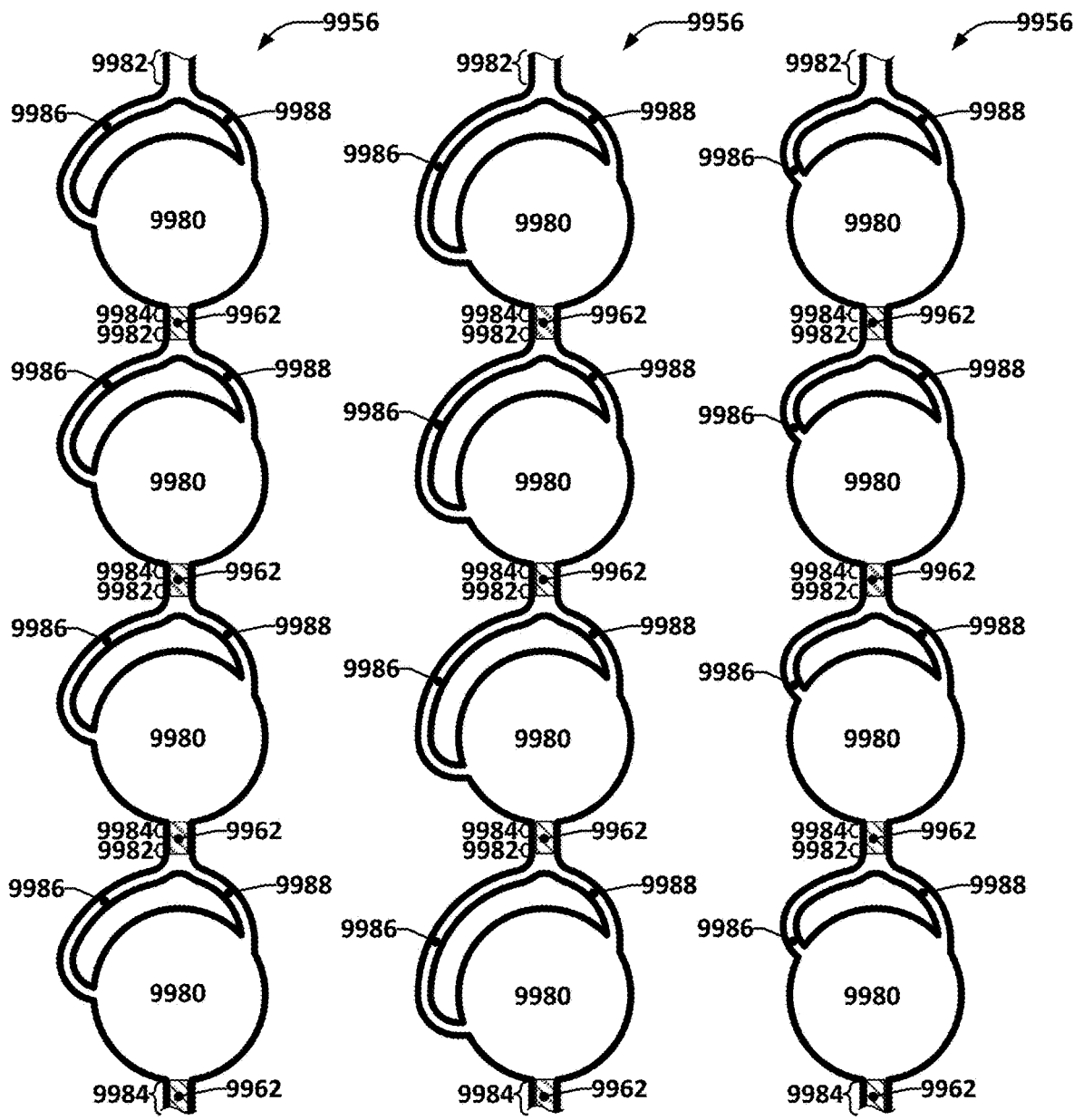

— Permanent Seal

— Permanent Seal

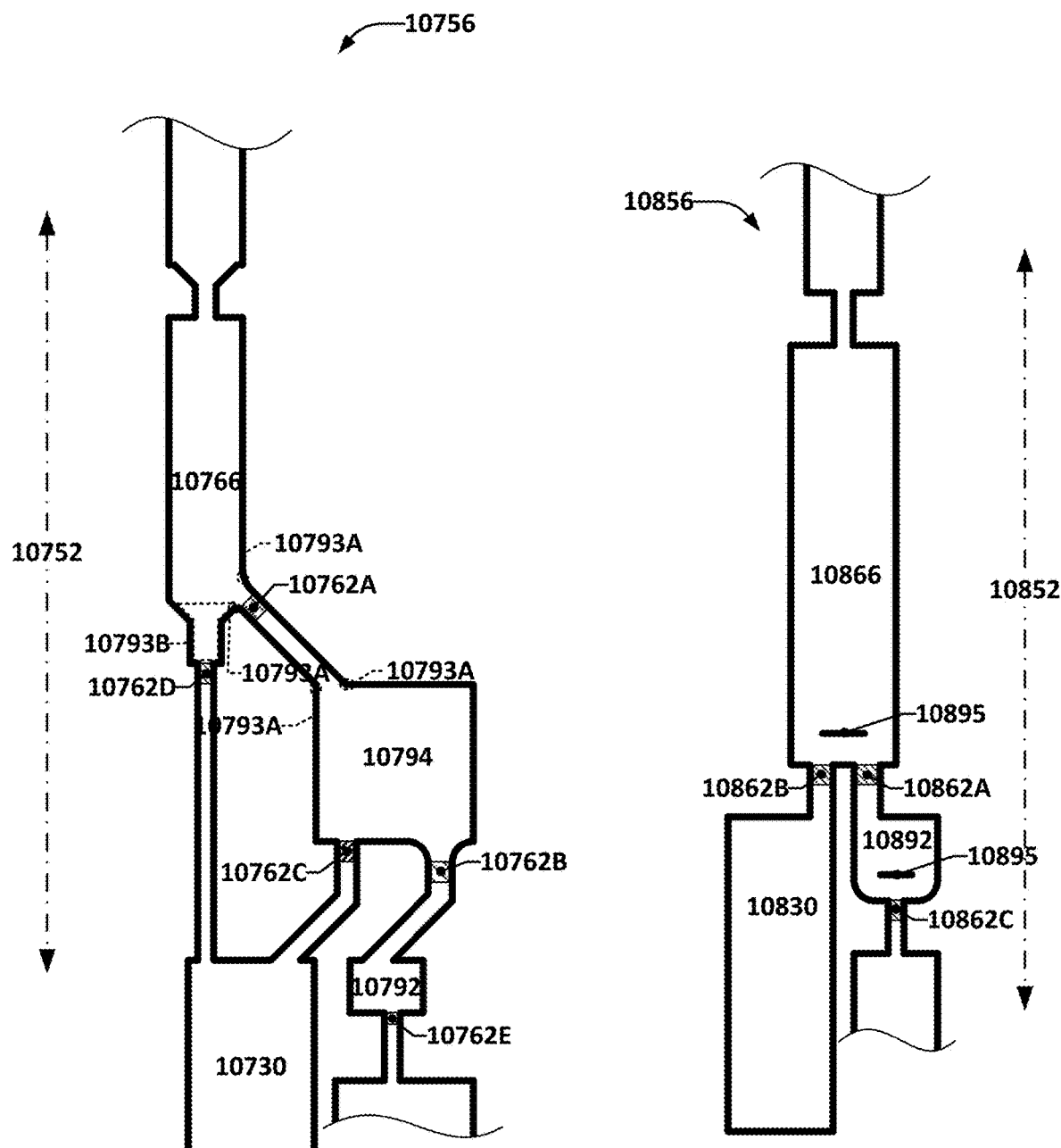

Symbol Legend for FIGS. 112A through 126D

*References to "above" and "below" in the legend below refer to relative positioning with respect to the orientation of the diagrams using the symbols summarized below.*

⊙────────────── Reference boundary (not necessarily a visible line)

Chamber Symbols

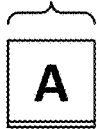 At least a portion of chamber must be above the closest reference boundary below the chamber symbol. The chamber can optionally additionally extend above at least the closest reference boundary above the chamber symbol and/or optionally additionally extend below at least the closest reference boundary below the chamber symbol.

 At least a portion of chamber must be below the closest reference boundary above the chamber symbol. The chamber can optionally additionally extend above at least the closest reference boundary above the chamber symbol and/or optionally additionally extend below at least the closest reference boundary below the chamber symbol.

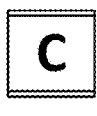 At least a portion of chamber must be both above the closest reference boundary below the chamber symbol and below the closest reference boundary above the chamber symbol. The chamber can optionally additionally extend above at least the closest reference boundary above the chamber symbol and/or optionally additionally extend below at least the closest reference boundary below the chamber symbol.

 Dotted boundary indicates that chambers and/or flow paths within boundary are backed by a recess or cavity in platen when being processed.

─┼─ Dynamic Seal

─✱─ Temporary Seal

─✦─ Dynamic or Temporary Seal (Pressure-Releasable Seal)

─╪─ Live Temporary Seal

─╪─ Live Permanent Seal

─╤─ Live Strong to Normal Dynamic Transition Seal/Floating Seal

FIG. 111

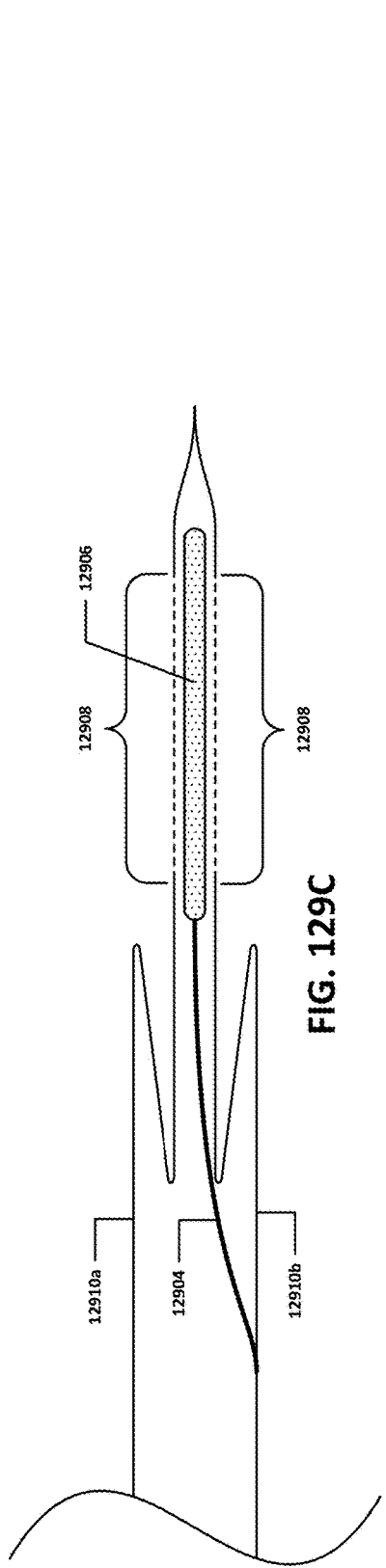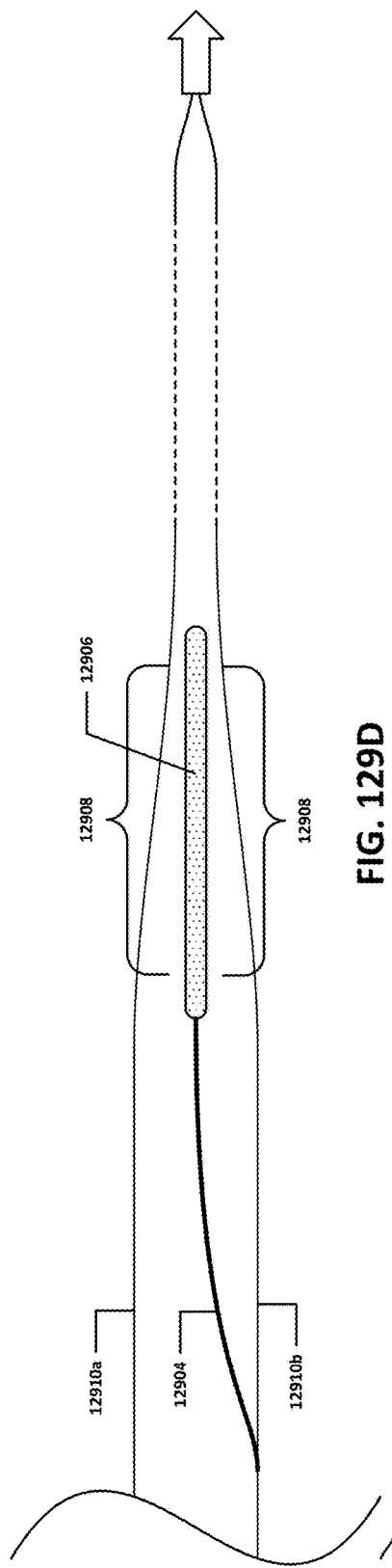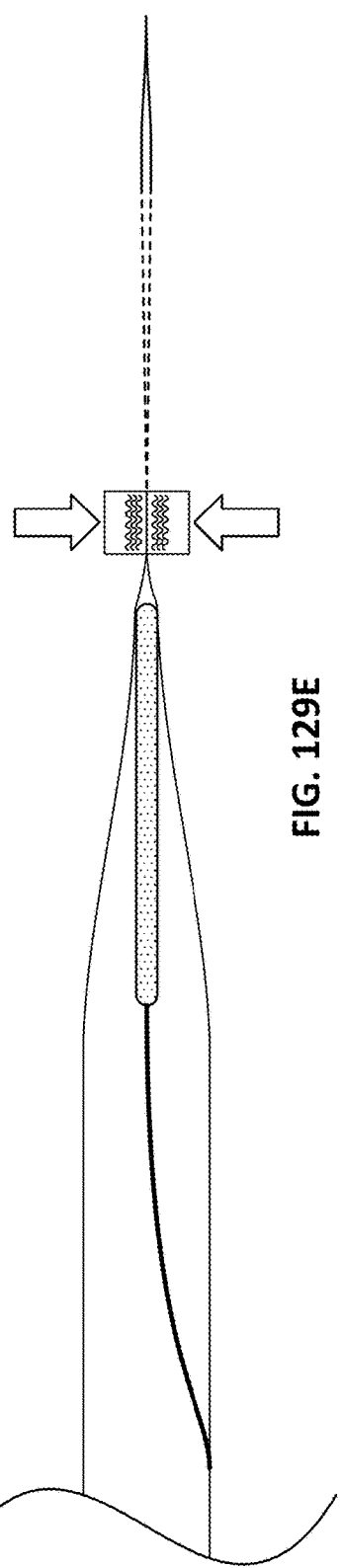

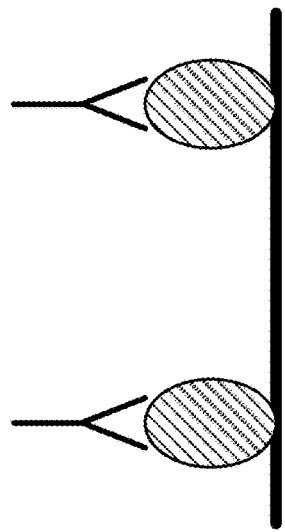
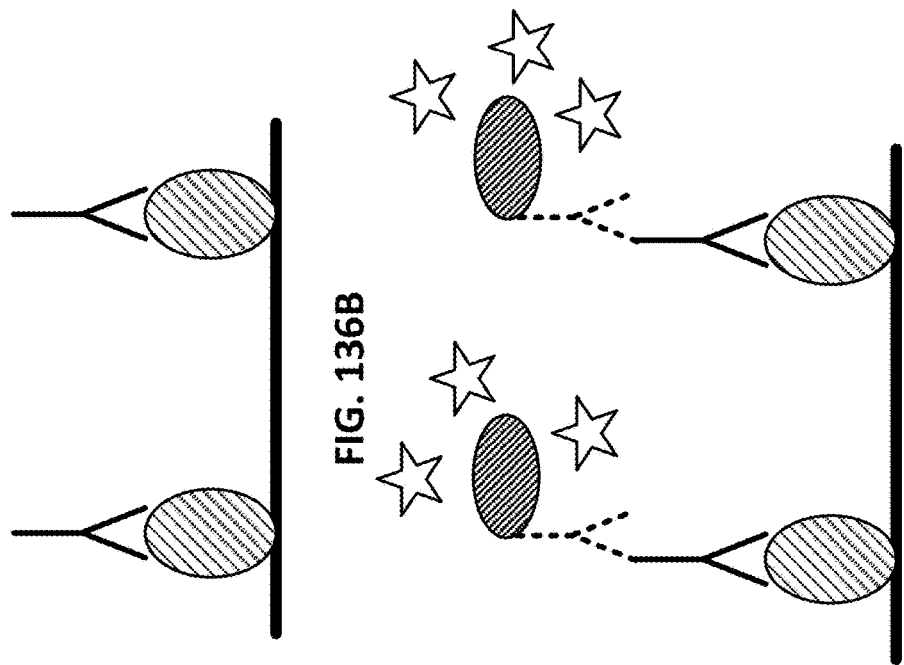
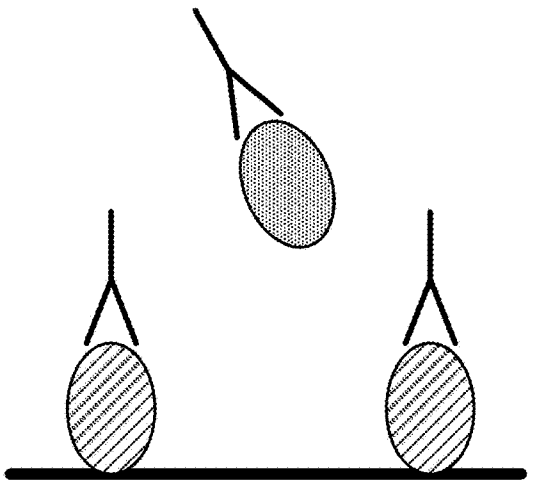
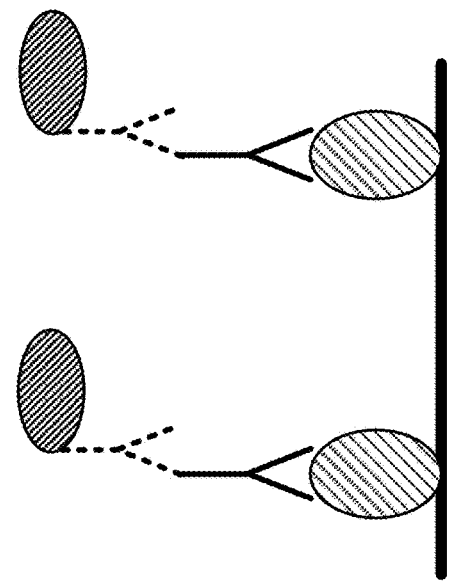

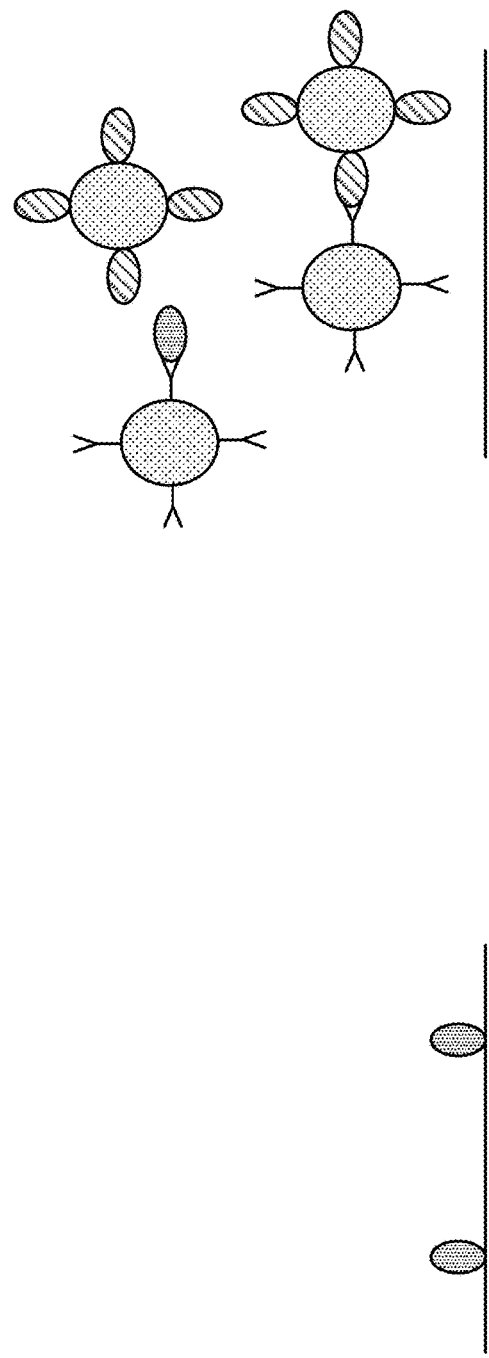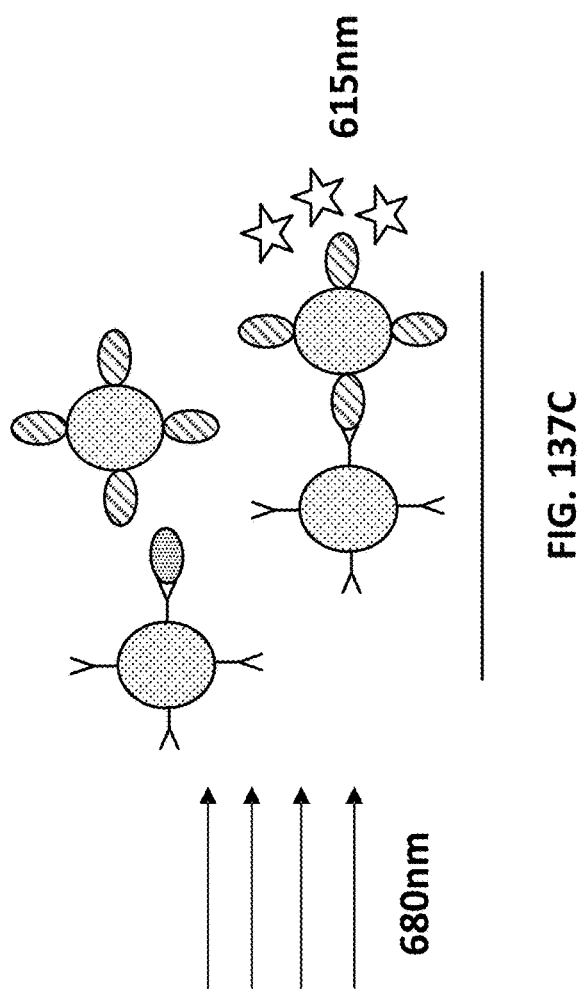

SYSTEMS, DEVICES, AND METHODS FOR FLUIDIC PROCESSING OF BIOLOGICAL OR CHEMICAL SAMPLES USING FLEXIBLE FLUIDIC CIRCUITS

RELATED APPLICATIONS

An Application Data Sheet is filed concurrently with this specification as part of the present application. Each application that the present application claims benefit of or priority to as identified in the concurrently filed Application Data Sheet is incorporated by reference herein in its entirety and for all purposes.

TECHNICAL FIELD

The present disclosure relates to systems and methods for analysis of a biological or chemical sample, e.g., as may be collected from the oral, nasal, anal or vaginal cavity of a patient. More particularly, the present disclosure relates to systems and methods that use a fluidic structure having collapsible elements, such as collapsible chambers, passages, and reservoirs to provide inexpensive, easily packaged, and reliable tools for performing chemical or biological assays.

BRIEF DESCRIPTION OF THE DRAWINGS

Implementations are illustrated by way of example and not limitation in the figures of the accompanying drawings, in which like references indicate similar elements.

FIGS. 27 through 29 depict a fluidic bypass structure during various stages of use.

FIGS. 30 through 32 depict an example of a feature that is implementable on a platen being instead implemented on a roller.

FIGS. 33 through 37 depict partitioning recess structure during various stages of use.

FIGS. 41 through 46 depict schematics of a portion of a fluidic structure with a fluidic circuit or sub-circuit that may be used to expose an area of interest to a particular fluid.

FIGS. 47 through 56 depict schematics of a portion of a fluidic structure with another fluidic circuit or sub-circuit that may be used to expose an area of interest to a particular fluid.

FIGS. 99-101 depict example fluidic structures for providing mixing capability in a fluidic system.

FIG. 107 depicts an example fluidic structure for providing metering capability in a fluidic system.

FIG. 108 depicts another example fluidic structure for providing metering capability in a fluidic system.

FIG. 111 depicts a legend for symbols used in FIGS. 112A through 126D.

FIG. 126A' depicts an actual example fluidic circuit that represents one implementation of the fluidic circuit of FIG. 126A. FIGS. 126C and 126D are both split across two pages and thus include FIGS. 126C-1 and 126C-2 and FIGS. 126D-1 and 126D-2.

FIGS. 129A through 129E depict example structures that may be used to provide another breath capture module.

FIGS. 136A-136F depict a surface-based antigen-down, heterogeneous, competitive two-antibody immunoassay.

FIGS. 137A-137C depict a homogeneous competitive immunoassay.

Figure 126A:
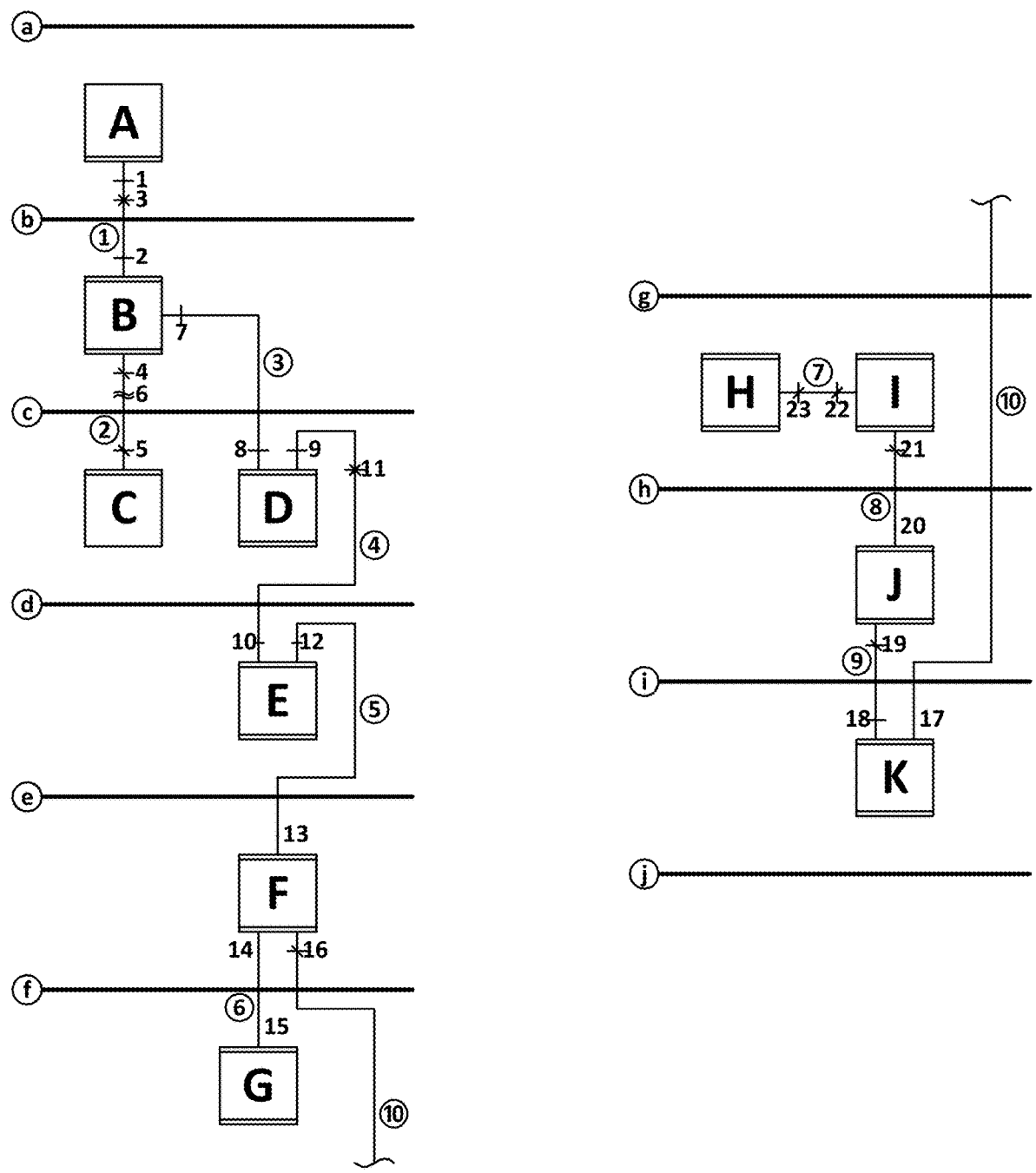
FIGS. 126A through 126H depict various example fluidic circuits that may be used to perform an assay on a sample.
Figure 126A:

At least FIGS. 126A', 126E, 126F, 126G, and 126H are all drawn to-scale.

DETAILED DESCRIPTION

The following detailed description includes references to the accompanying drawings, which form a part of the detailed description. The drawings show illustrations in accordance with example implementations. These example implementations, which are also referred to herein as "examples," are described in enough detail to enable those skilled in the art to practice the present subject matter. The implementations can be combined, other implementations can be utilized, or structural, logical, and electrical changes can be made without departing from the scope of what is claimed. The following detailed description is, therefore, not to be taken in a limiting sense, and the scope is defined by the appended claims and their equivalents.

Fluidic systems in certain embodiments are provided for analysis of small-volume biological or chemical samples, such as may be obtained using swabs that may be swabbed against moist tissue of a test subject, such as against the buccal surfaces, the tongue, the nasal meatuses, the nasopharyngeal cavity, the back of the throat, the anus, and the vagina. Examples of some such swabs are described in U.S. Patent Application Nos. 62/705,860, filed Jul. 17, 2020; 62/706,306, filed Aug. 7, 2020; 63/198,697, filed Nov. 5, 2020; and 63/199,610, filed Jan. 12, 2021, all of which are hereby incorporated herein by reference in their entireties.

A fluidic system may incorporate a fluidic structure and various systems or mechanisms for controlling how fluids flow within fluidic circuits defined within the fluidic structure. The fluidic structure of a fluidic system may be removable from the system in some cases, allowing for the fluidic structure to be replaced with a new fluidic structure in order to perform a subsequent analysis or fluid processing operation without risking contamination from the most recent previous such analysis or fluid processing operation. The fluidic circuits or flow paths within the fluidic structure may be configured to transport fluids processed within the fluidic system from one location within the fluidic structure to another responsive to inputs received from other components of the fluidic system. A fluidic circuit may be understood to be analogous to an electrical circuit, e.g., a collection of one or more fluid flow paths that fluidically connect together various other fluidic elements, e.g., reservoirs, chambers, etc., within a fluidic structure. In some instances, a fluidic circuit may be viewed as including a plurality of chambers, sets or subsets of which are fluidically connected by flow paths, e.g., to form a fluidic network, such that fluids may be moved in between chambers of the fluidic circuit. In some such instances, such flow paths may travel along different axes and/or may follow non-linear paths. In some implementations, fluidic circuits may include multiple flow paths that may lead from a single chamber to multiple different chambers, e.g., three or more different chambers.

In traditional mini- and microfluidic systems, the channels that define the various fluidic flow paths or circuits of a fluidic system are typically formed in a fluidic structure that is composed of a rigid (or at least self-supporting—it may, for example, be made of molded elastomer, such as PDMS) substrate, e.g., an etched or machined substrate or an injection molded substrate or housing. Such a substrate may then be interfaced with a rigid plate and/or elastomeric membrane that seals the channels and/or provides volume change within portions of the fluidic circuit(s) in order to provide for valving and pumping control. Fluid flow in such fluidic systems is accomplished by using pump structures located either within the substrate or offboard of the substrate, with the pressure produced by the pump structures being communicated through the flow paths in order to move fluid from one location in the fluidic structure to another.

In certain embodiments, micro- and minifluidic structures are provided using a flexible substrate. Instead of using a rigid substrate with channels formed therein (or a substrate in which the flow channels are otherwise self-supporting, e.g., such as may be the case in a substrate made of cured silicone), in certain embodiments, one or more fluidic circuits are defined between two (or more) flexible, but relatively inelastic, portions of material, such as sheets of Mylar, that are selectively joined together, e.g., using heat-sealing, in order to create seals that define the perimeter(s) of various chambers and fluidic paths that make up a particular fluidic circuit (as used herein, "inelastic" material refers to material that possess a modulus of elasticity and/or thickness that result in the material stretching by 1% or less when subjected to a 10 psi pressure field; in some contexts, the inelastic material may be replaced with relatively inelastic material, which may have an elasticity and/or thickness that result in the material stretching by 10% or less when subjected to a 10 psi pressure field). By avoiding the use of a rigid or self-supporting substrate to define the fluidic circuits and other fluidic elements, such fluidic structures are able to transition between a flat, collapsed state when unpressurized (or at sub-atmospheric pressure), and an inflated/semi-inflated or un-collapsed state when pressurized (with the term "inflate" in this context referring to filling such fluidic flow paths with liquid or gas). For example, if two portions of material are sealed or joined together when the space in between the two portions of material is held at a vacuum or otherwise sub-atmospheric pressure level, the resulting fluidic structure may provide a fluidic circuit having one or more portions thereof that are held at a vacuum or partial vacuum (or may be held at a zero volume) until they are fluidically connected with a higher-pressure environment. It will be understood that the portions of material can be from separate sheets, or may be portions of material from the same sheet, e.g., a sheet that has been folded over on itself, with each portion of material lying on an opposite side of the fold line and facing the other portion of material.

There is considerable flexibility in where such seals are placed, as will be evident from later discussion below relating to various examples, but some implementations may feature, for example, portions of material that are joined together along two parallel seal lines that define between them a passage running down the middle, or near the middle, of two portions of material. The passage may have a width equal to the gap between the two seal lines (when pressurized, the passage may expand into a more cylindrical shape if both portions of material are thin and flexible, thereby causing the passage width to contract but the passage height to increase). The portions of material in such examples may be additionally joined together in other locations as well, e.g., along lines that outline a fluid reservoir located on either side of the passage, or along parallel lines that define passages between such reservoirs and or other reservoirs or passages.

As a result, the working volumes of such collapsible fluidic structures, i.e., the volumes that contain fluids needed in the operation of the fluidic structure, are provided on-demand when pressurized fluid is introduced into such structures. In effect, the entire fluidic circuit may be viewed as a collection of discrete bladders that selectively transition between a "flat" state in which they have low, and in many cases, zero volume, and a "pressurized" state in which they have non-zero volumes. This avoids the need to displace a prior fluid, e.g., air, that was contained within such a fluidic structure prior to introduction of the sample of interest, thereby reducing the amount of fluids needed and/or reducing the likelihood of air bubbles being present in the fluid of interest. There is also the further benefit that by having the various fluidic chambers and passages of the fluidic circuit empty of fluid prior to use, there is no need to either provide a contained volume in which to capture such pre-existing fluids when displaced by the working fluids of the fluidic system or provide venting features that allow such pre-existing fluids to be vented outside of the fluidic system when displaced by the working fluids of the fluidic system. In the context of fluidic systems that are used for biological and chemical assays, the ability to omit vents, e.g., openings or passages that allow a fluid to enter or exit from a fluidic circuit in a fluidic structure, e.g., to ambient atmosphere, is particularly advantageous, as vents may serve as both potential points of entry for contaminants into the fluidic system, which may render any fluidic analysis that is performed less accurate, and leak sources that may allow potentially dangerous biological and/or chemical substances to escape from the fluidic system, thereby posing a hazard to operators.

Some such "on-demand" fluidic structures may also be operated without the need for traditional, discrete pumps. For example, since the fluidic structure itself may be constructed from a flexible material, fluid may be moved around with the fluidic structure through the application of pressure on different portions of the fluidic structure, essentially squeezing the fluid from one portion to another portion of the fluid structure.

In some such implementations, such fluidic structures may be positioned between two clamping structures so as to create one or more zones of increased pressure on one or more portions of the fluidic structure. In such implementations, the fluidic structure and/or one or both of the two clamping structures may be configured to permit for relative movement between the fluidic structure and one or both of the clamping structures to allow the one or more zones of increased pressure to be moved from one location to another on the fluidic structure.

For example, in some implementations, such a fluidic structure may be placed with one side against a platen or other rigid surface. A roller may then be placed against the opposite side of the fluidic system and used to press the fluidic system against the platen or other rigid surface (the roller and the platen would be considered the "clamping structures," thereby generating a zone of increased pressure where the roller contacts the fluidic structure and compresses it against the platen or other rigid surface. By rolling the roller across the fluidic structure, the zone of increased pressure may be caused to move across the fluidic structure in the same direction, i.e., along the axis of movement of the roller. Fluid that is contained within the fluidic structure in one or more portions that are subjected to the moving pressure zone may, for example, be squeezed into one or more adjacent portions of the fluidic structure when the zone of increased pressure is applied to such fluid. In this manner, it is possible to use a roller (or other structure that is able to provide for a zone of increased pressure that can be caused to move relative to the fluidic structure) to move fluids between various parts of such a fluidic structure.

Figure 1:
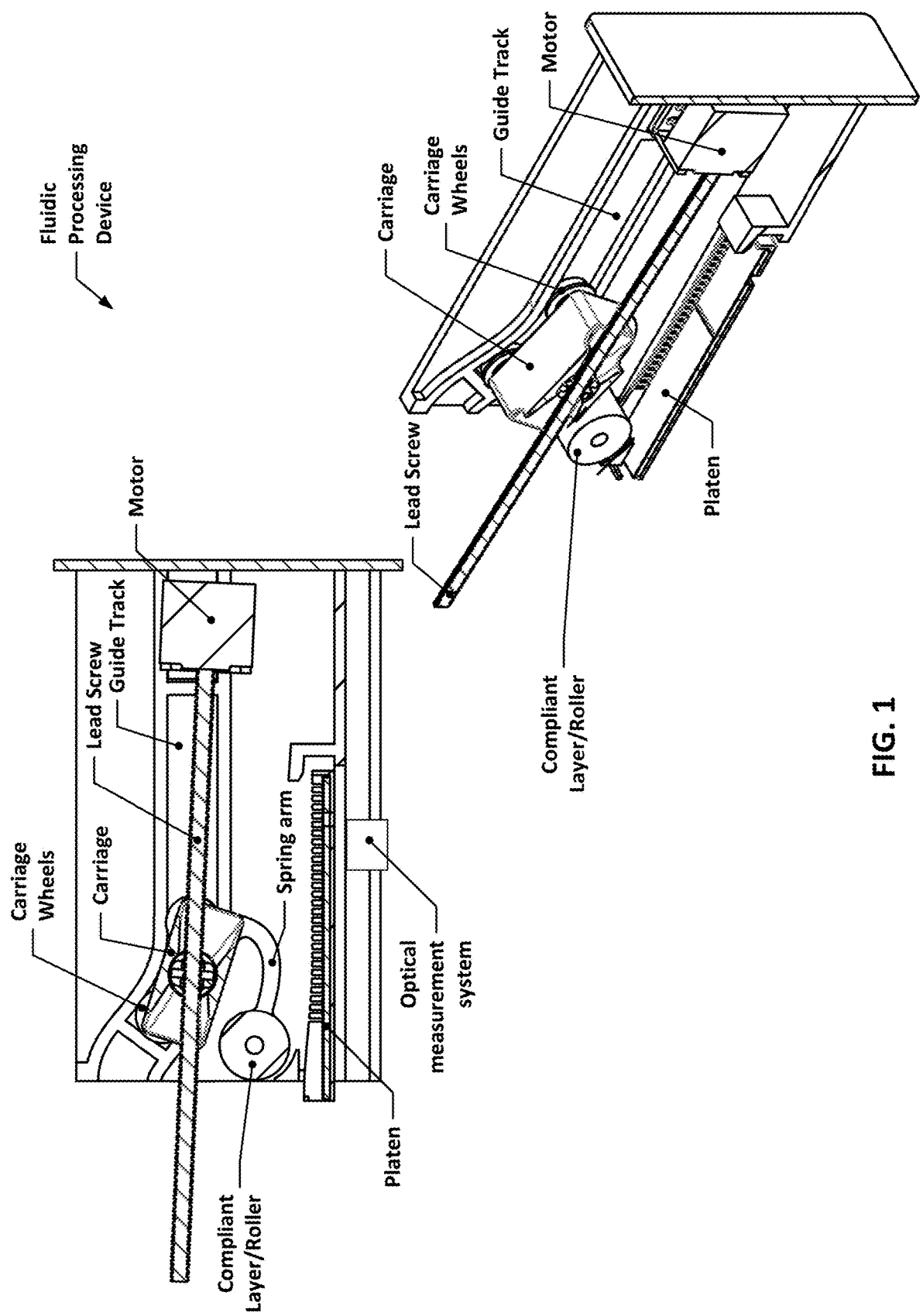
FIG. 1 depicts an example of a portion of a fluidic system that may be used to apply a movable clamping pressure zone to a fluidic structure.

FIG. 1 depicts cutaway views of a portion of an example fluidic system that may interface with the fluidic structures discussed herein and may be used to actuate the fluidic structures discussed herein. The depicted device may include a carriage that has wheels that are positioned within a guide track that may be configured to cause the carriage to move closer to, or further from (or maintain a constant distance from), a platen as the carriage is moved along the guide track. A motor may be used to actuate a lead screw that may be rotated in order to move the carriage along the lead screw, thus causing the carriage to transit along the guide track. The carriage may have a spring arm that may apply a spring force to a roller that may be pushed into contact with the platen as the carriage transits along the guide track. A fluidic structure may be placed in the fluidic system in between the platen and the roller, and the roller may be caused to apply a moving clamping pressure zone to the fluidic structure by actuating the motor and lead screw so as to cause the carriage to move along the guide track; as the carriage moves, the roller, which moves with the carriage, may exert a clamping pressure on the fluidic structure that generates the clamping pressure zone. Other mechanisms that provide similar functionality may also be used and are considered to be within the scope of this disclosure as well. Clamping pressure zones, as the term is used herein, may be understood to refer to generally linear pressure fronts, such as may be applied by the roller discussed above. Such linear pressure fronts may generally have a long axis and may, in some cases, have a short axis that is transverse to the long axis, e.g., be a long, thin rectangular or elongate region. The fluidic system of FIG. 1 may also include, for example, one or more optical measurements systems, as shown, that may be configured to obtain optical measurements, e.g., of color and/or illumination intensity, from a chamber or chambers within the fluidic structure. For example, the fluidic structure may have transparent portions that allow light to reach or escape from a particular chamber or chambers of the fluidic structure, and the optical measurement system may include one or more light sources and/or photodetectors, e.g., image sensors, that may be used to obtain data indicating an intensity level of an optical signal, which may be used as a proxy for a concentration of a particular target substance for which detection or quantification is sought.

It will be further understood that the system shown in FIG. 1 is but one example system that may be used to interface with, and act on, the fluidic structures discussed herein. In other implementations, systems with multiple rollers, which may be staggered relative to each other along an axis perpendicular to their rotational axes and/or which may be configured to be movable independently of one another along one or more axes, may be provided to allow for multiple clamping pressure zones to be simultaneously applied to a single fluidic structure, thereby providing greater flexibility in how the fluidic circuit(s) of the fluidic structure are able to be operated. In yet other implementations, the clamping pressure zones that are applied may be provided by mechanisms other than the rollers discussed herein. For example, a roller that can swivel, e.g., a caster, may be used to allow the direction of movement of the roller to be adjusted so as to support multi-directional roller movement. In yet other implementations, mechanisms other than, or in addition to, rollers may be used, e.g., solenoids may be used to apply some clamping pressure zones, e.g., to fluid reservoirs or other such areas. In some implementations, as discussed below with respect to some implementations, rollers (or other clamping zone application mechanisms) may be caused to reverse direction. This may facilitate various operations, e.g., sealing a previously traversed passage segment (the clamping pressure zone may act to push the to-be-sealed area of the fluidic structure into good thermal contact with the heating element used to make the seal), mixing (as discussed with respect to FIG. 17, in which the clamping pressure zone was reciprocated back and forth), and/or wash operations (e.g., to drive fluids back out of an area of interest).

In some such implementations, the use of a movable zone of increased pressure allows for such fluidic structures to be operated using much simpler equipment than is typically required. For example, a typical fluidic structure may require multiple pumps and valves to be provided in order to operate, with each such pump and valve typically requiring a separate actuator or other actuation mechanism. In contrast, fluidic structures such as those described above may be operated with only a single actuation mechanism that may be used to cause the roller (or other clamping structure that provides a movable zone of increased pressure) to move relative to the fluidic structure.

In addition to simplifying the actuation mechanism needed to operate such fluidic structures, fluidic structures such as those described above may also be easily manufactured using available materials. Suitable flexible materials, e.g., Mylar, BoPET, or cellophane, may be easily assembled, e.g., using heat welding, to produce the fluidic structures discussed above. Such structures may, for example, be provided by clamping two portions of such material between two heated platens that have raised patterns that define the desired bond lines between the two portions of material. The clamped portions of material may, in the regions of the raised patterns, be caused to bond together due to the localized application of heat in those areas, with the remainder of the portions of material remaining unbonded. Such fluidic structures are inexpensive to manufacture. In some implementations, non-polymeric materials, e.g., metal foils, may be used to provide a portion of material. For example, a thin aluminum, gold, or other film or foil may be used instead of a polymer like Mylar, BoPET, or cellophane. In such implementations, other types of joining operations may be used to provide permanent and temporary seals (temporary and permanent seals are discussed in more depth below with regard to FIG. 4), e.g., double-sided adhesive gaskets that adhere the portions of material together only in the regions where the seals are to be located or sandwiching a thin polymeric gasket defining the permanent and temporary seals in between such portions of material and then heat-sealing the polymeric gasket to both adjacent portions of material, thereby joining the two portions of material together. Techniques such as laser welding may also be used, when appropriate, to join the portions of material to one another to define the temporary and permanent seals.

Other benefits of such fluidic structures include reduced packaging size (for example, such fluidic structures may be stored in a rolled-up form, whereas traditional fluidic structures are rigid and cannot be transitioned to a more compact format), lighter weight, suitability for shipment via normal letter envelopes (as opposed to requiring a package), enhanced resistance to breakage, etc.

An example of a fluidic system using such a fluidic structure is discussed below with reference to FIGS. 4 through 15, although it will be apparent that a wide variety of fluidic structures or systems embodying one or more of the concepts discussed herein may fall within the scope of this disclosure, and the disclosure is not to be considered limited to this particular example.

Figure 4:
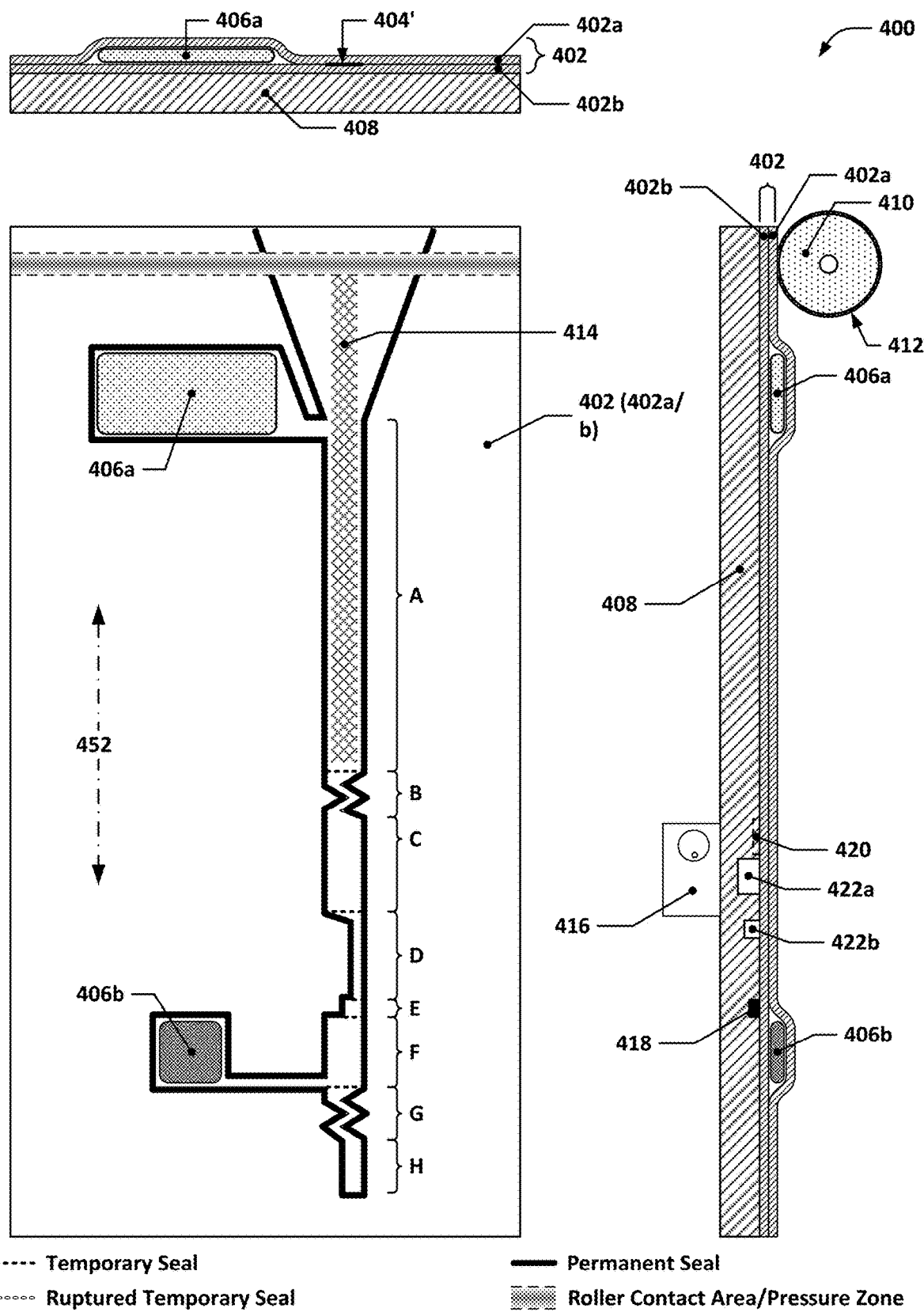
FIGS. 4 through 15 each depict various views of an example fluidic system in different operational states.

FIG. 4 depicts plan, side, and top views of an example fluidic system 400. The fluidic system 400 includes a fluidic structure 402 that is composed of two portions of material 402a and 402b of flexible, inelastic material, such as a polyester film like biaxially-oriented polyethylene terephthalate (BoPET, also sold as Mylar by DuPont de Nemours, Inc.) or similar material (alternatively, the separate portions of material 402a and 402b may also be different portions of the same material, e.g., a single sheet of such material that has been folded over on itself, with the two adjacent portions thereof sealed to one another). The portions of material 402a and 402b are shown having an observable thickness, but this is simply for illustration purposes and to allow them to be more easily discerned by the reader. In practice, such portions of material 402a and 402b may, in some implementations, be on the order of a few thousandths of an inch thick or less, e.g., several or tens of micrometers in thickness. The portions of material 402a and 402b may be sealed together, e.g., using thermal bonding, to create seals that define the perimeters or boundaries of one or more fluidic channels, reservoirs, and/or chambers that may be used in the fluidic structure 402. Techniques for thermal bonding of such materials, e.g., such as BoPET, are well known, and may include heat sealing, laser welding, ultrasonic welding, heat pressing, etc. The seals may be designed to be "permanent," i.e., not intended to fail structurally during normal use, or "temporary," i.e., intended to fail structurally under certain conditions during normal use, e.g., when a particular pressure is reached within the portion of the fluidic structure adjacent to such temporary seals. In FIG. 4, a permanent seal is provided along the dotted line bounded on either side by thin solid lines, while temporary seals are provided along the dotted lines that are not bounded on either side by thin solid lines. In the depicted example, the permanent seal can be observed to be a single, contiguous seal that, in effect, traces the perimeter or boundary of the fluidic circuit provided by the fluidic structure 402 shown. However, it will be understood that some fluidic structures 402 may feature multiple, discrete permanent seals that define, for example, separate flow paths that may have both inlets and outlets that are located along edges of the fluidic structure 402. It will also be understood that while the depicted permanent seals are linear in nature, such seal lines may also be curved or curvilinear. It will also be noted that while the depicted permanent seals are shown as thin lines, other implementations may use permanent seals with a greater width, including implementations in which all of the portions of material 402a and 402b that are outside of the fluidic circuit area are sealed together, i.e., the two portions of material 402a and 402b are completely sealed together except in regions where the fluidic circuit is intended to exist. Producing a permanent seal can be performed quite quickly; for example, in prototyping, permanent seals were able to be made between two 3 mil sheets of Mylar by using a 3 mm wide, 8 inch long thermal sealing element that was supplied with 200 W of power and used to press together the Mylar sheets for 5 seconds. Similarly, temporary seals were able to be made in a laboratory setting using a similar procedure, but with the thermal sealing element being applied for only 2.7 seconds instead of 5 seconds.

Each temporary seal may be placed so as to extend between two different portions of the permanent seal(s) and/or another temporary seal or seals. Such a temporary seal may be created by subjecting the portions of material 402a and 402b in the region of the temporary seal to a shorter duration and/or lower temperature heat sealing operation than is used to create the permanent seal(s), e.g., as discussed above. Alternatively, temporary seals may be formed by bonding the two portions of material 402a and 402b in the region of the temporary seal together using other bonding mechanisms, e.g., adhesives. The temporary seals may be used to create temporary chambers or working volumes that may, during use of the fluidic circuit, be fluidically isolated from one or more other chambers or working volumes adjacent thereto by way of such a temporary seal and which may then be caused to eventually fluidically connect with such one or more chambers or working volumes through intentional failure or bursting of the temporary seal, thereby allowing the contents thereof to be pumped or pushed, e.g., through movement of the roller or other force-application mechanism along axis 452, from that temporary chamber to a downstream fluidic structure, e.g., another chamber or a fluidic channel. In the fluidic structure 402, there are temporary seals located at the transitions between regions A and B, C and D, D and E, E and F, and F and G. The temporary seals may have a burst or rupture pressure that is less than that of the permanent seals (in fact, the permanent seals may even have a burst or rupture pressure that exceeds that of the portions of material 402a and/or 402b itself, i.e., the portion of material may fail before the permanent seal does)—this burst or rupture pressure may be significantly less, e.g., an order of magnitude or more less, than that of the permanent seals.

Figure 2:
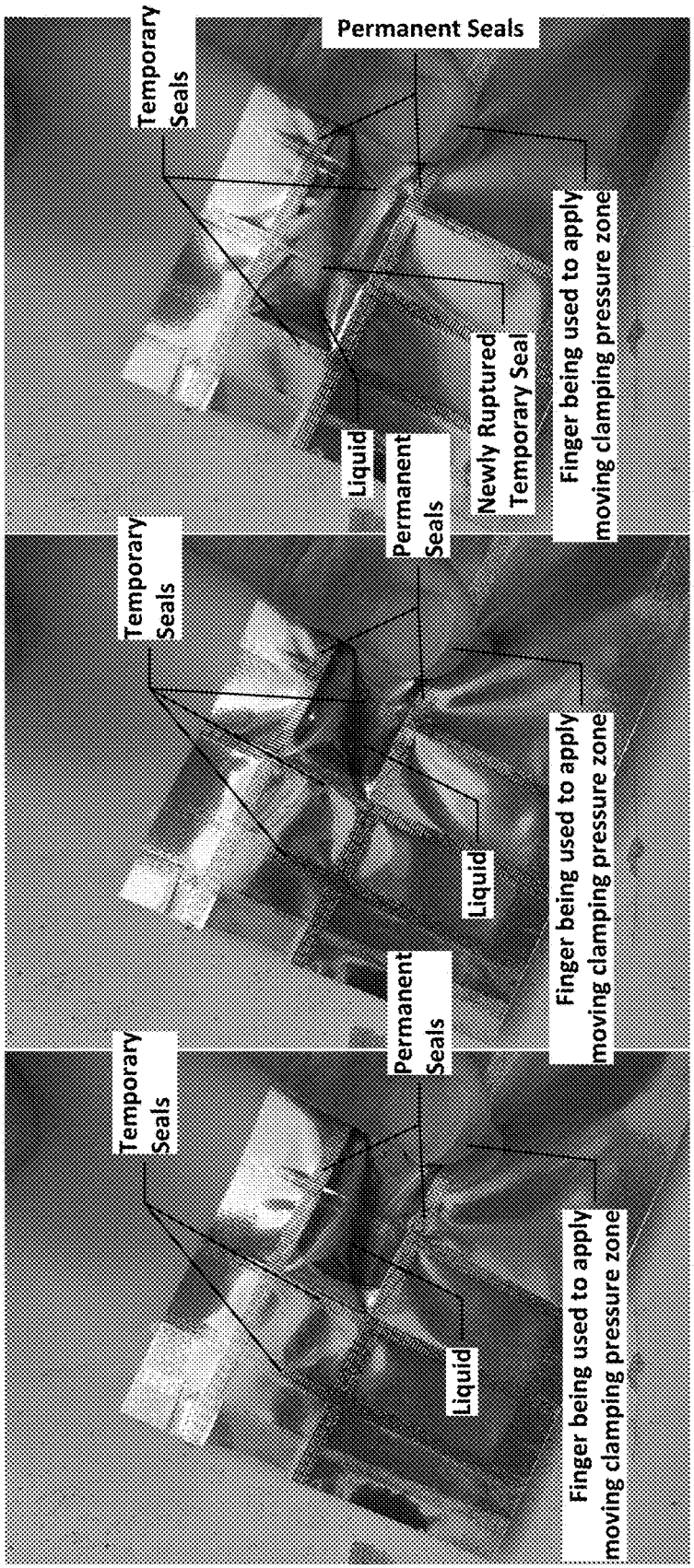
FIG. 2 depicts three sequential photographs of an example fluidic structure during rupture of a temporary seal.

FIG. 2 depicts three sequential photographs of an example fluidic structure having both temporary and permanent seals. Liquid is trapped in between two sheets of Mylar in a volume bounded by a temporary seal, two permanent seals on opposing sides of the temporary seal, and a person's finger, which is acting in place of a roller in this example and applying a moving zone of clamping pressure in a direction parallel to the permanent seals, e.g., in a direction extending upward to the left. As the person's finger moved upward to the left, the pressure applied on the fluidic structure causes the liquid to increase in pressure until the temporary seal that restrained it from moving suddenly ruptured (this happened so quickly that it was not possible to obtain an image of the temporary mid-rupture).

Temporary seals may also be designed to fail or rupture in various ways. For example, if two sheets of Mylar are thermally bonded together to form a temporary seal, such a temporary seal will tend to rupture along most or all of its length when subjected to a pressure greater than its rupture pressure, "popping" open to provide a passageway in which very little of the temporary seal remains. In material such as cellophane, however, the same type of temporary seal may tend to rupture by forming one or more pinholes through the seal area, leaving most of the temporary seal intact. As a result, the temporarily sealed passageway may still be relatively obstructed even after the temporary seal ruptures, although the velocity of the fluid that is forced through the pinholes in the ruptured temporary seal in such cases may be significantly higher than it would otherwise be, e.g., if the entire temporary seal had ruptured along its length (thus providing a single, large passage with little flow restriction compared to the pinholes). Such temporary seals may, in some instances, be used to promote jetting and/or mixing of fluids used in the fluidic systems discussed herein.

Fluidic structures such as those discussed herein may also utilize, in place of or in addition to temporary seals, dynamic seals. Dynamic seals are seals that are caused to come into being dynamically responsive to the pressurization of particular fluidic structure geometries; such dynamic seals effectively seal such a pressurized fluidic structure off from one or more downstream fluidic flow paths that would otherwise normally be fluidically connected with the pressurized fluidic structure. Various examples of such fluidic structures are shown in FIGS. 3A-3F, which are discussed further below. In each of FIGS. 3A through 3F, the dynamic seals are represented are represented by a sawtooth In FIG. 3A, a fluidic structure 356 is shown that has a reservoir 358 that has a passage 360 that is fluidically connected thereto. Another passage, not marked, may provide fluid to the fluidic structure 356. The fluidic structure 356 is, as with the previous fluidic structures discussed herein, composed of two portions of material that are sealed together using permanent seals along the paths indicated. The permanent seals define the reservoir 358, the passage 360, as well as the other passage. There may, of course, be other fluidic structures that are also defined between the two portions of material that are not depicted in FIG. 3A, such as any of the various other fluidic structures discussed herein, and that may be fluidically connected to, and upstream and/or downstream of, the fluidic structure depicted in FIG. 3A. This is similarly true for the fluidic structures of FIGS. 3B through 3F.

When the fluidic structure 356 is first pressurized, e.g., when fluid is introduced into the reservoir 358 through the inlet passage, the fluid will, through capillary action, wick into the reservoir 358 but will not initially flow into the passage 360 in any appreciable amount. In effect, a dynamic seal 362 forms at the junction between the passage 360 and the reservoir 358. As fluid continues to flow into the reservoir 358, the pressure in the reservoir 358 may continue to increase, causing at least one portion of material forming the top or bottom of the reservoir 358, if not both, to bulge outward. At the same time, the dynamic seal 362 may continue to prevent, or effectively prevent, fluid flow into the passage 360. However, at some point, the pressure within the reservoir 358 may reach a threshold level that causes the dynamic seal to fail, causing the passage 360 to become fluidically connected with the reservoir 358.

Thus, the dynamic seal 362 acts, in many respects, in a manner similar to the temporary seals discussed above. The two seals differ in that there is actually a non-permeable physical bond in the temporary seal that prevents fluid flow from occurring which is then ruptured or broken when the pressure on one side of the seal exceeds a threshold amount, whereas the dynamic seal does not have such a non-permeable physical bond and instead operates by, in essence, clamping the passage 360 shut.

While the mechanism behind the operation of such dynamic seals has not yet been fully characterized, it is believed that the sealing behavior of such dynamic seals is likely provided by a combination of capillary/surface tension effects and separate mechanical clamping effects that arise from the use of at least one portion of material that is thin and flexible, yet relatively inelastic.

When the fluid first flows into the reservoir 358 and encounters the location where the passage 360 fluidically connects with the reservoir 358, for example, there may be strong opposing capillary forces at play when the fluid tries to turn the corner (the corner or corners where passage 360 intersects with the permanent seal that defines the reservoir 358) that may act to discourage the fluid from flowing into the passage 360. In effect, the surface tension of the fluid, assuming the fluid is liquid, needs to be overcome in order for the fluid to flow into the passage 360. This effect may be particularly pronounced in fluidic systems formed between portions of material that are hydrophobic in nature. For example, fluidic systems defined by permanent seals formed between two sheets of flexible Mylar, for example, may be generally hydrophobic, and it was observed in such systems that a reservoir 358/passage 358 configuration as discussed above formed a dynamic seal even when the amount of fluid introduced into the reservoir 358 was quite small. For example, when fluid is initially introduced into the reservoir 358, the fluid may wick into the reservoir 358 through capillary action, without really requiring active pressurization through the application of a moving clamping pressure zone upstream of the reservoir 358. The dynamic seal may provide a sealing effect even under these low-pressure conditions.

When the reservoir 358 is further pressurized, however, the resulting outward bulging of at least one portion of material (if not both portions of material—as discussed above, one or both portions of material may be made from a flexible yet relatively inelastic material, e.g., Mylar) that defines the reservoir 358 results in sharp bends or creases to occur in the material portion(s) where the permanent seals are located that bound the reservoir 358. When there is a smaller-aperture passage that intersects with one of these permanent seals, e.g., the passage 360, it is believed that the creases that form along the boundaries of the reservoir 358 span transversely over the passage 360, thereby increasing the bending stiffness of the material portion(s) that spans over the intersection between the reservoir 358 and the passage 360. This is believed to prevent the material portion(s) that define the passage 360 from bulging upwards, as those material portion(s) are not able to easily bend in a plane that is perpendicular to the page (with respect to the orientation of FIG. 3A) and parallel to the edge of the reservoir 358 where the passage 360 connects. For example, the material portion(s) that are creased may act, in effect, like a piece or pieces of angle channel that have bending stiffnesses that far exceed that of un-creased material portions. The creased portion(s) spanning over the passage 360 may thus act like a rigid piece of material that presses against another rigid piece of material (such as another creased portion in the other material portion, or against a rigid material if one of the two material portions is rigid). While some small amount of fluid may still potentially squeeze past this clamped interface, such an amount may, for practical purposes, be negligible. When the pressure within the reservoir 358 reaches a particular threshold level, however, the fluid pressure will eventually push back on the creased portions that span the passage 360 and cause them to buckle, thereby allowing the material portions that define the passage 360 to bulge up and allow the fluid to flow into the passage 360 in a generally unobstructed manner.

Those with familiarity with traditional microfluidic systems looking at a structure that provides a dynamic seal in isolation, i.e., without the benefit of knowledge of how the fluid flow through the structure occurs and without the knowledge that the structure in question is part of a fluidic structure defined between two portions of material in which at least one, if not both, portions of material are made from a flexible, relatively inelastic material, may mistakenly believe that they are observing a "stop junction," which is a fluidic structure used in traditional microfluidic systems in a somewhat similar manner.

As noted earlier, traditional microfluidic systems are typically formed in a rigid fluidic structure, e.g., in an injection-molded housing or a laminated substrate or plate such that the fluidic passages and chambers within the microfluidic system retain their cross-sectional shapes regardless of whether there is liquid in them or not. As a result, small passages that are present in such traditional microfluidic structures may act, in effect, as capillary tubes, tending to try and retain fluid therewithin. This effect is typically enhanced further by the materials used in traditional microfluidic structures, which may be hydrophilic. As a result, when liquid is flowed through a small-size passage into a larger chamber in a traditional fluidic system, the liquid will tend to tend to "stop" at the junction between the small-size passage and the larger chamber, being encouraged to remain within the passage by capillary and surface tension forces. The liquid will, eventually, flow into the larger chamber once the pressure applied to the liquid is sufficient to overcome the capillary/surface tension forces that cause the liquid to remain at the mouth of the small passage. In contrast, liquid that is flowed into the small-size passage from the chamber, i.e., in the reverse direction, may tend to wick into the small-size passage-actively seeking to flow into the small-size passage as opposed to resisting flow into the small-size passage.

In contrast, dynamic seals in fluidic structures that are formed between two portions of material, with one or both portions of material being a flexible, relatively inelastic material, are provided when fluid is flowed from a chamber into a smaller-size passage (or from a passage into another passage that tees into the first passage). Thus, while both dynamic seals and stop junctions may be formed in regions where there are intersections of small passages with larger chambers, flow occurs in opposite directions with respect to each structure. Moreover, while stop junctions rely entirely on capillary effects, dynamic seals may derive additional sealing capability from the mechanical clamping effects that are believed to occur due to the creases formed at the permanent seals by the distension of the portion or portions of material that are flexible but relatively inelastic. This clamping effect may allow dynamic seals to obtain higher release pressures, i.e., the back pressure that must be applied to the fluid in order to cause the dynamic seal to release, than may be achievable with stop junctions that are used in traditional microfluidic structures (the release pressure for a stop junction being the back pressure that must be applied to the fluid in order to overcome the stop junction effect).

There may also be enhanced capillary forces in dynamic seals that arise in conjunction with a crease or creases formed in the portions of material that are flexible but relatively inelastic. As mentioned previously, capillary forces and surface tension may act to discourage a liquid from flowing from a larger chamber and into a smaller passage that fluidically connects therewith. This is believed to be due to such capillary forces and surface tension effects making it difficult for such a liquid to turn a corner, e.g., into the passage. When there is a relatively small amount of liquid present in the chamber leading to the passage, the structure may generally remain planar, with the "corners" being provided solely by the permanent seals that define the passage and the chamber. However, when the chamber is filled with sufficient liquid to cause the portion or portions of material that are flexible but relatively inelastic to distend and form creases, the creases may, in effect, act as additional corners that the liquid in the chamber must turn around in order to enter the passage. These additional corners may provide further opportunity for capillary and surface tension effects to act on the liquid so as to discourage the liquid from entering the passage.

Generally speaking, the smaller the width of the passage 360 where the passage 360 intersects with the permanent seals that define the reservoir 358, the higher the pressure at which the dynamic seal that is formed at the intersection of the passage 360 with the permanent seal that defines the reservoir 358 will release, allowing fluid to flow into the passage 358. For example, a dynamic seal that is formed where a passage 360 that is 0.4 mm wide intersects with a permanent seal that defines a reservoir 358 will release/open at a higher pressure than if the same passage 360 were 0.7 mm in width at that point. Similarly, a dynamic seal that is formed where a passage 360 that is 0.7 mm wide intersects with a permanent seal that defines a reservoir 358 will release/open at a higher pressure than if the same passage 360 were 1 mm in width at that point.

The length ($d_1$) of the permanent seal that defines part of the reservoir 358 where the passage 360 fluidically connects with the reservoir 358 should be larger than the width ($d_2$) of the passage 360 at that point. For example, a $d_1/d_2$ ratio as low as 1.5 was found to form a dynamic seal, but one that had a very low release pressure, e.g., a release pressure low enough that the reservoir 358 could not actually be pressurized to the point where it was at its maximum volume. A $d_1/d_2$ ratio of at least 3 was found to provide a sufficiently high enough release pressure that the reservoir 358 could be pressurized to the point where it was at, or very near to, its maximum volume (assuming no stretching of the portions of material), and a $d_1/d_2$ ratio of at least 8 was found to provide a release pressure that was high enough to cause a spring-loaded roller that was used to apply the moving clamping pressure zone by compressing the fluidic structure against a rigid platen to lift up off of the unpressurized portions of material/platen when traversing over the pressurized reservoir 358 (this spring-loaded roller was applying approximately a 15-20 pound compressive force to the clamping pressure zone). In such a situation, the movable clamping pressure zone may be unable to actually apply pressure to the reservoir 358 that is sufficient to overcome the release pressure, thereby causing the dynamic seal to remain sealed. In such situations, various approaches may be taken to address this issue—for example, the force exerted by the clamping pressure zone may be increased to meet the requirements of the higher release pressure. Alternatively, additional features may be included near the dynamic seal, such as the floating seals discussed elsewhere herein, to effectively limit or lower the release pressure for a particular dynamic seal.

The depth of the reservoir 358 in a direction perpendicular to the permanent seal at which the passage 360 fluidically connects with the reservoir 358 may also vary. In some implementations, the depth of the reservoir 358 in a direction perpendicular to the permanent seal at which the passage 360 fluidically connects with the reservoir 358 may be nominally equal to the width of the passage 360, as shown, for example, in FIG. 3B.

Figure 3:
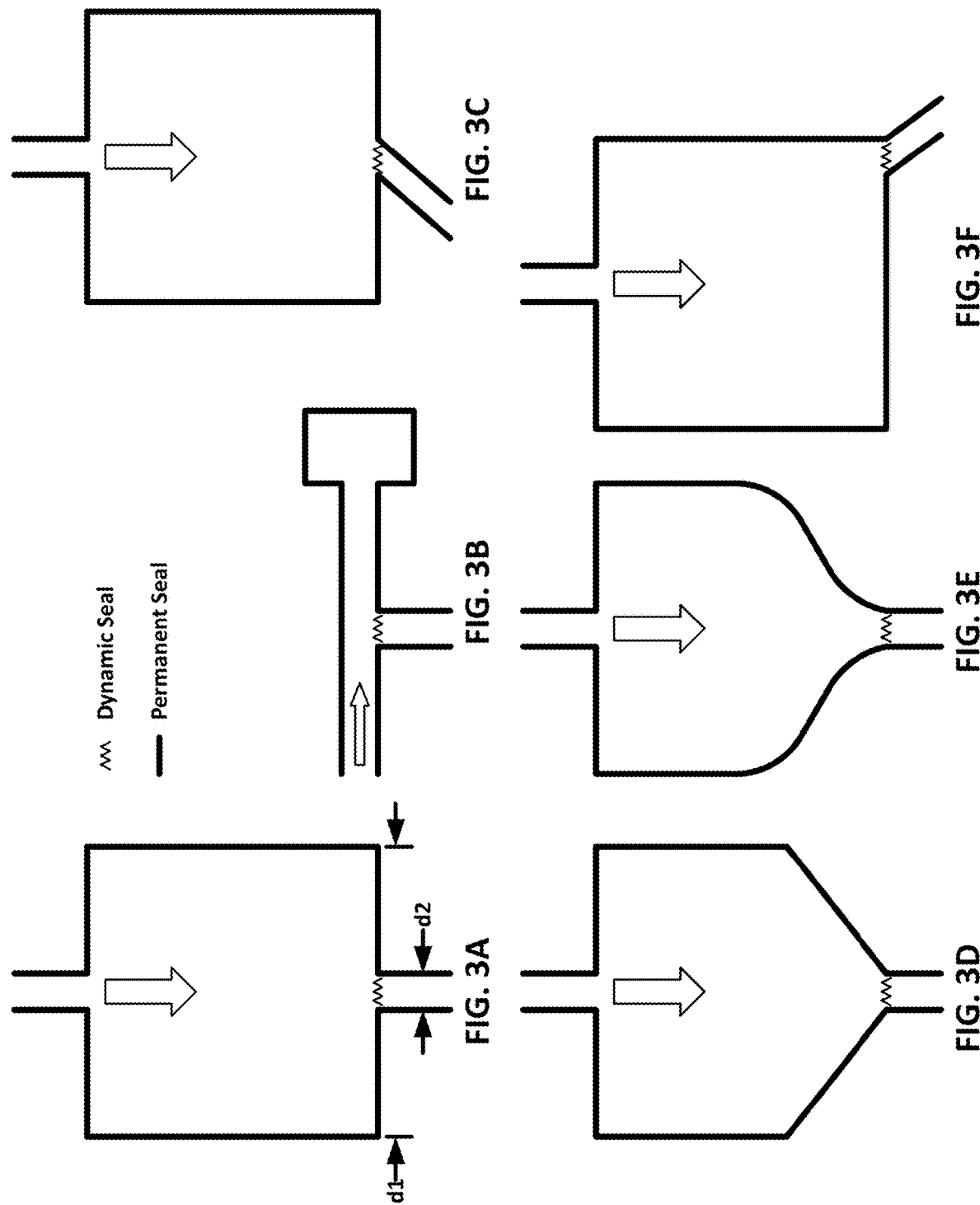
FIGS. 3A-3F depict example fluidic structures for providing dynamic seals.

In FIG. 3B, permanent seals define a passage 360A that is fluidically connected with a reservoir 358. A second passage 360B intersects with the passage 360A upstream of the reservoir 358 along one of the longer walls formed by the permanent seals that define the passage 360A. In such an arrangement, the passage 360A may act, in effect, like the reservoir 358 of FIG. 3A, causing a dynamic seal 362 to develop at the intersection of the passage 360B with the passage 360A. As a result, fluid flowing through the passage 360A will be constrained to flow into the reservoir 358 until the reservoir 358 (and the passage 358A) is pressurized to a first threshold amount. Once the first threshold amount is reached, the dynamic seal 362 that seals off the passage 360B will release, allowing the fluid that is subsequently flowed through passage 360A to flow into the passage 360B (assuming the clamping pressure zone continues to advance so as to maintain the pressurization of the fluid—if the fluid pressure drops sufficiently, e.g., to a first threshold amount lower than the release pressure, the dynamic seal may re-seal until the pressure is again increase to the release pressure). As with the passage discussed with respect to FIG. 3A, the smaller the width of the passage 360B where the passage 360B intersects with the permanent seal that defines the passage 360A, the higher the pressure at which the dynamic seal 362 that is formed at the intersection of the passage 360B with the permanent seal that defines the passage 360A will release.

In cases where a passage fluidically connects with a much larger chamber or reservoir, the distension or bulging of the larger chamber or reservoir may result in a dynamic seal that has too high a release pressure to operate reliably. In such cases, the addition of a floating seal, as discussed later herein with respect to FIG. 104, may be used to reduce the release pressure of the dynamic seal in that location.

The passages that are sealed by the dynamic seals discussed above do not necessarily need to intersect the permanent seal at which the dynamic seals are formed at a 90° angle, as shown in FIGS. 3A and 3B. In some implementations, the passages that are sealed by the dynamic seals discussed above may intersect the permanent seal that defines the upstream passage or reservoir that is sealed off from the downstream passage by a dynamic seal at an oblique angle, and thus have a smaller transverse width than the width of the dynamic seal. FIG. 3C depicts an example of this, where a passage 360 intersects with the permanent seal that defines a reservoir 358 at a 45° to form a dynamic seal 362. Regardless, the behavior of such a dynamic seal may generally be governed by the width of the gap in the permanent seal where the passage 360 fluidically connects with the reservoir 358 (or another passage 360, e.g., as shown in FIG. 3B). The reduced width of such a passage 360 downstream of the dynamic seal 362 may have little or no effect on the pressure at which the dynamic seal 362 may release, although it may affect the flow rate of the fluid through the passage for a given pressure once the dynamic seal 362 does release.

The permanent seal with which a passage fluidically connects to form a dynamic seal does not necessarily need to be straight, as shown in FIGS. 3A through 3C. Dynamic seals may also form where passages fluidically connect with a permanent seal that is non-linear-if the volume that is bounded by the permanent seal upstream of the passage represents, in effect, a large expansion in size of the passage, then a dynamic seal may still be caused to come into being where the passage starts to increase in size, e.g., at the intersection of the passage with the larger-cross-section upstream chamber or passage. FIG. 3D, for example, shows a reservoir 358 in which the permanent seals that define the reservoir 358 define a pentagonal shape instead of a rectangular shape. The two bottommost permanent seals of the reservoir 358 are perpendicular to each other, forming somewhat of a funnel shape before they meet the passage 360. A dynamic seal 362 is formed where the two bottommost permanent seals of the reservoir 358 meet with the passage 360. The dynamic seals formed in such arrangements may, for a given width of the dynamic seal, be weaker than the same width of dynamic seal in a fluidic structure such as is shown in FIG. 3A.

Dynamic seals may also be formed where passages transition to larger-width volumes in a more gradual manner, e.g., as shown in FIG. 3E. In FIG. 3E, a reservoir 358 is shown that is defined by permanent seals that smoothly transition from the larger width of the reservoir 358 to the smaller width of the passage 360. A dynamic seal 362 may nonetheless still form where the passage 360 ends, e.g., where the passage width starts to widen and expand in order to transition to the reservoir 358. In such an implementation, the pressure at which the dynamic seal releases for a given passage width may, for example, be less than the pressure at which a dynamic seal for a passage of similar width releases in configurations such as are shown in FIGS. 3A-3D. In some such implementations, if the smooth transition from the larger width of the reservoir 358 to the smaller width of the passage occurs over a long enough distance, e.g., the radii of curvature for such transitions is quite high, e.g., larger than the width of the reservoir 358, then there may actually be no or almost no dynamic seal effect generated at all.

As is likely evident from the implementations of FIGS. 3D and 3E, dynamic seals also do not necessarily need to be formed in the middle of a permanent seal. As shown in FIG. 3F, a dynamic seal 362 can also be formed at a corner of a reservoir, e.g., where a passage 360 intersects two permanent seal walls defining a reservoir 358. The dynamic seal of such an implementation may, in effect, behave similarly to the dynamic seal of the implementation of FIG. 3D.

It will be generally understood that implementations disclosed herein in which temporary seals or dynamic seals are used may also be practiced, with suitable modification, using dynamic or temporary seals instead (vice-versa) in many cases, and the use of either type of seal may be assumed in place of the other unless otherwise indicated.

Returning to FIG. 4, the fluidic structure 402 may also include reservoirs of one or more gaseous, liquid, and/or solid reagents or other materials that may be used during analysis. For example, the fluidic structure 402 shown in FIG. 4 includes a first fluid reservoir 406a and a second fluid reservoir 406b. In some such implementations, such as the depicted implementation, fluids may be contained within burstable blisters or pouches that are then sealed in between the portions of material 402a and 402b during formation of the fluidic structure 402. This may facilitate manufacturing, as the liquid or gas contents of the burstable blisters or pouches may be contained therewithin during the formation of the permanent and/or temporary seals, thereby preventing leakage. In some implementations, the fluid reservoirs 406a and/or 406b may be additionally equipped with temporary seals that may seal off the fluid reservoirs 406a and/or 406b from the remainder of the system-such temporary seals may, for example, be positioned so as to seal off the exit from the fluid reservoirs 406a and/or 406b, and may act to contain the fluid housed in the fluid reservoirs 406a and/or 406b should the burstable blisters or pouches prematurely rupture.

In some implementations, the fluid reservoirs 406a and/or 406b may be sized to have a maximum volume that exceeds the intended fluid volume that will be housed within those fluid reservoirs 406a and/or 406b by a significant margin, e.g., by 2X or more. While this may cause such fluid reservoirs 406a and/or 406b to occupy more surface area of the fluidic structure 402 than may be strictly necessary, this provides at least two benefits. The first benefit is provided during manufacturing, as the placement accuracy of the fluid blisters or pouches does not need to be as tightly controlled-such blisters or pouches may also be positioned further from any thermal bonding regions used to produce the permanent and temporary seals that define the fluid reservoirs 406a and/or 406b than would be the case if the blisters or pouches were sized only slightly smaller than the fluid reservoirs 406a and/or 406b. This reduces the risk of damage to the fluid reservoirs 406a and/or 406b during the thermal bonding operations that may be used to seal the blisters and pouches inside the fluidic structure 402. The other benefit is provided during handling by end users-since the potential free volume within the fluid reservoirs 406a and/or 406b may be considerably larger than the actual volume of fluid within each such reservoir, it is much more difficult to accidentally pressurize the fluid within such a reservoir to a level that causes the temporary seals that may be used to seal the fluid reservoirs 406a and/or 406b to rupture. This is because the pressure that is applied to the fluid reservoirs 406a and/or 406b in such a scenario must be applied over a much larger area than would otherwise be the case. This reduces the chances of a premature release of fluid from the fluid reservoirs 406a and/or 406b, even if the fluids therein are released from the blisters and/or pouches that houses them within the fluid reservoirs 406a and/or 406b.

Various types of burstable blisters or pouches may be used, including, for example, actual blisters that enclose the fluid in a thin membrane that stretches and ruptures when pressurized by a sufficient amount, pouches made using material similar to that used for the fluidic structure 402 (such pouches may, for example, be made by permanently sealing two small portions of such material together so as to form an open pocket, filling the pocket with the fluid, and then temporarily sealing the pocket to form a completely enclosed pouch that, when subjected to sufficient pressure, will rupture the temporary seal and thus release the fluid housed therewithin), and capsules made, for example, using liquid-gel capsules such as are used to encapsulate liquid pharmaceuticals or other ingestible liquids, such as fish oil.

Alternatively, such liquid or gas may be added after the fluidic structure 402 has been formed through the creation of the permanent and/or temporary seals, but this would require that such seals be in some way bypassed, which would require sealing or re-sealing the path through which such fluid was introduced. In such implementations, of course, a temporary seal would need to be used to seal off each such fluid reservoir from the remainder of the fluidic system until such fluid is pressurized such that the temporary seal is caused to rupture and supply the fluid to the adjoining portion of the fluidic circuit.

In the case of solid reagents, such implementations may typically also include a liquid carrier solution that may be provided, e.g., from a burstable blister, to a chamber or passage housing the solid reagent, where the liquid carrier solution may be caused to dissolve the solid reagent to facilitate flowing the reagent through the fluidic circuit. In such implementations, the solid reagent may be provided in granular or powder form or as one or more monolithic solid structures, e.g., a thin, brittle sheet, that are then dissolved through contact with the liquid release from the liquid carrier solution reservoir. In some implementations, the roller 410 may be caused to roll over the solid reagent, thereby crushing it and causing it to more rapidly dissolve in the carrier solution.

As can be seen in FIG. 4, the first fluid reservoir 406a and the second fluid reservoir 406b are both located within pre-sealed burstable pouches or blisters (indicated by the solid lines surrounding each shaded area). The burstable pouches or blisters act to contain the fluid housed within them until pressurized to the point where they burst.

Also shown in FIG. 4 is a platen 408 that provides support to the fluidic structure 402 when a roller 410 is pushed against the fluidic structure 402 and rolled from one end of the fluidic structure 402 to the other (alternatively, the roller 410 may be kept stationary and the platen 408 translated relative to the roller 410, or both the roller 410 and the platen 408 may be translated relative to each other—it will be understood that reference to moving the roller 410 herein is also inclusive of the other two possible movement scenarios discussed above). The platen 408 and the roller 410 may be rigid or otherwise designed to apply a zone of clamping pressure that can be caused to move across the fluidic structure 402. The platen 408 and/or the roller 410 may also, however, incorporate an element of compliance to allow for more uniform application of such clamping pressure across the fluidic structure 402. For example, one or both of the platen 408 and the roller 410 may be provided with a layer of elastomeric material that may come into contact with the fluidic structure 402. In FIG. 4, the roller 410 is shown having a compliant layer 412 that may compress to more evenly apply the clamping pressure that is provided by pushing the roller 410 against the platen 408.

In certain embodiments, the platen 408 may also include additional features to provide different functions during processing using the fluidic structure 402. For example, in the implementation of FIG. 4, the platen 408 also includes features for mounting a vibramotor 416 thereto, as well as a heater element 418 that is positioned so as to provide heat to region E of the fluidic structure 402. In some embodiments, a more forceful mechanism, such as a solenoid that may be used to provide sharp, percussive vibrations to a portion or portions of the fluidic structure 402 may be used in place of a vibramotor. The platen 408 also includes various recesses that may interact with the fluidic structure 402 in different ways to provide different fluidic effects. In FIG. 4, a fluidic bypass recess 420 is shown, as well as a first partitioning recess 422a and a second partitioning recess 422b. The function of such features and recesses is discussed further below with respect to later Figures.

The fluidic circuit provided by the fluidic structure 402 that is shown in FIG. 4 is linear in nature, but it will be appreciated that other, more complex fluidic circuits may be designed according to the principles and concepts disclosed herein, and the present disclosure is not to be viewed as being limited to only the specific fluidic structures discussed herein.

As the roller 410 is caused to roll across the fluidic structure 402, the zone of clamping pressure generated between the roller 410 and the platen 408 moves along the length of the fluidic circuit and is sequentially applied to zones A through H. Zone A is a region of the fluidic circuit in which a sample of material to be analyzed is extracted from a sample medium, e.g., a swab. Zone B is a region of the fluidic circuit in which the extracted sample material is caused to be mixed with a carrier medium. Zone C is a region of the fluidic circuit in which air bubbles trapped within the extracted sample/carrier medium may be removed and an aliquot of bubble-free (or relatively bubble-free) extracted sample/carrier medium metered out. Zone D is a region of the fluidic circuit in which a further aliquot of extracted sample/carrier medium may be obtained from the previously obtained aliquot. Zone E is a region of the fluidic circuit in which the aliquot obtained in zone D may be heated, while zone F is a region of the fluidic circuit in which the aliquot obtained in zone D may be mixed with the contents of the second fluid reservoir 406b before being pumped/pushed through zone G in order to further mix the aliquot of zone D with the contents of the second fluid reservoir 406b before being delivered to zone H, in which the sample may be subjected, for example, to optical analysis in order to detect the presence of one or more chemical or bio markers of interest.

It will be noted that zones B through H may, prior to use, be flat, as there is little or no fluid within them (aside from what may be contained within the fluid reservoirs 406a and 406b). Zone A may also be flat, although since zone A is fluidically connected with a portion of the fluidic circuit in the fluidic circuit 402 that has an edge that is unsealed, it is possible for the portions of material 402a and 402b to be locally separated from one another within zone A, e.g., if pressure was applied to zone A via the unsealed opening along the edge of the portions of material 402a and 402b (along the top edge thereof. However, zones B through H are all sealed off from the ambient environment by temporary seals, so they will remain unpressurized until the temporary seals are broken. Since there is little or no fluid within zones B through H until fluid from upstream in the fluidic circuit is forced into each of these zones, there is no preexisting fluid that needs to be displaced by the upstream fluid. There is thus no need to provide for venting to allow preexisting fluid to be displaced. This further simplifies the design of such fluidic systems, as such venting features typically required use of additional valve features and also introduced additional points where leakage could occur. If the materials being tested include infectious or toxic agents, such leakage could pose a safety risk.

In the case of the implementation of FIG. 4, the only zone in which there may be some significant introduction of fluid, e.g., air, other than the sample material (or fluid from the fluid reservoirs 406a/b) is zone A. For example, as shown in FIG. 4, the sample material may be provided in a sample medium 414 such as a swab, e.g., an absorbent sleeve as discussed in U.S. Patent Application Nos. 62/705,860, filed Jul. 17, 2020; 62/706,306, filed Aug. 7, 2020; 63/198,697, filed Nov. 5, 2020; and 63/199,610, filed Jan. 12, 2021, all of which were previously incorporated herein by reference in their entireties. In some implementations, the sample medium may include both an absorbent sleeve or other absorbent material as well as a rigid or semi-rigid core. In yet other implementations, the sample medium may simply be a liquid that may be pipetted or otherwise delivered into zone A.

In the case where the sample medium is a swab onto which the sample material has been absorbed, the material of the swab, when inserted into zone A, may force the portions of material 402a and 402b apart, thereby creating a gap in between the portions of material 402a and 402b in the region of zone A between the permanent seal(s) bounding zone A-some of that gap may be filled with sample material, but there may also be some amount of air contained within zone A after the swab is inserted therein. This air may then become trapped within the fluidic circuit of the fluidic structure 402, although the overall volume of such air may be relatively small.

After the sample medium 414 is introduced into zone A of the fluidic circuit, the roller 410 may be caused to roll across the fluidic structure 402 towards zone B, thereby causing the zone of clamping pressure generated between the platen 408 and the roller 410 to translate along zone A and towards zone B. This has the effect of compressing the portions of material 402a and 402b together again within the clamping zone, thereby preventing, or at least, reducing, the amount of fluid that may leak past the clamping zone. The compliant material that is provided on either or both of the roller 410 and/or the platen 408 may be selected so as to have at least a total thickness that allows for any incompressible portions of the sample medium, e.g., a semi-rigid core such as was described earlier, to be rolled over by the roller 410 while still maintaining a seal between the sample medium 414 and the portions of material 402a and 402b (the compliant material may act to push the portions of material 402a and/or 402b into close contact with all sides of the sample medium 414, thereby maintaining a relatively high degree of sealing).

In FIGS. 4 through 15, the fluidic system 400 is shown in three views. The lower left corner is a plan view of the fluidic system, e.g., viewed along an axis that is perpendicular to the platen 408; this view does not show the roller 410 or the platen 408, but best illustrates the various zones of the fluidic circuit. While the roller 410 is not shown in this view, the zone of clamping pressure provided thereby is shown in the form of a gradient bar bracketed by broken lines. The lower right corner shows a side view of the fluidic system taken along the long edge of the fluidic structure 402; both the roller 410 and the platen 408 are shown in this view. Finally, the upper right corner shows an end view of the fluidic system, but without the roller 410 shown.

Figure 5:
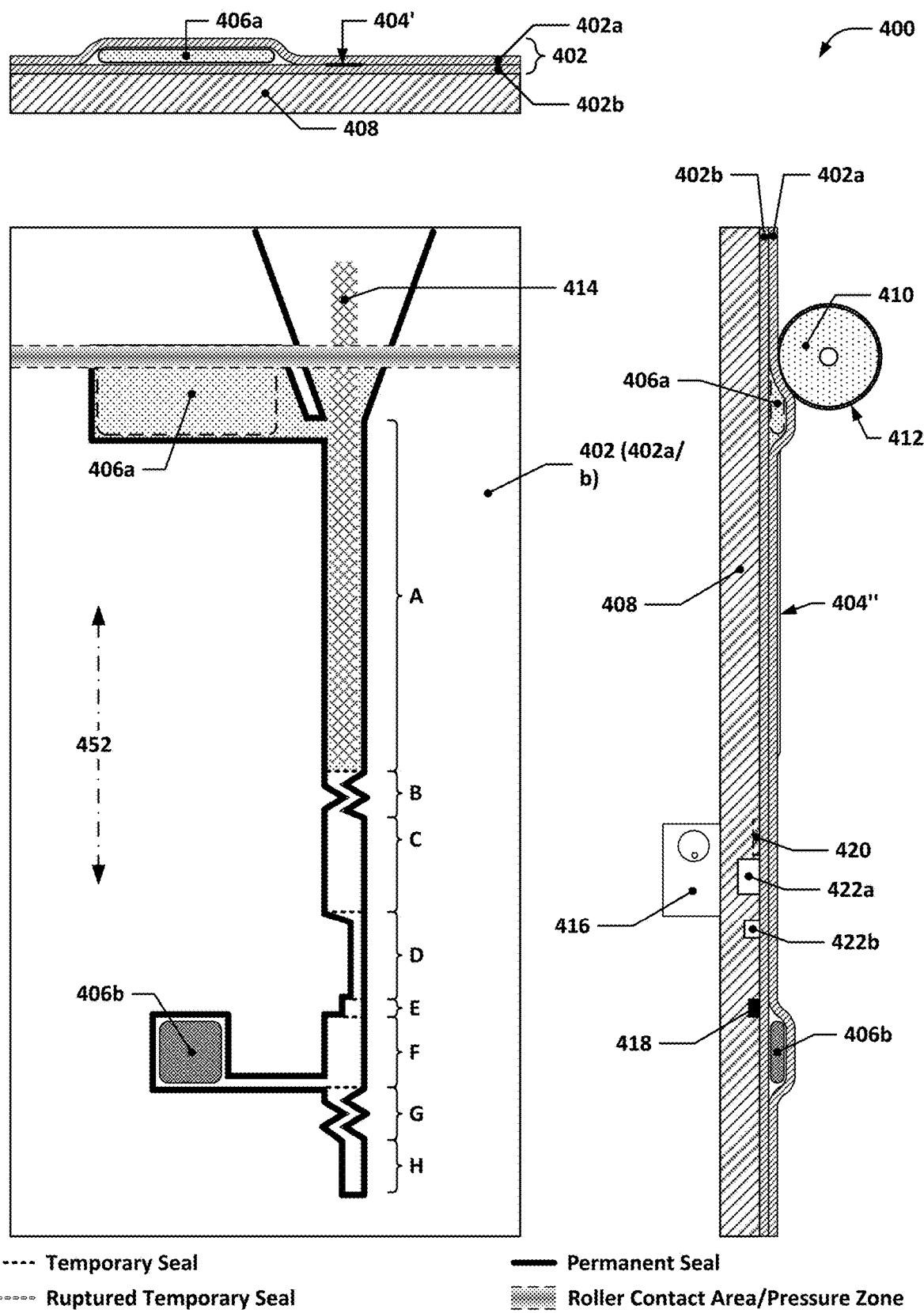

In FIG. 5, the roller 410 has been rolled somewhat towards zone B such that the zone of clamping pressure has started to press on the first fluid reservoir 406a, causing a liquid within the first fluid reservoir 406a to burst out of the pouch or bladder that contained it (the boundary of which is now shown in dashed lines to indicate that it has burst) and been pushed into main passage 404 (main passage 404 is not specifically called out, but includes the various zones A-H; flat or unpressurized portions of the main passage 404 are indicated with callouts 404', whereas distended or pressurized portions of the main passage 404 are indicated with callouts 404"—it will be noted that the flat or unpressurized portion 404 of the main passage is really only explicitly indicated in the end view, although it may be assumed that any portion of the main passage 404 not shown as pressurized or distended, i.e., as 404", is flat or unpressurized, i.e., 404'.

Figure 6:
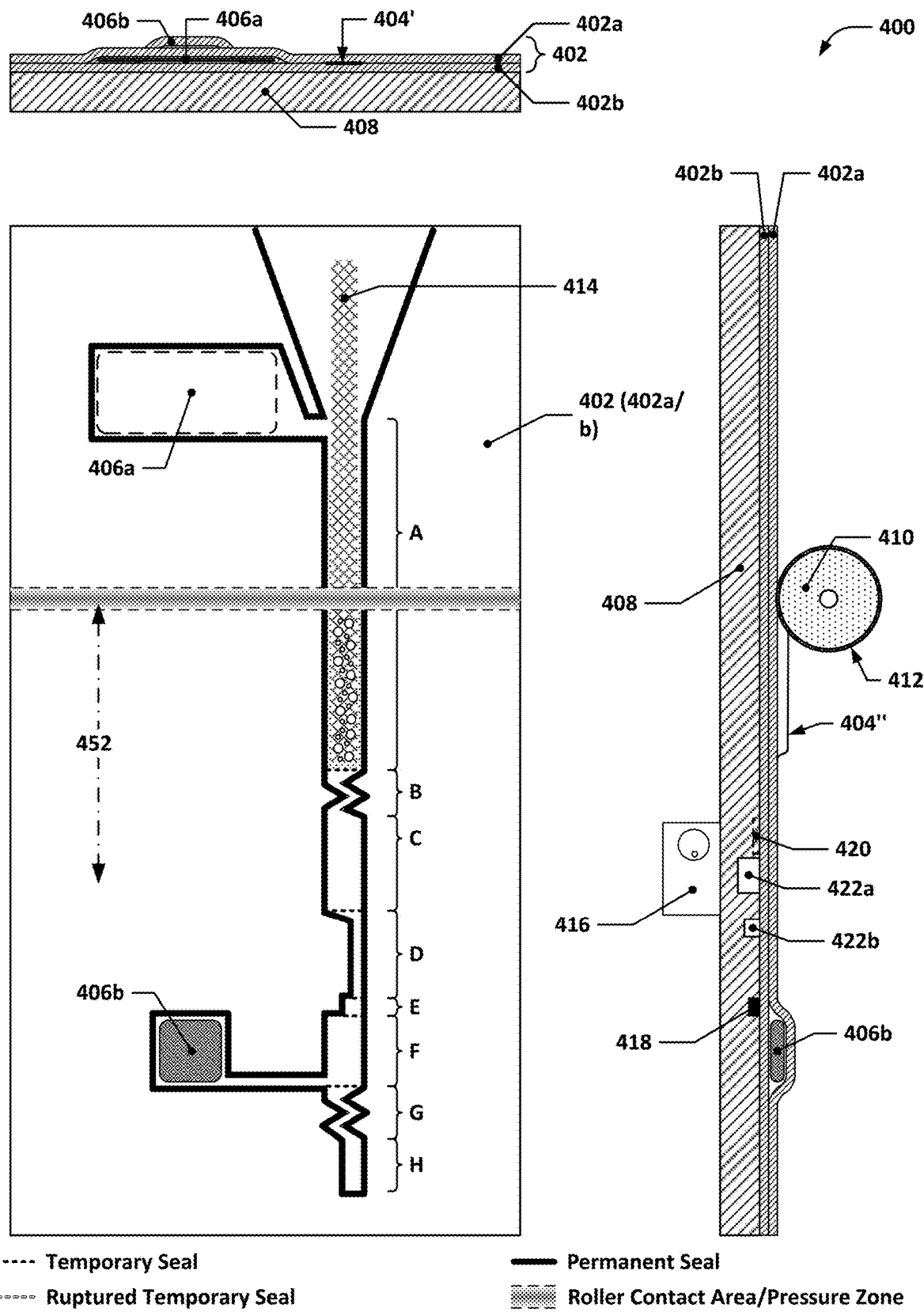

As can be seen in FIG. 6, the liquid from the first fluid reservoir 406a that is forced into zone A may wet the sample medium 414, thereby eluting sample material that may be absorbed onto the sample medium 414. The liquid from the first fluid reservoir 406a may, as it is forced into zone A, cause the pressure in the main passage in between the roller 410 and the temporary seal between zones A and B to increase, thereby producing a distended portion 404" of the main passage. As the roller 410 continues to roll towards zone B, the remainder of the liquid in the first fluid reservoir 406a may be forced into zone A until the first fluid reservoir 406a is emptied of liquid. As the roller 410 approaches the temporary seal between zones A and B, the pressure within the distended portion 404" of the main passage may continue to increase, thereby causing the distended portion 404" of the main passage to distend more and more. At the same, time, the liquid that is present within the distended portion 404" may also include air bubbles from the sample medium 414 that were trapped within the liquid (represented by small circular bubbles in FIG. 6).

Figure 7:
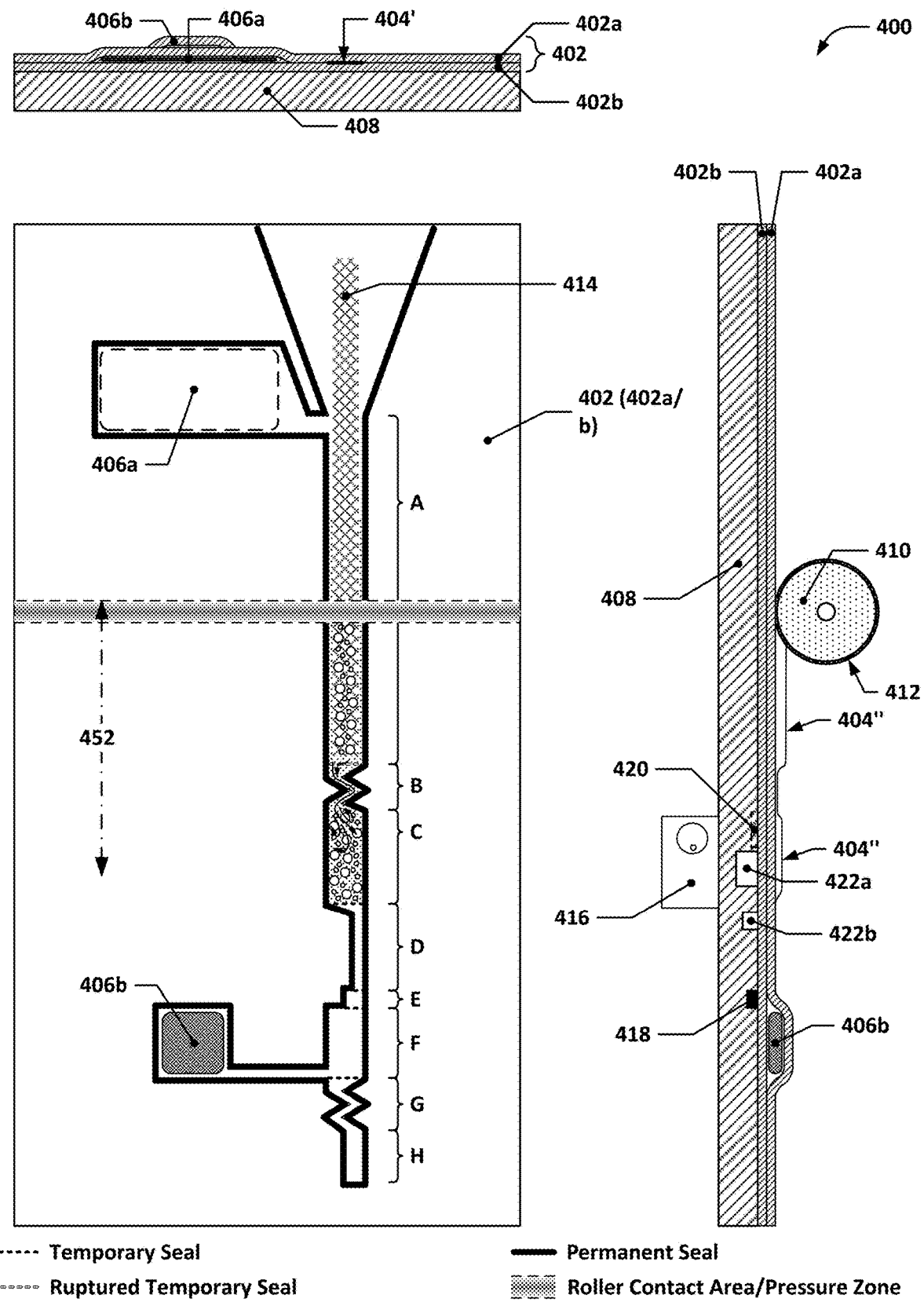

After the pressure within the distended portion 404" of the main passage reaches the burst pressure of the temporary seal between zones A and B, e.g., after the roller 410 moves to the position shown in FIG. 7, the temporary seal between zones A and B may rupture, allowing the fluid mixture from zone A to flow into zone B and then into zone C. Ruptured temporary seals in FIG. 7 onwards are indicated by greyed-out dotted lines.

Zone B, it will be noted, includes a zig zag or switchback flow path with a smaller width than zone A's width. The smaller width causes the fluid that is forced through zone B to accelerate relative to the speed of the fluid in zone A (the fluid in zone A will be moving at the same speed as the roller 410's translation speed, whereas the fluid flowing through zone B will be at a higher speed than the roller 410's translation speed owing to the reduced width of the flow passage in zone B. This higher fluid velocity, combined with one or more reversals of flow direction provided by the switchback or zig zag flow path, may serve to mix such fluid more thoroughly, thereby homogenizing the sample material with the liquid from the first fluid reservoir 406a. The transition from the narrower channel width of the zig zag portion back to the wider channel width in the immediately downstream region of the fluidic circuit may also cause vortices to be generated within that immediately downstream region, thereby further mixing the fluids introduced into that downstream region.

Figure 8:
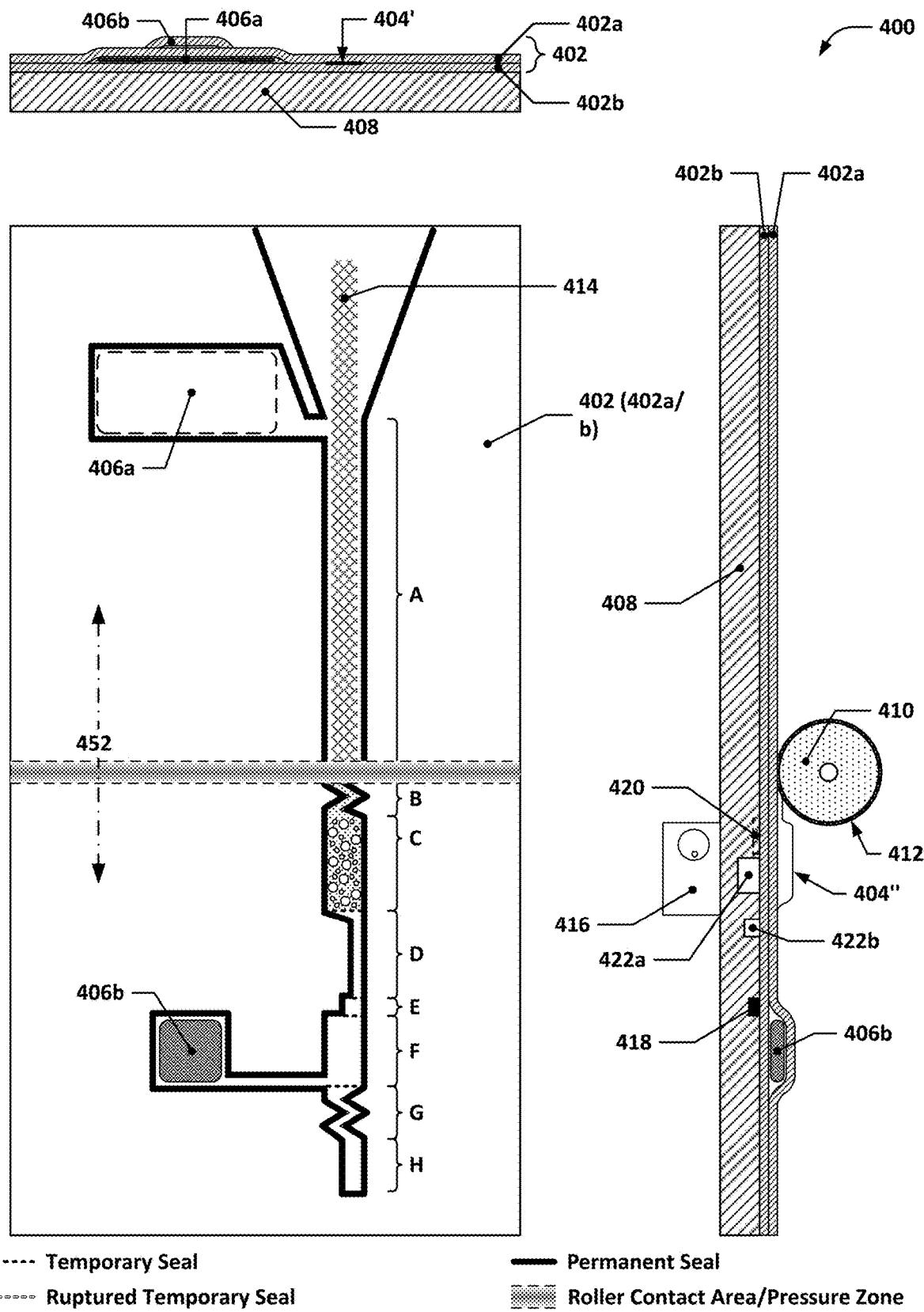

In FIG. 8, the roller 410 has rolled such that most or all of the fluid in zone A has been pushed into zones B and C, and the zone of clamping pressure is past (or at the end of) zone A. At this stage, the fluid that is in zones B and C may be a mixture of sample material, liquid from the first fluid reservoir 406a, and air bubbles introduced via the sample medium 414. The amount of fluid that is contained within zones B and C may be more than is needed. To reduce the amount of such fluid that is present, a fluidic bypass feature may be provided that allows for the roller 410 to be advanced further towards zones C and D without causing the temporary seal between zones C and D to rupture. The fluidic bypass feature may include a fluidic bypass recess 420, which may be a shallow recess in the platen 408 that is designed to generate an "engineered" leak path to allow fluid that is trapped within the pressurized portion 404" of the main passage to escape past the roller 410 (while the roller 410 continues to be moved towards zones C and D) and flow upstream with respect to the roller, i.e., towards portions of the fluidic circuit that the roller has already passed over, while still generally maintaining a constant pressure on the fluid downstream of the roller 410. This keeps the distended or pressurized portion 404" of the main passage at full or nearly full capacity in terms of fluid level while allowing extra fluid to flow past the roller 410 in order to prevent further pressure build-up that might rupture the temporary seal.

The fluidic bypass recess 420 may be configured to have a width along a direction that is parallel to the axis of rotation of the roller 410 that is less than the width, along that same direction, of the portion of the roller that is in contact with the fluidic structure 402 such that the roller 410 is supported on both ends by portions of the platen 408 that are offset from the bottom of the fluidic bypass recess by a small amount such that when the roller 410 is pressed against the platen 408, most or all of the force exerted on the roller 410 by the platen 408 (through the fluidic structure 402) is provided by these portions of the platen 408. This helps ensure that a small gap remains between the roller 410 and the bottom of the fluidic bypass recess 420 to allow excess fluid to escape during movement of the roller 410 across the fluidic bypass recess 420.

Figure 9:
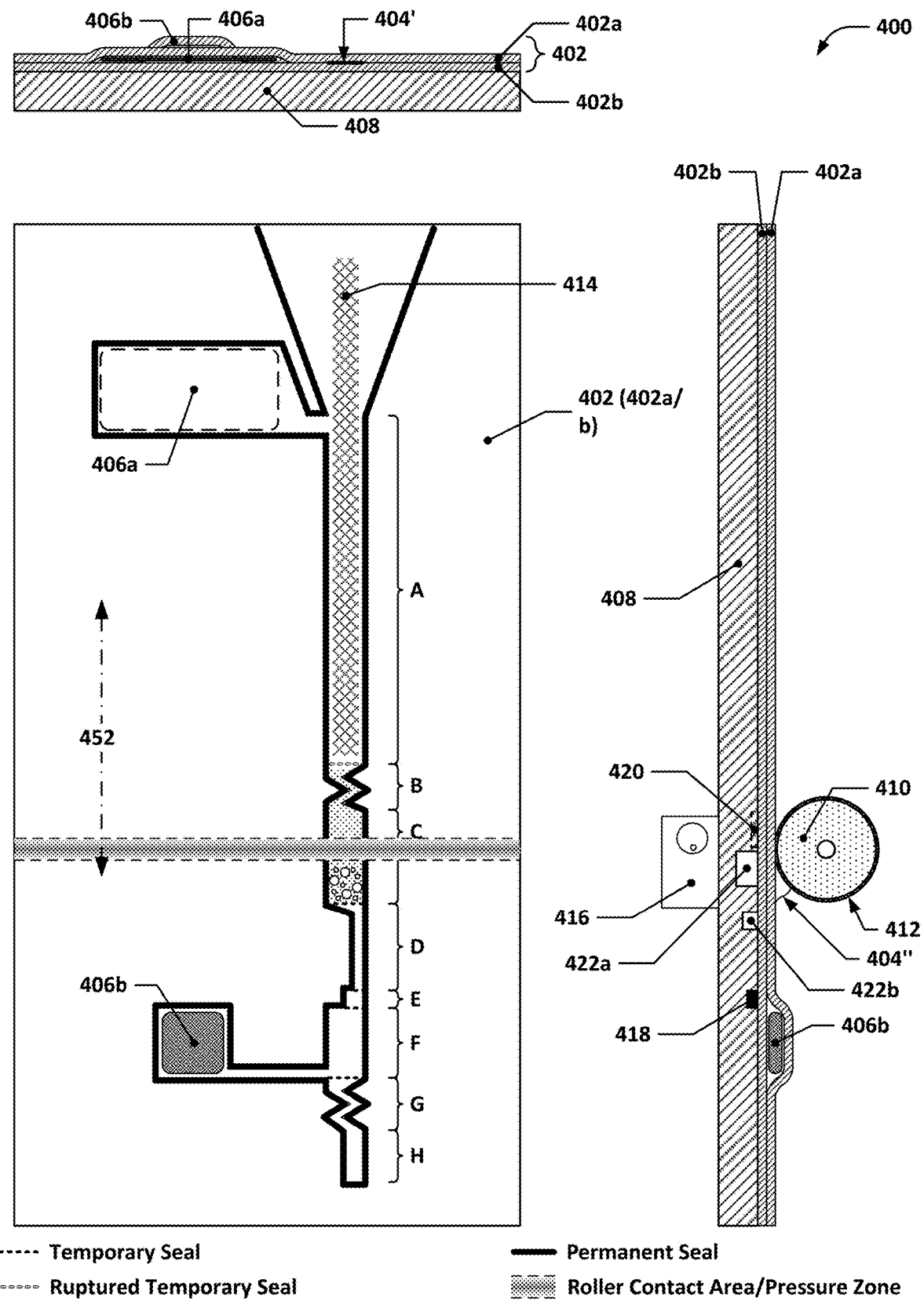

After draining off excess fluid via the fluidic bypass recess 420, the roller 410 may by in the position shown in FIG. 9, where the platen 408 has a short segment that separates the fluidic bypass recess 420 and the first partitioning recess 422a. This short segment may seal off the fluid downstream of the segment from the fluid that remains in the fluidic bypass recess 420, thereby "knifing" it off from the excess fluid. At the same time, part of the distended portion 404" of the main passage may be pushed into the first partitioning recess 422a by the roller 410.

Figure 10:
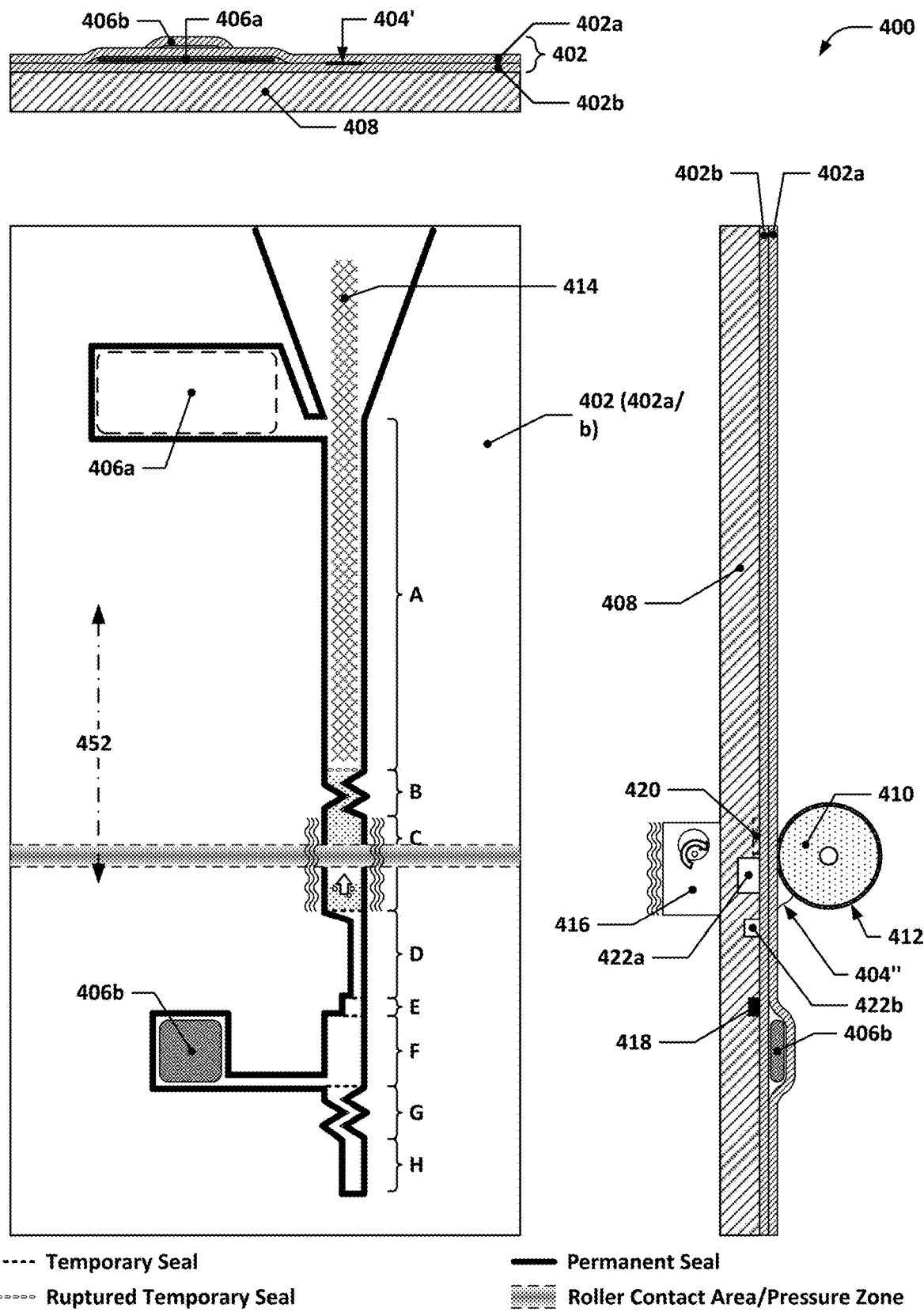

In FIG. 10, the roller may be caused to stop moving temporarily to allow time for air bubbles that are trapped within the fluid to settle out and collect in a portion of the main passage that is closest to the roller 410 (the fluidic structure 402 may be oriented much as in the plan and side views of FIG. 4 so that gravity exerts a downward force from zone A towards zone H in order to facilitate this). In some implementations, a vibratory input may be provided via the vibramotor 416 (indicated by the wavy lines and rotation motion in the vibramotor 416 shown in FIG. 10; alternatively, a solenoid may be used to provide vibratory or mechanical shock input) in order to help dislodge such bubbles and encourage their upward migration.

Figure 11:
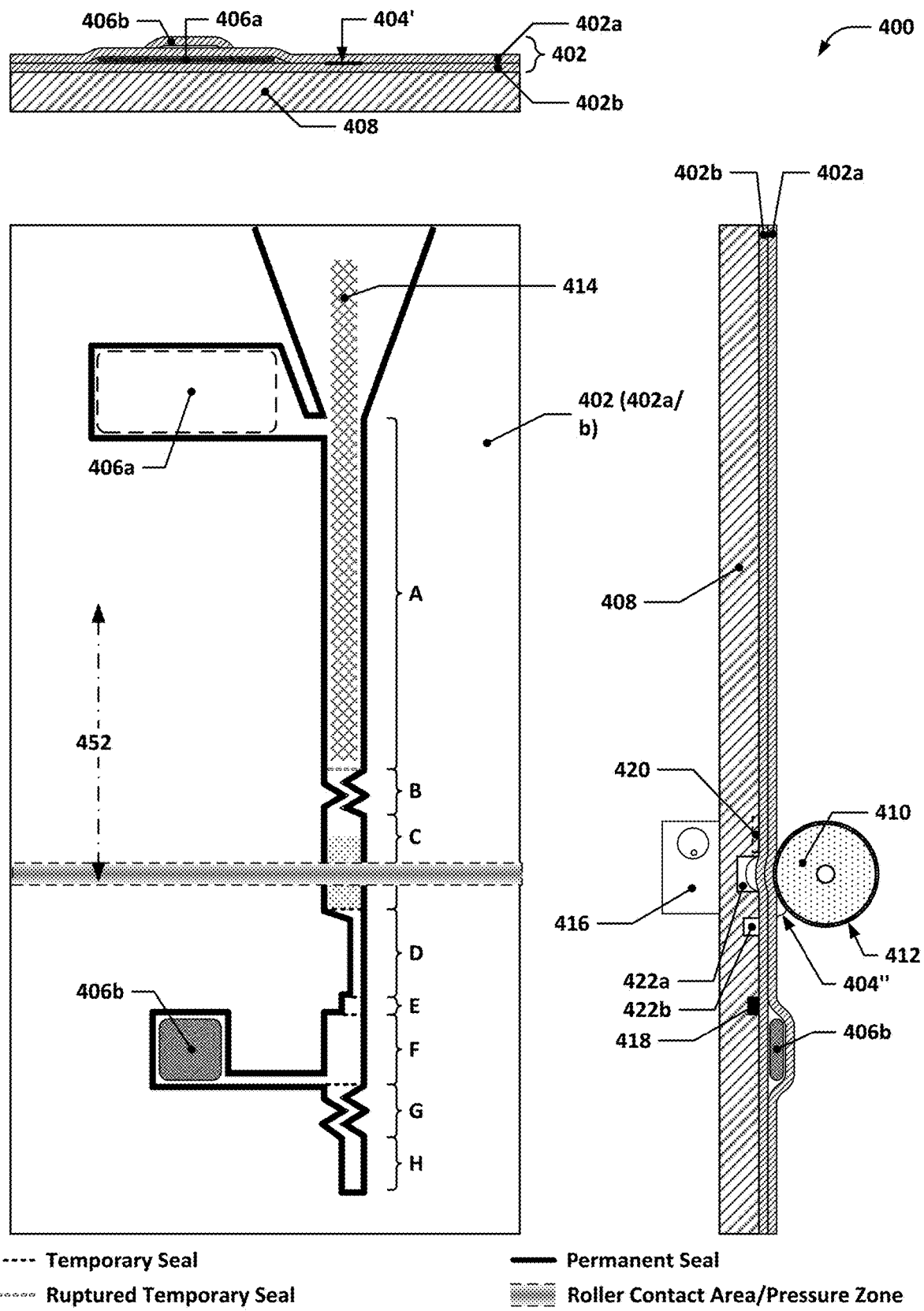

After time has passed such that the entrapped air has largely or wholly separated from the fluid in zone C, the roller 410 may be caused to continue rolling towards zone D, as shown in FIG. 11. As can be seen, as the roller 410 rolls over the first partitioning recess 422a, the roller 410 is allowed to translate towards the first partitioning recess 422a slightly such that the roller 410 remains in contact with the short segment between the fluidic bypass recess 420 and the first partitioning recess 422a as it also comes into contact with the opposing edge of the first partitioning recess 422a. Thus, the roller 410 may, in effect, simultaneously form two seals that are spaced apart from one another by approximately the width of the first partitioning recess 422a. The first partitioning recess 422a may be relatively deep (e.g., at least 4 to 5 times or more deeper than the fluidic bypass recess 420), thereby providing a recess that allows the pressurized portion 404" of the main passage that overlaps the first partitioning recess 422a, i.e., the portion that is eventually trapped between two seals formed by the roller 410 and the edges of the first partitioning recess 422a, to bulge into the first partitioning recess 422a. The partitioning recess may also have a width such that the roller 410 has a length along its axis of rotation that is less than the width of the partitioning recess width, e.g., such that both of the ends of the roller 410 lie in between the ends of the partitioning recess that lie along an axis that is parallel to the rotational axis of the roller 410. The partitioning recess also has a width along the axis of translation of the roller 410 that is less than a diameter of the roller 410 (thus allowing the roller 410 to contact the opposing edges of the partitioning recess simultaneously. At the same time, the pressurized portion 404" of the main passage that is downstream of the first partitioning recess 422a may be trapped between the bottom-most seal formed between the roller 410 and the edge of the first partitioning recess 422a that is closest to zone D. The dimensions of the first partitioning recess 422a may be selected such that the first partitioning recess 422a is sized so that the air that has been separated from the fluid sample, e.g., using a vibratory input, is located in the pressurized portion 404" that is in the first partitioning recess 422a and is thus similarly "knifed" off from the remaining pressurized portion 404" that is interposed between the roller 410 and the temporary seal between zones C and D.

Figure 12:
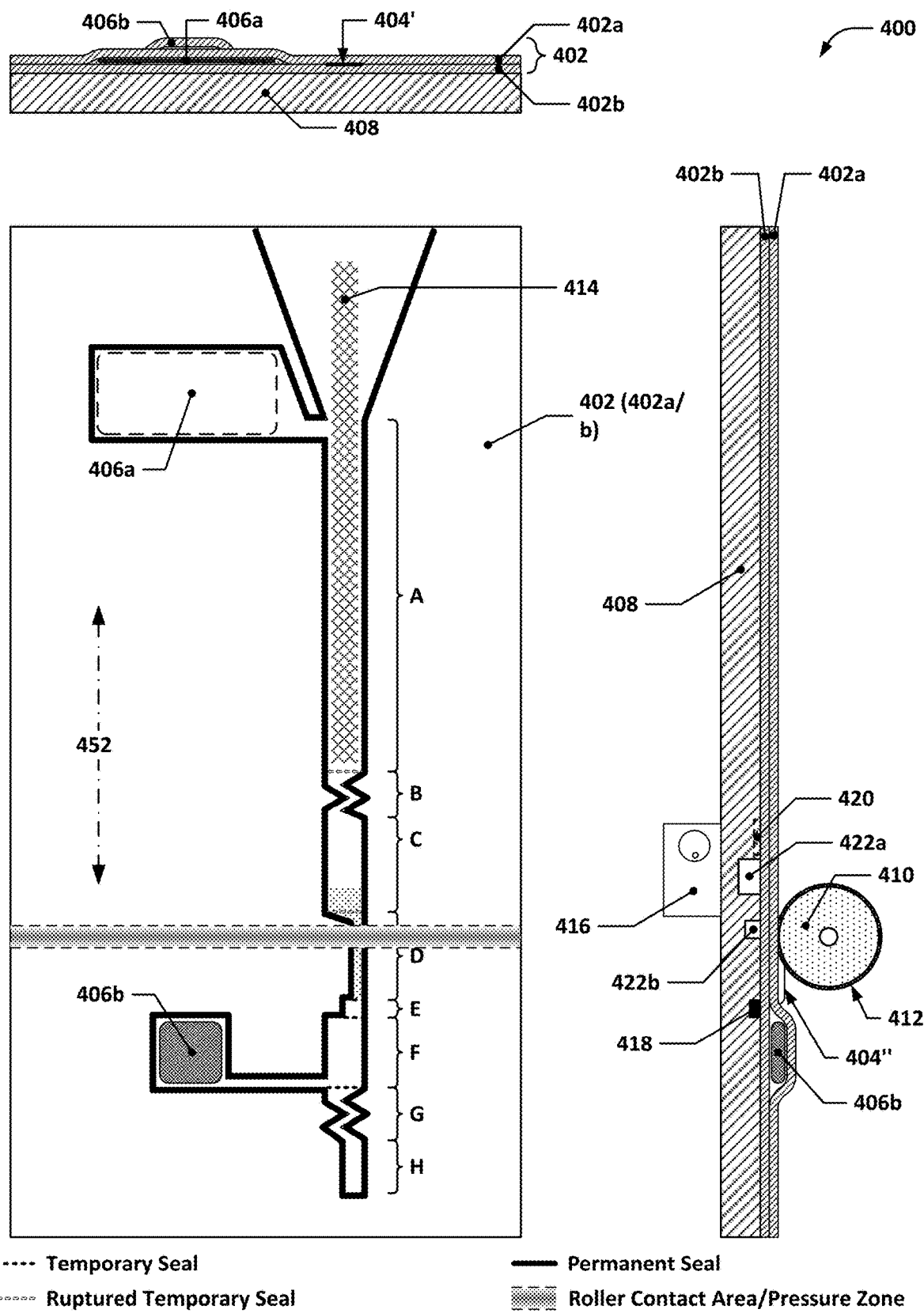
Figure 13:
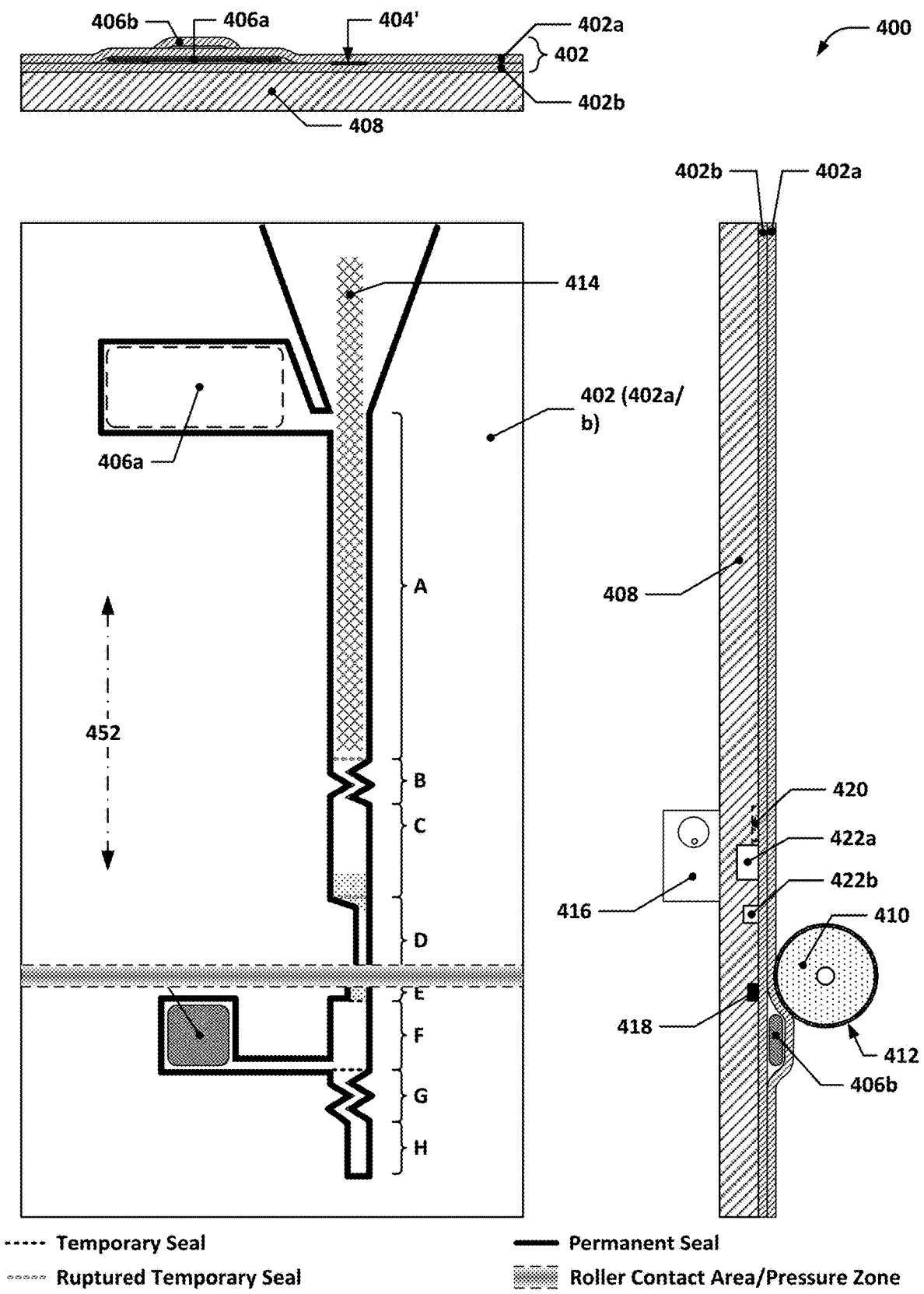

In FIG. 12, the roller 410 has been further advanced such that the temporary seal that separates zones C and D has been caused to rupture due to the increasing pressure applied to the fluid that is trapped downstream of the roller 410, thereby allowing this fluid to flow into zone D, where it is subjected to a second aliquoting operation using the second partitioning recess 422b. The second partitioning recess 422b, for example, may be used in a similar operation to that performed using the first partitioning recess 422a, although while the goal of the first aliquot operation may be thought of as being primarily used to produce a volume of sample material that is free or largely free from entrapped air bubbles, the goal of the second aliquot operation may be thought of as being primarily to separate a volumetrically precise amount of fluid from that bubble-free (or largely bubble-free) sample material for further downstream processing operations. The portion of the fluid that is downstream of the roller 410 after the second aliquot operation may then be pressurized further by further advancement of the roller 410 until the temporary seal between zones D and E ruptures, allowing the fluid to flow into zone E, as shown in FIG. 13. Zone E may optionally, as shown in FIG. 12, be designed to be square or otherwise exhibit radial symmetry so as to encourage the fluid that is forced into zone E to adopt a generally spherical or radially symmetric volume (or at least to have a size and shape that is generally spherical, e.g., within ±40% of spherical, e.g., such as a three-dimensional volume that shares the visual attributes of a squircle). This aspect ratio of zone E may allow for more even and rapid heating of the fluid in zone E by the heater element 418, which may optionally be used to heat the aliquoted sample fluid up to a particular temperature that may be required by the particular assay being used (if necessary). This decreases the time needed to heat the sample and also reduces the temperature variation within the sample by reducing the surface area-to-volume ratio of the aliquoted sample fluid, thereby increasing the diffusion speed and allowing for more even heating of the aliquoted sample fluid.

Figure 14:
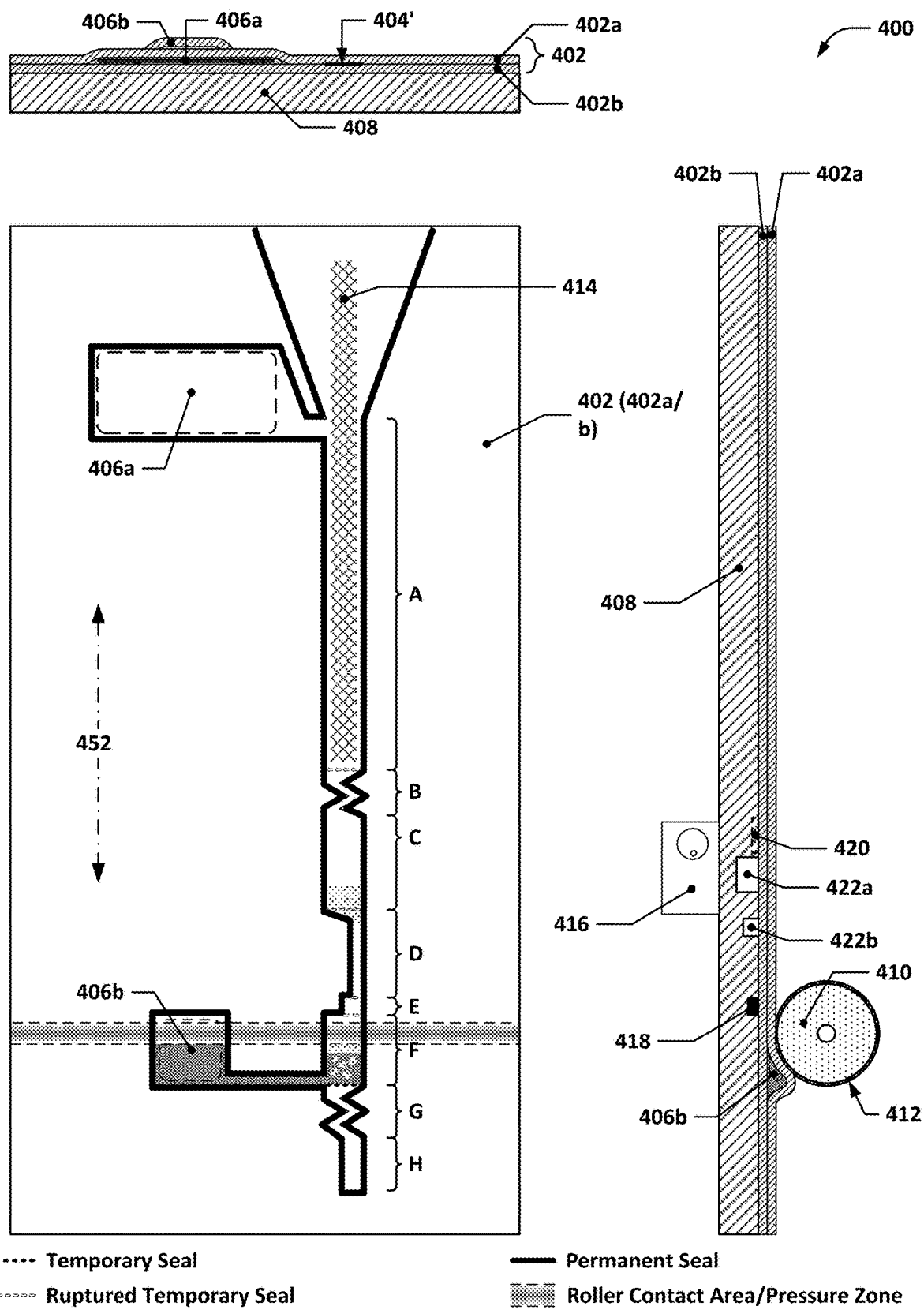

The aliquoted sample contained within zone E may subsequently be moved to zone F through further advancement of the roller 410, which may cause the pressure of the aliquot in zone E to increase until the temporary seal between zones E and F ruptures, allowing the aliquoted sample to flow into zone F. The roller 410 may, as part of this further advancement, also compress the second fluid reservoir 406b, causing it to eventually rupture (as happened with the first fluid reservoir 406a; similarly, the ruptured state of the second fluid reservoir 406b is indicated through the use of a broken line) and a liquid contained therein to flow into zone F as well, as shown in FIG. 14. As shown in FIG. 14, the aliquot is pushed into zone F in the "downstream" direction, whereas the liquid from the second fluid reservoir 406b is pushed into zone F in the opposite "upstream" direction since the horizontal passage that links the second fluid reservoir 406b is positioned so as to introduce the liquid from the second fluid reservoir 406b at a location that is adjacent to the temporary seal that is between zones F and G, whereas the aliquot fluid is introduced into zone F from a location coincident with the (now ruptured) temporary seal between zones E and F. By introducing the fluids from opposing ends of zone F, the fluids are caused to flow in opposing directions such that when they flow together in zone F, mixing between the two fluids is encouraged. If desired, another zig zag segment, similar to that provided in zone B, or other tortuous flow path structure may be fluidically interposed between zones E and F in order to provide for enhanced cooling of the recently heated aliquoted sample fluid. Such cooling may, for example, be desirable in some instances in which the elevated temperature of the aliquoted sample fluid may cause detrimental effects when the aliquoted sample fluid is mixed with the fluid of the second fluid reservoir 406b in zone F.

Figure 15:
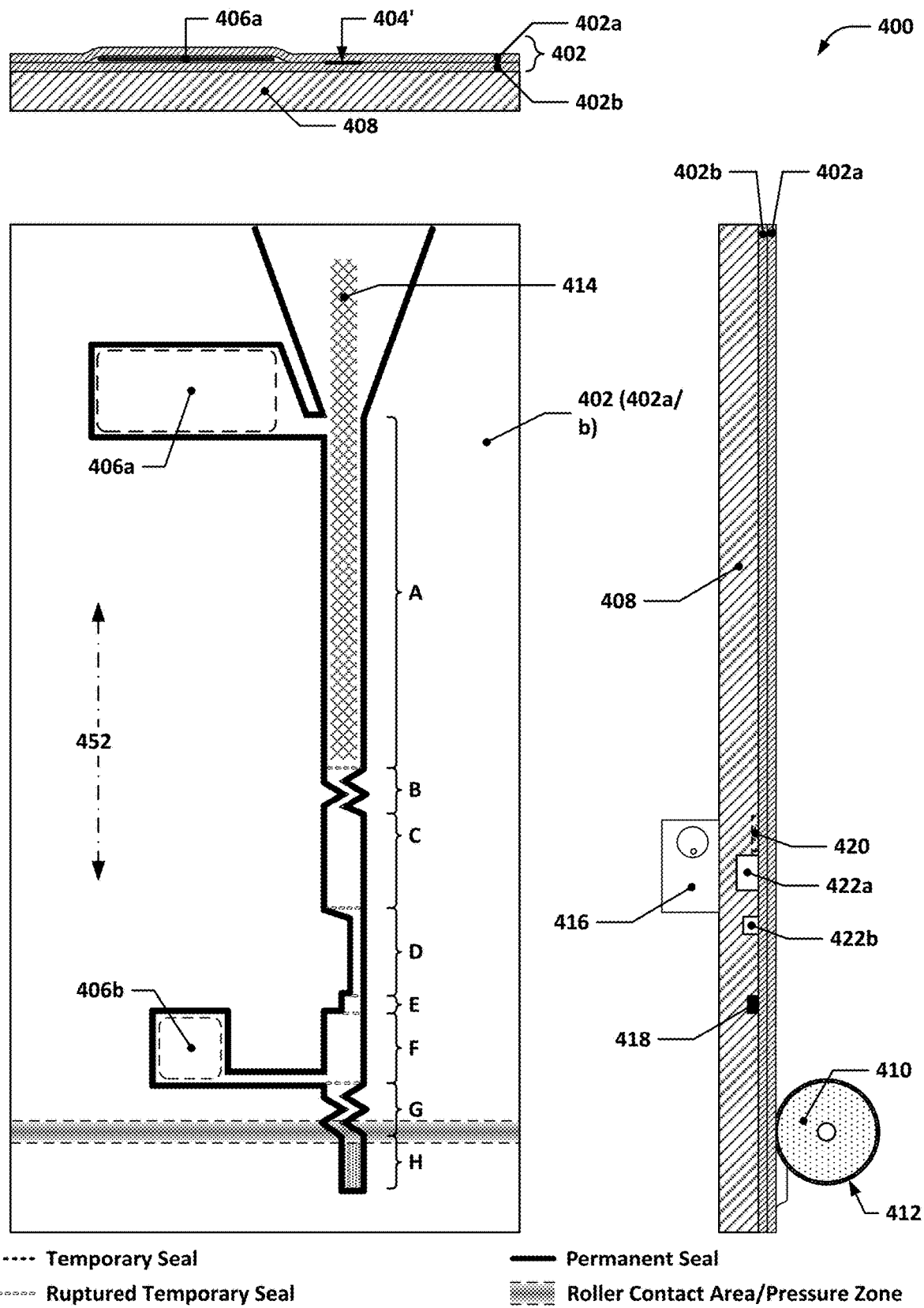

As the roller 410 is advanced further, the fluid mixture in zone F may be further pressurized until the temporary seal between zones F and G ruptures, allowing the fluid mixture to be driven through zone G, which may act to further mix the aliquoted fluid from zone E with the fluid from the second fluid reservoir 406b (similar to how zone B acted to mix the fluid from the first fluid reservoir 406a with the sample material earlier) before flowing the fluid mixture in zone H, as shown in FIG. 15.

Zone H, for example, may be configured such that it may be interrogated by an optical scanning device (not shown) of the fluidic system, e.g., one or both portions of material 402a and 402b may be optically transmissive in the region of zone H so as to allow light to be emitted from, and introduced to, the fluid mixture in zone H. For example, in some analyses, reagents introduced into zone H may react with a material of interest that may be present in a sample and emit light as a byproduct of a chemical reaction; this light may then be measured to determine a relative amount of such a reaction, which may, in turn, indicate the amount of the material of interest that is present. In other analyses, reagents introduced into zone H may react with a material of interest to produce a byproduct that emits a particular wavelength of light when stimulated in some manner, e.g., by exposure to light of a different wavelength.

While not described above, it will be understood that the above-discussed fluidic system may be used to perform an assay on a collected biological sample, such as the assays discussed in U.S. Patent Application No. 63/198,388, which is hereby incorporated herein by reference in its entirety and for all purposes. For example, the first fluid reservoir 406a may contain a volume of eluent that may be used to elute the material of interest that may be on the sample media and the second fluid reservoir 406b may contain a volume of fluid that may be used to perform an assay. For example, the first fluid reservoir 406a may contain a solution of 40 millimolar Tris, 1 millimolar ethylenediaminetetraacetic acid (EDTA), 5 millimolar tris(2-carboxyethyl)phosphine (TCEP), and an optional 40 millimolar guanidine thiocyanate with possibly one or more additives, including, for example, RNase inhibitor, dsDNase, trypsin, LysC, and/or proteinase K included to facilitate enzymatic digestion of inhibitors and RNases in the sample. Similarly, the second fluid reservoir 406b may contain a solution of LAMP (loop-mediated isothermal amplification) enzyme mix, primers, and one or more fluorophores. In such an example, there may also be a heater element located in zone H, for example, to allow the fluid from the second fluid reservoir to be heated to initiate a LAMP reaction that produces fluorescence that may then be measured by an optical measurement system to obtain an indication of the presence of a virus, such as COVID-19, or other biomarker.

Figure 16:
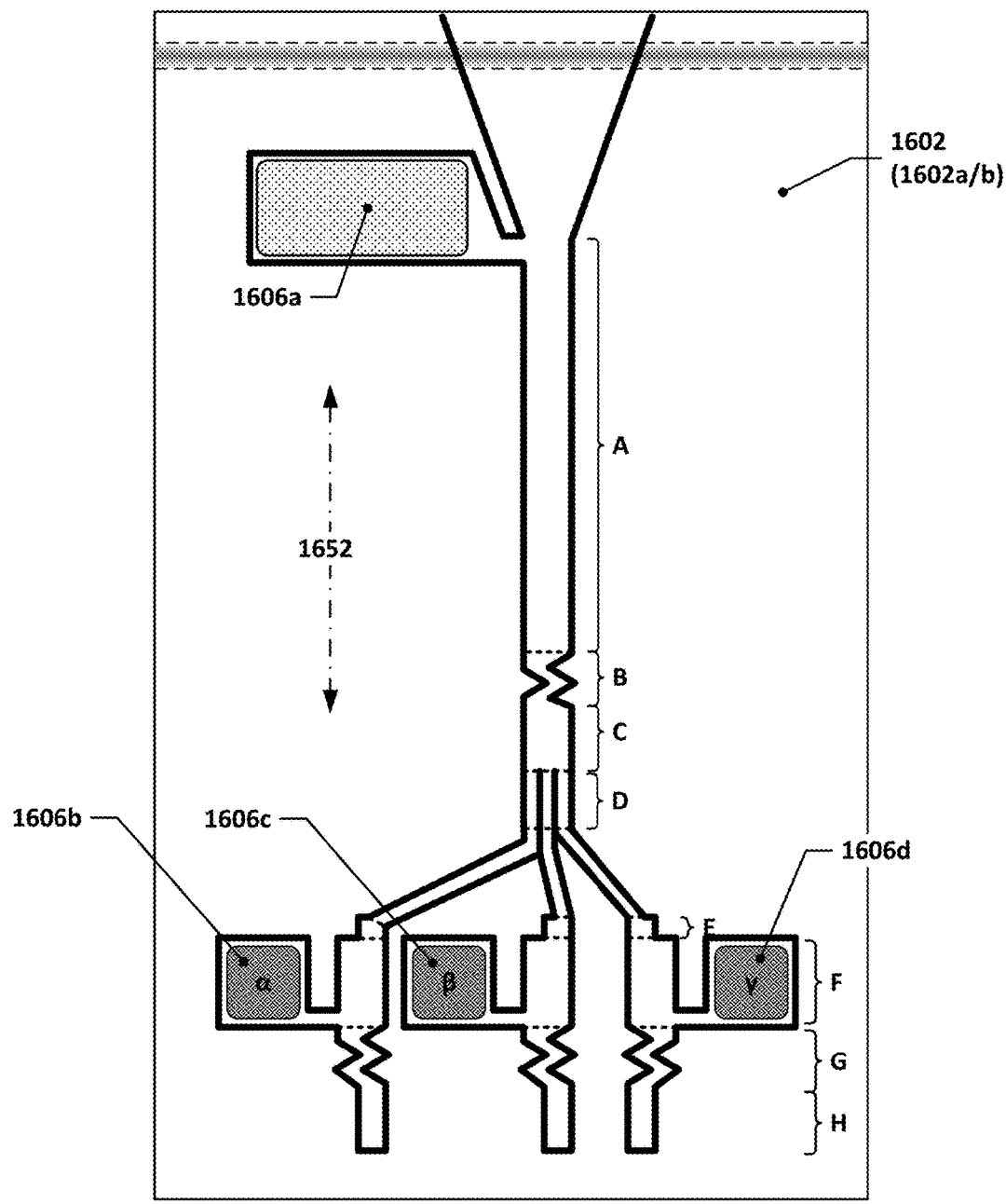
FIG. 16 depicts an example fluidic structure that may be used to perform multiple, different analyses.

While above-discussed example may be used to perform a single analysis on a sample, the fluidic structure architecture discussed herein may also be used to facilitate performing multiple analyses in parallel. FIG. 16 depicts a fluidic structure 1602 that has features that are similar to that of the fluidic structure 402. For example, the fluidic structure 1602 includes a first fluid reservoir 1606a, as well as similar zones A, B, and C. However, the fluidic structure 1602 differs from the fluidic structure 400 in that zone D features three metering volumes that will each receive generally equal volumes of fluid once the temporary seal between zones C and D ruptures and which will then provide those volumes of fluid to branching flow paths in between zones D and E instead of to a single flow path (in the event that different volumes of fluid are desired to be delivered to each branching flow path, the widths of each volume where the temporary seal between zones C and D is located may be adjusted to proportionately deliver more or less fluid to each volume). Each flow path leads to a different downstream fluidic circuit, each of which may be configured to perform different types of analysis or assays. For example, the three second fluid reservoirs 1606b/c/d may each contain different reagents or immunoassay materials ($\alpha$, $\beta$, and $\gamma$) that may be used to perform different analyses on the fluid that is provided to each downstream fluidic circuit. It will be apparent that the roller, as it causes the pressure zone to move along the fluidic circuit by moving along axis 1652, will cause the fluids within the fluidic structure 1602 to flow into all three downstream fluidic circuits. It will also be apparent that more or fewer such downstream circuits may be provided.

Figure 17:
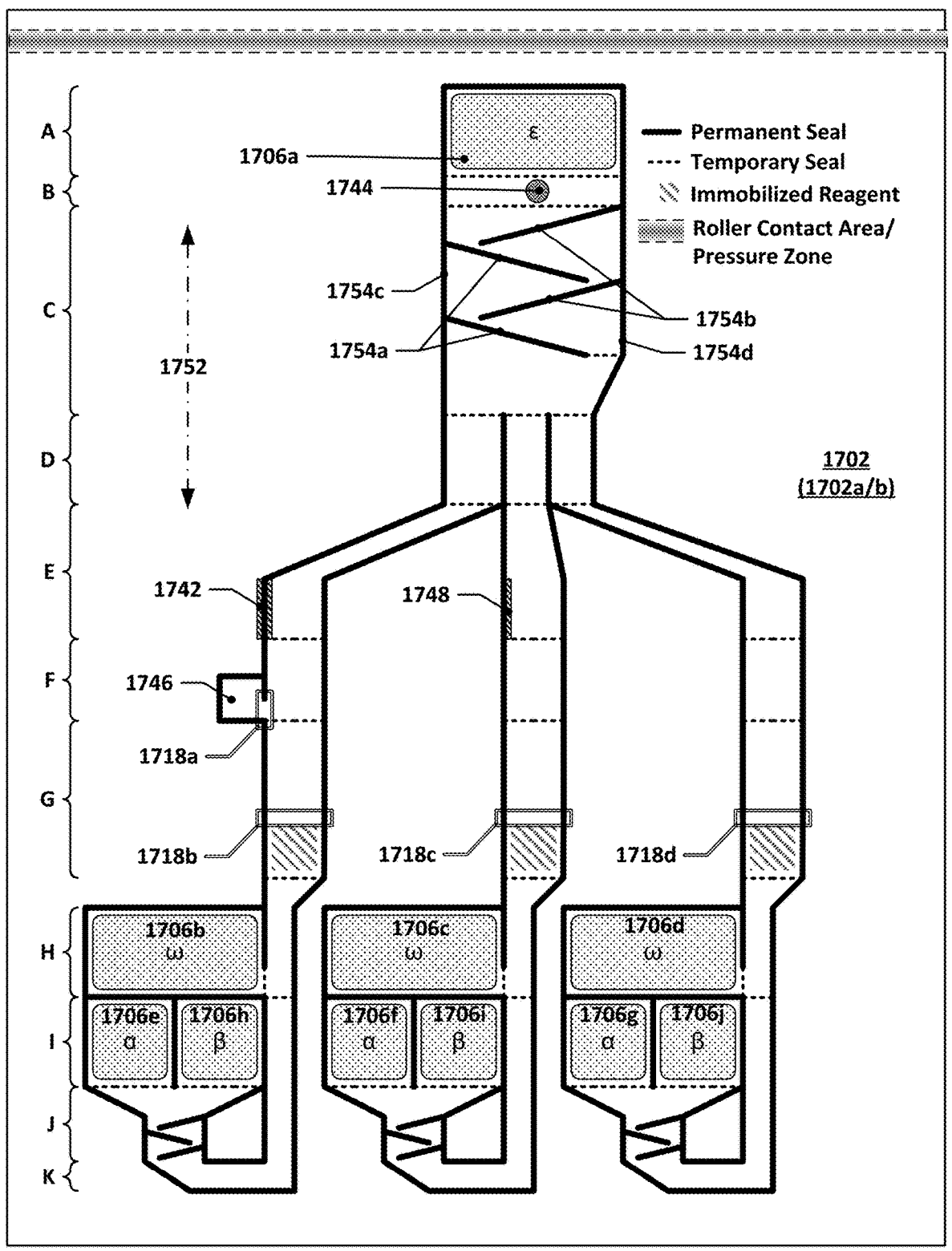
FIG. 17 depicts an example fluidic structure that may be used to measure a concentration of a biomarker or other material of interest.

Another example of a fluidic structure that may be implemented using the architecture disclosed herein is shown in FIG. 17. The fluidic structure 1702, which may have two portions of material 1702a and 1702b, similar to the earlier fluidic structures discussed herein, of FIG. 17 is designed to be implemented using the flexible fluidic circuit paradigm discussed herein and includes a plurality of permanent seals that define a fluidic circuit having a plurality of zones that are arranged in a linear fashion along an axis 1752. When the fluidic structure is processed by applying a moving pressure zone to it, e.g., with a roller, the moving pressure zone may be moved in directions parallel to that axis 1752, thus causing the pressure zone to move from one zone of FIG. 17 to another.

In zone A, the fluidic structure has permanent seals that define a first fluid reservoir 1706a that contains fluid E; fluid E may be an eluent, such as a buffer. Fluid E may be contained within a burstable pouch or blister that is positioned within the first fluid reservoir 1706a.

Zone A is separated from zone B by a temporary seal that forms one wall of the first fluid reservoir 1706a. When zone A is subjected to a clamping pressure, e.g., such as may occur when a roller is clamped against the fluidic structure and translated from zone A towards zone K, the clamping pressure will cause fluid E to be pressurized, eventually causing the temporary seal between zones A and B to rupture.

Zone B is a chamber that may include a reagent or material 1744, e.g., a lyophilized antibody, that is specific to a particular biomarker of interest. The reagent or material may be solid, e.g., a dry powder or a thin wafer of dried material, or liquid (in which case it may also optionally be secondarily contained within a burstable pouch or blister). Zone B may optionally be separated from zone C by a further temporary seal. When fluid E is forced from the first fluid reservoir 1706a by rupturing the temporary seal in between zones A and B, fluid E will be pushed into zone B and will mix with the reagent or material located within zone B (if that reagent or material is liquid and housed within a burstable blister or pouch, then this may occur after this second burstable blister or pouch is ruptured). The fluid E/reagent mixture may optionally be prevented from flowing into zone C by the temporary seal that is provided between zones B and C. In some implementations, this temporary seal may be omitted, but it may be beneficial to allow fluid E and the reagent some time to mix before advancing the mixture through the fluidic circuit.

Once fluid E and the reagent have been allowed to mix in zone B, the clamping pressure may be advanced further towards zone K, thereby pressurizing the fluid E/reagent mixture to a point that causes the temporary seal (if used) between zones B and C to rupture. The fluid E/reagent mixture may then be forced through zone C, which may contain multiple walls 1754a/b provided by permanent seals that are arranged in a "broken chevron" configuration, e.g., with each such wall 1754a/b extending from one wall 1754c/d of the passage extending through zone C towards an opposing wall 1754c/d of the passage extending through zone C. Such walls 1754a/b may be arranged in an alternating pattern, e.g., the wall or walls 1754a or 1754b adjacent to any given wall 1754c or 1754d may extend from the opposite side of the passage from the side of the passage from which the given wall 1754c or 1754d extends. Moreover, the walls 1754a/b may overlap one another when viewed along a direction aligned with the path of travel of the pressure zone. Finally, the distance from the tip of each wall 1754a or 1754b to the closest adjacent wall 1754b or 1754a may increase as that wall 1754a or 1754b approaches the side of the passage from which that wall 1754a or 1754b extends. In the depicted arrangement of FIG. 17, the walls 1754a/b give the appearance of two nested chevrons that have been broken apart in the middle and the two sets of chevron halves then offset vertically relative to each other and then inward towards each other. Other arrangements may be used as well to provide a similar effect. Such configurations may provide a similar effect to the zig zag feature discussed earlier, forcing the fluid that flows therethrough to undergo multiple flow reversals to help promote improved mixing of such fluid. The arrangement discussed above may further enhance mixing since each pair of adjacent walls may, in effect, cause the fluid to flow through a narrower opening before flowing into a larger volume trapped between the two walls. Each such transition may result in vortices being generated as the fluid flows from the narrower opening into the larger volume that follows. When the fluid is flowed through multiple such transitions, this may cause the fluid to undergo further mixing that may not be achieved using a constant-width zig zag passage.

Once the fluid E/reagent mixture has flowed through the flow-reversal section of zone C, it may be further pressurized by further advancement of the clamping pressure zone so as to cause a temporary seal at the end of the flow reversal section to rupture, thereby allowing the fluid E/reagent mixture to be delivered to an antechamber portion at the end of zone C. The antechamber portion of zone C may be separated from zone D by a further temporary seal.

Zone D may be partitioned internally by multiple permanent seals that may be spaced apart so as to divide the fluid E/reagent mixture into separate portions having desired relative volumes. For example, in the implementation of FIG. 17, there are two internal divider walls provided by permanent seals within zone D, forming a total of three different volumes directly beneath the temporary seal that partitions zone C from zone D. When the fluid E/reagent mixture collects above that temporary seal and is pressurized such that that temporary seal ruptures, the fluid E/reagent mixture will then rush into the separate volumes defined by the permanent seals in zone D. This may cause the fluid E/reagent mixture to be divided into sub portions that are sized to be proportionate to the relative widths of the temporary seal portions capping each such volume. For example, in the depicted example, the temporary seal portion above the leftmost volume is 33% wider than the corresponding temporary seal portions above each of the middle and rightmost volumes, thereby causing approximately 33% more of the fluid E/reagent mixture to collect in the leftmost volume of zone D than in the middle or rightmost volumes thereof (this assumes that the total volume of the fluid E/reagent mixture is less than the total volume within zone D). In some implementations, if the total volume of the fluid E/reagent mixture is known to be larger than the total volume of zone D, then the temporary seal between zones C and D may be omitted, as each volume in zone D will fill completely with the fluid E/reagent mixture, with any surplus spilling over into the adjoining volumes until all of the volumes are filled.

Each of the volumes in zone D defined between the walls provided by the permanent seals in zone D may lead to a separate fluidic sub-circuit that may be fluidically isolated from the other fluidic sub-circuits. In this example implementation, the fluidic structure is configured to obtain a calibrated measurement of a biomarker of interest. In order to do so, the fluidic structure is configured to allow for three separate measurements to be obtained-one of the biomarker of interest in a sample, one of a positive control amount of the biomarker of interest, and one of a negative control (with the biomarker of interest absent). The leftmost fluidic sub-circuit in FIG. 17 is used to obtain a measurement of the biomarker of interest in the sample, the middle fluidic sub-circuit is used to obtain the positive control measurement, and the rightmost fluidic sub-circuit is used to obtain the negative control measurement.

When the clamping pressure zone is advanced further towards zone K, the fluid E/reagent mixture trapped in the volumes of zone D may be pressurized to a level that causes temporary seals that partition zone D from zone E to burst, allowing the separate portions of the fluid E/reagent mixture to be flowed into separate fluid passages defined by permanent seals within zone E. The leftmost fluid passage of zone E may have a sample collection interface 1742 that allows the fluid E/reagent mixture flowed into that fluid passage to come into contact with a previously collected sample of interest. For example, the sample collection interface may include surfaces of a breath collector module, such as is described in U.S. patent application Ser. No. 16/823,113, which is hereby incorporated herein for all purposes, configured to collect breath constituents from exhaled breath of a test subject. The fluid E/reagent mixture may act to elute such a collected sample from the sample collection interface 1742, thereby suspending it within the fluid E/reagent mixture.

Similarly, the middle passage may include a pre-defined amount of the biomarker of interest that is known with a particular accuracy; the fluid E/reagent mixture that is introduced into the middle passage may similarly elute the pre-defined amount of the biomarker within that passage, thereby suspending it within that fluid E/reagent mixture. The fluid E/reagent that is introduced into the rightmost passage does remains unadulterated.

After the biomarker in the leftmost and middle passages in zone E has been eluted by the fluid E/reagent mixture, henceforth simply referred to as "eluent," the clamping pressure zone may be advanced again to further pressurize the eluent in each of the three passages and cause temporary seals within each passage in between zone E and zone F to rupture, thereby allowing the eluent in each passage to advance to zone F. Zone F may be optional, and may be included if it is desired to isolate a portion of the collected sample for future analysis, e.g., to preserve a portion of the collected sample for future or subsequent use or analysis. As discussed above, zone F may be omitted and the eluent flowed directly into zone G. If zone F is used, a portion of the eluent (with whatever eluted biomarker is contained within it) in the leftmost passage may be directed into chamber 1746 by the pressure applied by the clamping pressure zone as the clamping pressure zone moves towards zone K. A heater element 1718*a* may be activated to locally heat the fluidic structure around the opening of the chamber 1746, thereby thermally bonding it to form a permanent seal. After the chamber 1746 is sealed shut, the clamping pressure zone can be advanced further towards zone K, causing temporary seals between zones F and G to rupture and allowing the eluent in each passage to advance to zone G.

Zone G may have several features that are replicated for each of the three fluidic sub-circuits. For example, each fluidic sub-circuit may have an area (represented by diagonal cross-hatching) in which another reagent that is specific to the reagent mixed with fluid E may be immobilized. For example, if the reagent mixed with fluid E is an antibody, the reagent that is immobilized in the cross-hatched area may be an antigen to that antibody that may bind with any unbound antibodies in the eluent, thereby immobilizing such antibodies. Antibodies in the eluent that previously bound with the eluted biomarker, however, would not bind to the immobilized antigen as their binding site(s) would already have bound to the biomarker.

The diagonal hatched area may also represent an optical window area, e.g., an optically transmissive region, that may be used to introduce light to and/or emitted from the region having the immobilized reagent. As discussed later below, the optical window area may eventually be used to obtain optical measurements of fluorescence or chemiluminescence (or other optical characteristic) of material that is located within the optical window area, thereby allowing for a measurement relating to the concentration and/or presence of the biomarker to be made. Finally, a heating element may be provided such that at least a portion of the immobilized reagent is located between the heating element and zone H.

The heating element may be used to provide a localized thermal bond in the fluidic structure that acts to seal the passage within zone G. As noted, each of the passages in zone G may have a corresponding immobilized reagent, optical window area, and heater element.

Once the eluent has been pushed into zone G by advancement of the clamping pressure zone, the clamping pressure zone may optionally be moved back and forth by a small amount to promote circulation of the eluent over the area with the immobilized reagent. After the eluent has been allowed to incubate for a period of time such that most or all of the reagent in the eluent that is not bound to the biomarker of interest binds to the immobilized reagent, the clamping pressure zone may be advanced towards zone K again, causing the eluent to re-pressurize and cause the temporary seal separating zone G from zone H to be ruptured, thereby allowing the eluent to be pushed into zone H.

Zone H includes second fluid reservoirs 1706*b/c/d*, each of which may include a corresponding amount of fluid ⍵, and a portion of the passage that is sealed off from the corresponding second fluid reservoir 1706*b*, 1706*c*, or 1706*d* by a corresponding temporary seal. The portions of the passage in zone H may be positioned, for example, over a fluid bypass recess, such as the example discussed earlier (and discussed in more detail below), that allows the eluent to escape past the clamping pressure zone within zone H. Thus, as the clamping pressure zone moves through zone H, the eluent that is trapped between the clamping pressure zone and the temporary seals between zones H and I may escape and flow back up into zone G (and possible into zones F or E). At the same time, when the clamping pressure zone reaches the second fluid reservoirs 1706*b/c/d*, the second fluid reservoirs 1706*b/c/d* may be caused to release the fluid ⍵ portions contained therewithin and the resulting pressurization of the fluid ⍵ portions may cause the temporary seals associated with each of the second fluid reservoirs 1706*b/c/d* to rupture, allowing the fluid ⍵ to be pushed into the passage portions within zone H. As fluid ⍵ flows into the passage portions within zone H, it will act to push the eluent that is present in zone H past the clamping pressure zone, through zone G, and into zone F (and/or E). In some implementations, heater elements (not shown, but similar to the other heater elements discussed above) may be provided in locations corresponding to the locations of the ruptured temporary seals that existed between the second fluid reservoirs 1706*b/c/d* and the corresponding adjacent passages; these heater elements may be used to thermally bond the fluidic structure to as to produce permanent seals that replace the ruptured temporary seals at those locations once the fluid ⍵ is evacuated from the second fluid reservoirs 1706*b/c/d*. The clamping pressure zone may then be moved relatively rapidly backwards, thus pushing the eluent and fluid ⍵ towards zone A while allowing little of the eluent and fluid ⍵ to escape past the clamping zone and flow towards zone K, so as to align with the heater elements provided in zone G. The heater elements may then be activated so as to thermally bond corresponding areas of the fluidic structure so as to form permanent seals that seal off all or most of the eluent and/or fluid ⍵ from zones H/I/J/K and the portion of zone G that has the immobilized reagent.

The clamping pressure zone may then be further advanced to zone I; unlike previous such advancements, no fluid is driven forward through the passages into the adjoining passage segments in zone I; the temporary seals that exist at the boundary between zones I and J remain intact. Furthermore, the bypass recesses that were positioned under the passage segments in zone H may also extend into zone I and also into zone K.

As the clamping pressure zone moves into zone I, it may compress fluid α housed within third fluid reservoirs 1706e/f/g and fluid β housed within fourth fluid reservoirs 1706h/i/j, thereby causing the temporary seals sealing the third fluid reservoirs 1706e/f/g and the fourth fluid reservoirs 1706h/i/j at the boundary between zones I and J to rupture. The clamping pressure zone may then be advanced through zone I to drive fluids α and β into zone J, where they may mix within each fluidic sub-circuit. Fluids α and β may, for example, be substrates that, when mixed together, form an indicator that may be activated so as to emit light when exposed to the reagents bound to the immobilized reagents in zone G.

As fluids α and β are forced into zone J, they may mix, which may include mixing that occurs when fluids α and β are pushed through a zig zag fluid path, or similar feature (such as is shown in zone C). The α/β mixtures may then be forced into zone K, where they may, by way of the fluid bypass recesses extending into zone K, flow past the clamping pressure zone and up through the passages and into zone G, where the α/β mixtures may then come into contact with the immobilized reagent and any reagents bound thereto. An optical measurement may then be performed through each window area of each fluidic sub-circuit in order to ascertain the amount of biomarker that was provided to each immobilization site. The measurements of the positive and negative control amounts of the biomarker of interest may allow the measurement of biomarker in the sample to be calibrated based on the control amounts, e.g., the measured quantity of the biomarker in the sample may be interpolated between the measured quantities of the positive and negative controls, and the calibrated amount of biomarker in the measured sample may then be estimated based on interpolating between the positive and negative control amounts in a similar manner.

Figure 18:
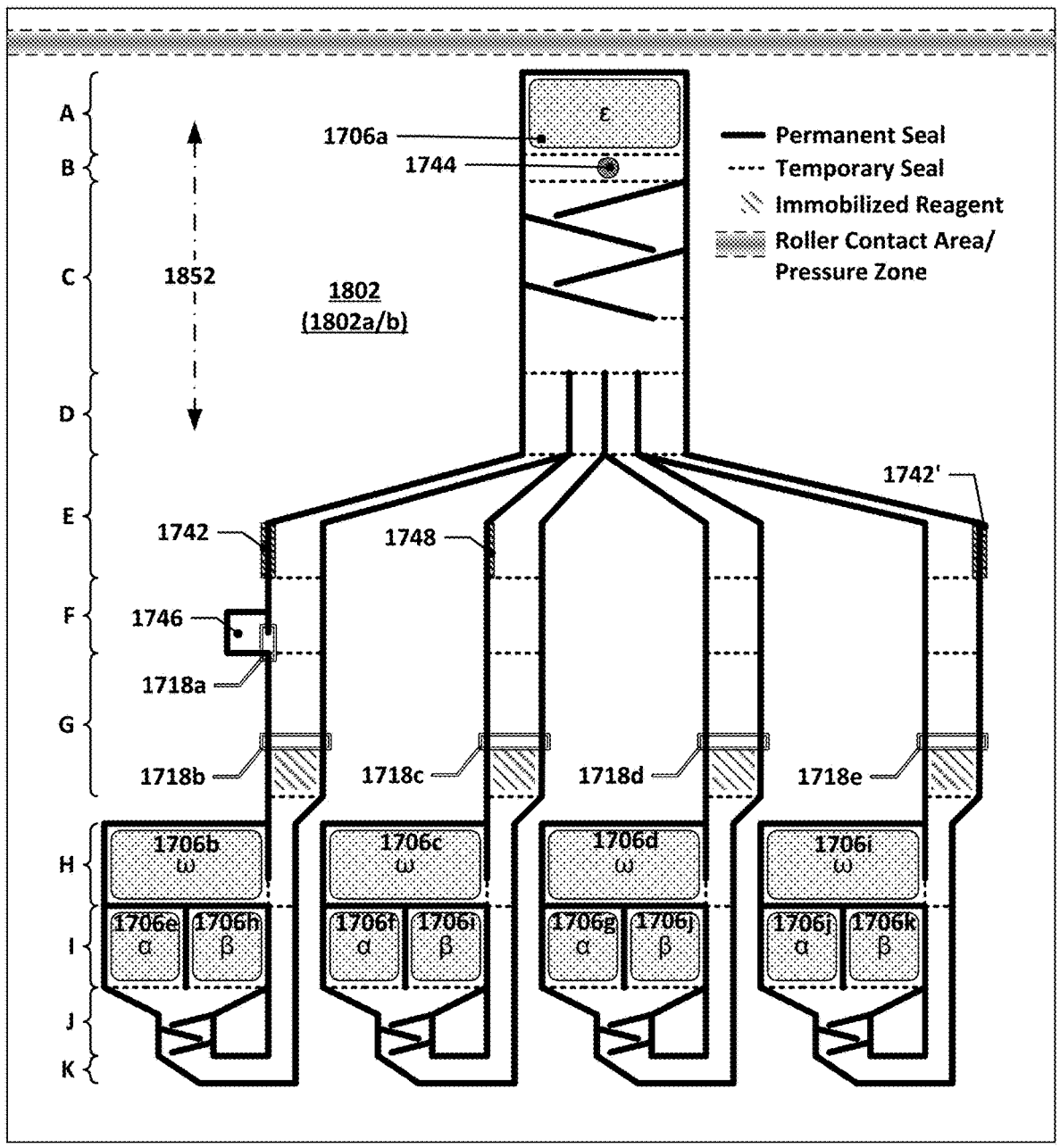
FIG. 18 depicts another example fluidic structure that may be used to measure a concentration of a biomarker or other material of interest.

FIG. 18 depicts a version of the fluidic structure of FIG. 17, but with four fluidic sub-circuits. The fourth fluidic sub-circuit, on the rightmost side, has a second sample collection interface 1742' that may, for example, be used to introduce a sample into the fluidic structure that has been collected from ambient air (as opposed to from a subject's lung exhalations), and to obtain similar measurements of that sample is obtained from the other three fluidic sub-circuits. Such a fluidic structure may be used to simultaneously obtain samples from, for example, a human subject's lungs, e.g., a breath sample, as well as from ambient air. In the latter case, a vacuum pump may be used to draw ambient air through a sampling system similar to that used to collect a breath sample from the test subject. Such a structure may permit the amount of biomarker in the test subject's sample to be adjusted to account for the amount of biomarker that may be in the ambient air. For example, if a reading of 40 units of biomarker is measured from the test subject's sample, but the ambient air is measured to have 30 units of biomarker present, then the test subject's biomarker measurement may be corrected to remove the portion thereof that may have been preexisting, i.e., 40 units minus 30 units, which would leave a corrected measurement of 10 units.

It will be understood that the fluidic structures of FIGS. 17 and 18 may use any of a variety of assays in order to identify a particular biomarker of interest, and that the basic architecture shown may be modified, as needed, to accommodate the fluidic requirements of any given assay, e.g., if an indicator that is stable in its final form is used, the dual fluid reservoirs containing the α and β fluids may be replaced with a single reservoir in each fluidic sub-circuit that contain that stable indicator; the mixing sections in zone J may also be omitted in some such cases since mixing may not be required. Alternatively, the dual fluid reservoirs of zone I may also be replaced with larger numbers of reservoirs, e.g., three or four reservoirs for each fluidic sub-circuit, allowing for more complex mixtures of reactants to be used.

In some implementations of the fluidic structures of FIGS. 17 and 18, the eluent may be N-cyclohexyl-2-hydroxyl-3-aminopropanesulfonic acid (CAPSO) mixed with 0.5% concentration dichloroacetic acid and the reagent or material 1744 may be a lyophilized anti-THC antibody that is conjugated to horseradish peroxidase (HRP). The immobilized reagent in such implementations may be bis(trimethylsilyl)acetamide (BSA)-THC that is adsorbed onto one or more surfaces of each passage in zone G of the fluidic structure, and the α and β fluids may be binary substrates that, when mixed, produce an HRP substrate. In such implementations, equal or near-equal volumes of eluted antibody are delivered to each fluidic sub-circuit, and varying amounts of the antibody in each such volume are bound to whatever THC is present within zone E of the corresponding fluidic sub-circuit. When the sample is then moved to zone G, whatever unbound antibody remains in the elution mixture is bound to the immobilized antibody, and the elution mixture is then washed out of zone G and the indicator (HRP) is introduced into zone G, where it binds to the immobilized antibody that remains. Subsequent luminescent or fluorescent emissions from the HRP may be measured to obtain an indication of the relative concentrations of immobilized antibody (and HRP) in each fluidic sub-circuit. Such concentrations will generally be inversely proportional to the amount of THC that was in zone E of each fluidic sub-circuit.

While the above specific examples provide some insight as to how particular fluidic circuits may be implemented in the context of the flexible fluidic circuit concepts discussed herein, it will be apparent that there may be many configurations of rollers and platens that may be suitable for use with the flexible substrate fluidic structures discussed above. FIGS. 19 through 24 depict several examples of example roller/platen configurations, including one that does not use any platen at all.

Figure 19:
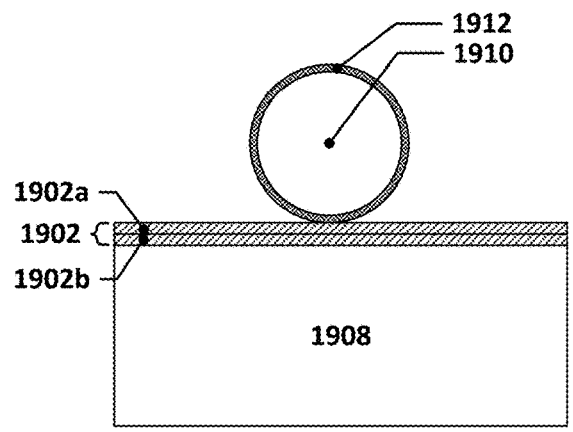
FIGS. 19 through 24 depict several examples of example roller/platen configurations, including one that does not use any platen at all.

FIG. 19 depicts a side view diagram of one such mechanism in which a roller 1910 is provided that has an elastomeric outer layer 1912. The roller 1910 is used in conjunction with a platen 1908 to apply clamping pressure to a fluidic structure 1902 having a first portion of material 1902a and a second portion of material 1902b. The use of the elastomeric outer layer 1912 allows for the compressive load applied between the roller 1910 and the platen 1908 to be spread out over a larger area, thus providing for a more complete seal to be generated within the fluidic structure 1902. The elastomeric outer layer 1912 also allows, as discussed earlier, for the roller 1910 to roll over incompressible objects, e.g., the semi-rigid core of a swab, while still maintaining a tight seal that prevents fluid from leaking past the roller 1910 (or that at least reduces the rate of such leakage, if present).

Figure 20:
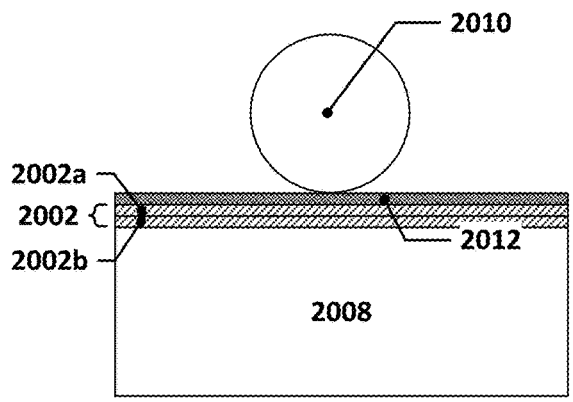

The implementation of FIG. 20 is similar to that of FIG. 15, except that the elastomeric layer 2012 is placed on top of the platen 2008, with the roller 2010 being made of a rigid material. The operating principle is similar, however, with the elastomeric layer 2012 being able to be elastically compressed in order to both spread out the compressive load imparted on the first portion of material 2002a and the second portion of material 2002*b* of the fluidic structure 2002 by the roller 2010 and to provide a more effective seal.

Figure 21:
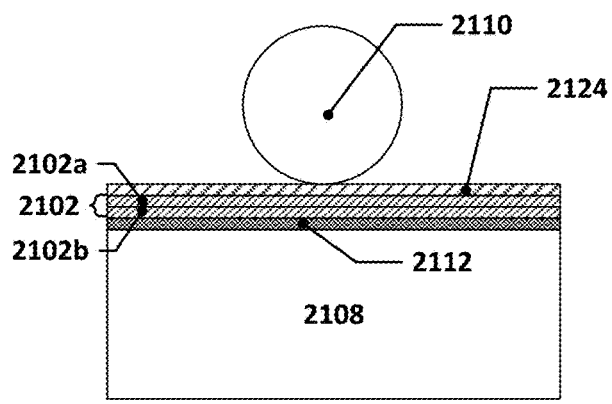

The implementation of FIG. 21 is similar to that of FIG. 20, except that the roller 2110 does not contact the fluidic structure 2102 directly, but instead presses against a separate, semi-flexible roller plate 2124 that is pressed into contact with the first portion of material 2102*a* of the fluidic structure 2102. The roller plate 2124 may be used, in effect, as a second platen 2108—except one that is flexible. Such a roller plate 2124 may, for example, be used to provide features, such as the fluidic bypass recess and/or the partitioning recess, discussed earlier that may cooperate with features in the fluidic structure that allow for particular fluidic operations to be performed.

Figure 22:
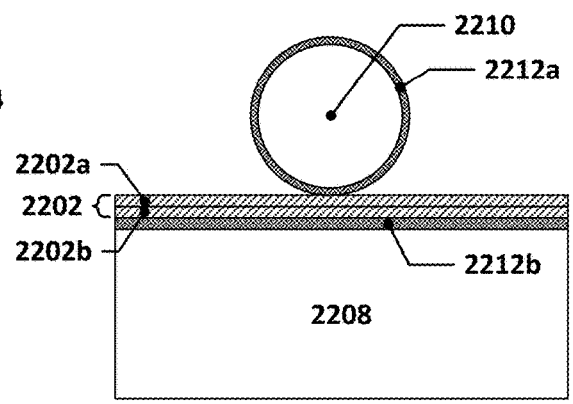

The implementation of FIG. 22 includes two compliant layers—a first elastomeric layer 2212*a* that is provided on the exterior circumference of the roller 2210 and that contacts the first portion of material 2202*a* of the fluidic structure 2202 and a second elastomeric layer 2212*b* that is provided on the upper surface of the platen 2208 that contacts the second portion of material 2202*b* of the fluidic structure 2202.

Figure 23:
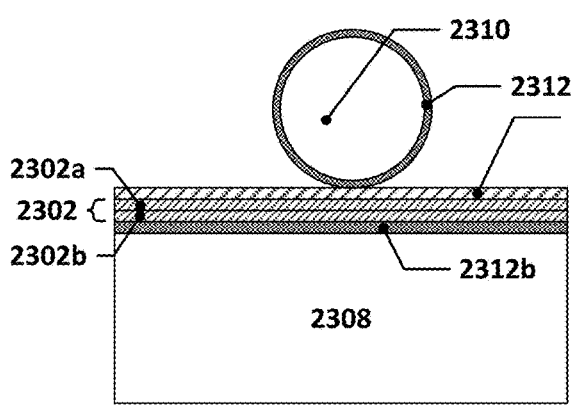

The implementation of FIG. 23 is, in effect, a blend of the implementations of FIGS. 21 and 22, including not only a first elastomeric layer 2312*a* that is provided on the exterior circumference of the roller 2310 and that contacts the first portion of material 2302*a* of the fluidic structure 2302 and a second elastomeric layer 2312*b* that is provided on the upper surface of the platen 2308 that contacts the second portion of material 2302*b* of the fluidic structure 2302, but which also includes a roller plate 2324 that may function in much the same way as the roller plate 2124.

Figure 24:
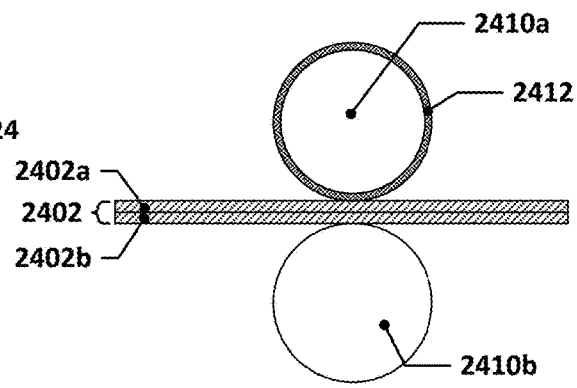

The implementation of FIG. 24 differs from the previously discussion implementations in that there is no platen; in its place, the implementation of FIG. 24 uses two rollers 2410*a* and 2410*b*, at least one of which has an elastomeric layer 2412 on the outer circumference thereof. The first portion of material 2402*a* and the second portion of material 2402*b* of the fluidic structure 2402 are clamped in between the two rollers 2410*a* and 2410*b*, with the elastomeric layer 2412 being used to more evenly distribute the clamping load on the fluidic structure 2402. The advantage of such a configuration is that the size of the mechanism that is used to apply the clamping pressure to the fluidic structure may be considerable smaller than in implementations that use a platen. However, such implementations may also prove somewhat more challenging to design, as any fluidic bypass recesses and/or partitioning recesses may need to be designed into one or both of the rollers 2410*a* and 2410*b*. In some implementations, a roller plate or roller plates may be used to provide such features, thereby avoiding the need to include such features in the rollers 2410*a* and 2410*b* themselves.

As discussed above, some implementations of the fluidic systems discussed herein may utilize a "roller plate," which may be a rigid, semi-rigid, or flexible plate that may be interposed between the roller and the platen (or between two rollers) in addition to the fluidic structure. The roller plate may serve multiple purposes. For example, the roller plate may include fluidic-circuit-specific features, e.g., partitioning or fluid bypass recesses such as are discussed below in more detail, raised portions, etc., that could also be included directly on the roller and/or the platen. Placing such features on a roller plate, however, allows for such features to be easily swapped out without needing to change the platen or the roller. Instead, different roller plates with different feature configurations may be provided, each tailored for use with a different fluidic circuit.

Another benefit of using a roller plate is that it may, in effect, act as a "virtual" roller that is much larger than the actual roller. For example, a roller may be sized such that it completes multiple revolutions as it traverses across a particular fluidic structure. As a result, any features that are included on the roller, e.g., recesses or protrusions, may repeatedly engage with the fluidic structure as the roller traverses across the fluidic structure. This may result in the functionality provided by such features being repeatedly applied to the fluidic circuit, even when not desired. However, if a roller plate is used, the roller plate may be viewed as representing a portion of a much larger diameter virtual roller of which only a portion is clamped against the fluidic structure at any given time. This virtual roller is sized such that no portion of it would come into contact with the fluidic structure more than once, thereby avoiding the issue of having features repeatedly engage with the fluidic structure.

Figure 25:
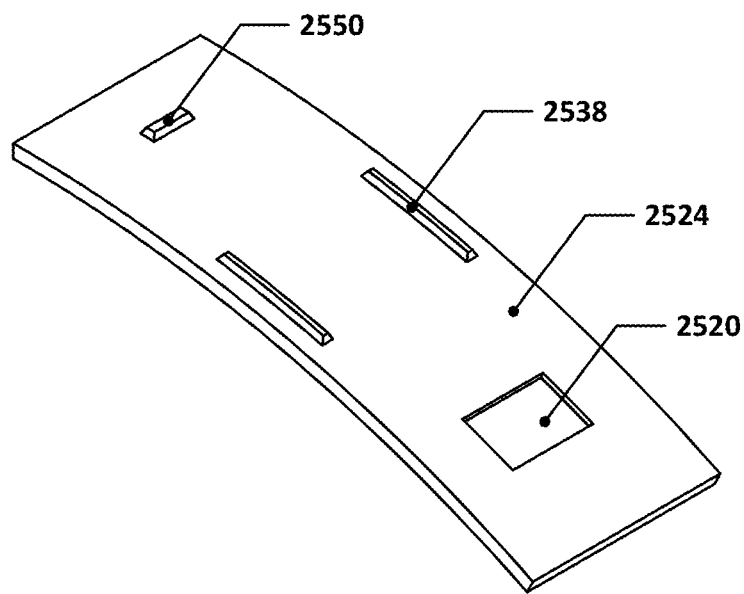
FIG. 25 depicts an example roller plate.

An example of such a roller plate is shown in FIG. 25. As shown in FIG. 25, the roller plate 2524 is a curved, rigid plate, although this is not necessary. The roller plate 2524 may also be made of a flexible material or semi-rigid material.

The roller plate 2524 includes a protrusion feature 2550, a pair of rail features 2538 (see later discussion below regarding rails), and a fluid bypass recess 2520.

Figure 26:
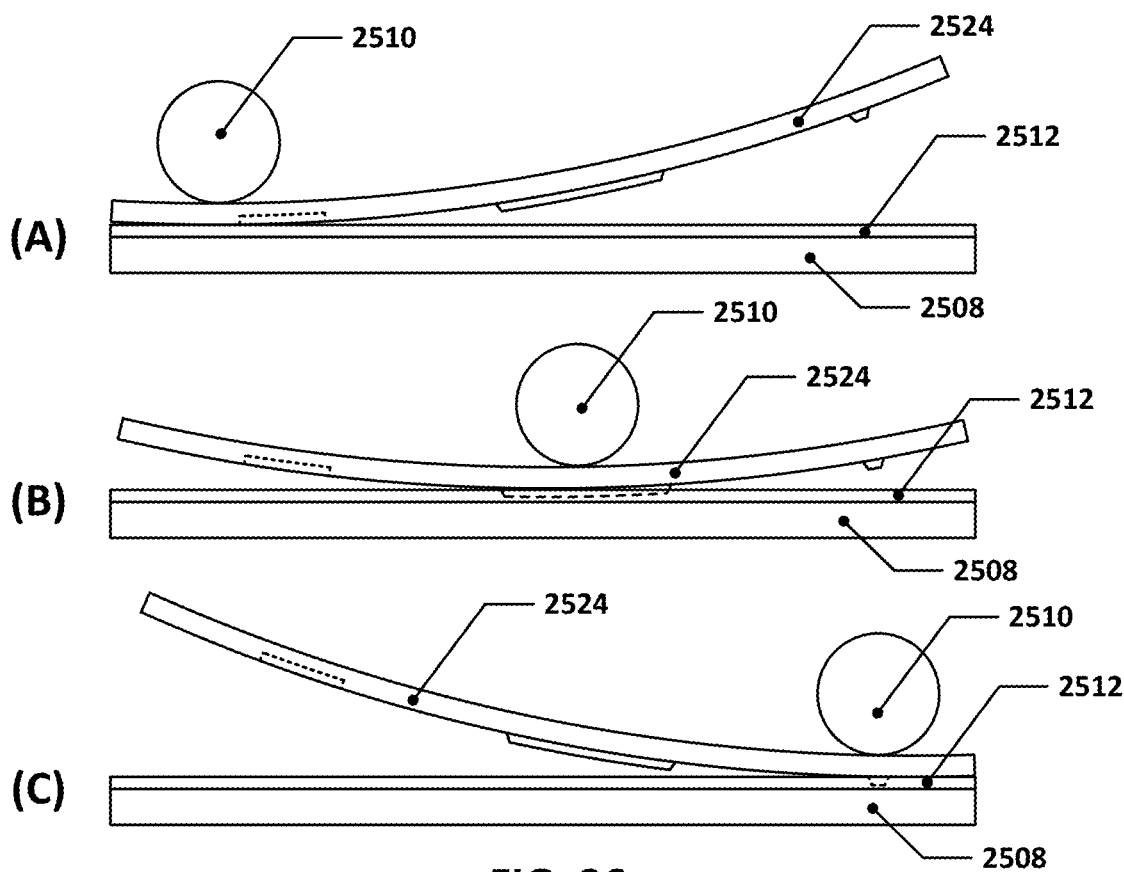
FIG. 26 depicts the example roller plate of FIG. 25 in various stages of use.

As can be seen in FIG. 26, the roller plate 2524 may be pressed into contact with a fluidic structure (not shown, but would be positioned between the roller plate 2524 and the platen 2508) by a roller 2510. A compliant layer 2512 may be interposed between the platen 2508 and the fluidic structure as well. When the roller 2510 is advanced along the platen 2508, it causes the roller plate 2524 to rotate (if rigid) and the portion of the roller plate 2524 following the roller 2510 to lift off of the fluidic structure (or at least no longer be subjected to a compressive force by the roller 2510 and the platen 2508) and the portion of the roller plate 2524 preceding the roller 2510 to come into contact with the fluidic structure. In this manner, the features that are provided on the roller plate 2524 may, as shown in stages (A), (B), and (C) of FIG. 26, sequentially come into and out of contact with the fluidic structure. The features that protrude from the roller plate 2524 may, for example, deform the compliant layer 2512, resulting in higher-pressure regions that may be applied to the fluidic structure, whereas the features that are recessed into the roller plate 2524 may result in lower-pressure regions that may be applied to the fluidic structure.

It will also be recognized that the platens discussed herein may be provided using any suitable material such as a printed circuit board, which may have embedded within it various electrical systems that may be configured to provide functionality that may be used by the fluidic system. For example, a printed circuit board may be equipped with resistive heating traces or other heat-generating features that may be used to provide for heating operations discussed herein. A printed circuit board may also include light sources and/or light detectors, temperature sensors, etc., that may all be used to assist with analysis steps that may be performed using such fluidic structures.

It will be recognized that fluidic systems such as those discussed above may incorporate various functional blocks that may be combined, as desired, to provide various fluidic operations. The following discussion focuses on several examples of such functional blocks and the structures that may be used to provide them.

FIGS. 27 through 29 depict an example of a fluidic bypass structure, which may be used to allow a smaller amount of fluid to be isolated from a larger amount of fluid. Such a structure may be useful when the exact volume of the larger amount of fluid may fluctuate due to various factors, e.g., when the amount of fluid in a sample that is provided to the fluidic structure may not be known in advance. In the depicted example, a platen 2708 is provided that has a bypass recess 2720 in it. A roller 2710 with a compliant layer 2712 may be used to compress a fluidic structure having a first portion of material 2702a and a second portion of material 2702b against the platen 2708. The first portion of material 2702a and the second portion of material 2702b may be similar to those discussed earlier and may be thermally bonded together to define one or more fluidic flow paths and/or chambers, including a fluidic passage that extends across the bypass recess 2720. A temporary seal 2734 may seal off the fluidic passage, thereby trapping a fluid within the passage in between the temporary seal 2734 and the clamping pressure zone exerted on the first portion of material 2702a and the second portion of material 2702b by the roller 2710. While the length of the bypass recess 2720 may be of any length, the width of the bypass recess 2720 in a direction perpendicular to the direction of travel of the roller 2710 may be designed to be less than the width of the roller 2710 in that same direction, such that the portion of the roller 2710 that applies pressure to the platen 2708b extends beyond the sides of the bypass recess 2720.

Thus, as the roller 2710 traverses across the first portion of material 2702a and the second portion of material 2702b and over the bypass recess 2720, the roller 2710 will push the first portion of material 2702a downward towards the bottom of the bypass recess 2720, thereby reducing the volume of the passage and increasing the pressure of the fluid therewithin. The roller 2710, however, may be prevented from falling into the bypass recess 2720 itself since the ends of the roller are supported by portions of the platen 2708 that are outside of the bypass recess 2720. The pressure exerted on the fluid within the passage due to the advancement of the roller 2710 may cause the second portion of material 2702b to bulge downward into the bypass recess 2720, thereby causing a small gap to come into being between the first portion of material 2702a and the second portion of material 2702b, as shown in FIG. 28. Some of the higher-pressure fluid (>p1) that is located between this gap and the temporary seal 2734 may escape through the gap into a lower-pressure region behind the roller 2710, thereby preventing the pressure within the higher-pressure fluid from exceeding the rupture pressure of the temporary seal 2734. Once the roller 2710 reaches the end of the bypass recess 2720, as shown in FIG. 29, the first portion of material 2702a and the second portion of material 2702b may again be clamped together by the clamping pressure exerted by the roller 2710, thereby causing the gap that existed within the bypass recess 2720 to close and the passage to again be sealed. The fluid that is trapped within the passage between the clamping zone exerted by the roller 2710 and the temporary seal 2734 may then be advanced through the fluidic circuit by further advancing the roller 2710, thereby increasing the pressure within that fluid to the point where the temporary seal 2734 ruptures, allowing the fluid to be pushed further down the passage. Through selection of the distance between the temporary seal 2734 and the edge of the bypass recess 2720 closest thereto (and factoring in the maximum volume of fluid that can be trapped therebetween within the passage), a sub-portion of the fluid within the passage having a given volume can be isolated even if the volume of fluid in the passage prior to the above-discussed operations is not precisely known.

In the example of FIGS. 27 through 29, the gap between the first portion of material 2702a and the second portion of material 2702b provided by the bypass recess 2720 allows for fluid to flow freely past the clamping pressure zone; the roller 2710 must keep moving in order to maintain the higher-pressure environment in the fluid between the clamping pressure zone and the temporary seal 2734. If the roller slows down sufficiently, the higher-pressure fluid may escape through the gap quickly enough that the higher-pressure and lower-pressure fluid on either side of the gap may start to equalize, which may result in some fluctuation in the amount of fluid that is ultimately isolated between the temporary seal 2734 and the edge of the bypass recess 2720 closest thereto.

If more precise partitioning of an amount of fluid from a larger amount of fluid is desired within such a fluidic structure, a feature such as that shown in FIGS. 33 through 37 may be used. In the depicted example, a platen 3308 is provided that has a partitioning recess 3322 in it. A roller 3310 with a compliant layer 3312 may be used to compress a fluidic structure having a first portion of material 3302a and a second portion of material 3302b against the platen 3308. The first portion of material 3302a and the second portion of material 3302b may be similar to those discussed earlier and may be thermally bonded together to define one or more fluidic flow paths and/or chambers, including a fluidic passage that extends across the partitioning recess 3322. A temporary seal 3334 may seal off the fluidic passage, thereby trapping a fluid within the passage in between the temporary seal 3334 and the clamping pressure zone exerted on the first portion of material 3302a and the second portion of material 3302b by the roller 3310. The length of the partitioning recess 3322 along the direction that the roller 3310 travels may be selected so as to be less than the diameter of the roller 3310, while the width of the partitioning recess 3322 in a direction perpendicular to the direction of travel of the roller 3310 may be designed to be more than the width of the roller 3310 in that same direction, such that the roller 3310, which may be pressed against the first portion of material 3302a and the second portion of material 3302b, as well as the platen 3308, by springs 3336, is able to dip into the partitioning recess 3322 as it traverses over the partitioning recess 3322. Also shown in FIG. 33 is the dotted outline of a bypass recess 3320, which may be used to reduce a much larger amount of fluid within the passage to the smaller amount shown as being trapped within the passage in FIG. 33. The mechanism shown in FIG. 33 may then be used to partition off an even smaller portion of that fluid with higher precision than may be possible using the bypass recess 3320. The use of a bypass recess in this context is not always necessary depending on the particular context but can provide part of a useful two-stage partitioning mechanism in which the bypass recess is used for gross fluid partitioning and the partitioning recess is used for more refined partitioning.

As shown in FIG. 34, as the roller 33 rolls across the partitioning recess 3322, the roller 3310 is pressed downward by the spring 3336 so that the first portion of material 3302a and the second portion of material 3302b are pinched between the roller 3310 and the edge of the partitioning recess 3322 that is furthest from the temporary seal 3334. This prevents the fluid that is trapped between this clamping region and the temporary seal 3334 from escaping, and keeps the trapped fluid at an elevated pressure that ensures that the passage stays pressurized in between the roller 3310 and the temporary seal 3334. The downward movement of the roller 3310 may also cause the portion of the passage beneath the roller 3310 to be pushed into the partitioning recess 3322; the partitioning recess 3322 may be sized to permit such downward movement of the passage.

In FIG. 35, the roller 3310 has advanced such that it is now centered over the center of the partitioning recess 3322 and has extended into the partitioning recess 3322 so that it is now pinching the first portion of material 3302a and the second portion of material 3302b together at two locations, each located along a different opposing transverse edge of the partitioning recess 3322. This results in the fluid within the passage being partitioned into two pressurized volumes—one that is fluidically interposed between the two pinch points and is located within the partitioning recess 3322, and the other of which is fluidically interposed between the temporary seal 3334 and the pinch point closest thereto.

In FIG. 36, the roller 3310 has advanced further (and has now started to climb back up out of the partitioning recess 3322), allowing the first pinch point that was formed to relax, thereby releasing the pressurized fluid that was trapped within the passage in the partitioning recess 3322 to flow in the opposite direction from the roller 3310 motion. The other pinch point, however, remains clamped, thereby preserving the pressurized state of the fluid trapped between that pinch point and the temporary seal 3334.

As the roller 3310 continues to advance, the pressure of the fluid that is still trapped in the passage will continue to increase until the rupture pressure of the temporary seal 3334 is reached, causing the temporary seal 3334 to burst, as shown in FIG. 37, and releasing the fluid that was previously trapped in between the burst temporary seal 3334 and the remaining pinch point to flow downstream for further fluidic operations.

Similar to the bypass recess 2720, through appropriate selection of the distance between the temporary seal 3334 and the edge of the partitioning recess 3322 closest thereto (and factoring in the maximum volume of fluid that can be trapped therebetween within the passage), a sub-portion of the fluid within the passage having a given volume can be isolated with precision.

The partitioning recess feature discussed above allows for more precise partitioning of a portion of fluid than can be achieved by using the bypass recess feature discussed earlier since the partitioning recess mechanism does not permit a gap to be generated within the fluidic structure that permits free flow of the trapped fluid past the clamping pressure zone. As a result, the fluid that is trapped between the temporary seal 3334 and the pinch point closest thereto is always kept in a pressurized state, regardless of the velocity of the roller 3310 relative to the platen 3308.

The partitioning mechanism discussed with respect to FIGS. 33 through 37 may, in some implementations, be particularly useful for separating two non-homogenous zones of fluid without causing undue mixing between the zones. For example, if the fluid that is trapped within the passage in FIG. 33 is a mixture of liquid and air (and air bubbles within the liquid) is allowed to separate out, e.g., by orienting the platen 3308 such that the direction of travel of the roller 3310 is in the vertical direction and the temporary seal 3334 is beneath the roller 3310, the result may be a bottom layer of relatively bubble-free fluid that occupies the portion of the passage closest to the temporary seal 3334, a layer of bubbles that floats on top of that bottommost layer, and a layer of free air in the space above the bubble layer. If the partitioning operation is performed with the mechanism is this orientation, the partitioning recess 3322 may be dimensioned so as to cause the portion of the fluid that includes the bubble layer and the free air layer, as well as a portion of the bubble-free layer, to be trapped within the partitioning recess 3322, thereby leaving only the remaining bubble-free fluid trapped in between the lower pinch point and the temporary seal. Thus, the fluid that is advanced further through the fluidic circuit once the temporary seal 3334 is ruptured may be free or relatively free of bubbles. While the bypass recess 3320 may be used to achieve a similar effect, the increased amount of fluid movement that occurs in conjunction with the use of the bypass recess 3320 may interfere with the bubble separation and cause some bubbles to flow or be reintroduced into the bottommost layer, which may be undesirable.

Figure 38:
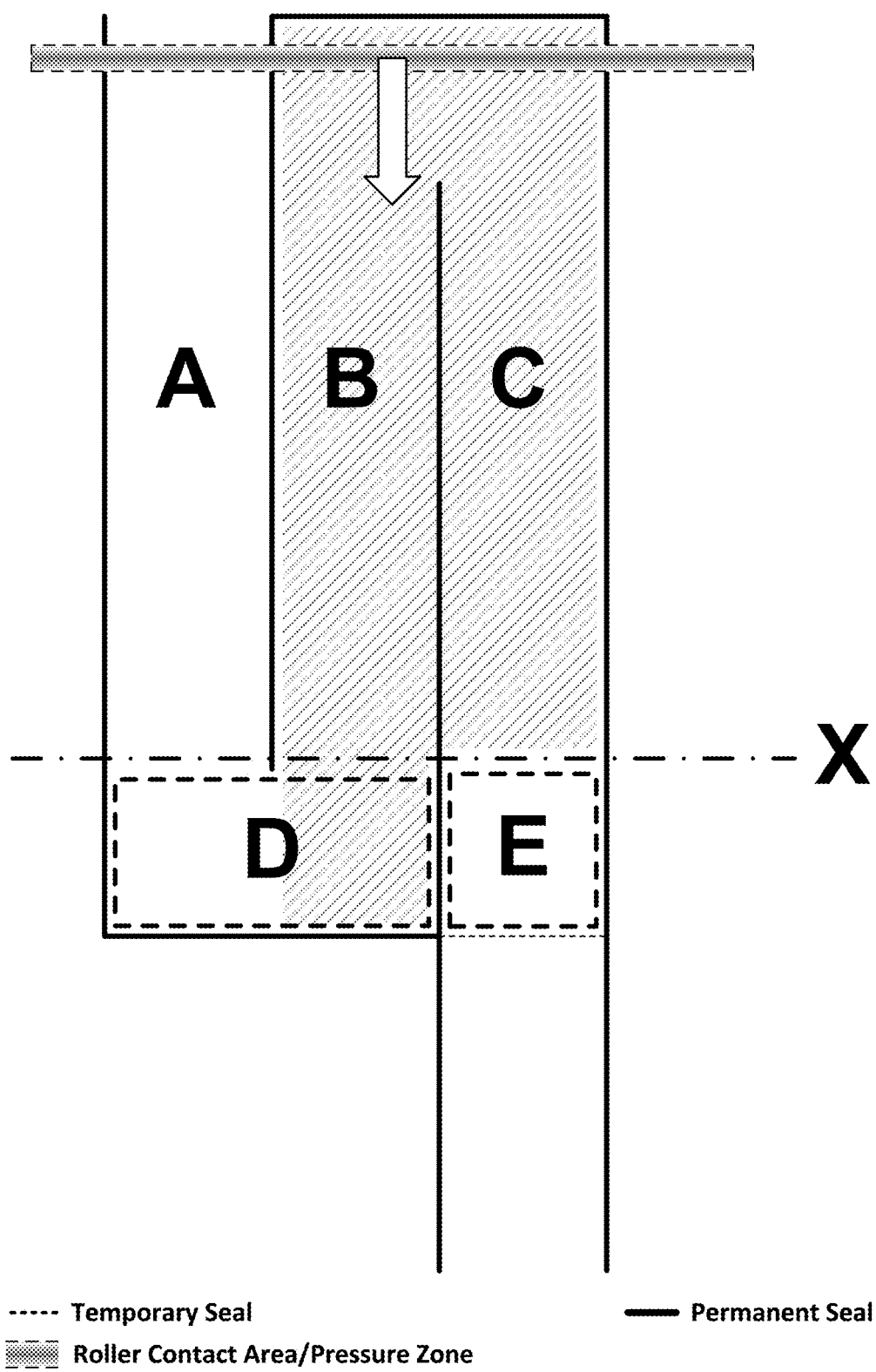
FIG. 38 depicts a functional block that may be used in fluidic systems discussed herein.

FIG. 38 depicts another example of a functional block that may be used to partition off a portion of the fluid being flowed therethrough. In FIG. 38, a fluidic path 3804 is shown that undergoes two or more changes in direction, e.g., the fluidic path may have switchback sections A, B, and C (or more than this number of switchback sections, if desired). Section A may be the initial section through which fluid flows when pushed by the clamping pressure zone as the clamping pressure zone advances across the fluidic structure from the top of the page to the bottom. The fluid may then flow through the remaining switchback sections, e.g., section B, before reaching the last switchback section, which is section C in this example. The functional block may also include a fluid bypass region, e.g., that may be designed to interface with a fluid bypass recess in the fluidic system that provides the clamping pressure zone as discussed earlier, as shown, that extends from at least the flow reversal section (region D) that bridges between sections A and B and through the switchback section or sections between the initial and last switchback sections as well as part of the last switchback section (section C in this example). The fluidic bypass region, however, may be configured to stop in the last switchback section such that there is an offset, e.g., offset 3803, along the direction of travel of the clamping pressure zone between the end of the bypass region in the last switchback section and the end of a wall 3806 that exists between sections A and B.

The various switchback sections A, B, . . . . C may generally have equal widths and may be separated from each adjacent such switchback section by one or more permanent seals/walls that extend generally along parallel axes.

By having such a geometry, as the clamping pressure zone moves along the fluidic circuit, e.g., from the top of the Figure to the bottom, the fluid may be pushed by the clamping pressure zone so as to flow through the switch-backed flow path. While the clamping pressure zone makes a tight seal in section A, thereby forcing the fluid to move forward through the fluidic circuit and to a portion of switchback section C that serves as metering chamber E, the fluidic bypass region allows the fluid, once the metering chamber is full, to flow past the clamping pressure zone in sections B and most of section C, thereby avoiding over-pressurizing metering chamber E and prematurely rupturing the temporary seal that forms one or more walls of the metering chamber. Thus, as the clamping pressure zone moves down along section A, the fluid is able to push past the clamping pressure zone in sections B and C even though the clamping pressure zone is travelling over those sections as well.

When the clamping pressure zone reaches the dash-dot-dash line X, the fluidic bypass region of section C has been replaced by a normal (full-seal clamping, as in section A)

region. Thus, when the clamping pressure zone is centered on line X (as shown on the right side of FIG. 38), there will be a liquid-tight seal in both sections A and C. Such an implementation permits for a precisely metered amount of fluid to be pressurized within the metering chamber E of section C between the line X and the temporary seal shown at the bottom of section C; further advancement of the clamping pressure zone towards the bottom of the page may then cause the temporary seal to rupture, thereby forcing the isolated portion of fluid trapped behind the now-ruptured temporary seal to be pushed onward through the fluidic circuit to downstream destinations.

Such implementations may, in addition to providing a reliable and precise way to meter a desired amount of fluid from a larger sample, also provide a useful mechanism for facilitating bubble removal from the fluid. For example, if the switchback feature is subjected to vibration or shock while oriented such that the sections A-C are oriented to be vertical (or at least semi-vertical), any bubbles that are present within the switchback sections may be shocked loose and may migrate upwards, e.g., towards the direction that the clamping pressure zone comes from in FIG. 38.

It will be noted that the various features discussed herein that may be implemented in the context of a platen may often also be susceptible to being implemented as similar features on the roller instead. Indeed, it is contemplated that any of the features discussed herein in the context of being platen features may also be implemented as features on the roller, e.g., if the surface of a platen having various fluidic control features, e.g., a bypass recess and/or partitioning recess, on it were to be wrapped around a cylinder, the resulting cylindrical surface would have cylindrical analogues of the platen-based features.

FIGS. 30 through 32 depict one example of such an implementation. In FIG. 30, a roller 3010 is shown that has a partitioning recess 3022 in it; the partitioning recess 3022 may, for example, be a slot that is milled in the cylindrical surface along a direction parallel to the axis of rotation of the roller 3010. The roller 3010 may be pushed down by a spring 3036 to compress a fluidic structure having a first portion of material 3002a and a second portion of material 3002b against a platen 3008. The platen 3008 may have a compliant layer 3012. The first portion of material 3002a and the second portion of material 3002b may be similar to those discussed earlier and may be thermally bonded together to define one or more fluidic flow paths and/or chambers, including a fluidic passage that extends between the clamping pressure zone provided by the roller 3010 and a temporary seal 3034. The temporary seal 3034 may seal off the fluidic passage, thereby trapping a fluid within the passage in between the temporary seal 3034 and the clamping pressure zone exerted on the first portion of material 3002a and the second portion of material 3002b by the roller 3010.

In FIG. 31, the roller 3010 has been advanced so that the outermost transverse edge of the partitioning recess 3022 closest to the temporary seal 3034 has come into contact with the first portion of material 3002a and started to pinch down on the passage formed between the first portion of material 3002a and the second portion of material 3002b. At the same time, the outermost transverse edge of the partitioning recess 3022 that is furthest from the temporary seal 3034 has pinched the first portion of material 3002a and the second portion of material 3002b together to form a seal that prevents the fluid from escaping.

In FIG. 32, the roller 3010 has been advanced even further such that both outermost transverse edges of the partitioning recess 3022 are pinching the first portion of material 3002a and the second portion of material 3002b together against the platen 3008. Further advancement of the roller 3010 may cause fluid that is trapped between the temporary seal 3034 and the transverse edge of the partitioning recess 3022 that is closest thereto to increase in pressure until the temporary seal 3034 ruptures, much in the same manner that occurred in the example of FIGS. 33 through 37.

Figure 39:
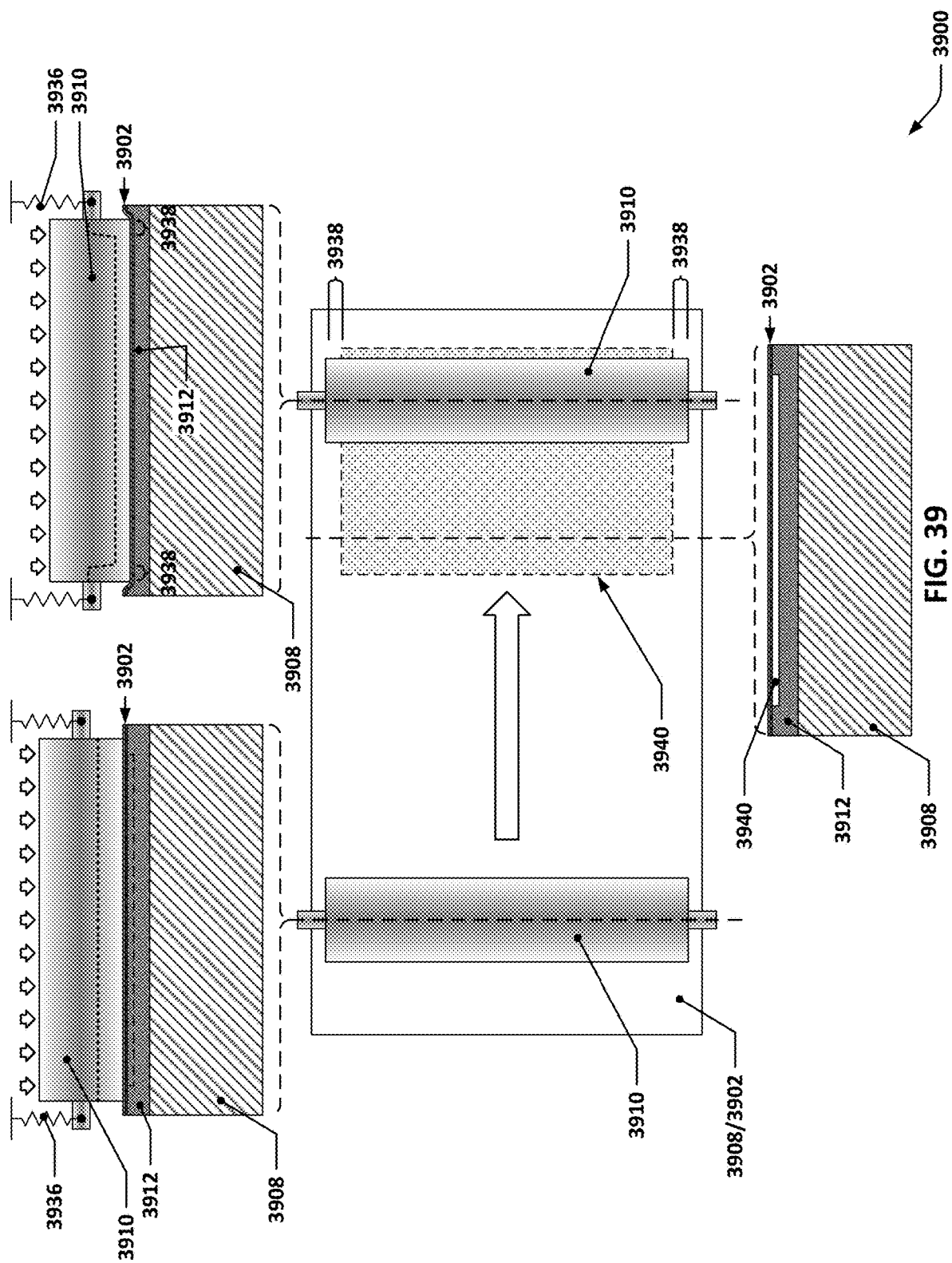
FIG. 39 depicts an example of features that act to adjust a clamping force exerted on a fluidic structure.

A further fluidic feature that may be used in some implementations is shown in FIG. 39. The implementation of FIG. 39 allows for fluid that is located ahead of the roller in the direction of travel to be maintained at a particular pressure as the roller advances, but still allows excess fluid to be evacuated to prevent over-pressurization. In this sense, it is somewhat of a hybrid of the functionality provided by the bypass recess and partitioning recess.

In FIG. 39, system 3900 is shown that has a roller 3910 that is pushed against a platen 3908 with a shallow recess 3940 in it by springs 3936; the shallow recess 3940 may be similar to the bypass recesses discussed earlier, but may be designed to have a shallower depth, e.g., on the order of thousands of an inch. Moreover, the platen 3908 (or, alternatively, the roller 3910) may be equipped with a compliant layer 3912.

When the roller 3910 is located on a portion of the platen 3908 that is unbroken, e.g., that does not have the shallow recess 3940 in it (such as at upper left in FIG. 39), the pressure profile that is applied to the platen (and a fluidic structure 3902, similar to those discussed earlier) may be generally constant, as represented by the dotted line that extends across the roller 3910. This is because the downward force applied to the roller 3910 is evenly applied across the underside of the roller 3910 that is in contact with the fluidic structure 392.

When the roller 3910 is moved to a position over the shallow recess 3940, however, the downward force that is applied to the roller 3910 is primarily applied to the portions of the compliant layer 3912 that support the ends of the roller 3910. The spring force applied to the roller 3910 may be selected such that the pressure applied to the portions of the compliant layer 3912 that support the ends of the roller 3910 compresses those portions such that the roller 3910 may come into contact with the bottom of the shallow recess 3940 along most or all of its length, as shown in the above-right cross-section. These portions of the compliant layer may be thought of, in effect, as compressible rails 3938 along which the roller 3910 rides while traversing the shallow recess 3940. In this configuration, the pressure field that is generated between the roller 3910 and the fluidic structure 3902 may be varying, with increased pressure towards the ends of the roller 3910 supported by the rails 3938, and reduced pressure in the middle of the roller 3910. This allows for the pressure exerted by the roller 3910 on portions of the fluidic structure to be changed as the roller traverses the fluidic structure. With appropriate selection of the various parameters involved, e.g., depth of the shallow recess 3940, spring force applied to the roller 3910, degree of contact between the ends of the roller 3910 and the compliant layer 3912 when the roller 3910 is over the shallow recess 3940, etc., it is possible to tune the amount of clamping force that is applied to the fluidic structure 3902 at various points along the travel of the roller 3910. This, in turn, allows for tuning of the pressure that can be applied to a fluid within the fluidic structure 3902 by the roller 3910 before the fluid pressure causes a portion of the fluid to escape by squeezing past the clamping pressure zone.

Figure 40:
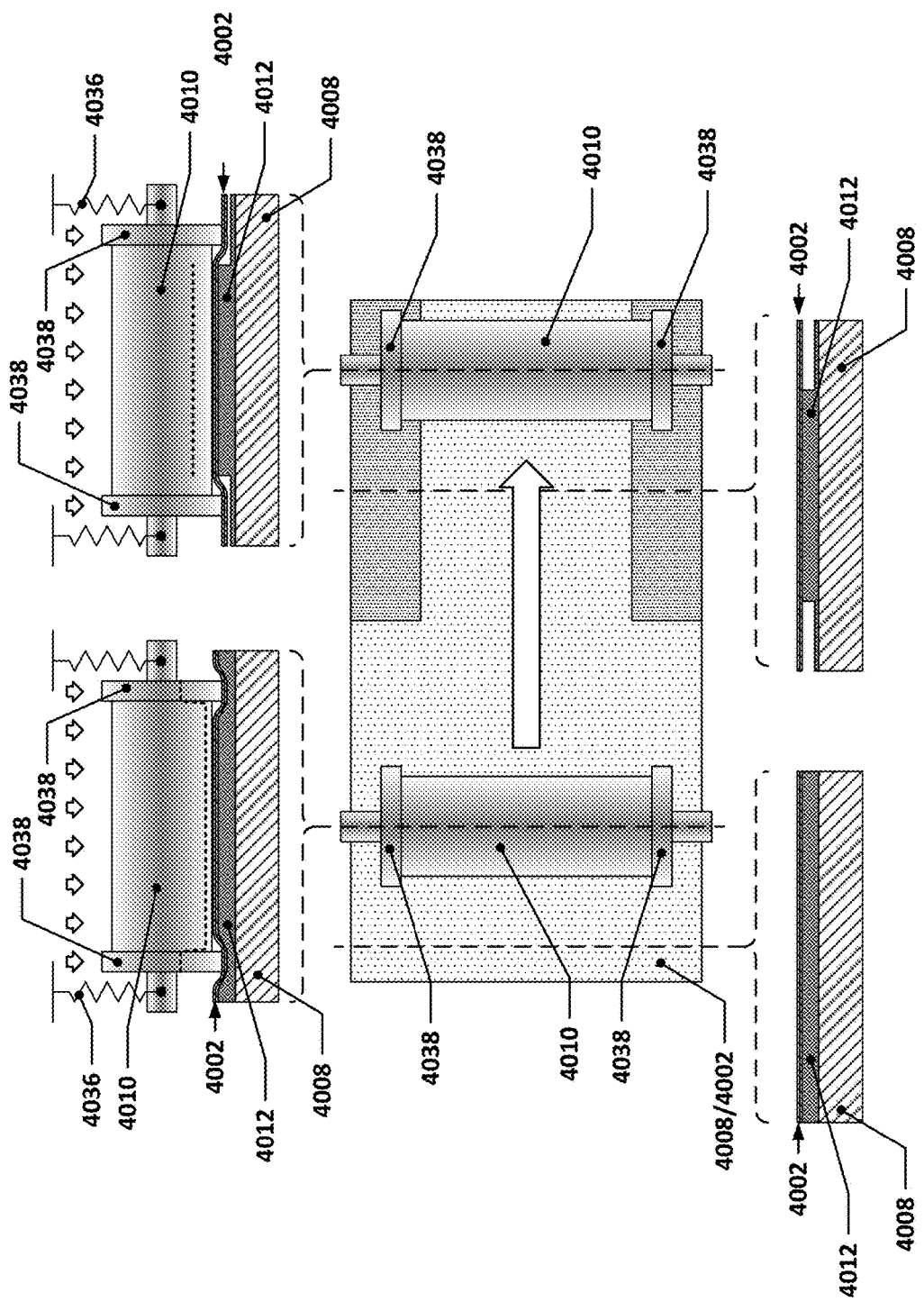
FIG. 40 depicts another example of features that act to adjust the clamping force exerted on a fluidic structure.

FIG. 40 depicts a further example in which a similar effect may be achieved using circumferential rails 4038 that are part of a roller 4010. In the implementation of FIG. 40, a platen 4008 is provided that has a compliant layer 4012. The roller 4010 may be pressed by springs 4036 against a fluidic structure 4002 that is supported by the platen 4008. In regions of the platen where the rails 4038 are able to compress the fluidic structure 4002 against the compliant layer 4012 of the platen 4008, the compliant layer 4012 may compress from the state shown in the lower left cross-section to a state such as is shown in the above left cross-section. The compressive loading provided by the springs 4036 may be selected such that the portion of the roller 4010 that lies between the rails 4038 may eventually be caused to come into contact with the fluidic structure 4002 as well due to increased deformation of the compliant layer 4012 under the rails 4038. Since the majority of the load being applied to the roller 4010 is directed into the compliant layer 4012 via the rails 4038, the pressure profile that is generated in the fluidic structure 4002, as represented by the dotted line extending across the roller 4010, is higher in the regions under the rails 4038 than in the regions in between the rails 4038.

If the roller 4010 is moved across the fluidic structure 4002 to a different portion thereof that has recesses in the compliant layer 4012 that are sized so that the rails 4038 are not able to compress the fluidic structure 4002 against the compliant layer 4012, as shown in the right-hand cross-sections, the downward force applied to the roller 4010 by the springs 4036 will be evenly distributed.

As with the example of FIG. 39, the arrangement of FIG. 40 allows for the amount of pressure exerted by the roller 40 to be adjusted by altering the pressure profile exerted by the roller, e.g., from a linear pressure profile to one that has higher-pressure zones near the ends of the roller and lower-pressure zones towards the interior of the roller.

While the above functional blocks have focused on features that may be implemented on the roller and/or platen in order to provide for particular functionalities, other functional blocks may primarily be provided by features within the fluidic structure itself.

For example, FIGS. 41 through 46 depict schematics of a fluidic circuit or sub-circuit that may be used to expose an area of interest to a particular fluid and to then wash that fluid away with a wash fluid and optionally replace it with a third fluid. Such an arrangement may be useful in performing assays in which the area of interest has, for example, a binder that may immobilize biomarkers, chemicals, or other particles or molecules of interest that may be suspended in the particular fluid. After the binder has been allowed to bind to the constituents of interest, the remainder of the particular fluid may need to be washed away before introducing an indicator into the area of interest; the indicator may then react with the bound (or unbound) molecules of the binder to provide a visual indication of the presence or absence of the constituents of interest. However, it may be desirable to ensure that the area of interest is free of any unbound constituents in the particular fluid before introducing the indicator to avoid having the unbound constituents of interest in the particular fluid interfere with the analysis.

In FIG. 41, a fluidic structure 4102 is shown that includes a first portion of material and a second portion of material that have been thermally bonded together to define a generally linear passage. Prior fluid processing operations have resulted in an amount of a fluid A being present in the passage. Fluid A occupies the passage between the point where the pressure zone is shown (just above a first fluid reservoir 4106*a*) and the point just upstream of the first of a series of temporary seals that are provided in a sequential seal region 4128. An area of interest 4126 is located within the passage and is exposed to fluid A.

The passage has a first fluid reservoir 4106*a* and a second fluid reservoir 4106*b*, each of which is joined to the passage by a short passage that terminates in a temporary seal, thereby fluidically isolating the fluid reservoirs 4106*a/b* from fluid A.

The sequential seal region 4128 may include a relatively large number of temporary seals that are arranged, one after the other, within a fluid passage of the fluidic structure 4102. The temporary seals of the sequential seal region may be configured to have a lower rupture pressure than those used to seal off the first and second fluid reservoirs 4106*a/b*. The sequential seal region 4128 may optionally empty into a waste reservoir 4130.

In FIG. 42, the roller that provides the pressure zone has been caused to move towards the sequential seal region 4128 along axis 4152 so as to compress a fluid blister within the first fluid reservoir 4106*a* and cause it to burst, thereby releasing fluid B into the first fluid reservoir 4106*a*. The temporary seal that separates the first fluid reservoir 4106*a* from fluid A, however, prevents fluids A and B from mixing. At the same time, the pressure zone has forced fluid A towards the sequential seal region 4128 until the pressure in fluid A is causes the first temporary seal in the sequential seal region to rupture. The roller may then advance some more, re-pressurizing fluid A until another temporary seal in the sequential seal region ruptures. This process may repeat with advancement of the roller/pressure zone towards the sequential seal region 4128.

In FIG. 43, the roller has advanced further and caused the pressure zone to pressurize fluid B to the point where the temporary seal that seals the first fluid reservoir 4106*a* has ruptured, allowing fluid B to flow into the passage. At the same time, more of fluid A has been pushed into the sequential seal region 4128, causing further temporary seals therein to rupture. Fluid B has now pushed fluid A out of the area of interest 4126, although some amount of fluids A and B will mix at the interface between the two fluids (as indicated by "AB" in the figure). The amount of fluid B that is provided may be adjusted or tuned to ensure that the area of interest 4126 is free of fluid A.

There may be some implementations in which the second fluid reservoir 4106 (and associated operations) may be omitted, e.g., if the assay process that the fluidic structure is designed to perform is does not wash away fluid A and replace it with fluid B.

Figure 44:

In FIG. 44, the zone of pressure has been advanced even further, causing the fluid blister containing fluid C in the second fluid reservoir 4106*b* to be released. The temporary seal that seals the second fluid reservoir 4106*b* has also been ruptured, allowing fluid C to flow into the passage and displace fluid B into the sequential seal region 4128. This causes further temporary seals in the sequential seal region 4128 to rupture.

Figure 45:
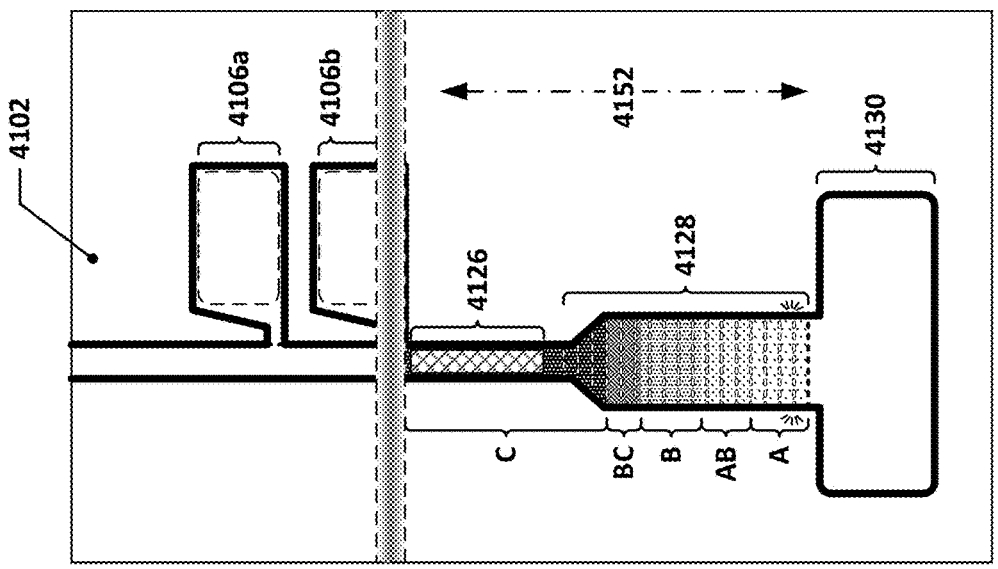

In FIG. 45, the zone of pressure has been advanced again so as to drive all of fluid C into the passage, thereby pushing fluids B and A further into the sequential seal region and causing the area of interest 4126 to be primarily exposed only to fluid C.

Figure 46:
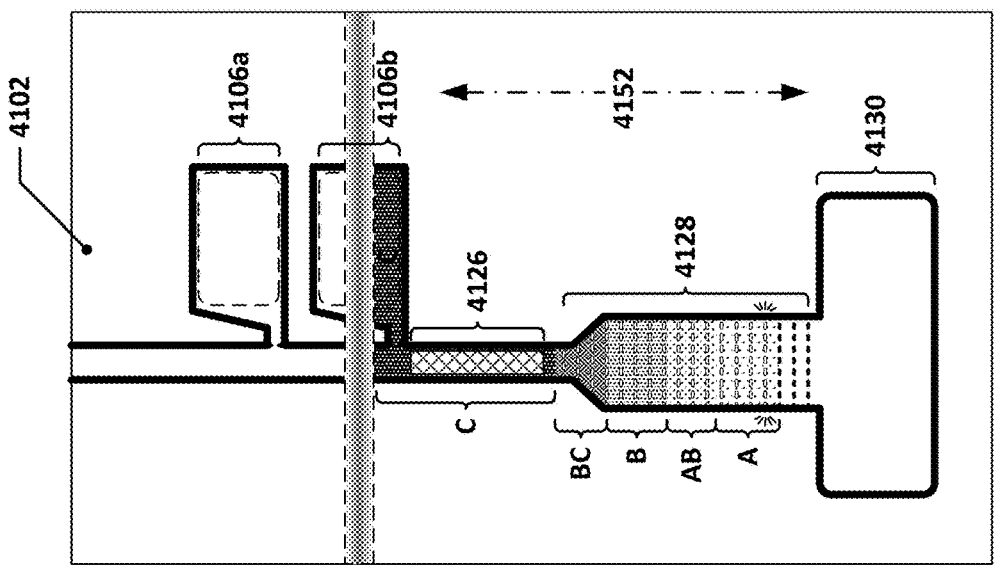

If desired, the zone of pressure may be advanced yet again to cause the last temporary seal in the sequential seal region 4128 to rupture, thereby releasing the fluids accumulated in the sequential seal region into the waste reservoir 4130, as shown in FIG. 46.

By using the sequential seal region, it is possible to incrementally move a fluid, such as fluid A, further and further from the area of interest 4126 while still maintaining a pressurized state (or at least the capability to enter into a pressurized state with little movement of the roller). This can be advantageous when it is desirable to maintain a relatively large amount of fluid within the area of interest, e.g., to ensure that the area of interest is completely and evenly exposed to a particular reagent or reactant that might be contained in fluid C, for example.

In FIGS. 41 through 46, fluids A, B, and C flow through the passage in the same direction throughout, with fluid B following fluid A, and fluid C following fluid B.

FIGS. 47 through 54 depict an alternative design in which fluid A reverses its flow direction, and fluids B and C are caused to flow in a direction opposite that initially taken by fluid A.

Figure 47:
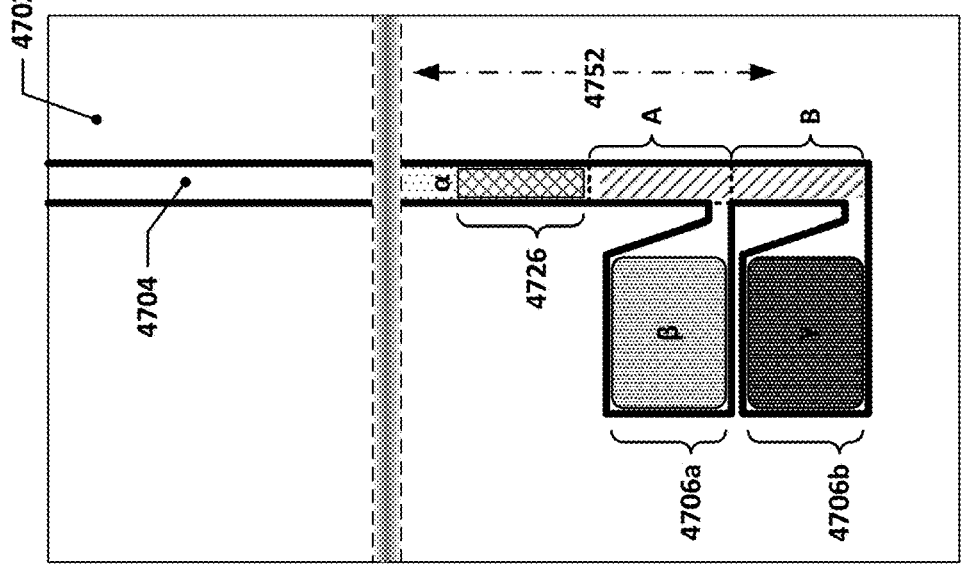

In FIG. 47, a fluidic structure 4702 is shown that has a flow passage 4704. The flow passage has an area of interest 4726 in it that terminates at a temporary seal that is interposed between the area of interest 4726 and zone A of the flow passage 4704. The flow passage 4704 also includes a zone B that is partitioned from zone A by another temporary seal. A bypass feature, such as was described earlier in conjunction with FIGS. 27 through 29, may be provided in zones A and B.

As shown in FIG. 47, the flow passage 4704 already has an amount of fluid α in it from a prior fluidic operation; the fluid α may fill the flow passage 11204 and is in contact with the area of interest 4726.

Figure 48:
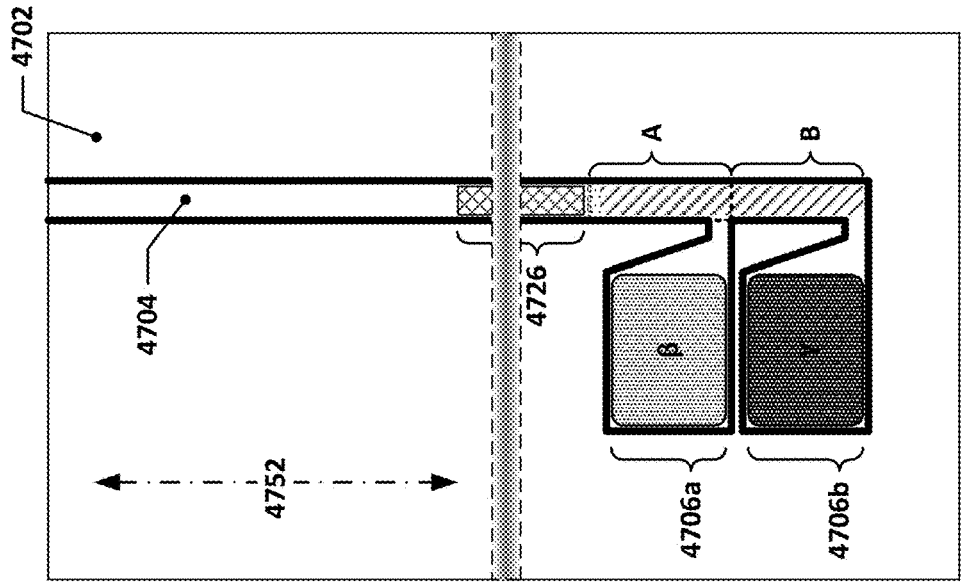

In FIG. 48, the pressure zone has been moved closer to zone B, e.g., by moving a roller that produces the pressure zone along an axis 4752, thereby causing fluid α to increase in pressure until the temporary seal between the area of interest 4726 and zone A ruptures, allowing fluid α to enter zone A.

Figure 49:
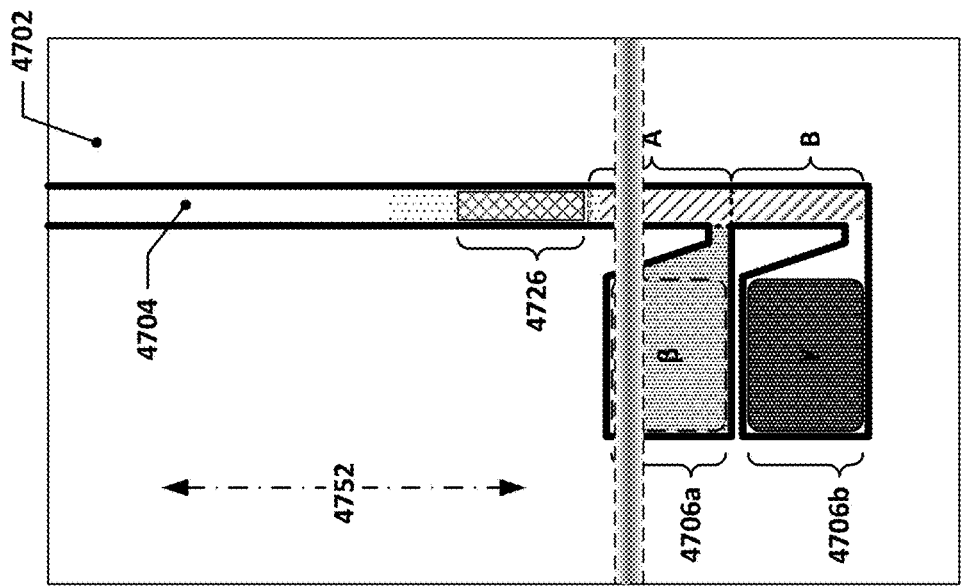

In FIG. 49, the pressure zone has been moved even closer to zone B, and has now advanced into zone A. As a result, fluid A that is retained within zone A is now able to flow back towards the area of interest 4726 via the bypass feature. Thus, as the pressure zone advances towards zone B, fluid A will flow through the bypass feature and away from zone B. At the same time, the pressure zone has also caused a blister containing fluid β to rupture within the first fluid reservoir 4706a. A temporary seal sealing the first fluid reservoir 4706a is, however, intact.

In FIG. 50, the pressure zone has advanced again, thereby causing fluid β to increase in pressure until the temporary seal that isolates the first fluid reservoir 4706a from zone A ruptures, thereby allowing fluid β to flow into zone A. Fluid β, when it flows into zone A, may do so at the "bottom" of zone A, i.e., directly adjacent to the temporary seal that is positioned between zones A and B. As a result, fluid β may almost immediately begin pushing fluid α further away from zone B and the area of interest 4726.

In FIG. 51, the pressure zone has been advanced to a position that covers the now-ruptured temporary seal between zone A and the first fluid reservoir 4706a. This causes all of fluid β to be driven into zone A and the flow passage 4704, thereby pushing fluid α further away from the zone of interest 4726. At this point, fluid β fills all of zone A and surrounds the area of interest 4726.

In FIG. 52, the pressure zone (and thus the roller that provides it) is caused to remain stationary while a heater element, e.g., provided in the platen that is used to support the fluidic structure 4702 during application of the pressure zone, is activated to cause localized heating of the fluidic structure 4702 in the location of the ruptured temporary seal between the first fluid reservoir 4706a and zone A, thereby causing a permanent seal to be formed to replace the ruptured temporary seal in that location. This seals the now-empty first fluid reservoir 4706a off from zone A.

Figure 53:
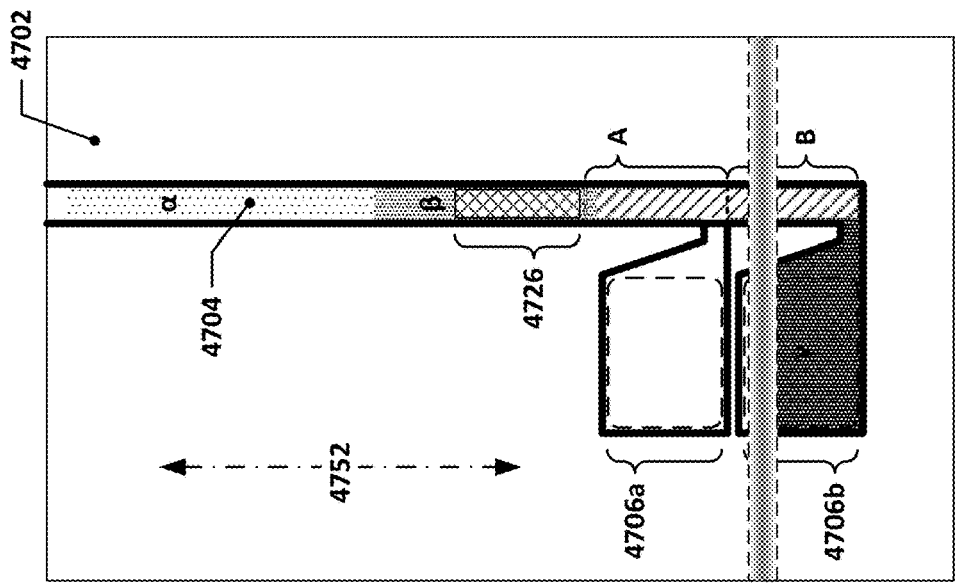

In FIG. 53, the pressure zone is again caused to advance, pressing on a fluid blister containing fluid γ in the second fluid reservoir 4706b and causing it to rupture.

Figure 54:
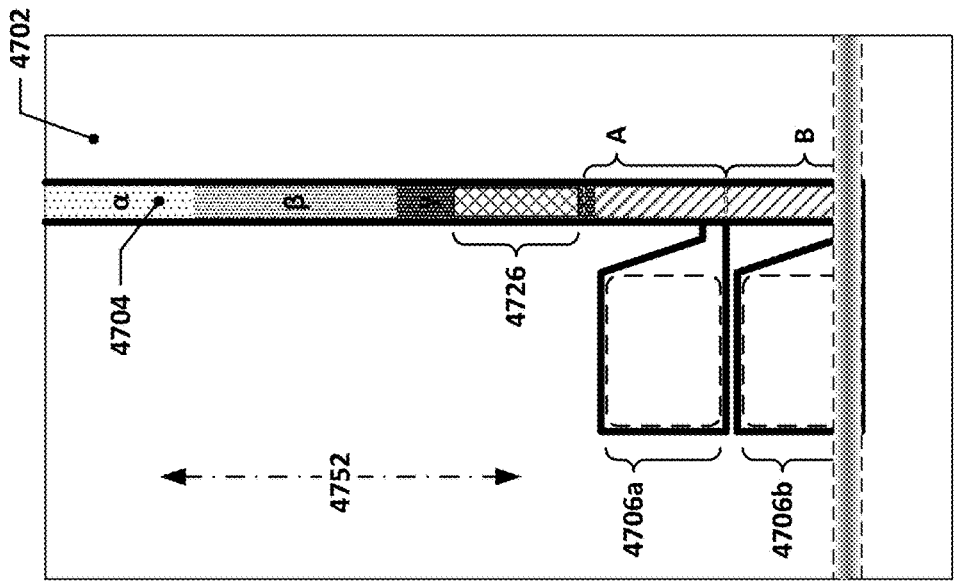

In FIG. 54, the pressure zone has been advanced to the end of zone B, thereby forcing the fluid γ from the second fluid reservoir 4706b to rupture the seal between the second fluid reservoir 4706b and zone B, and eventually the temporary seal between zones A and B as well. Fluid γ then flows from the very bottom of the flow passage 4704 upwards and past the area of interest. Fluids α and β are accordingly pushed further up the flow passage and further from the area of interest.

Figure 55:
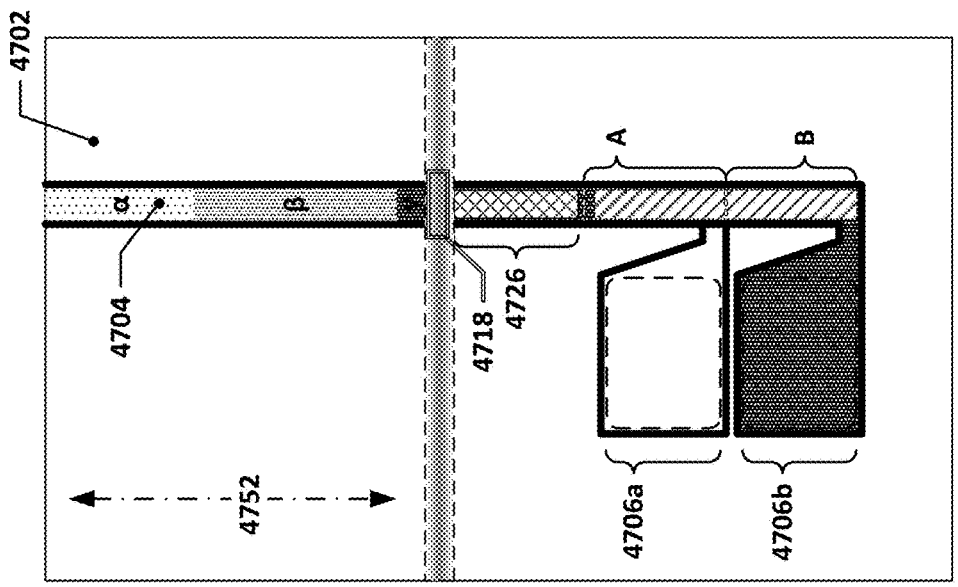
Figure 56:

In some implementations of the fluidic structure of FIGS. 47 through 54, a heating element may be provided in the platen that supports the fluidic structure, e.g., as shown in FIG. 55. The heating element, e.g., heating element 4718, may be positioned so as to be able to provide localized heating to the fluidic structure on the other side of—and typically adjacent to—the area of interest 4726. After fluid γ is flowed out of the second fluid reservoir 4706b and pushes fluid β out of the area of interest 4726, the clamping pressure zone may be moved backwards so that it is positioned above the heating element 4718, which may be activated in order to locally heat the material of the fluidic structure in that location and thereby thermally bond the fluidic structure together to form a permanent seal that seals off the flow path upstream of the area of interest 4726. Thus, when the clamping pressure zone is then returned to its previous position and then advanced further towards the end of the second fluid reservoir 4706b, as shown in FIG. 56, the resulting increase in pressure of fluid γ will cause the fluidic passage in the area of interest to inflate or otherwise become pressurized, thereby increasing the amount of fluid that the area of interest 4726 is exposed to. This may increase the exposure of the area of interest 4726 to fluid γ, which may increase the binding of fluid γ to the area of interest, for example, and may increase the signal-to-noise ratio of a detector that uses the depicted fluidic structure.

The implementations of FIGS. 47 through 54 or 56 reduces the likelihood for the various fluids to mix with one another by eliminating situations in which two simultaneously flowing fluids are combined as a mixed flow in a common passage.

FIGS. 57 through 64 depict various operational states of another example functional block that may be used in fluidic structures such as those discussed herein. The functional block of FIGS. 57 through 64 may be used to provide for staged flow of fluids through or past an area of interest, e.g., a binding site, filter, or other region, such that the two fluids do not mix or only minimally mix.

Figure 57:

FIGS. 57 through 64 depict an example functional block.

As seen in FIG. 57, a fluid α is present in a main passage (for clarity, the "main passage" in this example may be considered to be the straight passage that extends from the top of the diagram to the bottom of the diagram) within zone A of the depicted function block. The fluid α has also flowed through/past a zone of interest 5726 and has started to flow into a waste reservoir 5730. The waste reservoir may be empty of fluid when the fluid α starts to flow into it, and may actually wick, e.g., through capillary action, into the waste reservoir 5730 to a much greater extent than pictured.

As the zone of clamping pressure that is depicted moves from zone A to zone B, the fluid α may be pushed through the zone of interest 5726 and into the waste reservoir 5730 until nearly all of the fluid α has been moved into the waste reservoir 5730.

Figure 58:

In FIG. 58, the clamping pressure zone has advanced to the point in between zones A and B; the roller or other structure that provides the clamping pressure zone is then caused to pause while heat from a heating element 5718 that may be embedded in a platen of the fluidic system that may be used to apply the clamping pressure zone to the fluidic structure that includes the depicted functional block. The combination of heat from the heating element and pressure from the clamping pressure zone may act to perform a localized sealing operation at the location indicated, thereby forming a permanent seal at that location. The seal that is created at the boundary between zones A and B is not used immediately but will play a role during later operations when fluid β is caused to flow into the main passage.

Figure 59:

In FIG. 59, the clamping pressure zone has been caused to advance further towards zone D, thereby pushing all of the remaining fluid α into the waste reservoir 5730 (the permanent seal across the main passage at the transition between zones A and B discussed above with respect to FIG. 58 can be seen as well). At this point, the waste reservoir 5730 may be sealed off using another heating element 5718 that may, similar to the one discussed above, be positioned and configured so as to be able to provide localized heating to the opening to the waste reservoir 5730 that lies in between zones B and C, thereby allowing a permanent seal to be formed at that location, sealing the waste reservoir 5730.

Figure 60:

In FIG. 60, the clamping pressure zone may be optionally caused to reverse direction. At the same time, another heating element 5718 may be caused to again generate a localized heating of the fluidic structure of which the depicted functional block may be a part. As the clamping pressure zone traverses over this heating element 5718, it causes a permanent seal to be created, thereby sealing off a small alcove that may exist between the waste reservoir 5730 and the main passage. This may be desirable when precise volumes of fluid are desired to be isolated; sealing off the alcove may cause the main passage to have a generally constant cross-section, which may make it easier to isolate small, highly accurate volumetric samples. It will be understood, of course, that such a step may be optional if the volume of fluid that will flow into the alcove is not necessarily of great importance.

Figure 61:
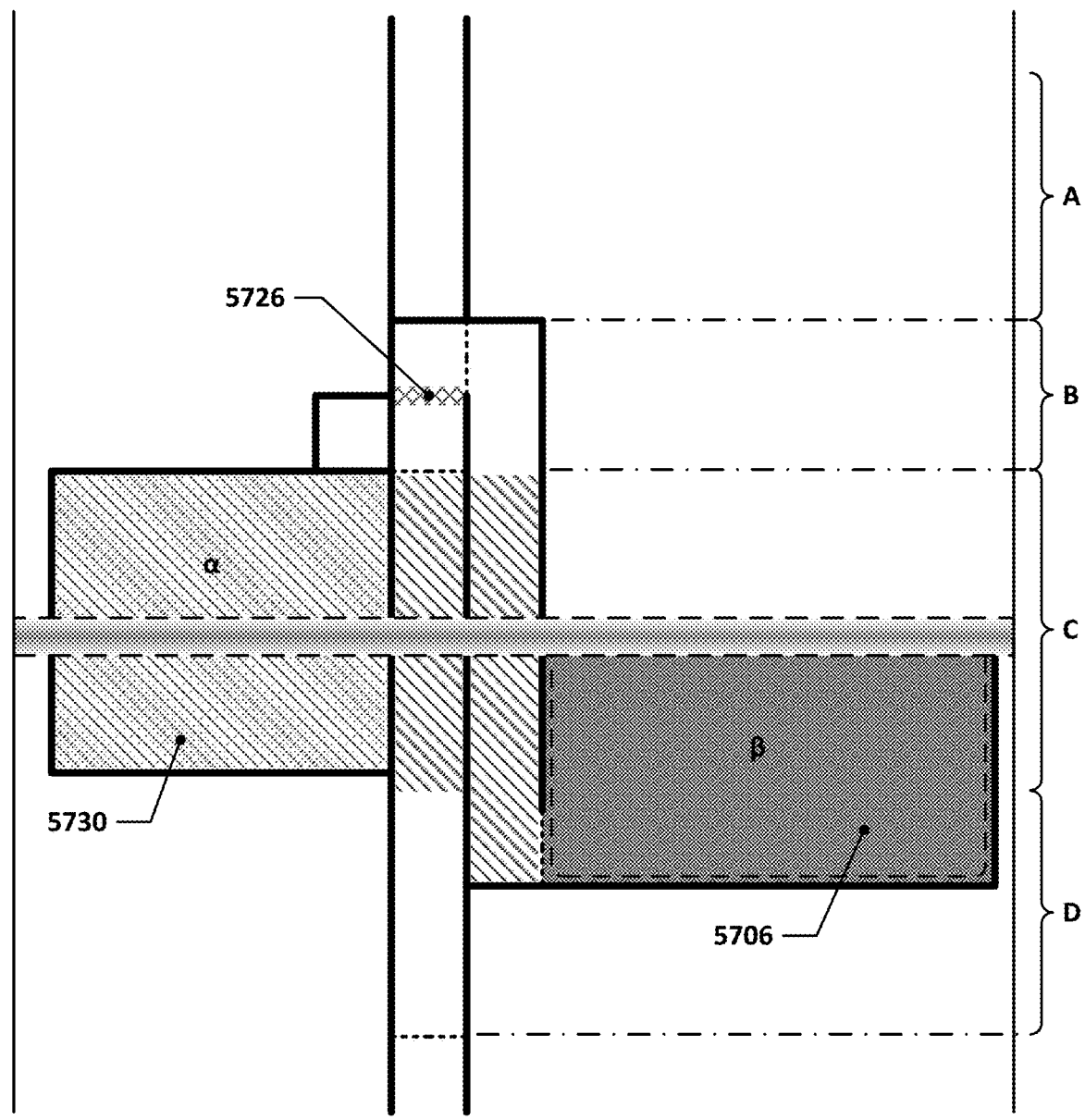

In FIG. 61, the clamping pressure zone has advanced further towards zone D and has now started to compress a burstable fluid blister or pouch in fluid reservoir 5706, causing the liquid therein to fill the fluid reservoir 5706. Furthermore, the waste reservoir 5730 may have, as shown, a bypass region, e.g., with the platen having a small recess in it to allow for a limited gap to form under the roller or other structure that provides the clamping pressure zone so that fluid can flow past the roller or other structure, if need be. This allows the roller or other structure that provides the clamping zone pressure to travel across the waste reservoir 5730 without causing it to rupture. In some other implementations, a similar effect may be achieved through making the waste reservoir 5730 larger (sized so that by the time the zone of pressure has completed its traversal of at least the functional block, the fluid held within it is still at pressure levels that do not cause leakage). Yet another possibility is that the waste reservoir may simply drain out of the fluidic structure, e.g., it may lead to the side of the fluidic structure, thereby allowing the fluid routed therethrough to simply leak out of the side of the fluidic structure.

Figure 62:

In FIG. 62, the clamping pressure zone has progressed further towards zone D and has pressurized fluid β such that the temporary seals that seal both ends of the short, vertical (with respect to the orientation of the Figure) passage that links the fluid reservoir 5706 to the main passage have ruptured, thereby allowing the fluid β to flow in a direction opposite the path of the clamping pressure zone (and past the clamping pressure zone) and into the main passage, where it may the reverse direction and flow through the zone of interest 5726 before again flowing past the clamping pressure zone again in the opposite direction. It will be noted that the short vertical passage, as well as the main passage, are aligned with a bypass feature, e.g., as discussed above, that allows a small gap to open up between the structure that applies the clamping pressure zone and the platen. This allows fluid to escape past the clamping pressure zone. In the depicted configuration, the pressure exerted on the fluid reservoir 5706 is such that the fluid cannot flow past the clamping pressure zone within the fluid reservoir 5706. However, once the fluid β exits the fluid reservoir 5706 and begins flowing up the short vertical passage and into the main passage, the presence of the bypass features may allow the fluid β to flow past the roller or other structure in either direction.

Figure 63:
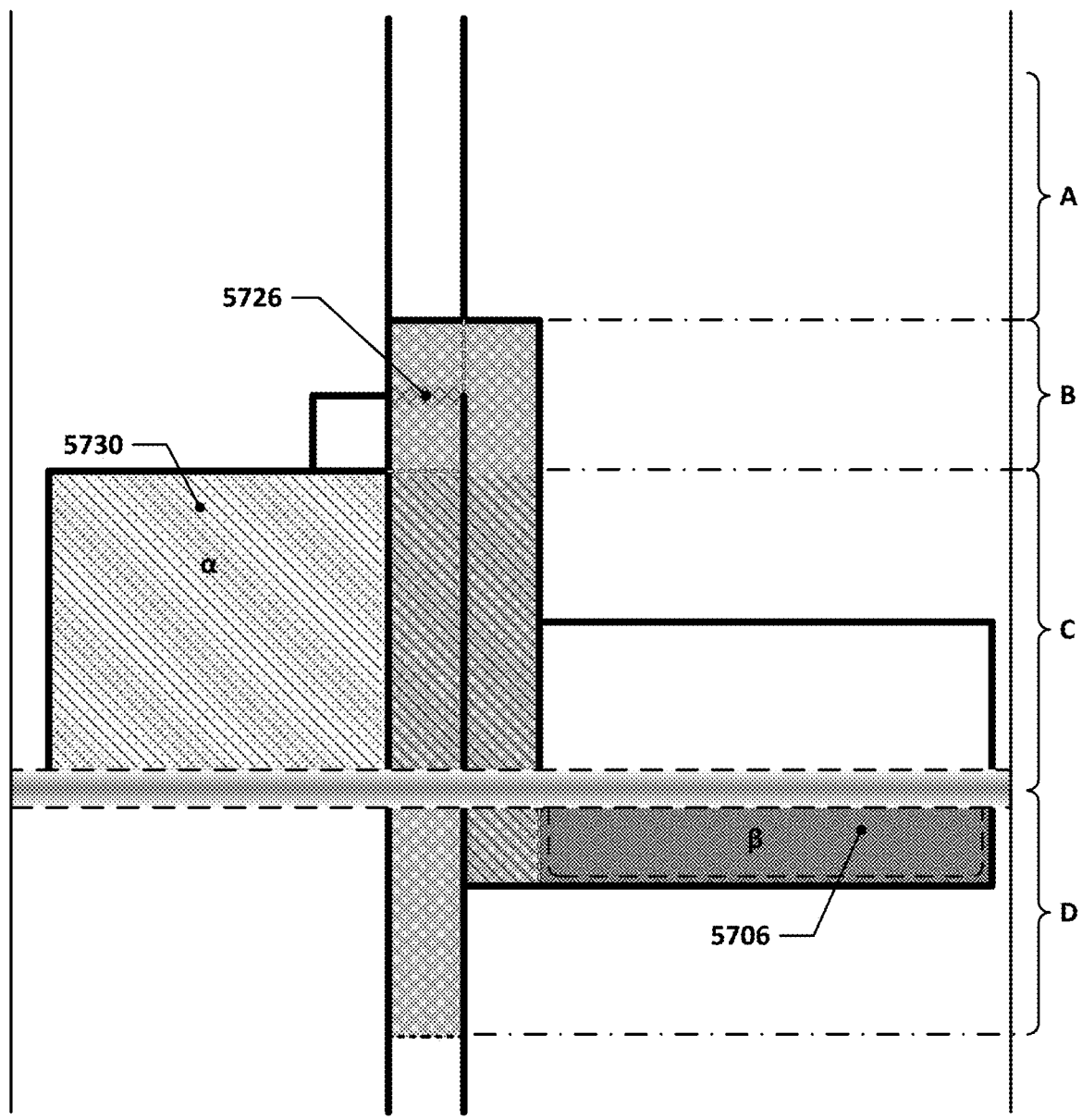
Figure 64:
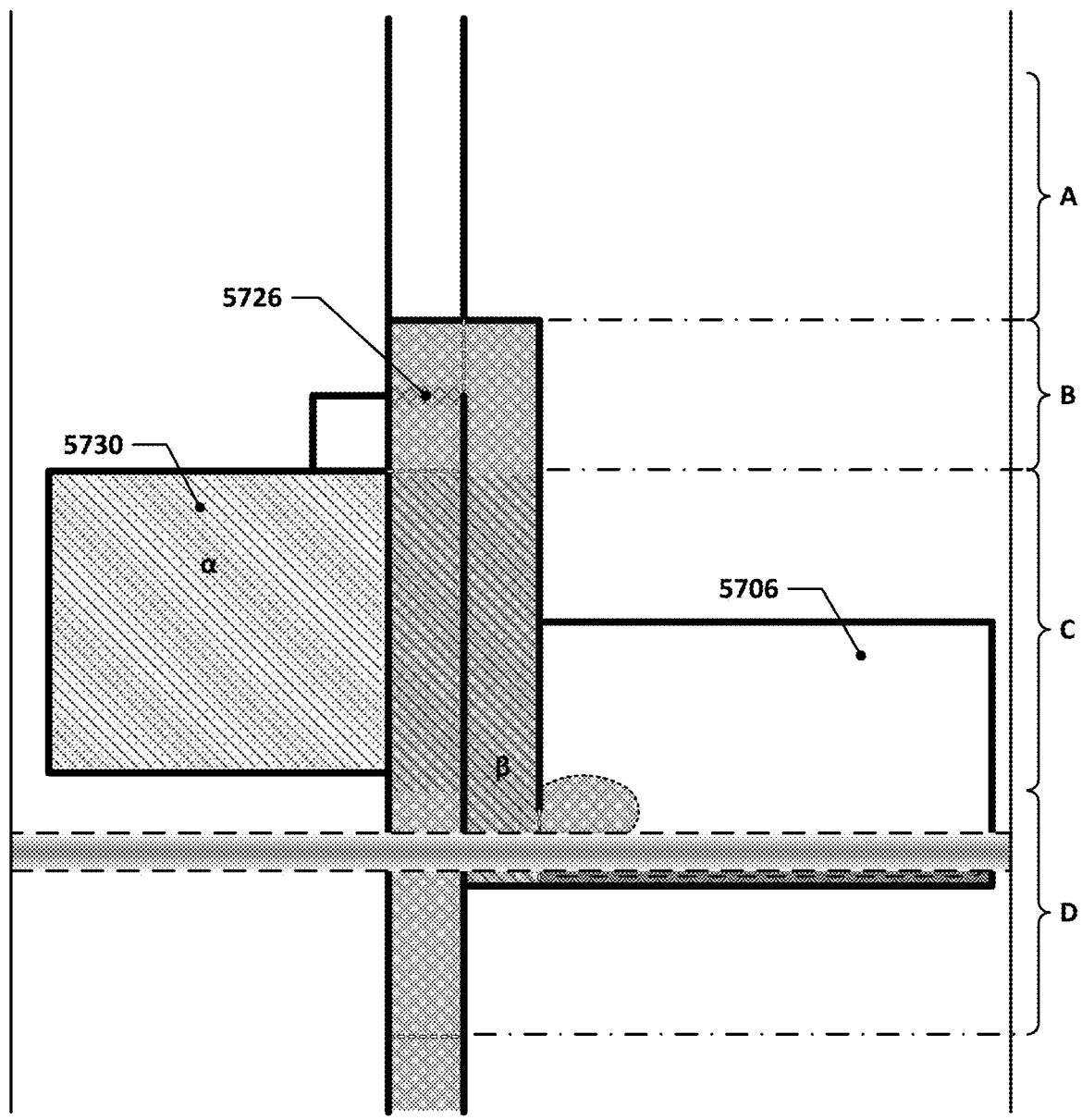

FIG. 63 depicts the clamping pressure zone located at the end of the bypass zone(s); this location is just before the end of the wall 5754 that formed a barrier, in conjunction with the now-ruptured seal that sealed off the fluid reservoir, between the fluid reservoir 5706 and the main vertical passage 5755 to the main passage. At this point, the bypass features in the bypass regions may no long be interacting with the clamping pressure zone, thus causing the clamping pressure zone to again form a tight seal within the fluidic structure that houses the functional block. At this point, whatever fluid is trapped within zone D will have been pressurized and further advancement of the clamping pressure zone towards the end of zone D, as shown in FIG. 64, may cause the temporary seal that is located at the end of zone D to rupture, thereby allowing the bolus of fluid β trapped between it and the clamping pressure zone to advance to a further stage of processing. As can be seen there may also be some backflow of fluid β back into the fluid reservoir 5706 since some of the fluid β that was trapped "behind" the clamping pressure zone may start to flow backwards and wick into the fluid reservoir 5706.

One example fluidic structure that may be implemented using such a functional block may be used for bacterial detection, e.g., for detecting sexually transmitted diseases such as gonorrhea or chlamydia that are caused by bacteria. FIGS. 65 through 78 depict various operational states of such a fluidic structure.

Vaginal, anal, or oral biological material samples may be collected using a swab or similar device that is brought into contact with surfaces of the vagina, anus, or mouth. For such samples, a fluidic structure similar to the structures discussed above with respect to COVID testing may be used to similarly elute sample material from such a sample collection device and then process it using the fluidic structure. For urine samples, however, such techniques are not as effective. Urine samples, by their nature, tend to be volumetrically much larger than swab samples, i.e., there is far more fluid in a urine sample than in a swab sample. As a result, the biological material in a urine sample for which testing is desired may be at a much lower concentration than the biological material in a swab might be.

Figure 65:
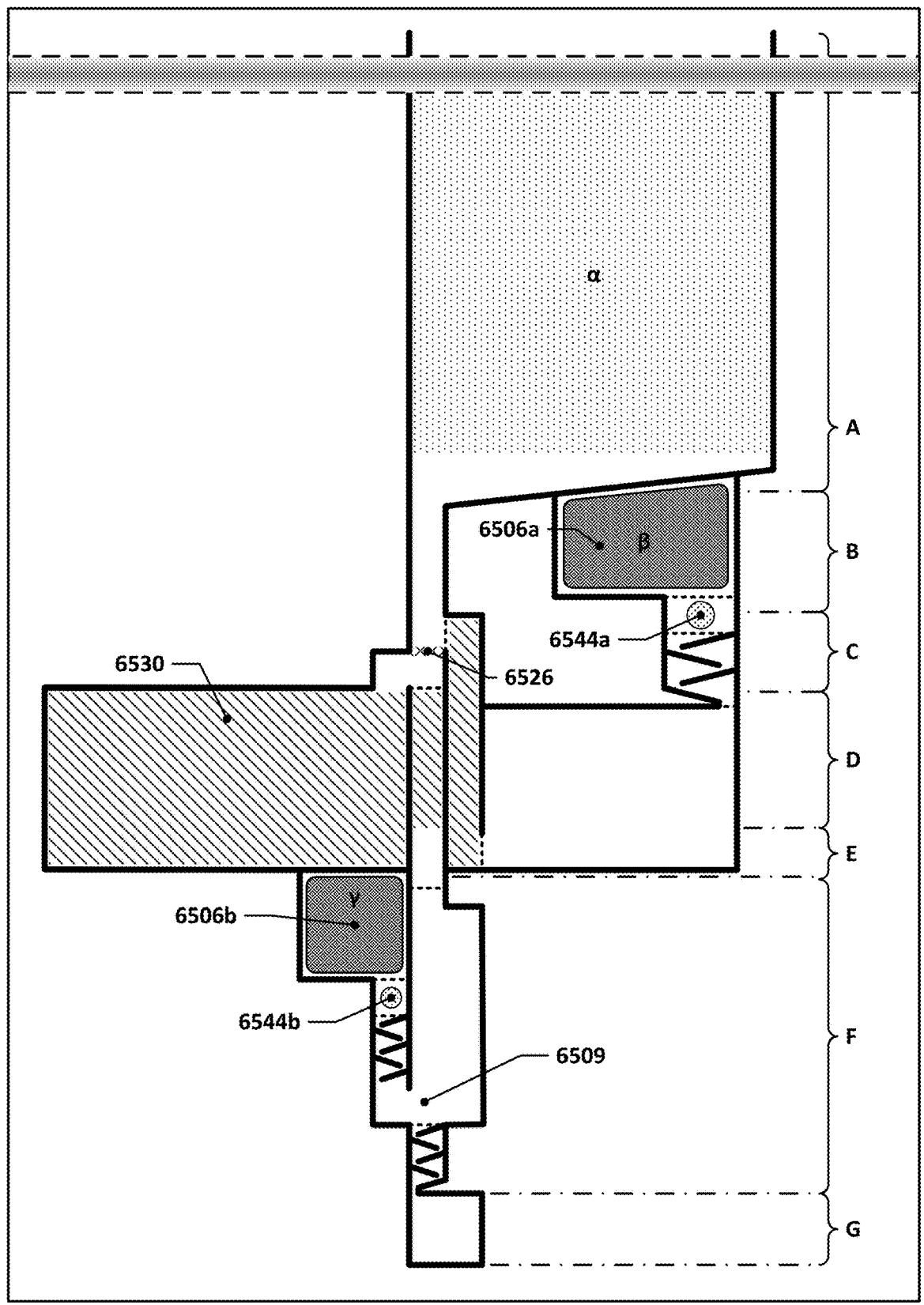
FIGS. 65 through 78 depict an example fluidic structure that may be well-suited to detecting bacterial infections from samples such as urine samples.

The implementation of FIG. 65 provides a fluidic structure that may be particularly well-suited to processing fluidic samples such as urine. In FIG. 65, a fluid sample a, e.g., urine is introduced into the top (from the perspective of the page) of the depicted fluidic structure. The fluid α may be a liquid that is pipetted or otherwise delivered directly into the depicted volume or may be a fluid that has been absorbed into a sponge or other compressible medium.

Figure 66:
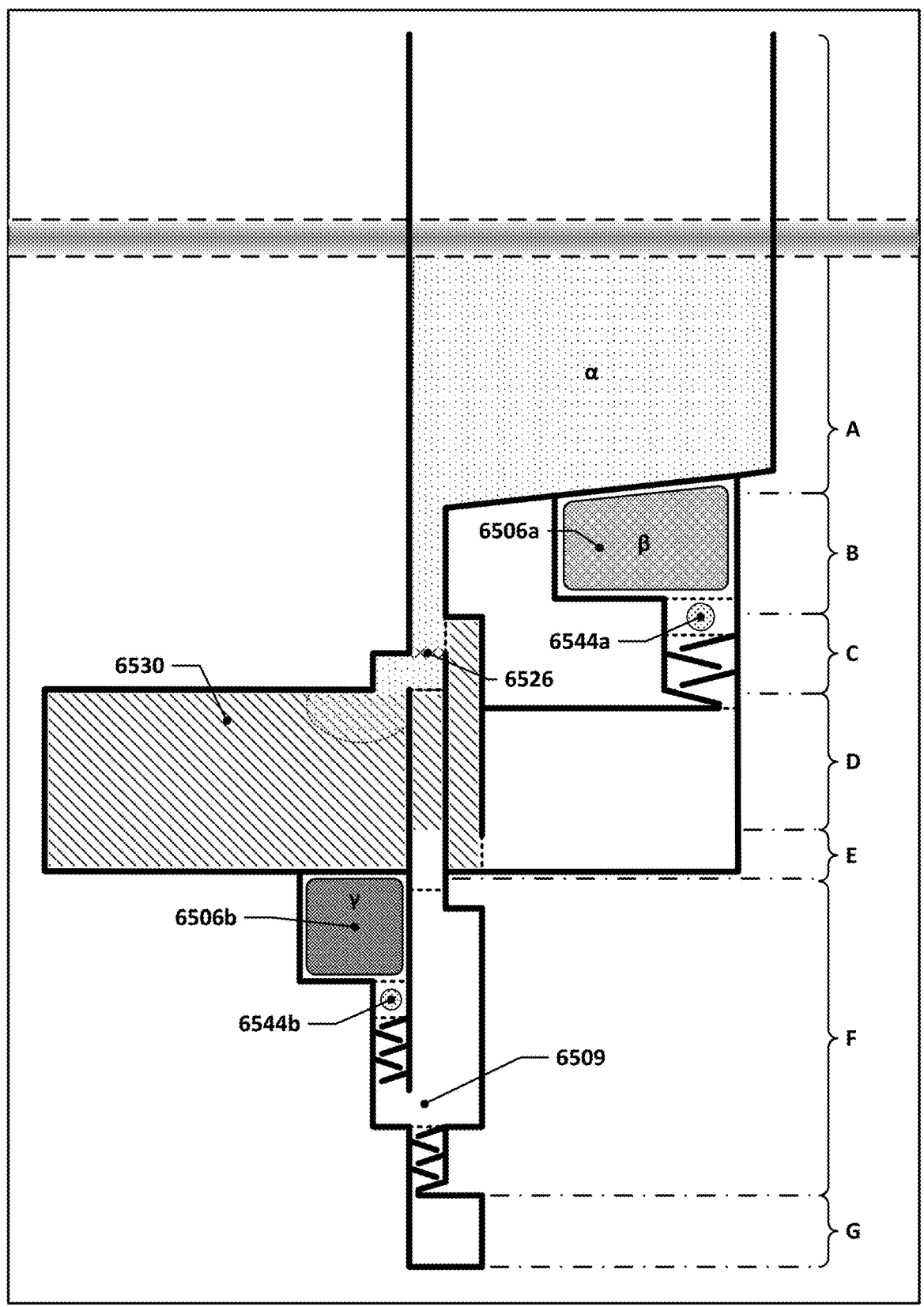

In FIG. 66, the clamping pressure zone has moved towards zone B, thereby applying pressure on the fluid α and pushing it through a zone of interest 6526. The zone of interest 6526 in this case is a filter that may be sized such that microbes, such as target bacteria of interest, are unable to pass through the filter while the urine in which the bacteria are suspended is able to pass through. The fluid α that flows through the zone of interest 6526 then flows into a waste reservoir 6530. If the assay is intended for use in detecting, for example, gonorrhea or chlamydia, the filter may, for example, be a 0.2 micron filter, as such bacteria may be on the order of 0.5 micron in diameter on average. Other filter sizes may be selected as appropriate, however. The filter may, for example, be a rigid frit filter or a bead plug filter that is heat-sealed in place within the fluidic structure, e.g., between two portions of material that are each heat-sealed to the frit on opposing sides of the frit, thereby securing the frit in a location that forces the fluid flowed through a fluidic circuit of the fluidic structure to flow through the frit and be filtered. In some implementations, there may be multiple filters positioned at different locations along the main passage, with each filter encountered by fluid pushed by the clamping pressure zone as it proceeds from towards zone B having having progressively smaller pore sizes such that the first filter(s) encountered by the fluid filter out larger particles, and the later filter(s) encountered by the fluid filter out smaller particles. This may avoid potential clogging issues.

Figure 67:
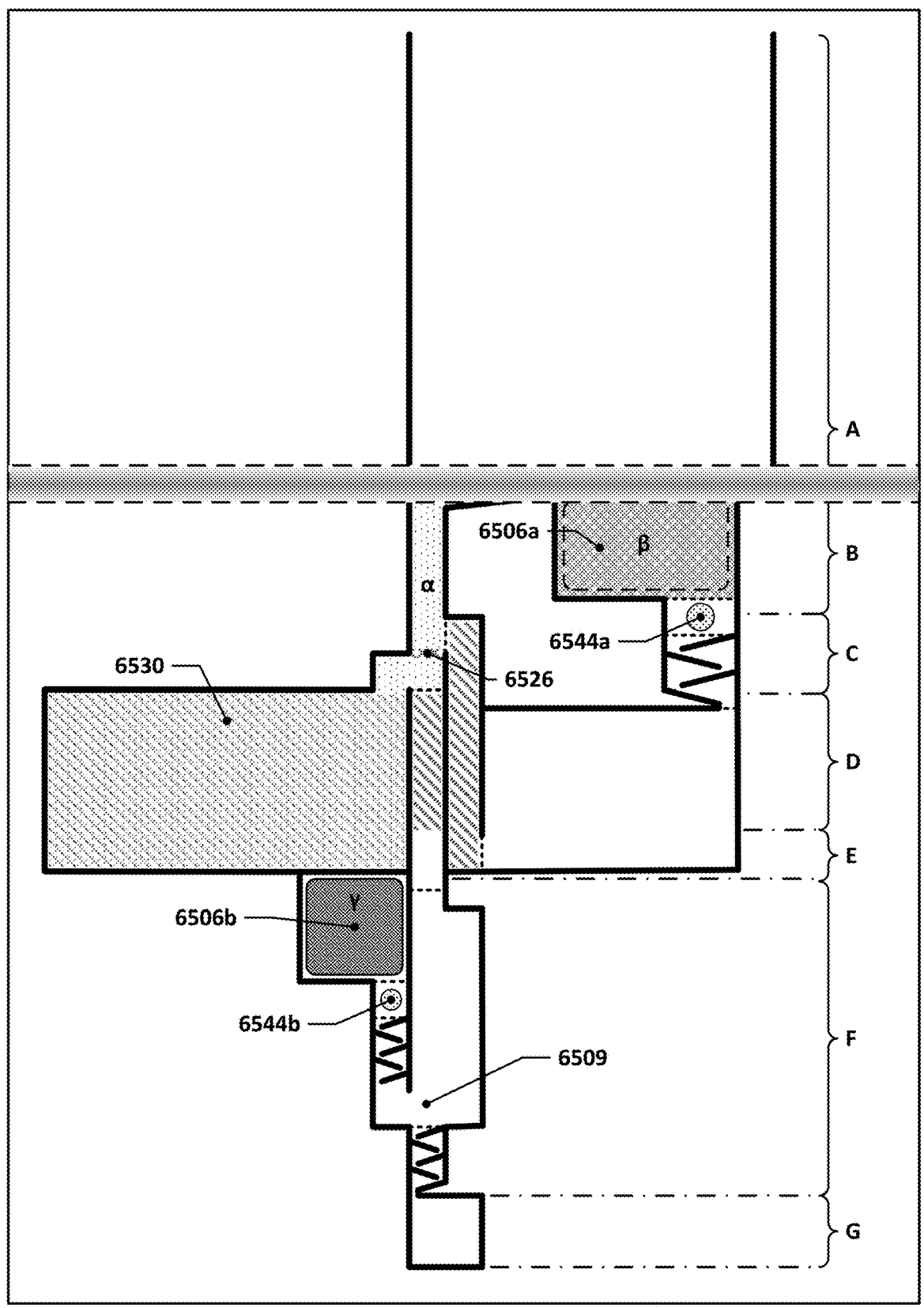

In FIG. 67, the clamping pressure zone has continued on to the transition between zones A and B, where the pressure exerted by the clamping pressure zone on the fluidic structure has caused a burstable fluid pouch or blister to rupture, thereby releasing fluid β into fluid reservoir 6506a. Nearly all of the fluid that was present in zone A has now been moved into the waste reservoir.

Figure 68:
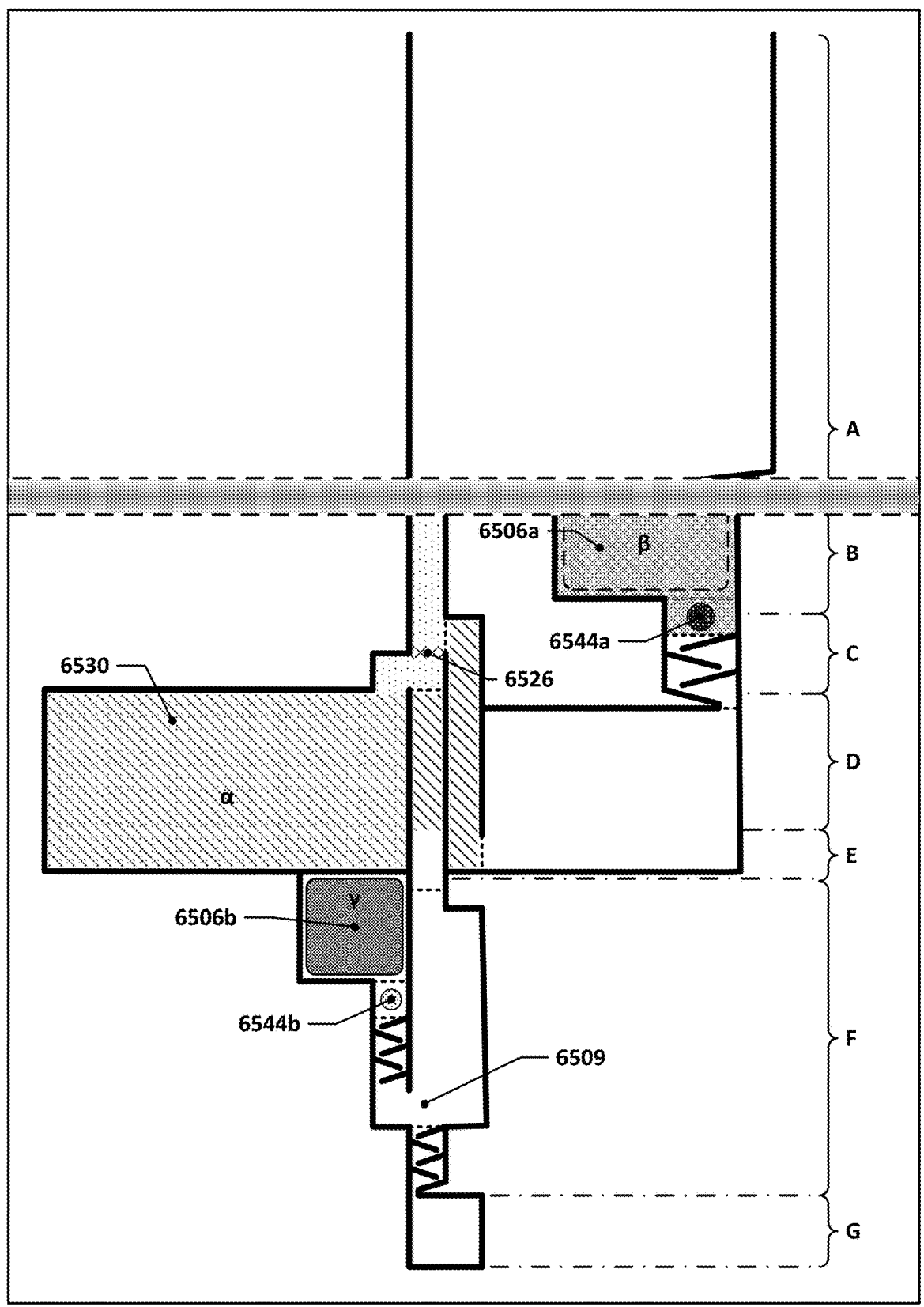

In FIG. 68, the clamping pressure zone has advanced slightly further, causing the pressurized fluid β in the fluid reservoir 6506a to rupture the temporary seal that sealed the fluid β into the fluid reservoir 6506a and allowing the fluid β to, for example, optionally mix with a material 6544a that may be housed within the chamber downstream of the fluid reservoir 6506a, e.g., a lyophilized material that may combine with the fluid β. After allowing the fluid β to dissolve the lyophilized material for some period of time, the clamping pressure zone may be caused to advance again towards zone C, as shown in FIG. 69.

Figure 69:
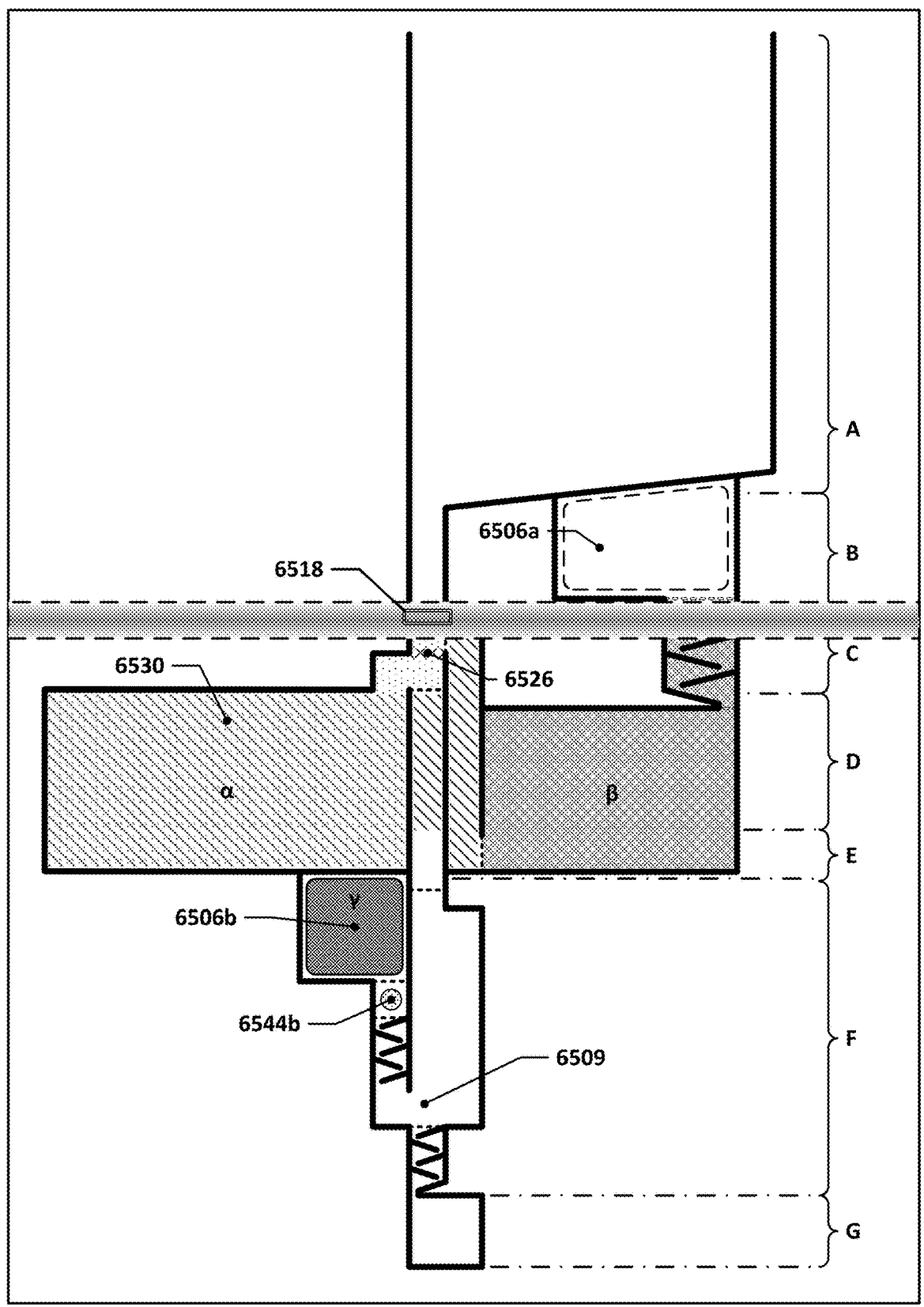

In FIG. 69, the clamping pressure zone has pressurized the fluid β so that the temporary seal that held the fluid β in place within the chamber that housed the material 6544a ruptures, allowing the fluid β to flow through a mixing passage that extends across the bulk of zone C, e.g., similar to those discussed earlier with respect to zig zag or broken chevron passages. The fluid β may, upon reaching the end of the mixing passage, cause a further temporary seal to rupture and may then flow into the reservoir 6507. In some implementations, the fluid β may not require any mixing with any other material prior to use, in which case the fluid β may simply be housed within reservoir 6507 to begin with (which may instead be viewed as the fluid reservoir 6506a) and the chamber with the material 6544a, as well as the mixing passage that fluidically connects that chamber with reservoir 6507, may be omitted. In some implementations, a heating element (not shown) may be provided in the platen or other portion of the fluidic system used to apply the clamping pressure zone and may be used to apply heat to the reservoir 6507 in order to bring the fluid housed therein up to a desired temperature level.

Also visible in FIG. 69 is a heating element 6518 that may, similar to the heating element 5718, provide for localized heating of the fluidic structure in the depicted location (the heating element 6518 may, for example, be located in the platen of the fluidic system used to apply the clamping pressure zone. The heating element 6518 may be used to create a permanent seal that may seal off the main passage just before the area of interest 6526.

Figure 70:
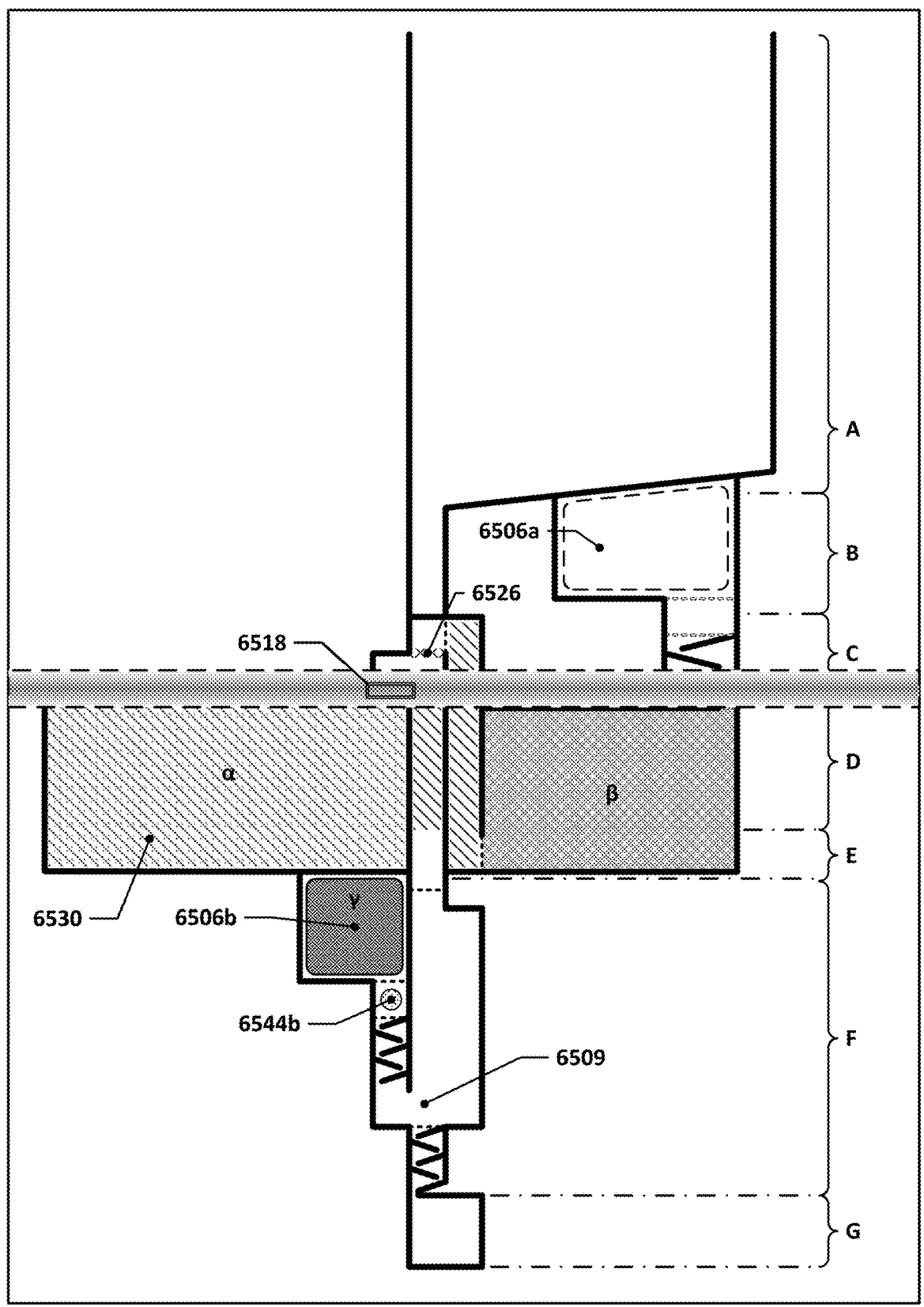

In FIG. 70, the clamping pressure zone has been advanced to the end of zone C, thereby pushing the last of the fluid β into the reservoir 6507 and positioning the roller or other structure that is used to produce the clamping pressure zone over another heating element 6518, which may be heated in order to cause a permanent seal to develop, thereby sealing all of the fluid α into the waste reservoir 6530 that passed through the filter in the area of interest 6526. The only remaining portion of the fluid α that remains in the main passage would be those particulates or organisms that were too large to fit through the filter.

Figure 71:
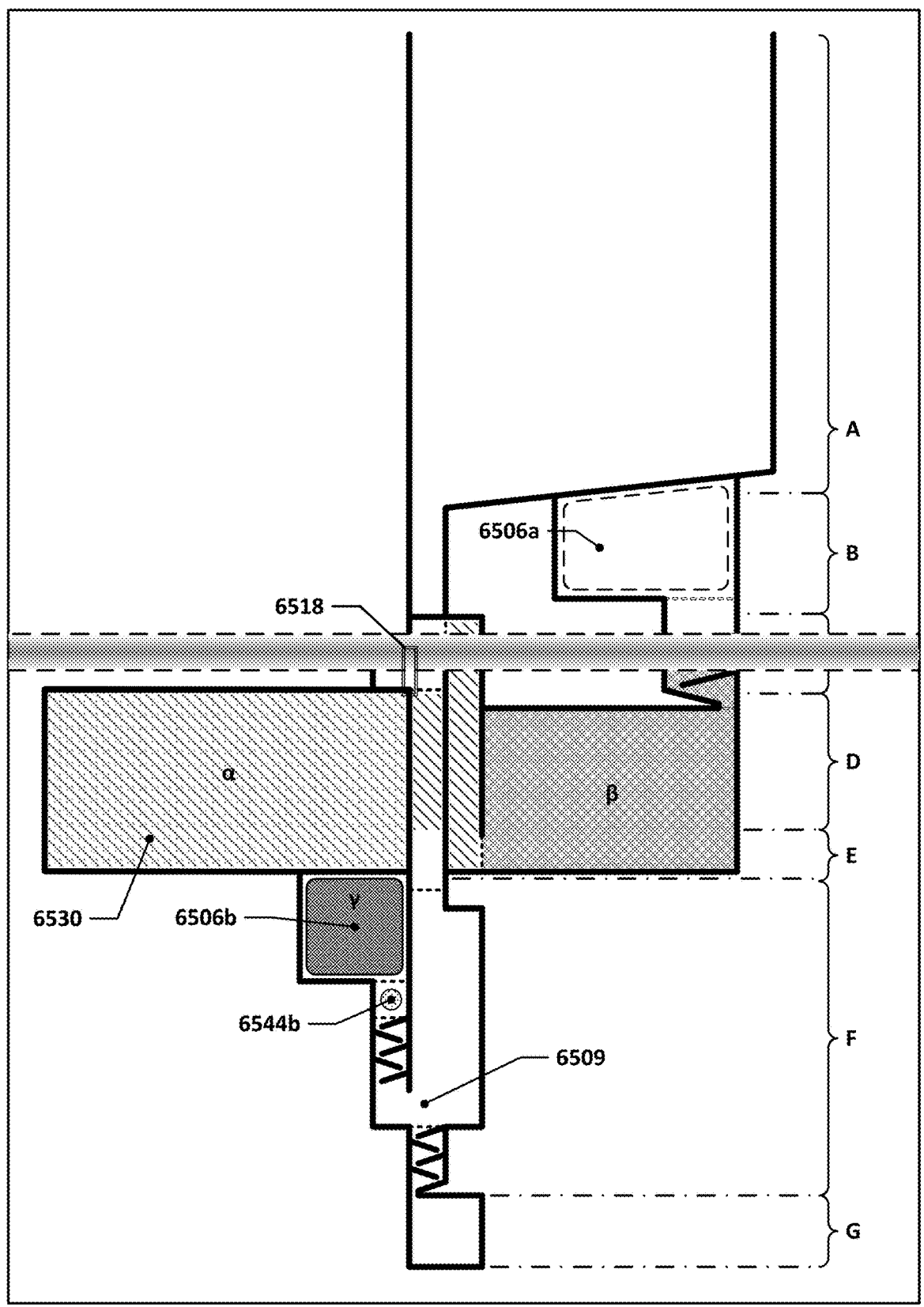

In FIG. 71, the clamping pressure zone has been caused to reverse direction, and another heating element 6518 has been activated to establish another permanent seal that seals off the "alcove" that leads to the waste reservoir 6530. Such an operation may be optional in some implementations.

Figure 72:
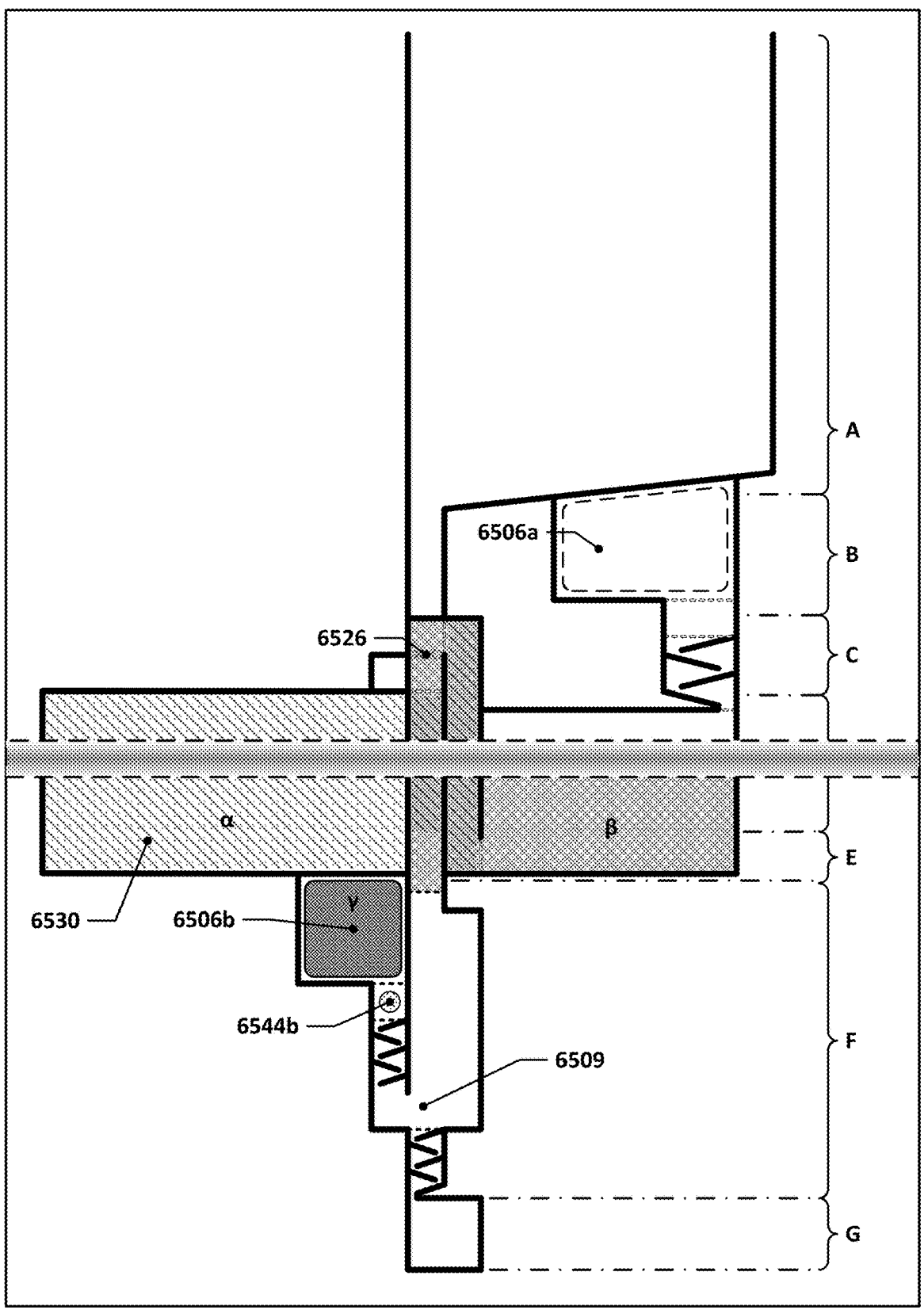

In FIG. 72, the clamping pressure zone has resumed traveling towards zone E and has now pressurized the fluid β so that the fluid β has caused the two temporary seals sealing off the reservoir 6507 from the area of interest 6526, as well as the temporary seal just downstream of the area of interest 6526, to rupture. This allows the fluid β to flow through the bypass region in the vertical passage that fluidically connects the reservoir 6507 with the area of interest 6526 and past the clamping pressure zone (in a direction opposite the direction of travel of the clamping pressure zone). At the same time, the fluid β is then able to reverse direction when it enters the main passage and may again flow past the clamping pressure zone due to the presence of the bypass region in that main passage as well.

Figure 73:
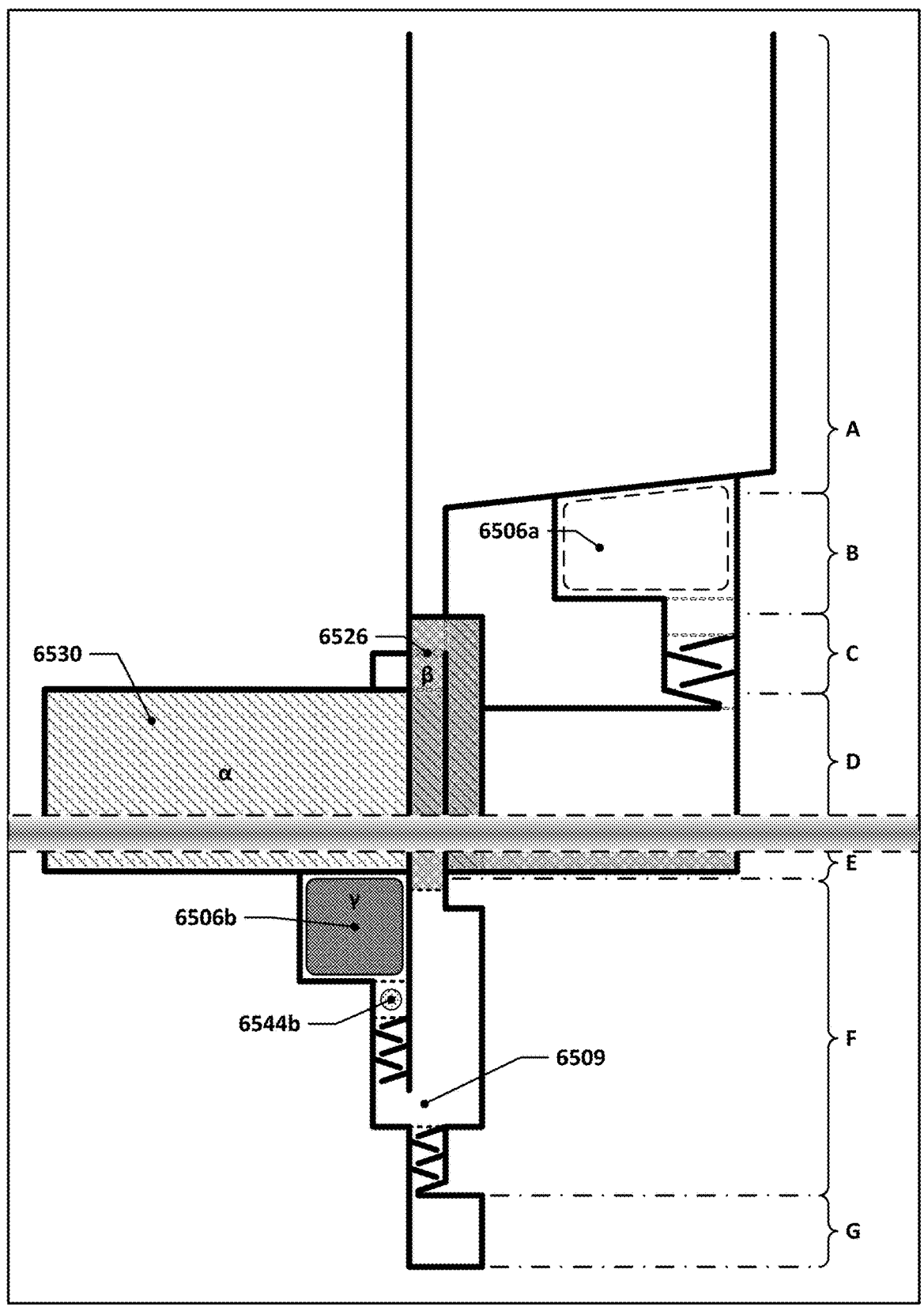

In FIG. 73, the clamping pressure zone has advanced to the transition between zones D and E. At this point, the clamping pressure zone still overlaps with the end of the wall 6554 that is closest to zone E. Moreover, the bypass region that exists in the main passage, e.g., downstream of the area of interest, is caused to not extend past the end of the wall 6554 discussed above. As a result, the clamping pressure zone, in the position shown, may act to pressurize the fluid β that is in between the clamping pressure zone and zone F.

Figure 74:
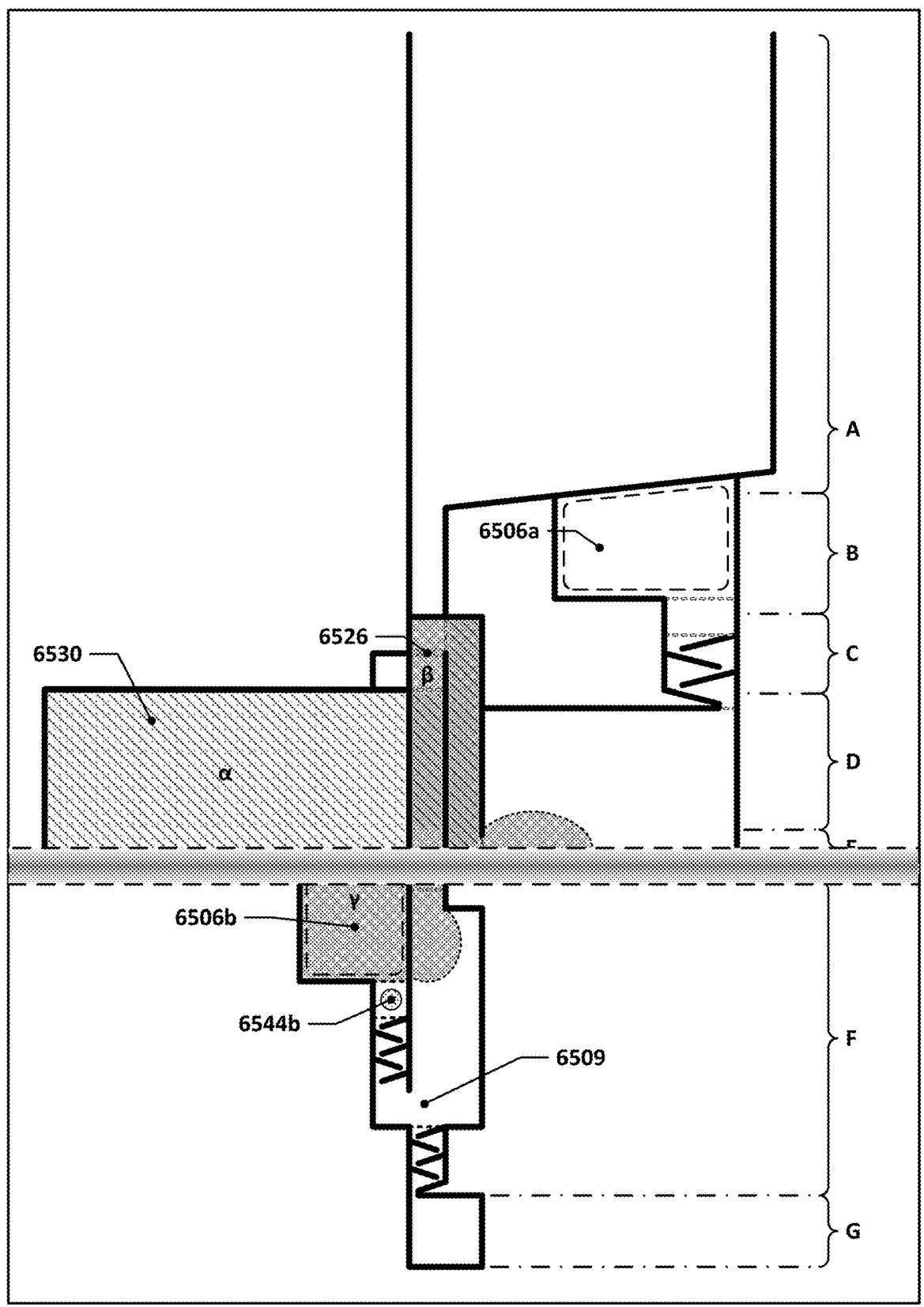

In FIG. 74, the clamping pressure zone has been advanced again towards zone F, thereby causing the temporary seal that held the bolus of fluid β that was between the clamping pressure zone and zone F to rupture, thus allowing the fluid β to flow into a chamber downstream. It will be noted that the fluid β that is located upstream of the clamping pressure zone may be unpressurized but may also be able to wick into previously traversed passages within the fluidic structure, e.g., as shown by the fluid β that is re-entering the reservoir 6507.

At the same time, the clamping pressure zone may also pressurize a fluid reservoir 6506b that has a fluid γ in it, e.g., held in a burstable blister within the fluid reservoir 6506b.

As shown in FIG. 74, the pressure exerted by the clamping pressure zone on the fluidic structure 6506b has caused the burstable fluid pouch or blister to rupture, thereby releasing fluid γ into fluid reservoir 6506b.

Figure 75:
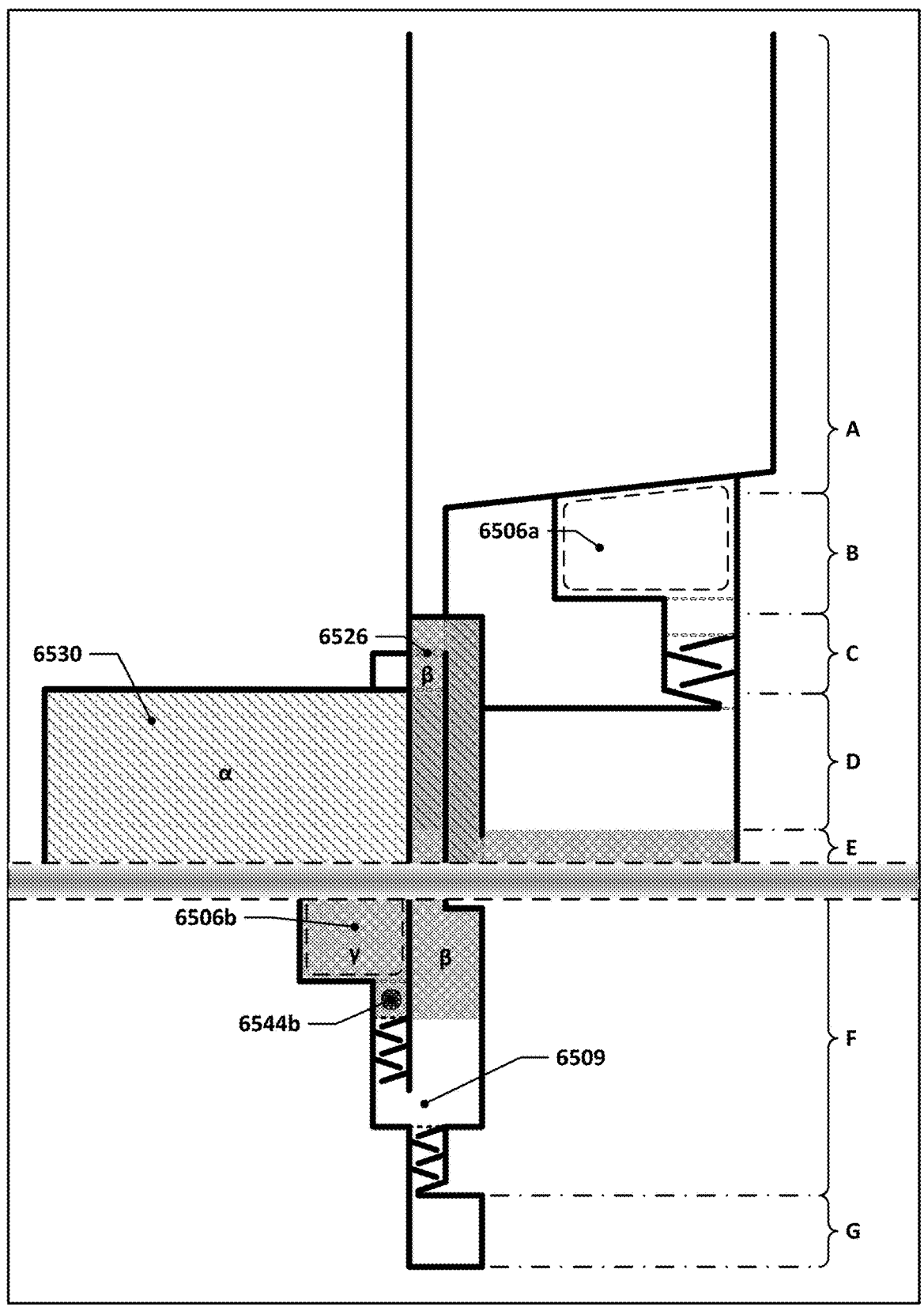

In FIG. 75, the clamping pressure zone has advanced slightly further, causing the pressurized fluid γ in the fluid reservoir 6506b to rupture the temporary seal that sealed the fluid γ into the fluid reservoir 6506b and allowing the fluid γ to, for example, optionally mix with a material 6544b that may be housed within the chamber downstream of the fluid reservoir 6506b, e.g., a second lyophilized material that may combine with the fluid γ. After allowing the fluid γ to dissolve the second lyophilized material for some period of time, the clamping pressure zone may be caused to advance again towards zone G, as shown in FIG. 76.

Figure 76:
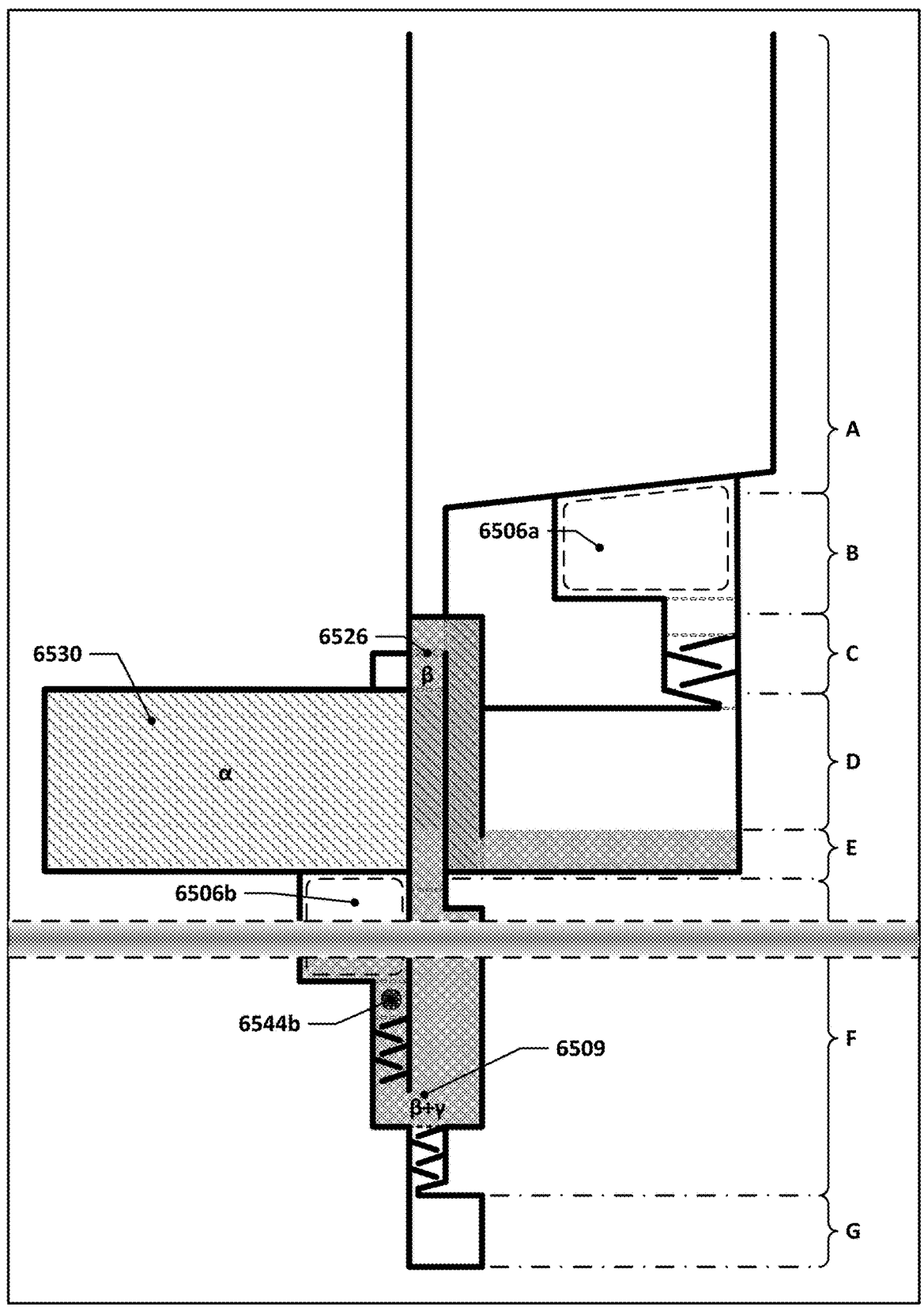

In FIG. 76, the clamping pressure zone has pressurized the fluid γ such that the temporary seal that held the fluid γ in place within the chamber that housed the material 6544b has ruptured, allowing the fluid γ to flow through a mixing passage that extends across part of zone F, e.g., a passage similar to those discussed earlier with respect to zig zag or broken chevron passages. The fluid γ may, upon reaching the end of the mixing passage, cause a further temporary seal to rupture and may then flow into the mixing chamber 6509, where it may mix with the fluid β that had also been flowed into the same chamber.

Figure 77:
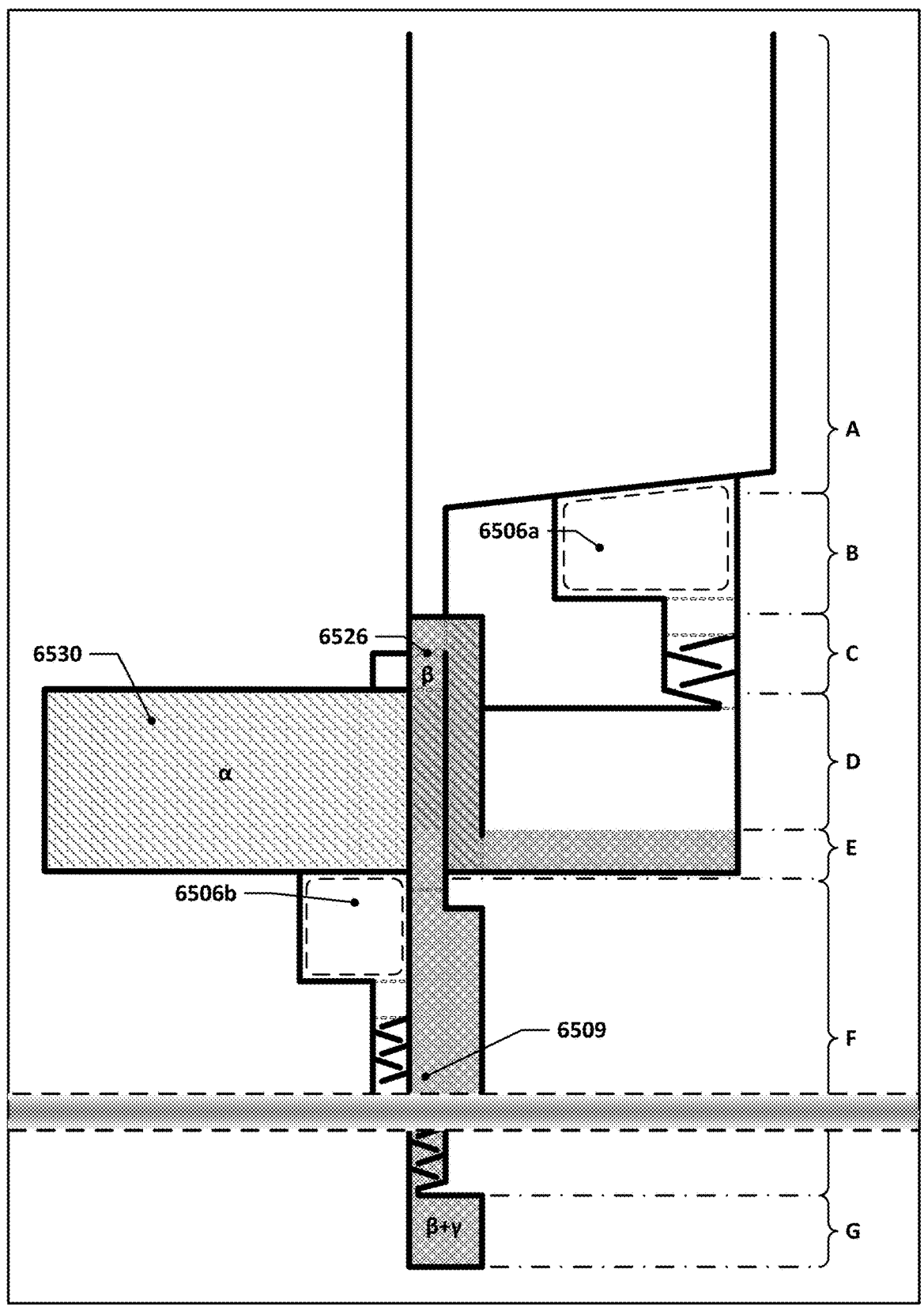
Figure 78:
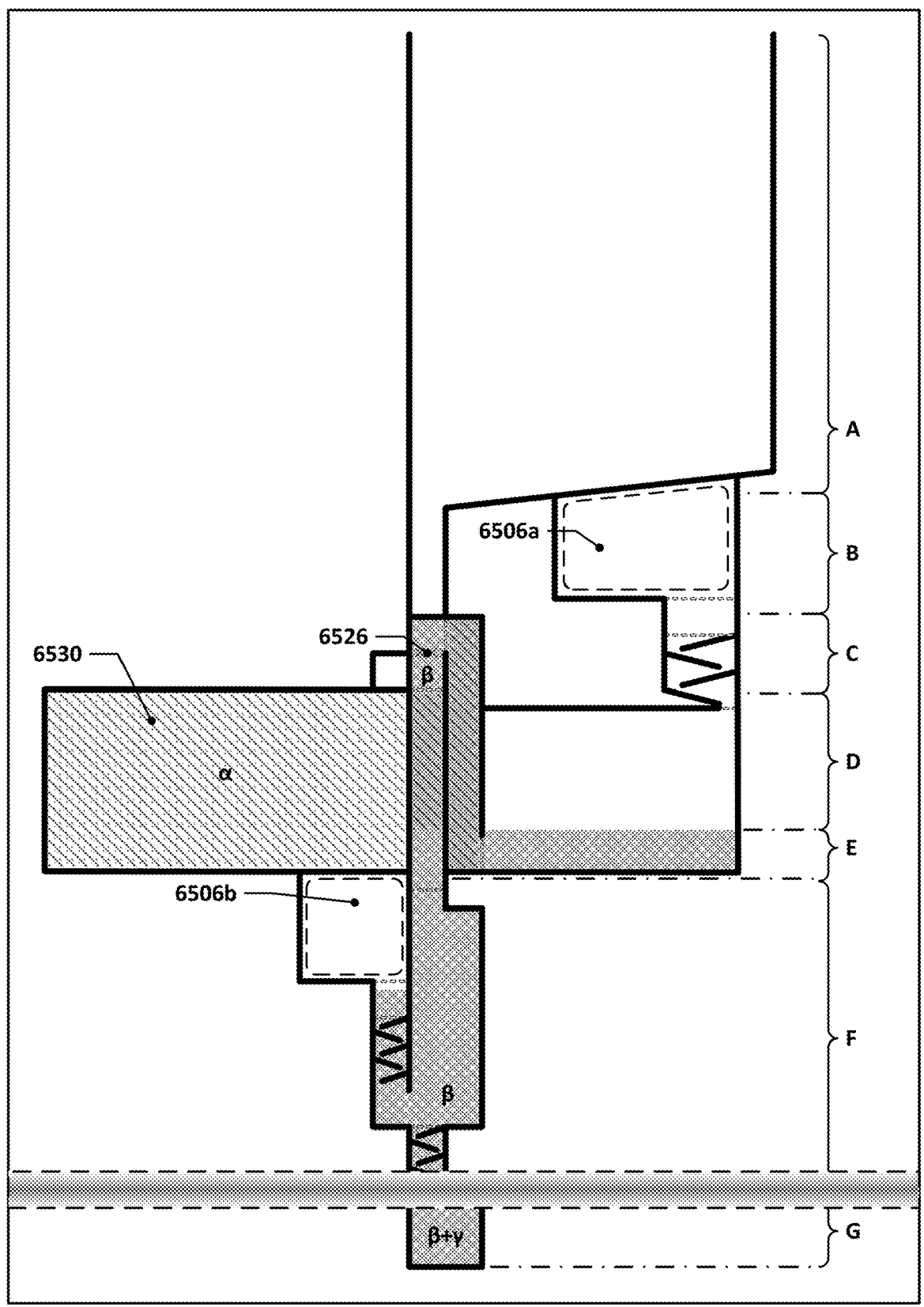

In FIG. 77, the clamping pressure zone has been further advanced towards zone G such that the mixed fluids β+γ are pressurized again so as to burst another temporary seal that seals off the mixing chamber 6509 from the mixing passage (zig zag or broken chevron) that is immediately downstream thereof. Upon rupturing this temporary seal, the β+γ mixture may then flow through another mixing passage before flowing into a measurement chamber in zone G, as shown in FIG. 78, at which point the clamping pressure zone may be advanced so as to seal the β+γ mixture into the chamber in zone G. At this point one or more measurements, e.g., optical measurements, of the β+γ mixture may be obtained, e.g., using fluorescent or luminescent techniques (similar to those discussed earlier herein) in order to ascertain whether or not the sample included biological material of interest, e.g., certain bacteria.

While not specified above, the fluid β may be a lysing agent, e.g., an enzyme that acts to break down any bacteria that may have been trapped by the filter in the area of interest 6526. For example, the fluid β may include one or more of an aqueous buffer, such as, for example, PBS or Tris, a detergent, such as, for example, Triton X100 or Tween 20, and a lyophilized lysozyme (which may be obtained through reconstitution of the material 6544a). Once lysed, the resulting crude lysate that results may be sized so that it can pass through the filter. Thus, flow of fluid α may result in an accumulation of trapped bacteria behind the filter of the area of interest, thus separating such bacteria out from the bulk of the fluid α, and flow of fluid β after fluid α has stopped flowing and is isolated within the waste reservoir 6530 may act to disintegrate the trapped bacteria and wash the constituent elements thereof downstream. This allows for a very concentrated sample of bacteria to be recovered from a much more dilute sample.

Similarly, while not specified above, the fluid γ may be any of a variety of LAMP (loop-mediated isothermal amplification) agents, such as, for example, RT enzyme, strand-displacing polymerase, primers, or intercalating fluorophores (such as, for example, Eva/SYBR green).

FIGS. 79 through 83 depict operational states of another functional block that may be used to provide for sequential flow of fluids through an area of interest, with the last fluid flowed being completely or nearly completely fluidically isolated from the two previous fluids.

Figure 79:
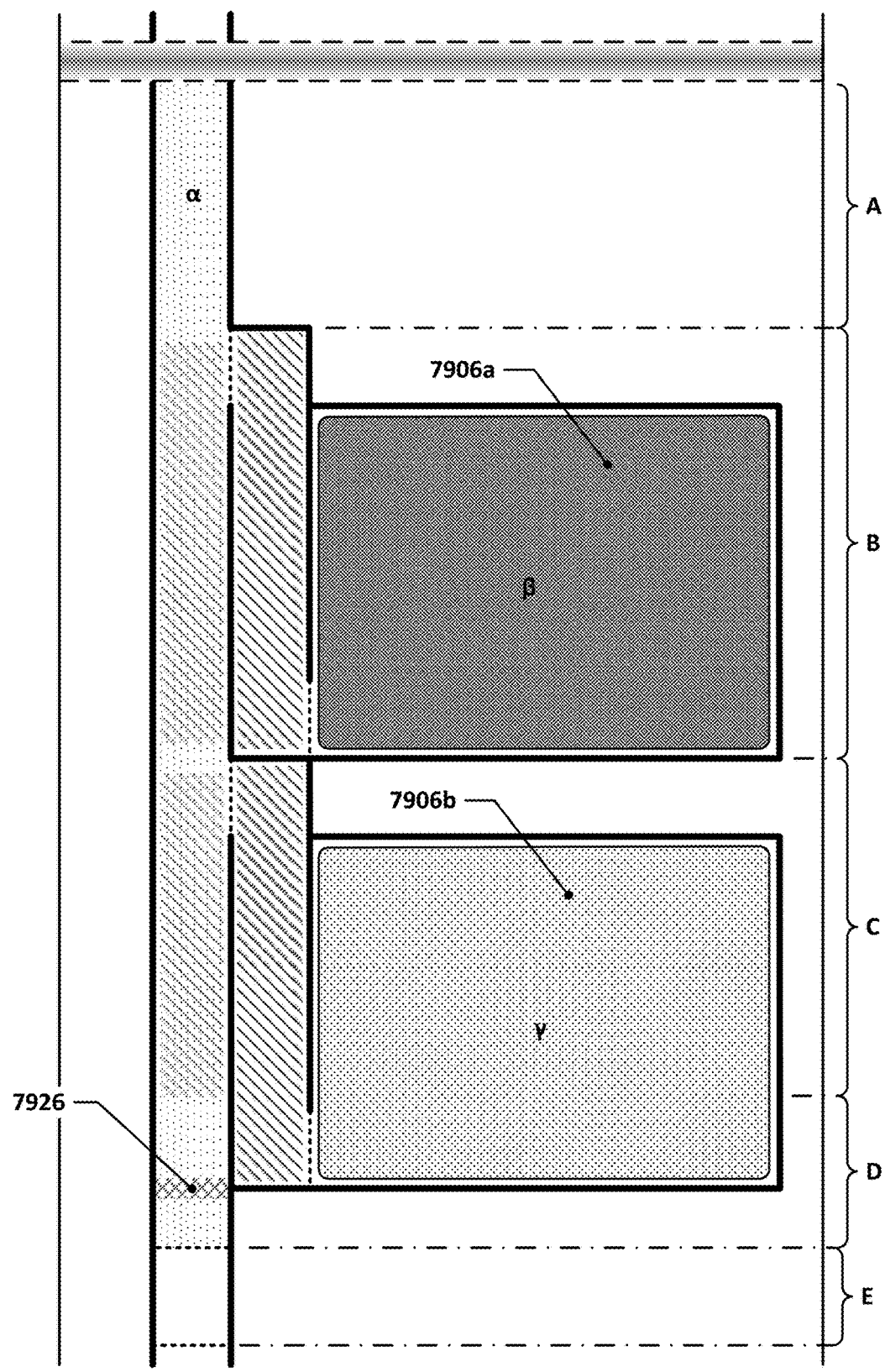
FIGS. 79 through 83 depict another example functional block.

In FIG. 79, a main passage is shown that is filled with fluid α. A first fluid reservoir 7906a may contain a second fluid β that may be housed within a burstable blister or pouch; a second fluid reservoir 7906b may contain a third fluid γ that may be housed within a burstable blister or pouch. An area of interest 7926 may be located within the main passage, as shown. Each fluid reservoir 7906a/b may have a short passage. The short passage may extend from a temporary seal that seals an opening in that fluid reservoir 7906 that is farthest from the clamping pressure zone (when the clamping pressure zone is in its initial, starting position used for processing the fluidic structure) to an opening in the main passage that is sealed off by a temporary seal and is located closer to the clamping pressure zone (again, when the clamping pressure zone is in its initial starting position) than the corresponding fluid reservoir 7906.

Figure 80:
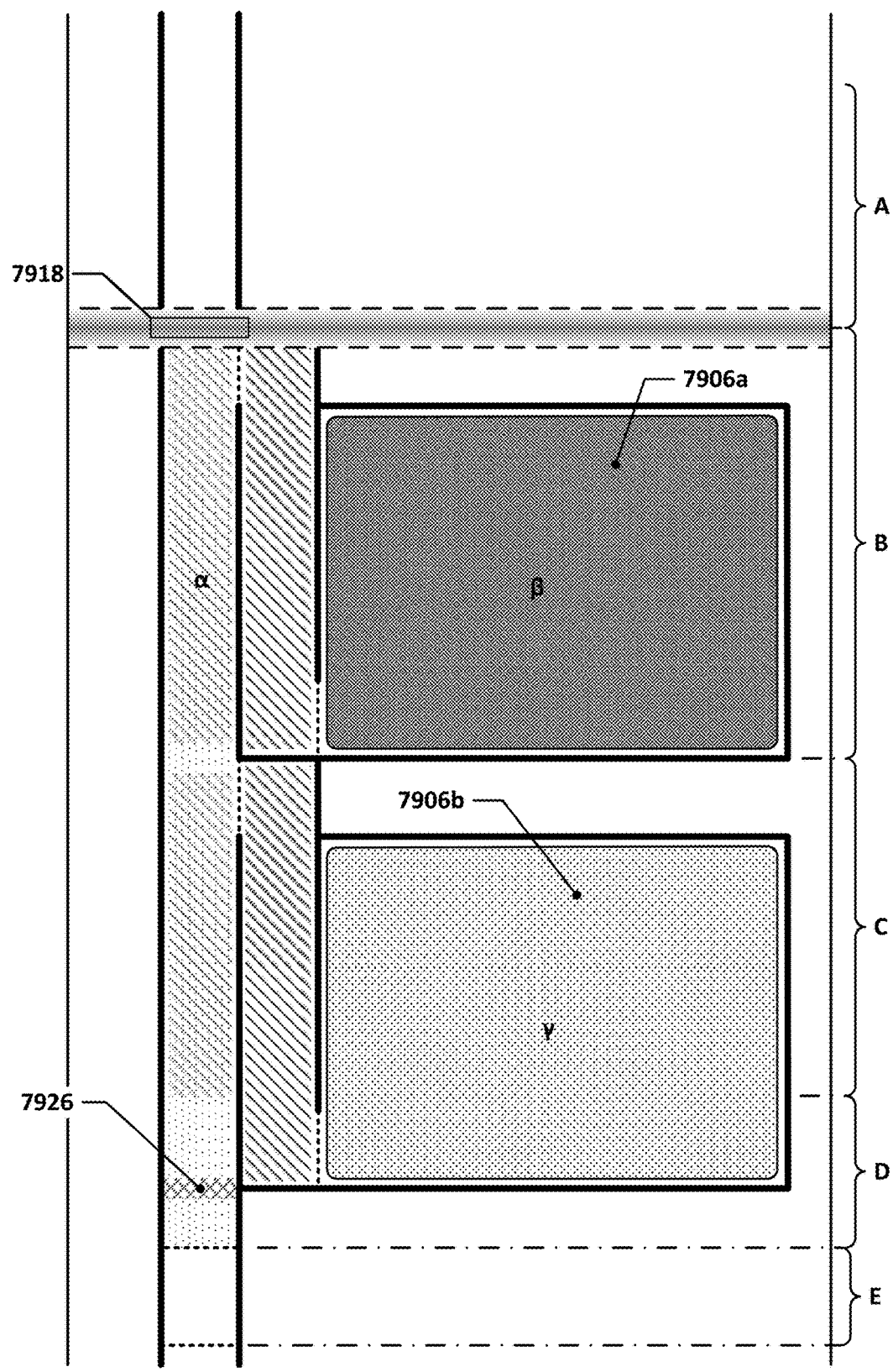

In FIG. 80, the clamping pressure zone has been moved towards zone E such that it has drawn generally even with the transition between zones A and B. A heating element 7918, similar to those discussed in above examples, may be used to seal the main passage at the indicated location (just before the temporary seal that seals the short passage for the fluid reservoir 7906a from the main passage) with a permanent seal.

Figure 81:
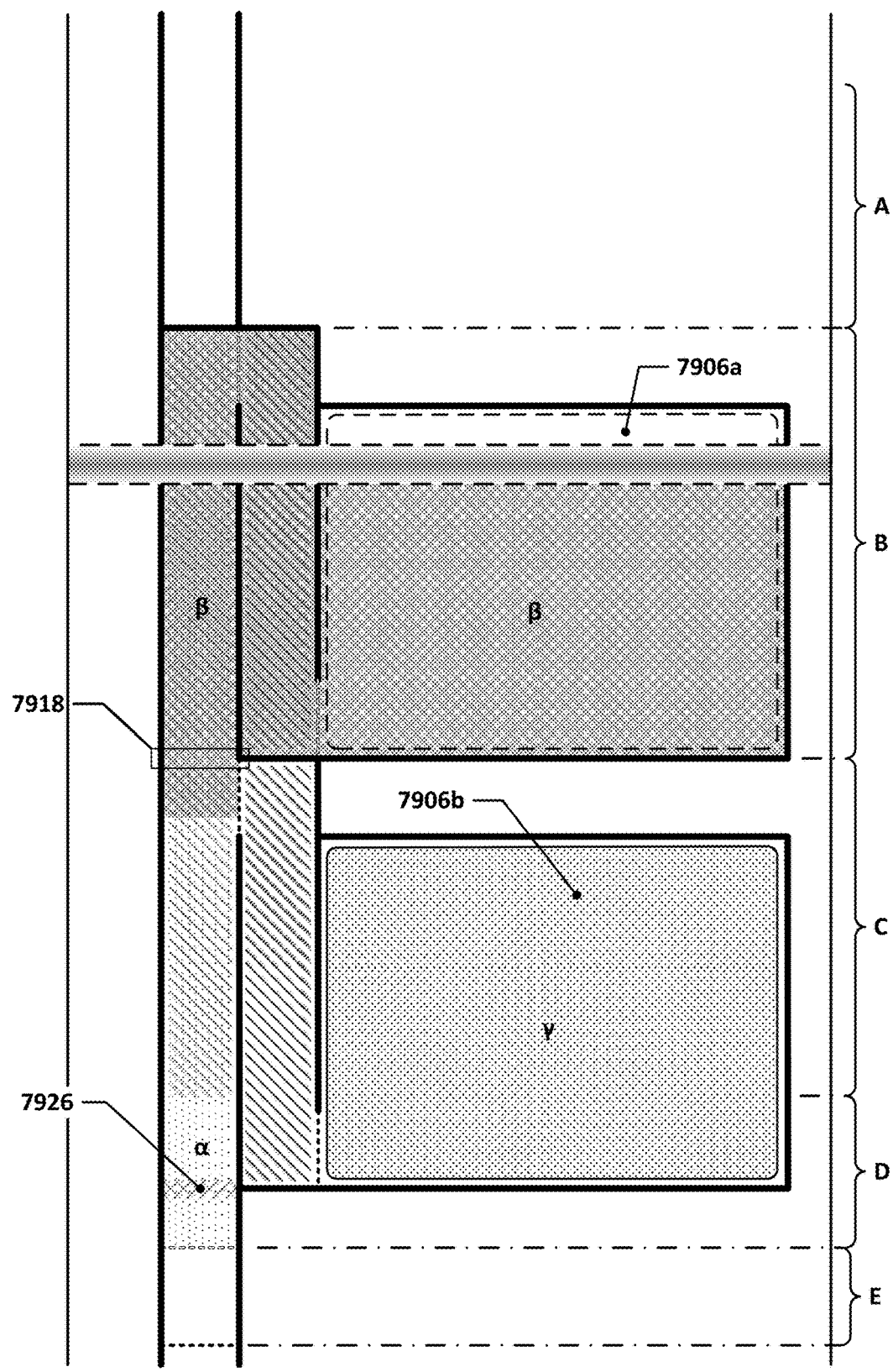

In FIG. 81, the clamping pressure zone has been advanced to a position that causes the fluid in the first fluid reservoir 7906a to be pressurized, thus causing the burstable blister housing the fluid β to burst. The continued movement of the clamping pressure zone also causes the fluid β to burst through the temporary seals that seal both ends of the short passage between the main passage and the first fluid reservoir 7906a, thereby allowing the fluid β to flow past the clamping pressure zone in a direction opposite the direction of travel of the clamping pressure zone while in the short passage, and then again past the clamping pressure zone in the same direction as the clamping pressure zone. Such fluid flow may, for example, be enabled through the use of bypass regions, as indicated in the Figures. In FIG. 81, it can be seen that fluid β has largely swept all of fluid α out of the upper part of the main passage.

Figure 82:
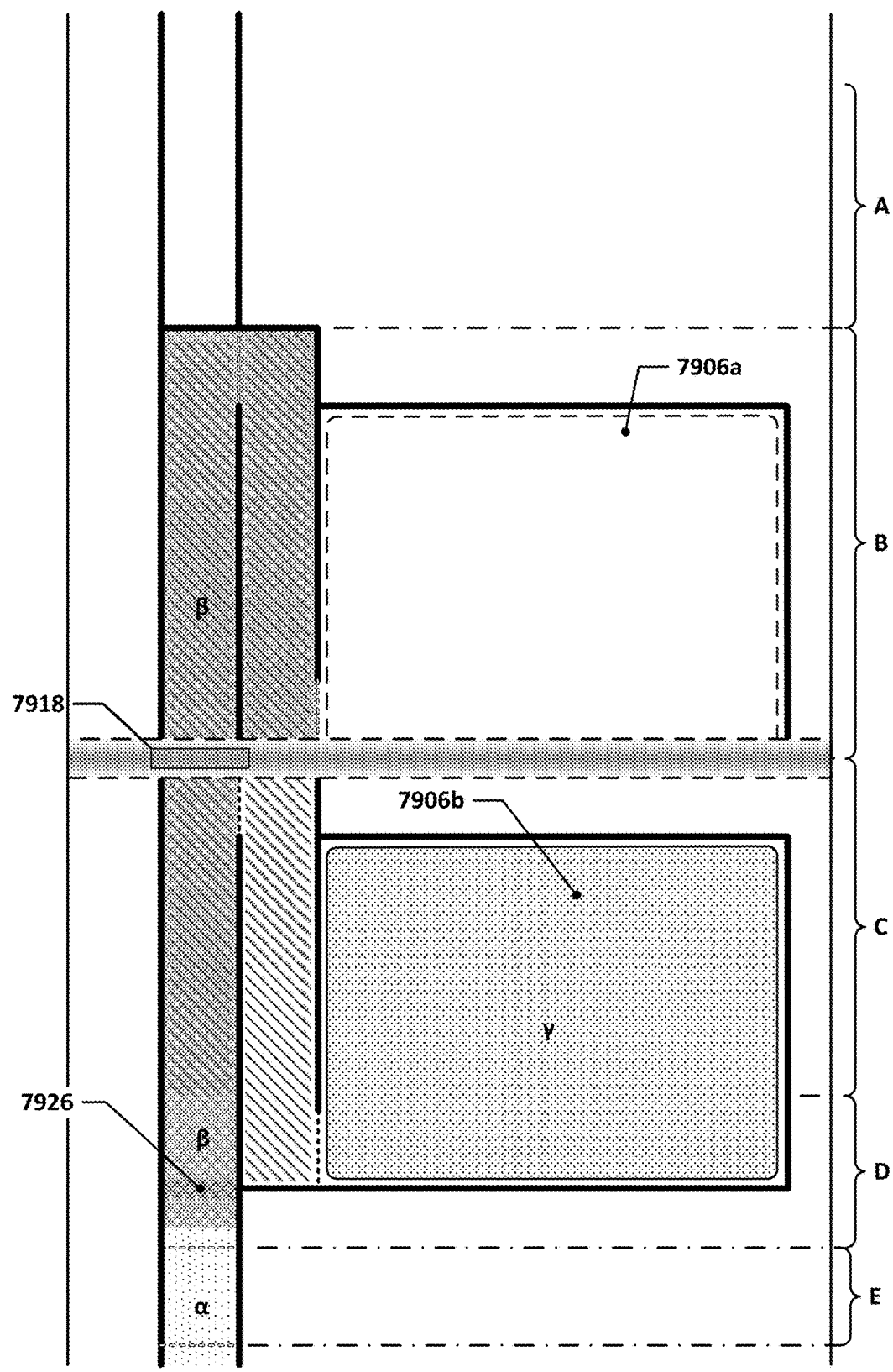

In FIG. 82, the clamping pressure zone has been moved towards zone E such that it has drawn generally even with the transition between zones B and C. A heating element 7918, similar to that discussed earlier with respect to FIG. 80, may be used to seal the main passage at the indicated location (just before the temporary seal that seals the short passage for the fluid reservoir 7906b from the main passage) with a permanent seal.

Figure 83:
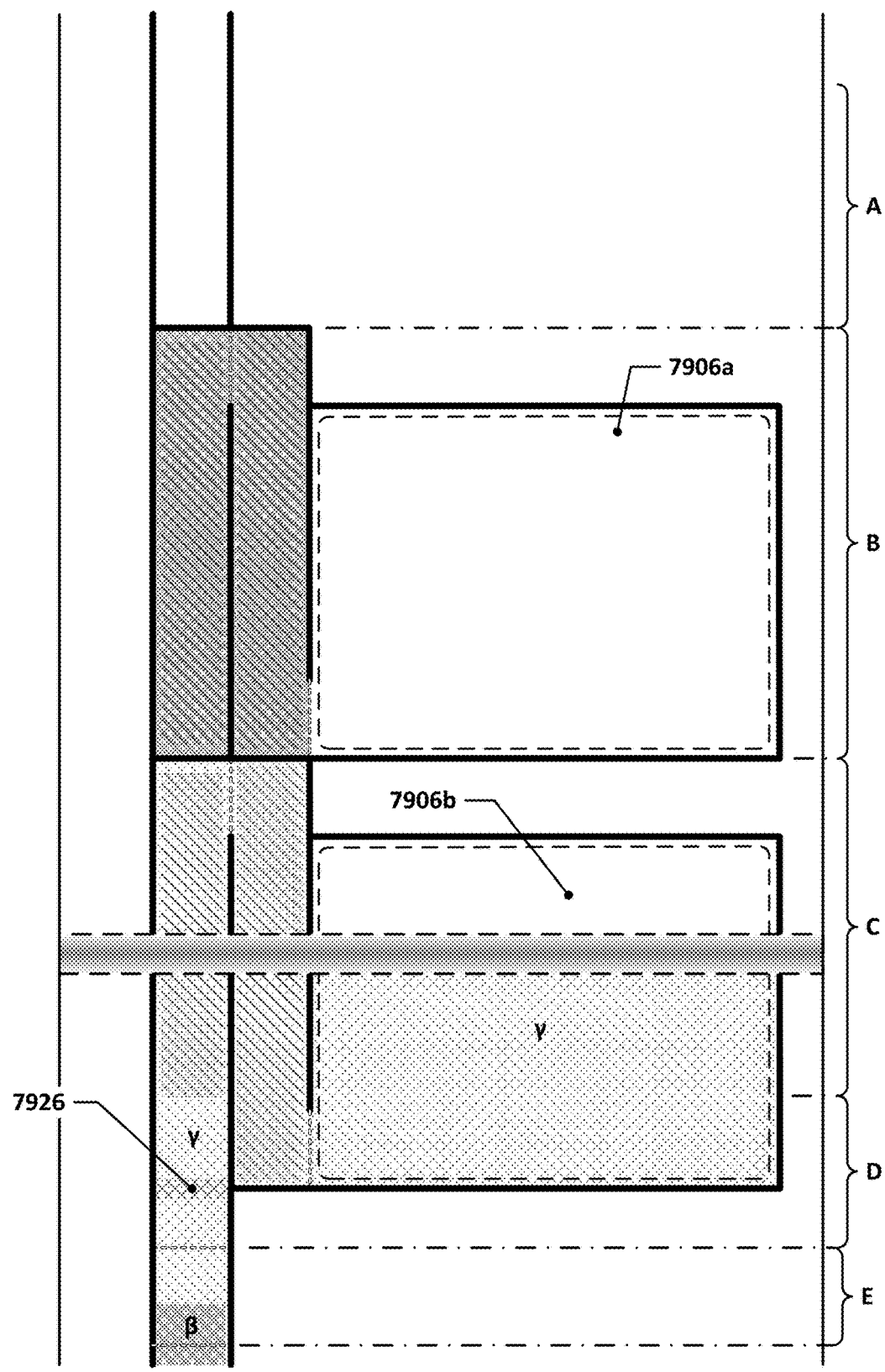

In FIG. 83, the clamping pressure zone has been advanced to a position that causes the fluid in the second fluid reservoir 7906b to be pressurized, thus causing the burstable blister housing the fluid γ to burst. The continued movement of the clamping pressure zone also causes the fluid γ to burst through the temporary seals that seal both ends of the short passage between the main passage and the second fluid reservoir 7906b, thereby allowing the fluid γ to flow past the clamping pressure zone in a direction opposite the direction of travel of the clamping pressure zone while int the short passage, and then again past the clamping pressure zone in the same direction as the clamping pressure zone. Such fluid flow may, for example, be enabled through the use of further bypass regions (or extensions of the earlier discussed bypass regions), as indicated in the Figures. In FIG. 83, it can be seen that fluid γ has largely swept all of fluid β out of most of the main passage.

The functional block discussed above with respect to FIGS. 79 through 83 may be used in a fluidic structure such as is shown in FIGS. 84 through 95. The fluidic structure of FIGS. 84 through 95 may be used to perform assays that may involve biological materials that are too small to be feasibly filtered out from a larger fluid specimen, e.g., viruses.

Figure 84:
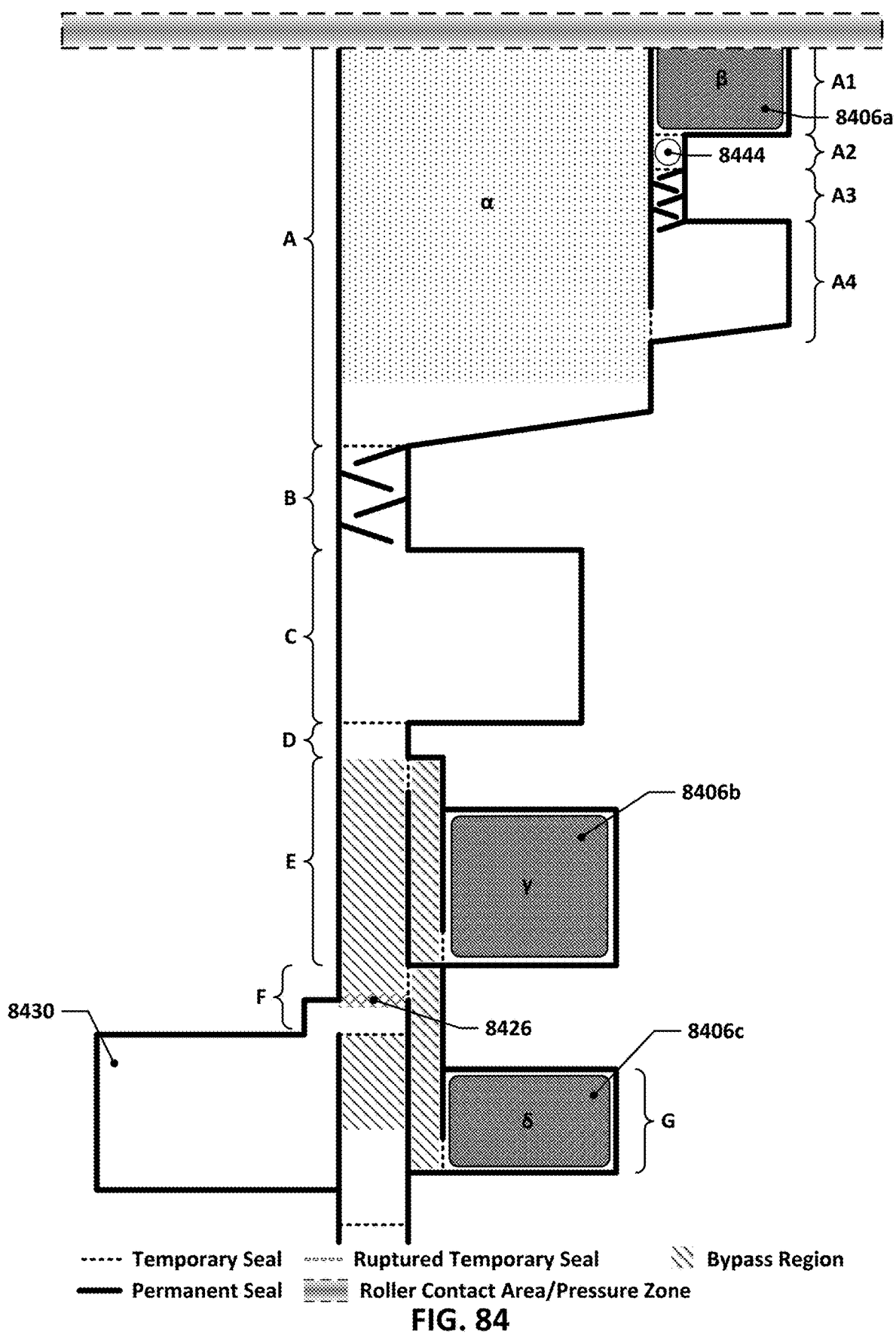
FIGS. 84 through 95 depict an example fluidic structure that may be well-suited to detecting viral infections from samples such as urine samples.
Figure 85:
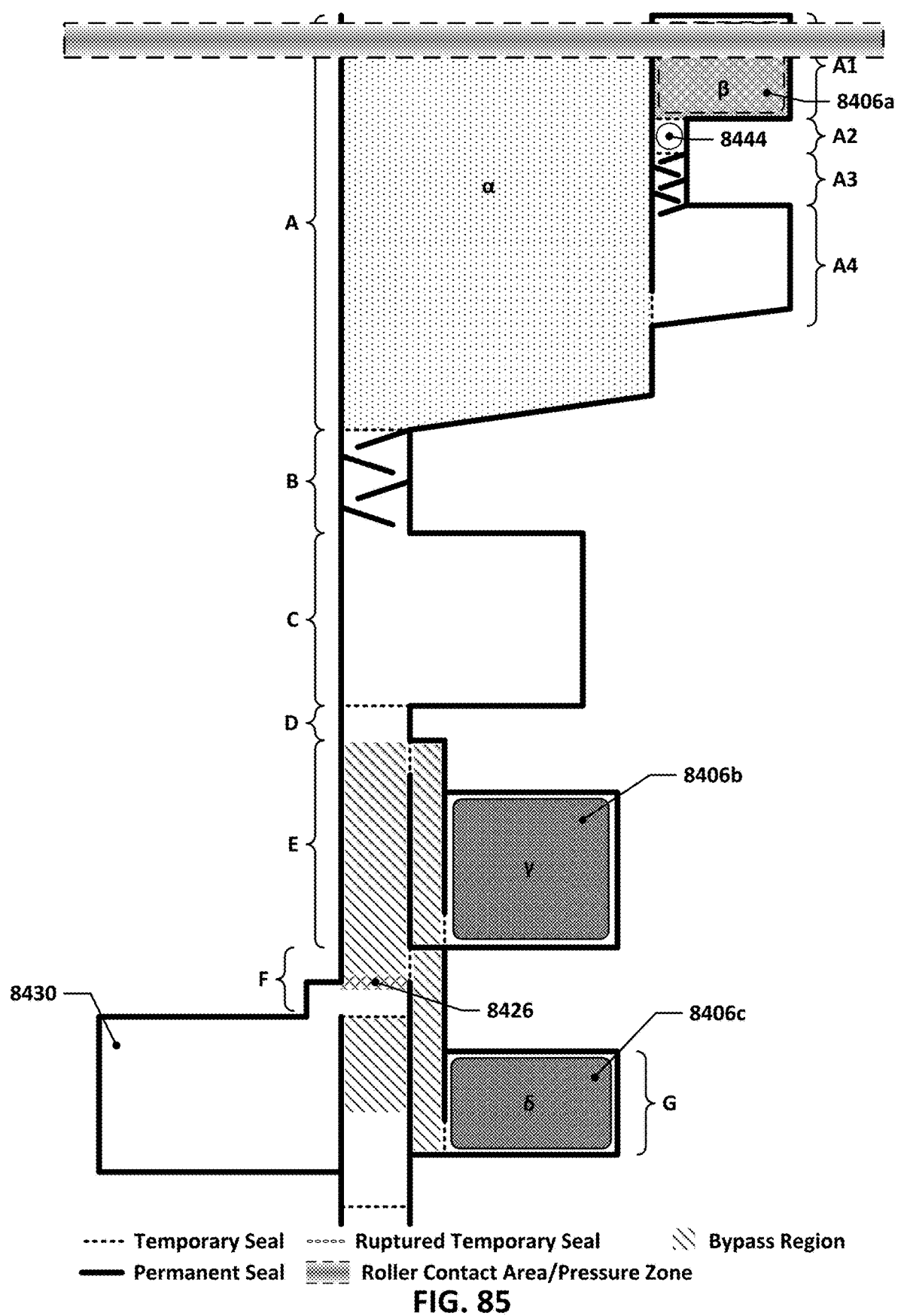

In FIG. 84, a fluid α, e.g., urine, may be provided in zone A. Also located in zone A may be a first fluid reservoir 8406*a* (zone $A_1$) that may contain a fluid β within a burstable blister or pouch, for example, a lyophilized material 8444 (zone A), a mixing passage (zone $A_3$), and a mixing chamber (zone $A_4$). When the clamping pressure zone is caused to advance through zone A, the pressurization of the burstable blister or pouch in zone $A_1$ may be pressurized by the clamping pressure zone until it ruptures, thereby releasing the fluid β contained therein, as shown in FIG. 85. At the same time, the fluid α may be pushed into zone A further.

Figure 86:
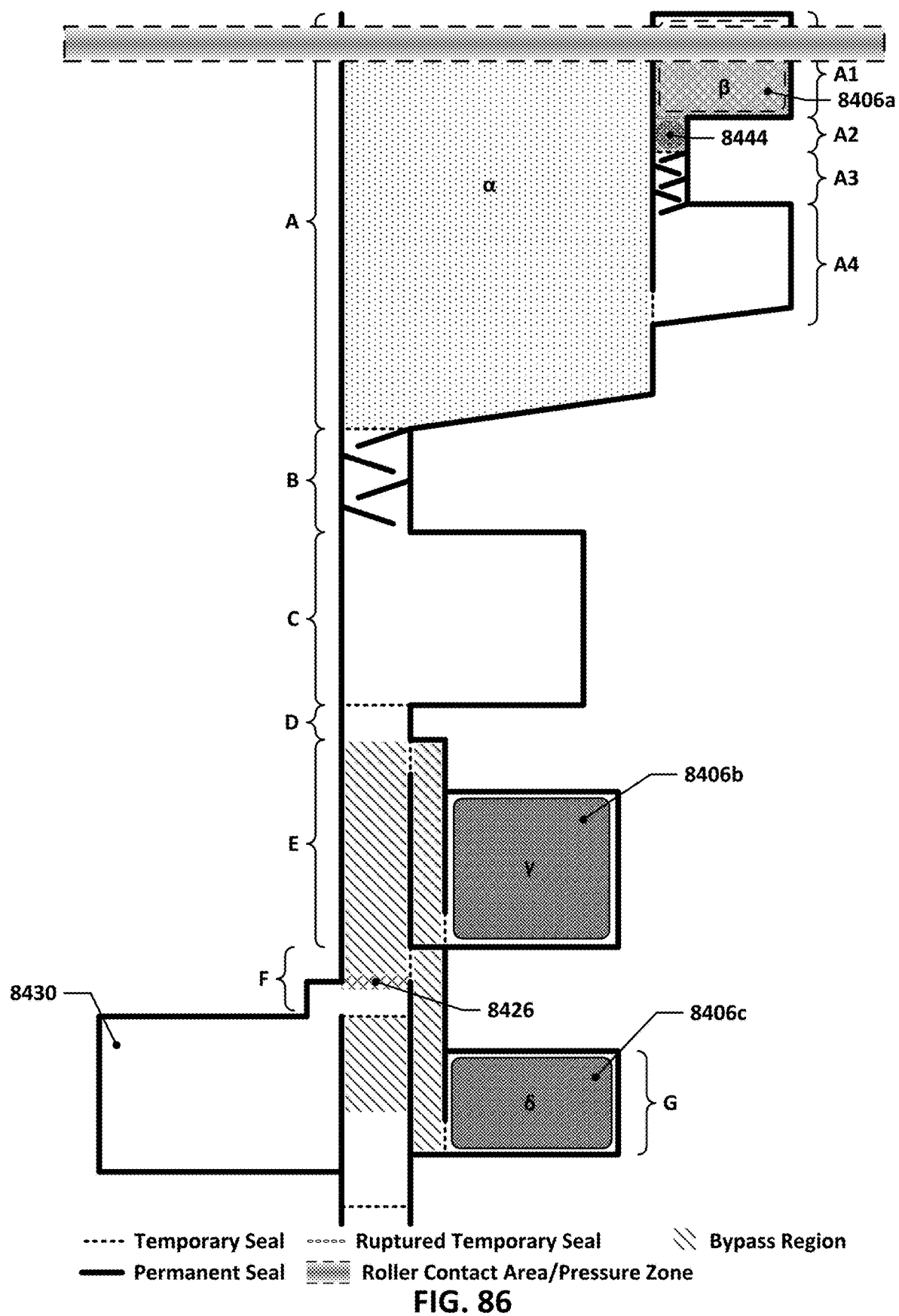

In FIG. 86, the clamping pressure zone has been advanced slightly, thereby pressurizing the fluid β and causing it to rupture the temporary seal that kept is in the first fluid reservoir 8406*a* and flow into a chamber (in zone $A_2$) where the lyophilized material 8444 is housed. The clamping pressure zone may be kept stationary for a period of time to allow fluid β to mix with/reconstitute the lyophilized material 8444. The mixture of the fluid β with the lyophilized material 8444 may, for example, turn fluid β into a lysing agent or enhance its ability to lyse. In some implementations, fluid β may, in its initial state, be a lysing agent and the lyophilized material 8444 may be omitted. In some implementations, for example, the fluid β may be an aqueous buffer with a detergent and guanidine hydrochloride or thiocyanate added.

Figure 87:
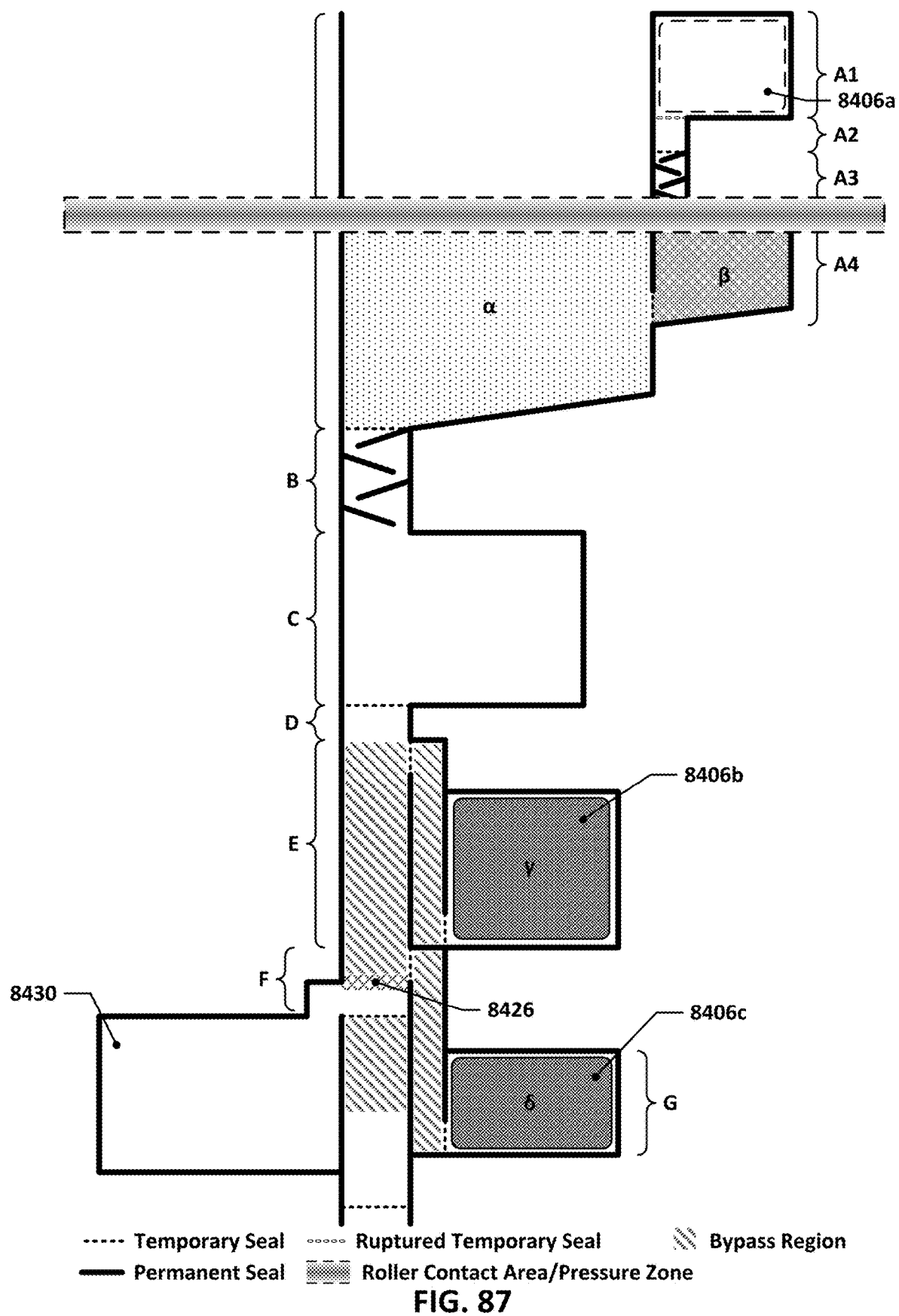
Figure 88:
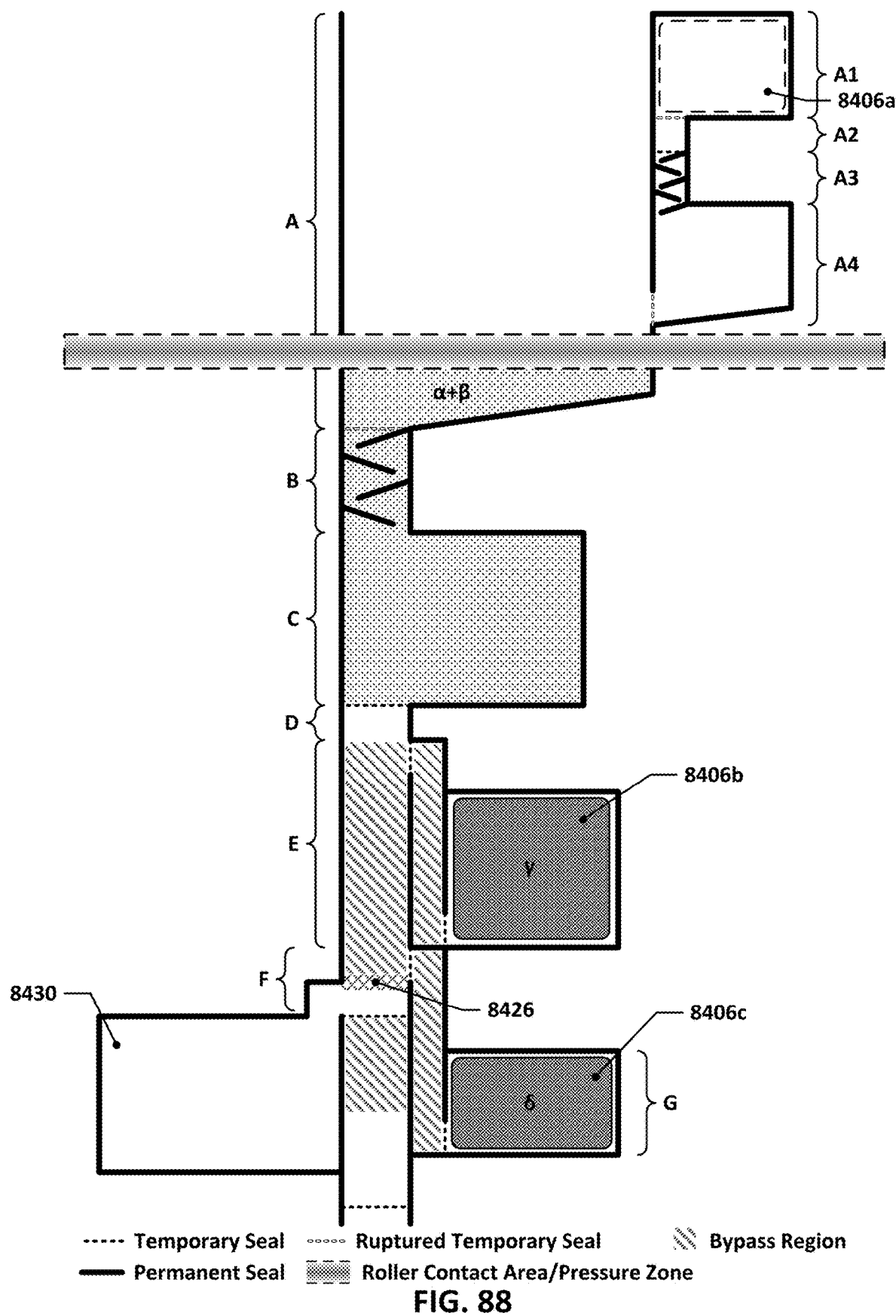

In FIG. 87, the clamping pressure zone has been further advanced, thereby forcing the fluid β to burst through the temporary seals provided at the top and bottom of the mixing passage ($A_3$) and flow into the mixing chamber ($A_4$). After allowing the mixture of fluid β and the lyophilized material 8444 to mix in the mixing chamber for some time, the clamping pressure zone may be caused to advance further, as shown in FIG. 88, thus causing the temporary seal between the mixing chamber with fluid β and the chamber containing fluid α to rupture. This allows the fluid β to flow into the chamber with the fluid α such that the two fluids mix together. As the clamping pressure zone continues to move towards the transition between zones A and B, the increasing pressure on the α+β fluid mixture trapped within zone A causes the temporary seal between zones A and B to rupture, thereby allowing the α+β fluid mixture to flow through the mixing passage in zone B and into a second mixing chamber in zone C, where it may be optionally heated, if desired, using a heating element (not shown) that may be part of the fluidic system used to apply the clamping pressure zone. Such heating, for example, may increase the efficacy of the fluid β in reacting with the fluid α. For example, if the fluid β is a lysing agent that may be used to break down the cell membranes of bacteria that are present within the sample, heating the fluid α and β mixture may facilitate such cell lysing.

Figure 89:
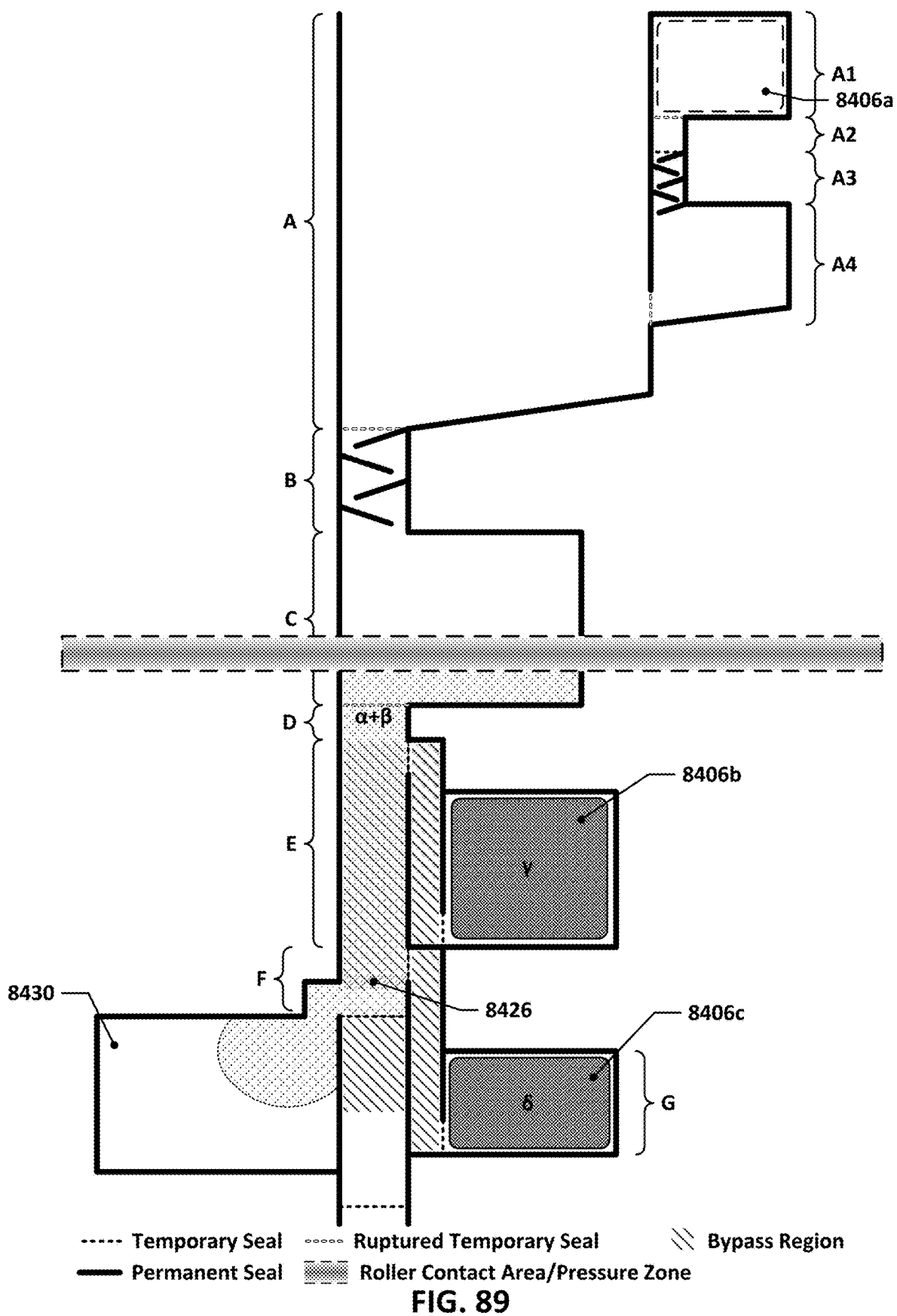

After optionally allowing the α+β fluid mixture to dwell in the second mixing chamber of zone C, the clamping pressure zone may be again moved closer to zone F, as shown in FIG. 89, thereby pressurizing the α+β fluid mixture again and causing the α+β fluid mixture to burst through the temporary seal between zones C and D. The α+β fluid mixture may then flow into a functional block similar to that discussed with reference to FIGS. 79 through 83.

For example, in FIG. 89, the α+β fluid mixture is flowed through a main passage, through an area of interest 8426, and into a waste reservoir 8430. In some implementations, the lysed α+β fluid mixture may include nucleic acids that are exposed through lysing of the bacteria that may be in fluid α, and the area of interest 8426 may, in such examples, have silica beads or other silica structures; the nucleic acids that are present in the lysed α+β fluid mixture may, in the presence of guanidine or other suitable substance, bind to the silica beads, thereby becoming immobilized in the area of interest 8426. In other implementations, the area of interest 8426 may have silica beads or other silica structures that may have antibodies immobilized thereon that may bind directly to the particular material(s) of interest that were in fluid α.

Figure 90:
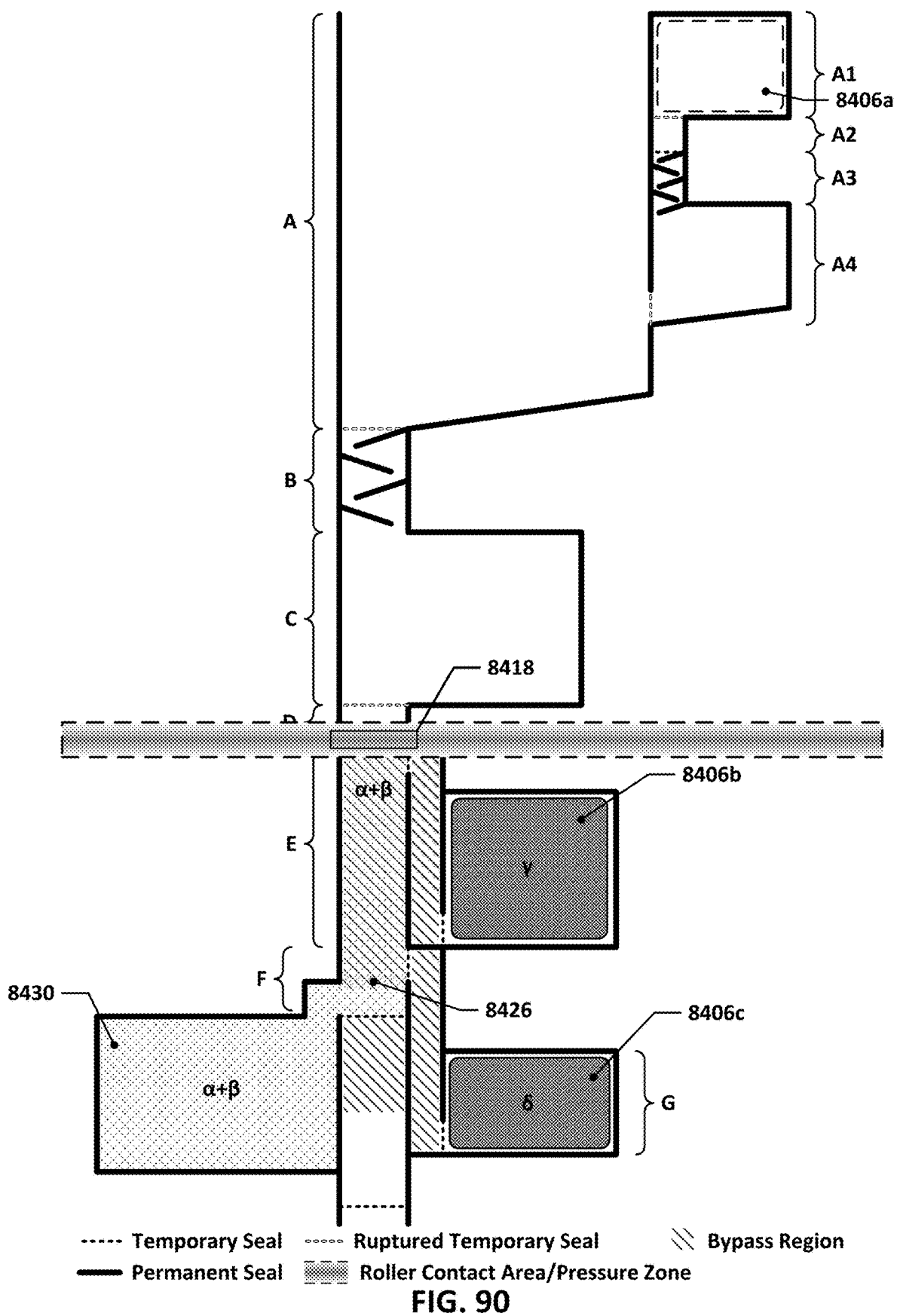

In FIG. 90, the clamping pressure zone has been advanced further to the transition between zones D and E. A heating element 8418, similar to those discussed in above examples, may be used to seal the main passage at the indicated location (just before the temporary seal that seals the short passage for the second fluid reservoir 8406*b* from the main passage) with a permanent seal.

Figure 91:
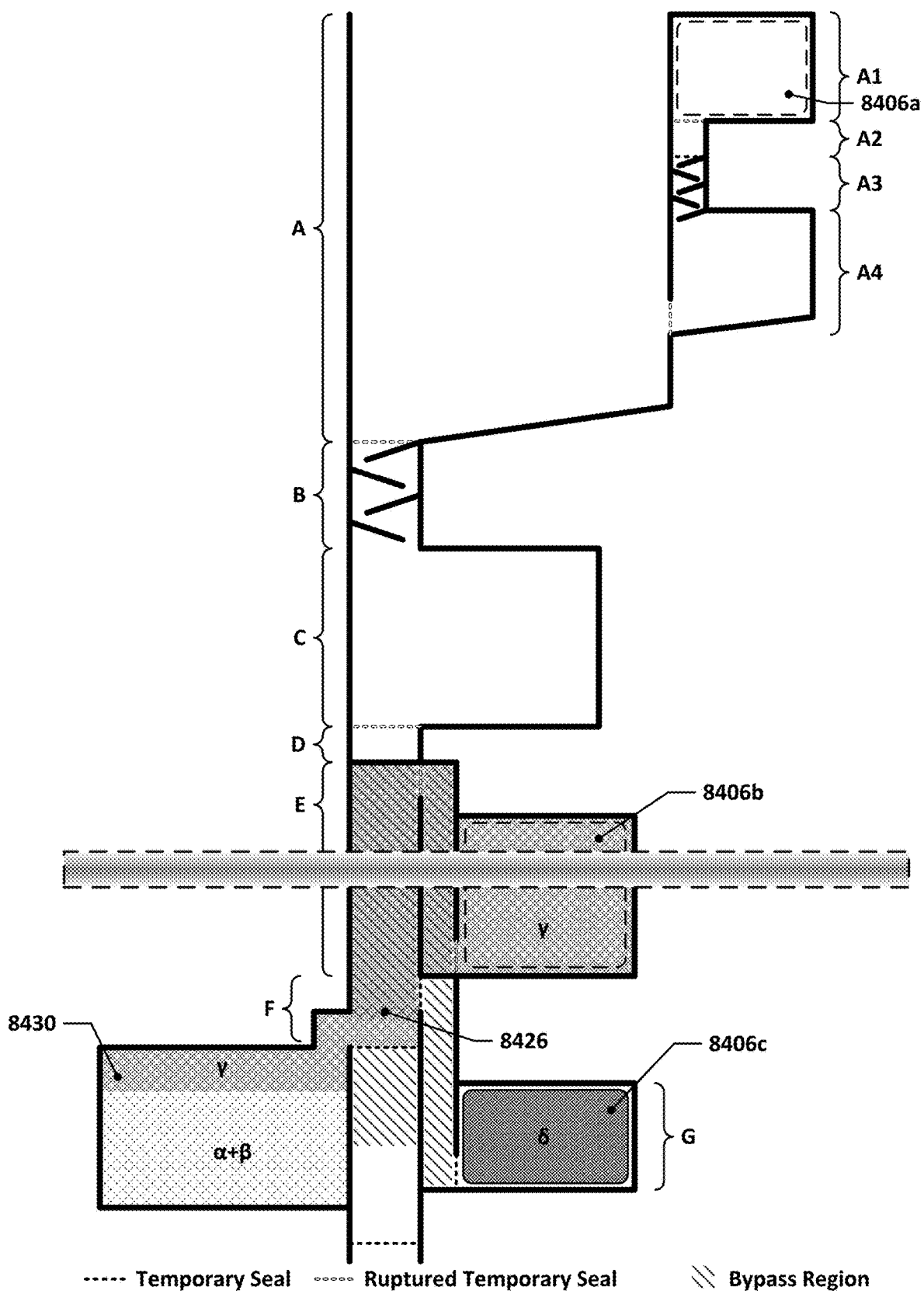

In FIG. 91, the clamping pressure zone is advanced through zone E, where it pressurizes and then bursts a burstable blister or pouch containing a fluid γ in the second fluid reservoir 8406*b*, which may then become further pressurized and cause temporary seals to burst in between the second fluid reservoir 8406*b* and the main passage. The fluid γ may then be pushed out of the second fluid reservoir 8406*b*, past the clamping pressure zone (by way of bypass regions that are provided in the main passage and the short passage between the main passage and the second fluid reservoir 8406*b*) through the area of interest 8426, and into the waste reservoir 8430. While the α+β mixture and the fluid γ are shown as different discrete layers in the waste reservoir 8430, they would likely mix within the waste reservoir 8430.

Figure 92:
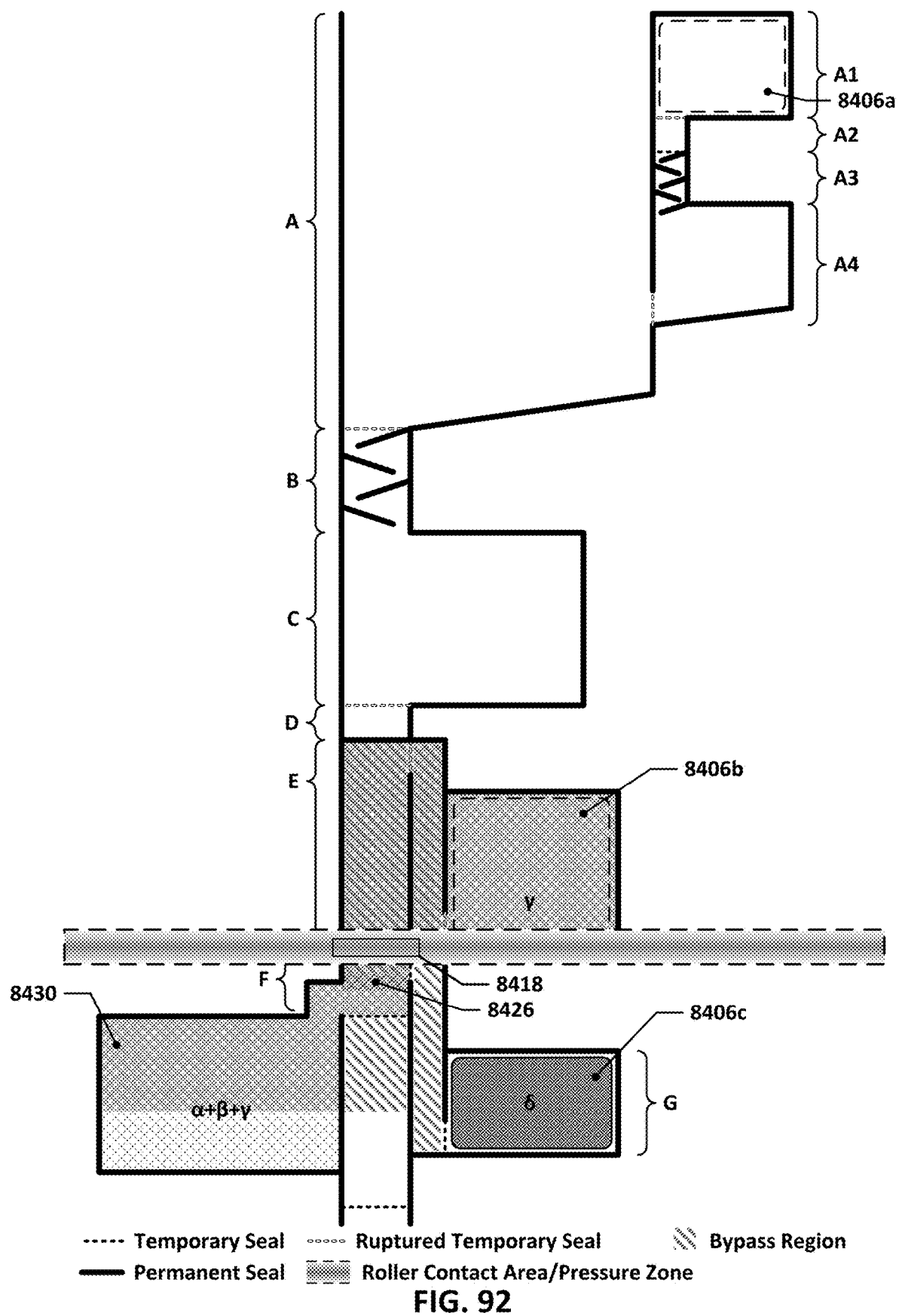
Figure 93:
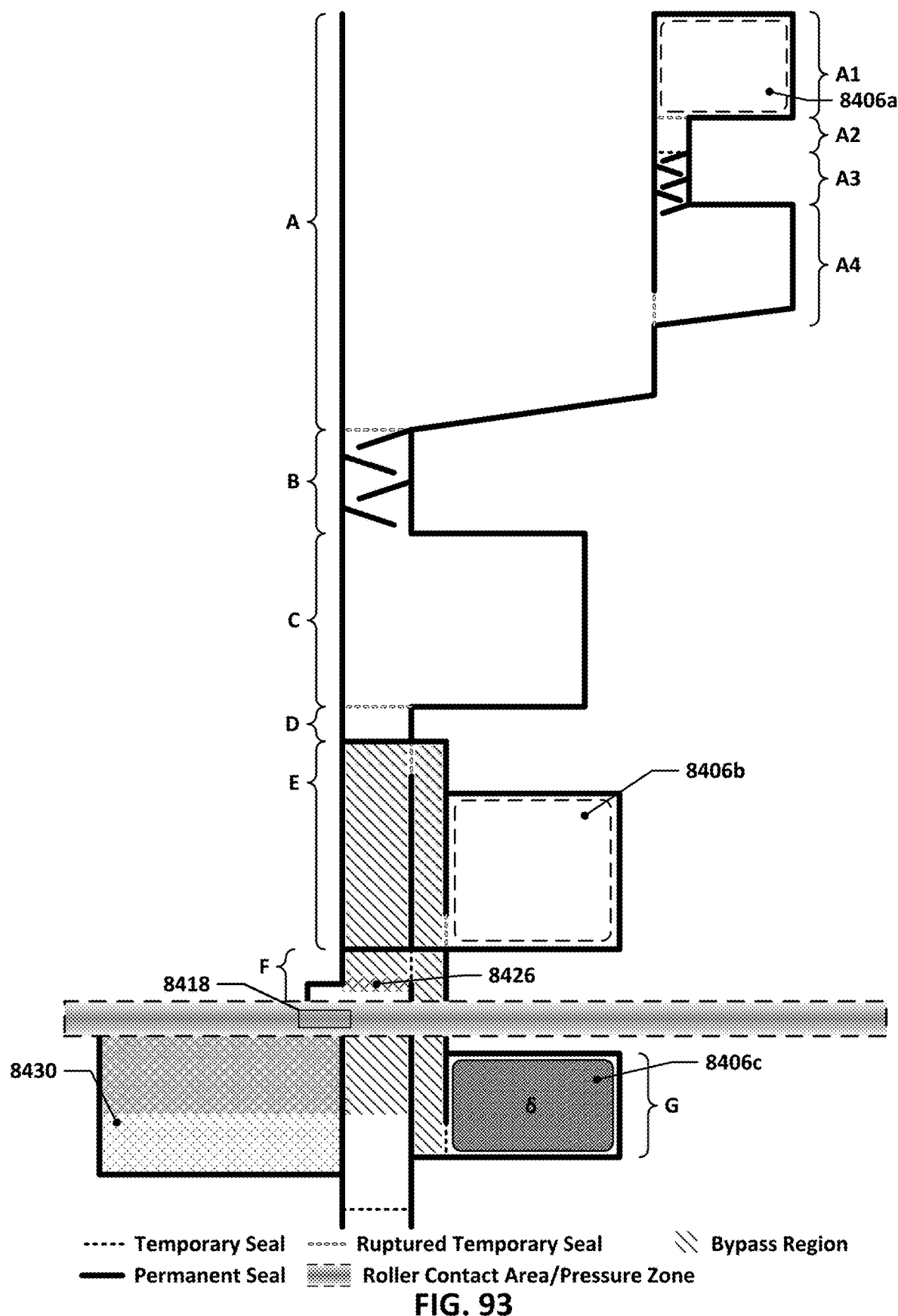

The fluid γ may, for example, be a wash solution, e.g., ethanol or a solution of >70% ethanol, that is used to wash away any remaining mixture of α+β that may remain in the area of interest while leaving the immobilized elements thereof in place. After the clamping pressure zone is advanced to the transition point between zones E and F, another heating element 8418, similar to those discussed in above examples, may be used to seal the main passage at the indicated location (just before the temporary seal that seals the short passage for the third fluid reservoir 8406*c* from the main passage) with a permanent seal, as shown in FIG. 92. The clamping pressure zone may then advance further towards zone G, as shown in FIG. 93. After the clamping pressure zone is advanced to the end of zone F, yet another heating element 8418, similar to those discussed in above examples, may be used to seal the waste reservoir 8430 at the indicated location; as discussed previously, a further sealing operation may optionally be performed (but is not shown as being performed here) to further permanently seal the alcove that is fluidically interposed between the main passage and the waste reservoir 8430.

Figure 94:
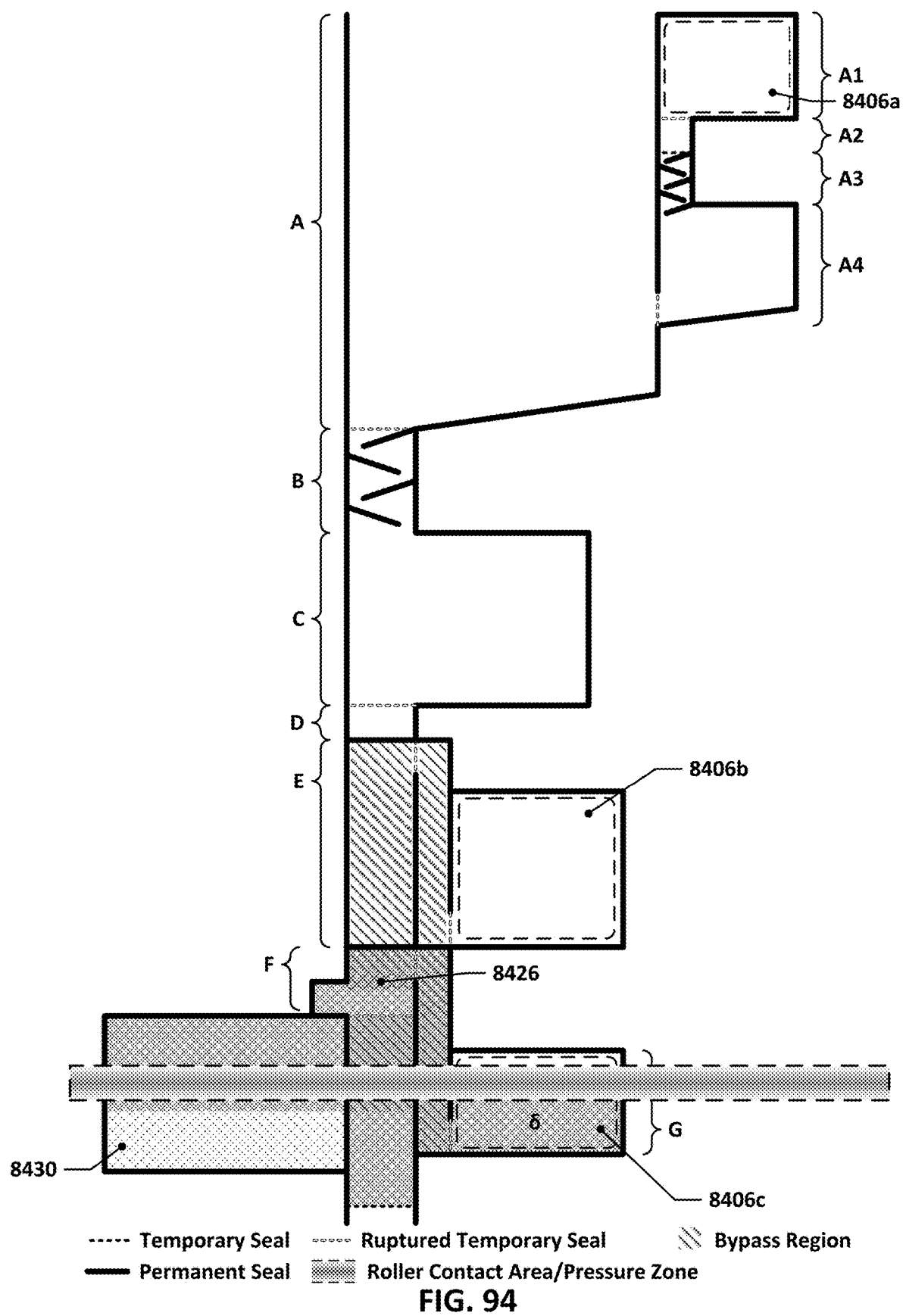

In FIG. 94, the clamping pressure zone has again been advanced and is now in zone G. In advancing, the clamping pressure zone has pressurized a burstable blister or pouch containing a liquid δ that is located within a third fluid reservoir 8406*c* and caused it to rupture. The pressurized fluid δ has also caused temporary seals between the third fluid reservoir 8406*c* and the area of interest 8426, as well as a further temporary seal downstream of the area of interest 8426, to rupture, thus allowing the fluid δ to flow through the area of interest 8426. The fluid δ is able to flow past the clamping pressure zones by way of the bypass regions that are shown.

Figure 95:
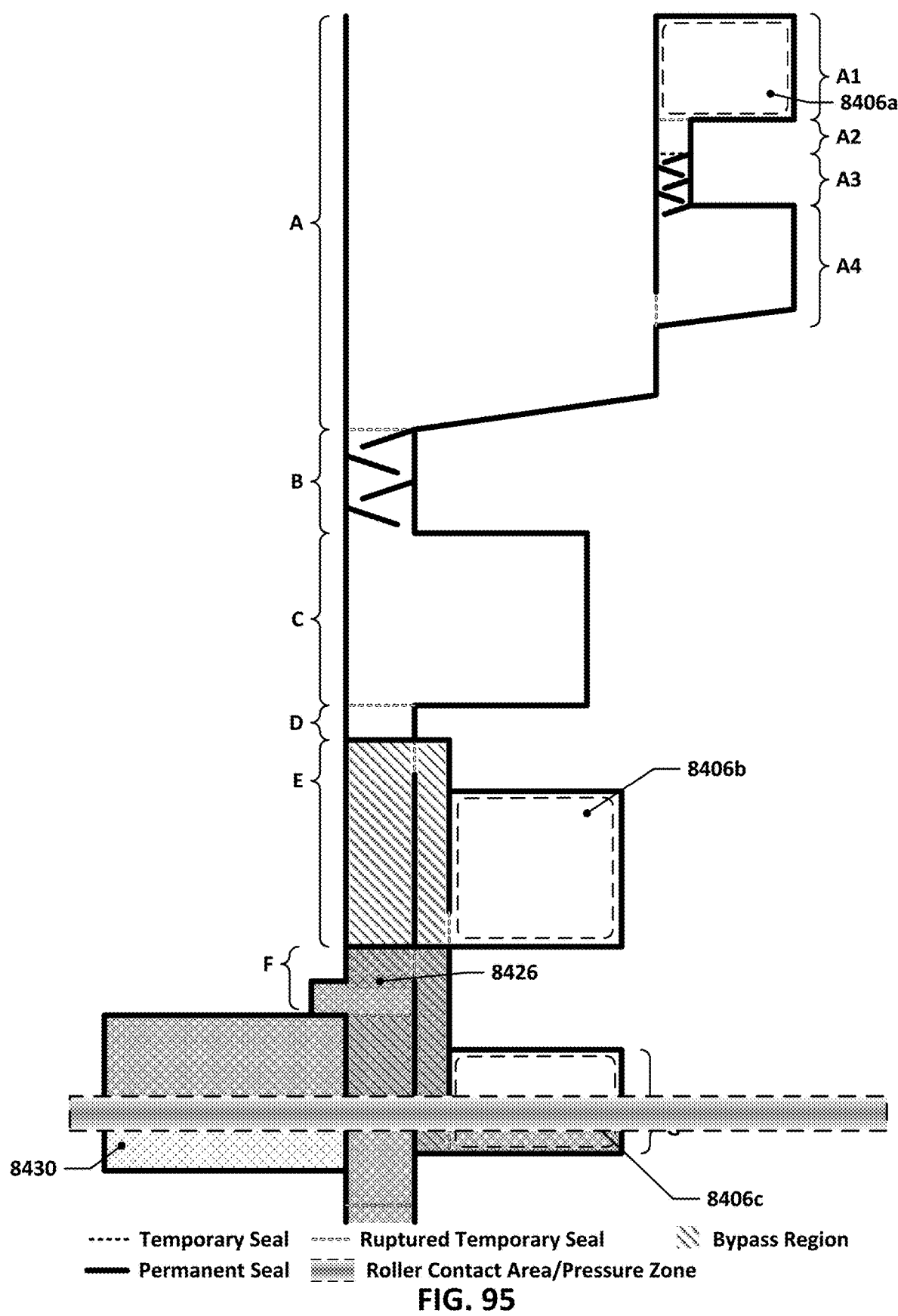

In FIG. 95, the clamping pressure zone has been advanced again such that the clamping pressure zone is moved past the bypass region in the main passage, thus sealing the main passage again. A bolus of the fluid δ was trapped between the clamping pressure zone and another temporary seal (visible below the clamping pressure zone) that has now been ruptured, thereby allowing the bolus of fluid δ to flow into subsequent portions of the depicted fluidic circuit. The fluid δ may, for example, be a solvent, e.g., an aqueous elution buffer such as, for example, water and/or TE pH 8, that may act to elute immobilized antibodies from the area of interest 8426 and then transport the eluted material to downstream functional blocks that may prepare the eluted antibodies for further processing, such as for a LAMP assay.

For example, the portion of the fluidic structure that is downstream of what is shown in FIGS. 84 through 95 may be similar to what is shown in zones F and G of FIGS. 65 through 78. Moreover, it will be recognized that some implementations may include multiplexing features, e.g., such as are shown in zones C through E of FIG. 16 or zones C through E of FIGS. 17 and 18, to allow for the fluidic sample that is provided using the structure of FIGS. 84 through 95 to be subdivided into multiple different sub-portions, each of which may be routed to its own fluidic sub-circuit for separate processing and analysis. For example, the exit flow path of the fluidic circuit of FIGS. 84 through 95 may be fluidically connected with the inlet of a fluidic multiplexing functional block, e.g., such as is shown in zones C through E of FIGS. 17 and 18, and each of the branching flow paths of the fluidic multiplexing functional block may, in turn, be fluidically connected with a different fluidic sub-circuit for performing different types of analysis. Such different types of analyses may include, for example, testing for strains of bacteria/viruses, different bacteria/viruses, different diseases, mixtures of viruses, etc.

A similar strategy may also be pursued for the implementation of FIGS. 65 through 78, e.g., the portion of the depicted fluidic circuit in zones F and G may be replicated multiple times as different fluidic sub-circuits, with each instance thereof being configured with different reactants to allow for different assays to be performed. Each such sub-circuit may be fluidically connected with zone E of the implementation of FIGS. 65 through 78 by way of such a multiplexing feature.

It will also be understood that some implementations may be configured to facilitate performing multiple different tests/analyses of the material that is within a single fluidic sub-circuit, e.g., performing analyses in which different materials of interest within the measurement chamber may produce different visual responses, e.g., providing light of different colors in response to different excitation stimuli. In some of these implementations, a fluidic multiplexing functional block may be used to subdivide the sample to be processed, and then one or more of the fluidic sub-circuits that are provided with a sub-portion of the sample to be processed may be configured to support the performance of multiple different analyses on the sub-portion contained therein.

In some implementations of the implementations of FIGS. 65 through 78 and 84 through 95, an air separation feature, e.g., similar to that discussed above with reference to zone C in the implementation of FIGS. 4 through 15, may be included in the main channel in between the areas of interest and the location where fluid α is introduced into the fluidic circuit.

It will be appreciated that references to lyophilized material herein may also include reference to any of a variety of different types of material that may be suitable for mixing or reconstituting with a fluid, e.g., a liquid. Such materials may include powdered substances, liquid concentrates, etc.

While multiple examples of fluidic structures have been described above with respect to various figures, various additional example fluidic structures are discussed below to provide further examples of the flexibility and capabilities offered by the technologies discussed herein.

In addition to earlier examples discussed herein in which wash operations were supported, various other fluidic structures that facilitate wash operations may be implemented in a fluidic circuit. For example, FIG. 96 depicts an example of an alternative fluidic structure that may be used to facilitate wash operations.

Figure 96:
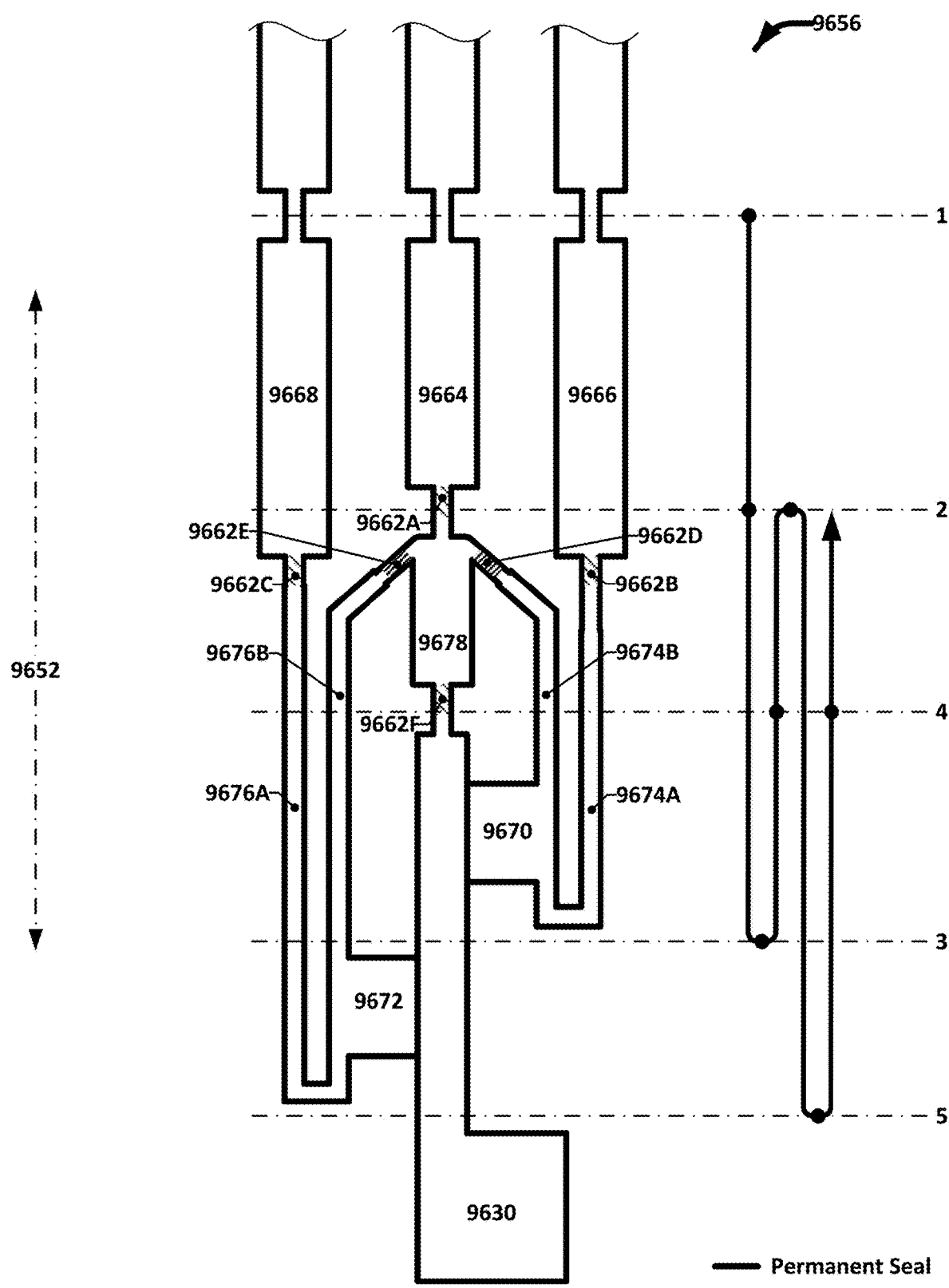
FIG. 96 depicts an example fluidic structure for providing wash capability in a fluidic system.

The fluidic structure of FIG. 96 includes three fluid reservoirs—a sample reservoir 9664, first reservoir 9666, and second reservoir 9668. The sample reservoir 9664 may, for example, contain an analysis sample, e.g., eluted breath sample or other biological sample. The first reservoir 9666 may, for example, contain a first wash fluid, and the second reservoir 9668 may, for example, contain a second wash fluid.

As with other fluidic structures discussed herein, the fluidic structure 9656 may be actuated by applying a moving clamping pressure zone, e.g., via a roller that is pressed into contact with the fluidic structure, to the fluidic structure. In this example, the clamping pressure zone may extend all the way across the depicted fluidic structure and may move along an axis 9652. To avoid undue visual clutter, the clamping pressure zone is not shown in FIG. 96, but broken lines are provided to show various positions that the clamping pressure zone may be moved between during use. Each such broken line is associated with a number that indicates an example order for movements of the clamping pressure zone, as discussed in more detail below.

When the fluidic structure 9656 is actuated, the clamping pressure zone may, for example, move from position 1 to position 2. In doing so, the clamping pressure zone may force the analysis sample from the sample reservoir 9664 into an immobilization chamber 9678, the first wash fluid from the first reservoir 9666 through a first passage 9674A and into a first bolus reservoir 9670, and the second wash fluid from the second reservoir 9668 through a second passage 9676A and into a second bolus reservoir 9672. Dynamic seals 9662A, 9662B, and 9662C having a first release pressure, e.g., having a first width, may seal the sample reservoir 9664, the first reservoir 9666, and the second reservoir 9668 off from the downstream elements of the fluidic structure 9656, e.g., the immobilization chamber 9678, the first passage 9674A and first bolus reservoir 9670, and the second passage 9676A and second bolus reservoir 9672, until the sample reservoir 9664, the first reservoir 9666, and the second reservoir 9668 have been pressurized to a desired threshold.

The first passage 9674A may be fluidically interposed between the first reservoir 9666 and the first bolus reservoir 9670; a continuation of the first passage 9674B may be fluidically interposed between the first bolus reservoir 9670 and the immobilization chamber 9678. A dynamic seal 9662D may be located at the junction of the first passage 9674B with the immobilization chamber 9678. Similarly, the second passage 9676A may be fluidically interposed between the second reservoir 9668 and the second bolus reservoir 9672; a continuation of the second passage 9676B may be fluidically interposed between the second bolus reservoir 9672 and the immobilization chamber 9678. A dynamic seal 9662E may be located at the junction of the second passage 9676B with the immobilization chamber 9678. The dynamic seals 9662D and 9662E may both have a release pressure that is lower than that of the dynamic seals 9662A-C (for example, the dynamic seals 9662D and 9662E may both have widths that are larger than the widths of the dynamic seals 9662A-C). Another dynamic seal 9662F similar to the dynamic seals 9662A-C may be located on an opposite end of the immobilization chamber 9678 from the dynamic seal 9662A so as to retain the sample fluid that is pushed into the immobilization chamber 9678 in the immobilization chamber 9678.

After the analysis sample is pushed into the immobilization chamber 9678, it may, in some instances, be allowed to incubate or otherwise reside in the immobilization chamber 9678 for a period of time. For example, the immobilization chamber may have a biomarker-specific substance that is immobilized on one or more surfaces thereof, such that any biomarker that is in the analysis sample binds to the biomarker-specific substance, thereby immobilizing the biomarker within the immobilization chamber 9678.

After the analysis sample has resided in the immobilization chamber 9678 for a period of time sufficient to immobilize biomarker that is present in the analysis sample, the clamping pressure zone may be moved from position 2 to position 3, thereby increasing the pressure in the immobilization chamber 9678 to the point where the dynamic seal 9662F releases, forcing the sample fluid that is within the immobilization chamber 9678 into a waste reservoir 9630.

At the same time, the clamping pressure zone may also exert clamping pressure on both the first bolus reservoir 9670, the first passage 9674A, and the first passage 9674B. Due to the U-shaped flow path provided by these elements, the fluid that is trapped therewithin is effectively in a state of equilibrium when the clamping pressure zone moves across such elements. Accordingly, the fluid that is present in the first bolus reservoir 9670, the first passage 9674A, and the first passage 9674B will tend to remain stationary as the clamping pressure zone traverses from position 2 to position 3.

After the sample fluid has been evacuated from the immobilization chamber 9678, the clamping pressure zone may be moved from position 3 to position 4, thereby pushing the first wash fluid that is within the first bolus reservoir 9670 up through the first passage 9674B (some amount of first wash fluid may also be pushed back through the first passage 9674A as well, but this is immaterial). The first passage 9674B may be pressurized by the clamping pressure zone to the point where the dynamic seal 9662D is released, allowing the first wash fluid to flow into the immobilization chamber 9678. In some implementations, the volume of fluid contained in the first bolus reservoir 9670 may be larger than the maximum volume of the immobilization chamber 9678. In such implementations, the excess fluid that is pushed into the immobilization chamber 9678 from the first bolus reservoir 9670 and through the dynamic seal 9662D may simply be forced through the dynamic seal 9662A and into the sample reservoir 9664 and/or into the waste reservoir 9630 via the dynamic seal 9662F. The excess fluid that may be pushed into the waste reservoir 9630 may, as the clamping pressure zone traverses from position 3 to position 4, be pushed back into the immobilization chamber 9678 through the dynamic seal 9662F. In some implementations, the dynamic seal 9662F may be designed to have a higher release pressure than the dynamic seal 9662A such that the excess fluid that may be pushed into the immobilization chamber 9678 from the first bolus reservoir 9670 (or the second bolus reservoir 9672, for that matter) may be forced only into the sample reservoir 9664.

It is noted that clamping pressure zone in position 3 may not pressurize the first wash fluid in the first bolus reservoir 9670 or the first passage 9674A or 9674B at all, thus ensuring that when the clamping pressure zone is moved from position 3 to position 4, all of the first wash fluid that is in the first bolus reservoir 9670, the first passage 9674A, and the first passage 9674B will be driven ahead of the advancing clamping pressure zone, with no first wash fluid in the first bolus reservoir 9670, the first passage 9674A, or the first passage 9674B being left behind the advancing clamping pressure zone. This may help ensure that there is no residual first wash fluid that may leak into the immobilization chamber 9678 after the clamping pressure zone is moved from position 4 to position 2. At the same time, position 3 may also be selected such that the clamping pressure zone is not applying pressure to the second bolus reservoir 9672 either, thereby preventing the second wash fluid from being pressurized (aside from by the small amount that may be compressed by the clamping pressure zone within the second passages 9676A and 9676B).

After the first wash fluid has been allowed to wash the immobilization chamber 9678, the clamping pressure zone may be moved from position 4 back to position 2, thereby pushing the first wash fluid from the immobilization chamber 9678 into the sample reservoir 9664 (which may now act as a secondary waste reservoir).

After the first wash fluid is moved into the sample reservoir 9664, the clamping pressure zone may be moved from position 2 to position 5. In doing so, the clamping pressure zone may exert clamping pressure on both the second bolus reservoir 9672, the second passage 9676A, and the second passage 9676B. As with the first bolus reservoir 9670, the first passage 9674A, and the first passage 9674B, due to the U-shaped flow path provided by these elements, the fluid that is trapped therewithin is effectively in a state of equilibrium when the clamping pressure zone moves across such elements. Accordingly, the fluid that is present in the second bolus reservoir 9672, the second passage 9676A, and the second passage 9676B will tend to remain stationary as the clamping pressure zone traverses from position 2 to position 5.

After the clamping pressure zone has been moved to position 5, the clamping pressure zone may be moved from position 5 to position 4, thereby pushing the second wash fluid that is within the second bolus reservoir 9672 up through the second passage 9676B (some amount of second wash fluid may also be pushed back through the second passage 9676A as well, but this is immaterial). The second passage 9676B may be pressurized by the clamping pressure zone to the point where the dynamic seal 9662E is released, allowing the second wash fluid to flow into the immobilization chamber 9678.

The second wash fluid may, for example, be an indicator that is activated in the presence of the immobilized biomarker so as to luminesce (or fluoresce when stimulated by a suitable excitation source, such as by exposure to a particular wavelength of light), while the first wash fluid may be used to wash out the immobilization chamber 9678 prior to introduction of the indicator (second wash fluid). The immobilization chamber 9678 may thus serve as an optical measurement chamber, e.g., light that is emitted, either passively or in response to external stimulation, by the contents thereof after the second wash fluid is delivered thereto may be measured and used to detect the presence and/or quantity of biomarker that was present in the sample.

The arrangement of the first passage 9674A and the first bolus reservoir 9670 and first passage 9674B so as to both be pressurized simultaneously by the clamping pressure zone as it moves along the axis 9652 may, in effect, act as a type of fluidic diode. When the clamping pressure zone traverses over the first passage 9674A and the first bolus reservoir 9670 and the first passage 9674B and towards the short transverse passage that spans between a) the first passage 9674A and b) the first bolus reservoir 9670 and first passage 9674B, the fluid that is contained in the first bolus reservoir 9670 may remain largely stationary, with little bulk fluid flow. When the clamping pressure zone movement is subsequently reversed, however, the fluid that is in the first bolus reservoir 9670 may be caused to flow, in bulk, through the first passage 9674B. The second passage 9676A and the second bolus reservoir 9672 and the second passage 9676B may be similarly configured, although the first bolus reservoir 9670 and the second bolus reservoir 9672 are positioned at spaced apart locations along the axis 9652 such that they do not overlap with one another when viewed along a direction perpendicular to the axis 9652 and parallel to the plane of the Figure.

The size of the first bolus reservoir 9670 may be selected to be large enough that most or all of the fluid that is in the first reservoir 9666 can be contained therewithin (with the remainder, if any, being contained within the first passages 9674A/B). The size of the second bolus reservoir 9672 may similarly be selected to be large enough that most or all of the fluid that is in the second reservoir 9668 can be contained therewithin (with the remainder, if any, being contained within the second passages 9676A/B).

Figure 97:
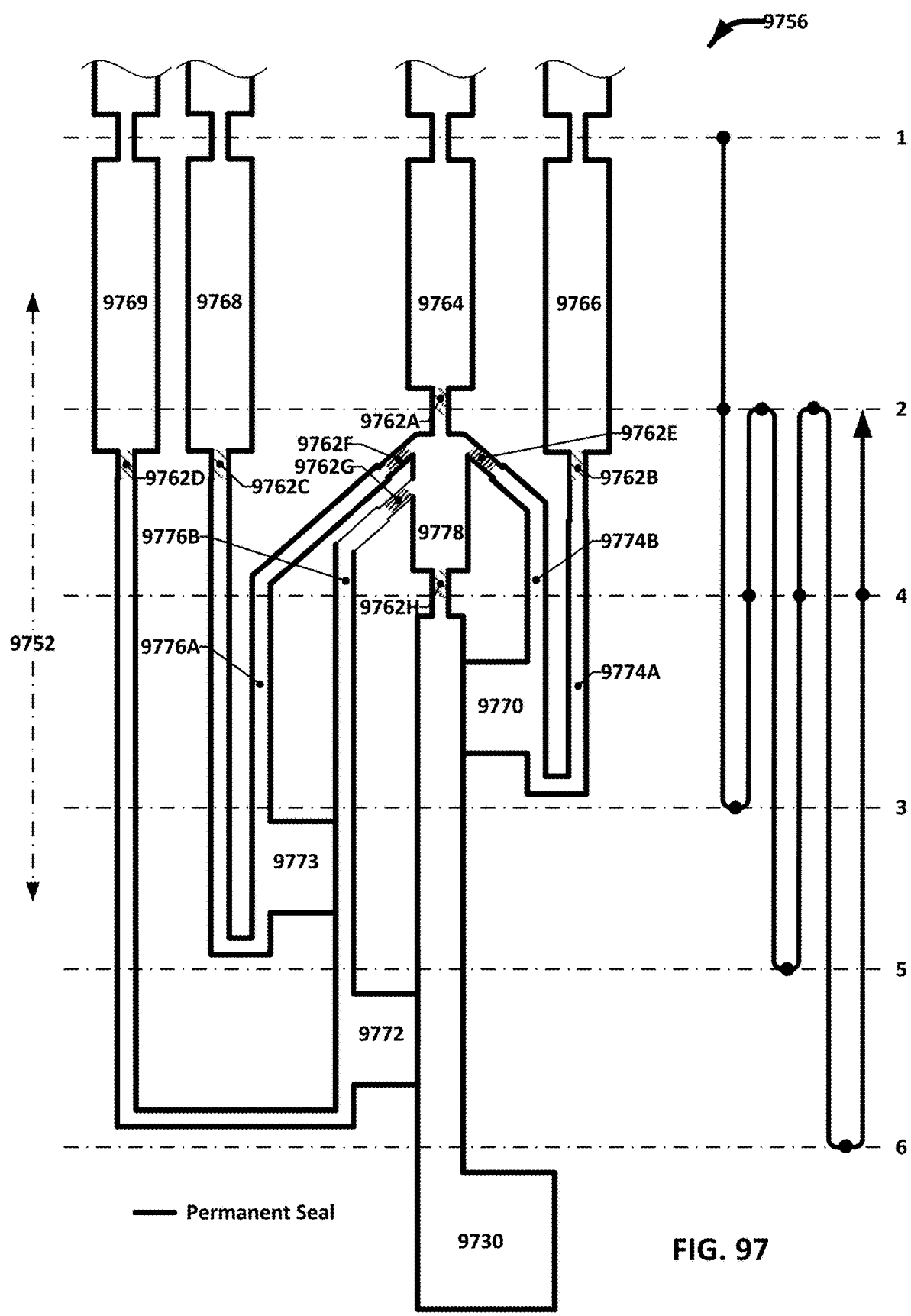
FIG. 97 depicts another example fluidic structure for providing wash capability in a fluidic system.

It is to be understood that while the example of FIG. 96 provided for two separate wash fluid reservoirs, such a fluidic structure may be easily modified to include larger numbers of wash fluid reservoirs (it is also to be understood that while the term "wash fluid" is used herein, the fluids in question may be any type of fluid, e.g., fluids for washing, fluids for performing a reaction, fluids for producing a chemiluminescent response, etc.). FIG. 97, for example, depicts a fluidic structure 9756 that includes a sample reservoir 9764, a first reservoir 9766, a second reservoir 9768, and a third reservoir 9769. Each of the first, second, and third reservoirs 9766, 9768, and 9769 may be fluidically connected with a respective dynamic seal 9762B, 9762C, or 9762E, that leads to a respective first bolus reservoir 9770, second bolus reservoir 9772, or third bolus reservoir 9773, respectively, via a first passage 9774A, second passage 9776A, or third passage 9777A, respectively. The first bolus reservoir 9770, the second bolus reservoir 9772, and the third bolus reservoir 9773 may each respectively be fluidically connected with immobilization chamber 9778 via a first passage 9774B, second passage 9776B, or third passage 9777B, respectively, which may each, in turn, have a dynamic seal 9762E, 9762F, or 9762G, respectively, that connects them with the immobilization chamber 9778.

The various operations that may be performed using the fluidic structure 9756 are not described in great detail as they are very similar to the operations discussed above with respect to FIG. 96. The fluidic structure 9756 may, as with the fluidic structure 9656, be actuated by advancing a clamping pressure zone across the fluidic structure 9756 along axis 9752, moving the clamping pressure zone between various positions so as to sequentially and separately deliver a first wash fluid from the first reservoir 9766, a second wash fluid from the second reservoir 9768, and a third wash fluid from the third reservoir 9769 to the immobilization chamber 9778. For example, the clamping pressure zone may be moved from position 1 to position 2, from position 2 to position 3, from position 3 to position 4, from position 4 back to position 2, from position 2 to position 5, from position 5 back to position 4, from position 4 back to position 2, from position 2 to position 6, from position 6 back to position 4, and then from position 4 back again to position 2. Such a sequence of clamping pressure zone movements may sequentially deliver sample fluid that is in the sample reservoir 9764, the first wash fluid that is in the first reservoir 9766, the second wash fluid that is in the second reservoir 9768, and the third wash fluid that is in the third reservoir 9769 into the immobilization chamber 9778 with little or no mixing between each fluid. This approach, in which different fluidic paths for different fluids may be nested inside each other, e.g., with the passages for one fluidic path/wash fluid interposed between passages for one or more other fluidic paths/wash fluids, may be scaled up to include support for using more than three wash fluids as well.

Figure 98:
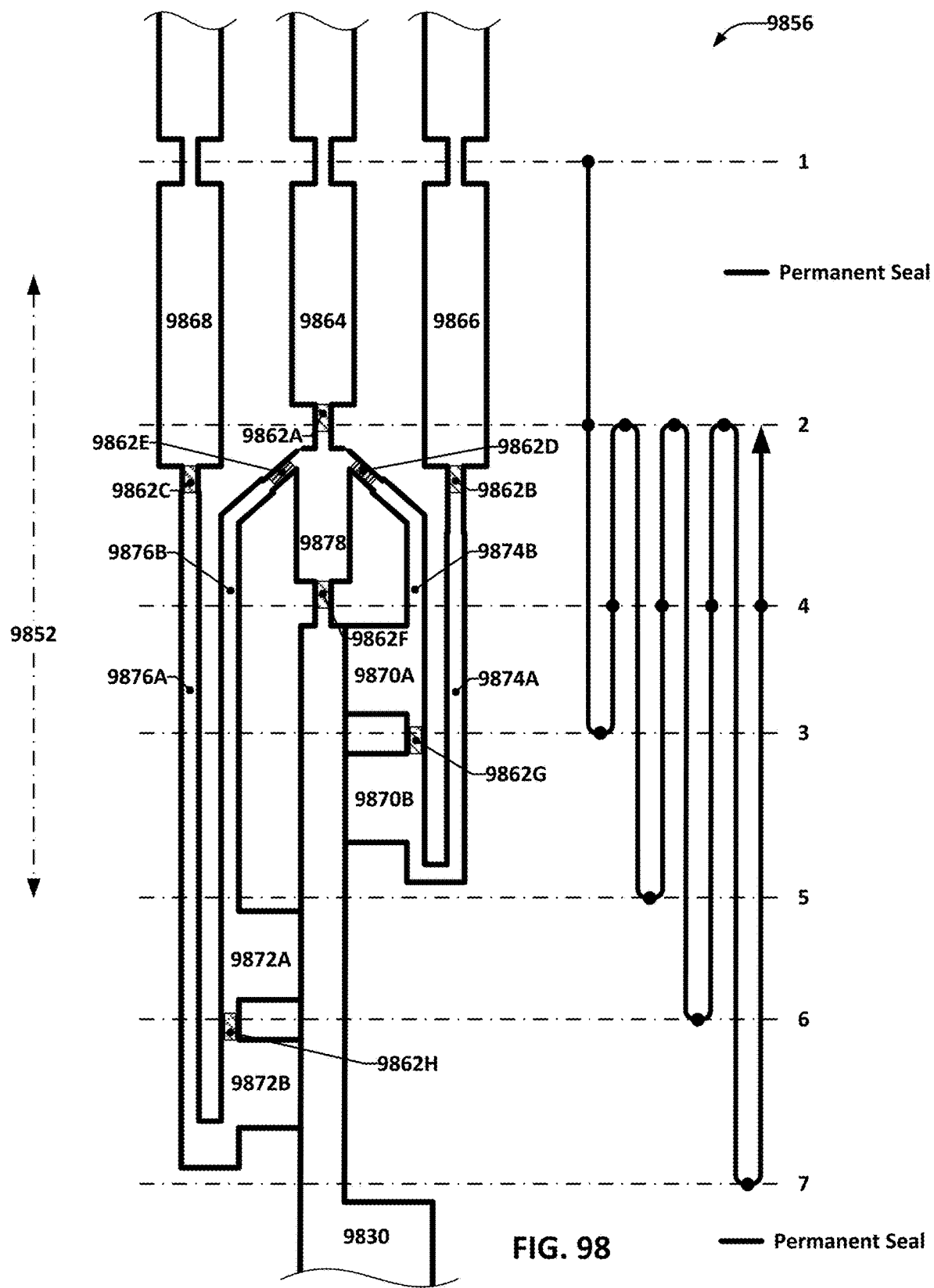
FIG. 98 depicts yet another example fluidic structure for providing wash capability in a fluidic system.

In some implementations, the delivery of wash fluids from reservoirs may be performed in a staged manner, with multiple bolus reservoirs provided for each reservoir flow path (or, alternatively, for only a subset of reservoir flow paths, e.g., one flow path might have a single bolus reservoir, and another might have two or three). FIG. 98 depicts an example of a fluidic structure for providing multi-stage wash capabilities. A fluidic structure 9856 is shown that is very similar to the fluidic structure of FIG. 96. To avoid needless discussion of elements in FIG. 98 that have analogous structures in FIG. 96, the discussion above of elements in FIG. 96 that share the same last two digits (and, where applicable, letter suffix) as similar-appearing elements in FIG. 98 may be considered to be equally applicable to the corresponding elements in FIG. 98 unless indicated otherwise below.

The fluidic structure 9856 of FIG. 98 may be actuated by causing a clamping pressure zone to move along the axis 9852 between various positions 1-7 (as indicated by the dash-dot-dash lines and the numeric callouts to the right of those lines). In contrast to the fluidic structure 9656 of FIG. 96, which had a single first bolus reservoir 9670 and a single second bolus reservoir 9672, the fluidic structure 9856 has two first bolus reservoirs 9870A and 9870B and two second bolus reservoirs 9872A and 9872B. The first bolus reservoirs 9870A and 9870B are fluidically connected in series and are fluidically interposed between the first passage 9874A and the first passage 9874B. Similarly, the second bolus reservoirs 9872A and 9872B are fluidically connected in series and are fluidically interposed between the second passage 9876A and the second passage 9876B. Similar to the first bolus reservoir 9670 and the second bolus reservoir 9672 of FIG. 96, the first bolus reservoirs 9870A/B and the second bolus reservoirs 9872A/B (as well as the immobilization chamber 9878) are positioned at spaced apart locations along the axis 9852 such that they do not overlap with one another when viewed along a direction perpendicular to the axis 9852 and parallel to the plane of the Figure. This allows the bolus reservoirs to be sequentially actuated by the clamping pressure zone as it moves back and forth, by increasingly larger amounts, across the fluidic structure 9856.

The first bolus reservoirs 9870A and 9870B may be sized so as to, collectively, be large enough that most or all of the fluid that is in the first reservoir 9866 can be contained therewithin. At the same time, the first bolus reservoirs 9870A and 9870B may also each be sized such that the total amount of fluid in the first reservoir 9866 does not fit entirely within either of the first bolus reservoirs 9870A or 9870B. This may ensure that each first bolus reservoir 9870A and 9870B contains a separate portion of the fluid from the first reservoir 9866 after the fluid from the first reservoir 9866 is moved to the first bolus reservoirs 9870A and 9870B. The second bolus reservoirs 9872A and 9872B may be similarly configured with respect to the second reservoir 9868.

During operation, a clamping pressure zone may be applied to the fluidic structure 9856 at position 1 and then moved to position 2, thereby pushing the fluids in sample reservoir 9864, first reservoir 9866, and second reservoir 9868 through dynamic seals 9862A, 9862B, and 9862C and into immobilization chamber 9878, the first bolus reservoirs 9870A and 9870B, and the second bolus reservoirs 9872A and 9872B, respectively. In some implementations, such as that shown, there may still be some fluid left in the first reservoir 9866 and/or the second reservoir 9868, at this stage (the same was true for the fluidic structure 9656 as well).

After sample fluid from the sample reservoir 9864 has been allowed to incubate in the immobilization chamber 9878, the clamping pressure zone may be advanced from position 2 to position 3, thereby forcing the sample fluid from the immobilization chamber 9878 past dynamic seal 9862F and towards waste reservoir 9830.

The clamping pressure zone may then be moved from position 3 to position 4, thereby forcing the fluid, e.g., first wash fluid, that is in the first bolus reservoir 9870A to pressurize dynamic seal 9862D (which is designed to have a higher release pressure than that of the dynamic seals 9862A-C) such that the dynamic seal 9862D releases, allowing the pressurized fluid to flow into the immobilization chamber 9878.

After the first wash fluid has been allowed to reside in the immobilization chamber 9878 for some period of time, e.g., sufficient to complete a wash step, the clamping pressure zone may then be moved from position 4 back to position 2, thus driving the first wash fluid through the dynamic seal 9862A (which may have re-sealed once the first wash fluid was initially pushed into the immobilization chamber 9878) into the sample reservoir 9864 (which may, as with the sample reservoir 9664, be used as a secondary waste reservoir).

After the first wash fluid from the first bolus reservoir 9870A is moved to the sample reservoir 9864, the clamping pressure zone may be moved from position 2 to position 5, after which the clamping pressure zone may be moved in the opposite direction from position 5 back to position 4. This will act to pressurize the first wash fluid that is in the first bolus reservoir 9870B such that a dynamic seal 9862G that is fluidically interposed between the first bolus reservoirs 9870A and 9870B releases (the dynamic seal 9862G may, for example, have a release pressure that is similar to that of the dynamic seals 9862A-C), thereby allowing the first wash fluid to flow into the first bolus reservoir 9870A and then subsequently into the immobilization chamber 9878. After this further amount of first wash fluid has been allowed to reside in the immobilization chamber 9878 for some period of time, e.g., to complete a second, repeat wash operation, the clamping pressure zone may again be moved from position 4 to position 2, thus driving the additional first wash fluid in the immobilization chamber 9878 through the dynamic seal 9862A and into the sample reservoir 9864, e.g., to waste.

The clamping pressure zone may then be moved from position 2 to position 6 and then from position 6 to position 4, thereby forcing the fluid, e.g., second wash fluid, that is in the second bolus reservoir 9872A to pressurize dynamic seal 9862E (which is designed to have a higher release pressure than that of the dynamic seals 9862A-C) such that the dynamic seal 9862E releases, allowing the pressurized fluid to flow into the immobilization chamber 9878.

After the second wash fluid has been allowed to reside in the immobilization chamber 9878 for some period of time, e.g., sufficient to complete a wash step, the clamping pressure zone may then be moved from position 4 back to position 2, thus driving the second wash fluid through the dynamic seal 9862A into the sample reservoir 9864.

After the second wash fluid from the second bolus reservoir 9872A is moved to the sample reservoir 9864, the clamping pressure zone may be moved from position 2 to position 7, after which the clamping pressure zone may be moved in the opposite direction from position 7 back to position 4. This will act to pressurize the second wash fluid that is in the second bolus reservoir 9872B such that a dynamic seal 9862H that is fluidically interposed between the second bolus reservoirs 9872A and 9872B releases (the dynamic seal 9862H may, for example, have a release pressure that is similar to that of the dynamic seals 9862A-C), thereby allowing the second wash fluid to flow into the second bolus reservoir 9872A and then subsequently into the immobilization chamber 9878.

It will be appreciated that any number of bolus reservoirs may be used for either wash fluid flow path, depending on the number of repeat wash cycles that may be desired for each wash fluid with respect to the immobilization chamber 9878. It will also be appreciated that other dynamic seals may form within various portions of the fluidic structure 9856 other than those specifically indicated, for example, where the first passage 9874A fluidically connects with the first bolus reservoir 9870A, and that such dynamic seals may also be caused to release by the above-described movements of the clamping pressure zone as appropriate.

In contrast to fluidic structures such as those discussed with respect to FIGS. 96 and 98 that provide the capability to flow multiple different fluids through a common chamber while generally keeping such fluids from mixing, some fluidic structures may be specifically designed to promote mixing. For example, the zig zag or switchback fluidic structures discussed elsewhere herein may provide fluid flow characteristics that may facilitate mixing of two fluids that are provided from separate input flow paths. In addition to such zig zag or switchback fluidic structures, various other types of fluidic structures that may be used to facilitate fluid mixing are depicted in FIGS. 99-106.

FIGS. 99-101 depict three different examples of fluidic structures 9956 that each include a plurality of vortex chambers 9980 that are fluidically connected to one another in series. Each vortex chamber may be provided a fluid through an input passage 9982 that splits into multiple passages including at least one crossflow passage 9986 and at least one tangential flow passage 9988. Each vortex chamber 9980 may have an overall shape, as defined by permanent seals that join two portions of materials together (one or both of which is flexible), that is generally circular or otherwise conducive to supporting recirculating fluid flow within the vortex chamber 9980. Each tangential flow passage 9988 may be fluidically connected with a corresponding vortex chamber 9980 such that the fluid that is flowed from the tangential flow passage 9988 into the corresponding vortex chamber 9980 tends to flow in a circumferential manner, e.g., along the permanent seals that define the vortex chamber 9980. In some implementations, a permanent seal that defines one side of a tangential flow passage 9988 may meet with (or transition to) a permanent seal that defines part of the vortex chamber 9980 in a tangential manner, and the fluid that flows out of such a tangential flow passage 9988 and into the vortex chamber 9980 may flow in a direction that is generally tangential to the permanent seal that defines the vortex chamber 9980 at that point. It will be understood that the tangential flow passage 9988 does not, despite its name, need to fluidically connect with the permanent seal that defines the vortex chamber 9980 in a perfectly tangential manner, but can also fluidically connect therewith in a manner that is not perfectly tangential. For example, the tangential flow passage 9988 may direct fluid that flows out of the tangential flow passage 9988 along a vector that forms an angle of 100 or less, 20° or less, 300 or less, 40° or less, or 450 or less with a reference line that is tangential to the outer boundary of the vortex chamber 9980 where the tangential flow passage 9988 fluidically connects. Thus, fluid that is flowed into the vortex chamber 9980 through the tangential flow passage 9988 may tend to swirl within the vortex chamber 9980.

In contrast, the fluid that is flowed through the crossflow passage 9986 may be directed into the vortex chamber 9980 along a direction that is more radial in nature, e.g., directed along a vector that forms an angle of 100 or less, 200 or less, 300 or less, 400 or less, or 450 or less with a reference line that extends from a center point of the vortex chamber 9980 out to where the crossflow passage 9986 intersects with the permanent seal that defines the vortex chamber 9980. As a result, the fluid flow from the crossflow passage 9986 may generally be caused to flow "across" the swirling flow field of the fluid that is flowed into the vortex chamber 9980 by the tangential flow passage 9988. This intersection of two fluid flows travelling along non-aligned flow paths results in turbulence within the vortex chamber 9980 that promotes more effective mixing of the two fluid flows as the vortex chamber 9980 is filled with fluid and pressurized. The vortex chamber 9980 may also be fluidically connected with an output passage 9984 that is sealed off from the vortex chamber by a dynamic seal 9962. Once the fluid in the vortex chamber 9980 has been pressurized to a first threshold amount, e.g., exceeding the release pressure for the dynamic seal 9962, the dynamic seal 9962 will release and the fluid may then flow into a subsequent downstream location. In the example of FIG. 99, there are four vortex chambers 9980 arranged in series, with the output passage 9984 of each transitioning to the input passage 9982 of the next vortex chamber 9980 in the series. As the fluid mixture passes through each vortex chamber 9980, it will become more and more evenly mixed, although it is understood that fluidic structures such as the fluidic structure 9956 may include fewer vortex chambers 9980, including as few as a single vortex chamber 9980, or more vortex chambers 9980 depending on the degree of mixing desired.

FIGS. 100 and 101 depict similar vortex mixer fluidic structures, but in the case of the FIG. 100, the fluidic structure 9956 includes crossflow passages 9986 that intersect with the permanent seal that defines the vortex chamber 9980 at different locations, e.g., offset closer to the output passage 9984. In the case of FIG. 101, the crossflow passages 9986 are offset closer to the input passage 9982. All three fluidic structures 9959 of FIGS. 99-101 may provide effective mixing, however.

The vortex chambers and tangential/crossflow passages discussed in the above examples may be sized such that the maximum volume of each vortex chamber and tangential/crossflow passages is approximately equal to the volume of fluid that is to be mixed, thereby avoiding potential situations in which there may be a portion of one fluid or the other that is not able to be present in the vortex chamber or tangential/crossflow passages during mixing and would therefor potentially not be mixed.

Figures 102, 103:
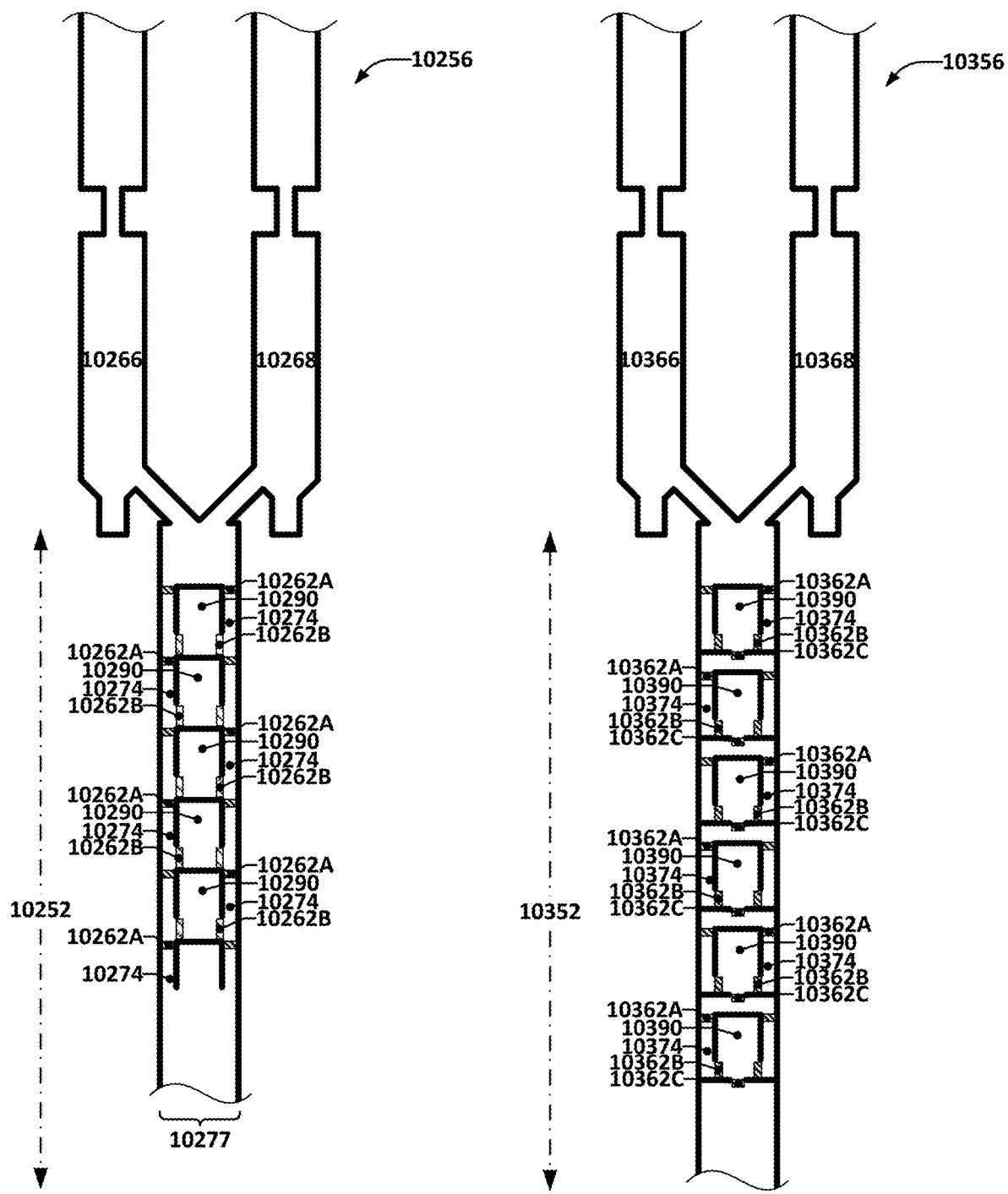
FIG. 102 depicts another example fluidic structure for providing mixing capability in a fluidic system.
FIG. 103 depicts another example fluidic structure for providing mixing capability in a fluidic system.

FIG. 102 depicts an example of a fluidic structure 10256 that includes a plurality of mixing chambers 10290 that are each positioned between two passages 10274 in a generally linear array along an axis 10252; in use, a clamping pressure zone may be advanced along the fluidic structure 10256 from the "top" of the fluidic structure 10256 to the "bottom" of the fluidic structure 10256 (with respect to the orientation of the Figure). Two different fluids stored in first reservoir 10266 and 10268 may be forced from their respective reservoirs by the advancement of the clamping pressure zone and then sequentially through the mixing chambers 10290. Each mixing chamber 10290 may be defined by two permanent seals: an upstream seal and a downstream seal. The upstream seal, which in FIG. 102 has the appearance of a sharp-cornered, upside-down U, may have opposing sidewalls that approach, but do not intersect with, the downstream seal of that mixing chamber 10290. The opposing sidewalls of the upstream seal may be connected together with a transverse segment such that the mixing chamber 10290 is defined, at least in part, between the upstream seal and the downstream seal thereof. In the implementation of FIG. 102, it will be observed that the transverse segments of the five lower upstream seals also serve as the lower seals for the mixing chambers immediately above each of the transverse segments. In other implementations, however, the transverse segments and the lower seals for the various mixing chambers 10290 may actually be provided by entirely separate permanent seals.

Each passage 10274 may generally be defined by two sidewalls-one that is provided by, or proximate to, one of the sidewalls of the upstream seal that defines a corresponding mixing chamber 10290, and the other that is defined by a wall of a much larger passage or chamber that the corresponding mixing chamber 10290 is located within. For example, in the depicted fluidic structure 10256, the two reservoirs 10266 and 10268 are both fluidically connected with a larger passage 10277 that contains the linear array of mixing chambers 10290. The larger passage 10277 has a width transverse to the axis 10252 for at least part of its length that is wider than the width of the upstream seals of the mixing chambers 10290. The passages 10274 are, as depicted, each defined by one of the sidewalls of the larger passage 10277 and one of the sidewalls of the upstream portion of a corresponding one of the mixing chambers 10290.

Each passage 10274 may be sized such that a dynamic seal 10262A comes into being in each such passage 10274 at location that is generally in between the downstream seal for a given mixing chamber 10290 and ends of the upstream seal for that mixing chamber 10290 that are proximate to the downstream seal for that mixing chamber 10290.

At the same time, dynamic seals 10262B may also be found sealing off each mixing chamber 10290 from the passages 10274. Each dynamic seal 10262B may form in between the upstream seal and the downstream seal for each mixing chamber 10290. The dynamic seals 10262B for a given mixing chamber 10290 may be positioned on opposite sides of the mixing chamber 10290 and generally at the same axial position along the axis 10252 such that fluid flowing through either or both dynamic seals 10262B of a mixing chamber 10290 after those dynamic seals 10262B are released will flow, at least initially, towards the other of those dynamic seals 10262B. When such fluid flows through both dynamic seals 10262B for a given mixing chamber 10290 simultaneously, the two fluid flows will tend to collide with each other, thereby generating turbulence within the mixing chamber 10290 and causing the combined fluid flow to reverse direction and flow towards the transverse segment of the upstream seal of the mixing chamber 10290.

The dynamic seals 10262A may be designed to have a higher release pressure than the dynamic seals 10262B, e.g., the dynamic seals 10262A may have narrower widths than the dynamic seals 10262B, such that fluid that is forced into the passages 10274 by movement of the clamping pressure zone towards the bottom of the fluidic structure 10256 (with respect to the Figure orientation) will, in pressurizing the passages 10274 for a given mixing chamber 10290, cause the dynamic seals 10262B to release and the mixing chamber 10290 to fill with fluid prior to causing the dynamic seals 10262A for the next downstream mixing chamber 10290 to release and allow the fluid to flow into the next downstream passages 10274. In some implementations, the dynamic seals 10262B may be omitted, e.g., the gaps between permanent seals that are present in the locations where the dynamic seals 10262B are located may be large enough that no dynamic seal forms at those locations. Regardless, as the clamping pressure zone continues to advance along the fluidic structure 10256, the fluid that is contained within the fluidic structure 10256 will be caused to jet into each mixing chamber 10290, mix and reverse direction to flow in a direction opposite the direction of travel of the clamping pressure zone, and then be re-pressurized as the clamping pressure zone applies pressure to the mixing chamber 10290 and forces the fluid contained therein to move in the direction of advancement of the clamping pressure zone. The re-pressurized fluid may be prevented from advancing further by the dynamic seals 10262A that seal off the passages 10274 for the next downstream mixing chamber 10290 until the fluid has been pressurized to the point there those dynamic seals 10262A release, thereby allowing the fluid to proceed to the next downstream passages 10274. This process may be repeated for each mixing chamber 10290, with the fluid becoming more and more mixed after passage through each mixing chamber 10290. In some implementations, the interior corners of the mixing chambers 10290 may be filleted or rounded to promote more effective mixing by eliminating or reducing the dead zones where fluid flow may stagnate.

FIG. 103 depicts an example of a fluidic structure 10356 that operates in a manner similar to how the fluidic structure 10256 operates. In the fluidic structure 10356, a first reservoir 10366 and a second reservoir 10368 that respectively stored two different fluids are provided. When a clamping pressure zone is advanced across the fluidic structure 10356 along axis 13252 and from the reservoirs 10366 and 10368 across mixing chambers 10390, the fluids contained within the reservoirs 10366 and 10368 will be pushed through each of the mixing chambers 10390 in sequence. As in the fluidic structure 10256, the mixing chambers 10390 are each bounded by an upstream seal, but the downstream seal of the mixing chambers 10390 is provided by two separate permanent seals that each extend inwards from the sides of a larger passage 10377 within which the mixing chambers 10390 are located.

As in the fluidic structure 10256, each mixing chamber 10390 of the fluidic structure 10356 may be positioned between two passages 10374 that allow fluid to move past the mixing chamber 10390 so that the fluid can then be redirected by the downstream seal for that mixing chamber 10390 so as to flow into that mixing chamber 10390 before being directed on to the next downstream mixing chamber 10390.

Each passage 10374 may generally be defined by two sidewalls-one that is provided by, or proximate to, one of the sidewalls of the upstream seal that defines a corresponding mixing chamber 10390, and the other that is defined by a wall of the larger passage 10377 that the corresponding mixing chamber 10390 is located within. For example, in the depicted fluidic structure 10356, the two reservoirs 10366 and 10368 are both fluidically connected with a larger passage 10377 that contains a linear array of mixing chambers 10390. The larger passage 10377 has a width transverse to the axis 10352 for at least part of its length that is wider than the width of the upstream seals of the mixing chambers 10390. The passages 10374 are, as depicted, each defined by one of the sidewalls of the larger passage 10377 and one of the sidewalls of the upstream portion of a corresponding one of the mixing chambers 10390.

As shown in FIG. 103, dynamic seals 10362A, 10362B, and 10362C for each mixing chamber 10390 are provided at various locations. As fluid is pushed through each mixing chamber 10390, the fluid will first encounter the dynamic seals 10362A which, when pressurized to their release pressure, will open to allow the fluid to flow into the passages 10374 immediately downstream. The fluid will then pressurize the passages 10374 until the pressure causes the dynamic seals 10362B for that mixing chamber 10390 to release and allow the fluid to enter the mixing chamber 10390. The dynamic seal 10362C will prevent the fluid from leaving the mixing chamber 10390 until the clamping pressure zone has advanced sufficiently far enough along the axis 10352 to cause the pressure within the mixing chamber 10390 to reach the release pressure for the dynamic seal 10362C, at which point the fluid will be pushed onwards through the fluidic structure 10356 to the next mixing chamber 10390.

Unlike in the fluidic structure 10256, the dynamic seals used in the fluidic structure 10356 may all, if desired, have the same release pressure, as each stage of dynamic seals (A/B/C) is pressurized and released in sequence regardless of what release pressure is used for each dynamic seal stage. In contrast, in the fluidic structure 10256, the dynamic seals 10262A need to have higher release pressures than the dynamic seals 10262B so as to force the fluid from the passages 10274 and into the mixing chambers 10290 before the fluid is allowed to proceed onwards to the next passages 10274.

Figure 104:
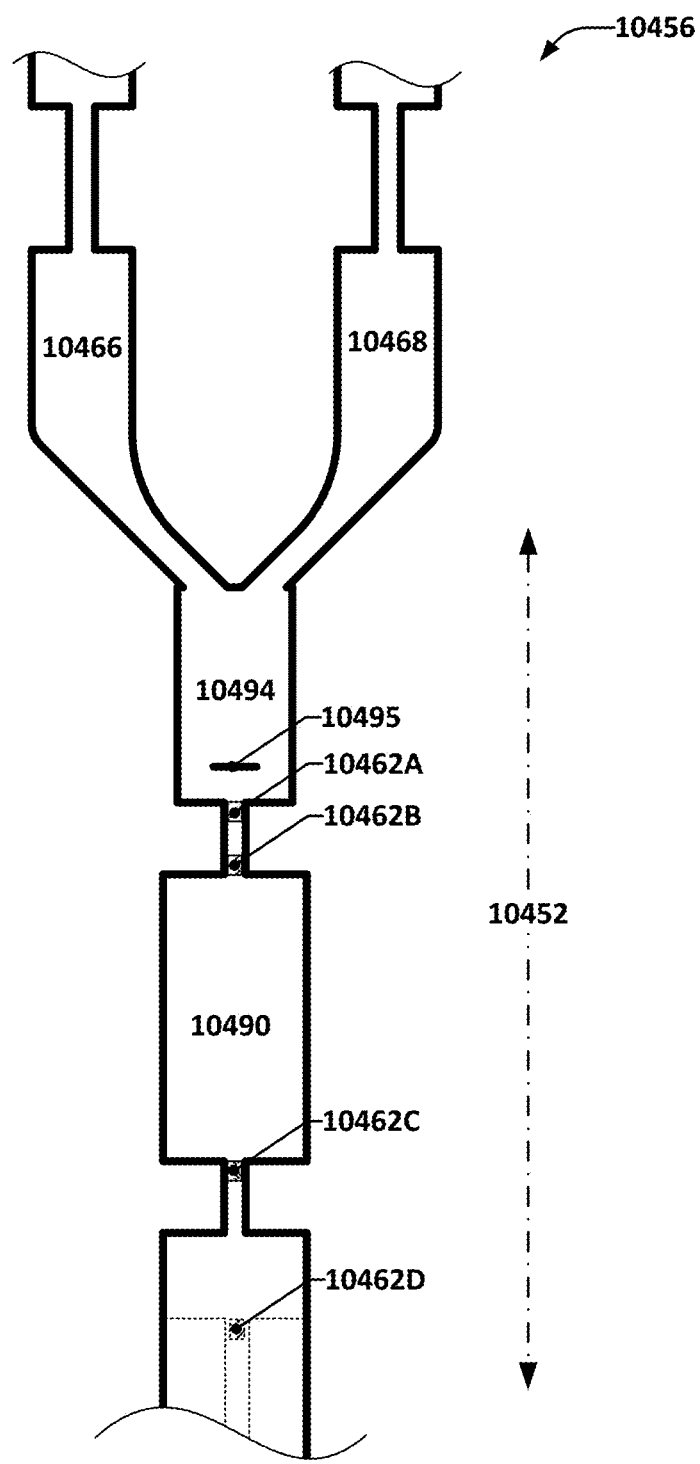
FIG. 104 depicts another example fluidic structure for providing mixing capability in a fluidic system.

FIG. 104 depicts an example of a fluidic structure 10456 that may be used to provide for mixing of two or more fluids. The fluidic structure 10456 may include a first reservoir 10466 and a second reservoir 10468 that may both be fluidically connected with a staging chamber 10494 that is fluidically connected with a mixing chamber 10490. A short passage may fluidically connect the end of the mixing chamber 10490 closest to the staging chamber 10494 with the staging chamber 10494, and another short passage may fluidically connect the end of the mixing chamber 10490 furthest from the staging chamber 10494 with various fluidic features (not shown) downstream of the mixing chamber 10490. As with many other example fluidic structures discussed herein, the fluidic structure 10456 may be actuated by causing a clamping pressure zone to advance across the fluidic structure 10456 and, for at least some portions of the fluidic structure 10456, move back-and-forth along the fluidic structure. The clamping pressure zone may move along axis 10452.

In the example of FIG. 104, different fluids may be driven from the first reservoir 10466 and the second reservoir 10468 and into the staging chamber 10494 by the advancement of the clamping pressure zone towards the mixing chamber 10490. The staging chamber 10494 may be pressurized through further advancement of the clamping pressure zone until the release pressure for a dynamic seal 10462A is reached, at which point the dynamic seal 10462A may be released and fluid from the staging chamber 10494 may be caused to flow into the mixing chamber 10490.

It will be noted that in FIG. 104, the staging chamber 10494 features a floating seal 10495, which is a permanent seal that is not used as a seal, e.g., to prevent fluid flow from reaching a particular part of the fluidic structure 10856, but is instead used to mechanically limit the amount of distension that may occur in the portions of material in the immediate vicinity of a dynamic seal when subjected to pressurization.

For example, it was found that in some instances, a dynamic seal might not reliably release at a particular pressure. Without being bound by theory, it is believed that a dynamic seal that is located where a passage fluidically connects with a much larger chamber or reservoir may not reliably release potentially due to the higher "wall height" and/or increased verticality formed by the bulging of the flexible material portion(s) that define the reservoir or chamber. The portion(s) of flexible material in the vicinity of the dynamic seal may, due to the magnitude with which the flexible material may bulge, form creases that are sufficiently stiff that they may release at much higher pressures. Such higher pressures may, in turn, make such dynamic seals more sensitive to variations in construction in terms of release pressure, thereby making them potentially less reliable in some circumstances. In other situations, the amount of pressure required to achieve the release pressure for a dynamic seal may be so high that the apparatus used to provide the clamping pressure zone may have difficulty in advancing the clamping pressure zone along the fluidic structure due to the presence of pressurized fluids acting as "speedbumps."

Use of floating seals, such as the floating seals 10895, may allow for dynamic seals to be used at the junctions between smaller-width passages, e.g., 1 mm, 0.9 mm, 0.8 mm, 0.7 mm, 0.6 mm, 0.5 mm, 0.4 mm, 0.3 mm, etc., and much larger chambers or reservoirs, e.g., having widths in line with the passage that are 4×, 5×, 6×, or higher than the widths of the passage. By locating a floating seal 10895 within the larger reservoir or chamber in a location spaced apart, e.g., by a distance of 1-2 mm, e.g., 1.2-1.6 mm, e.g., 1.3-1.5 mm, e.g., 1.4 mm, from the permanent wall of that reservoir or chamber in which a dynamic seal is located and in close proximity to where that dynamic seal is located, e.g., centered on the dynamic seal or overlapping at least a portion of the dynamic seal when viewed along an axis generally perpendicular to the transverse width of the dynamic seal, the portions of material that define the reservoir or chamber and are able to flex or bulge may be limited to the extent that they may do so, thereby limiting the size of the crease that can develop in the portions of material spanning the dynamic seal area due to pressurization of the reservoir or chamber. The floating seals, in effect, may act as a stitch that prevents the portions of material defining the reservoir or chamber from fully inflating and ballooning outwards too much. By limiting the amount that the portions of material may distend, the release pressure of the dynamic seals adjacent thereto may be prevented from becoming too high, thereby ensuring more reliable operation.

In the case of the fluidic structure 10456, the staging chamber 10494 is equipped with a floating seal so as to cause the dynamic seal 10462A to operate reliably at a predictable and manageable release pressure. When the dynamic seal 10462A is released, the fluid in the staging chamber 10494 is flowed into the mixing chamber 10490. The mixing chamber 10490, as mentioned earlier, may be fluidically connected at either end with short passages, e.g., leading to the staging chamber 10494 and various fluidic features (not shown) downstream of the mixing chamber 10490. Each such passage may have a corresponding dynamic seal where it fluidically connects with the mixing chamber 10490. For example, a dynamic seal 10462B may be located where the passage from the staging chamber 10494 fluidically connects with the mixing chamber 10490, and a dynamic seal 10462C may be located where the passage from the staging chamber 10494 to the downstream fluidic structures fluidically connected with the mixing chamber 10490. Since the mixing chamber 10490 has no floating seal structures that limit the amount of distension in the vicinity of the dynamic seals, pressurization of the mixing chamber 10490 may cause the dynamic seals 10462B and 10462C to seal shut and have release pressures that are too high to be reliably actuated. In effect, the dynamic seal 10462B acts as a form of fluidic diode or one-way valve, allowing fluid to flow into the mixing chamber 10490 from the staging chamber 10494, but generally preventing the reverse flow from occurring.

Once the fluid is moved into the mixing chamber 10490, the fluid may be subjected to one or more back-and-forth applications of the clamping pressure zone. For example, a roller that is used to apply the clamping pressure zone may be caused to move back and forth across the mixing chamber 10490 so as to displace the fluid housed therein from one end of the mixing chamber 10490 to the other, thereby increasing the amount of mixing experienced by the fluid. While this has the effect of pressurizing the fluid that is trapped ahead of the clamping pressure zone with respect to the direction of motion thereof, the pressurized fluid may, in general, be insufficient to cause the dynamic seals 10462B and 10462C from releasing.

It will be understood that some small amount of fluid may still leak out through a closed dynamic seal-even when the dynamic seal's release pressure is not exceeded and especially when the clamping pressure zone gets close to the dynamic seal. This is because the clamping pressure zone, if applying sufficient clamping force, may act to push the portion(s) of material that are used to form the fluidic structure downward, i.e., thus reducing the bulge height of the fluidic structure in the location of the clamping pressure zone. As a result, the creases that form where the portion(s) of material that define the mixing chamber 10490 intersect with the passages where the dynamic seals 10462B and 10462C are located when the mixing chamber 10490 is pressurized may be less steep/sharp and of a lower height, thereby reducing the bending moment of such creases and allowing for a lower release pressure. The clamping pressure zone may thus, in effect, act as a temporary floating seal, allowing the adjacent dynamic seal to open and release a small amount of fluid. Such release may be avoided or mitigated by reducing the stroke of the clamping pressure zone, e.g., moving the clamping pressure zone back-and-forth over the mixing chamber 10490 by an amount that is less than the length of the mixing chamber 10490 along the axis 10452 such that the clamping pressure zone is kept from approaching within a certain distance of either dynamic seal and the crease height/stiffness is prevented from decreasing too much, and/or by changing the speed with which the clamping pressure zone traverses back and forth over the mixing chamber 10490, e.g., the quicker the clamping pressure zone moves, the less opportunity there will be for potential leaks to occur through either dynamic seal 10462B and 10462C.

Once the fluid within the mixing chamber 10490 has been mixed a desired number of times, the fluid may be pushed through the dynamic seal 10462C and into further fluidic structures (not shown) downstream of the mixing chamber 10490. As mentioned above, the dynamic seal 10462C may generally be resistant to releasing due to the size of the mixing chamber 10490. However, repeated movements of the clamping pressure zone to the dynamic seal 10462C may nonetheless cause a small amount of fluid to leak past the dynamic seal 10462C with each such movement, thereby allowing the contents of the mixing chamber 10490 to be moved in small portions over a period of time.

In an alternative implementation, a heater may be provided in a location near the dynamic seal 10462C (e.g., within a platen used to support the fluidic structure during application of the clamping pressure zone), similar to the relative positioning of the floating seal 10495 relative to the dynamic seal 10462A and may, when the clamping pressure zone is applying pressure to that region of the portions of material that form the fluidic circuit, be activated to form a thermal bond between the portions of material sandwiched between the clamping pressure zone and the heater element. This may, in effect, create another floating seal that operates in a manner similar to the floating seal 10495. In another or alternative implementation, the dynamic seals 10462A/B may be augmented by, or replaced by, a seal that is formed in-situ using a heating element in the platen that supports the fluidic structure 10456 and clamping pressure from the clamping pressure zone. Such a thermally bonded seal creates a permanent seal that seals off the staging chamber 10494 from the mixing chamber 10490, thereby preventing the fluid provided to the mixing chamber 10490 from flowing back into the staging chamber 10494. In some implementations, the mixing chamber 10490 may be connected via the passage with the dynamic seal 10462C to an optional downstream "catch basin" chamber, e.g., a 5×5 mm chamber, that acts to catch any fluid that might leak past the dynamic seal 10462C. The catch basin chamber may, in turn, be connected with another passage via another dynamic seal 10462D that may act to retain such leaked fluid within the catch basin until mixing is completed, at which point the clamping pressure zone may be advanced to push all of the fluid in the mixing chamber 10490 through the catch basin, reuniting (and mixing) the fluid in the catch basin with the fluid from the mixing chamber.

In addition to the chamber-based mixing examples discussed above, various other types of mixing structures may be provided according to the disclosure contained herein. Some examples of such mixing structures are discussed below.

Figure 105:
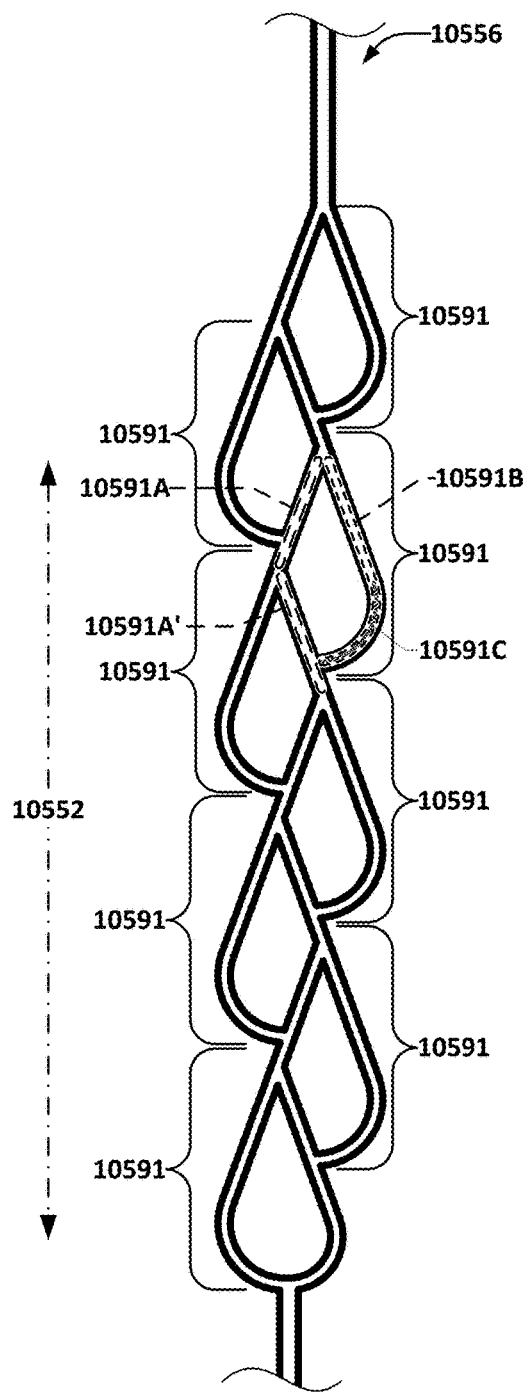
FIG. 105 depicts an example fluidic structure with etrier mixing features.
Figure 106:
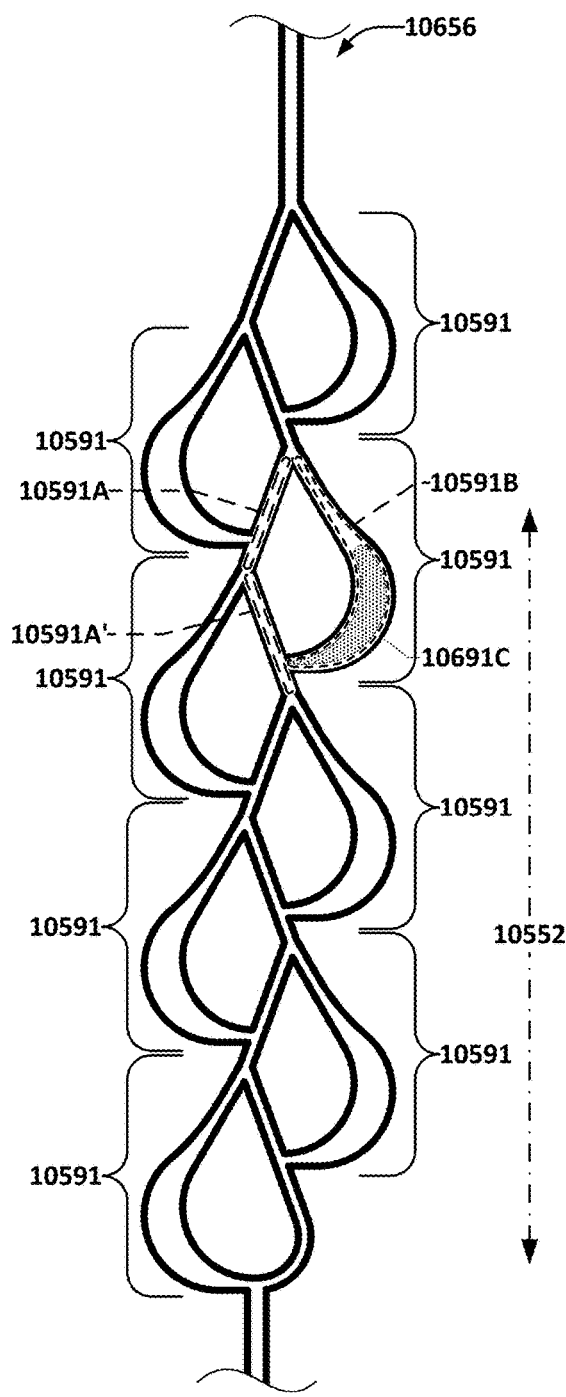
FIG. 106 depicts another example fluidic structure with etrier mixing features.

FIGS. 105 and 106 depict fluidic structures incorporating etrier mixers, which appear somewhat similar to one-way Tesla valves but, importantly, do not provide the one-way valve functionality that a Tesla valve does. In FIG. 105, a fluidic structure 10556 is shown that features an etrier mixer. An etrier is a ladder used in rock climbing which is typically made of alternating loops of webbing or other material that are connected together to form a shape similar to that of the etrier mixer shown in FIG. 105.

The fluidic structure of FIG. 105 features a chain of etrier mixing elements 10591 that generally (the first and last etrier mixing elements in an etrier mixer may differ slightly) each include at least one first short segment 10591A, a second short segment 10591A', a long segment 10591B, and a curved portion 10591C that forms part of the longer segment 10591B. As with other fluidic mixing structures discussed herein, a clamping pressure zone may be advanced along the fluidic structure 10556 and along the axis 10552, e.g., from the top towards the bottom (relative to the orientation of FIG. 105), in order to cause the fluidic structure 10556 to mix two or more fluids more effectively.

Various specific characteristics of etrier mixing elements are discussed below, but it will be appreciated that the first and last etrier mixing elements in a chain of etrier mixing elements may have somewhat differing characteristics from the general characteristics discussed below by virtue of their placement at the opposing ends of the chain.

The short segment 10591A of each etrier mixing element 10591 may fluidically connect with the other short segment 10591A' of the etrier mixing element 10591 so as to form a "V" shape, i.e., the fluid that flows through the short segments 10591A and 10591A' may have a flow component that is in one direction perpendicular to the axis 10552 when flowing through the short segment 10591A and a flow component that is in the opposite direction perpendicular to the axis 10552 when flowing through the short segment 10591A'. It will be appreciated that the short segment 10591A' for one etrier mixing element 10591 may also be the short segment 10591A for the etrier mixing element 10591 immediately downstream of that etrier mixing element 10591. Similarly, the short segment 10591A for one etrier mixing element 10591 may also be the short segment 10591A' for the etrier mixing element 10591 immediately upstream of that etrier mixing element 10591.

The long segment 10591B of an etrier mixing element 10591 may, in the meantime, fluidically connect at one end with the upstream end of the short segment 10591A and may fluidically connect at the other end with the short segment 10591A' of that etrier mixing element 10591. A curved portion 10591C of the long segment 10591B may fluidically connect with the short segment 10591A', while another portion of the long segment 10591B upstream of the curved portion 10591C may fluidically connect with the short segment 10591A. The portion of the long segment 10591B that connects with the short segment 10591A may be generally straight or have a shallow radius of curvature or otherwise have a shallow amount of non-linearity to its path, and may fluidically connect with the end of the short segment 10591A such that the centerline of the long segment 10591B at that junction is generally parallel with the centerline of the short segment 10591A' of the immediately upstream etrier mixing element 10591. Thus, fluid that flows through each short segment 10591A and into the immediately downstream long segment 10591B may do so with little or no change in direction. In contrast, the fluid that flows through each short segment 10591A and into the immediately downstream short segment 10591A' may undergo a change in flow direction, e.g., as discussed earlier.

The fluid that flows through the long segments 10591B may, as it flows therethrough, have its flow direction changed in the curved portion 10591C such that when the curved portion 10591C fluidically connects with the short segment 10591A' of the corresponding etrier mixing element 10591, the fluid flow entering the short segment

10591A' may do so at an oblique or perpendicular angle to the centerline of the short segment 10591A' and may, in fact, have a flow direction component that points opposite the flow direction of the fluid flowing through the short segment 10591A'. This causes the fluid that flows through the short segments 10591A' and the fluid that flows through the long segments 10591B to flow in opposite directions from each other when they first meet, although the fluid will eventually, due to the advancement of the clamping pressure zone along the axis 10552, force the fluid to continue to flow downstream. At each junction of a long segment 10591B with a short segment 10591A', there will be some amount of counterflow and turbulence that causes the fluids present to intermix and become more homogenous.

FIG. 106 depicts a similar arrangement in the form of fluidic structure 10656, which also has etrier mixing elements 10591 with short segments 10591A and 10591A' and long segments 10591B, but the long segments 10591B have curved portions 10691C that change in cross-sectional width along their lengths, bulging thicker in the middle than at the ends. This extra volume provides additional room for vortex mixing to occur within the long segments 10591B and also allows for a larger amount of fluid to be mixed in each mixing element 10591 without necessarily increasing the length of the mixing element 10591 along the axis 10552.

It will be noted that in both fluidic structures 10556 and 10656, there is no point in the etrier mixing elements where fluid would become trapped as a clamping pressure zone that extends along a line perpendicular to the axis 10552 is moved in either direction. In contrast, the construction of a Tesla valve involves curved passages that, when they intersect with short segments similar to those in the etrier mixing elements discussed herein, generally do so at such a large oblique angle, e.g., on the order of potentially as much as 150° or more between the flow through the short segments and the flow that exits the curved passages into the short passages, that the curved portions thereof effectively form a U-shape, allowing fluid to become trapped in the bottom of the U if a clamping pressure zone were to be advanced across a Tesla valve structure along, for example, an axis such as axis 10552 in a particular direction. Tesla valves require the use of such large oblique angles so that the flow direction of the fluid that is directed into the short segments from the curved portions of the longer segments is almost entirely in the opposite direction from the flow of fluid through the short segments. In contrast, etrier mixing elements use smaller oblique or perpendicular angles, e.g., such as ±45°, ±35°, ±25°, or ±15° from perpendicular to the short passage centerline such that the flow of fluid out of the curved portions of the long segments is generally transverse to the flow of fluid through the short segments. While such transverse flow may include a directional component that is in the opposite direction from the flow through the short segments, this directional component is not the dominant directional component of the curved portion flow where it enters the short segment.

Fluidic structures, such as the examples depicted in FIGS. 107 and 108, that provide the ability to partition off, or meter, a smaller amount of fluid from a much larger amount of fluid are also discussed herein. For example, an assay may only require an amount of 10 microliters from a much larger sample volume that may have considerable variation in size. The examples of FIGS. 107 and 108 use various configurations of dynamic seals to allow for such a smaller-volume sample to be split off from a larger sample volume.

In FIG. 107, a fluidic structure 10856 is depicted that includes a reservoir 10766 that may contain a volume of fluid that is of interest. A clamping pressure zone may be applied to the fluidic structure 10756 and advanced along the fluidic structure 10756 in a direction aligned with the axis 10752, e.g., from the reservoir 10766 and moving towards waste reservoir 10730, in order to force the fluid of interest through the fluidic structure 10756 and meter off a portion thereof for further processing, e.g., within other fluidic structures (not shown) downstream of FIG. 107.

The reservoir 10766 may be fluidically connected with a staging chamber 10794, which may be sized such that the fluid that is directed into the staging chamber 10794 from the reservoir 10766 may act to fill the staging chamber 10794, by a short passage. Thus, for example, the size/dimensions of the staging chamber may be selected such that the pressurized volume of the staging chamber 10794 is less than or equal to the expected minimum volume of fluid that may be contained within the reservoir 10766. The passage that fluidically connects the reservoir 10766 to the staging chamber 10794 may be sealed where it fluidically connects with the reservoir 10766 by a dynamic seal 10762A.

The staging chamber 10794 may, in turn, be fluidically connected with a metering chamber 10792 by another short passage. A dynamic seal 10762B may be provided where the short passage to the metering chamber 10792 fluidically connects with the staging chamber 10794. The metering chamber 10792 may be sized so as to have a pressurized volume that is of the desired size for the portion of the fluid that is to be separated from the larger volume of fluid, e.g., 10 microliters. This pressurized volume may be inclusive of the pressurized volume of the passage that fluidically connects the metering chamber 10792 with the staging chamber 10794, as the fluid that is trapped within this passage will typically also be pushed through the metering chamber 10792 eventually. The metering chamber 10792 may also have a second passage that leads from the metering chamber 10792 to further downstream fluidic structures (not shown) in which further fluidic processing of the metered amount of fluid may occur. This second passage may be sealed by a dynamic seal 10762E where it fluidically connects with the metering chamber 10792.

The staging chamber 10794 may also be fluidically connected with the waste reservoir 10730 via another short passage. The waste reservoir may be sized, for example, such that it has a pressurized volume that is at least large enough to receive the maximum amount of fluid that can be expected to be in the reservoir 10766 minus the pressurized volume of the metering chamber 10792. The waste reservoir may, for example, be positioned such that the clamping pressure zone, as it moves across the waste reservoir 10730, experiences a reduced amount of clamping pressure or force. For example, the clamping pressure zone may be generated by rolling a roller across a platen, with two portions of flexible material defining the fluidic structure 10756 positioned therebetween. The platen may have a recess that is positioned so as to align with the waste reservoir 10730 and deep enough that the platen does not press on the waste reservoir 10730 when the roller is applying pressure thereto, thereby reducing the amount of pressure that can be generated in the waste reservoir 10730.

The short passage that fluidically connects the waste reservoir 10730 to the staging chamber 10894 may be sealed by a dynamic seal 10762C where that passage fluidically connects with the staging chamber 10794. The dynamic seal 10762E may be designed to have a higher release pressure than the dynamic seal 10762C, and the dynamic seal 10762C may be designed to have a higher release pressure than the dynamic seal 10762B. Thus, as fluid is pushed into the staging chamber 10794 through advancement of the clamping pressure zone along the axis 10752, the fluid will first be retained within the staging chamber 10794 until the release pressure for the dynamic seal 10762B is reached within the staging chamber 10794. Upon release of the dynamic seal 10762B, the pressurized fluid will then flow into the metering chamber 10792, filling it. Once the metering chamber 10792 is full, further advancement of the clamping pressure zone along the axis 10752 will cause the pressure within the metering chamber 10792 and the staging chamber 10794 to increase further until the release pressure for the dynamic seal 10762C is reached, at which point the dynamic seal 10762C will release and allow the fluid that is within the staging chamber 10794 to be pushed into the waste reservoir 10730. The fluid that is trapped within the metering chamber 10792 will remain trapped therein until the clamping pressure zone reaches the location where the dynamic seal 10762B is located. Once the clamping pressure zone reaches this point, further advancement of the clamping pressure zone will cause the fluid that is trapped within the metering chamber 10792 to increase further in pressure until the release pressure for the dynamic seal 10762E is reached, at which point the dynamic seal 10762E will release and allow the metered fluid that is within the metering chamber 10792 to be pushed downstream into other fluidic structures (not shown) for further processing.

In some implementations, the fluidic structure 10756 may also include a bypass passage that directly fluidically connects the reservoir 10766 to the waste reservoir 10730; the bypass passage may have a dynamic seal 10762D where it fluidically connects with the reservoir 10766. The dynamic seal 10762D may have a higher release pressure than the dynamic seals 10762A, 10762B, and 10762C such that when the reservoir 10766 is pressurized, fluid is first flowed through the staging chamber 10794 before the dynamic seal 10762D is released, allowing fluid flow through the bypass passage.

The bypass passage may be provided to facilitate bubble removal. As can be readily envisaged, when metering precise volumes of liquid for further use in a fluidic system, any bubbles that are present within the metering volume will reduce the amount of the desired liquid that is present. As such, it may be desirable to include features that discourage the transport of bubbles into the metering chamber 10792.

During testing, the present inventors observed that bubbles tended to congregate at dynamic seal locations, e.g., at locations where there was a small opening in a relative long permanent seal that led to a passage. Such bubble collection was observed to occur not only at the upstream ends of passages that were sealed by dynamic seals at their upstream termini, but also at downstream ends of such passages, e.g., where they fluidically connect with a larger volume. For example, for the short passage that fluidically connects the reservoir 10766 with the staging chamber 10794, bubbles would tend to collect at the throat of the passage, e.g., spanning between the surfaces 10793A of the reservoir 10766 adjoining where the short passage fluidically connects with the reservoir 10766 as well as spanning between surfaces 10793A within the staging chamber 10794 adjoining where the short passage fluidically connects with the staging chamber 10794.

The testing also revealed that bubbles tended to collect in regions of the fluidic structure 10756 in which fluid tended to have stagnant flow characteristics. Thus, for example, bubbles would tend to collect in corner regions, pockets, cul-de-sacs, etc. In the fluidic structure 10756, the portion 10793B of the reservoir 10766 interposed between the dynamic seals 10762A and 10762D may act as a bubble trap since it is an area of generally stagnant flow while fluid is flowing through the dynamic seal 10762A and the short passage connected thereto. Bubbles that are present in the fluid in the reservoir 10766 may thus tend to collect in the bubble trap region 10793B in addition to on surfaces 10793A. The bypass passage that extends from the bubble trap region 10793B of the reservoir 10766 to the waste reservoir 10730 is provided to allow whatever stagnant fluid is trapped within the bubble trap region 10793B to be pushed into the waste reservoir 10730 once the clamping pressure zone passes by the dynamic seal 10762A positioned upstream of the bubble trap region 10793B. Similar bubble trap regions are also visible at the bottoms of the reservoirs 10266, 10268, 10366, and 10368 discussed earlier, although those bubble traps are not connected with bypass passages.

The staging chamber 10794 may, in effect, act as a large bubble removal structure, providing a relatively large volume in which bubbles may be removed from the fluid prior to the fluid reaching the metering chamber 10792. To further facilitate such bubble removal, the passage that fluidically connects the staging chamber 10794 with the metering chamber 10792 may fluidically connect with the staging chamber 10794 at a location that is generally opposite from the location of where the fluidic connection of the staging chamber 10794 to the reservoir 10766 occurs, e.g., the two connection points may generally be at opposite corners and/or sides of the staging chamber 10794.

As noted earlier, dynamic seals may often be substituted for temporary seals (and vice-versa) and the various examples herein that feature dynamic seals may, unless logic dictates otherwise, substitute temporary seals in place of any of the dynamic seals. For example, in some implementations, the dynamic seal 10762E may be replaced by a temporary seal that simply seals across the entire width of the metering chamber 10792, thereby allowing the short passage in which the dynamic seal 10762E is located to be omitted, if desired.

FIG. 108 depicts another example fluidic structure for metering. In FIG. 108, features such as the bubble-trapping features of the fluidic structure 10756 are omitted but could be added if desired. The fluidic structure 10856 of FIG. 108 includes a reservoir 10766 that is fluidically connected to a waste reservoir 10830 (similar to waste reservoir 10730) and a metering chamber 10892. A dynamic seal 10862A may be formed in a short passage that fluidically connects the metering chamber 10892 with the reservoir 10866, another dynamic seal 10862B may be formed in another short passage that fluidically connects the waste reservoir 10830 with the reservoir 10866, and a third dynamic seal 10862C may be formed in a short passage that leads from the metering chamber 10892 to downstream fluidic structures (not shown). The dynamic seal 10862A may have a lower release pressure than the dynamic seal 10862B, and the dynamic seal 10862B may have a lower release pressure than the dynamic seal 10862C. Thus, when the reservoir 10866 is pressurized, e.g., through advancement of a clamping pressure zone across the fluidic structure and along the axis 10852, the pressurized fluid will cause the dynamic seal 10862A to release when the pressure reaches the release pressure of the dynamic seal 10862A, thus allowing the fluid to flow into the metering chamber 10892. Once the metering chamber 10892 is full and the fluid therein subjected to further pressurization by the advancement of the clamping pressure zone, the further increased pressure will eventually reach the release pressure for the dynamic seal 10862B, allowing the remaining fluid in the reservoir 10866 to be pushed into the waste reservoir 10830 by the advancing clamping pressure zone.

When the clamping pressure zone reaches where the dynamic seals 10862A and 10862B are located, the clamping pressure zone will seal off both passages leading to the waste reservoir 10830 and the metering chamber 10892. Further advancement of the clamping pressure zone will increase the pressure within the metering chamber 10892 until the release pressure of the dynamic seal 10862C is reached, at which point the metered volume of fluid that is in the metering chamber 10892 will be pushed through the short passage in which the dynamic seal 10862C is located and into other downstream fluidic elements (not shown).

Also visible in the fluidic structure 10856 are floating seals 10895, which, as discussed earlier, are permanent seals that are not used as seals, e.g., to prevent fluid flow from reaching a particular part of the fluidic structure 10856, but are instead used as mechanical stabilization to facilitate more reliable dynamic seal operation.

Figures 109, 110:
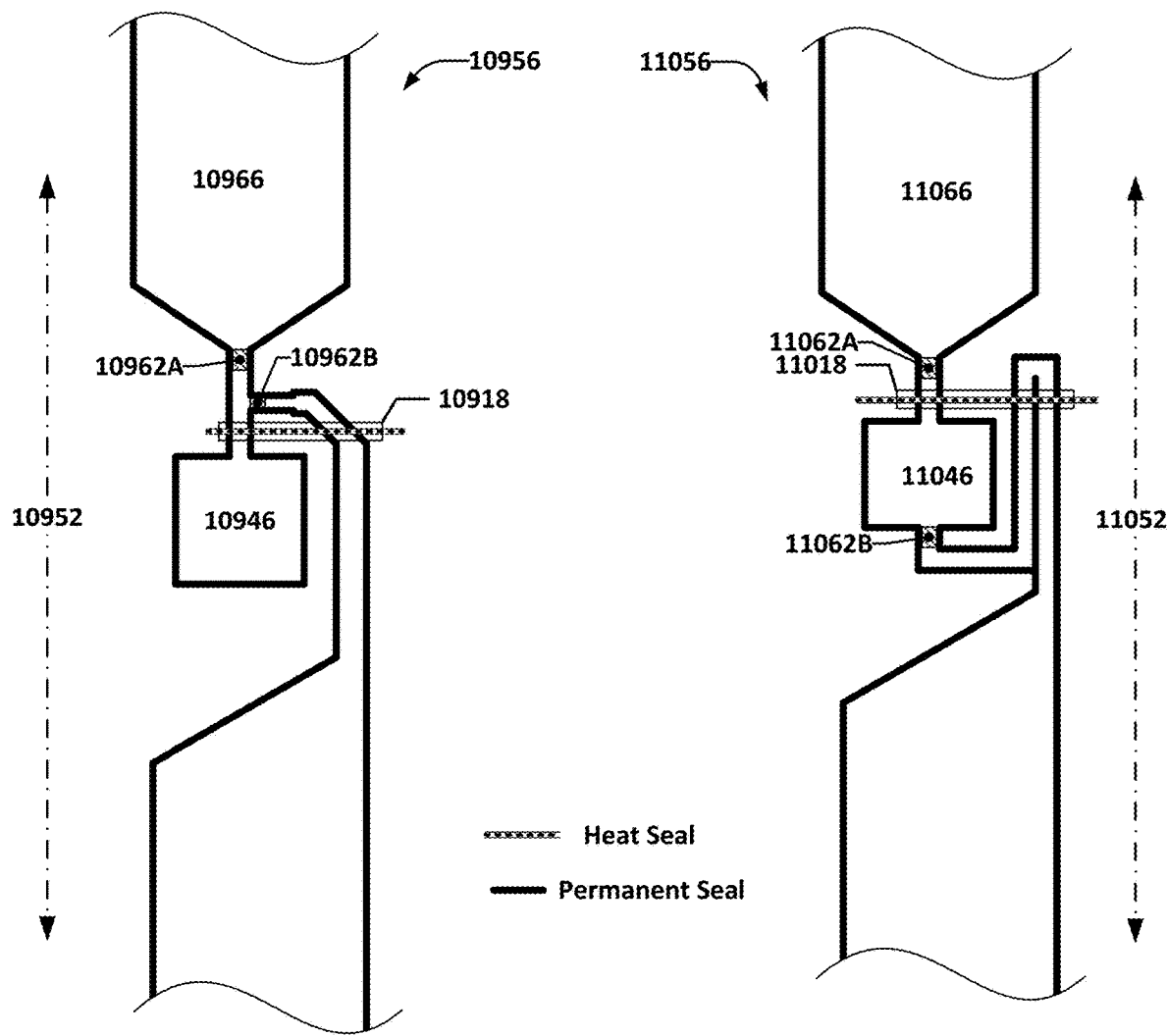
FIG. 109 depicts an example fluidic structure for providing sequestration capability in a fluidic system.
FIG. 110 depicts another example fluidic structure for providing sequestration capability in a fluidic system.

In some implementations, specially configured fluidic structures may be user to sequester or reserve a portion of fluid for later use, e.g., days or months later. For example, it may be desirable to sequester a portion of a sample for later testing in a laboratory, such as for pathology or evidentiary purposes. FIGS. 109 and 110 depict two different examples of such fluidic structures.

In FIG. 109, a fluidic structure 10956 is depicted. The fluidic structure 10956 includes a reservoir 10966 and a sequestration chamber, e.g., evidence chamber, pathology chamber, etc., 10946. The sequestration chambers discussed herein may, in some implementations, be filled with a material that may allow for easier removal of any sequestered fluid or substance at a later date. For example, in some implementations, the sequestration chamber 10946 may contain a nitrocellulose material (or other absorbent material, such as foam or a sponge) that may act to soak up the fluid so that the fluid sample is easier to remove in a laboratory setting, e.g., the fluidic structure may be cut open to allow the nitrocellulose material (and the fluid captured therewithin) to be removed, e.g., using tweezers, and deposited in a liquid medium for analysis). A short passage fluidically connects the sequestration chamber 10946 with the reservoir 10966. A dynamic seal 10962A may be provided where the passage meets with the reservoir 10966. A second passage, e.g., a spur passage, may tee into the passage that spans between the reservoir 10966 and the sequestration chamber 10946. The spur passage may have a dynamic seal 10962B that is formed where the spur passage tees into the passage that spans between the reservoir 10966 and the sequestration chamber 10946. When a clamping pressure zone is advanced along the fluidic structure 10956, e.g., along the axis 10952 from the reservoir 10966 towards the sequestration chamber 10946, the fluid that is in the reservoir 10966 may be pushed through the dynamic seal 10962A and into the sequestration chamber 10946. Once the fluid that is in the reservoir 10966 and the sequestration chamber 10946 has been pressurized to the release pressure for the dynamic seal 10962B, the dynamic seal 10962B may release and allow the additional fluid that is being forced from the reservoir 10966 to flow into the spur passage and downstream to further fluidic structures, e.g., for further processing. The apparatus that applies the clamping pressure zone may, for example, include a heating element 10918 that may be used to apply heat to the fluidic structure 10956 while the clamping pressure zone is held in a location that applies compressive force to the heating element 10918. Heat from the heating element 10918 may be used to generate a localized thermal bond (shown by the dotted line) between the portions of material forming the fluidic structure 10956 in the location of the heating element 10918, thus sealing off the sequestration chamber 10946 from the remainder of the fluidic structure 10956 with a permanent seal.

In FIG. 110, a fluidic structure 11056 is depicted. The fluidic structure 11056 includes a reservoir 11066 and a sequestration chamber, e.g., evidence chamber, pathology chamber, etc., 11046. A first passage fluidically connects the sequestration chamber 11046 with the reservoir 11066. A dynamic seal 11062A may be provided where the first passage meets with the reservoir 11066. A second passage may exit the sequestration chamber 1104 and may follow a path that passes through a point that is interposed between the reservoir 11066 and the sequestration chamber 11046 and which crosses over a heating element 11018. The first passage may also pass over the heating element 11018 or a similar heating element.

The second passage may have a dynamic seal 11062B that is formed where the second passage fluidically connects with the sequestration chamber 11046. When a clamping pressure zone is advanced along the fluidic structure 11056, e.g., along the axis 11052 from the reservoir 11066 towards the sequestration chamber 11046, the fluid that is in the reservoir 11066 may be pushed through the dynamic seal 11062A and into the sequestration chamber 11046. Once the fluid that is in the reservoir 11066 and the sequestration chamber 11046 has been pressurized to the release pressure for the dynamic seal 11062B, the dynamic seal 11062B may release and allow the additional fluid that is being forced from the reservoir 11066 to flow into the sequestration chamber 10946, thereby pushing the fluid that was in the sequestration chamber 10946 through the second passage and downstream to further fluidic structures, e.g., for further processing. The apparatus that applies the clamping pressure zone may, for example, include the heating element 11018 that may be used to apply heat to the fluidic structure 11056 while the clamping pressure zone is held in a location that applies compressive force to the heating element 11018. Heat from the heating element 11018 may be used to generate a localized thermal bond (shown by the dotted line) between the portions of material forming the fluidic structure 11056 in the location of the heating element 11018, thus sealing off the portions of the first and second passages with the sequestration chamber 11046 being fluidically interposed between the two localized thermal bonds.

It will be noted that FIGS. 107-110 all depict fluidic structures that facilitate sequestration or partitioning of a portion of a fluidic sample from a larger volume. However, the fluidic structures of FIGS. 107 and 108 allow the sequestered fluidic sample to then be directed to further downstream fluidic structures for further processing, whereas the fluidic structures of FIGS. 109 and 110 isolate the sequestered fluid sample from all further movement within the fluidic system, requiring removal from the fluidic system through some other mechanism, e.g., by cutting open the fluidic structure, puncturing it with a probe or tube, etc.

The previous discussions and examples have provided an extensive overview of many different types of fluidic circuits that may be implemented using the techniques discussed herein. In addition to the implementations discussed above, a large number of additional implementations are discussed below with respect to FIGS. 112A through 126D. FIGS. 112A through 126D depict such additional example fluidic circuits using a symbolic coding language that is used to describe various structural characteristics of the depicted fluidic circuits.

FIG. 111 depicts a legend that gives a broad overview of the various symbols used in FIGS. 112A through 126D. To begin with, FIGS. 112A through 126D each feature a number of reference boundaries that are represented in the Figures by a heavy-weight, horizontal, solid line that terminates at a circled letter callout, as shown at the top of FIG. 111. Each such reference boundary represents, in effect, a location (or zone of locations) along an axis that runs perpendicular to the reference boundaries to which a clamping pressure zone may be moved during fluidic processing operations performed with the fluidic circuit. For example, if a clamping pressure zone is applied to a depicted fluidic circuit, the clamping pressure zone may be moved along the fluidic circuit from one reference boundary to another. It will be understood, of course, that the reference boundaries that are shown in the Figures do not need to be visible boundaries but can be invisible reference geometry, e.g., similar to how a center axis of a shaft is not necessarily visible. It will also be understood that the reference boundaries, while depicted as lines, may also be zones. For example, if a clamping pressure zone is moved to a particular reference boundary during one phase of operation of a fluidic circuit and is then later moved again to that same reference boundary during a subsequent phase of operation of that fluidic circuit, it is contemplated that the clamping pressure zone may actually be in different locations during both phases of operation, but that both locations may meet whatever conditions are placed on that reference boundary. Thus, for example, reference boundaries for a given fluidic circuit may, for the sake of clarity, include a number of rectangular regions spaced along an axis, each oriented such that two opposing edges thereof are perpendicular to the axis. Each reference boundary corresponds to a different rectangular region and moving a clamping pressure zone to any location within a given one of those rectangular regions is to be understood to be equivalent to moving the clamping pressure zone to the corresponding reference boundary. Moreover, the rectangular regions may have zero or non-zero widths along directions parallel to the axis and different reference boundaries for a given fluidic circuit may be associated with rectangular regions of different widths in directions parallel to the axis.

It will be further understood that, in some implementations, clamping pressure zones may, when transiting from one reference boundary to another, do so in a continuous manner or may stop one or more times at different locations in between the two reference boundaries (unless otherwise suggested).

FIG. 111 also depicts symbols representing three different types of chambers A, B, and C. In FIGS. 112A through 126D, the chambers are all represented by squares of the same size, regardless of their actual relative volumes. Thus, no assumptions should be made as to relative sizes of the chambers represented by chamber symbols in FIGS. 112A through 126D based on the sizes of the symbols used in these Figures. In some instances, the relative volumes of two or more such chambers in a given Figure may be specified separately in the discussion below.

The chamber symbols may each represent a different type of chamber, as noted above. The different symbols that may be used for the types of chambers provide insight as to the positioning of each chamber relative to one or more reference boundaries. For example, a square symbol with a double solid line along the bottom edge, e.g., as shown in the chamber symbol marked "A" in FIG. 111, in a fluidic circuit diagram represents a chamber in which at least a portion of the chamber must be above the closest reference line below that chamber. It is to be understood that the terms "above" and "below" (or similar terms indicating a vertical ordering), as used herein with respect to FIGS. 112A through 126D, are used relative to the orientation of the Figure as determined by the orientation of the Figure label text. Such a chamber may optionally extend above the closest reference boundary above the chamber symbol and/or optionally extend below at least the closest reference boundary below the chamber symbol. It is also to be understood, however, that it is explicitly contemplated that any given chamber represented by the symbol for chamber "A" in FIG. 111 may also, in at least some implementations, be a chamber that does not extend below the closest reference boundary below that chamber. It is also further to be understood that it is explicitly contemplated that any given chamber represented by the symbol for chamber "A" in FIG. 111 may also, in at least some implementations, be a chamber that does not extend above or below the closest reference boundaries bracketing that chamber in the Figure.

A square symbol with a double solid line along the top edge, e.g., as shown in the chamber symbol marked "B" in FIG. 111, in a fluidic circuit diagram represents a chamber in which at least a portion of the chamber must be below the closest reference line above that chamber. Such a chamber may optionally extend above the closest reference boundary above the chamber symbol and/or optionally extend below at least the closest reference boundary below the chamber symbol. It is also to be understood, however, that it is explicitly contemplated that any given chamber represented by a square having a double solid line along the top edge (and a single line along the bottom edge) may also, in at least some implementations, be a chamber that does not extend above the closest reference boundary above that chamber. It is also further to be understood that it is explicitly contemplated that any given chamber represented by a square having a double solid line along the top edge (and a single line along the bottom edge) may also, in at least some implementations, be a chamber that does not extend above or below the closest reference boundaries bracketing that chamber in the Figure.

A square symbol with double solid lines along both the top and bottom edge, e.g., as shown in the chamber symbol marked "C" in FIG. 111, in a fluidic circuit diagram represents a chamber in which at least a portion of the chamber must be between the closest reference boundary above that chamber and the closest reference boundary below that chamber. Such a chamber may optionally extend above the closest reference boundary above the chamber symbol and/ or optionally extend below at least the closest reference boundary below the chamber symbol. It is also to be understood, however, that it is explicitly contemplated that any given chamber represented by a square having double solid lines along both the top and bottom edges may also, in at least some implementations, be a chamber that does not extend above or below the closest reference boundaries bracketing that chamber in the Figure.

It will be understood that when a chamber symbol is used to represent a chamber, this may also be inclusive of one or more chambers that are fluidically connected and positioned, in aggregate, consistent with the rules regarding chamber placement discussed above. For example, a single chamber may be divided into three sub-chambers by two spaced-apart temporary seals; in practice, as soon as the sub-chambers are pressurized by the application of a clamping pressure zone to them, such temporary seals may burst relatively quickly, thereby allowing the three sub-chambers to almost immediately merge into one large chamber. Alternatively, such an arrangement may allow the fluid in a chamber to be partitioned into smaller sub-portions, with the clamping pressure zone applied to each portion, as needed, in order to force it to flow to a particular part of the fluidic circuit.

It is also to be understood that, in some implementations, chambers that are shown according to the conventions above may be understood to have 80% or 90% or more of their total volume located between the closest adjacent reference boundaries to such chambers' symbols in such diagrams.

Each chamber depicted by a chamber symbol in a given fluidic circuit diagram may be connected with one or more other chambers depicted by chamber symbols in the fluidic diagram by lines indicating flow paths. Many such flow paths may have one or more symbols along their lengths, as shown in the bottom half of FIG. 111. Each such symbol may indicate the position (or at least relative placement along the flow path) of a seal feature and may be accompanied by a numeric callout that may be referenced in discussion of the Figure. For example, a dynamic seal may be indicated by a single line segment that is transverse to the line representing a flow path. Such a dynamic seal, as discussed earlier, may be provided at the point where the flow path fluidically connects with a chamber when the width of the flow path at that point is significantly smaller than a corresponding width of the chamber at that point. Similar numeric callouts are also generally provided at locations where flow paths fluidically connect with chambers even if a diagram does not indicate a seal feature at that location. In some Figures, some or all flow paths may have a circled number next to them that corresponds to the ordinal indicator used in the text to refer to such a flow path. For example, if the text refers to a flow path as the "third flow path," then a circled number 3 may be positioned proximate to that flow path in the corresponding Figure. Such circled callouts are not to be confused with numeric callouts for seal features or connection points for flow paths that are not circled, as are discussed earlier above. It will also be understood that in some instances, flow paths may have a zero length, e.g., two chambers that share a common wall may have a dynamic seal or temporary seal that may act to seal an opening in that common wall. Such an opening may be considered to simultaneously be both a flow path and a releasable seal (or two releasable seals with a zero-length flow path fluidically interposed therebetween) for the purposes of this disclosure. Generally speaking, when a flow path is shown as connecting to a chamber symbol in the fluidic circuit diagrams discussed below, such a connection generally indicates that the flow path may fluidically connect with that chamber at any location of the chamber, although it is also explicitly contemplated that the flow path may fluidically connect with that chamber at a location that is constrained in the same manner as the chamber is constrained relative to the closest reference boundaries thereto, e.g., at a location between the two closest reference boundaries or on one side or the other of a particular reference boundary.

Another type of symbol that may be used in the fluidic circuit diagrams discussed herein is a single line segment that is transverse to the flow path and has two diagonally crossing, shorter line segments (making an X) centered on it. Such symbols represent temporary seals, as discussed earlier herein.

Yet another type of symbol that may be used in the fluidic circuit diagrams discussed herein is a single segment that is transverse to the flow path and has a single diagonally crossing, shorter line segment centered on it. Each such symbol may represent either a dynamic seal or temporary seal. The term "releasable seal" is used herein to refer to such seals and is to be understood to refer generally to seals that can be either dynamic seals or temporary seals. It is to be understood that where multiple releasable seals are shown in a given fluidic circuit diagram, then such releasable seals may all be dynamic seals, all be temporary seals, or be a combination of dynamic and temporary seals. The term "pressure-releasable seal" may also be used in place of "releasable seal" in some instances.

Three other types of seals are represented by symbols that feature at least one wavy line that is transverse to a given flow path. Such seals may be caused to come into existence during fluidic processing using the fluidic circuit depicted in a given diagram, but may not otherwise exist prior to such processing. For example, a live temporary seal may be caused to form across a chamber or within a passage or other flow path through the application of pressure and heat along a line defining the temporary seal. For example, such pressure and heat may act to thermally bond together the material portions between which the fluidic circuit is defined. In the case of a live temporary seal, the amount of thermal bonding may be less than in a live permanent fluidic seal such that the live temporary seal may later be caused to release responsive to the fluid on one side of the live temporary seal being pressurized to a level greater than the release pressure of the live temporary seal. In a live permanent seal, the amount of heat and pressure applied to form the seal may be such that the thermal bond is permanent, i.e., not releasable responsive to pressurizing the fluid restrained thereby.

A live strong to normal dynamic transition seal is a dynamic seal that is located where a passage fluidically connects with a chamber and is able to be transitioned between a high release pressure and a low release pressure by thermally bonding two portions of the chamber proximate to where the dynamic seal is located together, e.g., using a thermal "stitch," to form a "floating seal" (as discussed earlier herein). Live strong to normal dynamic transition seals are represented in the Figures by a short line segment and a short wavy line segment that are both transverse to the line representing the flow path.

Generally speaking, flow paths that do not have a seal symbol located at one or both ends thereof may be assumed to be "open" flow paths at the locations where they do not have a seal symbol. In other words, fluid may be relatively free to flow in or out of the flow path at that end with little or no resistance. It will be understood that while such flow paths are shown as "open" flow paths, this does not necessarily mean that such flow paths do not have releasable seals at such locations. For example, it will be understood that the indication of a flow path as being "open" at a particular location should be understood to be inclusive of the flow path being open at that location or having a releasable seal at that location that has a release pressure that is low enough that it, in effect, does not act to change the sequence of how fluids flow through a particular circuit. For example, a flow path that is indicated as being "open" at one end and as having a releasable seal at the other end that has a release pressure of X could potentially be implemented with one or more additional releasable seals between the indicated releasable seal having a release pressure of X and the "open" end of that flow path; such additional releasable seals may, for example, have release pressures that are lower than X, such that fluid flow that is sufficient to breach the indicated releasable seal will also be sufficient to breach the additional releasable seals.

One last symbol that may be used in the fluidic circuit diagrams discussed below is a dotted boundary line that may be provided around one or more chambers and/or one or more flow paths. Such dotted boundary lines indicate portions of the fluidic circuit that, when processed using a system, e.g., an analysis system, that is configured to apply a clamping pressure zone to the portions of material forming the fluidic circuit, may be aligned with a cavity or recess (or cavities or recesses) in a platen or other support structure against which the clamping force may be developed. As a result, regions of the fluidic circuit that align with the cavities or recesses may experience lower or non-existing clamping pressure that results from the application of the clamping pressure zone to such regions.

It will be generally understood that the following fluidic circuit Figures are schematic in nature and are generally not indicative of relative scale, flow path lengths, etc. It is also to be understood that the relationships that are depicted, e.g., relative positioning of the various chambers relative to the various reference boundaries, are depicted with respect to the fluidic circuit when the fluidic circuit is laid out in a flat configuration. As indicated earlier, the portions of material between which the fluidic circuit is defined may both be flexible, which may allow the fluidic circuit to be folded into any number of configurations, which may allow the relative positioning of the chambers located therein to be reconfigured into any number of configurations depending on how one folds the portions of material. For consistency, it is to be understood that the fluidic circuits depicted in the following Figures represent the structural aspects of the fluidic circuits when in their flattened, unfolded, or unrolled state.

It will be further understood that the left-right relative positioning of chambers, and relative vertical positioning of chambers with symbols located between the same pair of adjacent reference boundaries, as shown in the Figures may be modified as desired unless otherwise indicated. Moreover, it is to also be understood that the structural nature of each flow path indicated may be dependent on the particular nature of the seals that may be used along such flow paths. For example, dynamic seals generally require that the flow paths along which they are located have smaller cross-sectional widths than the chambers to which they fluidically connect. Accordingly, a flow path that features a dynamic seal where it connects with a chamber may be provided by a narrow passage (as compared with the width of the chamber in that same direction), whereas a flow path that uses some form of temporary or live seal in the same location may have a width that is, in some cases, as wide or wider than the chamber width at that point (this is because dynamic seals are dependent on the geometry of the transition between the chamber and the flow path, whereas temporary and live seals are generally geometry-independent and only rely on the thermal bond that provides the seal). Moreover, while dynamic seals must generally be located at the ends of a flow path, e.g., where the flow path transitions from a narrow passage to a larger chamber, temporary seals are not so constrained, as they rely on a thermal bond or other bond (e.g., adhesive bond) that may be created at any of a variety of locations along a flow path's length. Accordingly, temporary seals, when indicated as being present along a flow path, may generally be positioned at a variety of locations therealong rather than just at one end or the other.

It will be understood that the fluidic circuit diagrams discussed below convey a variety of different types of information. On one level, the fluidic circuit diagrams communicate structural information regarding chamber locations, flow paths, and seal locations that are evident in the fluidic circuit prior to use (such as prior to potentially being pre-loaded with fluids). On another level, the discussion regarding each Figure may describe how the fluidic circuits are to be operated during fluidic processing operations, including structural features that come into play during such operative use. On yet another level, the discussion regarding each Figure may describe potential uses for the depicted and described fluidic circuit.

It will be understood that the fluidic circuits discussed below may be presented in isolation but may, nonetheless, be suitable for inclusion in a larger fluidic circuit if suitable flow paths are included to allow integration of such fluidic circuits into the larger fluidic circuit. It will also be understood that all of the fluidic circuits discussed below may be implemented as a fluidic structure that includes the fluidic circuit. Such fluidic structures may include, for example, a first portion of material that is flexible yet inelastic and a second portion of material which may be rigid or may also be flexible yet inelastic, as discussed earlier herein. Such portions of material may be sealed together, e.g., using laser welding or other heat-based bonding so as to provide one or more permanent seals that define one or more boundaries of the fluidic circuit interposed between the first portion of material and the second portion of material.

Figure 126B:
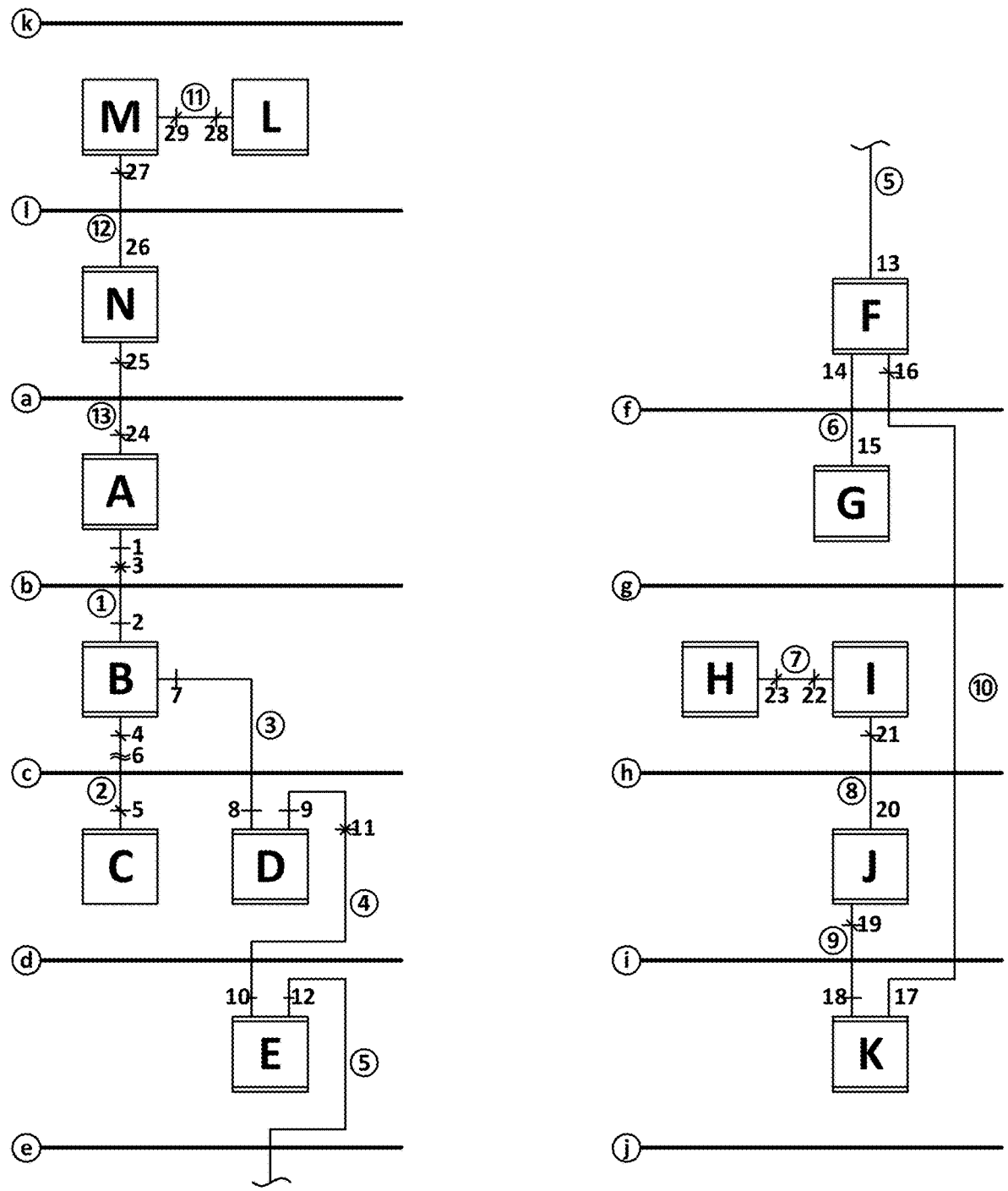
Figures 1, 126C:
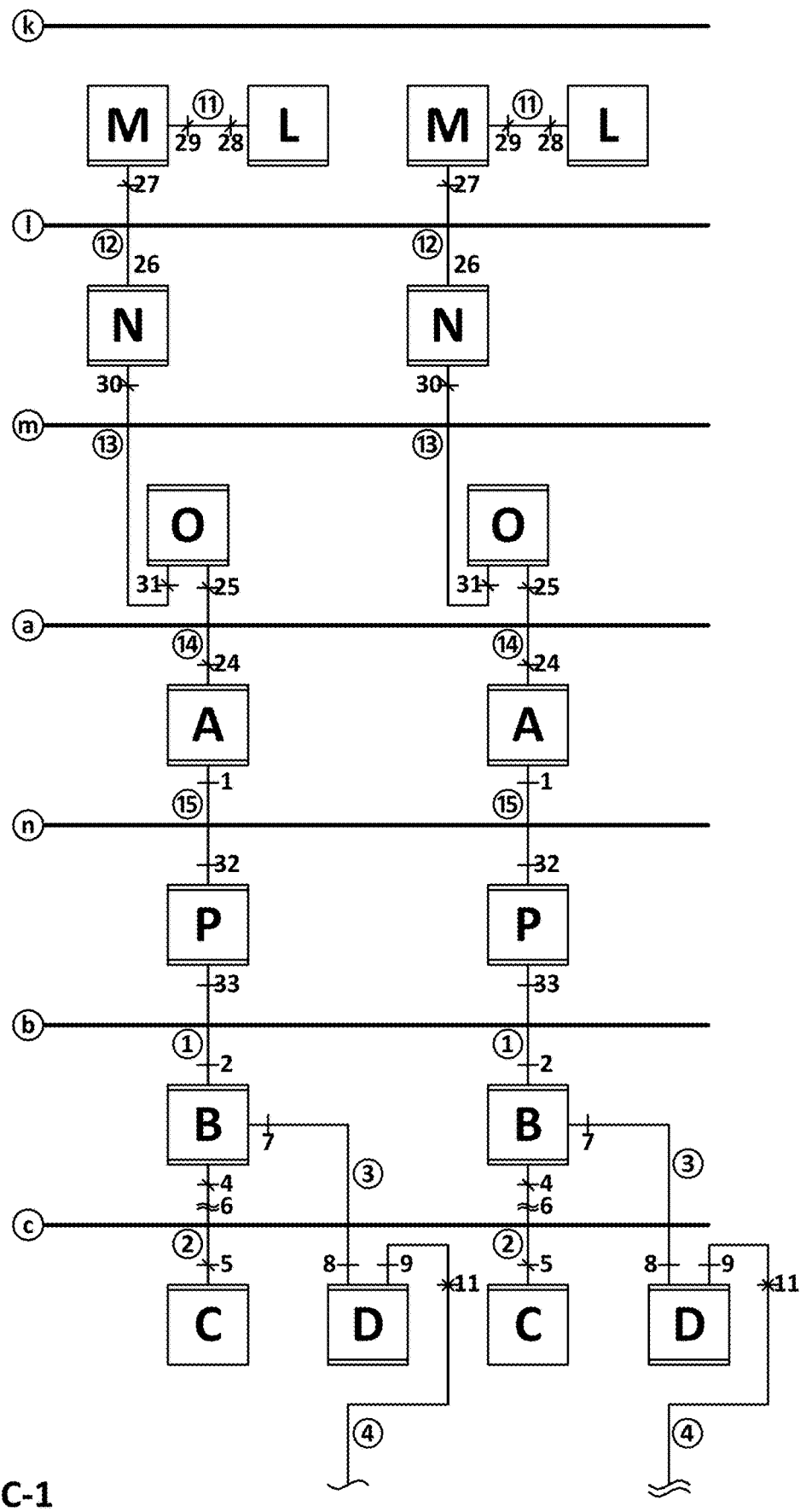
Figures 2, 126C:
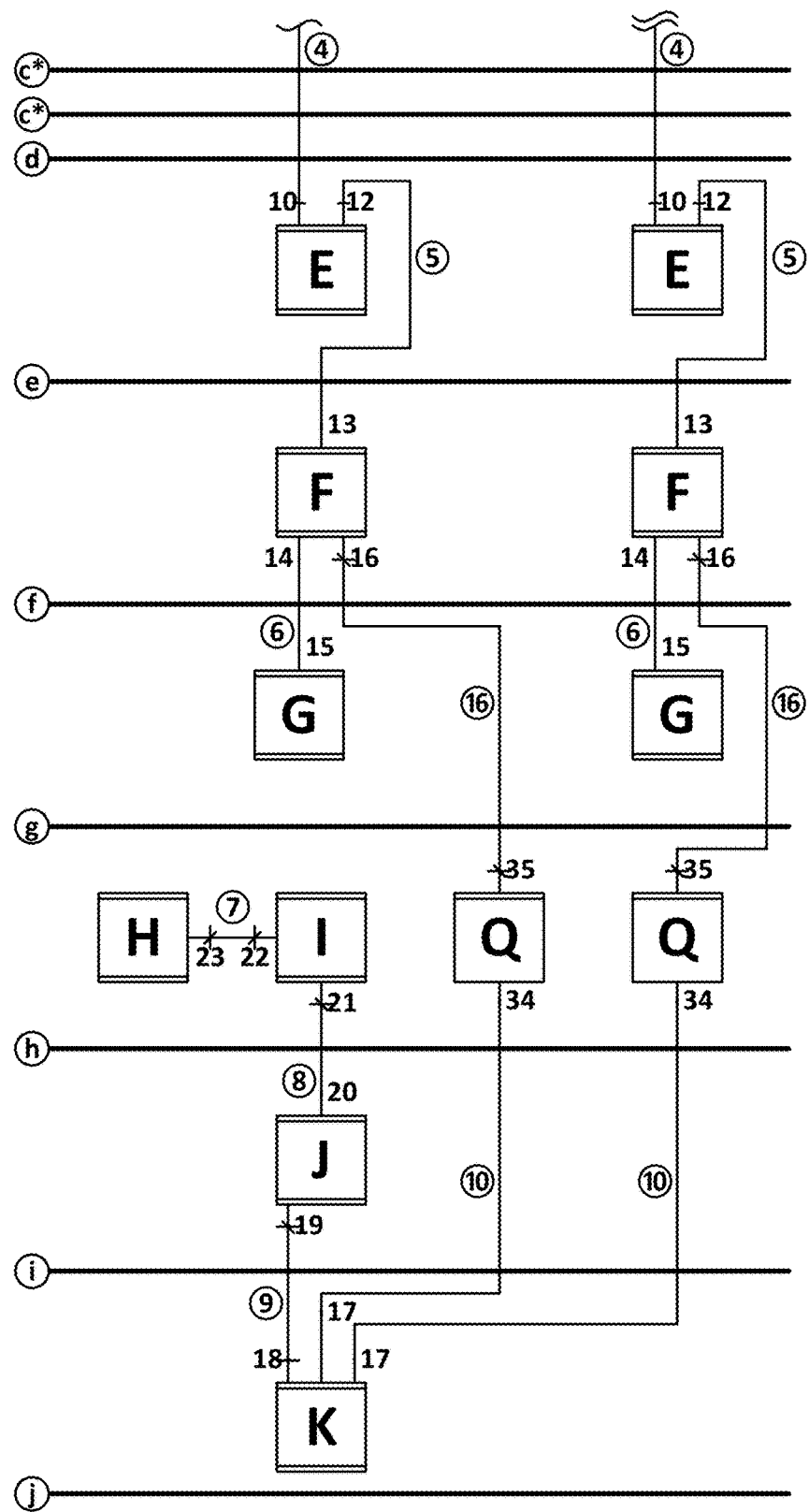
Figures 1, 126D:
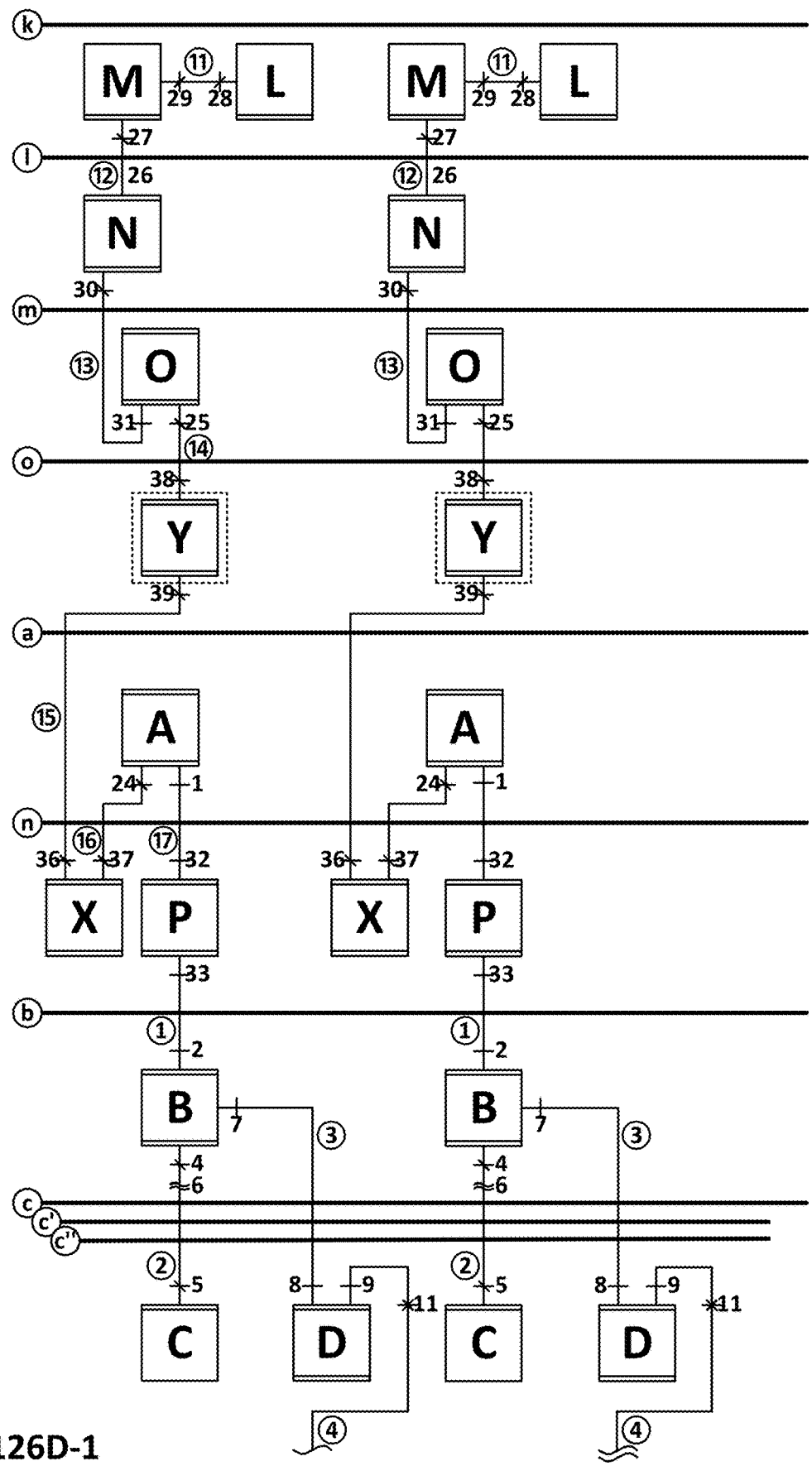
Figures 2, 126D:
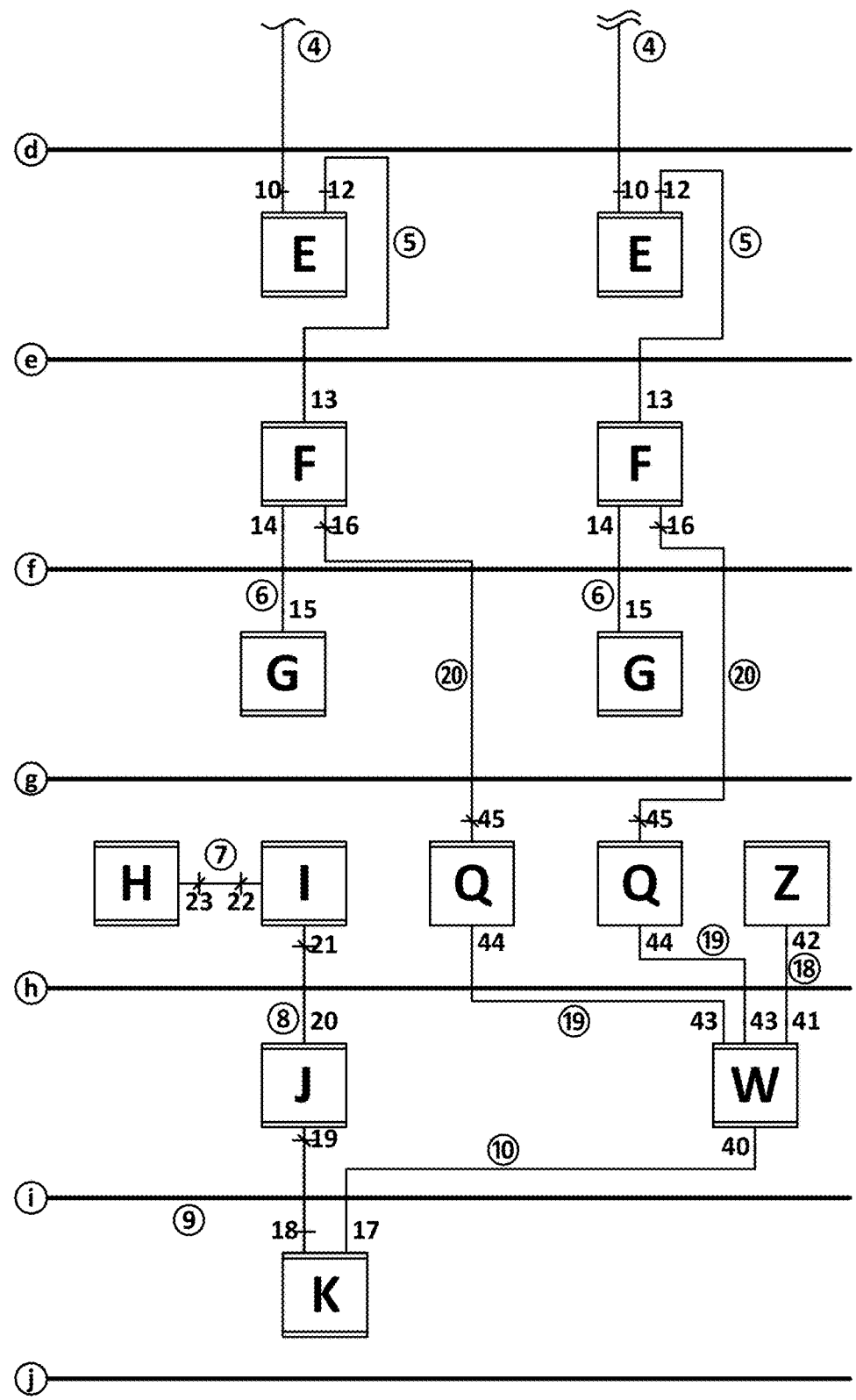

It will also be understood that the reference boundaries for each Figure are each labeled with a different lowercase letter and are, starting with "a" as (usually) the topmost reference boundary at the top of each fluidic circuit, presented in alphabetical order (the only deviation in this is in FIGS. 126B, 126C, and 126D, for reasons that will become apparent). Chambers are each labeled with a different upper-case letter, and seals (or end of flow paths that are open flow paths) are each labeled with a non-circled number.

In many of the Figures discussed below, reference may be made to a chamber with a surface of interest, which is to be understood to refer to a chamber in which one or more surfaces of the chamber, or surfaces of objects within the chamber, may be prepared with a particular surface treatment that may be used to perform one or more steps of an assay or other analysis technique. For example, such surfaces may, in some cases, be coated with a substance that is used in the assay in some manner, e.g., the substance may be the same target substance that the assay is designed to detect or measure (such that antibodies that are mixed with the sample but that are not able to bind to (or that otherwise do not bind to) any target substance that may be in the sample instead bind to the immobilized target substance when the sample is allowed to incubate within the chamber having the surface of interest), or may be a substance that binds to the target substance, e.g., antibodies that are specific to the target substance. Such substances may, for example, include antibodies, fluorophores, proteins, the target substance, etc.

Figure 112A:
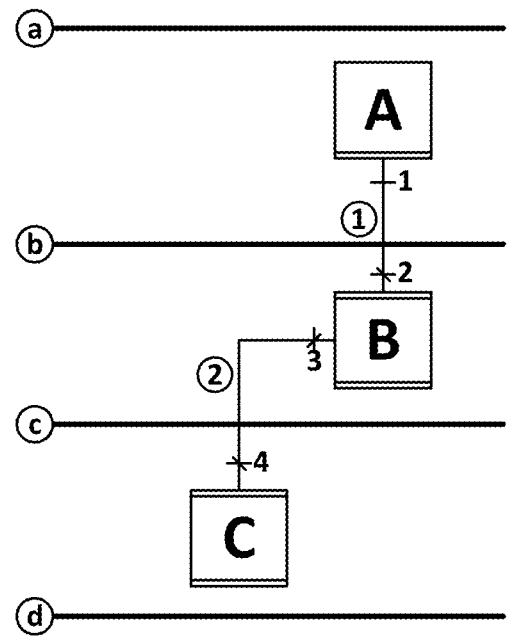
FIGS. 112A through 112F depict various fluidic circuits that may be used to sequentially expose a surface of interest with two or more different fluids.

FIG. 112A depicts a diagram of an example fluidic circuit that may be used to inundate a surface of interest within a chamber with two different fluids at two different times and with minimal or no mixing of the fluids. For example, the first fluid may be a sample that may bind to the surface of interest and the second fluid may be an indicator that may bind to any portions of the surface of interest that have not already bound to the sample. The surface of interest may be immobilized within the chamber B. The fluidic circuit of FIG. 112A has a first chamber A, a second chamber B, and a third chamber C. The chambers A and C may be provided with respective fluids, either through preloading the fluidic circuit prior to operation of the fluidic circuit or via one or more earlier fluidic circuit operations that act to deliver such fluids to the chambers A and C, e.g., via other flow paths not shown, during operation (for example, there may be other fluidic circuits that are fluidically connected with the chambers A and C that may be actuated prior to actuation of the depicted fluidic circuit in order to cause chamber A and C to be filled with their respective fluids; this is generally the case with all of FIGS. 112A through 112F). The chamber B may initially be empty of fluids. It will be understood that while this discussion refers to chambers A through C, such references also, as mentioned earlier, include implementations in which one or more of chambers A through C are provided by multiple chambers that are fluidically connected together and still, in aggregate, satisfy the structural aspects discussed below.

Per the conventions discussed above, at least a portion of the chamber A is on a side of the reference boundary "b" that faces the reference boundary "a," at least a portion of the chamber B is between the reference boundary "c" and the reference boundary "b," and at least a portion of the chamber C is between the reference boundary "d" and the reference boundary "c." In some implementations, all of chamber A may be on the side of the reference boundary "b" that faces the reference boundary "a," all of chamber C may be in between the reference boundaries "c" and "d," and/or all of chamber B may in between the reference boundaries "b" and "c."

A first flow path may fluidically connect the chamber A with the chamber B. The first flow path may fluidically connect with the chamber A at a location in between the reference boundaries "a" and "b," and may fluidically connect with the chamber B at a location in between the reference boundaries "b" and "c." A second flow path may fluidically connect the chamber B with the chamber C. The second flow path may fluidically connect with the chamber B at a location in between the reference boundaries "b" and "c," and may fluidically connect with the chamber C at a location in between the reference boundaries "c" and "d." Thus, the chamber B may be fluidically interposed between the chambers A and C by way of the first and second flow paths, respectively.

The first flow path may include a dynamic seal at location 1 where the first flow path fluidically connects with the chamber A and may include a pressure-releasable seal, e.g., a dynamic seal or a temporary seal, in between the dynamic seal at location 1 and the chamber B, e.g., at location 2. The second flow path may include two pressure-releasable seals, e.g., dynamic or temporary seals, in between the chambers B and C, e.g., at locations 3 and 4. The seal provided at location 3 may be designed to have a higher release pressure than the seal provided at location 2.

The chambers A through C may generally be sized such that the maximum volume of chamber B is at least greater to or equal to the total amount of fluid that is in, or is anticipated to be in, chamber A during operation of the fluidic circuit and such that the combined maximum volume of chambers A and B is greater than or equal to the combined total amounts of fluid that are in, or are anticipated to be in, the chambers A and C.

During operation, a clamping pressure zone may be applied to the fluidic circuit of FIG. 112A. The clamping pressure zone may be generally transverse in nature, e.g., extending along a line parallel to the reference boundaries (a) through (d), and may be moved along an axis perpendicular to the reference boundaries (a) through (d); the other fluidic circuits discussed below may be subjected to similar movable clamping pressure zones during fluidic operation.

During fluidic operation, the clamping pressure zone may be caused to move from the reference boundary "a" to the reference boundary "b," thereby pressurizing the chamber A until the release pressure for the dynamic seal at location 1 is reached, thereby causing the dynamic seal at location 1 to release and allow the fluid to be pushed through the first flow path to pressurize the releasable seal at location 2 until the release pressure for that seal is reached. At this point, the further movement of the clamping pressure zone to the reference boundary "b" may cause the fluid from the chamber A to be pushed into the chamber B. The clamping pressure zone may then be caused to pause at the reference boundary "b" to allow the fluid from chamber A to incubate or soak the surface of interest in chamber B. The clamping pressure zone may then be advanced to the reference boundary "c"; in some implementations, the speed with which the clamping pressure zone is moved from reference boundary "b" to reference boundary "c" may be maintained at a level that avoids transient pressures that may exceed the release pressure of the releasable seal at location 3. In other or additional such implementations, the location where the second flow path fluidically connects with the chamber B may be positioned close to the reference boundary "b" or, in some implementations, as close to the reference boundary "b" as possible. In such implementations, as the clamping pressure zone traverses the chamber B from the reference boundary "b" to the reference boundary "c," the clamping pressure zone will nearly immediately move past the fluidic connection point between the second flow path and chamber B—thus, any pressure that subsequently builds up in the fluid that is trapped between the clamping pressure zone and the reference boundary "c" in the chamber B during such movement does not get applied to the releasable seal at location 3.

The clamping pressure zone may then be caused to move from reference boundary "c" back to reference boundary "b," thereby driving the fluid from chamber A back through the first flow path and into chamber A, leaving chamber B empty of fluid (or practically empty of fluid). The clamping pressure zone may then be caused to reverse direction and move to the reference boundary "d" and then, after reaching the reference boundary "d," move back to the reference boundary "c." During such motion, the fluid in chamber C may be pressurized so as to cause the releasable seals on the second flow path to release, thereby allowing that fluid to enter the chamber B and flow onto the surface of interest. If desired, the clamping pressure zone may also optionally be moved to reference boundary "b" after this to purge the fluid from chamber C from chamber B; in such an implementation, the maximum total volume of chamber A may be set to be greater than or equal to the total combined fluid volumes of the fluids in chambers A and C. The fluid from chamber A that was returned to chamber A may, during these operations, be prevented from flowing back down into chamber B by the operation of the dynamic seal at location 1.

The implementation of FIG. 112A may be optionally implemented with various revisions to the above. For example, the fluidic circuit shown in FIG. 112A may use dynamic seals at each of the four locations 1-4 shown; in fact, the fluidic circuits shown in FIGS. 112A through 112F may optionally use dynamic seals at all seal locations in some implementations. In some implementations, the second flow path may omit the releasable seal that is at location 3, e.g., location 3 may be an open flow path, and the releasable seal at location 4 may be a dynamic seal. Generally speaking, where a flow path features releasable seals at both ends of the flow path, i.e., both ends of the flow path may have either dynamic seals or temporary seals, if a temporary seal is used as one of the releasable seals, then the other of the two releasable seals may optionally be simply omitted, e.g., replaced with an open flow path. In the context of FIG. 112A, while this may result in some of the fluid from chamber A potentially flowing down the second flow path and mixing with the fluid from chamber B during later clamping zone movements, moving the clamping pressure zones slowly and/or locating the location where the second flow path fluidically connects with chamber B near the reference boundary "b" may reduce this possibility.

In some implementations, the first flow path may be subjected to a live seal after the fluid from chamber A is returned to chamber A instead of using a dynamic seal at location 1 to prevent the fluid from flowing back out of chamber A.

Generally speaking, in the implementations of FIGS. 112A through 112F (and in other Figures in which similar issues may develop), if temporary seals are used at fluidic connections with a chamber with a surface of interest in it, e.g., chamber B, it may be advantageous during application of the clamping pressure zone to cause the speed with which the clamping pressure zone traverses the fluidic circuit to increase when the clamping pressure zone is used to supply fluid to such a chamber so as to maintain an elevated back pressure in the fluid within that chamber that causes the portion or portions of flexible inelastic material between which that chamber is located to bulge outward, thereby providing additional volume within the chamber that may help facilitate exposure of the entire surface of interest within that chamber to the fluid introduced into that chamber.

Figure 112B:
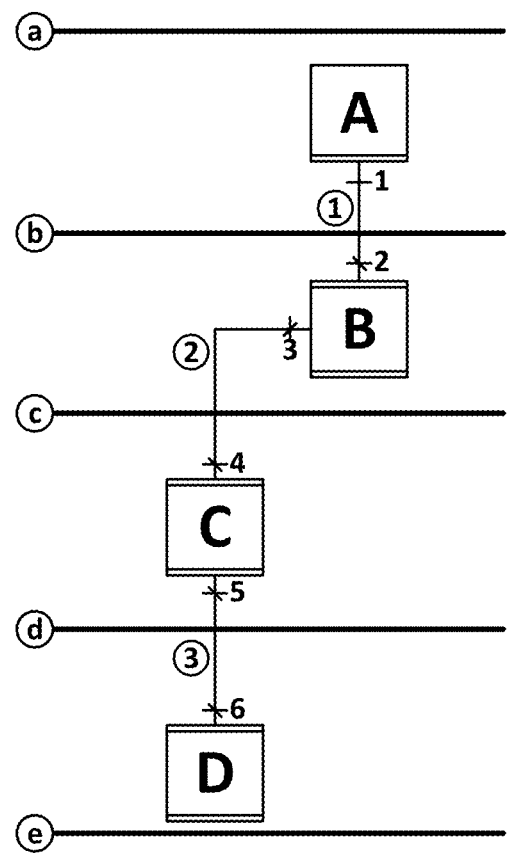

FIG. 112B depicts a fluidic circuit that is similar to that of FIG. 112A but adds on an additional chamber, reference boundary, and flow path to provide for the sequential but separate introduction of fluids from three different chambers into chamber B and the surface of interest contained within with minimal to no mixing between the fluids. The above discussion of FIG. 112A is equally applicable to the implementation of FIG. 112B and is not repeated here with respect to FIG. 112B in the interest of brevity. The reader is referred to the previous discussion for elements of FIG. 112A that are also in FIG. 112B.

As can be seen, the fluidic circuit of FIG. 112B further includes a chamber D, at least a portion of which is between the reference boundary "d" and a reference boundary "e." In some implementations, all of chamber D may lie between the reference boundaries "d" and "e." It will be understood that the chamber D may also be provided by multiple chambers or sub-chambers, similar to as described above with respect to chambers A through C. Chamber D may be preloaded with fluid, e.g., loaded prior to operation of the fluidic circuit, or may be loaded with fluid during operation of the fluidic circuit. A third flow path may be fluidically connected with chamber C at a location between the reference boundary "c" and the reference boundary "d" and with chamber D at a location between the reference boundary "d" and the reference boundary "e." The third flow path may have releasable seals at locations 5 and 6.

The location where the third flow path fluidically connects with chamber C may be positioned closer to the reference boundary "c" than the location where the third flow path fluidically connects with the chamber C such that fluid that is forced from chamber D through chamber C will be unimpeded in its subsequent flow to chamber B. The chamber size relationships discussed earlier may be somewhat modified in this implementation, with the maximum total combined volume of chambers A and B being equal to or greater than the combined total amounts of fluid that are in, or are anticipated to be in, the chambers A, C and D.

The operation of the fluidic circuit of FIG. 112B may initially parallel that of the fluidic circuit of FIG. 112A, with the optional final movement of the clamping pressure zone to the reference boundary "b." At this point, the chamber B has sequentially had fluids from chambers A and C flowed therethrough without mixing, with both fluids eventually being directed into chamber A, which now serves as a waste reservoir. However, after the movement of the clamping pressure zone to the reference boundary "b," the clamping pressure zone may then be moved to the reference boundary "e" before being moved back to the reference boundary "c." During such movement of the clamping pressure zone, the fluid that is present within chamber D, which may be preloaded or may be loaded during operation of the fluidic circuit, may be pressurized so as to cause the releasable seals at locations 5 and 6 to release and allow the fluid present within chamber D to be pushed through chamber C and into chamber B. If desired, a subsequent optional movement of the clamping pressure zone from the reference boundary "c" to the reference boundary "b" may be performed to drive the fluid from chamber D out of chamber B and into chamber A.

Such fluidic circuits may thus permit the surface of interest in chamber B to be sequentially and separately exposed to separate fluids from chambers A, C, and D during operation of the fluidic circuit of FIG. 112B. It will be appreciated that, if desired, additional chambers and flow paths similar to chamber D and the third flow path may be chained together off of chamber D to allow for any number of different fluids to be sequentially and separately introduced into chamber B.

In some implementations, the releasable seals at locations 5 and 6 on the third flow path may be replaced with open flow paths, thereby allowing for potential fluid flow between chambers C and D along the third flow path without requiring that releasable seals be released on the third flow path. While this may allow some fluid from chamber D to prematurely enter chamber B, e.g., while the fluid from chamber C is present within chamber B, the magnitude of such fluid flow may be relatively small.

In some implementations, e.g., implementations where it is desirable to deliver multiple separate boluses of the fluid to chamber B, the chambers C and D may be viewed as a single long chamber (containing one type of fluid). As the clamping pressure zone moves to reference boundary "d," which may be located, for example, along the length of chamber C/D, an amount of fluid in the portion of the chamber C/D corresponding to chamber C of the fluid may be caused to flow into chamber B. When the clamping pressure zone then moves to the reference boundaries "e" and then "c," the remainder of the fluid in the C/D chamber may be pushed into chamber B. This may allow, for example, multiple wash cycles to be performed of chamber B.

Figure 112C:
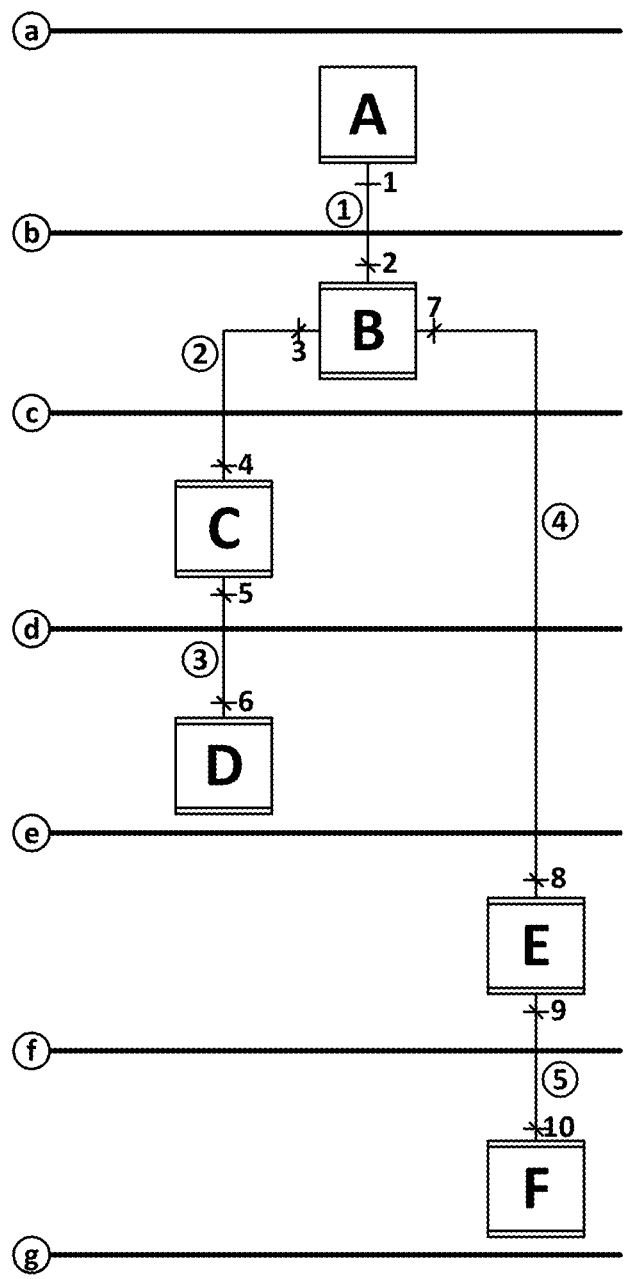

FIG. 112C depicts a fluidic circuit that builds on the fluidic circuit of FIG. 112B but allows for multiple doses of each fluid to be delivered from separate chambers. The fluidic circuit of FIG. 112C includes, for example, a chamber E, at least a portion of which is between the reference boundary "e" and a reference boundary "f." In some implementations, all of chamber E may lie between the reference boundaries "e" and "f." It will be understood that the chamber E may also be provided by multiple chambers or sub-chambers, similar to as described above with respect to chambers A through D. Chamber E may be preloaded with fluid, e.g., loaded prior to operation of the fluidic circuit, or may be loaded with fluid during operation of the fluidic circuit. A fourth flow path may be fluidically connected with chamber B at a location between the reference boundary "b" and the reference boundary "c" and with chamber E at a location between the reference boundary "e" and the reference boundary "f." The fourth flow path may have releasable seals at locations 7 and 8. The releasable seal at location 7 may, for example, have a release pressure that is greater than that of the releasable seal at location 2. In some implementations, the location where the fourth flow path fluidically connects with chamber B may be positioned to be close to, or as close as possible to, the reference boundary "b," similar to as discussed with respect to the location where the second flow path fluidically connects with chamber B (and for similar reasons).

The fluidic circuit of FIG. 112C may also include a chamber F, at least a portion of which is between the reference boundary "f" and a reference boundary "g." In some implementations, all of chamber F may lie between the reference boundaries "f" and "g." It will be understood that the chamber F may also be provided by multiple chambers or sub-chambers, similar to as described above with respect to chambers A through E. Chamber F may be preloaded with fluid, e.g., loaded prior to operation of the fluidic circuit, or may be loaded with fluid during operation of the fluidic circuit. A fifth flow path may be fluidically connected with chamber E at a location between the reference boundary "e" and the reference boundary "f" and with chamber F at a location between the reference boundary "f" and the reference boundary "g." The fifth flow path may have releasable seals at locations 9 and 10.

The location where the fourth flow path fluidically connects with chamber E may be positioned closer to the reference boundary "e" than the location where the fifth flow path fluidically connects with the chamber E such that fluid that is forced from chamber F through chamber E will be unimpeded in its subsequent flow to chamber B. The chamber size relationships discussed earlier may be somewhat modified in this implementation, with the maximum total combined volume of chambers A and B being equal to or greater than the combined total amounts of fluid that are in, or are anticipated to be in, the chambers A, C, D, E, and F.

The operation of the fluidic circuit of FIG. 112C may initially parallel that of the fluidic circuit of FIG. 112B, with the optional final movement of the clamping pressure zone to the reference boundary "b." At this point, the chamber B has sequentially had fluids from chambers A, C, and D flowed therethrough without mixing, with all three fluids eventually being directed into chamber A, which now serves as a waste reservoir. However, after the movement of the clamping pressure zone to the reference boundary "b" to drive the fluid that originated from chamber D into chamber A, the clamping pressure zone may then be moved to the reference boundary "f" before being moved back to the reference boundary "c." During such movement of the clamping pressure zone, the fluid that is present within chamber E, which may be preloaded or may be loaded during operation of the fluidic circuit, may be pressurized so as to cause the releasable seals at locations 8 and 9 to release and allow the fluid present within chamber E to be pushed into chamber B. The clamping pressure zone may then be moved back to the reference boundary "b" to drive the fluid from chamber E from chamber B into chamber A before being moved to the reference boundary "g" and then moved to the reference boundary "c" again, thereby driving the fluid in chamber F into chamber B. If desired, the clamping pressure zone may be subsequently moved to the reference boundary "b" again to drive the fluid from chamber F that is in chamber B into chamber A so as to leave chamber B empty.

Such fluidic circuits may thus permit the surface of interest in chamber B to be sequentially and separately exposed to separate fluids from chambers A, C, D, E, and F during operation of the fluidic circuit of FIG. 112B. It will be appreciated that, if desired, additional chambers and flow paths similar to chambers E and F and the fourth and fifth flow paths may be fluidically connected with chamber B in a manner similar to that used to fluidically connect chambers C and D or E and F to chamber B, although with the additional chambers each located in between additional corresponding reference boundary lines such that each chamber may be individually subjected to clamping zone pressure in order to drive the contents thereof into chamber B. Such arrangements may allow for any number of different fluids to be sequentially and separately introduced into chamber B. It will also be appreciated that the locations of any two or more of the chambers C through F (or other such chambers) may be positioned such that those chambers have portions thereof (or the entireties thereof) that are interposed between a common adjacent pair of reference boundaries. In such implementations, the movement of the clamping pressure zone may act to simultaneously convey the fluids from the chambers that share a position in between the same adjacent pair of reference boundaries to chamber B. Such implementations may be used when, for example, it may be desirable to simultaneously introduce different substances into chamber B, e.g., to produce a particular chemical reaction. It will also be appreciated that chambers C-F, instead of being arranged C-D-E-F, may be arranged C-E-D-F, so as to cause the fluids from C/D to be interleaved with fluids from E/F; in such implementations, it may be desirable to have the releasable seals at locations 3 and 7 be dynamic seals.

Figure 112D:
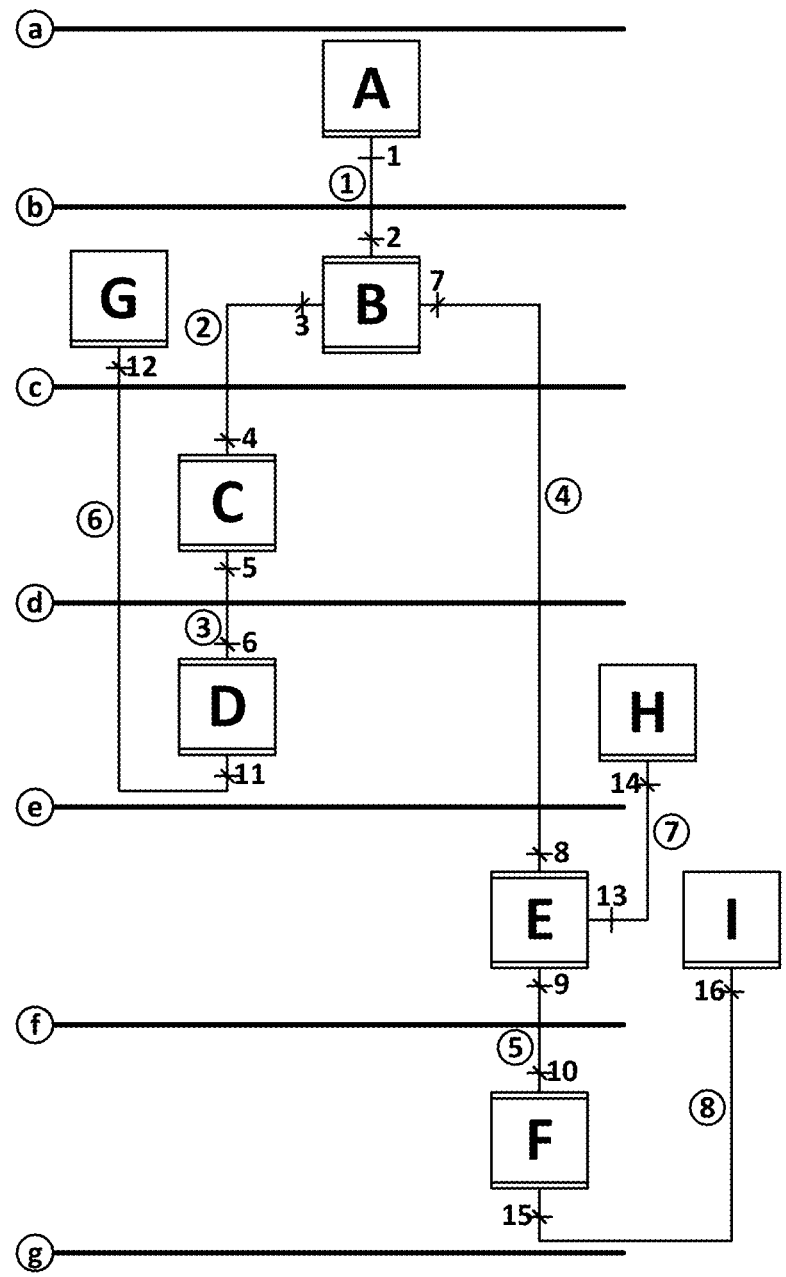

FIG. 112D depicts another fluidic circuit that builds further on the fluidic circuits depicted in FIGS. 112A through 112C. In particular, the fluidic circuit of FIG. 112D includes the chambers and flow paths of the fluidic circuit of FIG. 112C, but also includes chamber G, at least a portion of which is above the reference boundary "c." In some implementations, all of chamber G may be above the reference boundary "c." It will be understood that the chamber G may also be provided by multiple chambers or sub-chambers, similar to as described above with respect to chambers A through F. Chamber G may be preloaded with fluid, e.g., loaded prior to operation of the fluidic circuit, or may be loaded with fluid during operation of the fluidic circuit (for example, earlier fluidic flow operations using other flow paths and/or chambers not depicted in FIG. 112D may be used to load chamber G with fluid—this may also be applicable to the other chambers H and I discussed below). A sixth flow path may be fluidically connected with chamber D at a location between the reference boundary "d" and the reference boundary "e" with chamber G at a location on the side of the reference boundary "c" that faces towards the reference boundary "b." The sixth flow path may have releasable seals at locations 11 and 12. In some implementations, the location where the sixth flow path fluidically connects with chamber D may be positioned to be further from the reference boundary "d" than the location where the third flow path fluidically connects with chamber D; in some such implementations, the sixth flow path may fluidically connect with chamber D at a location on chamber D farthest from the reference boundary "d" and/or the third flow path may fluidically connect with chamber D at a location on chamber D farthest from the reference boundary "e." In some alternative implementations, the releasable seal at location 11 may be a dynamic seal and the release pressure of the dynamic seal at location 11 may be higher than the release pressure of the releasable seal at location 6.

The fluidic circuit of FIG. 112D may also include a chamber H, at least a portion of which is above the reference boundary "e." In some implementations, all of chamber H may lie above the reference boundary "e." It will be understood that the chamber H may also be provided by multiple chambers or sub-chambers, similar to as described above with respect to chambers A through G. Chamber H may be preloaded with fluid, e.g., loaded prior to operation of the fluidic circuit, or may be loaded with fluid during operation of the fluidic circuit. A seventh flow path may be fluidically connected with chamber H at a location on a side of the reference boundary "e" that faces the reference boundary "e" and with chamber E at a location between the reference boundary "e" and the reference boundary "f." The seventh flow path may have releasable seals at locations 13 and 14. The release pressure for the releasable seal at location 13 may be higher than that of the releasable seal at location 8.

The fluidic circuit of FIG. 112D may also include a chamber I, at least a portion of which is above the reference boundary "f." In some implementations, all of chamber I may lie above the reference boundary "f." It will be understood that the chamber I may also be provided by multiple chambers or sub-chambers, similar to as described above with respect to chambers A through H. Chamber I may be preloaded with fluid, e.g., loaded prior to operation of the fluidic circuit, or may be loaded with fluid during operation of the fluidic circuit. An eighth flow path may be fluidically connected with chamber I at a location on a side of the reference boundary "f" that faces the reference boundary "e" and with chamber F at a location between the reference boundary "f" and the reference boundary "g." The eighth flow path may have releasable seals at locations 15 and 16. In some implementations, the location where the eighth flow path fluidically connects with chamber F may be positioned to be further from the reference boundary "f" than the location where the fifth flow path fluidically connects with the chamber F; in some such implementations, the eighth flow path may fluidically connect with chamber F at a location on chamber F farthest from the reference boundary "f" and/or the fifth flow path may fluidically connect with chamber F at a location on chamber F farthest from the reference boundary "g." In some alternative implementations, the releasable seal at location 15 may be a dynamic seal and the release pressure of the dynamic seal at location 15 may be higher than the release pressure of the releasable seal at location 10.

It will be appreciated that any number of additional chambers, flow paths, and reference boundaries may be included in such fluidic circuits, with each set of additional chambers, flow paths, and reference boundaries generally being implemented in a manner similar to as described herein. It will also be appreciated that in some implementations some chambers may be placed so as to be simultaneously compressed by the clamping pressure zone so as to simultaneously push fluids in such chambers into chamber B. In some implementations, the chambers may be arranged so that the clamping pressure zone may traverse chambers that deliver fluids to chamber B through different flow paths in an alternating fashion, e.g., chamber C, followed by chamber E, followed by chamber D, followed by chamber F.

The operation of the fluidic circuit of FIG. 112D, at least with respect to clamping pressure zone movements, may parallel that of the fluidic circuit of FIG. 112C. In the fluidic circuit of FIG. 112D, however, the fluids that are directed through the various fluidic paths in the fluidic circuit may all be stored in chambers A and G through I, with chambers B through F initially being empty of fluids; chamber B may have a surface of interest, as in earlier example fluidic circuits. The fluidic circuit of FIG. 112D may be used to provide functionality similar to the fluidic circuit of FIG. 112C, but with the ability to load the fluids used in the various chambers B through F via the chambers A and G through I, which may, for example, optionally extend all the way to (or past) the reference boundary "a," thus allowing, for example, such fluids to be introduced through openings along a top edge of the fluidic structure. It will be understood that in some such implementations, some fluids may be pre-loaded into one or more of chambers A and G through I while other fluids in chambers A and G through I may be loaded through operation of the fluidic circuit, e.g., via flow paths (not shown) to earlier fluidic elements. For example, chambers within fluidic circuits such as those discussed herein that are "pre-loaded" with fluid may be fluidically connected to passages leading to ports that may be located at various locations; after such chambers are loaded with their respective fluids via such ports, the passages leading from such ports to those chambers may be permanently sealed, e.g., via thermal bonding, to seal the fluid into the chamber until application of a clamping pressure zone to the fluidic circuit causes such fluid to move. Such ports may, in some instances, be located along an edge of the fluidic structure that is generally transverse to the direction of travel of the clamping pressure zone and may, in other instances, be located along an edge of the fluidic structure that is generally parallel to the direction of travel of the clamping pressure zone. In yet other instances, such ports may even be located within the interior of the fluidic structure, e.g., a passage that leads to a hole in one of the portions of material between which the fluidic circuit is defined. It will also be appreciated that a given fluidic structure may have pre-loaded chambers that are pre-loaded via passages that lead to a mix of two or more such ports, e.g., some leading to ports in the interior of the fluidic structure, some leading to ports on one or both edges of the fluidic structure that are transverse to the intended direction of clamping zone translation, and/or some leading to ports on one or both edges of the fluidic structure that are parallel to the intended direction of clamping zone translation. In particular, loading ports that are located along the edge of the fluidic structure that is generally transverse to the direction of clamping zone movement (such as in FIG. 112D) may be particularly advantageous since such configurations allow for all of the fluids that are to be pre-loaded into such fluidic circuits to be introduced to the fluidic circuit from one side of the fluidic structure and then pushed downstream into various other staging chambers (such as chambers D, E, or F in FIG. 112D) by motion of the clamping pressure zone. In contrast, if such staging chambers were instead directly filled through ports located on edges of the fluidic structure that are parallel to the clamping pressure zone direction of travel (see FIG. 112C, for example), it may be necessary, depending on the fluidic circuit layout, to perform separate fluid delivery operations on different sides of the fluidic structure, thereby increasing manufacturing complexity and potential cost.

It will be understood that chamber G is configured to provide sequential filling of chambers D and C with the same fluid, whereas chambers H and I may be configured to sequentially fill chambers E and F, respectively, with separate and potentially different fluids. It will be further understood that chambers C and D may be provided fluids from chambers similar to chambers H and I, and/or that the chambers E and F may be provided fluids from a chamber similar to chamber G, if desired.

In some implementations, the sixth flow path between chambers G and D may preferably fluidically connect with chamber D at a location along an edge of chamber D that faces towards the reference boundary "e" and then travel sideways before turning to cross at least the reference boundaries "c" and "d" to fluidically connect with chamber G. Similarly, the eighth flow path between chambers I and F may preferably fluidically connect with chamber F at a location along an edge of chamber F that faces towards the reference boundary "g" and then travel sideways before turning to cross the reference boundary "f" to fluidically connect with chamber I.

In some implementations, the location where the seventh flow path may fluidically connect with the chamber E may be positioned close to the reference boundary "e" or, in some implementations, as close to the reference boundary "e" as possible.

Subjecting the fluidic circuit of FIG. 112D to clamping pressure zone movements such as are described with reference to the fluidic circuit of FIG. 112C may first cause the fluid in chamber A to be pushed into chamber B, followed by the fluid from chamber A that is resident in chamber B being pushed back in to chamber A when the clamping pressure zone is moved to reference boundary "c" and then back to reference boundary "b." As the clamping pressure zone is moved from reference boundary "b" to reference boundary "c," the fluid in chamber G may reach the release pressure associated with the releasable seal 12 on the sixth flow path, thereby allowing the fluid in chamber G to be pushed into chambers D and C. This ensures that when the clamping pressure zone is subsequently moved to reference boundary "d" and then to reference boundary "c," the fluid that is now in chamber C is caused to be pushed into chamber B. Similarly, when the clamping pressure zone is later moved to reference boundary "e" and then to reference boundary "c" again, the fluid that is now in chamber D is caused to be pushed into chamber B. During movement of the clamping pressure zone from the reference boundary "d" to the reference boundary "e," the clamping pressure zone may apply pressure to the fluid in chamber H such that the releasable seal 14 on the seventh flow path releases and allows the fluid in chamber H to flow into chamber E. When the clamping pressure zone is then subsequently moved from the reference boundary "e" to the reference boundary "c" in order to cause the fluid in chamber E to be moved to chamber B, the pressure that is also applied to chamber I may cause the fluid contained therein to reach the release pressure for the releasable seal 16 on the eighth flow path, thereby allowing the fluid in chamber I to flow into chamber F.

There may be a number of variations of the fluidic circuit of FIG. 112D. For example, if it is beneficial to prevent the fluids in chambers H and I from mixing, e.g., if such fluids might undergo an undesirable chemical reaction if mixed, then chamber E may be sized such that the maximum total volume of chamber E is greater than or equal to the anticipated maximum total amount of fluid that will be held in chamber H, and chamber F may be sized such that the maximum total volume of chamber F is greater than or equal to the anticipated maximum total amount of fluid that will be held in chamber I. In some such implementations, the maximum total volume of chamber F may be sized to be equal to, or substantially equal to, the anticipated maximum total amount of fluid that may be contained within chamber I.

In some implementations, the third flow path may fluidically connect with chamber C at a location on chamber C that is closest to the reference boundary "c" so as to reduce the possibility that fluid will be pushed from chamber C to chamber D during movement of the clamping pressure zone from reference boundary "c" to reference boundary "d." Similarly, the fifth flow path may fluidically connect with chamber E at a location on chamber E that is closest to the reference boundary "e" so as to reduce the possibility that fluid will be pushed from chamber E to chamber F during movement of the clamping pressure zone from reference boundary "e" to reference boundary "f."

In some implementations, chamber H and E and/or chamber I and F may be moved further from the reference boundary "a," e.g., such that, for example, at least a portion of chamber H is on a side of reference boundary "f" that is closest to reference boundary "e" and such that at least a portion of chamber E is between reference boundaries "f" and "g" and/or such that, for example, at least a portion of chamber I is on a side of reference boundary "g" (or another reference boundary, not depicted, that is "below" reference boundary "g") that is closest to reference boundary "f" and such that at least a portion of chamber F is between reference boundary "g" and the undepicted reference boundary. Such implementations may allow the combined maximum total volumes of chambers E and F to be greater than or equal to the anticipated maximum total fluid volume that is to be held in chamber H and to be greater than or equal to the anticipated maximum total combined fluid volume that is to be held in chambers I and E.

Other or additional such variants may include, for example, fluidic circuits in which one or more of the releasable seals at locations 4, 14, and/or 16 may optionally be replaced with open flow paths. In some implementations, some releasable seals may instead be replaced by live seals, e.g., on the second, sixth, seventh, and/or eighth flow paths.

In some implementations, the sixth flow path may extend to a location that is farther from the reference boundary "a" than any portion of chamber D before reversing direction to fluidically connect with chamber D. In some such implementations, the sixth flow path may fluidically connect with chamber D at a location on chamber D that is closest to the reference boundary "a." In some implementations, chambers C and D may instead be a single chamber, and the sixth flow path may be similarly configured.

FIG. 96 depicts an example of a fluidic circuit such as that depicted in FIG. 112D.

Figure 112E:
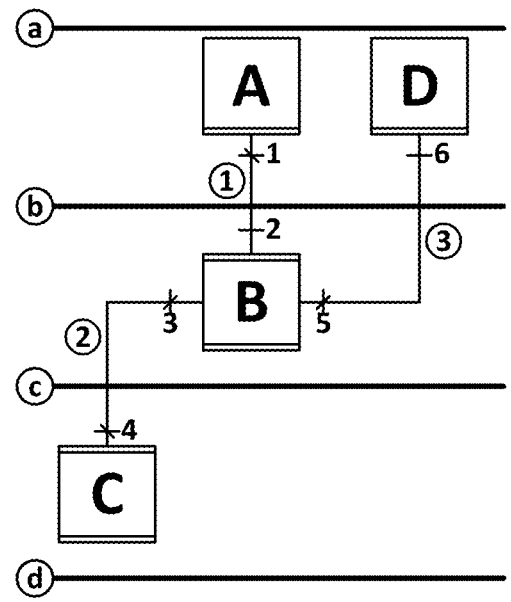

FIG. 112E depicts another fluidic circuit that is a variant of the fluidic circuit depicted in FIG. 112A; in the depicted variant, fluids are flowed into chamber D instead of chamber A after flowing through chamber B. In FIG. 112E, the fluidic circuit of FIG. 112A is augmented with an additional chamber D, of which at least a portion thereof is located on a side of the reference boundary "b" that faces towards the reference boundary "a." Chamber D, which may be empty of fluid prior to operation of the fluidic circuit in order to deliver fluids from chambers A and C to chamber B, may have a total combined maximum volume that is greater than or equal to the anticipated maximum amount of fluid in chamber A prior to the fluid in chamber A being moved to chamber B (or, in the case where chamber B is to be ultimately emptied of the fluid from chamber C, the total combined maximum volume of chamber D may be greater than or equal to the anticipated combined maximum fluid volumes that will be in chambers A and C prior to any of such fluids being moved to chamber B). In some implementations, all of chamber D may be located on the side of the reference boundary "b" that faces towards the reference boundary "a." A third flow path may fluidically connect to chamber D at a location on the side of the reference boundary "b" that faces towards the reference boundary "a" and may fluidically connect to chamber B at a location that lies between the reference boundaries "b" and "c." The third flow path may feature a dynamic seal at location 6, e.g., where the third flow path fluidically connects with chamber D, and a releasable seal at location 5, e.g., in between chamber B and the dynamic seal at location 6. In such an implementation, the dynamic seal at location 6 may be configured to have a release pressure that is higher than the pressure that the clamping pressure zone may be able to generate within chamber D, thus allowing fluid to flow into chamber D, but preventing it from flowing out. The fluidic circuit of FIG. 112E also features a slight revision from that of FIG. 112A in that location 1 features a releasable seal (instead of a dynamic seal) and location 2 features a dynamic seal (instead of a releasable seal). The releasable seal at location 3 in the fluidic circuit of FIG. 112E has a release pressure that is higher than the dynamic seal at location 2. Similarly, the dynamic seal at location 2 has a higher release pressure than the releasable seal at location 5.

The fluidic circuit of FIG. 112E may be used in much the same manner as that of FIG. 112A, except that the fluid that is delivered into chamber B from chamber A is instead delivered to chamber D after being delivered to chamber B. In some implementations, the fluid from chamber C may also optionally be delivered to chamber D after being delivered to chamber B.

The operation of the fluidic circuit of FIG. 112E may proceed in a manner largely similar to that of the fluidic circuit of FIG. 112A, with the major difference being that movement of the clamping pressure zone from reference boundary "c" to reference boundary "b" will cause the fluid in chamber B to be directed to chamber D instead of to chamber A. This is due to the releasable or dynamic seals used at locations 2 and 3 having higher release pressures than the releasable seal at location 5. In some implementations, the third flow path may fluidically connect with chamber B at a location that is close to the reference boundary "b" or, in some implementations, as close to the reference boundary "b" as possible. In such implementations, as the clamping pressure zone traverses the chamber B from the reference boundary "b" to the reference boundary "c," the clamping pressure zone will nearly immediately move past the fluidic connection point between the third flow path and chamber D—thus, any pressure that subsequently builds up in the fluid that is trapped between the clamping pressure zone and the reference boundary "c" in the chamber B during such movement does not get applied to the releasable seal at location 5.

In some implementations, the first flow path and/or the third flow path may optionally be sealed with a live seal of some type, in which case one or both of the seals that are indicated as being associated with either of those flow paths may be omitted.

Figure 112F:
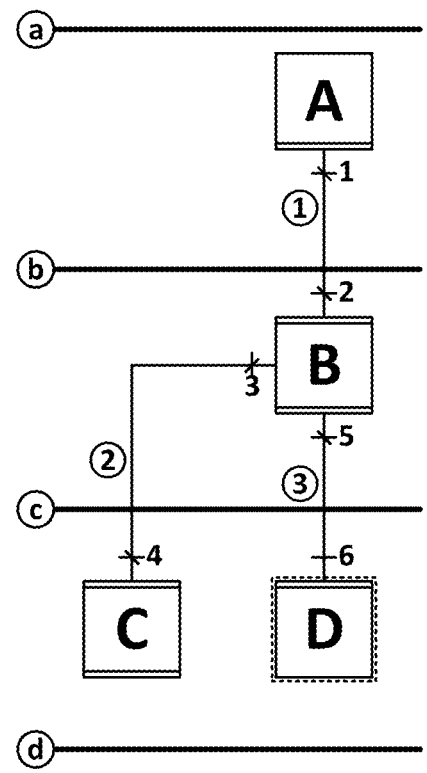

FIG. 112F depicts another variant of the fluidic circuit of FIG. 112A.

In FIG. 112F, the fluidic circuit of FIG. 112A is also augmented with an additional chamber D, of which at least a portion thereof is located on a side of the reference boundary "c" that faces towards the reference boundary "d." Chamber D, which may be empty of fluid prior to operation of the fluidic circuit in order to deliver fluids from chambers A and C to chamber B, may have a total combined maximum volume that is greater than or equal to the anticipated maximum amount of fluid in chamber A prior to the fluid in chamber A being moved to chamber B. In some implementations, all of chamber D may be located on the side of the reference boundary "c" that faces towards the reference boundary "d."

A third flow path may fluidically connect to chamber D at a location on the side of the reference boundary "c" that faces towards the reference boundary "d" and may fluidically connect to chamber B at a location that lies between the reference boundaries "b" and "c." The third flow path may feature a dynamic seal at location 6, e.g., where the third flow path fluidically connects with chamber D, and a releasable seal at location 5, e.g., in between chamber B and the dynamic seal at location 6. The third flow path may, for example, fluidically connect with chamber B at a location that is farther from reference boundary "a" than where the second flow path may fluidically connect with chamber B.

As with the fluidic circuit of FIG. 112E, the dynamic seal at location 6 may be configured to have a release pressure that is higher than the pressure that the clamping pressure zone may be able to generate within chamber D, thus allowing fluid to flow into chamber D, but preventing it from flowing out. The releasable seal at location 3 in the fluidic circuit of FIG. 112F has a release pressure that is higher than the releasable seal at location 2. Similarly, the releasable seal at location 2 has a higher release pressure than the releasable seal at location 5.

The fluidic circuit of FIG. 112F may be used in much the same manner as that of FIG. 112A, except that the fluid that is delivered into chamber B from chamber A is instead delivered to chamber D after being delivered to chamber B. In some implementations, the fluid from chamber C may also optionally be delivered to chamber A after being delivered to chamber B.

Variants of the fluidic circuit of FIG. 112F may include, for example, versions in which the first flow path and/or the third flow path may be subjected to a live seal of some type after fluid has been caused to flow through such flow paths, in which case one of the seals indicated on either or both flow paths may be optionally omitted. For example, the first flow path may be live sealed when the clamping pressure zone first moves the reference boundary "b," and/or the third flow path may be live sealed when the clamping pressure zone first moves to reference boundary "c."

Chamber D may, as shown in FIG. 112F by the dotted line boundary around chamber D, be positioned so as to be located over a hole or recess in a platen used to support the fluidic circuit during application of the clamping pressure zone to the fluidic circuit. The cavity or recess in the platen may reduce or virtually eliminate the force or pressure that is applied to chamber D when the clamping pressure zone moves from reference boundary "c" to reference boundary "d." This may prevent fluid from chamber A that has been delivered to chamber D after passing through chamber B from being pushed back out of chamber D when the clamping pressure zone is moved to reference boundary "d" in preparation for moving the fluid in chamber C into chamber B.

Alternatively, the recess or hole in the platen may be omitted and chamber D may instead be located on the side of reference boundary "d" that faces away from reference boundary "c" such that chamber C may be subjected to pressure from the clamping pressure zone without the fluid in chamber D being similarly pressurized. This may be preferable in situations where chamber D is fluidically connected with further fluidic circuits further "downstream," e.g., fluidic circuits that are below (with respect to the Figure orientation) the lowest portion of the depicted fluidic circuit.

The third flow path may, in some implementations, connect with chamber B at a location that is close to the reference boundary "b" or, in some implementations, as close to the reference boundary "b" as possible. In such implementations, as the clamping pressure zone traverses the chamber B from the reference boundary "b" to the reference boundary "c," the clamping pressure zone will nearly immediately move past the fluidic connection point between the third flow path and chamber D-thus, any pressure that subsequently builds up in the fluid that is trapped between the clamping pressure zone and the reference boundary "c" in chamber B during such movement does not get applied to the releasable seal at location 5. Such an implementation may be particularly useful in the event that the total maximum volume of chamber D is not greater than or equal to the anticipated maximum fluid volume contained in chamber A prior to movement of the fluid in chamber A to chamber B. In such an implementation, the clamping pressure zone may, instead of being moved between reference boundaries a-b-c-b-d-c, be moved between reference boundaries a-b-c-b-d-c, thereby driving back into chamber A whatever fluid from chamber A still remains in chamber B after chamber D has been filled with fluid from chamber A via chamber B before proceeding to cause fluid from chamber C to be moved to chamber B.

It will be understood that the fluidic circuit of FIG. 112F may be modified to allow for additional fluids from additional chambers to be flowed through chamber B as well. For example, one or more additional chambers may be fluidically connected in series to chamber C, e.g., similar to the arrangement in FIG. 112B, in order to provide additional fluid flows. In such implementations, the releasable seal at location 1 may preferably be a dynamic seal or, optionally, a live seal that may be formed through application of heat to location 1 from a heater in a platen against which the clamping pressure zone is pressing.

FIG. 96, discussed previously, depicts an example of a fluidic circuit such as that depicted in FIG. 112F.

In the fluidic circuits of FIGS. 112A through 112F, the clamping pressure zone is moved between reference boundaries such that the direction of travel of the clamping pressure zone reverses course at least once. FIGS. 113A through 113D depict various fluidic circuits that allow for a surface of interest to be sequentially exposed to different fluids using only, or primarily, unidirectional clamping pressure zone movement.

Figure 113A:
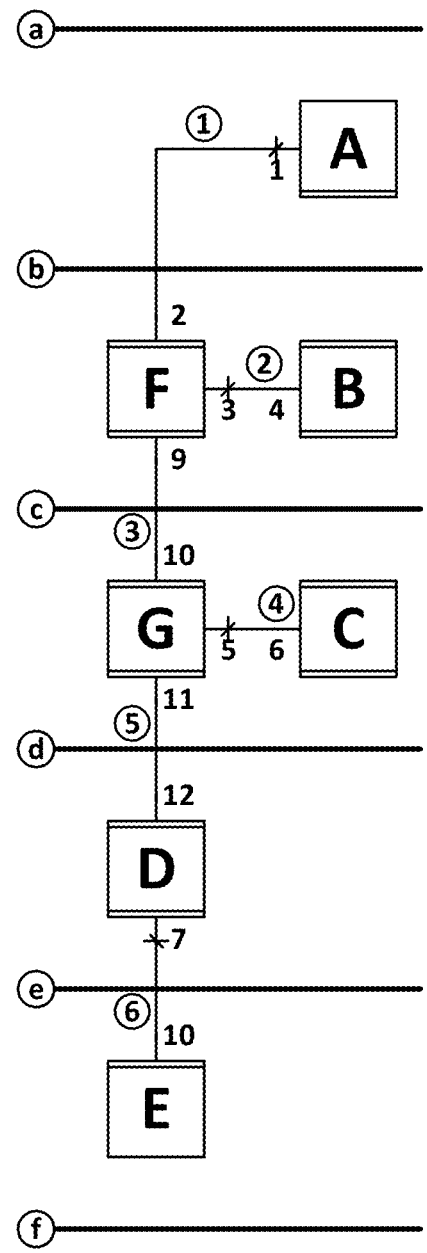
FIGS. 113A through 113C depict two fluidic circuits that may be used to expose a surface to two or more fluids in sequence.

FIG. 113A depicts a diagram of an example fluidic circuit that may be used to inundate a surface of interest within a chamber with two different fluids at two different times and with little mixing of the fluids. It will be understood that the fluidic circuit of FIG. 113A may, for example, be extended by inserting additional instances of some chambers/flow paths, e.g., the fluidic elements between reference boundaries "b" and "c" may be repeated one or more times in series in order to extend the capabilities of the depicted fluidic circuit to allow for more than two separate fluids to be flowed past the surface of interest. The fluidic circuit of FIG. 113A includes seven chambers A through G. Per the conventions discussed above, at least a portion of the chamber A is on a side of the reference boundary "b" that faces the reference boundary "a," at least portions of chambers F and B are between the reference boundaries "b" and "c," at least portions of chambers G and C are between the reference boundaries "c" and "d," at least a portion of the chamber D is between the reference boundaries "d" and "e," and at least a portion of chamber E is on a side of reference boundary "e" facing towards reference boundary "f." In some implementations, all of chamber A may be on the side of the reference boundary "b" that faces the reference boundary "a," all of chambers F and/or B may be in between the reference boundaries "b" and "c," all of chambers G and/or C may be in between the reference boundaries "c" and "d," all of chamber D may be in between reference boundaries "d" and "e," and/or all of chamber E may on the side of reference boundary "f" that faces towards the reference boundary "f."

Chambers A-C may be preloaded with fluids and chambers D-G may be empty prior to operation of the fluidic circuit of FIG. 113A. Chamber D may have a surface of interest that is immobilized within it. It will be understood that chambers F and G may actually be quite small in nature, e.g., chambers F and G may, in some instances, be a small volume where one flow path tees into another or where three flow paths meet.

The various chambers of the fluidic circuit of FIG. 113A may be fluidically connected with each other by a plurality of flow paths. For example, chamber A may be fluidically connected with a first flow path at a location that is on a side of the reference boundary "b" that faces towards the reference boundary "a." The other end of the first flow path may be fluidically connected with chamber F at a location in between the reference boundaries "b" and "c." Chamber F may also be fluidically connected with chamber B by a second flow path that fluidically connects with both chambers at locations in between reference boundaries "b" and "c." A third flow path also may fluidically connect with chamber F at a location in between the reference boundaries "b" and "c." An opposing end of the third flow path may fluidically connect with chamber G at a location that is between the reference boundaries "c" and "d."

Chamber G may, in turn, be fluidically connected with chamber C by a fourth flow path that fluidically connects with both chambers, as well as with a fifth flow path, at locations that are between the reference boundaries "c" and "d." The fifth flow path may fluidically connect at an opposing end with chamber D at a location in between reference boundaries "d" and "e." A sixth flow path may also fluidically connect with chamber D at a location in between reference boundaries "d" and "e" and with chamber E at a location on a side of reference boundary "e" that faces towards reference boundary "f."

The various chambers of the fluidic circuit shown in FIG. 113A may, for example, have volumes such that the total combined maximum volume of chambers D and E is greater than or equal to the anticipated total combined volume of fluid in chambers A, B, and C.

In some implementations, the locations where the first, second, and/or fourth flow paths respectively fluidically connect with the chambers A, B, and/or C may be positioned close to the reference boundaries "b," "c," and/or "d," respectively, or, in some implementations, as close to the reference boundaries "b," "c," and/or "d," respectively, as possible. In such implementations, as the clamping pressure zone traverses such chambers in moving from reference boundary "a" through reference boundaries "b" and "c" to reference boundary "d," the clamping pressure zone will move past such fluidic connection points either shortly before it stops applying pressure to the corresponding chamber, or contemporaneously therewith. This may ensure that the fluids that are housed in chambers A, B, and/or C are completely driven out of such chambers and into chamber D. In some implementations, the locations where the second and fourth flow paths fluidically connect with chambers F and G, respectively, may be positioned closer to, or at the same distance from, the reference boundaries "c" and "d" as are the locations where those same flow paths fluidically connect with the chambers B and C, respectively. It will also be appreciated that, for example, some implementations of the fluidic circuit may have chambers B and/or C positioned closer to reference boundaries "b" and "c," respectively, than chambers F and G, respectively. In one such implementation, a clamping pressure zone being moved from reference boundary "b" to reference boundary "d" may pass completely over chamber B before reaching chamber F, and, similarly, completely over chamber C before reaching chamber G. Similar variants are to be understood as being contemplated for other similar fluidic circuits discussed later below, such as with reference to FIG. 113B.

In some further such implementations, the locations where the second and/or fourth flow paths respectively fluidically connect with the chambers F and/or G may be positioned at a distance from the reference boundaries "c" and/or "d," respectively, that is less than or equal to a corresponding distance between the locations where the second and/or fourth flow paths, respectively, and those same reference boundaries, respectively. This may help ensure that the fluid that flows through such flow paths is able to completely be drained into the chambers F and/or G as the clamping pressure zone traverses chambers B and C in moving from reference boundary "a" through reference boundaries "b" and "c" to reference boundary "d,"

The various flow paths that are depicted may have various seal or open flow path features along their lengths. For example, the first flow path may have a releasable seal at location 1, which may be on a side of the reference boundary "b" that faces towards the reference boundary "a," and an open flow path at location 2, which may be between the reference boundaries "b" and "c." The second and fourth flow paths may each have a releasable seal located at some point along their lengths, while the third and fifth flow paths may each be open flow paths along their lengths, e.g., with no obstacles to flow between chamber A and chamber D. The sixth flow path may, for example, have a releasable seal with the remainder of the sixth flow path being an open flow path.

During operation of the fluidic circuit of FIG. 113A, a clamping pressure zone may be caused to move from reference boundary "a" to reference boundary "b" and then to reference boundary "c" and reference boundary "d"; in some implementations, the clamping pressure zone may also move to reference boundary "e" (which may be done if it is desired to drain or purge chamber D of fluids after the fluids from chamber C are delivered thereto). Such clamping pressure zone movement may cause the fluids that are stored in chambers A, B, and C to sequentially be driven into chamber D and then into chamber E with little or minimal mixing between the two fluids.

In some variations on such implementations, the various open flow paths that are shown along the combined flow path from chamber A to chamber E may, alternatively, be provided by dynamic seals or temporary seals. In such implementations, the release pressures for such dynamic seals or temporary seals may be less than the release pressures for any releasable seals on the second and fourth flow paths, thereby ensuring that fluid from chamber A that is pushed into chamber F is caused to move to chamber G rather than into chamber B, and that fluid from chamber F that is pushed into chamber G is caused to move to chamber D rather than into chamber C. The releasable seals located on the second and fourth flow paths may, for example, be dynamic seals with release pressures that exceed the pressures in chambers F and G that the clamping pressure zone may be able to provide.

In implementations in which the releasable seal at location 7 is a temporary seal, it may be desirable to use a sequential seal region, e.g., as shown in FIGS. 44 through 46, of multiple temporary seals arranged in sequence across the sixth flow path/chamber E so as to allow the volume of the sixth flow path to incrementally be expanded as each temporary seal in sequence releases during pressurization of the sixth flow path. This may allow chamber D to remain inflated until the fluid therein is forced out through movement of the clamping pressure zone across chamber D, thereby allowing for the surface of interest in chamber D to be more effectively wetted by the fluid that is introduced therein by keeping the portions of material between which chamber D is defined separated. Alternatively, the temporary seal at location 7 may be a single seal that is relatively thick, e.g., having a thickness along an axis parallel to the direction of travel of the clamping pressure zone that extends along a substantial portion of the sixth flow path. In such a temporary seal, pressurization of chamber D may cause the temporary seal to incrementally open (in a manner somewhat analogous to that of the temporary seals in a sequential seal region, but in a continuous fashion rather than in an incremental step fashion). In such implementations, the sixth flow path may be sized, for example, to be able to hold the anticipated combined fluid volumes of the fluids in chambers A, B, and C just prior to fluidic operation of the fluidic circuit.

FIG. 41, discussed previously, depicts one example of a fluidic circuit that is compatible with the fluidic circuit of FIG. 113A.

Figure 113B:
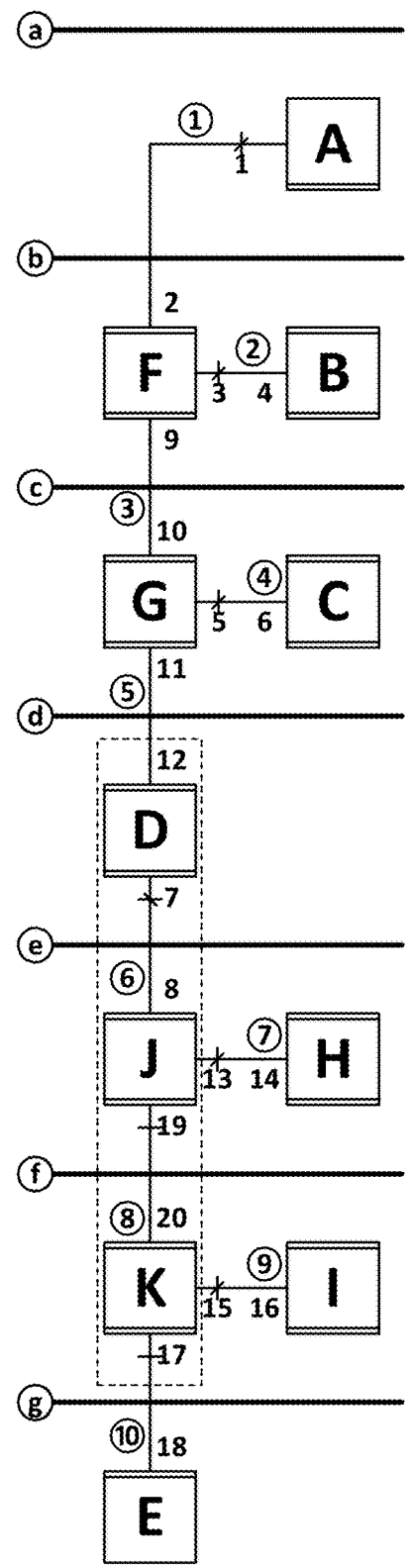

FIG. 113B depicts another fluidic circuit that builds on the fluidic circuit of FIG. 113A. As can be seen, the fluidic circuit of FIG. 113B has the same configuration of chambers A-C, F, and G as the fluidic circuit of FIG. 113A, but exhibits differences in how chambers D and E are configured. In particular, there are additional chambers H-K that are part of the fluidic circuit that allow for additional fluids to be introduced into chamber D, which may contain a surface of interest, from locations "downstream" of chamber D. For example, at least portions of chambers J and H are between the reference boundaries "e" and "f," and at least portions of chambers K and I are between the reference boundaries "f" and "g." Chambers H and I may, for example, each hold an amount of fluid that is to be sequentially introduced into chamber D as a clamping pressure zone is moved from reference boundary "e" to reference boundary "g." Chambers J and K, like chambers F and G, may be sized quite small, e.g., may be chambers resulting from a tee intersection between two passages, or an intersection between three passages (and thus have sizes governed by the widths of those passages).

In the fluidic circuit of FIG. 113B, the sixth flow path may, instead of fluidically connecting chamber D with chamber E, fluidically connect chamber D with chamber J. Thus, for example, the sixth flow path may fluidically connect with chamber D at a location in between reference boundaries "d" and "e" at one end and, at the opposite end, with chamber J at a location in between the reference boundaries "e" and "f." A seventh flow path may fluidically connect chambers J and H in a manner similar to how the second and fourth flow paths fluidically connect chambers F and B and G and C, respectively. An eighth flow path may fluidically connect with chamber J at a location in between reference boundaries "e" and "f" at one end and may have an opposite end that fluidically connects with chamber K at a location in between reference boundaries "f" and "g." A ninth flow path may fluidically connect chambers K and I in a manner similar to how the second, fourth, and seventh flow paths fluidically connect chambers F and B, G and C, and J and H, respectively. A tenth flow path may fluidically connect with chamber K at a location that is between the reference boundaries "f" and "g" and may fluidically connect with chamber E at a location that is on a side of the reference boundary "g" that faces away from the reference boundary "f."

The seventh and ninth flow paths may be similarly configured to the second and fourth flow paths, e.g., with respect to releasable seals and with respect to the positioning of the fluidic connections of those flow paths relative to the closest reference boundaries thereto in the direction of the reference boundary "g." However, the eighth flow path may have a dynamic seal at location 19 that has a release pressure that is lower than the release pressure of the releasable seal at location 13. Somewhat similarly, the tenth flow path may have a dynamic seal at location 17 that has a release pressure that is lower than the release pressure of either of the releasable seals at locations 13 and 15. Thus, when fluid from chamber D is caused to flow into chambers J and K responsive to movement of a clamping pressure zone towards reference boundary "g," the dynamic seals at locations 19 and 17, having lower release pressures, will release before the releasable seals at locations 13 and 15 release, thereby constraining such fluid flow to move into chamber E. However, when chambers H or I are pressurized, the fluid that is pushed out of those chambers into chambers J or K, respectively, will be prevented from flowing towards chamber E due to the dynamic seals at locations 19 and 17, respectively. In other words, the fluid from chambers H and I may flow past the clamping pressure zone and in a direction opposite the direction of travel of the clamping pressure zone. This is made possible by the presence of an opening or recess (as indicated by the dotted outline) in the platen against which that clamping pressure zone is developed that overlaps with at least the chambers J and K, the eighth flow path, and, optionally, chamber D. The opening or recess reduces or eliminates the clamping pressure that may be exerted on chambers J and K, for example, when the clamping pressure zone transits across those chambers, while still allowing the clamping pressure zone to pressurize chambers H and I. If it is desired that chamber D be purged of any fluids from chambers A-C prior to the introduction of fluid from chamber H to chamber D, then the opening or recess in the platen may be caused, for example, to not overlap with chamber D.

As with the fluidic circuit of FIG. 113A, the fluidic circuit of FIG. 113B may be operated by applying a clamping pressure zone to the fluidic circuit and then moving that clamping pressure zone from reference boundary "a" through reference boundary "g." Such clamping pressure zone movement results in the fluids in chambers A, B, and C to be sequentially flowed into (and out of) chamber D and then through chambers J and K before flowing into chamber E. When the clamping pressure zone reaches chamber H, however, the fluid that flows from chamber H into chamber J may, due to the presence of the dynamic seal at location 19 and the reduction or absence of clamping pressure on chamber J due to the cavity or opening in the platen against which the clamping pressure zone is applied, flow in the opposite direction as the movement of the clamping pressure zone, eventually flowing through chambers G and F (or G alone) and into, for example, one or more of chambers A-C. A similar fluidic flow may happen with respect to chambers I and K when the clamping pressure zone moves to reference boundary "g." In implementations in which the fluidic circuit of FIG. 113B is interfaced with a platen having a recess or opening it that overlaps with chambers J and K but not chamber D, the unidirectional movement of the clamping pressure zone may optionally be reversed during some portions of the operation of the depicted fluidic circuit in order to perform additional purging operations on chamber D. For example, the clamping pressure zone, on reaching reference boundary "f" and causing the fluid from chamber H to be delivered to chamber D, may be caused to reverse direction and move back to reference boundary "d" such that the fluid from chamber H that is in chamber D is caused to move through the fifth flow path and into chamber G prior to the clamping pressure zone being moved to reference boundary "g" in order to cause the fluid in chamber I to be moved to chamber D. In such implementations, the total maximum volume of chamber E may be greater than or equal to the anticipated total combined fluid volume contained within chambers A-C prior to operation of the fluidic circuit, and the total combined maximum volumes of chambers A-D may be greater than or equal to the anticipated combined fluid volume contained within chambers H and I prior to operation of the fluidic circuit. If chamber D is not purged, e.g., the cavity or opening in the platen is to overlap chamber D during operation of the fluidic circuit, then the total maximum combined volume of chambers D and E may be greater than or equal to the anticipated total combined fluid volume contained within chambers A-C prior to operation of the fluidic circuit, and the total combined maximum volumes of chambers A-C may be greater than or equal to the anticipated combined fluid volume contained within chambers H and I prior to operation of the fluidic circuit.

It will be appreciated that the various seals that may be present may generally be selected such that the flow paths between chambers F and B, G and C, J and H, and K and I have a higher release pressure than whatever releasable seals may be present along the flow paths between chambers F and G, G, and D, D and J, J and K, and K and E. To that end, in some implementations, any of the releasable seals at locations 3, 5, 13, and/or 15 may have relative high release pressures. It will also be appreciated that the "open flow path" locations that are shown may optionally be replaced with releasable seals, e.g., temporary or dynamic seals, that are consistent with this guidance.

In some variations of the fluidic circuit of FIG. 113B, the open flow path at location 12 may instead be replaced with a dynamic seal such that when fluid from chambers H or I is moved into chamber D, the dynamic seal at location 12 may act to seal chamber D and prevent such fluid from flowing out of chamber D until such fluid has been pressurized to the release pressure of that dynamic seal. Such a variation may be used when it is desirable to maintain a back pressure in chamber D, e.g., to maintain a particular volume of fluid within chamber D, thereby allowing for the surface of interest in chamber D to be more effectively wetted by the fluid that is introduced therein by keeping the portions of material between which chamber D is defined separated. In some other or additional variations of the fluidic circuit of FIG. 113B, the open flow path at location 18 may instead be replaced with a dynamic seal such that when fluid from chambers A, B, or C is moved into chamber E, the dynamic seal at location 18 may act to seal chamber E and prevent such fluid from flowing out of chamber E.

In some variations of the fluidic circuit of FIG. 113B, releasable seals, e.g., such as the releasable seal at location 13, may, for example, be temporary seals. In some such implementations, a live seal may be provided on the same flow path during operation of the fluidic circuit, e.g., after the fluid that was restrained by the temporary seal is caused to flow through the temporary seal (by pressurizing the fluid to the release pressure for the temporary seal), a heater in the platen against which the fluidic circuit may be placed may be activated so as to cause localized heating of the flow path through n which the temporary seal was located so as to, in conjunction with pressure applied by the clamping pressure zone, re-seal the flow path to prevent fluid from flowing back through the flow path. The clamping pressure zone, in such implementations, may be caused to reverse course after causing the desired fluid flow so as to apply pressure to the flow path along which the fluid flow occurred during the heat sealing process. For example, if such a paradigm is practiced with respect to the releasable seal at location 13, the clamping pressure zone may move from reference boundary "e" to reference boundary "f" to pressurize the fluid that is in chamber H so as to reach the release pressure for the releasable seal (temporary seal, in this case) at location 13 and then cause the fluid to move to chamber J and then chamber D. The clamping pressure zone may then be caused to reverse course and move to a location that causes it to apply pressure to location 13, at which point a heater that may be provided in the platen may be caused to apply heat to location 13 such that the combination of heat and clamping pressure causes the portions of material at location 13 to fuse together, thus forming a seal and preventing fluid flow back into chamber H.

In implementations in which the releasable seal at location 7 is a temporary seal, it may be desirable to use a sequential seal region, e.g., as shown in FIGS. 44 through 46, of multiple temporary seals arranged in sequence across the sixth flow path/chamber J so as to allow the volume of the sixth flow path to incrementally be expanded as each temporary seal in sequence releases during pressurization of the sixth flow path. This may allow chamber D to remain inflated until the fluid therein is forced out through movement of the clamping pressure zone across chamber D, thereby allowing for the surface of interest in chamber D to be more effectively wetted by the fluid that is introduced therein by keeping the portions of material between which chamber D is defined separated. Alternatively, the temporary seal at location 7 may be a single seal that is relatively thick, e.g., having a thickness along an axis parallel to the direction of travel of the clamping pressure zone that extends along a substantial portion of the sixth flow path. In such a temporary seal, pressurization of chamber D may cause the temporary seal to incrementally open (in a manner somewhat analogous to that of the temporary seals in a sequential seal region, but in a continuous fashion rather than in an incremental step fashion). In such implementations, the sixth flow path may be sized, for example, to be able to hold the anticipated combined fluid volumes of the fluids in chambers A, B, and C just prior to fluidic operation of the fluidic circuit.

It will be appreciated that the fluidic circuit of FIG. 113B may be extended to include any number of additional chambers, e.g., such as additional instances of chambers F and B, G and C, J and H, or K and I, that may be placed in series with similar instances of such chambers consistent with the implementation of FIG. 113B. It will also be appreciated that one or more sets of chambers may be omitted from the fluidic circuit of FIG. 113B. For example, chambers J and I may be omitted, with the flow path between chambers D and J instead fluidically connecting chambers D and K.

FIGS. 47 and 79, discussed previously, depict examples of fluidic circuits such as those that are depicted in FIG. 113B.

Figure 113C:
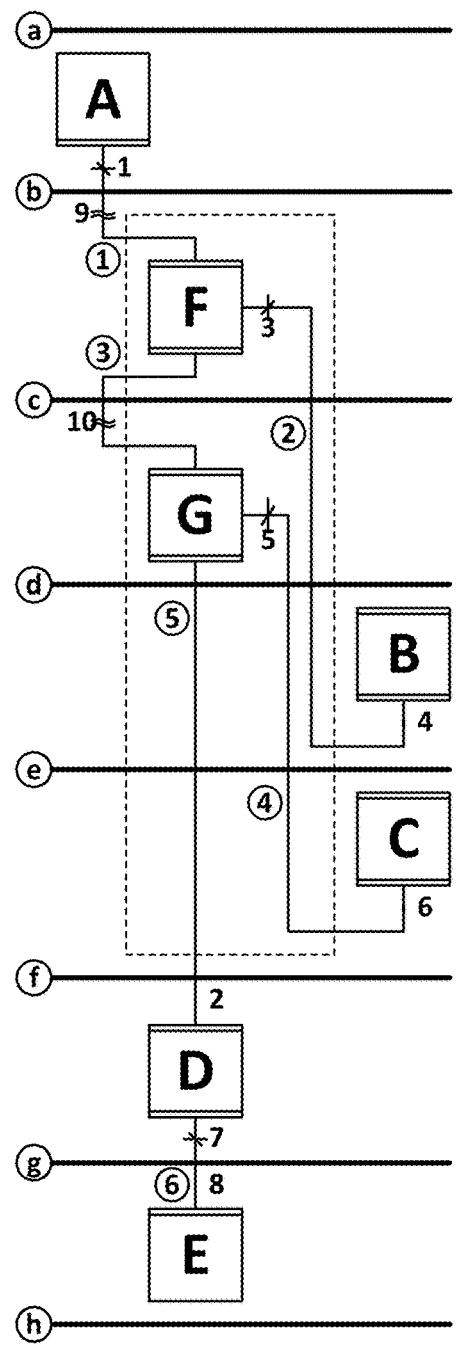

FIG. 113C depicts a fluidic circuit that builds on and modifies the fluidic circuit of FIG. 113A, offering further reductions in potential fluid mixing as compared with the fluidic circuit of FIG. 113A. Like the fluidic circuit of FIG. 113A, the fluidic circuit of FIG. 113C has chambers A-G. Per the conventions discussed above, at least a portion of the chamber A is on a side of the reference boundary "b" that faces the reference boundary "a," at least a portion of chamber F is between the reference boundaries "b" and "c," at least a portion of chamber G is between the reference boundaries "c" and "d," at least a portion of chamber B is between the reference boundaries "d" and "e," at least a portion of chamber C is between the reference boundaries "e" and "f," at least a portion of the chamber D is between the reference boundaries "f" and "g," and at least a portion of chamber E is on a side of reference boundary "g" facing towards reference boundary "h." In some implementations, all of chamber A may be on the side of the reference boundary "b" that faces the reference boundary "a," all of chamber F may be in between the reference boundaries "b" and "c," all of chamber G may be in between the reference boundaries "c" and "d," all of chamber B may be in between the reference boundaries "d" and "e," all of chamber C may be between the reference boundaries "e" and "f," all of chamber D may be in between reference boundaries "f" and "g," and/or all of chamber E may on the side of reference boundary "g" that faces towards the reference boundary "h."

Chambers A-C may be preloaded with fluids and chambers D-G may be empty prior to operation of the fluidic circuit of FIG. 113C. Chamber D may have a surface of interest that is immobilized within it. It will be understood that chambers F and G, similar to the chambers F and G in FIGS. 113A and 113B, may actually be quite small in nature, e.g., chambers F and G may, in some instances, be a small volume where one flow path tees into another or where three flow paths meet.

The various chambers of the fluidic circuit of FIG. 113C may be fluidically connected with each other by a plurality of flow paths. For example, chamber A may be fluidically connected with a first flow path at a location that is on a side of the reference boundary "b" that faces towards the reference boundary "a." The other end of the first flow path may be fluidically connected with chamber F at a location in between the reference boundaries "b" and "c." Chamber F may also be fluidically connected with chamber B by a second flow path that fluidically connects with chamber F at a location in between reference boundaries "b" and "c" and with chamber B at a location in between reference boundaries "d" and "e." A third flow path also may fluidically connect with chamber F at a location in between the reference boundaries "b" and "c." An opposing end of the third flow path may fluidically connect with chamber G at a location that is between the reference boundaries "c" and "d."

Chamber G may, in turn, be fluidically connected with chamber C by a fourth flow path that fluidically connects with chamber G at a location that is between reference boundaries "c" and "d" and with chamber C at a location that is between reference boundaries "e" and "f." Chamber G may also be fluidically connected with a fifth flow path at a location that is between the reference boundaries "c" and "d." The fifth flow path may fluidically connect at an opposing end with chamber D at a location in between reference boundaries "f" and "g." A sixth flow path may also fluidically connect with chamber D at a location in between reference boundaries "f" and "g" and with chamber E at a location on a side of reference boundary "g" that faces towards reference boundary "h."

The various chambers of the fluidic circuit shown in FIG. 113C may, for example, have volumes such that the total combined maximum volume of chambers D and E is greater than or equal to the anticipated total combined volume of fluid in chambers A, B, and C.

In some implementations, the locations where the first, second, and/or fourth flow paths respectively fluidically connect with the chambers A, B, and/or C may be positioned close to the reference boundaries "b," "e," and/or "f," respectively, or, in some implementations, as close to the reference boundaries "b," "e," and/or "f," respectively, as possible. In such implementations, as the clamping pressure zone traverses such chambers in moving from reference boundary "a" through reference boundaries "e" and "f," the clamping pressure zone will move past such fluidic connection points either shortly before if stops applying pressure to the corresponding chamber, or contemporaneously therewith. This may ensure that the fluids that are housed in chambers A, B, and/or C are completely driven out of such chambers and into chamber D. Similarly, the location where the fifth flow path fluidically connects with chamber D may be closer to reference boundary "a" than where the sixth flow path fluidically connects with chamber D.

The various flow paths that are depicted may have various seal or open flow path features along their lengths. For example, the first flow path may have a releasable seal at location 1, which may be on a side of the reference boundary "b" that faces towards the reference boundary "a," and an open flow path at location 9 which may be positioned such that a live seal may be generated at location 9, which may be between the reference boundaries "b" and "c," during fluidic operations with the fluidic circuit of FIG. 113C. The second and fourth flow paths may each have a releasable seal located at some point along their lengths, e.g., where such flow paths fluidically connect with chambers F and G (at locations 3 and 5, for example), respectively, while the third and fifth flow paths may each be open flow paths along their lengths, e.g., with no obstacles to flow between chamber A and chamber D. The third flow path may, however, be configured such that a live seal may be generated at location 10 during fluidic operations of the fluidic circuit. It will be understood that the live seals shown at locations 9 and 10 may optionally be formed at any position along the respective flow paths that feature them and that the specific depicted locations are not limiting. The sixth flow path may, for example, have a releasable seal with the remainder of the sixth flow path being an open flow path.

The fluidic circuit of FIG. 113C is intended to be used with a platen having a cavity or opening represented by the dotted/dashed region. The cavity or opening may, for example, overlap with at least part, if not all of, chambers F and G and overlap at least with the portions of the second and fourth flow paths that extend between the points of those flow paths closest to the reference boundary "h" and the locations where those flow paths fluidically connect with chambers F and G, respectively. The cavity or opening may not, however, overlap with chambers B and C.

During operation of the fluidic circuit of FIG. 113C, a clamping pressure zone may be caused to move from reference boundary "a" to reference boundary "b" and then to location 9 (or location 9 and then reference boundary "b" if location 9 is closer to reference boundary "a' than is reference boundary "b"). In doing so, the fluid in chamber A may be pushed through chambers F and G and into chamber D; releasable seals at locations 3 and 5 may prevent such fluid from flowing into chambers B or C during such flow. When the clamping pressure zone at location 9, a heating element in the platen against which the clamping pressure zone clamps the fluidic circuit may be activated to heat location 9 and generate a live seal thereat.

Once the live seal at location 9 is formed, the clamping pressure zone may then be caused to move to reference boundary "e," which may apply pressure to chamber B, thereby driving the fluid in chamber B through the releasable seal at location 3, into chamber F and then chamber G, and then into chamber D, thereby driving the fluid from chamber A that was in chamber D into chamber E. The clamping pressure zone may then move back to location 10, where a corresponding heater in the platen may be used in conjunction with the clamping pressure zone to create a live seal at location 10. It will be noted that locations 9 and 10 are not located in the region of the platen with the opening or cavity so as to ensure that a) heat can be applied to locations 9 and 10 by the platen heater(s) and b) such that both heat and pressure from the clamping pressure zone may be simultaneously applied to the portions of material in which the fluidic circuit is formed at locations 9 and 10. Once the live seal at location 10 is formed, the clamping pressure zone may then be moved to reference boundary "f," at which point the fluid in chamber C will be driven through the releasable seal at location 5 and through chamber G and into chamber D, thus driving the fluid from chamber B that was in chamber D into chamber E.

In some implementations, the operation of the fluidic circuit may further include moving the clamping pressure zone to reference boundary g so as to drive the fluid from chamber C that is in chamber D into chamber E. In such an implementation, the total volume of chamber E may be greater than or equal to the anticipated combined total volumes of fluid that are contained in chambers A-C prior to operation of the fluidic circuit.

The fluidic circuit of FIG. 113C may allow for multiple different fluids to be flowed through chamber D, thus gaining exposure to the surface of interest located therein. The fluidic circuit of FIG. 113C allows for such fluids to be sequentially flowed through chamber D with little or a minimal amount of mixing between any two of such fluids.

In some variants of the fluidic circuit of FIG. 113C, the first, third, and fifth flow paths may initially be open flow paths, whereas in other implementations, there may be one or more releasable seals placed along one or more such flow paths. In such implementations, such releasable seals may have release pressures that are less than the release pressures for the releasable seals that may be along the second and fourth flow paths, thereby preventing fluid that is pushed into chambers F or G from flowing into chambers B or C, respectively. For example, in some variations, a releasable seal may be provided at location 2; the releasable seal at location 2 may have a release pressure that is lower than the release pressures for the releasable seals at locations 3 and 5, for example. Releasable seals may also optionally be provided in other locations, such as at locations 4 and/or 6.

In implementations in which the releasable seal at location 7 is a temporary seal, it may be desirable to use a sequential seal region, e.g., as shown in FIGS. 44 through 46, of multiple temporary seals arranged in sequence across the sixth flow path and/or chamber E so as to allow the volume of the sixth flow path/chamber E to incrementally be expanded as each temporary seal in sequence releases during pressurization of the sixth flow path. This may allow chamber D to remain inflated until the fluid therein is forced out through movement of the clamping pressure zone across chamber D, thereby allowing for the surface of interest in chamber D to be more effectively wetted by the fluid that is introduced therein by keeping the portions of material between which chamber D is defined separated. Alternatively, the temporary seal at location 7 may be a single seal that is relatively thick, e.g., having a thickness along an axis parallel to the direction of travel of the clamping pressure zone that extends along a substantial portion of the sixth flow path. In such a temporary seal, pressurization of chamber D may cause the temporary seal to incrementally open (in a manner somewhat analogous to that of the temporary seals in a sequential seal region, but in a continuous fashion rather than in an incremental step fashion).

As noted above, chambers F and G may be quite small, e.g., they may simply be provided at the intersection between two or three flow paths. As a result, chambers F and G, as well as the various seals 9, 10, 3, and 5 that are proximate thereto may be located as close to one another as feasibly possible so as to minimize the amount of volume that is present within the third flow path and to reduce the amount of volume that may be lost to the second and fourth flow paths. Put another way, in such implementations, it may be desirable have the reference boundaries "b", "c," and "d" as close together as possible.

It will be understood that the fluidic circuit of FIG. 113C may be extended to allow additional volumes of different fluids to be flowed into/through chamber E, e.g., by replicating chambers F and B or chambers G and C and configuring them in a manner similar to that shown for chambers F and B or chambers G and C, e.g., with the additional chambers corresponding to chambers F or G being fluidically interposed between chamber A and chamber D. The opening or cavity may be extended to include the additional chambers that correspond to chambers F or G, as well as similar portions of the flow paths that lead to those additional chambers from the additional chambers that correspond to chambers B and C. The opening or cavity may also, in some cases, be extended to also overlap with chamber D and potentially chamber E, e.g., if, for some reason, one were to relocate chambers B and/or C to be on the side of reference boundary "f" that faces aware from reference boundary "a." It will also be understood that in some variations, the chamber pairs F-B and G-C, for example, may be arranged such that only one reference boundary separates each pair of chambers instead of two reference boundaries (as depicted). For example, chamber B's symbol may be positioned in the diagram of FIG. 113C in between reference boundaries "c" and "d" instead of between reference boundaries "d" and "e." Similarly, chamber C's symbol may be positioned in the diagram of FIG. 113C in between reference boundaries "d" and "e" instead of between reference boundaries "f" and "e." Such implementations may provide similar functionality but with an increased risk of mixing between the fluids of the various chambers. In some implementations, the chamber pairs may be positioned such that the fluidic connections between each chamber pair lie between the same reference boundaries. This applies to subsequent versions of this fluidic circuit as well.

In some implementations of the fluidic circuit of FIG. 113C, locations 9 and 10 may, instead of having a live seal formed thereat, may instead feature dynamic seals that may prevent flow of fluid from chamber B, C, or D into chambers A or B. Thus, accordingly, the dynamic seals at locations 9 and 10 may have release pressures that are greater than the release pressure of the releasable seal at location 7.

FIG. 57, discussed previously, depicts an example of an implementation of the fluidic circuit of FIG. 113C.

It will be appreciated that there may be a variety of different configurations, including various permutations of live or releasable seals that may be designed in accordance with FIGS. 113A through 113C, e.g., using different combinations of live seals, temporary seals, and dynamic seals. Such variations are considered within the scope of this disclosure.

Figure 114A:
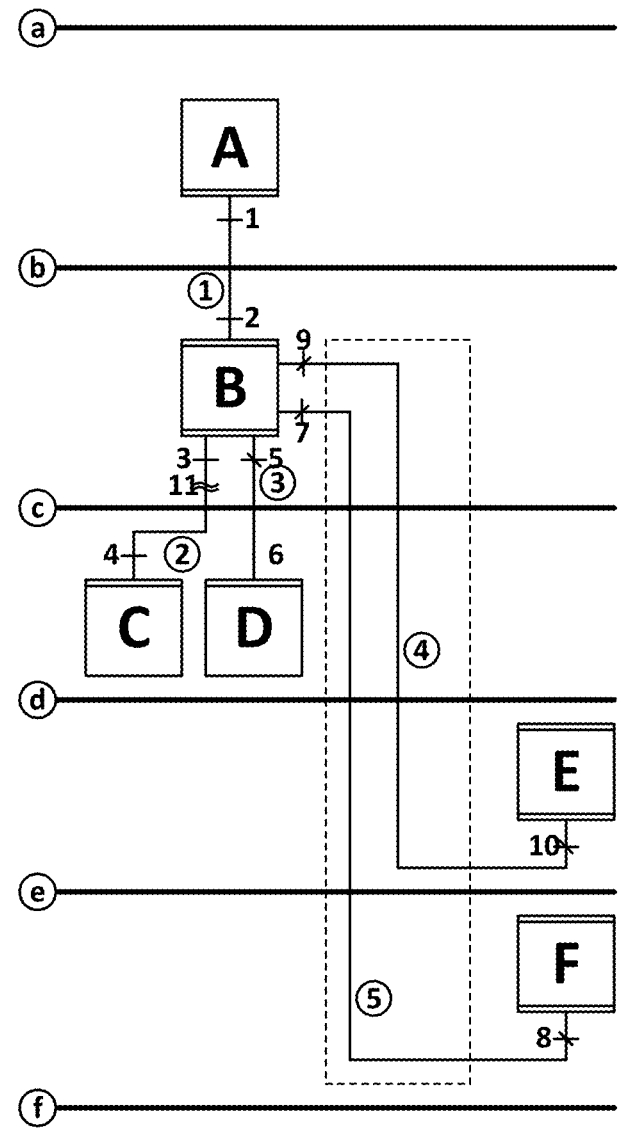
FIGS. 114A and 114B depict another two fluidic circuits that may be used to expose a surface to two or more fluids in sequence.

FIG. 114A depicts an example fluidic circuit that features six chambers A-F. The fluidic circuit depicted in FIG. 114A allows for a surface of interest in chamber B to be sequentially exposed to fluids from chambers A, E, and F using a generally unidirectional clamping pressure zone movement. The fluidic circuit is configured to prevent or reduce mixing between the fluids from chambers A, E, and F, and also to retain the last fluid introduced into B for use in one or more downstream fluidic circuits.

As noted above, in the depicted fluidic circuit, chambers A, E, and F may be preloaded with fluids (or loaded during earlier fluidic circuit operations using other fluidic circuits not depicted here). As shown in FIG. 114A, at least a portion of chamber A may be on a side of reference boundary "b" that faces towards reference boundary "a," at least a portion of chamber B may be in between reference boundaries "b" and "c," at least portions of chambers C and D may be on a side of reference boundary "c" that faces towards reference boundary "d," at least a portion of chamber E may lie between reference boundaries "d" and "e," and at least a portion of chamber F may lie between reference boundaries "e" and "f." It will be understood that in some implementations, all of chamber A may be on a side of reference boundary "b" that faces towards reference boundary "a," all of chamber B may be in between reference boundaries "b" and "c," all of chambers C and/or D may be on a side of reference boundary "c" that faces towards reference boundary "d," all of chamber E may lie between reference boundaries "d" and "e," and/or all of chamber F may lie between reference boundaries "e" and "f."

Chamber A may be fluidically connected with chamber B by a first flow path that fluidically connects with chamber A at a location that is on the side of reference boundary "b" that faces towards reference boundary "a" and with chamber B at a location that is in between reference boundaries "b" and "c." Chamber B may be fluidically connected with chambers C, D, E, and F by, respectively, second, third, fourth, and fifth flow paths, all of which may fluidically connect with chamber B in between reference boundaries "b" and "c." The other ends of the second and third flow paths may fluidically connect with chambers C and D, respectively, at locations in between reference boundaries "c" and "d," while the other end of the fourth flow path may fluidically connect with chamber E at a location between reference boundaries "d" and "e," and the other end of the fifth flow path may fluidically connect with chamber F at a location between reference boundaries "e" and "f." In some implementations, the fourth and fifth flow paths may fluidically connect prior to reaching chamber B and the resulting combined flow path may fluidically connect with chamber B at a location between locations "b" and "c."

In some implementations, the locations where the second and third flow paths fluidically connect with chamber B may be positioned close to the reference boundary "c" or, in some further such implementations, as close to the reference boundary "c" as possible. Similarly, in some implementations, the location where the fourth flow path fluidically connects with chamber E may be positioned close to the reference boundary "e" or, in some further such implementations, as close to the reference boundary "e" as possible, and the location where the fifth flow path fluidically connects with chamber F may be positioned close to the reference boundary "f" or, in some further such implementations, as close to the reference boundary "f" as possible.

In some further or additional implementations, the fourth and/or fifth flow paths may fluidically connect with chamber B at locations that are positioned close to the reference boundary "b" or, in some further such implementations, as close to the reference boundary "b" as possible.

During operations of the fluidic circuit of FIG. 114A, a clamping pressure zone may be applied at reference boundary "a" and then moved to reference boundary "b" to pressurize the fluid that is in chamber A and drive it into chamber B. The clamping pressure zone may then be moved to reference boundary "c" to drive the fluid from chamber A that is in chamber B into chamber C; to facilitate this, the second flow path may have a releasable seal, e.g., a temporary or dynamic seal, at location 3 with a release pressure that is lower than the release pressures of releasable seals on the third through fifth flow paths, e.g., releasable seals at locations 5, 7, and 9. Chamber C may be sized to have a total maximum volume that is greater than or equal to the anticipated combine maximum volume of fluid in chambers A and E (or all fluid-containing chambers for this fluidic circuit except for the last fluid-containing chamber to be emptied into chamber B during operation of the fluidic circuit) prior to operation of the fluidic circuit. Thus, chamber C may serve to receive all of the fluids that are passed through chamber B except for the last bolus of fluid that is passed through chamber B.

The second flow path may also be equipped with a dynamic seal at location 4 to facilitate retention in chamber C of fluids received from chamber B during one or more subsequent fluidic flow operations. The release pressure of the dynamic seal that is used at location 4 may be selected so as to be very high, i.e., higher than the amount of pressure that may be applied to chamber C's contents when the clamping pressure zone transits over chamber C. Thus, the dynamic seal at location 4 may act as a type of fluidic diode (or one-way valve) that allows fluid to be pushed into chamber C from chamber B via the second flow path but prevents fluid from flowing out of chamber C to chamber B via the second flow path.

Once the fluid from chamber A has passed through chamber B and passed into chamber C, the clamping pressure zone may be caused to advance to reference boundary "d" and then reference boundary "e," passing over chambers C and D in the process. Since chamber D is empty at this point, there is no fluidic pressure developed therein, and, as discussed above, the fluid that is contained in chamber C, while pressurized by the clamping pressure zone, may be pressurized to a level that is lower than the release pressure of the dynamic seal at location 4 and therefor remains in chamber C despite the pressure applied by the clamping pressure zone. If desired, the platen against which the clamping pressure zone is developed may include a cavity or opening that overlaps some or all of chamber C to reduce, or entirely eliminate, the pressure that is applied to chamber C by the clamping pressure zone as it traverses over chamber C.

As the clamping pressure zone moves from reference boundary "d" to reference boundary "e," the pressure applied to the contents of chamber E by the clamping pressure zone may pressurize the fluid contained therein such that the release pressure of the releasable seal(s) that is(are) on the fourth flow path, e.g., at locations 10 and 9, is reached and the fluid then caused to flow into chamber B. The platen against which the fluidic circuit of FIG. 114A is compressed by the clamping pressure zone may include cavities or openings that overlap the portions of the fourth and fifth flow paths that extend between the points of those flow paths closest to the reference boundary "f" and locations along those flow paths that are closest to the reference boundary "b." In some implementations, the cavity or opening may not, however, overlap with chambers E and F. Such a cavity or opening may allow fluids from chambers E and F to "bypass" the clamping pressure zone and move to chamber B.

After the clamping pressure zone reaches reference boundary "e," it may be caused to return to location 11, where it may be used, in conjunction with heat provided by a heater in the platen against which the fluidic circuit is pressed, to create a live seal at location 11, e.g., by thermally bonding the portions of material between which the fluidic circuit is defined together at location 11.

When the fluidic operation of the depicted fluidic circuit reaches the point where all boluses but the last bolus of fluid that is to be flowed through chamber B have been moved through chamber B and into chamber C, the second flow path, somewhere along its length, may be subjected to heat, e.g., from a heating element in a platen against which the fluidic circuit is pressed by the clamping pressure zone, to form a live seal, e.g., at location 11.

In variants in which only a single additional fluid-filled chamber E or F is used instead of both fluid-filled chambers E and F (or even further additional fluid-filled chambers similar to chambers E or F), the optional seal at location 4 may be omitted.

It will be understood that the fluidic circuit of FIG. 114A may be implemented in a variety of ways that may deviate from the above implementations while still providing equivalent or substantially similar functionality. For example, the fourth and fifth flow paths may not have any seals at all at locations 8 and 10, e.g., they may only be sealed at locations adjacent to chamber B, e.g., at locations 7 and 9. In other or additional variants, a dynamic or temporary seal may be provided where the first flow path fluidically connects with chamber A to prevent the fluid in chamber A from prematurely flowing into chamber B, e.g., prior to application of the clamping pressure zone to chamber A. In some variants, the first flow path may be provided with a dynamic seal at location 2, e.g., where it fluidically connects with chamber B, so as to prevent fluid in chamber B from potentially flowing into chamber A when pressure is applied to chamber B; in some such implementations, the release pressure for the dynamic seal at location 2 may be higher than the release pressures for one or more, or all, of the seals that may be at locations 3, 5, 7, and/or 9. In some implementations, the first flow path may, instead of being sealed with a dynamic seal where it fluidically connects with chamber B, be subjected to heat, e.g., from a heating element in a platen against which the fluidic circuit is pressed by the clamping pressure zone, somewhere along its length to form a live seal, e.g., at location 2, thereby sealing off chamber A from chamber B.

It will be appreciated that chamber D may, for example, be fluidically connected with one or more additional fluidic circuits (not shown) that are positioned "downstream" of chamber D which may perform further fluidic operations using the fluid that is delivered to chamber D by the fluidic circuit of FIG. 114A. It will be further appreciated that chamber D may, in some implementations, simply be a flow path that leads to such further fluidic circuits.

In some variants of the fluidic circuit depicted in FIG. 114A, the clamping pressure zone may be caused to move to reference boundary "b" after being used to create the live seal on the second flow path, thereby pushing whatever fluid may remain in chamber B into chamber A. In such implementations, the first flow path may include a dynamic seal at location 1 to prevent such fluid from then flowing back out of chamber A and into chamber B.

It will also be appreciated that additional chambers may be included in a similar manner in order to provide for delivery of additional fluids to chamber B prior to reaching the last fluid, e.g., from chamber F.

Figure 114B:
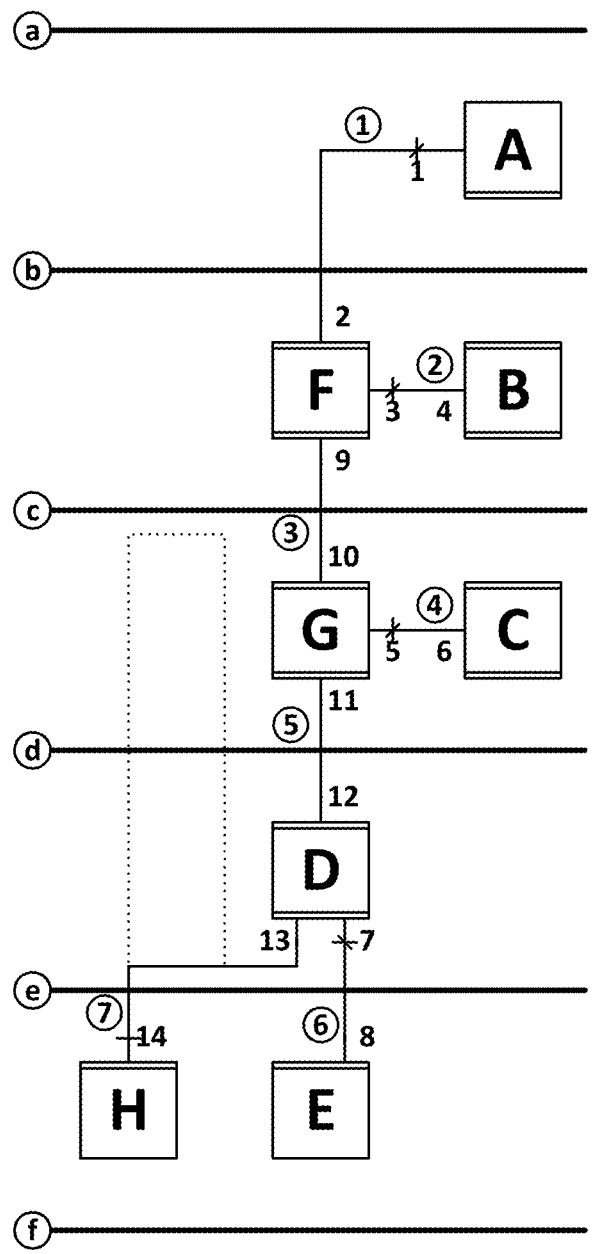

FIG. 114B depicts another fluidic circuit that is similar in construction and operation to the fluidic circuit of FIG. 113A but is designed to allow the last fluid flowed past the surface of interest to be kept separate from the earlier fluids flowed past the surface of interest; the discussion of the fluidic circuit of FIG. 113A is to be understood to also be applicable to the corresponding structures in FIG. 114B. The fluidic circuit of FIG. 114B, as with the previous fluidic circuit, may be operated through unidirectional linear movement of a clamping pressure zone. The fluidic circuit of FIG. 114B includes chambers A-H, of which chambers A-G may be configured in a manner similar to how the corresponding chambers A-G of FIG. 113A may be configured. For example, chambers A, B, and C may contain volumes of fluid prior to operation of the fluidic circuit, chamber D may contain a surface of interest, and chambers F, G, D, and E may initially be empty. It will be further appreciated that chambers F and G may be quite small, e.g., no larger than an intersection between two or three channels, as noted earlier with respect to FIG. 113A.

The primary difference between the fluidic circuit of FIG. 114B and that of FIG. 113A is the inclusion of chamber H, which may be fluidically connected with chamber D by a seventh flow path that fluidically connects with chamber D at a location in between reference boundaries "d" and "e" and with chamber H at a location on the side of reference boundary "e" that faces reference boundary "f." In the implementation of FIG. 114B, chamber H may be sized to have a maximum total volume that is greater than or equal to the anticipated combined volumes of fluid present in chambers A and B prior to operation of the fluidic circuit, but smaller than the anticipated combined volumes of fluid present in chambers A through C prior to operation of the fluidic circuit. The releasable seal that is on the sixth flow path may have a higher release pressure than the releasable seal that is on the seventh flow path, thereby causing fluid that is forced from chamber D and towards reference boundary "e" to first flow into chamber H. Thus, all of the fluid from chambers A and B that is flowed into chamber D will eventually be pushed into chamber H. Fluid from chamber C that is then flowed into chamber D and then flowed towards the reference boundary "e" may, at first, also be delivered to chamber H, but when chamber H is completely full and unable to accept additional fluid, this may cause the fluid from chamber C still remaining in chamber D to increase in pressure until the release pressure on the sixth flow path is exceeded, thereby causing the remaining fluid from chamber C that is in chamber B to flow into chamber E.

In some implementations, the eighth flow path may, as represented by the dotted alternate path shown in FIG. 114B, include one or more portions that travel across the reference boundary "d" to a location that is closer to reference boundary "c" than the portions of chambers C and G that are closest thereto. In such an implementation, the clamping pressure zone may, as it moves from reference boundary "c" to reference boundary "d," apply pressure to the eighth flow path, thereby preventing fluid flow through it, prior to the fluid from chamber C being driven into chamber D by the clamping pressure zone. Such an arrangement may allow the fluid from chamber C to be kept entirely separate from the fluids from chambers A and B that are housed in chamber H during operation of the fluidic circuit.

As with other fluidic circuits discussed herein, various variants of the fluidic circuit of FIG. 114B may be implemented as well. For example, a releasable seal may be provided at location 13 on the seventh flow path if the releasable seal at location 13 is designed to have a release pressure that is less than that of the releasable seal on the sixth flow path.

It will be appreciated that chamber E may, for example, be fluidically connected with one or more additional fluidic circuits (not shown) that are positioned "downstream" of chamber E which may perform further fluidic operations using the fluid that is delivered to chamber E by the fluidic circuit of FIG. 114B. It will be further appreciated that chamber E may, in some implementations, simply be a flow path that leads to such further fluidic circuits.

In some implementations, any of the open channels, e.g., at locations 7-9 on the main flow path between chambers A and D, may be replaced with releasable seals that have release pressures that are less than the release pressures of any releasable seals that may be the flow paths that span between chambers where the chamber symbols therefor are between the same two reference boundaries.

In implementations in which the releasable seal at location 7 is a temporary seal, it may be desirable to use a sequential seal region, e.g., as shown in FIGS. 44 through 46, of multiple temporary seals arranged in sequence across the sixth flow path so as to allow the volume of the sixth flow path to incrementally be expanded as each temporary seal in sequence releases during pressurization of the sixth flow path. This may allow chamber D to remain inflated until the fluid therein is forced out through movement of the clamping pressure zone across chamber D. Alternatively, the temporary seal at location 7 may be a single seal that is relatively thick, e.g., having a thickness along an axis parallel to the direction of travel of the clamping pressure zone that extends along a substantial portion of the sixth flow path. In such a temporary seal, pressurization of chamber D may cause the temporary seal to incrementally open (in a manner somewhat analogous to that of the temporary seals in a sequential seal region, but in a continuous fashion rather than in an incremental step fashion). In such implementations, the sixth flow path may be sized, for example, to be able to hold the anticipated combined fluid volumes of the fluids in chambers A, B, and C just prior to fluidic operation of the fluidic circuit.

It will also be appreciated that the depicted fluidic circuit may also be extended to provide support for the flow of additional fluids past the surface of interest, e.g., by providing additional repetitions of chamber pairs F and B or G and C.

Figure 115:
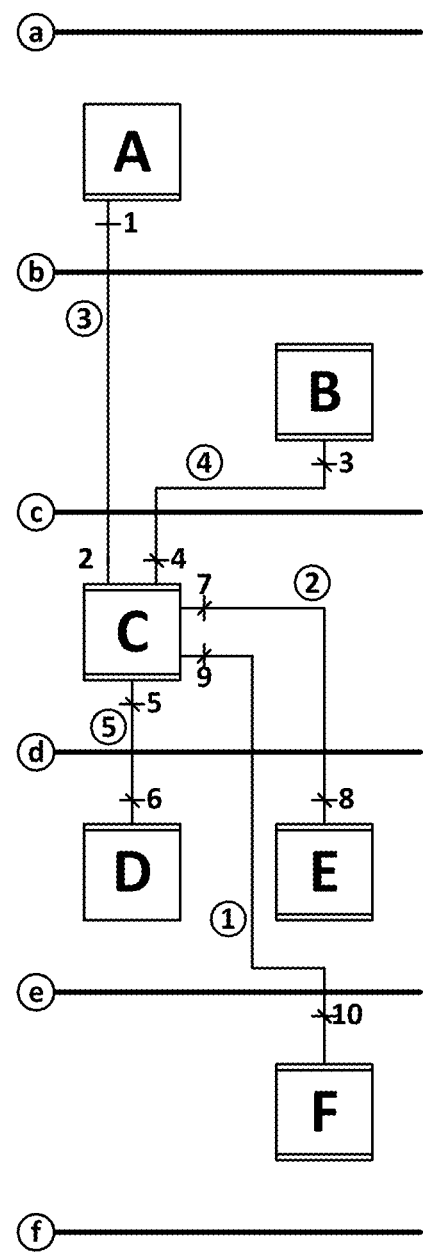
FIG. 115 depicts a fluidic circuit that allows multiple fluids to be flowed past a surface of interest in sequence, with the last fluid flowed past the surface of interest being separated from the other fluids for later use.

FIG. 115 depicts an example fluidic circuit in which multiple fluids may be flowed through a chamber having a surface of interest and in which the last fluid flowed therethrough may then be flowed isolated from the previous fluids to allow for later downstream fluidic operations to be performed on the last fluid. The fluidic circuit of FIG. 115 includes chambers A-F. Chambers B, E, and F may contain fluids prior to operation of the fluidic circuit, while chambers A, C, and D may be empty; chamber C may contain a surface of interest that is to be sequentially exposed to fluids from chambers F, E, and B. Chamber F, for example, may be a chamber that receives fluids from upstream fluidic circuits (not shown) that are operated prior to the depicted circuit. Chamber D may, for example, be a chamber that leads to downstream fluidic circuits (not shown) that may perform further fluidic operations using the fluid from chamber D. At least a portion of chamber A may lie on a side of reference boundary "b" that faces towards reference boundary "a," at least a portion of chamber B may lie between reference boundaries "b" and "c," at least a portion of chamber C may lie between reference boundaries "c" and "d," at least a portion of chamber E may lie between reference passages "d" and "e," at least a portion of chamber F may lie between reference passages "e" and "f," and at least a portion of chamber D may lie on a side of reference boundary "d" that faces towards reference boundary "e." In some implementations, all of chamber A may lie on a side of reference boundary "b" that faces towards reference boundary "a," all of chamber B may lie between reference boundaries "b" and "c," all of chamber C may lie between reference boundaries "c" and "d," all of chamber E may lie between reference passages "d" and "e," all of chamber F may lie between reference passages "e" and "f," and/or all of chamber D may lie on a side of reference boundary "d" that faces towards reference boundary "e."

In the fluidic circuit of FIG. 115, first through fifth flow paths may fluidically connect with chamber C at a location in between reference boundaries "c" and "d." The first flow path may, at the other end, fluidically connect with chamber F at a location that lies on the side of the reference boundary "e" that faces towards reference boundary "f," while the other end of the second flow path may fluidically connect with chamber E at a location between reference boundaries "d" and "e." It will be understood that the first and second flow paths may, in some implementations, fluidically connect with each other prior to their connection with chamber C. The other end of the third flow path may fluidically connect with chamber A at a location that lies on a side of reference boundary "b" that faces towards reference boundary "a," while the other end of the fourth flow path may fluidically connect with chamber B at a location in between reference boundaries "b" and "c." Finally, the other end of the fifth flow path may fluidically connect with chamber D at a location on a side of reference boundary "d" that faces towards reference boundary "e."

During operation of the fluidic circuit of FIG. 115, a clamping pressure zone may be applied to reference boundary "f" and advanced to reference boundary "e," which may cause the fluid in chamber F to be pressurized to a release pressure of, for example, a releasable seal at location 10 on the first flow path, thereby allowing the fluid in chamber F to be pushed into chamber C. Releasable seals on the third through fifth flow paths may act to prevent the fluid flowed into chamber C from flowing out of chamber C into any of chambers B, D, and E. When the clamping pressure zone is subsequently moved to reference boundary "d," the fluid in chamber E may be pressurized to a release pressure of a releasable seal at location 8 on the second flow path to allow the fluid in chamber E to be pushed into chamber C, thereby displacing the fluid from chamber F that is in chamber C and causing it to be pushed to chamber A via the third flow path. The third flow path may, for example, have a dynamic seal at the end that connects with chamber A so as to prevent fluid that is flowed into chamber A via the third flow path from later flowing back down the third flow path to chamber C. The other end of the third flow path may, as shown, have no seal or may be equipped with a releasable seal having a release pressure that is lower than the release pressures of the releasable seals used for the first, second, fourth, and fifth flow paths from chamber C. After pushing the fluid from chamber E into chamber C via the second flow path, the clamping pressure zone may be caused to advance to reference boundary "c," thereby pushing the fluid from chamber E that is in chamber C to chamber A via the third flow path. Once the clamping pressure zone is advanced to reference boundary "c," the clamping pressure zone may be simultaneously applying clamping pressure to the third flow path, thereby effectively preventing fluid flow from chamber C to chamber A along the third flow path as it advances to reference boundary "b" and applies pressure to chamber B. In doing so, the fluid in chamber B may be pressurized to a release pressure associated with a releasable seal at location 3 on the fourth flow path, causing the releasable seal at location 3 to open and allow the fluid in chamber B to be pushed to chamber C. The clamping pressure zone may then be caused to reverse course and move to reference boundary "d" so as to push the fluid from chamber B that is in chamber C into chamber D via the fifth flow path (the clamping pressure zone may still clamp the third flow path shut, thereby preventing fluid flow from chamber C to chamber A during such clamping pressure zone movement). The fifth flow path may have a releasable seal at location 5 that has a release pressure that is greater than that of the releasable seal at location 2 (if present) and smaller than that of the releasable seals at locations 7 and 9. The fifth flow path may optionally have a dynamic seal at location 6 to prevent fluid flowed into chamber D from potentially flowing back into chamber C after being delivered to chamber D.

It will be further understood that the fluidic circuit of FIG. 115 may be expanded to include the capability to flow additional fluids through chamber C prior to the flow of the fluid from chamber B therethrough. For example, additional chambers similar to chambers E or F may be provided, with each being located between a pair of adjacent reference boundaries that is further from chamber C than the last and each having a flow path that fluidically connects it with chamber C in a manner similar to how chambers E and F fluidically connect with chamber C.

Figure 116A:
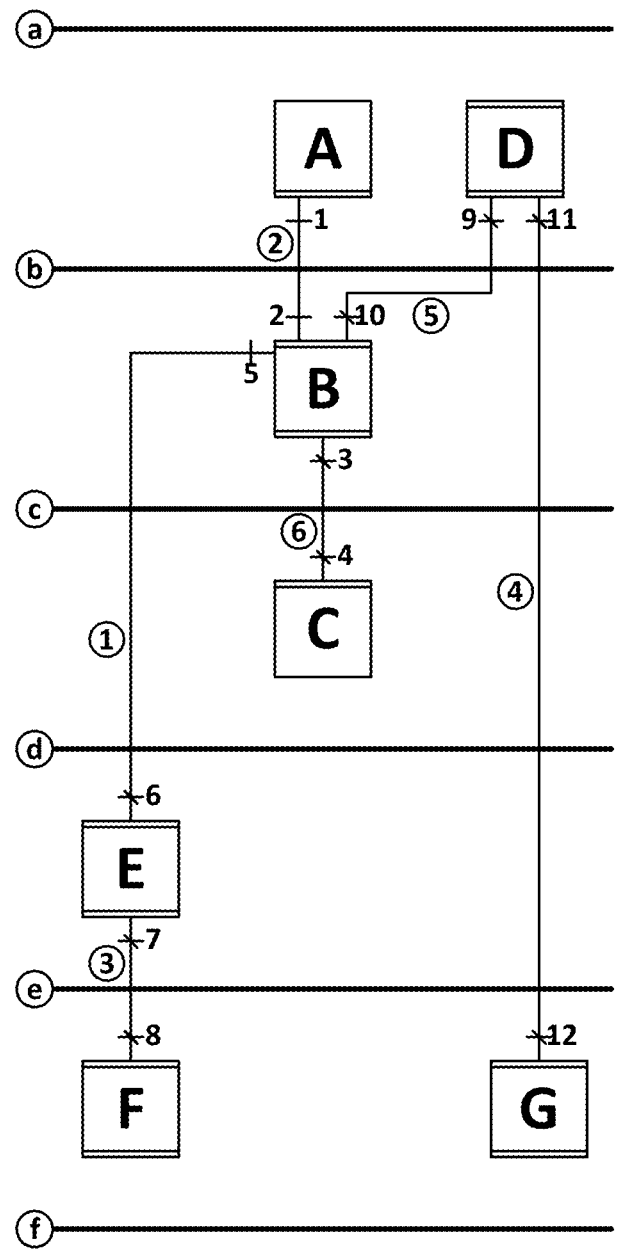
FIGS. 116A through 116C depict other fluidic circuits that allow multiple fluids to be flowed past a surface of interest in sequence, with the last fluid flowed past the surface of interest being separated from the other fluids for later use.

FIG. 116A depicts another fluidic circuit in which fluids may be sequentially flowed past a surface of interest with the last fluid that is flowed past the surface of interest being sequestered from the previous fluids and preserved for later fluidic processing. The fluidic circuit of FIG. 116A includes chambers A through G. Chambers E, F, and G may be pre-filled with fluids prior to operation of the depicted fluidic circuit, e.g., through prior fluidic operations performed by other fluidic circuits (not shown) or during creation of the fluidic circuit. Chamber B may contain a surface of interest past which the fluids in chambers E, F, and G are to be flowed, and chambers A-D may be free of fluids prior to the operation of the depicted fluidic circuit. Chamber C may be fluidically connected with other fluidic circuits (not shown) that are configured to perform various fluidic operations using the last fluid that is flowed through chamber B. Chamber D may be sized to have a maximum total volume that is greater than or equal to the anticipated fluid volume that will be in chamber G prior to operation of the fluidic circuit, while chamber A may be sized to have a maximum total volume that is greater than or equal to the anticipated total combined fluid volume that will be in chambers E and F prior to operation of the fluidic circuit. In some implementations, chamber D may have a maximum total volume that is less than the anticipated fluid volume that will be in chamber G prior to operation of the fluidic circuit—in such cases, chamber G may be positioned on the opposite side of reference boundary "f," and the operation of the fluidic circuit as described below modified accordingly to facilitate movement of the fluid in chamber G to chamber D.

At least a portion of chamber A may be located on a side of reference boundary "b" that faces towards reference boundary "a," while at least a portion of chamber D may be located in between reference boundaries "a" and "b." At least a portion of chamber B may be located in between reference boundaries "b" and "c," while at least a portion of chamber C may be located on a side of reference boundary "c" that faces towards reference boundary "d." At least a portion of chamber E may be located between reference boundaries "d" and "e," while at least portions of chambers F and G may be located between reference boundaries "e" and "f." In some implementations, all of chamber A may be located on a side of reference boundary "b" that faces towards reference boundary "a," all of chamber D may be located in between reference boundaries "a" and "b," all of chamber B may be located in between reference boundaries "b" and "c," all of chamber C may be located on a side of reference boundary "c" that faces towards reference boundary "d," all of chamber E may be located between reference boundaries "d" and "e," and/or all of chambers F and/or G may be located between reference boundaries "e" and "f."

A first flow path may fluidically connect with chamber B at a location in between reference boundaries "b" and "c" and with chamber E at a location between reference boundaries "d" and "e." A second flow path may fluidically connect with chamber B at a location between reference boundaries "b" and "c" and with chamber A at a location on a side of reference boundary "b" that faces towards reference boundary "a." A third flow path may fluidically connect with chamber E at a location between reference boundaries "b" and "c" and with chamber F at a location between reference boundaries "e" and "f." A fourth flow path may fluidically connect with chamber G at a location between reference boundaries "e" and "f" and with chamber D at a location in between reference boundaries "a" and "b." A fifth flow path may fluidically connect with chamber D at a location in between reference boundaries "a" and "b" and with chamber B at a location between reference boundaries "b" and "c." A sixth flow path may fluidically connect with chamber B at a location between reference boundaries "b" and "c" and with chamber C at a location on a side of reference boundary "c" facing towards reference boundary "d."

The locations where the various fluidic paths fluidically connect with some chambers may, in some cases, be selected to provide for more effective operation of the fluidic circuit. For example, the locations where the first flow path and the second flow path fluidically connect with chamber E may be positioned close to the reference boundary "b" or, in some implementations, as close to the reference boundary "b" as possible. The location where the second flow path fluidically connects with chamber F may be positioned close to the reference boundary "e" or, in some implementations, as close to the reference boundary "e" as possible. The location where the third flow path fluidically connects with chamber B may be positioned close to the reference boundary "b" or, in some implementations, as close to the reference boundary "b" as possible. The location where the fourth flow path fluidically connects with chamber D may be positioned close to the reference boundary "a" or, in some implementations, as close to the reference boundary "a" as possible. The location where the fourth flow path fluidically connects with chamber G may be positioned close to the reference boundary "e" or, in some implementations, as close to the reference boundary "e" as possible. Similarly, the locations where the fifth and sixth flow paths fluidically connect with chamber B may be positioned close to the reference boundary "c" or, in some implementations, as close to the reference boundary "c" as possible.

During operation of the fluidic circuit of FIG. 116A, a clamping pressure zone may be caused to move from reference boundary "a" to reference boundary "e." In traversing from reference boundary "a" to "d," the clamping pressure zone may cause little or no fluidic movement since chambers A-D may be empty of fluids. However, when transitioning from reference boundary "d" to reference boundary "e," the clamping pressure zone may pressurize the fluid in chamber E until the release pressure of a releasable seal on the first flow path, e.g., at location 6, is reached, thereby causing the fluid in chamber E to flow up the first flow path and into chamber B. Chamber E may also have a releasable seal at location 7 that has a higher release pressure than that of the releasable seal at location 6, thereby causing the fluid in chamber E to be flowed through the first flow path rather than the second flow path when pressurized by the clamping pressure zone. The clamping pressure zone may also, in implementations in which the second flow path fluidically connects with chamber E closer to, or as close as possible to, reference boundary "d," apply a clamping pressure to chamber E and to the second flow path simultaneously that may prevent fluid from flowing down the second flow path and into chamber F as the clamping pressure zone traverses chamber E to reference boundary "e." The clamping pressure zone may then be moved to reference boundary "b" so as to pressurize the fluid in chamber B to a level that exceeds a release pressure of the dynamic seal at location 2 and drive the fluid from chamber E that is in chamber B through the second flow path and into chamber A.

Once the fluid in chamber E has been pushed into chamber A, the clamping pressure zone may be caused to reverse its direction of travel and move to reference boundary "f" before reversing direction and traversing to reference boundary "c" again, thereby pressurizing the fluid in chamber F so as to exceed a release pressure of the releasable seal at location 8 and driving the fluid in chamber F through chamber E and into chamber B. At the same time, the fluid in chamber G may be pressurized to a pressure that exceeds a release pressure for a releasable seal at location 12 and then driven into chamber D by the movement of the clamping pressure zone to reference boundary "c." After the fluid from chamber F has been allowed to reside in chamber B for a desired period of time, the clamping pressure zone may then be moved to reference boundary "b" so as to pressurize the fluid in chamber B to a level that exceeds a release pressure of the dynamic seal at location 2 and drive the fluid from chamber F that is in chamber B through the second flow path and into chamber A. Subsequent to this, the clamping pressure zone may then be advanced to reference boundary "a" and then reversed in direction so as to return to reference boundary "b," thereby pressurizing the fluid in chamber D such that the release pressure of a releasable seal at location 9 is exceeded, thereby allowing the fluid in chamber D that originated from chamber G to flow into chamber B. The fluid in chamber D may be prevented from flowing back to chamber G during such movement via any of several mechanisms, e.g., using a dynamic seal at location 11 that has a release pressure that exceeds that of the releasable seal at location 9 or by positioning the connection point where the fourth flow path connects with chamber D at a location on chamber D that is closest to reference boundary A. After the fluid from chamber G has been allowed to reside in chamber B for a desired period of time, the clamping pressure zone may be advanced to reference boundary "c" to cause the fluid from chamber G that is in chamber B to pressurize to a level that exceeds a release pressure of the releasable seal at location 3 (and location 4) and then be flowed into chamber C, which may be connected with downstream fluidic elements (not shown) that may allow for further processing of the fluid from chamber G.

It will be understood that while FIG. 116A depicts releasable seals at locations 4, 7-9, and 11, any or all such locations may instead, optionally, be free of any such seals, e.g., be open flow paths at those locations. It will also be understood that in some implementations, the fluidic connection of the third flow path with chamber A at location 1 may be equipped with a dynamic seal that has a relatively high release pressure, e.g., a release pressure that is higher than the pressure that the clamping zone pressure can generate on the fluid within chamber A, thereby allowing fluid from chambers E and F to be passed into chamber A, but preventing such fluid from later being flowed out of chamber A should chamber A's fluid be pressurized by the clamping pressure zone. In some additional or alternative implementations, the platen against which the fluidic circuit is pressed by the clamping pressure zone may have a cavity or opening in a region that contains chamber A so as to allow the clamping pressure zone to traverse chamber A without applying significant or any clamping pressure thereto. For example, if a cavity or opening is used in the platen in the location where chamber A is located during fluidic operations, a dynamic seal with a lower release pressure than that noted above may be used at location 1.

It will be further understood that the fluidic circuit of FIG. 116A may be expanded to include the capability to flow additional fluids through chamber B prior to the flow of the fluid from chamber G therethrough. For example, additional chambers may be provided in series with chambers E and F with additional fluids that are to be flowed in sequence through chamber B, and the fluidic operations described above may be repeated, with appropriate modification, to cause the fluid from each such additional chamber to be flowed through chamber B in sequence before the fluid from chamber G is caused to flow through chamber B. For example, the portion of the fluidic circuit between reference boundaries "d" and "e" may be replicated multiple times in between chamber C and chambers F and G to provide additional chambers E (with different and/or the same fluids therein).

Figure 116B:
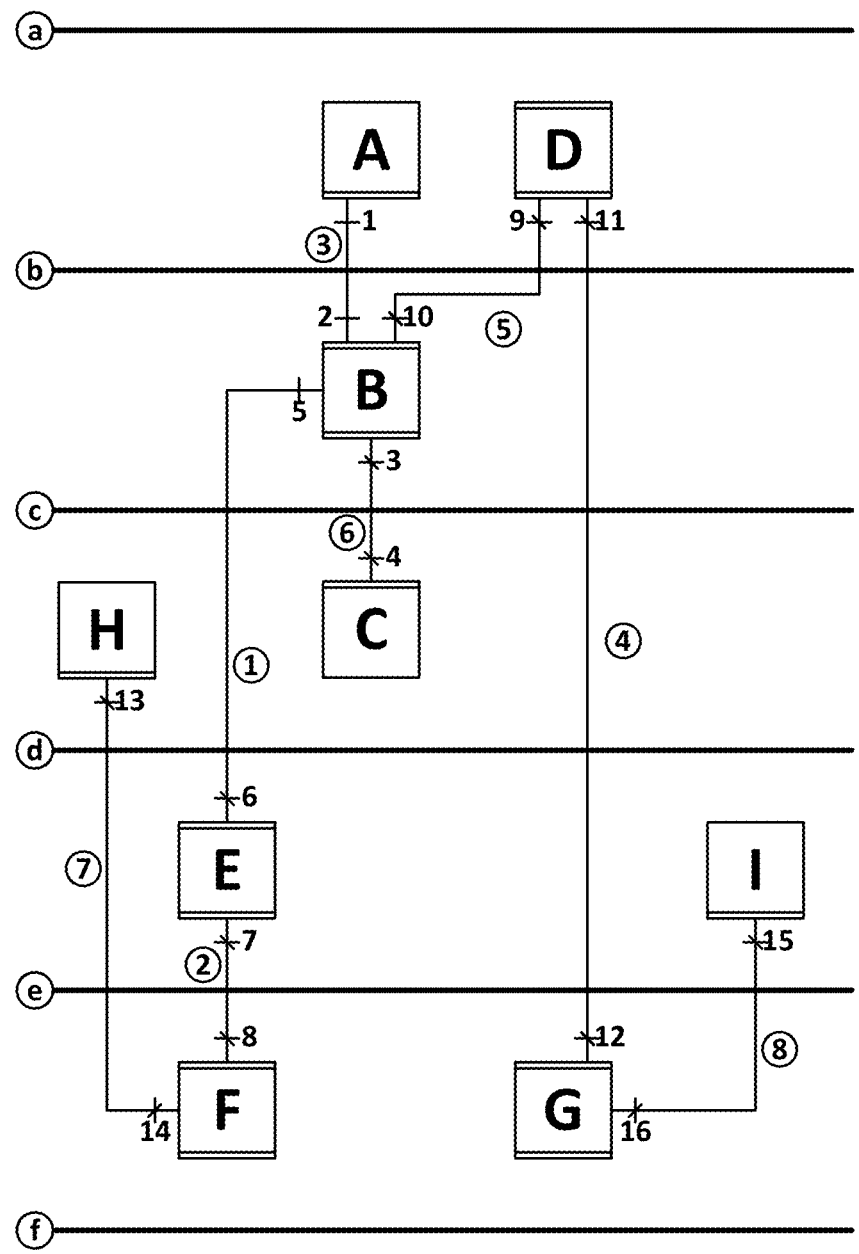

FIG. 116B depicts a variant of the fluidic circuit of FIG. 116A in which additional chambers H and I are provided to initially hold the fluids that are, in the fluidic circuit of FIG. 116A, contained in chambers F and G. Such an implementation may allow for such additional chambers to be located, for example, alone a common edge of the portions of material between which the fluidic circuit is defined, thereby allowing the fluids to be loaded into the fluidic circuit along such an edge and facilitating pre-loading of the fluidic circuit with fluids. For example, if reference boundary "a" is located at the top edges of the portions of material between which the depicted fluidic circuit is defined, then that top edge may have a series of chambers (e.g., chambers H and I, for example) that lie along the top edge and are open along the top edge. Fluids that are destined for transfer to chambers F and G may be placed into those chambers, e.g., via a pipette, syringe, or other transfer device, and the top edge then sealed, e.g., heat-sealed, to seal the fluids into the chambers H and I.

The operation of the fluidic circuit of FIG. 116B may be identical to that of the fluidic circuit of FIG. 116A except that chambers F and G may initially be empty of fluids but are then filled with fluid from chambers H and I that are pushed into chambers F and G when the clamping pressure zone moves from reference boundary "a" to reference boundary "e." The flow paths that fluidically connect chambers H and I with chambers F and G, respectively, may be configured to fluidically connect with chambers F and G, respectively, at locations on chambers F and G, respectively, that are close to, or as close as possible to, reference boundary "f"; in such implementations, the fluidic connections at those locations may optionally not include any seals. Such a configuration may cause the clamping pressure zone to also clamp such flow paths shut as it applies pressure to the fluid that has been transferred to chambers F and G, thereby preventing backflow of such fluids to chambers H and I. Alternatively, or additionally, the flow paths leading to chambers F and G from chambers H and I, respectively, may be equipped with dynamic seals at locations 14 and 16, respectively, that have release pressures that are above the pressure that the clamping pressure zone is able to apply to chambers F and G, thereby allowing fluid to flow into chambers F and G from chambers H and I, respectively, but not permitting the reverse.

It will also be appreciated that chamber E may be similarly provided with fluid from a chamber similar chamber H, although such a configuration is not depicted. In some implementations, the fluidic circuit of FIG. 116A may be expanded to include additional fluid sources, e.g., in a manner similar to that discussed above with respect to FIG. 112D.

Figure 116C:
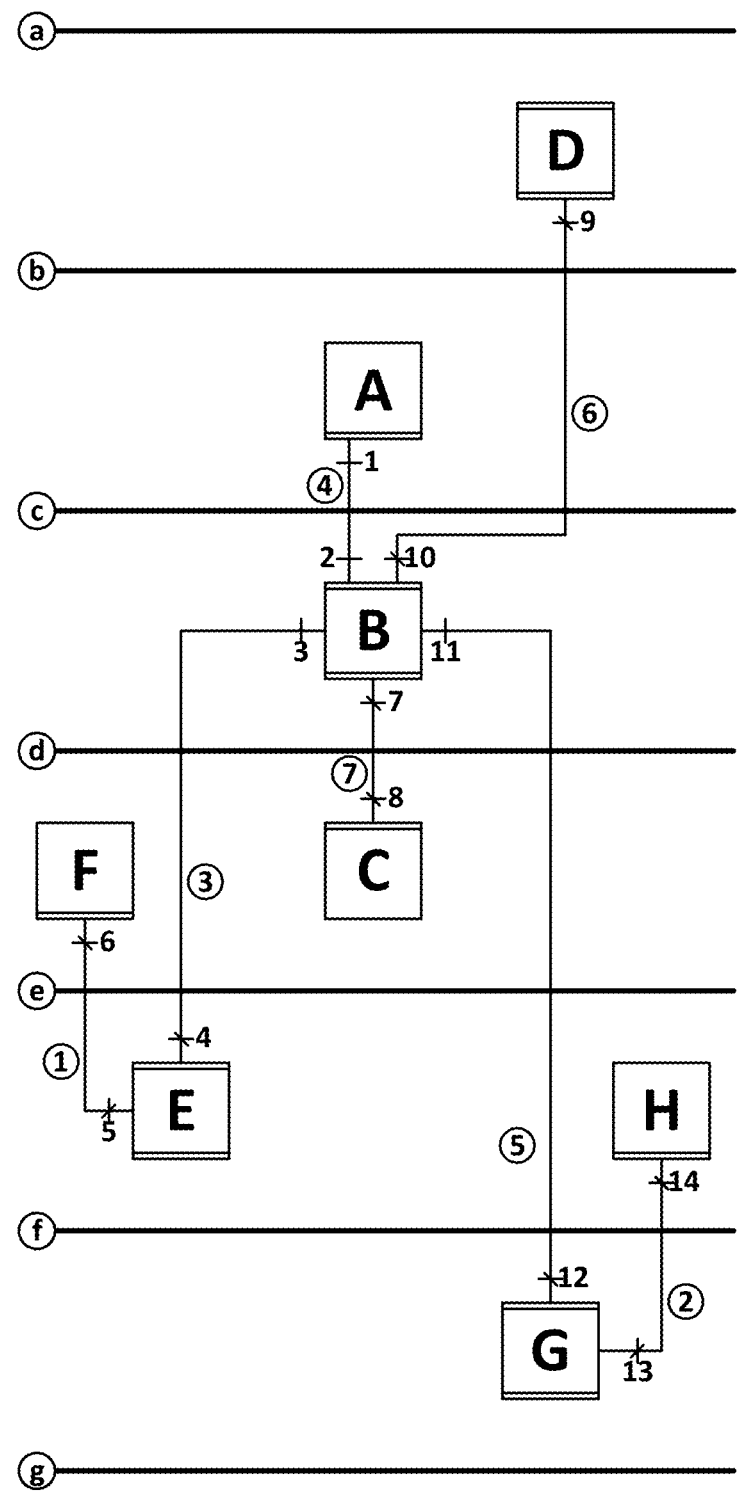

FIG. 116C depicts another fluidic circuit that may be used to sequentially flow a series of fluids past a surface of interest with the last fluid that is flowed past the surface of interest being sequestered from the previous fluids and preserved for later fluidic processing. The fluidic circuit of FIG. 116C includes chambers A-H. Chambers D, F, and H may be pre-loaded with fluids, e.g., during earlier fluidic operations performed with fluidic circuits (not show) upstream of the depicted fluidic circuit or during creation of the depicted fluidic circuit, whereas chambers A-C, E, and G may be empty of fluids. Chamber B may have a surface of interest that is to be sequentially exposed to the fluids in chambers F, H, and then D. Chamber C, it will be understood, may be fluidically connected to additional fluidic circuits (not shown) downstream of the depicted fluidic circuit and may, in some instances, simply be a flow path to such downstream elements. Chamber C may, for example, receive, via chamber B, the fluid that is contained in chamber D and is the last fluid of the fluids in chambers F, H, and D to be flowed through chamber B. The fluids from chambers F and H, however, may be routed to chamber A for disposal/sequestration.

At least a portion of chamber D may lie between reference boundaries "a" and "b," while at least a portion of chamber A may lie on a side of reference boundary "c" that faces towards reference boundary "b." At least a portion of chamber B may lie between reference boundaries "c" and "d," while at least a portion of chamber F may lie on a side of reference boundary "e" that faces towards reference boundary "d." At least a portion of chamber C may lie on a side of reference boundary "d" that faces towards reference boundary "e," while at least a portion of chamber H may lie on a side of reference boundary "f" that faces towards reference boundary "e." At least a portion of chamber E may lie in between reference boundaries "e" and "f," while at least a portion of chamber G may lie in between reference boundaries "f" and "g." In some implementations, all of chamber D may lie between reference boundaries "a" and "b," all of chamber A may lie on a side of reference boundary "c" that faces towards reference boundary "b," all of chamber B may lie between reference boundaries "c" and "d," all of chamber F may lie on a side of reference boundary "e" that faces towards reference boundary "d," all of chamber C may lie on a side of reference boundary "d" that faces towards reference boundary "e," all of chamber H may lie on a side of reference boundary "f" that faces towards reference boundary "e," all of chamber E may lie in between reference boundaries "e" and "f," and/or all of chamber G may lie in between reference boundaries "f" and "g."

Chamber E may be sized to have a maximum volume that is greater than or equal to the anticipated maximum volume of fluid that will be in chamber F prior to operation of the fluidic circuit, while chamber G may similarly be sized to have a maximum volume that is greater than or equal to the anticipated maximum volume of fluid that will be in chamber H prior to operation of the fluidic circuit. Chamber A may be sized to have a maximum total volume that is greater than or equal to the anticipated maximum combined total volume of fluid that will be in chambers F and H prior to operation of the fluidic circuit.

A first flow path may fluidically connect with chamber F at a location that lies on the side of reference boundary "e" that faces towards the reference boundary "d" and with chamber E at a location that is between reference boundaries "e" and "f." A second flow path may fluidically connect with chamber H at a location on the side of reference boundary "f" that faces towards reference boundary "e" and with chamber G at a location between reference boundaries "f" and "g." A third flow path may fluidically connect with chamber E at a location that is between reference boundaries "e" and "f" and with chamber B at a location that is between reference boundaries "c" and "d." A fourth flow path may fluidically connect with chamber B at a location that is between reference boundaries "c" and "d" and with chamber A at a location that is on the side of reference boundary "c" that faces towards reference boundary "b." A fifth flow path may fluidically connect with chamber G at a location in between reference boundaries "f" and "g" and with chamber B at a location in between reference boundaries "c" and "d." A sixth flow path may fluidically connect with chamber B at a location between reference boundaries "c" and "d" and with chamber D at a location that is on the side of reference boundary "b" that faces towards reference boundary "a." A seventh flow path may fluidically connect with chamber C at a location on the side of reference boundary "d" that faces towards reference boundary "e" and with chamber B at a location between reference boundaries "c" and "d."

During operation of the fluidic circuit of FIG. 116C, a clamping pressure zone may be moved from reference boundary "b" to reference boundary "f," thereby pressurizing first the fluid in chamber F and then the fluid in chamber H. When the fluid in chamber F is pressurized to a release pressure for a releasable seal for the first flow path, e.g., located at location 6, the fluid in chamber F may be pushed along the first flow path and into chamber E. When the clamping pressure zone is subsequently moved from reference boundary "e" to reference boundary "f," the clamping pressure zone may pressurize the fluid in chamber H to a release pressure for a releasable seal on the second flow path, e.g., at location 14, and cause the fluid in chamber H to flow through the second flow path into chamber G. The clamping pressure zone may also, during such movement, cause the fluid that was flowed into chamber E from chamber F to be pressurized to a release pressure for a releasable seal on the third flow path, e.g., at location 4. In some implementations, a dynamic seal may be provided at location 5 on the first flow path; such a dynamic seal may have a release pressure that exceeds the pressure that the clamping pressure zone may cause to be developed within chamber E so that fluid that is introduced via the first flow path into chamber E is unable to be caused by the clamping pressure zone to flow back into chamber F. In other or additional such implementations, the first flow path may fluidically connect with chamber E at a location on chamber E that is close to, or as close as possible to, the reference boundary "f." In such implementations, the clamping pressure zone may pinch the first flow path shut as it applies pressure to chamber E, thereby preventing or discouraging flow of fluid from chamber E to chamber F. It will be understood that a similar arrangement or configuration may be practiced with respect to the second and fifth flow paths and chamber G. For example, the clamping pressure zone may during later movement across chamber G, cause the fluid that was flowed into chamber G from chamber H to be pressurized to a release pressure for a releasable seal on the fifth flow path, e.g., at location 12. In some implementations, a dynamic seal may be provided at location 13 on the second flow path; such a dynamic seal may have a release pressure that exceeds the pressure that the clamping pressure zone may cause to be developed within chamber G so that fluid that is introduced via the second flow path into chamber G is unable to be caused by the clamping pressure zone to flow back into chamber H. In other or additional such implementations, the second flow path may fluidically connect with chamber G at a location on chamber G that is close to, or as close as possible to, the reference boundary "g." In such implementations, the clamping pressure zone may pinch the second flow path shut as it applies pressure to chamber G, thereby preventing or discouraging flow of fluid from chamber G to chamber H.

The pressurized fluid from chamber F that is in chamber E may then be caused to flow into chamber B. Chamber B may have dynamic or releasable seals at each of its fluidic connections to one of the flow paths, e.g., dynamic seals at locations 2, 3, and 11, and releasable seals for the sixth and seventh flow paths, e.g., at locations 10 and 7. The release pressure of the dynamic seal at location 2 may be lower than the release pressures associated with the other fluidic connections to chamber B, and the release pressures of the dynamic seals at locations 3 and 11 may be higher than the release pressure of the releasable seal for the seventh flow path. Such an arrangement of seals may act to prevent fluids from chambers F and H that are flowed into chamber B from exiting chamber B except via the fourth flow path into chamber A, while allowing the fluid from chamber D that is flowed into chamber B to exit chamber B via the seventh flow path into chamber C.

The clamping pressure zone may then be caused to reverse direction of its traversal, traveling from reference boundary "f" to reference boundary "d," thereby driving what fluid from chamber F via chamber E is in the third flow path into chamber B. The clamping pressure zone may then be caused to move to reference boundary "c" in order to pressurize the fluid from chamber F that is in chamber B to a level that exceeds the release pressure of the dynamic seal at location 2, thereby allowing the fluid from chamber F that is in chamber B to be flowed through the fourth flow path and into chamber A. Chamber A, for example, may have a dynamic seal at location 1 that has a release pressure that exceeds the pressure that the clamping pressure zone is able to apply to the contents of chamber A.

After purging chamber B of the fluid from chamber F, the clamping pressure zone may be caused to reverse course and traverse the fluidic circuit to reference boundary "g" and then reverse course to return to reference position "d" so as to push the fluid from chamber H that was in chamber G into chamber B. The clamping pressure zone may then be caused to move to reference boundary "c" in order to push the fluid from chamber H that is in chamber B into chamber A.

Once chamber B is purged of the fluid from chamber H, the clamping pressure zone may then be caused to move to reference boundary "a" and then return to reference boundary "c." During such movement, the fluid in chamber D may be pressurized by the clamping pressure zone to a pressure that causes releasable seal(s) at locations 9 and 10 to release and allow the fluid in chamber D to flow into chamber B. The clamping pressure zone may then be caused to move to reference boundary "d" in order to push the fluid from chamber D that is in chamber B into chamber C. The clamping pressure zone may, as it traverses from reference boundary "c" to reference boundary "d," prevent fluid in chamber B from flowing back up to chamber A.

It will be understood that chamber A may, for example, be located in a position that aligns with a cavity or opening in a platen against which the fluidic circuit is pressed by the clamping pressure zone such that the pressure that the clamping pressure zone can apply to chamber A is reduced or eliminated when the clamping pressure zone traverses chamber A. Alternatively or additionally, the fourth flow path may be fluidically connected with chamber A at location 1 with a dynamic seal that has a release pressure that exceeds the maximum pressure that the clamping pressure zone can apply to the contents of chamber A. Either or both options may prevent fluid from chambers F or H that are introduced to chamber A from flowing back out of chamber A to chamber B.

The fluidic circuit of FIG. 116C may allow for sequential introduction of fluids similar to that provided by previous fluidic circuits discussed herein, but may also allow for more flexibility regarding lateral placement of the fluid-containing chambers F and H, i.e., they may be placed on either or both sides of chamber B having the surface of interest. Chambers F and H may also be positioned near an edge of the portions of material forming the fluidic circuit to allow for fluids to be easily loaded into those chambers after the fluidic circuit has been manufactured, e.g., an edge near reference boundary "a," for example.

It will also be understood that the fluidic circuit of FIG. 116C may be expanded to include additional fluid-containing chambers, e.g., chamber pairs F and E or H and G, as well as their associated flow paths, may be replicated and positioned in a similar staggered manner to allow for additional fluids to be introduced to chamber B as desired.

Figure 117A:
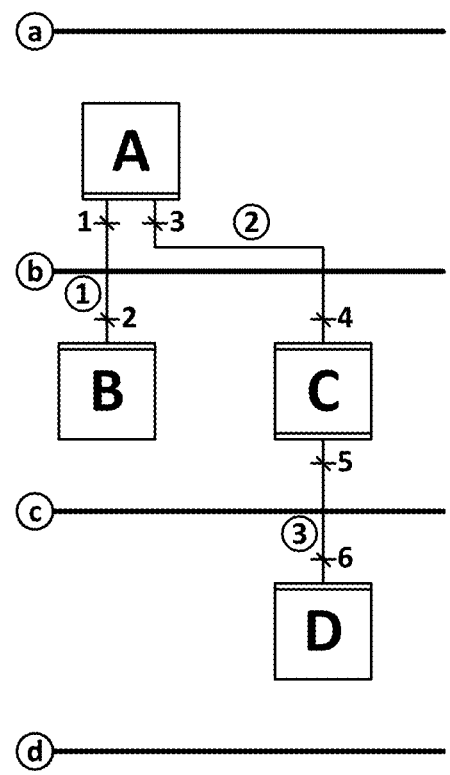
FIGS. 117A and 117B depict fluidic circuits that may be used to meter any amount of fluid.

FIG. 117A depicts a fluidic circuit that may be used to separate out, i.e., meter, a particular amount of fluid from a larger volume of fluid. In the fluidic circuit of FIG. 117A, four chambers A-D are depicted, with chamber A being filled with a volume of fluid to be metered (either pre-filled or filled during earlier fluidic operations using other fluidic circuits not shown) and chamber C having a maximum total volume equal to the desired amount of fluid to be separated out (the metering amount). Chamber D may be empty prior to operation of the depicted fluidic circuit and may lead to other fluidic circuit elements that may receive the metered amount of fluid; it will be understood that chamber D may thus be, for example, a flow path that leads to such downstream fluidic circuit elements and may not be a discrete chamber. Chamber B may also be empty prior to operation of the depicted fluidic circuit and may be used to receive whatever portion of the fluid from chamber A is left over after the metered portion of the fluid from chamber A has been obtained and sequestered in chamber C.

Chamber B may have a maximum volume that is greater than or equal to the anticipated maximum volume of fluid that will be contained in A prior to operation of the fluidic circuit minus the maximum total volume of chamber C. If it is desired to obtain exactly the maximum amount of fluid that may be contained within chamber C (the metering amount), then chamber A must understandably be filled with an amount of fluid at least equal to the maximum total volume of C; if an amount of metered fluid that is less than the metering amount is acceptable, then chamber A may be filled with a lesser amount of fluid. In some implementations, chamber B may, when the fluidic circuit is placed against a platen in order to have a clamping pressure zone applied thereto, be positioned such that cavity or opening in the platen overlaps therewith so as to reduce or eliminate the pressure that may be applied to chamber B by the clamping pressure zone.

At least a portion of chamber A may, for example, lie on a side of reference boundary "b" that faces towards reference boundary "a," while at least a portion of chamber B may lie on a side of reference boundary "b" that faces towards reference boundary "c" and at least a portion of chamber D may lie on a side of reference boundary "c" that faces towards reference boundary "d." At least a portion of chamber C may lie between reference boundaries "b" and "c." It will be understood that in some implementations, all of chamber A may lie on the side of reference boundary "b" that faces towards reference boundary "a," all of chamber B may lie on a side of reference boundary "b" that faces towards reference boundary "c," all of chamber C may lie between reference boundaries "b" and "c," and/or all of chamber D may lie on a side of reference boundary "c" that faces towards reference boundary "d."

Chambers A-D may be fluidically connected by a number of flow paths, each of which may include at least one releasable seal. For example, a first flow path and a second flow path may fluidically connect to chamber A at locations on a side of reference boundary "b" that faces towards reference boundary A. The first flow path may also fluidically connect with chamber C, and the second flow path with chamber B, at locations in between reference boundaries "b" and "c." A third flow path may fluidically connect with chamber C at a location in between reference boundaries "b" and "c" and with chamber D at a location on the side of reference boundary "c" that faces towards reference boundary "d."

The first flow path may, e.g., at location 3, have a releasable seal, e.g., a dynamic seal or temporary seal, that has a release pressure that is lower than the release pressure of a releasable seal that is provided on the second flow path, e.g., at location 1. Thus, when chamber A is pressurized by the application of a clamping pressure zone thereto, the pressurized fluid in chamber A will cause the releasable seal on the first flow path to open and allow the fluid in chamber A to travel to chamber C. The third flow path that leads from chamber C to chamber D may, in turn, have a releasable seal that has a release pressure that is higher than that of the releasable seal that seals the second flow path. Thus, once chamber C has reached its maximum volume due to the introduction of the fluid from chamber A, further advancement of the clamping pressure zone across chamber A and towards the reference boundary "b" may cause the pressure in fluid A to increase until it exceeds the release pressure for the releasable seal that prevents fluid flow along the second flow path. At this time, the releasable seal on the second flow path may release and the remaining fluid in chamber A may be forced to flow into chamber B. Thus, by the time the clamping pressure zone has reached the reference boundary "b," chamber A will be empty of fluid, chamber C will hold the desired metered amount of fluid from chamber A, and chamber B will hold the remaining fluid from chamber A.

The clamping pressure zone may then be advanced to reference boundary "c," which may cause the fluid trapped in chamber C to be pressurized until the release pressure for the releasable seal on the third flow path is reached, at which point the metered amount of fluid from chamber A may be pushed into chamber D for use in downstream fluidic circuits (not shown). If desired, one or more of the first through third flow paths may feature releasable seals at both ends thereof, as long as the releasable seal(s) on the first flow path have a release pressure or pressures that are lower than that or those of the releasable seal(s) on the second flow path and as long as the releasable seal(s) on the second flow path has or have a release pressure or pressures that are lower than that or those of the releasable seal(s) on the third flow path. However, if dynamic seals are used, for example, at any of locations 2, 4, and/or 6, then such dynamic seals may have release pressures that do not satisfy such constraints. For example, dynamic seals used at any of locations 2, 4, or 6 may have release pressures that exceed that of the releasable seal at location 5-since dynamic seals only seal when pressurized on a particular side (the chamber side), such dynamic seals may act to prevent fluid that has been delivered to chambers B, C, or D from flowing back towards chamber A, but may freely allow fluid to flow in the opposite direction, i.e., away from chamber A.

The first through third flow paths may also feature no seal features at locations 2, 4, and/or 6, if desired. This may have little effect on performance as long as the clamping pressure zone, when advancing from reference boundary "a" to reference boundary "c," provides sufficient clamping pressure to the chambers A through C and the first and second flow paths to prevent fluid from flowing past the clamping pressure zone towards chamber A.

In some implementations, a dynamic seal may be used on at least the first and/or second flow paths at locations 3 and/or 2 (and potentially at other locations as well). In some implementations, a dynamic seal may be used on the first flow path at location 3.

Figure 117B:
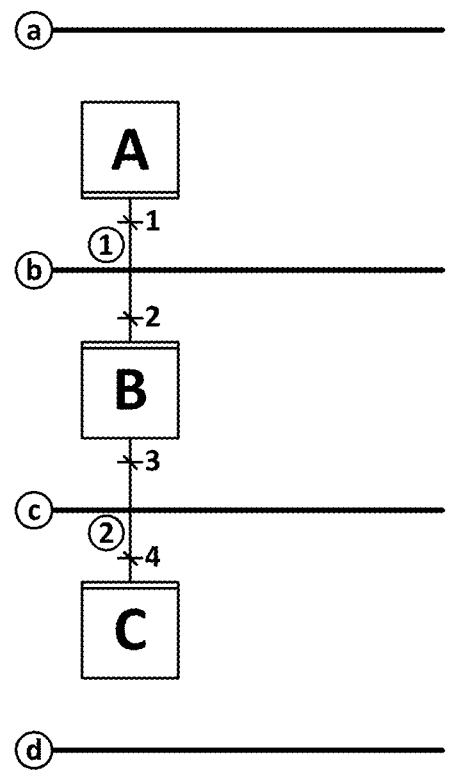

FIG. 117B depicts another example fluidic circuit that may be used for metering of a desired amount of fluid from a larger volume of fluid, with the remainder being discarded or sequestered. As with the fluidic circuit of FIG. 117A, the fluidic circuit of FIG. 117B includes three chambers A-C. At least a portion of chamber A may lie on a side of reference boundary "b" that faces towards reference boundary "a," at least a portion of chamber B may lie on a side of reference boundary "b" that faces towards reference boundary "c," and at least a portion of chamber C may lie on a side of reference boundary "c" that faces towards reference boundary "d." In some implementations, all of chamber A may lie on a side of reference boundary "b" that faces towards reference boundary "a," all of chamber B may lie on a side of reference boundary "b" that faces towards reference boundary "c," and/or all of chamber C may lie on a side of reference boundary "c" that faces towards reference boundary "d."

Chamber A, which may contain a volume of fluid from which a smaller volume of fluid is to be metered, may be fluidically connected with a first flow path that fluidically connects with chamber A at a location that is on the side of the reference boundary "b" that faces towards reference boundary "a." The first flow path may, in turn, be fluidically connected with chamber B at a location that is on the side of the reference boundary "b" that faces towards the reference boundary "c." Similarly, a second flow path may fluidically connect between chambers B and C.

Chamber C, it will be understood, may represent downstream fluidic circuits (not shown) or other fluidic elements that are to eventually receive a metered amount of fluid from chamber B. Chamber B, it will be realized, may be sized to have a maximum total volume that equals the desired amount of fluid, i.e., the metered amount of fluid volume. Chamber A may be sized to have a maximum total volume that is greater than or equal to the maximum total volume of chamber B.

During operation of the fluidic circuit, a clamping pressure zone may be moved from reference boundary "a" to reference boundary "c." During movement of the clamping pressure zone from reference boundary "a" to reference boundary "b," the fluid that is present in chamber A may be pressurized to the point where it exceeds the release pressure for one or more releasable seals on the first flow path, e.g., at locations 1 (and possibly 2), but does not exceed the release pressure for a releasable seal on the second flow path, e.g., at location 3. As a result, fluid from chamber A may be pushed into chamber B until chamber B is at maximum capacity (the metered amount). Further advancement of the clamping pressure zone towards reference boundary "b" may not cause any further fluid flow towards chamber A since the releasable seal at location 3 may have a release pressure than is higher than can be developed within chamber A. As a result, the remaining fluid in chamber A may simply flow backwards, underneath or past the clamping pressure zone, and towards the reference boundary "a."

Once the clamping pressure zone crosses reference boundary "b" and starts applying pressure directly to chamber B, the resulting pressure that arises from the clamping pressure zone may be sufficient to overcome the release pressure for the releasable seal at location 3, thereby allowing the fluid in chamber B to be driven into chamber C, e.g., for further processing via one or more downstream fluidic circuits (not shown).

While it may seem somewhat counterintuitive, the release pressures for releasable seals that are in series, e.g., such as releasable seals at locations 1 and 3, may be somewhat higher than for any one of those seals individually. As a result, the releasable seal at location 3 may have a higher release pressure when pressurized from chamber A (with the releasable seal at location 1 in between) as opposed to when pressurized via pressure applied directly to chamber B (bypassing the releasable seal at location 1). It will also be understood that the geometry of the chambers A and B relative to one another may allow the pressure provided by the clamping pressure zone to be modified so as to be lower when applied to chamber A as opposed to chamber B. For example, if the clamping pressure zone is provided by a spring-loaded roller, the amount of force applied to the roller may stay generally constant (varying only based on changes in the amount of deflection undergone by the spring), but the area over which that force is distributed by the roller may vary based on the width (in a direction parallel to the reference boundaries) of the chamber where the clamping pressure zone is applied. Thus, if chamber A is twice as wide as chamber B, the pressure arising from the clamping pressure zone within chamber A may, as a rough approximation, be approximately half what that same clamping pressure zone may produce when applied to chamber B. Accordingly, the releasable seal at location 3 may not be able to be released when pressurized from chamber A, but can be released when pressurized by pressure applied directly to chamber B.

Variants of the fluidic circuit of FIG. 117B include versions in which the releasable seals shown at locations 2 and/or 4 may be omitted, e.g., there may be no restrictions on the flow of fluids through such flow paths other than those provided at locations 1 and 3.

Figure 118A:
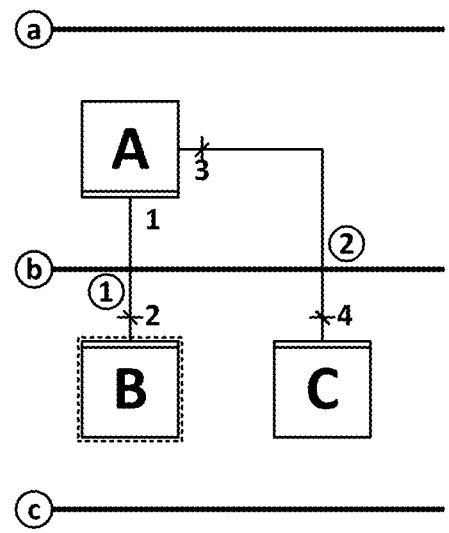
FIGS. 118A and 118B depict additional fluidic circuits that may be used to meter any amount of fluid.

FIG. 118A depicts another fluidic circuit that may be used for metering an amount of fluid from a larger volume of fluid. In the fluidic circuit of FIG. 118A, the metered amount of fluid is retained within a chamber for later use, e.g., retained for later analysis in a laboratory setting as opposed to being analyzed within the portions of material having the fluidic circuit.

The fluidic circuit of FIG. 118A includes chambers A through C. In the fluidic circuit of FIG. 118A, at least a portion of chamber A may be on a side of reference boundary "b" that faces towards reference boundary "a" and at least portions of chambers B and C may be on a side of reference boundary "b" that faces towards reference boundary "c." In some implementations, all of chamber A may be on the side of reference boundary "b" that faces reference boundary "a" and/or all of chambers B and/or C may be on the side of reference boundary "b" that faces reference boundary "c."

Chamber A may be sized to receive a fluid volume from other fluidic circuits (not shown) that may be upstream, e.g., previously operated. Alternatively, chamber A may simply be a fluidic path to such upstream fluidic circuits. Thus, when the fluidic circuit of FIG. 118A is operated, chamber A may be pre-filled with an amount of fluid that is larger than the desired amount of fluid to be metered. Chamber B may be empty and may be sized to have a maximum volume that is equal to the desired metering volume. Chamber C, which may be a chamber that is fluidically connected with other fluidic circuits downstream of the depicted fluidic circuit or which may simply be a flow path that fluidically connects with such a downstream fluidic circuit, may similarly be empty or may, alternatively, contain a fluid.

First and second flow paths may fluidically connect with chamber A at a location that is on the side of the reference boundary "b" that faces towards reference boundary "a." The first flow path may fluidically connect with chamber B, and the second flow path with chamber C, at locations on a side of the reference boundary "b" that faces towards the reference boundary "c."

During operation of the depicted fluidic circuit of FIG. 118A, a clamping pressure zone may be moved from reference boundary "a" to reference boundary "b" so as to cause the fluid in chamber A to be pushed into chamber B. To facilitate this, the first flow path may have either no seals, e.g., be an open flow path, or may, optionally, have a releasable seal, e.g., at location 1, that may have a release pressure that is lower than that of a releasable seal on the second flow path. In some implementations, the first flow path may have a dynamic seal at location 2 that has a higher release pressure than the releasable seal(s) on the second flow path, but such a dynamic seal will, by virtue of its configuration and positioning, not prevent fluid flowing along the first flow path from chamber A to chamber B.

Once chamber B has been filled to its maximum capacity from chamber A, any remaining advancement of the clamping pressure zone towards reference boundary "b" may cause the pressure in chamber A to further increase until the release pressure for the releasable seal on the second flow path is reached, thereby causing the releasable seal on the second flow path, e.g., at location 3, to release and allow the remainder of the fluid in chamber A to be directed to chamber C. The releasable seal at location 3 may, for example, be a dynamic seal.

If the first flow path has a dynamic seal at location 2, then this may act to seal the metered portion of the fluid from chamber A into chamber B, especially if the dynamic seal is configured to have a high release pressure, e.g., higher than can be provided by the clamping pressure zone. In such an implementation, when the clamping pressure zone moves from reference boundary "b" to reference boundary "c," the clamping pressure zone may simply traverse chamber B without ever exerting sufficient pressure on the contents thereof to cause the dynamic seal at location 2 to release. Alternatively, the fluidic circuit of FIG. 118A may be interfaced with a platen during fluidic operation that may have a cavity or opening around where chamber B is located such that the clamping pressure zone, in traversing chamber B, is not able to generate pressure within chamber B since there is no surface against which to compress chamber B. In a third alternative, the first flow path may be live sealed when the clamping pressure zone is, for example, at the reference boundary "b," e.g., by causing a heater in the platen against which the fluidic circuit is pressed when fluidic operations are performed to heat a portion of the first flow path while it is under compression by the clamping pressure zone. This last technique may provide the most secure mechanism for retaining the metered amount of fluid in chamber B, as the only way to remove the fluid after the live seal is created is to puncture the portions of material that bound chamber B.

The second flow path may, in some implementations, include a dynamic seal at location 4 that allows fluid directed into chamber C to pass into chamber C without issue, but which may prevent or resist fluid flow from chamber C to chamber B. Such a dynamic seal, for example, may have a release pressure that is greater than the maximum pressure that the clamping pressure zone may be capable of inducing in chamber C. In other implementations, there may be no seal at location 4, e.g., it may be an open flow path at that location.

Figure 118B:
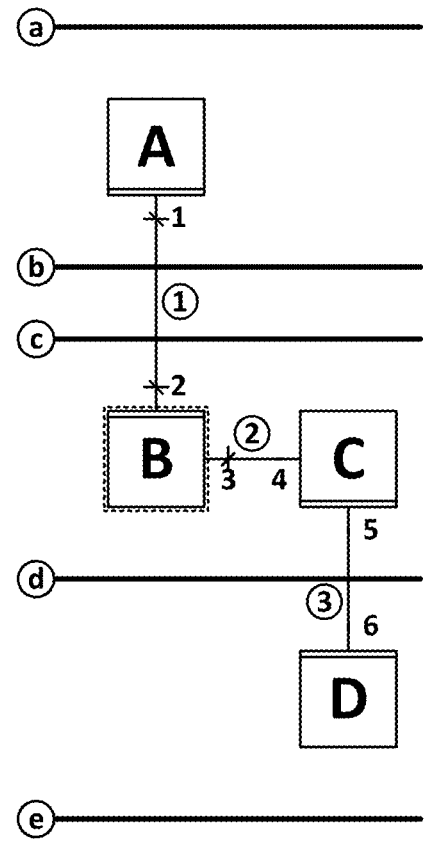

FIG. 118B depicts another fluidic circuit that may be used to meter a smaller, desired amount of fluid from a larger volume of that fluid. The fluidic circuit of FIG. 118B includes chambers A-D.

In the fluidic circuit of FIG. 118B, at least a portion of chamber A may be on a side of reference boundary "b" that faces towards reference boundary "a," at least a portion of chamber B may be on a side of reference boundary "c" that faces towards reference boundary "d," at least a portion of chamber C may be on a side of reference boundary "d" that faces towards reference boundary "c," and at least a portion of chamber D may be on a side of reference boundary "d" that faces towards reference boundary "e." In some implementations, all of chamber A may be on the side of reference boundary "b" that faces reference boundary "a," all of chamber B may be on the side of reference boundary "c" that faces reference boundary "d," all of chamber C may be on a side of reference boundary "d" that faces reference boundary "c," and/or all of chamber D may be on a side of reference boundary "d" that faces reference boundary "e."

Chamber A may be sized to receive a fluid volume from other fluidic circuits (not shown) that may be upstream, e.g., previously operated. Alternatively, chamber A may simply be a fluidic path to such upstream fluidic circuits. Thus, when the fluidic circuit of FIG. 118B is operated, chamber A may be filled with an amount of fluid that is larger than the desired amount of fluid to be metered. Chamber B may be empty and may be sized to have a maximum volume that is equal to the desired metering volume. Chamber C may be a small or zero-volume chamber and may optionally be positioned between reference boundaries "b" and "c." Chamber D may, for example, lead to downstream fluidic circuits (not shown) or may simply be a flow path to such fluidic circuits.

A first flow path may fluidically connect with chamber A at a location that is on the side of the reference boundary "b" that faces towards reference boundary "a." The first flow path may fluidically connect with chamber B at a location on a side of the reference boundary "c" that faces towards the reference boundary "d." A second flow path may fluidically connect with chamber B at a location that is on a side of the reference boundary "c" that faces towards reference boundary "d" as well as with chamber C at a location on a side of the reference boundary "d" that faces towards reference boundary "c." A third flow path may fluidically connect with chamber C at a location on a side of reference boundary "d" that faces towards reference boundary "c" and with chamber D on a side of reference boundary "d" that faces towards reference boundary "e."

During operation of the depicted fluidic circuit of FIG. 118B, a clamping pressure zone may be moved from reference boundary "a" to reference boundary "b" and then reference boundary "c" so as to cause the fluid in chamber A to be pushed into chamber B. The fluid that flows into chamber B, once chamber B is filled to capacity, may pressurize until the release pressure of the releasable seal at location 3 is reached, thereby allowing the fluid in chamber B to be pushed into and through chamber C to chamber D. Once the clamping pressure zone reaches location 3 or 4, however, and clamps down on the second flow path, the flow of fluid from chamber B into and through chamber C may be terminated due to the clamping pressure. The amount of fluid that is retained in B may be determined based on the location of chamber C and/or where locations 3 and 4 are. For example, if chamber C is located between reference boundaries "b" and "c" (and location 4 is similarly located) the clamping pressure zone may push fluid from chamber A into chamber B until chamber B is full, at which point additional fluid from chamber A that is pushed into chamber B may displace fluid in chamber B into chamber C (and then chamber D). Once the clamping pressure zone reaches reference boundary "c," it will be applying pressure to the second flow path that prevents fluid flow through the second flow path, thereby keeping the fluid that is in chamber B within chamber B even as the clamping pressure zone traverses over chamber B in moving to reference boundary "d." As noted above, chamber C may be quite small in volume, even to the point where chamber C is effectively non-existent, i.e., the second flow path and the third flow path may merge into a single flow path that passes through a location where chamber C is shown. Thus, in the example in which chamber C is in between reference boundaries "b" and "c," such a flow path would travel from location 3 on chamber B (between reference boundaries "c" and "d") up to a location in between reference boundaries "b" and "c" and then back down past reference boundaries "c" and "d" to chamber D. The same fluidic circuit may also work in a similar manner with other placement of chamber C—for example, if location 4 is either at the same distance from or farther from reference boundary "c" location 3, the depicted fluidic circuit may act to preserve whatever fluid is contained in the portion of chamber B that lies on the side of location 3 that faces towards reference boundary "d" within chamber B as the clamping pressure zone moves over chamber B towards reference boundary "d." Once the clamping pressure zone reaches location 3, further flow from chamber B into the second flow path may be caused to stop (or at least significantly decrease), thereby preventing the fluid remaining in chamber B from being pushed downstream.

Figure 119:
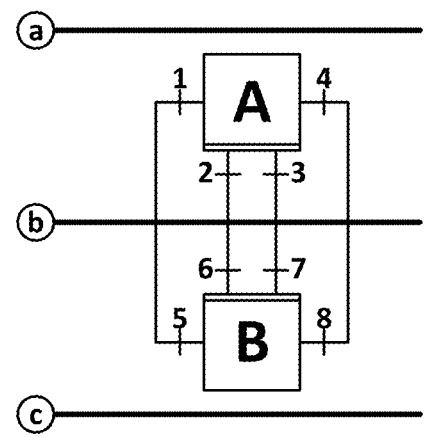
FIG. 119 depicts a fluidic circuit that may be used to remove bubbles from a fluid.

FIG. 119 depicts a fluidic circuit that may be used for bubble removal. As shown, the fluidic circuit includes chamber A, at least a portion of which may be on a side of reference boundary "b" that faces towards reference boundary "a," and chamber B, at least a portion of which may be on a side of reference boundary "b" that faces towards reference boundary "c." In some implementations, all of chamber A may lie on the side of reference boundary "b" that faces towards reference boundary "a" and/or all of chamber B may lie on the side of reference boundary "b" that faces towards reference boundary "c." Chamber A may be fluidically connected with one or more other fluidic circuit elements (not shown) that are located upstream of chamber A, and chamber B may be fluidically connected with one or more other fluidic circuit elements (also not shown) that are located downstream of chamber B. In some implementations, multiple instances of the fluidic circuit depicted in FIG. 119 may be arranged in series in order to perform multiple bubble removal operations in sequence, each such bubble removal operation further degassing the liquid that is present. In such implementations, chamber A of one fluidic circuit may be fluidically connected with chamber B of the previous upstream fluidic circuit or, alternatively, chamber B of one fluidic circuit may also serve as chamber A of the next downstream fluidic circuit.

Chambers A and B may be joined together by one or more flow paths; in FIG. 119, there are four such flow paths shown, although more or fewer flow paths may be used. Each flow path may fluidically connect with chambers A and B via dynamic seals; in some implementations, the dynamic seals for chamber A may be designed to all have the same release pressure. In some other implementations, the dynamic seals that fluidically connect with chamber A at locations that are the same distance from reference boundary "b" may all have the same release pressure, but different sets of such dynamic seals may have different release pressures depending on their distance from reference boundary "b." In such implementations, the release pressures of such dynamic seals may increase with decreasing distance between those dynamic seals and the reference boundary "b."

During operation, fluid may be pressurized within chamber A by a clamping pressure zone that moves from reference boundary "a" to reference boundary "b," thereby driving the fluid that is in chamber A through the dynamic seals that are present and into the flow paths to chamber B. Each dynamic seal may act as a bubble removal feature, as bubbles that are present within the fluid that is forced through the dynamic seals will tend to stick to the corners where the chamber transitions to a channel, with the transition from chamber to channel forming the dynamic seal. Such dynamic seals may be particularly effective at removing bubbles that have diameters larger than the width of the passages forming the dynamic seals at the locations where such passages fluidically connect with chamber A. The dynamic seals where the flow paths fluidically connect with chamber B may also act to capture bubbles that may make past the dynamic seals of chamber A. At some point during the clamping pressure zone's traversal of chamber A, all or nearly all of the liquid that is present may have been forced into chamber B or the flow paths, and chamber A may retain only gas, e.g., air. Further advancement of the clamping pressure zone may thus also push the gas that remains in chamber A through into chamber B, but the gas/liquid mixture in chamber B may, as a result of the bubbles being held back in chamber A and at the dynamic seals in chamber B, be less intermixed than the gas/liquid mixture was when introduced into chamber A. In some implementations, the movement of the clamping pressure zone may be constrained so as to keep the movement of fluid through the flow paths to a low speed. For example, for moving a fluid volume in the 10 µL to 20 µL range, a clamping pressure zone movement speed sufficient to drive such a fluid volume from chamber A to chamber B through the dynamic seals in a span of 10 seconds or more was found to produce good bubble removal performance, whereas pushing the same volume through the dynamic seals in a span of 5 seconds or less resulted in a significant number of bubbles being carried into chamber B as compared with the slow speed. In some such implementations, the clamping pressure zone may be caused to move across the fluidic circuit at a speed that is lower than the speed used to move the clamping pressure zone across another fluidic circuit or other fluidic circuits immediately upstream and/or immediately downstream of the fluidic circuit of FIG. 119. For example, in some implementations in which the clamping pressure zone may be moved at different speeds in different regions during the actuation of a particular fluidic circuit, a "low" clamping pressure zone speed may be a speed that is less than or equal to 1 mm/s. Conversely, as discussed with respect to some other implementations herein, the operation of some of the fluidic circuits disclosed herein may involve moving the clamping pressure zone at a higher or greater rate or speed in some regions. In some such implementations, such a speed may be on the order of 10 mm/s or greater. "Normal" clamping pressure zone speeds in either or both such instances may be in a speed regime between the "low" and "high" speeds.

After the clamping pressure zone is moved to reference boundary "b," the clamping pressure zone may be advanced further to reference boundary "c," thereby causing the liquid that is present in chamber B (and the gas that follows it) to move to a subsequent stage of fluidic processing via a flow path (not shown) leading from chamber B.

Figure 120A:
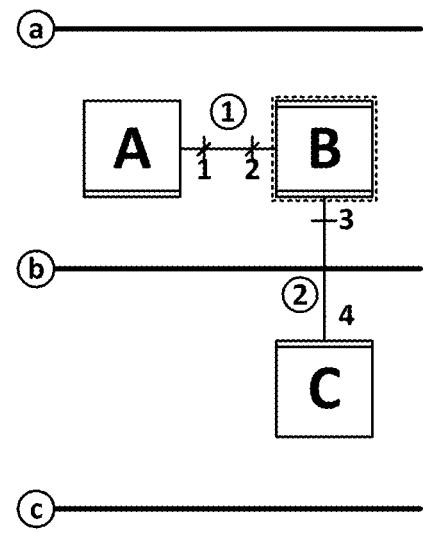
FIGS. 120A through 120C depict fluidic circuits that allows bubbles that may be present in a fluid within the circuits to be skipped over and not passed on downstream.

FIG. 120A depicts an example fluidic circuit that may be used to remove a large bubble or cluster of bubbles that follow a liquid flowed through the fluidic circuit such that the bubble or bubbles are not passed into downstream fluidic circuits. Such a fluidic circuit may, for example, be used to remove a large bubble or cluster of bubbles that may trail behind the liquid portion of a fluid that is flowed through the bubble removal fluidic circuit of FIG. 119.

In FIG. 120A, three chambers A-C are shown. At least a portion of chamber A may be positioned on a side of reference boundary "b" that faces towards reference boundary "a" and at least a portion of chamber C may lie on a side of reference boundary "b" that faces towards reference boundary "c." At least a portion of chamber B may lie between reference boundaries "a" and "b," although in some implementations, it may be preferable to locate chamber A such that all of chamber A is closer to reference boundary "a" than any of chamber B. In some implementations, all of chamber A may lie on the side of reference boundary "b" that faces reference boundary "a," all of chamber C may lie on the side of reference boundary "b" that faces reference boundary "c," and/or all of chamber B may lie between reference boundaries "a" and "b." As mentioned above, in some such cases, there may be an additional reference boundary in between chambers A and B, and all of chamber B may lie on one side of that additional reference boundary and all of chamber A may lie on the other side thereof (closer to reference boundary "a" than chamber B). The maximum total volume of chamber B may be less than, and, in many cases, much less than, the anticipated maximum total volume of liquid that will be in chamber A immediately prior to operation of the depicted fluidic circuit. Chamber B may also be positioned such that when the fluidic circuit is placed against a platen against which a clamping pressure zone is applied in order to operate the fluidic circuit, an opening or cavity in the platen aligns with chamber B.

A first flow path may fluidically connect with chamber A at a location that lies on the side of reference boundary "b" that faces towards reference boundary "a" and with chamber B at a location that is between reference boundaries "a" and "b." A second flow path may fluidically connect with chamber B at a location that is between reference boundaries "a" and "b" and with chamber C at a location that is on the side of reference boundary "b" that faces towards reference boundary "c."

Chamber A may be fluidically connected with one or more upstream fluidic circuit elements (not shown) via a flow path (not shown), while chamber C may be fluidically connected with one or more downstream fluidic circuit elements (also not shown) via a flow path (also not shown). During operation of the fluidic circuit of FIG. 120A, chamber A may receive, from an upstream fluidic element, a liquid bolus followed by an air or gas bubble (or cluster air or gas bubbles). A clamping pressure zone may then be moved from reference boundary "a" to reference boundary "b" (including, if present, travel through the reference boundary between chambers A and B). Such movement of the clamping pressure zone may cause the liquid that is in chamber A to be moved to chamber B, followed by the gas that is present in chamber A. For example, when the clamping pressure zone pressurizes the fluid/gas that are present in chamber A, the resulting pressure that is obtained may exceed the release pressure for a releasable seal that may be present on the first flow path, e.g., at location 1. The fluid may then flow through the first flow path (and optionally through a releasable seal at location 2, if present) and into chamber B. When the clamping pressure zone traverses across chamber B, however, there may be little or no pressurization of chamber B by the clamping pressure zone due to the cavity or opening in the platen against which the clamping pressure zone presses when traversing chamber B.

Due to the fact that chamber B is sized smaller, and likely much smaller, in maximum volume as compared with the total amount of liquid that is anticipated to be in chamber A at the start of operation of the depicted fluidic circuit, the movement of fluid from chamber A to chamber B may cause the liquid that is present in chamber A to flow to chamber B first until chamber B is full, at which point further liquid flow from chamber A into chamber B may cause the liquid that is present in chamber B to pressurize until the release pressure of a dynamic seal where the second flow path fluidically connects with chamber B, e.g., at location 3, is reached, thereby allowing the liquid that is present in chamber B to flow into chamber C. The dynamic seal at location 3 may be configured to have a low release pressure so that very little pressurization of the liquid in chamber B is required in order to cause that liquid to flow on to chamber C—in some cases, the dynamic seal that is formed at location 3 may be configured to have as low a release pressure as is possible given whatever local constraints may exist. When the clamping pressure zone then traverses from reference boundary "b" to reference boundary "c," it causes the liquid that has been sequestered in chamber C to be moved on to further downstream fluidic circuits (not shown) while allowing the separately sequestered air or gas bubble in chamber B to be left behind.

It will be understood that during operation, the fluidic circuit of FIG. 120A may optionally be oriented such that reference boundary "c" is vertically lower than reference boundary "b," e.g., so as to cause any air or gas bubbles that may be present in chamber A to congregate nearer to the reference boundary "a" than to the reference boundary "b."

In some implementations, locations 2 and 4 may feature dynamic seals that have release pressures that may, for example, be higher than what the clamping pressure zone may cause to develop within chambers B and C, thus preventing backflow of the fluids in question. In some alternate implementations, however, the first flow path may simply be an open flow path at the end that fluidically connects with chamber B. In some implementations, the fluidic connection between the first flow path and chamber A may be provided by a dynamic seal.

Figure 120B:
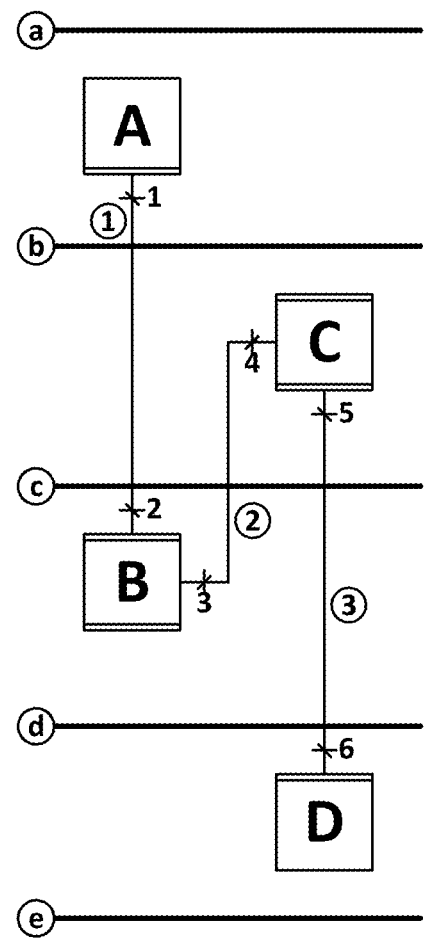

FIG. 120B depicts an example fluidic circuit that may be used to allow a clamping pressure zone to "skip" over bubbles that may be present in conjunction with a liquid so that the bubbles are not carried forward into other fluidic circuits with the liquid.

The fluidic circuit of FIG. 120B includes four chambers A-D. At least a portion of chamber A may lie on a side of reference boundary "b" that faces towards reference boundary "a," while at least a portion of chamber B may lie between reference boundaries "c" and "d." At least a portion of chamber C may lie between reference boundaries "b" and "c," while at least a portion of chamber D may lie on a side of reference boundary "d" that faces towards reference boundary "e." Chamber A may be prefilled with liquid or may receive liquid from various upstream fluidic circuits (not shown); chamber D may be fluidically connected with fluidic circuits (not shown) downstream of the depicted fluidic circuit; alternatively, chamber D may actually be part of the downstream fluidic circuits or a passage leading thereto. Chambers B and C may be sized to be relatively small compared to chamber A; chamber C may even be effectively a zero-volume chamber (in other words, the second and third flow paths-discussed below—may actually be a single flow path that passes through a location represented by chamber C).

A first flow path may fluidically connect with chamber A on the side of reference boundary "b" that faces towards reference boundary "a" and with chamber B at a location in between reference boundaries "c" and "d." A second flow path may fluidically connect with chamber B at a location in between reference boundaries "c" and "d" and with chamber C at a location between reference boundaries "b" and "c." A third flow path may fluidically connect with chamber C at a location between reference boundaries "b" and "c" and with chamber D at a location on the side of reference boundary "d" that faces towards reference boundary "e."

During fluidic operation of the depicted fluidic circuit, a clamping pressure zone may be caused to move from reference boundary "a" to reference boundary "b," thereby pressurizing fluid in chamber A such that a release pressure of a releasable seal at location 1 (and, if necessary, at location 2 as well) is exceeded, thereby driving the fluid into and through chambers B and C; any bubbles that are contained in chamber A may also be forced into chamber B, but may tend to remain trapped in chamber B. In particular, if the fluidic circuit of FIG. 120B is oriented with chamber A being elevated above chambers B-D, then any air bubbles in chamber A will tend to float upwards and thus be the last fluid from chamber A to be moved into chamber B. The clamping pressure zone may then be moved from reference boundary "b" to reference boundary "c," thereby sealing off the second and third flow paths and preventing the flow of fluid (air bubbles) from chamber B to chamber C, and causing any fluid that may be remaining in chamber C (if present) to be pushed into chamber D, which may represent downstream fluidic elements that may further process the fluid delivered to chamber D.

In some implementations, the releasable seals shown at locations 1, 4, and/or 5 may be omitted—in particular, if chamber C is effectively zero-volume (the second and third flow paths being, in effect, a single contiguous flow path), then the releasable seals at locations 4 and 5 may be omitted.

In some implementations, the releasable seals at locations 2 and/or 3 may be dynamic seals, e.g., to prevent back flow of fluid into chamber A and/or to prevent later flow of fluid from chamber B into chamber C after the clamping pressure zone passes chamber B. The releasable seal at location 6 may also be a dynamic seal in some implementations so that fluid that is delivered to chamber D is unable to flow back into chamber C. In some implementations featuring dynamic seals at locations 2 and/or 6, such dynamic seals may have a relatively high release pressure, e.g., high enough that the clamping pressure zone cannot pressurize the fluids contained in chambers B or D, respectively to a level sufficient to exceed the release pressure.

Figure 120C:
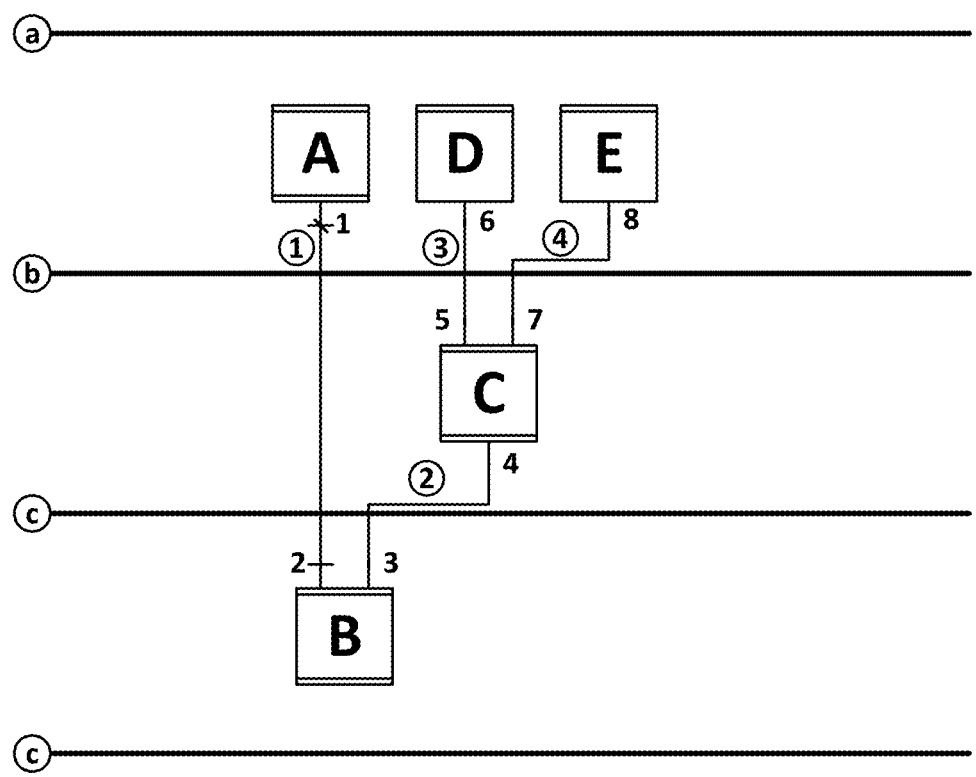

FIG. 120C depicts an example fluidic circuit that may be used to remove a quantity of bubbles from a fluid prior to metering an amount of the fluid for use in later fluidic elements. In the fluidic circuit of FIG. 120C, chamber A may be provided with a fluid that has bubbles contained therein. A clamping pressure zone may then be moved from reference boundary "a" to reference boundary "d," thereby driving the fluid (and bubbles) into chamber B via a first flow path. The first flow path may have a releasable seal at location 1 where it fluidically connects with chamber A, although if a temporary seal is used at location 1, the fluidic connection between the first flow path and chamber A may be configured so as to feature a relatively abrupt transition between a larger width of chamber A and a narrower width of the first flow path so as to encourage bubbles to congregate at the fluidic connection between chamber A and the first flow path.

The clamping pressure zone may then be caused to reverse course and move to reference boundary "b." In doing so, the fluid from chamber A that was moved to chamber B may be moved into chamber C via a second flow path. Chamber C, as can be seen, is connected with chambers D and E. Chamber D, for example, may be fluidically connected with chamber C via a third flow path, and chamber E may be fluidically connected with chamber C by a fourth flow path. While both the third and fourth flow paths are shown as being "open" flow paths, it will be understood that one or both such flow paths may be equipped with one or more releasable seals. Regardless of the particular configuration, the third and fourth flow paths may be configured such that the third flow path has a lower flow resistance than the fourth flow path (for example, if both the third and fourth flow paths have releasable seals located thereupon, the release pressure for the releasable seal(s) on the third flow path may be lower than the release pressure for the releasable seal(s) on the fourth flow path). Moreover, chamber C may, for example, be elongate, and the location where the third flow path fluidically connects with chamber C may be interposed between the fluidic connection of the second flow path to chamber C and the fluidic connection of the fourth flow path to chamber C. Thus, when fluid flows out of chamber C towards chambers D and E, such fluid will preferentially first flow into chamber D until chamber D is full, and will then flow into chamber E due to the flow restriction differences. Bubbles in the fluid may tend to travel at the forefront of the fluid flow and may therefor tend to flow into chamber D and become trapped there. This may be particularly the case if the fluidic circuit is oriented with chambers A, D, and E positioned higher than chamber C. The fluid that is in chamber E may then be caused to be pushed on to other elements of the fluidic circuit (not shown) by another flow path that fluidically connects with chamber E. If desired, addition chambers E may be used to meter additional amounts of fluid from the chamber A and/or provide for overflow. For example, if three chamber-E sized boluses of fluid are desired, three chambers E may be provided, each of which fluidically connects with chamber C such that the fluidic connection of the third flow path is in between the fluidic connection points of the fourth flow paths and the second flow path with respect to chamber C. Thus, chamber D may first fill up with a mixture of bubbles and fluid; once chamber A is full, further flow of fluid may pass into the chambers E until each chamber E is full. If desired, another chamber (not shown) but located in a similar manner to chamber E, but having a flow path that fluidically connects with chamber C such that all of the fluidic connection points of the fourth flow paths with chamber C are in between the fluidic connection point of the third flow path with chamber C and the fluidic connection point of the other chamber with chamber C; this additional chamber may be sized so as to contain all of the extra fluid that is anticipated to be present after chambers D and E have been filled.

Figure 121:
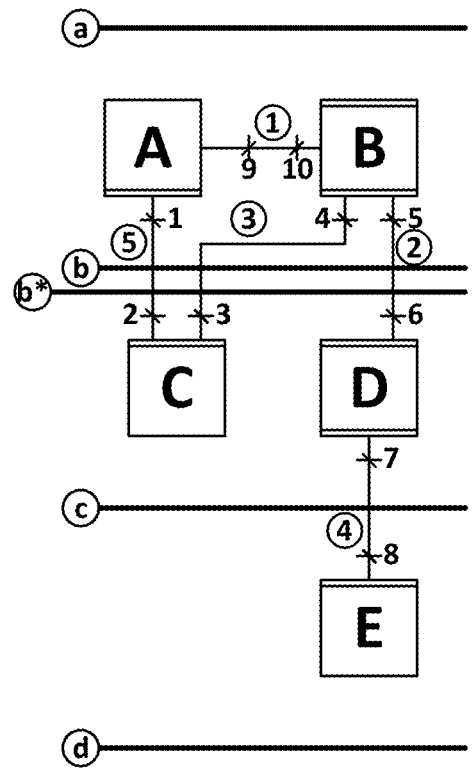
FIG. 121 depicts a fluidic circuit that allows bubbles that may be present in a fluid within the circuit to be skipped over and not passed on downstream.

FIG. 121 depicts an example fluidic circuit in which a desired quantity of liquid may be metered off from a larger volume of liquid while at the same time, a gas bubble or a cluster of gas bubbles that may accompany the liquid may be shunted to a different portion of the fluidic circuit so as to prevent such gas bubbles from, for example, accompanying the metered amount of liquid to downstream fluidic circuits.

The fluidic circuit depicted in FIG. 121 includes chambers A-E. At least a portion of chamber A may be located on a side of reference boundary "b" that faces toward reference boundary "a" and at least a portion of chamber B may lie between reference boundaries "a" and "b" (or "b*"). At least a portion of chamber C may lie on a side of reference boundary "b" that faces towards reference boundary "c," at least a portion of chamber D may lie between reference boundaries "b" and "c," and at least a portion of chamber E may lie on a side of reference boundary "c" that faces towards reference boundary "d." In some implementations, all of chamber A may be located on the side of reference boundary "b" that faces toward reference boundary "a," all of chamber B may lie between reference boundaries "a" and "b" (or "b*"), all of chamber C may lie on the side of reference boundary "b" that faces towards reference boundary "c," all of chamber D may lie between the reference boundaries "b" and "c," and/or all of chamber E may lie on the side of reference boundary "c" that faces towards reference boundary "d." In some implementations, all of chamber A may be located closer to reference boundary "a" than any of chamber B, e.g., chamber B may lie between reference boundaries "b" and "b*." Chamber D may be sized to have a maximum volume that equals the desired metering amount, and chamber E, which may ultimately receive the metered amount of fluid from chamber D, may be fluidically connected with additional fluidic circuits (not shown) positioned downstream.

In some implementations, chamber C may be positioned such that when the fluidic circuit is pressed against a platen, e.g., when a clamping pressure zone is applied to the fluidic circuit, chamber C may align with a cavity or opening in the platen that prevents the clamping pressure zone from applying pressure to chamber C (or that reduces the pressure that the clamping pressure zone can apply thereto).

A first fluidic path may fluidically connect with chamber A at a location that lies on the side of reference boundary "b" that faces towards reference boundary "a" and with chamber B at a location on chamber B that lies between reference boundaries "a" and "b*." A second fluidic path may fluidically connect with chamber B at a location between reference boundaries "a" and "b*" and with chamber D at a location in between reference boundaries "b" and "c." A third fluidic path may fluidically connect with chamber B at a location between reference boundaries "a" and "b*" and with chamber C at a location on chamber C on a side of reference boundary "b" that faces towards reference boundary "c." A fourth flow path may fluidically connect with chamber D at a location between reference boundaries "b" and "c" and with chamber E at a location on chamber E that is on a side of reference boundary "c" that faces towards reference boundary "d." A fifth flow path, which may be optional, may fluidically connect with chamber A at a location that lies on the side of reference boundary "b" that faces towards reference boundary "a" and with chamber C at a location on the side of reference boundary "b" that faces towards reference boundary "c."

It will be understood that during operation, the fluidic circuit of FIG. 121 may optionally be oriented such that reference boundary "d" is vertically lower than reference boundary "a," e.g., so as to cause any air or gas bubbles that may be present in chamber A to congregate nearer to the reference boundary "a" than to the reference boundary "b."

Prior to operation of the depicted fluidic circuit, a volume of liquid and a gas bubble or bubbles that may accompany it may be delivered to chamber A, e.g., by prior operation of one or more fluidic circuits (not shown) that are upstream of chamber A and fluidically connected thereto by a flow path (not shown); such an earlier fluidic circuit may, for example, be a fluidic circuit such as that shown in FIG. 119.

During operation of the fluidic circuit of FIG. 121, a clamping pressure zone may be moved from reference boundary "a" to reference boundary "b*," thereby pressurizing the fluid in chamber A to a pressure that exceeds a release pressure of a releasable seal that may be present on the first flow path, e.g., at location 9. The releasable seal on the first flow path may have a lower release pressure than a release pressure for another releasable seal that may be on the fifth flow path (if present), e.g., so as to prevent flow from chamber A along the fifth flow path if the first flow path is available.

As the clamping pressure zone traverses chamber A, first the liquid in chamber A, followed by the air or gas bubble(s) in chamber A, may be forced into chamber B. When the clamping pressure zone applies pressure to the contents of chamber B, e.g., when traversing from reference boundary "a" to "b" or from reference boundary "b" to "b*," depending on the configuration, the fluid within chamber B may be pressurized so as to exceed a release pressure for a releasable seal on the second flow path, e.g., at location 5. The third flow path may also have a releasable seal that may prevent fluid from flowing from chamber B to chamber C, but the releasable seal on the third flow path may have a release pressure that exceeds that of the release pressure of the releasable seal on the second flow path.

When the fluid in chamber B is forced through the second flow path into chamber D by the pressure applied to chamber B by the clamping pressure zone, the liquid that is present in chamber B may be the first to flow to chamber D, and may continue to do so until chamber D is at maximum capacity, i.e., until the desired metered volume of fluid has been delivered to chamber D. Once chamber D is full, a releasable seal on the fourth flow path may temporarily prevent the fluid within chamber D from flowing to chamber E. For example, the releasable seal on the fourth flow path, e.g., at location 7, may have a higher release pressure than the releasable seal on the third flow path, e.g., at location 4. Thus, when chamber D is full, further fluid flow from chamber B will switch to flowing along the third flow path into chamber C, which may be sized so as to be able to receive the remaining volume from chamber A (as well as the air or gas bubble(s) that may be present in chamber A.

The clamping pressure zone may then be advanced to reference boundary "c," thereby applying pressure to chamber D that causes the metered volume of fluid in chamber D to be flowed into chamber E, where it may then be used for downstream fluidic operations using other fluidic circuits.

In various implementations of the fluidic circuit of FIG. 121, the fluidic connections between passages and chambers at locations 2, 3, 5, 6, 8, and/or 10 may be temporary or dynamic seals or may, alternatively, simply be unsealed, e.g., open flow paths.

Figure 122:
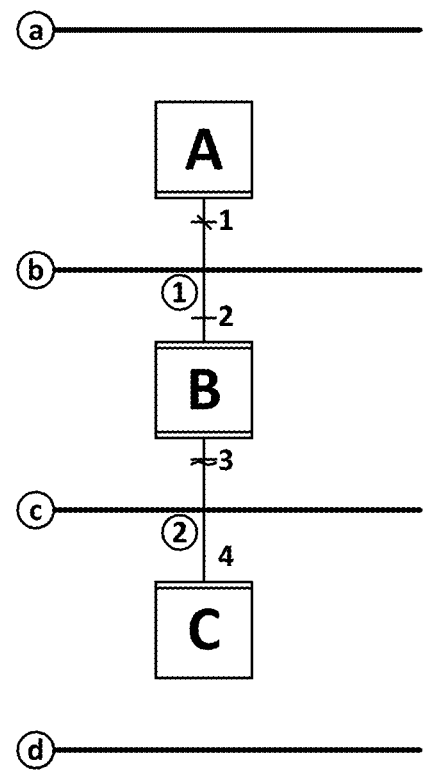
FIG. 122 depicts a fluidic circuit that may be used to mix two or more fluids.

FIG. 122 depicts an example fluidic circuit that may be used to perform mixing operations in which a clamping pressure zone is caused to traverse back and forth between two reference boundaries multiple times. The fluidic circuit depicted in FIG. 122 includes chambers A-C. Chamber A may be fluidically connected with upstream fluidic elements (not shown), typically via a single or, more commonly, multiple flow paths (also not shown). Chamber C may be fluidically connected with downstream fluidic elements (also not shown) via another flow path (also not shown).

At least a portion of chamber A may lie on a side of reference boundary "b" that faces towards reference boundary "a," at least a portion of chamber B may lie between reference boundaries "b" and "c," and at least a portion of chamber C may lie on a side of reference boundary "c" that faces towards reference boundary "d." In some implementations, all of chamber A may lie on the side of reference boundary "b" that faces towards reference boundary "a," all of chamber B may lie between reference boundaries "b" and "c," and/or all of chamber C may lie on the side of reference boundary "c" that faces towards reference boundary "d."

Chamber B may be sized to have a maximum total volume that is greater than or equal to an anticipated maximum amount of fluid that will be in chamber A prior to operation of the depicted fluidic circuit.

A first flow path may fluidically connect with chamber A at a location on the side of reference boundary "b" that faces towards reference boundary "a" and with chamber B at a location that lies between reference boundaries "b" and "c." A second flow path may fluidically connect with chamber B at a location that lies between reference boundaries "b" and "c" and with chamber C at a location that lies on the side of reference boundary "c" that faces towards reference boundary "d."

During operation, a clamping pressure zone may be traversed from reference boundary "a" to reference boundary "b" in order to cause a fluid mixture in chamber A to be pressurized to a release pressure of a releasable seal on the first flow path, e.g., at location 1. This may cause the fluid that is present in chamber A to be pushed into chamber B, which may serve as the mixing chamber.

The clamping pressure zone may then be caused to repeatedly move between reference boundary "b" and reference boundary "c," with each traversal of chamber B serving to further mix the contents thereof. The first flow path may fluidically connect with chamber B via a dynamic seal that is configured to have a release pressure that exceeds the pressure which the clamping pressure zone may cause to develop within chamber B, thereby preventing or discouraging the fluid to be mixed from leaking back into chamber A. Alternatively, the first flow path may be sealed with a live seal somewhere along its length after the clamping pressure zone has finished traversing chamber A. For example, a heating element in a platen against which the fluidic circuit is pressed by the clamping pressure zone may be caused to locally heat the portions of material between which the fluidic circuit is defined in order to, in combination with the pressure provided by the clamping pressure zone, form a heat seal across the first flow path.

The second flow path may fluidically connect with chamber B via a strong to normal dynamic transition seal, i.e., a dynamic seal that has a release pressure that, like that of the dynamic seal potentially used at location 2, may exceed the pressure that the clamping pressure zone may be able to develop in the fluids that are in chamber B but which may be transitioned to a dynamic seal with a lower release pressure by creating a "stitch" within chamber B that is near where the strong to normal dynamic transition seal is located. The stitch may, for example, be formed by thermally bonding together the portions of material between which the fluidic circuit is defined at a localized region within chamber B to create a "floating seal," as described earlier herein.

After the clamping pressure zone has been caused to repeatedly traverse chamber B to cause mixing to occur within the fluid contained therein, the clamping pressure zone may be caused to move to a location that is aligned with the location where the "stitch" is to be formed to cause the strong to normal dynamic transition seal to transition to its "normal" (lower release pressure) state. Once the clamping pressure zone is at this location, heat may be caused to be applied at that location, e.g., by a heater element that is in the platen against which the fluidic circuit is pressed by the clamping pressure zone, and to the portions of material between which the fluidic circuit is defined. Such application of heat and pressure may cause the portions of material to thermally bond together at that location, thereby forming the "stitch" that provides the floating seal.

After the strong to normal dynamic transition seal is transitioned to its "normal" state, the clamping pressure zone may be caused to move back to reference boundary "b" before moving towards reference boundary "c" in order to drive the fluid that is contained in chamber B into chamber C. The strong to normal dynamic transition seal, having been transitioned to its "normal" state, may have a release pressure that is below the pressure that the clamping pressure zone is able to cause to develop in chamber B and thus does not prevent the flow of fluid from chamber B.

In many implementations, the reciprocal motion of the clamping pressure zone across chamber B for mixing purposes may be caused to be performed rapidly, e.g., with the clamping pressure zone moving at a greater rate than the clamping pressure zone may move during other typical fluidic processing operations.

It will be understood that when a clamping pressure zone applied to a fluidic circuit is moved in order to cause fluid movement in the fluidic circuits discussed herein, such movement may generally be at a rate or speed that is low enough to avoid causing the clamping pressure zone to "skip" over fluid as it moves. For example, moving the clamping pressure zone too quickly may cause the fluid being pressurized to reach a pressure that causes the fluid to squirt underneath the clamping pressure zone, thereby allowing a portion of the fluid to travel in a direction opposite the direction of movement of the clamping pressure zone. While this is done deliberately in some of the fluidic circuits discussed herein (and may also be accomplished, for example, by locating a cavity or recess behind a portion of a fluidic circuit to reduce the amount of clamping pressure that may be applied thereto), it may generally be desirable to avoid such overly rapid movement of the clamping pressure zone when using the clamping pressure zone to move fluid from one chamber to another. However, in some implementations, it may also be desirable to cause the clamping pressure zone to move as quickly as possible (or almost as quickly as possible) during such movement without causing such fluid-skipping behavior, as this may allow for faster operation of the fluidic circuit as a whole. In some cases, such as in the reciprocal clamping pressure zone movement discussed above, it may actually be desirable to have the clamping pressure zone move fast enough that skipping of portions of the fluid occurs. For example, in the case where fluid is to be mixed by reciprocally moving the clamping pressure zone over a chamber or chambers where the fluid is located in order to push the fluid from one end of the chamber(s) to the other, it may actually be desirable to skip over portions of the fluid so as to allow the clamping pressure zone to then push the fluid from the other direction. In such implementations, the clamping pressure zone may be caused to move at a speed that causes such skipping behavior.

The above-described fluidic circuit may be used to cause a mixture of multiple fluids to be more homogenously mixed prior to being passed on to subsequent fluidic circuit elements. Various variants of the depicted fluidic circuit may also be used to similar effect. For example, the strong to normal dynamic transition seal may, in some implementations, be a dynamic seal at location 3 that has a release pressure that is slightly higher than the pressure that the clamping pressure zone may cause to be developed within chamber B. In such implementations, the dynamic seal at location 3 may, due to dynamic pressure effects caused by movement of the clamping pressure zone, leak slightly during at least part of some traversals of chamber B towards reference boundary "c" by the clamping pressure zone. This amount of leakage may be relatively small, with the bulk of the fluid being retained within chamber B for mixing, at least initially. However, such a dynamic seal may allow the clamping pressure zone to eventually, with sufficient reciprocations, cause the fluid in chamber B to be moved to chamber C. Such an implementation may forego the use of the floating seal/stitch, thereby allowing the thermal bonding step discussed earlier to be omitted.

In some variations, the second flow path may be equipped with a releasable seal at location 4, for example. For example, a dynamic seal may be provided at location 4 to prevent mixed fluid that is flowed into chamber C from potentially flowing back into chamber B. Additionally or alternatively, a temporary seal may be provided at location 4 to limit the amount of fluid that may prematurely leak out of chamber B (although this may need to be used in conjunction with the strong to normal dynamic transition seal at location 3, as the temporary seal may act to prevent the leakage of fluid that may allow the fluid in chamber B to be moved to chamber C, and it may be necessary to dynamically lower the release pressure for the dynamic seal at location 3 in order to allow the clamping pressure zone to apply sufficient pressure to the temporary seal at location 4 to cause the temporary seal to release.

In another variant, a fourth chamber D may be fluidically interposed between chambers B and C in order to catch any fluid that may leak past the strong to normal dynamic transition seal at location 3 and contain it prior to the clamping pressure zone then traversing chamber D to move the fluid to chamber C.

Figure 123:
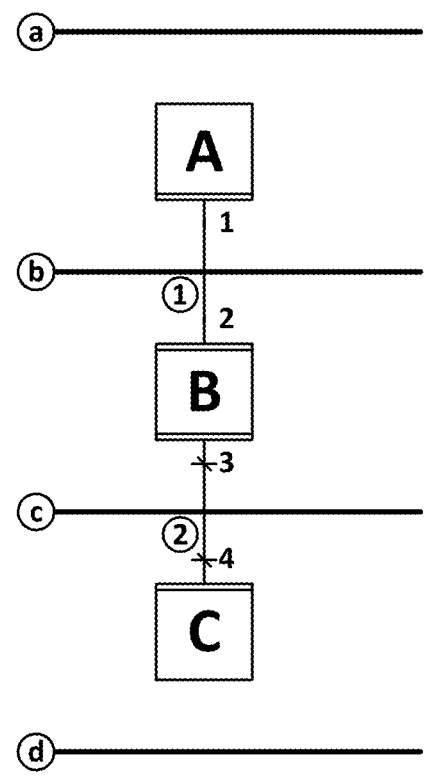
FIG. 123 depicts another fluidic circuit that may be used to mix two or more fluids.

FIG. 123 depicts another fluidic circuit that may be used for reciprocal mixing. In the depicted fluidic circuit, chambers A-C are provided. Chamber A may be fluidically connected with upstream fluidic elements (not shown), typically via a single or, more commonly, multiple flow paths (also not shown). Chamber C may be fluidically connected with downstream fluidic elements (also not shown) via another flow path (also not shown). Chamber B may be a relatively thin chamber in a direction crosswise to the nominal flow direction of fluid passing therethrough. For example, chamber B may have a width that causes chamber B, when loaded with fluid, to collapse when the back pressure that holds the fluid in chamber B is removed. Thus, for example, if fluid from chamber A is pushed into chamber B by a clamping pressure zone applying pressure to the fluid in chamber B, the fluid that is moved into chamber B will, without external application of pressure (or without external application of pressure other than atmospheric pressure) to chamber B, flow back out of chamber B into chamber A when the back pressure in chamber A is reduced, e.g., by removing the clamping pressure zone from chamber A or moving the clamping pressure zone closer to reference boundary "a"/further from reference boundary "b."

Chamber B may be a straight chamber, e.g., a chamber that generally follows a linear axis, a serpentine chamber, e.g., a chamber that follows a snaking path, or any other shape that does not prevent chamber B from collapsing and causing the fluid contained therein to automatically return to chamber A once the back pressure provided by chamber A via the clamping pressure zone is removed or, in some cases, reduced.

At least a portion of chamber A may lie on a side of reference boundary "b" that faces towards reference boundary "a," at least a portion of chamber B may lie between reference boundaries "b" and "c," and at least a portion of chamber C may lie on a side of reference boundary "c" that faces towards reference boundary "d." In some implementations, all of chamber A may lie on the side of reference boundary "b" that faces towards reference boundary "a," all of chamber B may lie between reference boundaries "b" and "c," and/or all of chamber C may lie on the side of reference boundary "c" that faces towards reference boundary "d."

Chamber B may be sized to have a maximum total volume that is greater than or equal to an anticipated maximum amount of fluid that will be in chamber A prior to operation of the depicted fluidic circuit.

A first flow path may fluidically connect with chamber A at a location on the side of reference boundary "b" that faces towards reference boundary "a" and with chamber B at a location that lies between reference boundaries "b" and "c." A second flow path may fluidically connect with chamber B at a location that lies between reference boundaries "b" and "c" and with chamber C at a location that lies on the side of reference boundary "c" that faces towards reference boundary "d."

During operation, a clamping pressure zone may be traversed from reference boundary "a" to reference boundary "b" in order to cause a fluid mixture in chamber A to be flowed into chamber B. The clamping pressure zone may then be caused to reverse course and return to reference boundary "a" or to a location between reference boundaries "a" and "b," thereby reducing the back pressure that pushed the fluid into chamber B. Chamber B, accordingly, may collapse, forcing the fluid therein to flow back into chamber A. This process may be repeated multiple times until a desired number of reciprocations of the fluid into and out of chamber B has occurred. The number of reciprocations may, for example, be selected to provide a desired amount of further mixing of the fluids in chamber A.

In many implementations, the reciprocal motion of the clamping pressure zone across chamber A for mixing purposes may be caused to be perform rapidly, e.g., with the clamping pressure zone moving at a greater rate than the clamping pressure zone may move during other typical fluidic processing operations. In some implementations, the clamping pressure zone may be moved at the highest speed possible before the clamping pressure zone, for example, begins to "skip" over fluid portions within chamber A, thereby allowing the fluid to escape to the side of the clamping pressure zone facing away from reference boundary "b."

Once the desired number of reciprocations of the clamping pressure zone have been provided, the clamping pressure zone may be caused to move to reference boundary "c" in order to force the fluid from chamber A to be pushed into chamber B one last time and pressurized to the point where the pressure in the fluid exceeds the release pressure for a releasable seal on the second flow path, e.g., at location 3. This causes the mixed fluid to then flow through the second flow path into chamber C, where it may then be passed on to further downstream fluidic elements (not shown).

In some variants of the depicted fluidic circuit, the maximum volume of chamber B may be less than the anticipated volume of fluid that may be within chamber A prior to operation of the depicted fluidic circuit. In such variants, the clamping pressure zone may be caused to move to a location along chamber A that drives fluid from chamber A into chamber B but that does not cause chamber B to be pressurized to the release pressure of the releasable seal on the second flow path. This allows the fluid in chamber A to be reciprocated in and out of chamber B without prematurely leaking into chamber B. Such implementations may, due to only a portion of the fluid being flowed into chamber B for any given reciprocation of the clamping pressure zone, offer less efficient mixing, but may still provide a desired amount of mixing if performed a sufficient number of times.

In FIG. 123, the first flow path is shown as having no seals, e.g., being an open flow path. However, it will be understood that releasable seals may potentially be used at locations 1 and/or 2 without affecting the performance of the fluidic circuit if care is taken to avoid such releasable seals having a release pressure that cannot be overcome by the pressure that chamber B may exert on the fluid when forcing the fluid back into chamber A. Thus, for example, if a dynamic seal is used at location 2, the dynamic seal may be selected to have a release pressure that is lower than the pressure that chamber B may exert on the fluid. It will also be understood that the second flow path may have an open flow path at location 4, i.e., the second flow path may have no releasable seal at location 4, although the use of a dynamic seal at location 4 may allow the depicted fluidic circuit to prevent backflow of the fluid that is introduced into chamber C to chamber B.

Figure 124A:
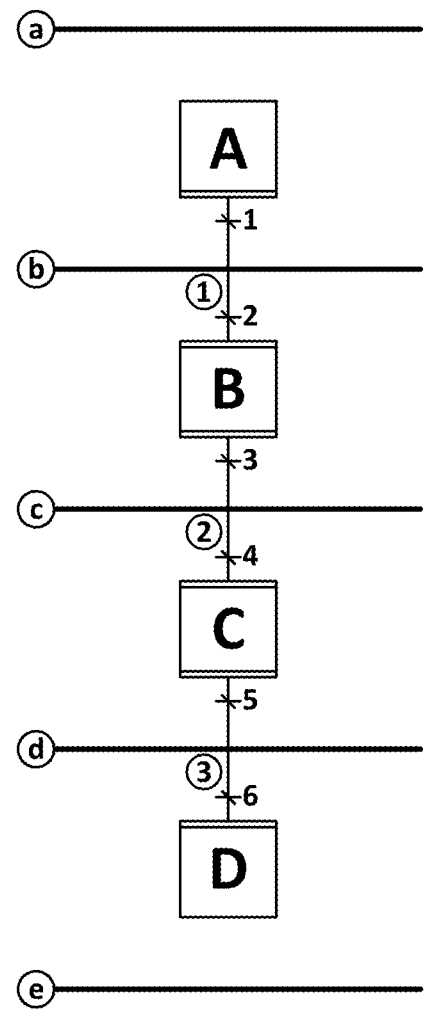
FIGS. 124A through 124C depict other fluidic circuits that may be used to mix two or more fluids.

FIG. 124A depicts an example fluidic circuit for mixing that uses a sequential chain of multiple chambers in order to provide for multi-staged turbulent mixing. As depicted, the fluidic circuit contains chambers A-D, although it will be appreciated that additional instances of chambers B and/or C may be fluidically interposed between chambers B and C, as desired, in order to provide for even more mixing. Each chamber may, for example, serve as a separate mixing stage, with the chain of chambers forming a chain of mixing stages. The chambers of each mixing stage may also be referred to herein as mixing chambers; this convention is applicable to other implementations discussed below as well.

Chamber A may be fluidically connected with upstream fluidic elements (not shown), typically via a single or, more commonly, multiple flow paths (also not shown). Chamber D may be fluidically connected with downstream fluidic elements (also not shown) via another flow path (also not shown). Chambers B and C may each be sized to have a maximum total volume that is greater than or equal to an anticipated maximum amount of fluid that will be in chamber A prior to operation of the depicted fluidic circuit, although in some implementations, chambers B and/or C may each have maximum total volumes that are less than the anticipated maximum amount of fluid that will be in chamber A prior to operation of the depicted fluidic circuit. In such implementations, the mixing that is performed at each chamber may be somewhat less efficient than when chambers B and C have a maximum total volume that is greater than or equal to the anticipated maximum amount of fluid that will be in chamber A prior to operation of the depicted fluidic circuit, but this inefficiency may, for example, be countered by including additional mixing stages, as discussed above.

At least a portion of chamber A may lie on a side of reference boundary "b" that faces towards reference boundary "a," at least a portion of chamber B may lie between reference boundaries "b" and "c," at least a portion of chamber C may lie between reference boundaries "c" and "d," and at least a portion of chamber D may lie on a side of reference boundary "d" that faces towards reference boundary "e." In some implementations, all of chamber A may lie on the side of reference boundary "b" that faces towards reference boundary "a," all of chamber B may lie between reference boundaries "b" and "c," all of chamber C may lie between reference boundaries "c" and "d," and/or all of chamber D may lie on the side of reference boundary "d" that faces towards reference boundary "e."

A first flow path may fluidically connect with chamber A at a location on the side of reference boundary "b" that faces towards reference boundary "a" and with chamber B at a location that lies between reference boundaries "b" and "c." A second flow path may fluidically connect with chamber B at a location that lies between reference boundaries "b" and "c" and with chamber C at a location that lies between reference boundaries "c" and "d." A third flow path may fluidically connect with chamber C at a location that lies between reference boundaries "c" and "d" and with chamber D at a location on the side of reference boundary "c" that faces towards reference boundary "d."

During operation, a clamping pressure zone may be traversed from reference boundary "a" to reference boundary "d" in order to cause a fluid mixture in chamber A to be sequentially flowed into chambers B, C, and then D. Releasable seals provided on the first through third flow paths, e.g., at locations 1, 3, and 5, may prevent the fluid flowed into each chamber B through D from flowing on to the next chamber in the series until the fluid in the chamber being filled reaches a pressure that equals the release pressure of the releasable seal blocking the flow path to the next chamber in the sequence. When each releasable seal releases, the fluid that was being restrained thereby may flow through the now-open flow path that it sealed and into the next chamber in the sequence. With each such fluid flow, turbulence within the next downstream chamber that arises due to such fluid flow may cause additional mixing to occur within the fluid.

It will be understood that the releasable seals shown at locations 2, 4, and 6 may optionally be omitted in some implementations, making the first through third flow paths be open flow paths after the releasable seals at locations 1, 3, and 5, respectively, as the clamping pressure zone may restrain fluid flow in the reverse direction.

Figure 124B:
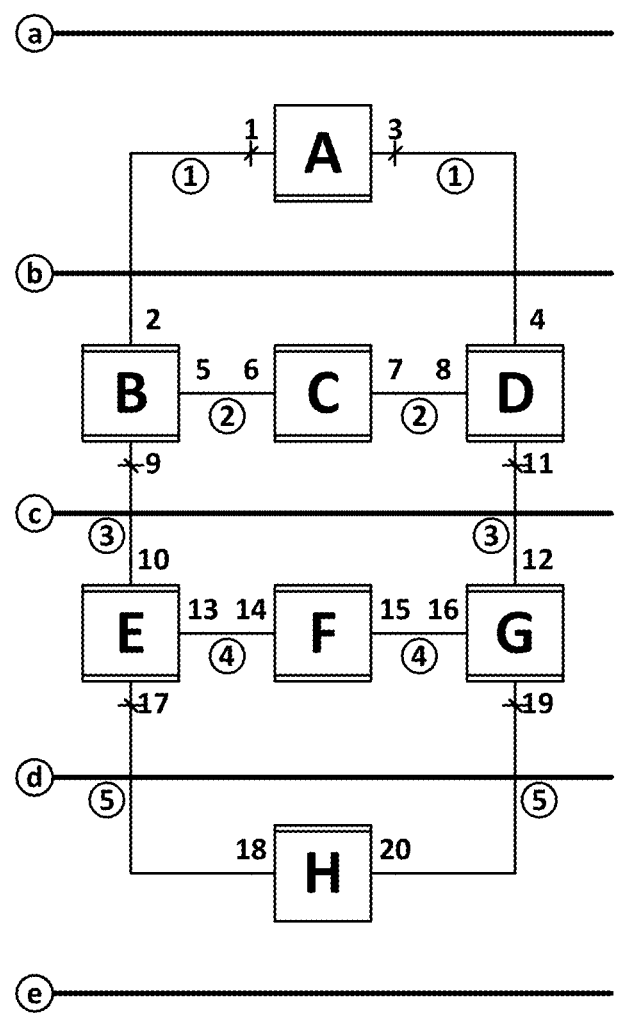

FIG. 124B depicts another example fluidic circuit for mixing that uses a sequential chain of multiple chambers in order to provide for multi-staged turbulent mixing. As depicted, the fluidic circuit contains chambers A-H, although it will be appreciated that additional instances of chambers B/C/D and/or E/F/G may be fluidically interposed between chambers B/C/D and/or E/F/G, as desired, in order to provide for even more thorough mixing.

The fluidic circuit of FIG. 124B is similar to that of FIG. 124A, except that instead of a single chain of chambers being fluidically interposed in sequence between chambers A and D in FIG. 124A, the fluidic circuit of FIG. 124B has multiple, e.g., two, chains of chambers fluidically interposed in sequence between chambers A and H. For example, chambers B and E are fluidically interposed between chambers A and H on one side of the fluidic circuit of FIG. 124B, while chambers D and G are similarly fluidically interposed between chambers A and H on the other side of the fluidic circuit of FIG. 124B. Moreover, additional chambers may be fluidically interposed in between chambers in adjacent chains of chambers, e.g., chamber C is fluidically interposed between chambers B and D, and chamber F is fluidically interposed between chambers E and G, in the depicted fluidic circuit. Chambers B, D, E, and G may, for example, be quite small in some implementations, e.g., representing the junction of two flow paths.

Chamber A may be fluidically connected with upstream fluidic elements (not shown), typically via a single or, more commonly, multiple flow paths (also not shown). Chamber H may be fluidically connected with downstream fluidic elements (also not shown) via another flow path (also not shown).

At least a portion of chamber A may lie on a side of reference boundary "b" that faces towards reference boundary "a," at least portions of chambers B, C, and D may lie between reference boundaries "b" and "c," at least portions of chambers E, F, and G may lie between reference boundaries "c" and "d," and at least a portion of chamber H may lie on a side of reference boundary "d" that faces towards reference boundary "e." In some implementations, all of chamber A may lie on the side of reference boundary "b" that faces towards reference boundary "a," all of one or more of chambers B, C, and D may lie between reference boundaries "b" and "c," all of one or more of chambers E, F, and G may lie between reference boundaries "c" and "d," and/or all of chamber H may lie on the side of reference boundary "d" that faces towards reference boundary "e." Thus, each pair of adjacent reference boundaries in FIG. 124B may be viewed as bracketing a different mixing stage of the fluidic circuit of FIG. 124B.

First flow paths may fluidically connect with chamber A at locations on the side of reference boundary "b" that faces towards reference boundary "a" and with chambers B and D, respectively, at locations that lie between reference boundaries "b" and "c." Second flow paths may fluidically connect chambers B and D with chamber C, with the second flow paths fluidically connecting with chambers B-D at locations that lie between reference boundaries "b" and "c." Third flow paths may fluidically connect chambers B and D with, respectively, chambers E and G, with the third flow paths fluidically connecting with chambers B and D in locations that lie between reference boundaries "b" and "c" and with chambers E and G at locations between reference boundaries "c" and "d." Fourth flow paths may fluidically connect chambers E and G with chamber F, with the fourth flow paths fluidically connecting with chambers E-G at locations that lie between reference boundaries "c" and "d." Fifth flow paths that fluidically connect with chambers E and G, respectively, at locations in between reference boundaries "c" and "d" may fluidically connect with chamber H at locations on the side of reference boundary "d" that faces towards reference boundary "e."

The second flow paths may, for example, fluidically connect with chamber C at locations on chamber C that are close to, or as close as possible to, reference boundary "c"; similarly, the fourth flow paths may, for example, fluidically connect with chamber F at locations on chamber F that are close to, or as close as possible to, reference boundary "d." Chambers C and F may also, in some implementations, be positioned such that the locations where the second and fourth flow paths, respectively, fluidically connect thereto are closer to reference boundary "a" than the locations where those same flow paths fluidically connect with chambers B/C or E/G, respectively.

During operation, a clamping pressure zone may be traversed from reference boundary "a" to reference boundary "d" in order to cause a fluid mixture in chamber A to be sequentially flowed into chambers B/D/C, E/F/G, and then D. Releasable seals provided on the first, third, and fifth flow paths, e.g., at locations 1, 3, 9, 11, 17, and 19, may prevent the fluid flowed into each of chambers B, D, E, and G from flowing on to the next chamber in the series, e.g., chambers E, G, or H, until the fluid in the chamber being filled reaches a pressure that equals the release pressure of the releasable seal blocking the flow path to the next chamber in the sequence. When each releasable seal releases, the fluid that was being restrained thereby may flow through the now-open flow path that it sealed and into the next chambers in the sequence. With each such fluid flow, turbulence within the next downstream chambers that arises due to such fluid flow may cause additional mixing to occur within the fluid.

It will be understood that the releasable seals shown at locations 9,11, 17, and 19 may optionally be omitted in some implementations, although the third and fifth flow paths in such implementations may be provided using very thin flow passages that have a high flow resistance so as to discourage significant fluid flow therethrough absent the fluid being pressurized to a first threshold level upstream of those flow paths.

During operation of the depicted fluidic circuit, a clamping pressure zone may be moved from reference boundary "a" to reference boundary "b" and then to reference boundary "c" and then reference boundary "d." As the clamping pressure zone applies pressure to chamber A and pressurizes the fluids contained within chamber A, the fluid pressure within chamber A may cause the release pressure for one or both of the releasable seals that may be located on the first flow paths to be reached, thereby causing one or both such releasable seals to release and allow the fluid in chamber A to flow to one or both of chambers B and D. As the clamping pressure zone continues to advance, the fluid that is flowed into chambers B and/or D may also flow into chamber C and, if the fluid has not already done so, into the other of chambers B or D via the second flow paths.

As the clamping pressure zone continues to advance to reference boundary "c," the fluid in chambers B-D may be pressurized to the point where the release pressure for one or both of the releasable seals on the third flow paths may be met, thereby causing one or both of the releasable seals on the third flow paths to open and release the fluid contained in chambers B-D to be pushed into chambers E-G in a manner generally similar to that described above with respect to chambers B-D. As the clamping pressure zone continues to advance, the fluid contained in chambers E-G may be pressurized to the point where the release pressure for the releasable seals on the fifth flow paths may be exceeded, thereby allowing the fluid to flow from chambers E-G into chamber H.

The symmetry evident in the fluidic circuit of FIG. 124B is optional; in some implementations, chambers B and E, D and G, B and G, or D and E may be omitted while still providing for adequate mixing of the fluids. Moreover, it will be understood that either flow path in each of the pair of first flow paths, the pair of second flow paths, and the pair of third flow paths may be omitted to similar effect.

Various versions of the fluidic circuit of FIG. 124B discussed above may be practiced as well. For example, in some implementations, releasable seals may also be used at any one or more of locations 5-8 and 13-16 as long as the release pressures are appropriately selected so as to allow for the fluidic operations discussed above. For example, the release pressures for such releasable seals along any given flow path may be selected such that the total release pressure along each flow path may be lower than the release pressure for the releasable seals that lie along the third or fifth flow paths, e.g., at locations 9, 11, 17, or 19, respectively. The releasable seals at locations 2, 4, 10, and 12 may be dynamic seals or temporary seals.

Figure 124C:
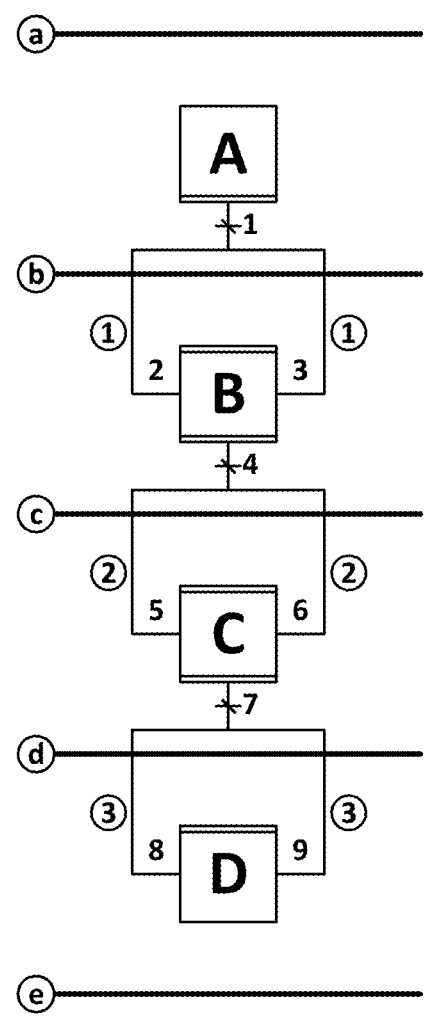

FIG. 124C depicts another fluidic circuit in which multi-stage turbulent mixing may be performed. In the fluidic circuit of FIG. 124C, a chain of chambers A-D is arranged in sequence. It will be understood that additional repetitions of chambers B and/or C may be fluidically interposed between the depicted chambers in order to add additional mixing stages to the mixer.

Chamber A may be fluidically connected with upstream fluidic elements (not shown), typically via a single or, more commonly, multiple flow paths (also not shown). Chamber D may be fluidically connected with downstream fluidic elements (also not shown) via another flow path (also not shown).

At least a portion of chamber A may lie on a side of reference boundary "b" that faces towards reference boundary "a," at least a portion of chamber B may lie between reference boundaries "b" and "c," at least a portion of chamber C may lie between reference boundaries "c" and "d," and at least a portion of chamber D may lie on a side of reference boundary "d" that faces towards reference boundary "e." In some implementations, all of chamber A may lie on the side of reference boundary "b" that faces towards reference boundary "a," all of chamber B may lie between reference boundaries "b" and "c," all of chamber C may lie between reference boundaries "c" and "d," and/or all of chamber D may lie on the side of reference boundary "d" that faces towards reference boundary "e."

First flow paths may fluidically connect with chamber A at locations on the side of reference boundary "b" that faces towards reference boundary "a" and with chamber B at locations that lie between reference boundaries "b" and "c." Second flow paths may fluidically connect with chamber B at a location that is between reference boundaries "b" and "c" and with chamber C at locations that lie between reference boundaries "c" and "d." Third flow paths may fluidically connect with chamber C at a location that is between reference boundaries "b" and "c" and with chamber C at locations that lie between reference boundaries "c" and "d" and with chamber D at locations that lie on the side of reference boundary "d" that faces towards reference boundary "e." As can be seen, the first through third flow paths may be branching flow paths, e.g., sharing a common fluidic connection to the chamber to which they are fluidically connected that is located closest to reference boundary "a" and while fluidically connecting with the other chamber to which they are fluidically connected via separate fluidic connection locations. In some implementations, such separate fluidic connection locations may, for each flow path, be located on opposing sides of the respective chamber such that the fluids flowed through each fluidic connection generally face each other and collide within the corresponding chamber.

The first through third flow paths may, for example, fluidically connect with chambers A through C, respectively, at locations on those respective chambers that are close to, or as close as possible to, reference boundaries "b," "c," or "d," respectively.

During operation, a clamping pressure zone may be traversed from reference boundary "a" to reference boundary "d" in order to cause a fluid mixture in chamber A to be sequentially flowed into chambers B, C, and then D, e.g., with each of chambers B, C, and D forming a separate mixing stage of the fluidic circuit. Releasable seals provided on the first through third flow paths may be caused to sequentially release as the clamping pressure zone moved from reference boundary "a" to reference boundary "d," thereby allowing the fluid in the fluidic circuit to move from chamber to chamber, thereby further mixing at each such chamber introduction.

Various versions of the fluidic circuit of FIG. 124C discussed above may be practiced as well. For example, in some implementations, releasable seals may also be used at any one or more of locations 2, 3, 5, 6, 8, and/or 9 as long as the release pressures for such releasable seals on each pair of flow paths are selected so as to be generally equal in magnitude (this is not necessarily needed, but doing so may promote more uniform mixing since it may avoid a release pressure imbalance that may cause fluid to only be introduced to one side of each chamber).

It will be understood that the releasable seals shown at locations 1, 4, and 7 may optionally be omitted in some implementations, although the third and fifth flow paths in such implementations may be provided using very thin flow passages, e.g., passages with volumes that are less than the volume of fluid pushed therethrough, that have a high flow resistance so as to discourage significant fluid flow therethrough absent the fluid being pressurized to a first threshold level upstream of those flow paths.

Figure 125A:
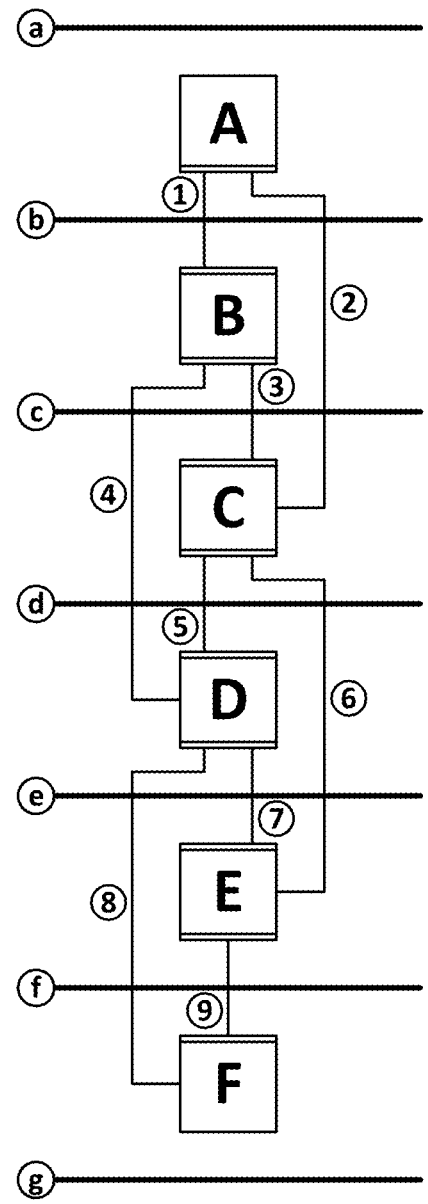
FIGS. 125A and 125B depict other fluidic circuits that may be used to mix two or more fluids.

FIG. 125A depicts another fluidic circuit for multi-stage turbulent mixing of fluids. In the fluidic circuit of FIG. 125A, a chain of chambers A-F is arranged in sequence. It will be understood that additional repetitions of any one or more of chambers B through E may be fluidically interposed between the depicted chambers, and fluidically connected in a similar manner, in order to add additional mixing stages to the mixer.

Chamber A may be fluidically connected with upstream fluidic elements (not shown), typically via a single or, more commonly, multiple flow paths (also not shown). Chamber F may be fluidically connected with downstream fluidic elements (also not shown) via another flow path (also not shown).

At least a portion of chamber A may lie on a side of reference boundary "b" that faces towards reference boundary "a," at least a portion of chamber B may lie between reference boundaries "b" and "c," at least a portion of chamber C may lie between reference boundaries "c" and "d," at least a portion of chamber D may lie between reference boundaries "d" and "e," at least a portion of chamber E may lie between reference boundaries "e" and "f," and at least a portion of chamber F may lie on a side of reference boundary "f" that faces towards reference boundary "g." In some implementations, all of chamber A may lie on the side of reference boundary "b" that faces towards reference boundary "a," all of chamber B may lie between reference boundaries "b" and "c," all of chamber C may lie between reference boundaries "c" and "d," all of chamber D may lie between reference boundaries "d" and "e," all of chamber E may lie between reference boundaries "e" and "f," and/or all of chamber F may lie on the side of reference boundary "f" that faces towards reference boundary "g."

Each of chambers A-D may be fluidically connected with each of the next two chambers in sequence via separate flow paths, with one flow path (which may be referred to as an inter-stage flow path) leading to the next chamber in sequence, and the other (which may be referred to as a bypass flow path, leading to the next chamber beyond that in the sequence. Thus, for example, chamber A may be fluidically connected with chamber B by a first flow path and with chamber C by a second flow path; both the first and second flow paths may fluidically connect with chamber A at a location on the side of reference boundary "b" that faces reference boundary "a." The first flow path may fluidically connect with chamber B at a location between reference boundaries "b" and "c," and the second flow path may fluidically connect with chamber C at a location between reference boundaries "c" and "d." Similarly, chamber B may be fluidically connected with chamber C by a third flow path and with chamber D by a fourth flow path; both the third and fourth flow paths may fluidically connect with chamber B at a location in between reference boundaries "b" and "c." The third flow path may fluidically connect with chamber C at a location between reference boundaries "C" and "d," and the fourth flow path may fluidically connect with chamber D at a location between reference boundaries "d" and "e." The remaining fluidic connections/flow paths between chambers may be similarly configured, as is evident from FIG. 125A. Chamber E may, due to there being only chamber F downstream of it, only be connected with the next downstream chamber as opposed to the next two downstream chambers. Each chamber may be viewed as a separate mixing stage of the fluidic circuit that is shown.

During operation, a clamping pressure zone may be traversed from reference boundary "a" to reference boundary "f" in order to cause a fluid mixture in chamber A to be sequentially flowed into chambers B, C, D, E, and then into chamber F. The flow paths in between the chambers A through F may be unrestricted, e.g., may not have any releasable seals.

It will be understood that chambers B through F may, for example, be very small chambers, e.g., representing the volumes where two passages intersect but not otherwise being larger than such passages. The fluidic circuit of FIG. 125A may, for example, be similar to the fluidic circuit of FIG. 105.

Figure 125B:
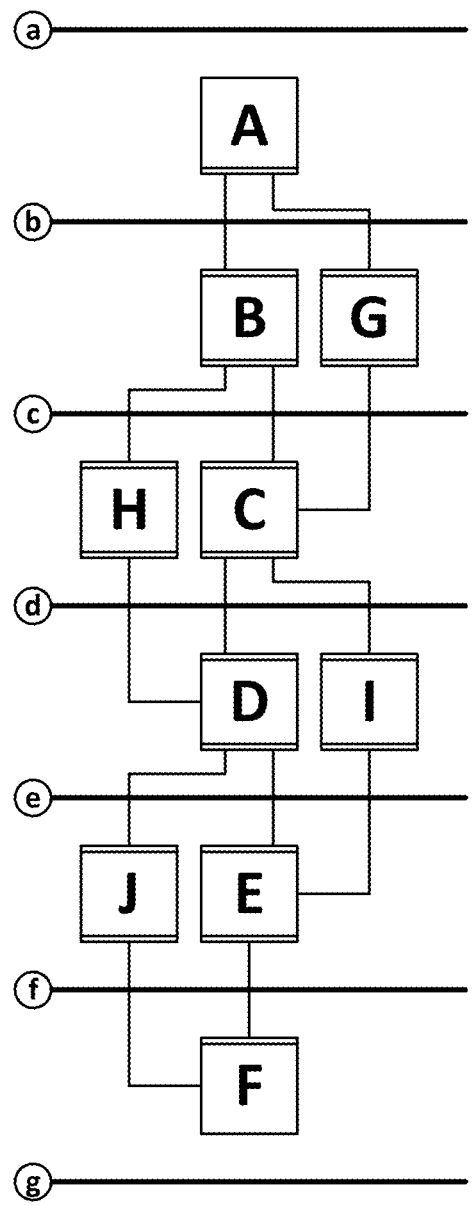

FIG. 125B depicts another fluidic circuit for mixing fluids. In the fluidic circuit of FIG. 125B, a chain of chambers A-F is arranged in sequence, with additional chambers G-J arranged such that each such additional chamber is fluidically interposed between near-adjacent pairs of the chambers A-F. It will be understood that the repeating pattern of chambers exhibited in FIG. 125B may be continued for any number of mixing stages in order to achieve a desired level of mixing.

Chamber A may be fluidically connected with upstream fluidic elements (not shown), typically via a single or, more commonly, multiple flow paths (also not shown). Chamber F may be fluidically connected with downstream fluidic elements (also not shown) via another flow path (also not shown).

At least a portion of chamber A may lie on a side of reference boundary "b" that faces towards reference boundary "a," at least portions of chambers B and G may lie between reference boundaries "b" and "c," at least portions of chambers C and H may lie between reference boundaries "c" and "d," at least portions of chambers D and I may lie between reference boundaries "d" and "e," at least portions of chambers E and J may lie between reference boundaries "e" and "f," and at least a portion of chamber F may lie on a side of reference boundary "f" that faces towards reference boundary "g." In some implementations, all of chamber A may lie on the side of reference boundary "b" that faces towards reference boundary "a," all of chambers B and G may lie between reference boundaries "b" and "c," all of chambers C and H may lie between reference boundaries "c" and "d," all of chambers D and I may lie between reference boundaries "d" and "e," all of chambers E and J may lie between reference boundaries "e" and "f," and/or all of chamber F may lie on the side of reference boundary "f" that faces towards reference boundary "g."

Each of chambers A-D may be fluidically connected with each of the next two chambers in sequence via separate flow paths, with one flow path leading to the next chamber in sequence, and the other leading to the next chamber beyond that in the sequence but with one of chambers G-H fluidically interposed therebetween. Thus, for example, chamber A may be fluidically connected with chamber B by a first flow path and with chamber C by second and third flow paths that meet at chamber G; both the first and second flow paths may fluidically connect with chamber A at a location on the side of reference boundary "b" that faces reference boundary "a." The first flow path may fluidically connect with chamber B at a location between reference boundaries "b" and "c," the second flow path may fluidically connect with chamber G at a location between reference boundaries "b" and "c," and the third flow path may fluidically connect with chamber C at a location between reference boundaries "c" and "d." Similarly, chamber B may be fluidically connected with chamber C by a fourth flow path and with chamber D by fifth and sixth flow paths that meet at chamber H; both the fourth and fifth flow paths may fluidically connect with chamber B at a location in between reference boundaries "b" and "c." The fourth flow path may fluidically connect with chamber C at a location between reference boundaries "c" and "d," the fifth flow path may fluidically connect with chamber H at a location between reference boundaries "c" and "d," and the sixth flow path may fluidically connect with chamber D at a location between reference boundaries "d" and "e." The remaining fluidic connections/flow paths between chambers may be similarly configured, as is evident from FIG. 125A. Chamber E may, due to there being only chamber F downstream of it, only be connected with the next downstream chamber as opposed to the next two downstream chambers.

During operation, a clamping pressure zone may be traversed from reference boundary "a" to reference boundary "f" in order to cause a fluid mixture in chamber A to be sequentially flowed into chambers B/G, C/H, D/I, E/J, and then into chamber F. The flow paths in between the chambers A through F may be unrestricted, e.g., may not have any releasable seals. It will be understood that this implementation is functionally similar to that in FIG. 125A, but with additional chamber volumes located along the flow paths that "skip" a chamber.

It will be further understood that chambers B through F may, for example, be very small chambers, e.g., representing the volumes where two passages intersect but not otherwise being larger than such passages. The fluidic circuit of FIG. 125A may, for example, be similar to the fluidic circuit of FIG. 106.

FIG. 126A depicts an example of a fluidic circuit that may be used to perform an assay for a target substance in a sample, e.g., for THC in a breath sample. The depicted fluidic circuit, which is shown split in half between reference boundaries "f" and "g" so as to fit on one page, includes chambers A through K and may be configured to perform a single-lane aqueous assay. Chamber A, at least a portion of which may lie on a side of reference boundary "b" that faces towards reference boundary "a," may be filled with a pre-mixed bolus of sample material, surfactant or elution fluid (which may act as a carrier to assist with transport of the sample material), and target-substance-specific antibody, e.g., an antibody that binds to THC in the case of a THC assay. The fluid mixture in chamber A may, for example, include more antibody than is anticipated to be needed in order to bind all of the target substance that could reasonably be expected to be present in the sample to such antibodies. Thus, the fluid will typically contain some unbound antibody and all of the target substance in the fluid will generally be bound to the antibody.

Chambers B, C, and D may, for example, be similarly arranged to the metering and sequestration fluidic circuit of FIG. 118A, where chamber C may receive a metered amount of the pre-mixed bolus fluid and sequester it to preserve it for later secondary analysis; chamber C may also be pre-loaded in some implementations with a stabilizer buffer to assist with preserving the metered sample portion. At least a portion of chamber B may lie between reference boundaries "b" and "c," at least a portion of chamber C may lie on a side of reference boundary "c" that faces towards reference boundary "d," and at least a portion of chamber D may lie between reference boundaries "c" and "d." Chamber B may, for example, be positioned so as to be able to be optically interrogated by an optical measurement device of an analysis system when the depicted fluidic circuit is interfaced with the analysis system in order to be fluidically operated. Chamber B may also have one or more surfaces thereof that may be coated, for example, with an immobilized substance that may be used during performance of an assay. For example, chamber B may have a surface or surfaces (referred to below as "surfaces of interest") that are coated with the target substance, e.g., THC, such that the target substance remains fixed in place in chamber B during exposure to various fluids that flow through chamber B during various stages of fluidic operation. In other implementations, the surfaces of chamber B may not be coated with such a substance, but surfaces of objects contained within chamber B may instead be coated with such a substance. For example, magnetic beads, e.g., beads made of a material that is susceptible to magnetism, may be provided within chamber B. Such beads may be coated with such a material, e.g., THC, and then caused to be held in place within chamber B during fluidic operations by, for example, a magnet that may be positioned proximate to chamber B when the fluidic circuit is interfaced with the analysis system that may be used to perform an assay with the fluidic circuit by causing the fluidic circuit to be fluidically operated.

Chamber D may be provided to capture whatever sample fluid from chamber A may remain after the portion of sample fluid that is retained in chamber C has been sequestered. Chamber D may be provided so as to serve as a catch basin that may capture the fluid from chamber A that is flowed through chamber B but which may, for whatever reason, not get pushed into chamber C. In conjunction with dynamic seals at locations 8 and 10, chamber D may also act as a rough pre-metering chamber for fluids located in other downstream chambers. For example, when fluid is pushed into chamber D from chamber E, the release pressure of the dynamic seal at location 8 may be higher than the pressure that may be applied to the fluid via compression of chamber E by the clamping pressure zone (due, for example, to additive effects of dynamic seals 8 and 10 being in series and/or to chamber E being wider in directions perpendicular to the clamping pressure zone direction of travel than chamber D, which may result in the pressure developed in chamber E when chamber E is being directly compressed by the clamping pressure zone being lower than the pressure that is developed in chamber D by direct compression thereof by the clamping pressure zone). As a result, once chamber D is filled with fluid from, for example, chamber E, the flow of fluid into chamber D may stop, and the clamping pressure zone's continued movement to reference boundary "d" may proceed generally without additional fluid flow into chamber D (there may still be some additional flow into chamber D due to dynamic effects or other contributing factors, but the bulk of the fluid remaining in chamber E once chamber D is filled may remain in chamber E). When the clamping pressure zone is applied directly to chamber D, however, the resulting pressure that is developed in chamber D may cause the dynamic seal at location 8 to release, allowing the fluid contained therein to flow into chamber B. This allows the amount of fluid from chamber E or other chambers, such as chambers H and I, for example, that is delivered to chamber B to be metered, at least somewhat, prior to being introduced to chamber B in order to constrain the amount of such fluid that is ultimately delivered to chamber B. A similar effect may occur during movement of other fluids through the same flow path during later stages of fluidic operation as well.

Chamber E, at least a portion of which may be between reference boundaries "d" and "e," may contain a wash buffer. Chamber F, at least a portion of which may be located between reference boundaries "e" and "f," may be quite small, e.g., a small chamber that arises at the junction of two flow paths or passages. Chamber G, at least a portion of which may be positioned between reference boundaries "f" and "g," may serve as a secondary sequestration chamber that may be used to temporarily catch any wash fluid or fluid from chamber A that might potentially make its way down the fifth flow path towards chamber F. Chambers H and I, at least portions of which may lie between reference boundaries "g" and "h," may each contain a different component of a two-component substrate, e.g., a luminol substrate that may be produced by mixing together two different components (either component may be placed in either chamber). For example, one of chambers H and I may contain a stable peroxide solution and the other of chambers H and I may contain an enhanced luminol-based substrate solution; when the two solutions are mixed, they may produce a chemiluminescent indicator or marker substrate that may be used to determine an amount of the target substance during later analysis steps. Chamber J, at least a portion of which may lie between reference boundaries "h" and "I," may be configured such that any fluid that is introduced therein may, absent back pressure to hold it in, flow into chamber I. Chambers J and I, for example, may act similar to chambers B and A, respectively, of the fluidic circuit of FIG. 123, i.e., chambers J and I may form a fluidic sub-circuit that is configured to provide for mixing of the fluids flowed into chamber J from chamber I. Accordingly, chamber J, for example, may be configured such that chamber J collapses when back pressure that serves to push fluid into chamber J, e.g., from chamber I, is removed, thereby causing the fluid that is in chamber J to flow back into chamber I. Chamber J may, for example, be a relatively long and narrow-width chamber, e.g., a chamber having a serpentine shape. The maximum total volume of chamber J may, in some implementations, be greater than or equal to the anticipated combined total volume of fluids in chambers H and I prior to operation of the fluidic circuit, although in other implementations, the maximum total volume of chamber J may be less than this. At least a portion of chamber K may lie between reference boundaries "i" and "j"; chamber K may act as a temporary containment chamber for the indicator or marker substrate mixture after mixing operations are performed with chambers I and J, for example. Chamber K may generally have a maximum total volume that is greater than the combined total volume of fluid contained in chambers H and I, although in some implementations, chamber K may have a lower volume (in which case some of the substrate mixture produced from the fluids of chambers H and I may become trapped in chambers H/I/J during the subsequent fluidic operations discussed below).

In some implementations, all of chamber A may lie on the side of reference boundary "b" that faces towards reference boundary "a," all of chamber B may lie between reference boundaries "b" and "c," all of chamber C may lie on the side of reference boundary "c" that faces towards reference boundary "d," all of chamber D may lie in between reference boundaries "c" and "d," all of chamber E may lie between reference boundaries "d" and "e," all of chamber F may lie between reference boundaries "e" and "f," all of chamber G may lie between reference boundaries "f" and "g," all of chambers H and/or I may lie between reference boundaries "g" and "h," all of chamber J may lie between reference boundaries "h" and "i," and/or all of chamber "K" may lie between reference boundaries "i" and "j."

Chamber A may have a maximum total volume that is greater than or equal to the amount of wash buffer that is within chamber E prior to operation of the fluidic circuit, while chamber C may have a maximum total volume that is greater than or equal to the anticipated amount of fluid that will be in chamber A and then moved to and through chamber B.

Various flow paths may fluidically connect the various chambers of the fluidic circuit of FIG. 126A. For example, a first flow path may fluidically connect with chamber A on a side of reference boundary "b" that faces towards reference boundary "a" and with chamber B at a location in between reference boundaries "b" and "c." A second flow path may fluidically connect with chamber B at a location between reference boundaries "b" and "c" and with chamber C on a side of reference boundary "c" that faces towards reference boundary "d." A third flow path may fluidically connect with chamber B at a location between reference boundaries "b" and "c" and with chamber D at a location in between reference boundaries "c" and "d." A fourth flow path may fluidically connect with chamber D at a location in between reference boundaries "c" and "d" and with chamber E at a location in between reference boundaries "d" and "e." A fifth flow path may fluidically connect with chamber E at a location in between reference boundaries "d" and "e" and with chamber F at a location in between reference boundaries "e" and "f." A sixth flow path may fluidically connect with chamber F at a location in between reference boundaries "e" and "f" and with chamber G at a location in between reference boundaries "f" and "g." A seventh flow path may fluidically connect chambers H and I at locations in between reference boundaries "g" and "h," and an eighth flow path may fluidically connect with chamber I at a location in between reference boundaries "g" and "h" and with chamber J at a location in between reference boundaries "h" and "i." A ninth flow path may fluidically connect with chamber J at a location in between reference boundaries "h" and "i" and with chamber K at a location in between reference boundaries "i" and "j." A tenth flow path may fluidically connect with chamber K at a location in between reference boundaries "i" and "j" and with chamber F at a location in between reference boundaries "e" and "f."

Some fluidic connections of flow paths to chambers may be constrained to particular locations on such chambers. For example, the first, second, sixth, eighth, and ninth flow paths may fluidically connect with chambers A B, F, I, and J, respectively, at locations thereon that are close to, or as close as possible to, reference boundaries "b," "c," "f," "h," and "i," respectively. The tenth flow path may also fluidically connect with chamber F at a location thereon that is close to, or as close as possible to, reference boundary "f." Similarly, the first, third, fourth, fifth, sixth, and ninth flow paths may fluidically connect with chambers B, D, E, G, J, and K, respectively, at locations thereon that are close to, or as close as possible to, reference boundaries "b," "c," "d," "f," "h," and "i." Additionally, the fourth, fifth, eighth, and tenth flow paths may fluidically connect with chambers D, E, F, and K, respectively, at locations thereon that are close to, or as close as possible to, reference boundaries "c," "d," "e," and "i."

During operation of the depicted fluidic circuit, a clamping pressure zone may be moved from reference boundary "a" to reference boundary "b," thereby pressurizing the sample-containing fluid in chamber A to a release pressure of a dynamic seal on the first flow path at location 1. An optional temporary seal may also be provided along the first flow path, e.g., fluidically interposed between the dynamic seal at location 1 and chamber B, such as at location 3. Such an optional temporary seal may serve to provide an additional level of protection that may help provide storage and/or transport stability, e.g., by preventing contaminants from potentially entering the fluidic circuit via chamber A (which may, for example, be fluidically connected with an upstream breath sampling module or other mechanism for introducing a sample for analysis). Once the pressure in the fluid in chamber A has reached the release pressure for the dynamic seal at location 1, the dynamic seal may release (as well as the optional temporary seal at, for example, location 3) and allow the fluid in chamber A to be pushed into chamber B.

Once the fluid from chamber A is pushed into chamber B, the fluid may be allowed to incubate for a period of time in chamber B. As discussed above, chamber B, for example, may have one or more surfaces of interest (or contain objects with surfaces of interest). The surface(s) of interest, for example, may have the target substance that the assay is intended to test for immobilized thereupon. Thus, when the fluid from chamber A is flowed into chamber B, the remaining unbound antibody in that fluid may bind to the immobilized target substance in chamber B and become immobilized. The antibody that was previously bound to whatever amounts of the target substance were present in chamber A initially will remain bound to that target substance and will thus not bind to the immobilized target substance in chamber B. The amount of target substance that is immobilized on the surface or surfaces of interest within chamber B may be selected such that it is sufficient to bind to all of the antibody that may be in the fluid from chamber A, i.e., sufficient to bind all of the antibody that may be in the fluid from chamber A assuming that the fluid from chamber A does not contain any of the target substance.

Further advancement of the clamping pressure zone to reference boundary "c" may cause the sample-containing fluid, minus the unbound antibody that was in the fluid but has now been bound to the immobilized target substance, in chamber B from chamber A to flow into chamber C. A releasable seal on the second flow path, e.g., at location 4, may be designed to have a release pressure that is lower than a dynamic seal on the third flow path at location 7. Accordingly, when chamber B is pressurized, the resulting fluid flow may be shunted into chamber C when the releasable seal at location 4 releases before the dynamic seal at location 7. Once the fluid from chamber A has passed through chamber B and then into chamber C, the clamping pressure zone may be moved to location 6, where a live seal may be formed on the second channel so as to permanently seal chamber C. For example, a heater in a platen that supports the fluidic circuit during fluidic processing operations may be caused to apply heat to a localized area that corresponds with location 6 while the clamping pressure zone is applying pressure to location 6, thereby causing the second passage to be thermally bonded shut, sealing the fluid from chamber A therewithin.

The clamping pressure zone may then be caused to advance to reference boundary "d" and then caused to move back and forth between reference boundaries "b" and "d" one or more times so as to force any potential remaining fluid from chamber A, e.g., that may have potentially leaked into chamber D, to be moved back into chamber A. The pressure applied by the clamping pressure zone may cause, for example, whatever fluid remains in chambers B and D to be pressurized to a release pressure of a dynamic seal on the first flow path, e.g., at location 1, thereby allowing such fluid to be pushed into chamber A. The other dynamic seal on the first flow path, e.g., at location 1, may act to prevent the fluid that is reintroduced to chamber A from flowing back out into chamber B.

After chambers B and D have been purged of fluid from chamber A, the clamping pressure zone may then be moved to reference boundary "e" and then caused to move back and forth between reference boundaries "e" and "b" one or more times so as to perform repeated wash operations using the wash buffer in chamber E. For example, the wash buffer in chamber E may be pressurized by the clamping pressure zone to a pressure that exceeds a release pressure for a dynamic seal on the fourth flow path, e.g., at location 10. Another dynamic seal on the fifth flow path at location 12 may have a higher release pressure than the dynamic seal at location 10, thereby preventing the wash buffer from flowing through the fifth flow path responsive to such pressurization. In some implementations, the clamping pressure zone may not be caused to move to reference boundary "e" from reference boundary "b" directly, but to instead move to intermediate positions along chamber E, with the clamping pressure zone being moved to an intermediate position along chamber E that is closer to reference boundary "e" with each such reciprocal movement. Thus, for example, with each transit of chamber E by the clamping pressure zone, more and more of the fluid from chamber E may be caused to flow into chambers D, B, and A, thereby allowing for multiple wash steps to be performed. In other implementations, the release pressure of the dynamic seal at location 8 may be set such that the pressure developed in chamber E through direct application of the clamping pressure zone thereto is below the release pressure but the pressure developed in chamber D through direct application of the clamping pressure zone thereto is above the release pressure. Thus, when the clamping pressure zone moves from reference boundary "e" to reference boundary "c," the pressure applied to chamber E may cause the wash buffer in chamber E to flow into chamber D until chamber D is full, at which point the clamping pressure zone may transit the rest of chamber D without further (or without significant) movement of fluid from chamber E into chamber D due to the blocking effect of the dynamic seals at locations 8 and 9. Once the clamping pressure zone reaches chamber D, however, and is able to directly pressurize the fluid contained therein, the pressure in the fluid may increase so as to exceed the release pressure for the dynamic seal at location 8, thereby allowing the wash buffer in chamber D to flow into chamber B. This process may be repeated for each cycle of clamping pressure zone movement between reference boundaries "b" and "e."

The wash operation(s) may serve to wash fluid from chamber A that may remain in chambers D or B into chamber A. During such wash operations, any wash fluid that may potentially leak through the dynamic seal at location 12 may flow into chamber G, which may act as a leak catch basin to prevent such fluid from flowing into any of chambers H-K, for example.

An optional temporary seal may also be provided along the fourth flow path, e.g., fluidically interposed between chamber D and the dynamic seal positioned, for example, at location 10. Such an optional temporary seal may serve a similar purpose to the optional temporary seal that may be used on the first flow path, for example.

The wash buffer that is pushed through chambers D and B as the clamping pressure zone moves from reference boundary "e" to reference boundary "b" may serve to flush out remaining fluid from chamber A and carry it back into chamber A.

After the desired wash operations have been completed, the clamping pressure zone may be moved to reference boundary "g" and then reciprocated between reference boundaries "g" and "b," there by purging any remaining wash fluid and/or fluid from chamber A that may be present and pushing it into chamber A. The sixth flow path may be an open flow path or may have a dynamic seal at location 14 that has a release pressure that is lower than a release pressure of a releasable seal at location 16 that leads to the tenth flow path. Accordingly, any wash fluid that may be pushed ahead of the clamping pressure zone during movement from reference boundary "b" to reference boundary "g" may be pushed into chamber G instead of the tenth flow path (and may then be pushed from chamber G to chamber A by a subsequent purge cycle).

After chambers B, D, E, and F have been purged of wash fluid, the clamping pressure zone may be caused to move to reference boundary "g" again and to then be reciprocated between reference boundaries "g" and "h" repeatedly. In doing so, the clamping pressure zone may cause the fluid components in chambers H and I to be pressurized such that the release pressure or pressures of a releasable seal or releasable seals on the seventh and eighth flow paths are exceeded, thereby allowing the fluids in chambers H and I to repeatedly flow into, and then out of, chamber J. In some implementations, chambers H and I may, in effect, be a single large chamber that is divided into two smaller chambers by a wall that is a temporary seal-thus the temporary seals shown at locations 22 and 23 on the seventh flow path may both be provided by the same temporary seal, and the seventh flow path may, in effect, have a zero length (or a length equal to the thickness of the temporary seal).

After the fluid components in chambers H and I have been mixed through reciprocating the clamping pressure zone a desired number of times, the clamping pressure zone may be caused to move to reference boundary "j," thereby pressurizing the substrate mixture from chambers H and I to a pressure that exceeds the release pressure for a releasable seal at location 19 on the ninth flow path and allowing the substrate mixture to be moved into chamber K.

The clamping pressure zone may then be caused to move from reference boundary "j" to reference boundary "c," thereby pressurizing the substrate mixture in chamber K to cause the substrate mixture to flow through the tenth flow path to chamber F. A dynamic seal at location 18 may be provided so as to cause the pressurized substrate mixture in chamber K to flow through the tenth flow path rather than back through the ninth flow path when pressurized in chamber K.

The movement of the clamping pressure zone from reference boundary "j" to reference boundary "c" may push the substrate mixture through chambers F, E, and D and into chamber B, where the substrate may, for example, react with the immobilized antibody that is bound to the surface(s) of interest in chamber B, thereby producing luminescence that may be measured using an optical measurement device in order to obtain a measurement, based on the intensity of the luminescence, of the amount of antibody that is present within chamber B. The amount of antibody that is present may, in combination with the amount of antibody that was known to have been introduced into chamber A initially, allow for a determination to be made as to how much antibody was bound to the target substance that was in the fluid from chamber A (and was thus not immobilized in chamber B). This, in turn, may allow for a determination to be made as to the amount and/or concentration of target substance in the sample material from chamber A to be made.

As with other fluidic circuits described previously, the fluidic circuit of FIG. 126A may be modified in a number of ways without changing the underlying functionality that it provides.

For example, in some implementations, chamber G may be positioned so as to align with a cavity or recess on a platen of the analysis system against which the fluidic circuit may be pressed by the clamping pressure zone during fluidic operations, thereby limiting the amount of pressure that the clamping pressure zone is able to apply to the contents of chamber G. In such implementations, all of chamber G may lie on a side of reference boundary "f" that faces towards reference boundary "g." In such implementations, the reciprocations of the clamping pressure zone between reference boundaries "b" and "g" may instead be performed between reference boundaries "b" and "f," with the fluids that are purged from chambers B through F being directed into one or both of chambers A and G. In some such implementations, the sixth flow path may have a dynamic seal at location 15 that may be used to prevent backflow of such fluid out of chamber G into chamber F.

In some implementations, chambers H and/or I may be located in between reference boundaries "e" and "f" or "f" and "g"—although chamber I should not be located H should generally be located such that the end of chamber H that is closest to reference boundary "j" is further from reference boundary "j" than the end of chamber I that is closest to reference boundary "j" to ensure that the fluid in chamber H can be fully transferred to chamber I through movement of the clamping pressure zone. Additionally, the seventh flow path may be positioned so as to fluidically connect with chambers H and I In some implementations, the releasable seal shown at location 5 on the second flow path may be omitted, with the second flow path being an open flow path where it fluidically connects with chamber C. In some implementations in which a dynamic seal is used at location 5 instead, the dynamic seal may have a release pressure that exceeds the pressure that the clamping pressure zone is able to generate within the fluid that will eventually be contained in chamber C.

In some implementations, the dynamic seal at location 8 along the third flow path may be omitted, leaving the third flow path to be an open flow path where it fluidically connects with chamber D. Such implementations may be used when metering capabilities for chamber D are not desired.

In some implementations, one or more of locations 13-15, 17, or 20 may, instead of having open flow paths at those locations, have releasable seals, e.g., dynamic or temporary seals. In such implementations, the release pressures of such releasable seals may be selected to as to not exceed the release pressures for any of the releasable, temporary, or dynamic seals shown in FIG. 126A at other locations. Additionally, if location 20 is provided with a releasable seal, the release pressure for that releasable seal may be selected so as to not exceed the back pressure that chamber J naturally applies to fluid contained within it. Conversely, in some implementations, the eighth flow path may, instead of a releasable seal at location 21, be an open flow path where it fluidically connects with chamber I.

In some implementations, as noted above, temporary seals may optionally be provided on some flow paths to provide stability that may prevent degradation of the fluidic circuit during long-term storage or transport. Temporary seals that may be used for similar purposes may also be provided as the releasable seals at one or more of locations 21-23, if desired.

In some implementations, the releasable seal at location 5 on the second flow path may be a dynamic seal with a release pressure that exceeds the pressure that the clamping pressure zone may exert on the fluids that are ultimately flowed into chamber C. In such an implementation, the releasable seal at location 4 may be a dynamic seal with a release pressure that is higher than that of the dynamic seal at location 2 such that wash buffer that is flowed into chamber B from chamber E via chamber D is caused to flow into chamber A instead of chamber C. In an alternative such implementation, chamber C may be sized such that the maximum total volume of chamber C is greater than or equal to the combined volume of wash buffer in chamber E prior to operation of the fluidic circuit and the anticipated volume of fluid that will be in chamber A prior to operation of the fluidic circuit; in such an alternative implementation, the releasable seal at location 4 may be either a temporary seal or a dynamic seal. In some further implementations, chambers C and A may be sized so as to have a combined total maximum volume that is greater than or equal to the anticipated combined total volume of fluids that will be contained in chambers A and E prior to operation of the depicted fluidic circuit. In such implementations, fluid from chamber E that flows through chamber B may flow into either chamber A or chamber C when forced from chamber B. However, when either chamber A or chamber C reaches maximum capacity, the remaining flow may naturally divert to the other of chambers A and C. Each of the above options may allow for chamber B to be exposed to the fluid in chamber A and then be washed clear of such fluid in a subsequent wash step using the wash buffer from chamber E.

In some other implementations, the third flow path between chambers B and D may instead span between chambers C and D such that chamber C is fluidically interposed between chambers B and D. In such implementations, the releasable seal at location 4 on the second flow path may be a dynamic seal so as to allow excess fluid from chamber A that is flowed into chamber B to escape into chamber C temporarily.

In yet some other implementations, chamber C and the second flow path may be omitted entirely. In such implementations, chamber D may be sized to have a maximum total volume that is greater than or equal to the anticipated volume of fluid that will be in chamber A prior to operation of the fluidic circuit such that the fluid from chamber A may be pushed into chamber D via chamber B. Due to such chamber sizing, the fluid that is forced into chamber D via the third flow path may be retained within chamber D by the dynamic seal at location 9. Moreover, when chamber D is pressurized directly by the clamping pressure zone, the placement of the locations where the third and fourth flow paths fluidically connect with chamber D may act to prevent the fluid in chamber D from being pushed down either flow path as the clamping pressure zone advances towards from the reference boundary "c" to reference boundary "d." When the clamping pressure zone direction of travel is then reversed, the resulting fluid flow may be through the third flow path, as the dynamic seal at location 9 may prevent such fluid flow from proceeding down the fourth flow path. In some other such implementations, the dynamic seal provided at location 7 may have a release pressure that is set such that direct application of the clamping pressure zone to chamber B produces causes the fluid pressure within chamber B to exceed the release pressure while direct application of the clamping pressure zone to chamber A does not cause the release pressure to be exceeded. The dynamic seal at location 7 has a higher release pressure than the dynamic seal at location 2 in this example.

In some implementations, an additional chamber, which may be smaller in size compared to chambers A and B, may be fluidically interposed between chambers A and B along the first flow path. The additional chamber may have relatively low-release-pressure dynamic seals at the locations where it fluidically connects with the first flow path and may, through such dynamic seals, provide a bubble-trapping function. In other implementations, a bubble trap such as that shown in FIG. 119 may be used in such a location, e.g., with two chambers connected by multiple flow paths with dynamic seals.

It will be understood the various purge operations performed above, which are described as involving multiple repeated cycles of clamping pressure zone movement may, in some implementations, be accomplished with only a single such clamping pressure zone movement. For example, one or more of the reciprocal motions of the clamping pressure zone between reference boundaries "b" and "d," "b" and "e," and/or "b" and "g," may be replaced by a single such motion.

It will also be understood that the clamping pressure zone may, at the conclusion of the above operations, be moved to any location in between, and inclusive of, the reference boundaries "c" through "j" if needed, e.g., to move the mechanism that provides the clamping pressure zone so as to be out of the way of chamber B in order to facilitate optical measurement of the contents of chamber B.

FIG. 126A' depicts a diagram of an example fluidic circuit that is generally configured to be consistent with the guidance provided by FIG. 126A. The equivalent chambers, flow paths, and seal locations have been indicated with letter callouts, circled number callouts, and non-circled number callouts. Such a fluidic circuit may, for example, be formed between two sheets of flexible, inelastic material, such as mylar, that have been thermally bonded together to form permanent seals along the solid outlines of FIG. 126A. The depicted fluidic circuit also includes load ports to allow the various fluids that may be contained within some chambers prior to fluidic operation to be loaded into the fluidic circuit after the thermal bonding process is complete.

FIG. 126B depicts a fluidic circuit that builds on the fluidic circuit of FIG. 126A; the depicted example may be used to provide an assay for THC, but it will be understood that it may be adapted to perform assays for other substances as well. Whereas the fluidic circuit of FIG. 126A is designed to receive a pre-mixed liquid solution of sample, antibodies, and surfactant, the fluidic circuit of FIG. 126A incorporates additional fluidic elements prior to chamber A that allow the depicted fluidic circuit to receive a sample and then cause the sample to be mixed with a lyophilized antibody that may be included within one of the additional chambers. Due to the size of the depicted diagram, the fluidic circuit has been split into two halves that are shown side-by-side, with one of the flow paths being shown in broken form, with each break represented by a wavy line; this wavy line is not to be confused with a live seal.

The depicted fluidic circuit of FIG. 126B is identical in construction to the fluidic circuit of FIG. 126A in between reference boundaries "a" and "j." Accordingly, the discussion above with regard to the fluidic circuit of FIG. 126A and its variants is equally applicable to the fluidic circuit of FIG. 126B.

The fluidic circuit of FIG. 126B includes additional chambers L-N. At least a portion of chamber N may be located between reference boundary "a" and reference boundary "l", while at least portions of chambers M and L may be located on a side of reference boundary "l" that faces towards reference boundary "k." In some implementations, all of chambers L and/or M may be located on the side of reference boundary "l" that faces towards reference boundary "k" and/or all of chamber N may lie in between reference boundaries "l" and "a." One of chambers L and M, for example, may contain a quantity of lyophilized antibody, while the other of chambers L and M may contain a quantity of elution fluid (or eluent). Chamber L may serve as a mixing chamber that may be used to more thoroughly mix the eluent and lyophilized antibody from chambers L and M. In some such implementations, the lyophilized antibody may be located proximate to or as close to the releasable seal at location 27.

Chambers L and M may be fluidically connected by an eleventh flow path that fluidically connects with locations on chambers L and M that lie on the side of the reference boundary "l" that faces towards reference boundary "k." A twelfth flow path may fluidically connect with chamber M at a location on chamber M that lies on the side of the reference boundary "l" that faces towards reference boundary "k" and with chamber N at a location in between reference boundaries "l" and "a." A thirteenth flow path may fluidically connect with chamber N at a location in between reference boundaries "l" and "a" and with chamber A at a location in between reference boundaries "a" and "b."

During operation of the fluidic circuit depicted in FIG. 126B, the clamping pressure zone may, instead of starting at reference boundary "a," start at reference boundary "k." The clamping pressure zone may initially move between reference boundaries "k" and "l" multiple times, thereby pressurizing the eluent that is in either chamber M or chamber L and causing the pressurized fluid to cause the releasable seal(s) at location(s) 29 and/or 28 to release (as with chambers H and I, chambers M and L may, for example, be provided in some implementations by a common chamber that is divided into two sub-chambers that are separated by a partition wall that is a temporary seal). This may allow the eluent and the lyophilized antibody in chambers L and M to mix, thereby allowing the eluent to dissolve/reconstitute the lyophilized antibody, and cause the eluent/antibody mixture to be moved into chamber N, e.g., by pressurizing the fluid to a release pressure of a releasable seal located on the twelfth flow path at location 27, for example.

Chamber N, for example, may be configured such that chamber N collapses when back pressure that serves to push fluid into chamber N, e.g., from chambers M and L, is removed, thereby causing the fluid that is in chamber N to flow back into chamber M. Chamber N may, for example, be a relatively long and narrow-width chamber, e.g., a chamber having a serpentine shape. Thus, each time the clamping pressure zone moves to reference boundary "l" and then back to reference boundary "k," the antibody/eluent mixture may be pushed into chamber N and then allowed to drain back out into chamber M. Such repeated movement may allow for more thorough mixing of the eluent and the antibody, thereby increasing the homogeneity of the resulting mixture.

Once a desired number of reciprocal movements of the clamping pressure zone between reference boundaries "k" and "l" have been performed, the clamping pressure zone may be caused to advance to reference boundary "a," thereby causing the fluid that is pushed into chamber N to be pressurized to a release pressure for a releasable seal at location 24 on the thirteenth flow path, thereby allowing the fluid to be pushed into chamber A.

In some such implementations, chamber A may contain the sample to be assayed. For example, chamber A may incorporate a breath collection module (BCM), e.g., capture media, and may include a plurality of interfaces that may be connected with equipment that allows a breath sample to be flowed therethrough, thereby allowing breath constituents that are present in the breath to be adsorbed onto the capture media and then eluted by the eluent/antibody mixture that is later flowed into chamber A (the interfaces that allow breath to flow therethrough may be sealed after the sample is collected). In some other implementations, an additional chamber may be fluidically interposed between chambers N and A and capture media for a BCM may be placed within the additional chamber such that the eluent/antibody mixture passes through the additional chamber on its way to chamber A, thereby eluting any breath constituents that may be absorbed onto the capture media and conveying them to chamber A. In such an implementation, the clamping pressure zone may be caused to pause—at an additional reference boundary that may be present between the additional chamber and chamber N-after traversing chamber N so as to allow the eluent/antibody mixture additional time in which to elute the breath constituents before moving on to chamber A.

In some implementations, the releasable seals at locations 27-29 may be configured so as to be temporary seals. Such implementations may provide for long-term stability of the fluidic circuit and may protect against accidental leakage, evaporative effects, and/or contamination. The releasable seal at location 24 may, in some implementations, be omitted, leaving location 24 to be an open flow path or channel. In other implementations, the releasable seal at location 24 may be a dynamic seal. In some such implementations, the releasable seal at location 24 may be a dynamic seal with a release pressure that is high enough that only direct application of pressure by the clamping pressure zone on chamber N may provide sufficient pressure to cause it to release.

The fluidic circuit of FIG. 126B may also be implemented without chambers M, L, and N, e.g., if no lyophilized antibody is needed for a particular assay. In such implementations, a single chamber may be provided that includes an eluent that may be pushed into chamber O in order to elute a sample that may be provided via chamber O.

FIG. 126C, which spans two sheets (showing FIG. 126C-1 and FIG. 126C-2), depicts a diagram of a fluidic circuit that is based on the fluidic circuit of FIG. 126B but modified so as to allow for two separate analyses on two separate samples to be performed in parallel. As such, two nearly identical and separate instances of the fluidic circuit of FIG. 126B are depicted, although there are some elements of each fluidic circuit that are shared between the two fluidic circuit instances, as discussed below. The depicted fluidic circuit may be used to perform assays, e.g., THC assays, on two different samples, e.g., a sample collected from exhaled breath from a test subject and a sample collected from ambient atmospheric air in the vicinity of where the breath sample was collected. Such a sampling paradigm may allow for the assay of the breath sample to be adjusted in order to compensate for amounts of the target substance that may be present in the ambient atmosphere, i.e., not actually produced by the subject. It will be understood that additional fluidic circuit instances similar may be added in a similar manner to provide for positive and/or negative controls that may be used to further fine-tune the assay results that may be obtained using the test subject sample.

It will also be understood that the fluidic circuits for performing assays discussed herein may also be used to perform assays on samples collected through other mechanisms, e.g., blood samples, urine samples, stool samples, saliva samples, sweat samples, vaginal samples, etc.

In FIG. 126C, the only new features that are depicted (aside from the inclusion of two parallel assay fluidic circuits) are chambers O, P, and Q. It will be understood that some of the flow paths have been relabeled, e.g., the thirteenth flow path no longer fluidically connects between chambers N and A, but instead fluidically connects between chambers N and O.

Chambers O, at least portions of which may lie between reference boundaries "m" and "a," may each be fluidically interposed between respective chambers N and A. Chambers O may, for example, be chambers that may contain a capture media for a breath collection module, as discussed above with respect to the fluidic circuit of FIG. 126B.

Chambers P, at least portions of which may lie between reference boundaries "n" and "b," may each be fluidically interposed between respective chambers A and B. Chambers P may, for example, be chambers (or multiple chambers) that may be used for bubble removal, e.g., such as are described above with respect to the fluidic circuit of FIG. 126A. Chambers P may, for example, each have a maximum total volume that is significantly smaller than the anticipated volume of fluid that will be in chamber A prior to the contents thereof being transferred through chamber P.

Chambers Q, at least portions of which may lie on a side of reference boundary "g" that faces towards reference boundary "h," may serve as metering chambers that allow fluid from chamber K (which may be the substrate mixture) to be flowed from chamber K to chambers Q via connection points 17 in a more or less evenly distributed manner. By having connection points 17 and 34 be non-sealed, the substrate mixture may be flowed into separate flow paths prior to significant pressurization. Thus, when the clamping pressure zone moves from, for example, reference boundary "h" to reference boundary "g" and pressurizes chambers Q, both chambers Q will have generally equal amounts of the substrate mixture that may then be driven on to their respective chambers F. In contrast, if locations 17 instead featured releasable seals, it would be most likely that one would release before the other, thus causing the fluid within to travel down only one of the two flow paths to a chamber Q. In some implementations, the flow paths to chambers Q may meet to form a single, common flow path prior to reaching chamber K. It will be appreciated that additional fluidic circuits may be provided in parallel with the two depicted fluidic circuits, with an additional chamber Q fluidically connected with chamber K provided for each such fluidic circuit.

Chambers H-K in the depicted fluidic circuit are not replicated, but are shared between both fluidic sub-circuits shown. This may ensure that each assay circuit receives an identical substrate mixture, thereby reducing the chances of measurement errors between assays due to different substrate mixtures potentially being used.

Due to the size of the depicted diagram, the fluidic circuit has been split into two halves that are shown on separate pages with two of the flow paths being shown in broken form, with each break represented by a wavy or double-wavy line; these wavy lines are not to be confused with live seals.

During fluidic operation, the fluidic circuit of FIG. 126C may be subjected to similar clamping pressure zone movements to those discussed previously with respect to FIG. 126B, although with some modification. For example, instead of the clamping pressure zone transiting from chambers N to A directly, it may pass over chambers O on its way from chambers N to A. Similarly, instead of the clamping pressure zone transiting from chambers A to B directly, it may pass over chambers P on its way from chambers A to B. If additional fluidic circuit instances are provided, e.g., for positive and/or negative controls, then the chambers O in those additional instances may be sealed (as opposed to having interfaces that may allow them to be interfaced with a breath collector module) and may contain positive or negative control amounts of the target substance.

FIG. 126D, which spans two sheets (showing FIG. 126D-1 and FIG. 126D-2), depicts a fluidic circuit that is similar to that of FIG. 126C (and which is similarly split into two separate pages due to its size). A large sub-portion of the fluidic circuit of FIG. 126D, e.g., a sub-portion similar to that of FIG. 126C, is replicated, in parallel, so as to provide two generally identical fluidic sub-circuits that span between the reference boundaries "k" and "g" and which then merge with another, common fluidic sub-circuit between reference boundaries "g" and "j." The fluidic circuit of FIG. 126D may, for example, be used to perform an assay, e.g., a THC assay-similar to the examples discussed above. Thus, for example, chambers M and L may respectively contain a lyophilized THC-specific antibody that is conjugated to horseradish peroxidase (HRP) and an eluent, e.g., a buffer that may be combined with the lyophilized antibody in order to reconstitute it and provide a liquid carrier for the reconstituted antibody, chamber E may contain a quantity of wash liquid, e.g., a buffer, and chambers H and I may contain reactants that are stable when separately stored but which, when mixed together, form an unstable indicator compound, such as luminol, that has a limited lifespan. Chambers O may initially be empty of fluid but may be configured to receive a sample to be analyzed. For example, chambers O may include a capture medium and may be configured so as to be able to have a breath sample flowed therethrough. Later sections of this disclosure provide several examples of chambers that may be used for such purposes. Alternatively, chambers O may be configured to receive a liquid sample, such as urine, blood, fecal matter suspended in solution, mucus samples, etc. Prior to operation of the fluidic circuit of FIG. 126D, chambers O may be sealed such that the contents within chambers O, as well as fluids that are later pushed into chambers O, cannot leak out. The remaining chambers that are shown may initially be empty of fluids.

During operation, a clamping pressure zone may be moved from the reference boundary "k" to the reference boundary "l" in order to pressurize the contents of chambers L and/or M, thereby causing any fluid contained in either chamber L or M to pressurize to a pressure that exceeds a release pressure for the releasable seals at locations 28 and 29, thereby allowing the contents of chambers L and M to mix. The clamping pressure zone may then be advanced to reference boundary "m" and then returned to reference boundary "l" to cause the fluid mixture in chamber M to flow into chamber N and then flow back into chamber M. This process may optionally be repeated one or more times, with each repetition serving to more thoroughly mix the antibody and eluent. Once a desired number of mixing operations have been performed, the clamping pressure zone may be advanced to reference boundary "m" to push the fluid mixture into chamber O, which may, as noted above, contain a sample to be analyzed. If the depicted fluidic circuit is used to analyze a breath sample, for example, one of chambers O may be used to collect a breath sample from a subject while the other of chambers O may, in some cases, be used to collect an ambient air sample, e.g., by using a pump to draw ambient air through the capture medium that may be located within chambers O. The liquid mixture that is forced into the chambers O may then be allowed to rest within the chambers O for a desired period of time, e.g., an incubation time period with a duration that is selected to allow for any of the target substance, e.g., THC or an associated compound, that may be in the sample to bind with the antibody that is in the mixture.

After the sample material and the antibody mixture have been allowed to incubate for the desired time period, the clamping pressure zone may be further advanced to reference boundary "o" and then to reference boundary "b" to push the liquid mixture into chambers B, which may have surfaces of interest to which the unbound antibodies are specific to. In doing so, the fluids may be pushed through chambers Y, X, A, and P, which may serve various purposes. For example, chambers A may be relatively large and may later be used to store waste fluids, i.e., fluids that are no longer needed to perform the assay. Chambers Y, X, and P may, for example, be relatively small-volume chambers (as compared with chambers A) that are used as bubble traps to help remove bubbles that may be present within the fluid that is moved from chambers O to chambers B.

After the fluid mixtures that are moved to chambers B are allowed to incubate in chambers B for desired periods of time, the clamping pressure zone may be caused to move to reference boundary "c" to cause the fluid that is in chambers B to first flow into chambers C, which may then be caused to be heat-sealed by applying the clamping pressure zone to location 6 while heat is applied to the fluidic structure in that same location, e.g., via a heater. Chamber C, for example, may be used to store a sub-portion of the collected sample which may subsequently be analyzed separately, e.g., in a lab using a separate analysis system.

Once the portion of the sample has been sequestered in chamber C and sealed therein, the clamping pressure zone may continue on to reference boundary "d." It will be noted that there are multiple reference zones "c" showing, including "c'" and "c"." The extra reference zones "c" may, for example, be used if multiple fluidic structures are processed simultaneously. For example, if the fluidic circuit of the fluidic structure is defined between two sheets of flexible yet inelastic material, e.g., such as Mylar, multiple such fluidic structures may be stacked on top of one another and simultaneously subjected to the clamping pressure zone. In such an implementation, the clamping pressure zone may apply clamping pressure to all of the fluidic structures, and the fluidic circuits and fluids housed therein, simultaneously. If the fluidic circuits in each fluidic structure are the same, or generally the same, then such an arrangement may allow for multiple such fluidic circuits to be operated in unison.

Figure 126E:
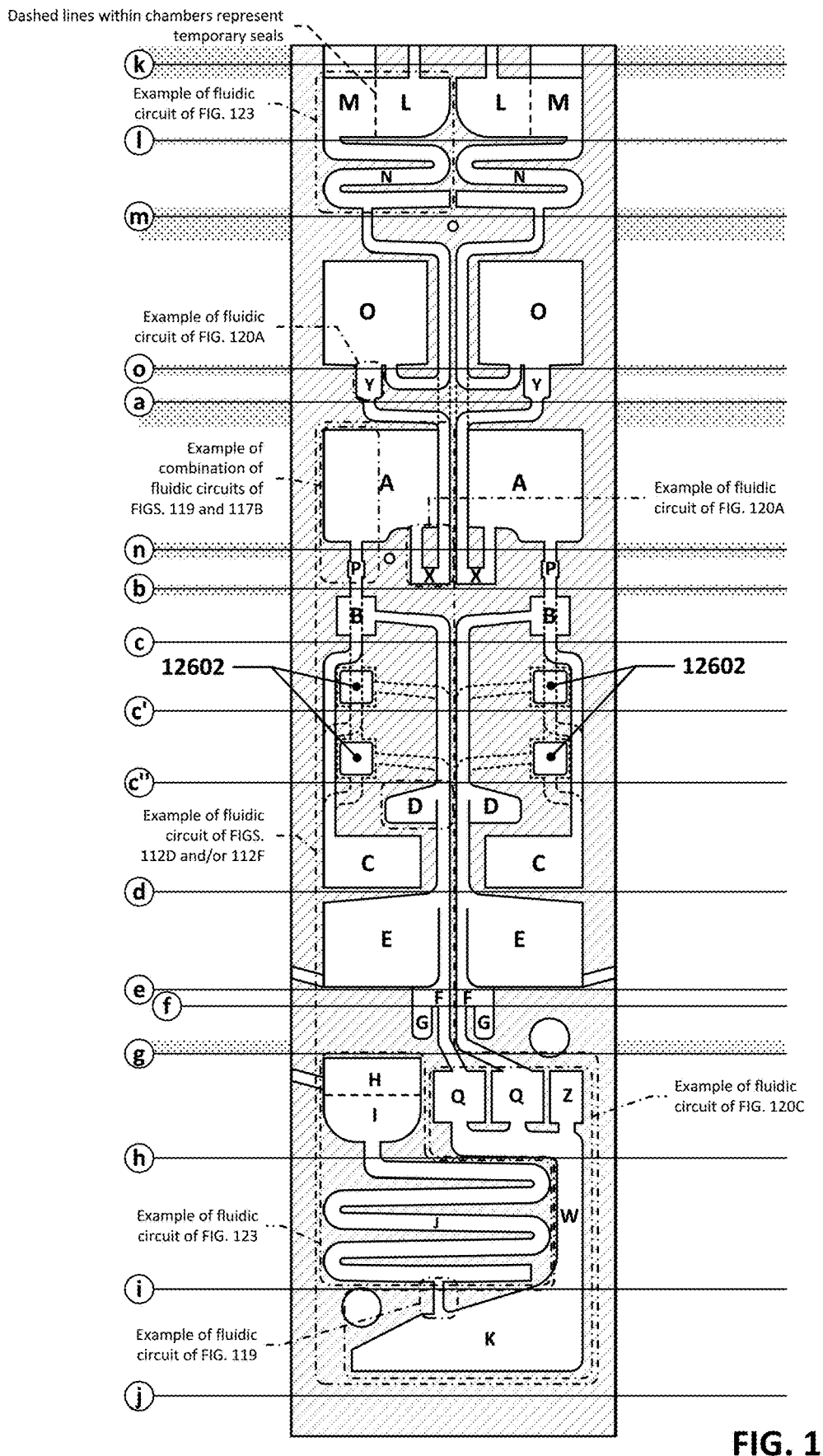
Figure 126F:
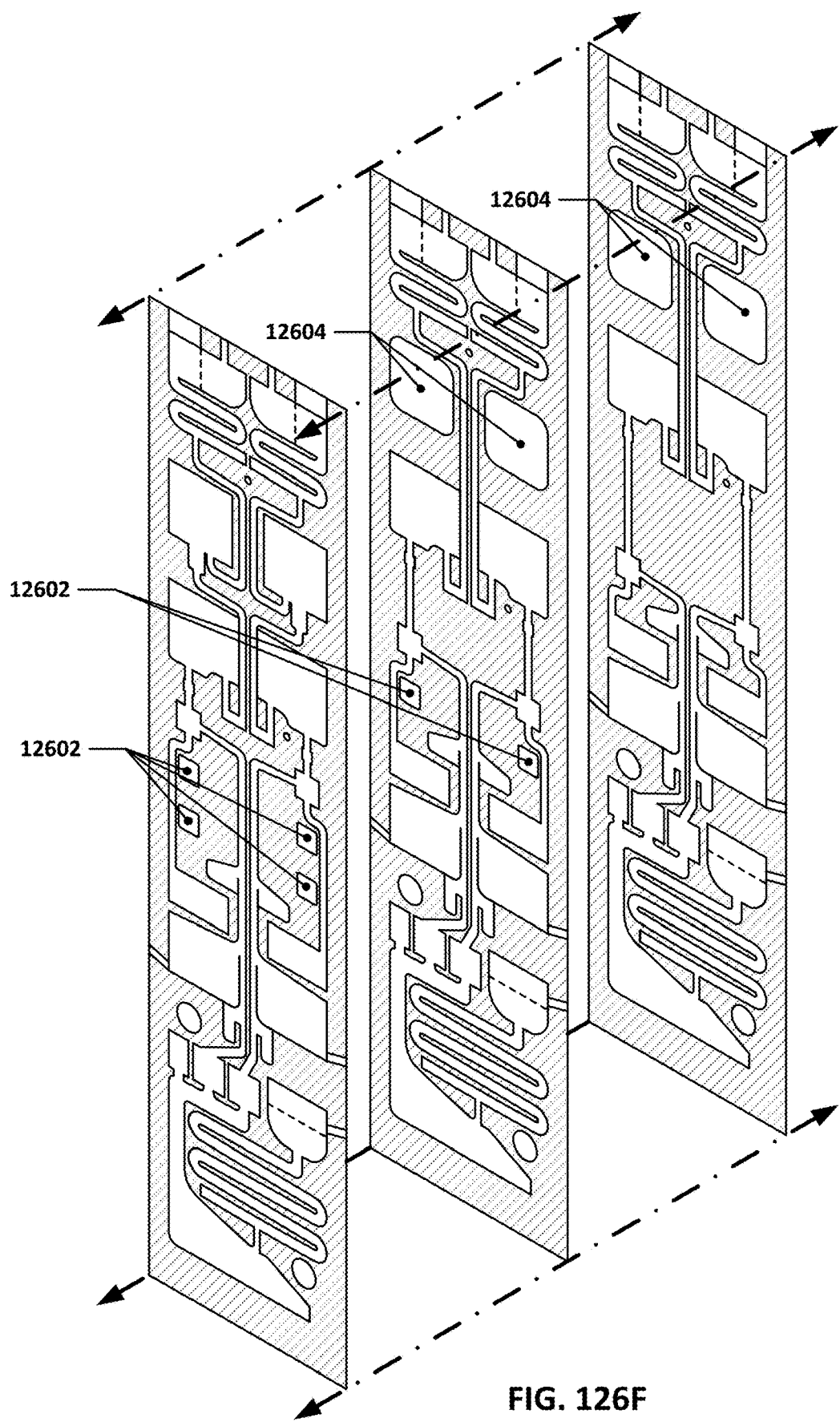

FIGS. 126E and 126F may illustrate this concept more clearly. FIG. 126E depicts an example fluidic structure (the crosshatched material) with a fluidic circuit defined therein. The solid black lines bounding the white areas generally correspond to permanent seals between the two portions of material, while the three dashed lines between chambers L and M and chambers H and I represent temporary seals. The chambers depicted in FIG. 126E may be assumed to contain substances similar to the substances discussed above with similarly labeled chambers with respect to the fluidic structure of FIG. 126D unless otherwise indicated. As can be seen, the two sub-portions of the fluidic circuit between reference boundary "k" and reference boundary "g" are mirror images of each other. However, the sub-portion of the fluidic circuit between reference boundary "g" and reference boundary "j" is fluidically connected with both of the sub-portions mentioned above. As can be seen in FIG. 126E, there are dotted outlines depicting additional chambers B that may be located on additional fluidic structures that are located behind the depicted fluidic structure, e.g., in a layered configuration. The fluidic circuits of the additional fluidic structures may be identical to that depicted in FIG. 126E except in certain limited respects. For example, the chambers B in each other fluidic structure may be located in a different location such that none of the chambers B overlap one another when the fluidic structures are otherwise aligned and in the stacked configuration (thus, the clamping pressure zone may need to be moved to a different reference boundary "c" for each of the three sets of chambers B depicted). Another difference in the fluidic circuits of the other fluidic structures is that chambers O and Y may simply be omitted, with chambers N being directly connected with chambers X via flow paths that travel down the middle of the fluidic structure (as indicated by the dotted lines that cross reference boundary "a").

FIG. 126F shows an isometric view of such a stacked arrangement of fluidic structures, but with the fluidic structures spaced apart for easier viewing—in practice, all three fluidic structures of FIG. 126F would be placed proximate to one another. The similarities and differences of the three fluidic structures is readily apparent in FIG. 126F. Other notable features visible in FIG. 126F are various cutouts, e.g., such as optical cutouts 12602 and breath capture module cutouts 12604. Each optical cutout 12602 may be positioned so as to align with one of the chambers B in one of the other fluidic structures. For example, the front-most fluidic structure in FIG. 126F has four optical cutouts, each of which aligns with a different one of the four chambers B in the other two fluidic structures when the fluidic structures are aligned and stacked together. Similarly, the middle fluidic structure has two optical cutouts that align with the chambers B in the rear-most fluidic structure when the fluidic structures are arranged in an aligned stacked configuration. Thus, when the stacked arrangement of fluidic structures is viewed such that the left-most fluidic structure of FIG. 126F is closest to the viewer, the optical cutouts 12602 provide direct line-of-sight to each of the six chambers B (the material of the fluidic structures may, for example, include a transparent material, e.g., transparent Mylar, on the side of the fluidic structure facing towards the viewer in FIG. 126F, and an opaque and/or reflective material, e.g., metallized Mylar, on the other. Such an arrangement may allow for each chamber B, and the contents thereof, to be optically interrogated during performance of an assay in order to determine, for example, an amount of fluorescence or luminescence that may be exhibited by the contents thereof, thereby indicating, either directly or indirectly, an amount of the target substance that was present within that sub-portion of the fluidic circuits. The optical cutouts 12602 may also optionally simply be optically transparent regions, e.g., windows, of each corresponding fluidic structure.

The breath capture module cutouts 12604 in the two rear-most fluidic structures in FIG. 126F may be provided to allow for physical access to both sides of the front-most fluidic structure in FIG. 126F, thereby allowing, for example, fluid (breath or air) to be flowed through the chambers O in directions perpendicular to the fluidic structures (such techniques are, as mentioned above, discussed later herein). It will be understood that in some examples of a multi-layer fluidic circuit stack such as that shown in FIG. 126F that are designed to collect breath samples in-situ, the portion of each of the fluidic structures that overlaps with a breath sample collection chamber (or breath collection module) of another fluidic structure may be omitted or configured to be able to be moved so as to not overlay that breath sample collection chamber during breath sample collection. For example, in the depicted configuration, the chambers O that are located on the front-most fluidic structure could instead be located on the middle or rear-most fluidic structure, and the other two remaining fluidic structures would include the corresponding breath capture module cutouts 12604. Alternatively, one of the chambers O may be located in one fluidic structure, while the other of chambers O may be located in another fluidic structure. In such an implementation, the fluidic structure without a chamber O would include two breath capture module cutouts 12604, and the other two fluidic structures would each include one breath capture module cutout 12604.

Such a stacked arrangement allows all of the fluidic structures, and the fluidic circuits contained therein, to be subjected to the same clamping pressure movements, thereby resulting in generally consistent fluidic movement within each of the three fluidic structures and reducing the potential for variation in the data provided by each fluidic circuit due to each fluidic circuit potentially being operated in a different manner.

The stacked arrangement of fluidic structures of FIG. 126F may, for example, allow for the simultaneous collection of a breath sample and an ambient air sample in the chambers O of the front-most fluidic structure, while the middle and rear fluidic structures may, for example, each contain two different control amounts of the target substance. When such an implementation is operated, a total of six samples (one from the subject, one from ambient, and four with control amounts) may be provided to the different chambers B and then evaluated, e.g., to detect an amount of luminescence that is indicative of the amount of the target substance (or equivalent thereof), e.g., THC, that was present within each corresponding fluidic circuit sub-portion. The use of four control amounts may allow for multiple control measurements to be obtained that may be used to produce a calibration curve (two control amounts could be used as well, but may not prove to be sufficient to accurately calibrate the assay since the calibration curve may be non-linear-however, no-control and dual-control implementations are nonetheless considered to be within the scope of this disclosure).

Returning to FIG. 126E, as the clamping pressure zone moves to reference boundary "c" and causes chambers C to fill with fluid from chamber B, once each chamber C is full, the remaining fluid from the chambers B may be pushed into chambers D, which may temporarily hold the fluid as the clamping pressure zone traverses chambers D to reach reference boundary "d." The clamping pressure zone may then be caused to return to reference boundary "b" (or "n") to then push the fluid in chambers D back through chambers B and into chambers A, which may act as waste reservoirs. The fluid that is contained in the chambers C, however, may not be moved by such clamping pressure zone movement due to the permanent seals that were placed at locations 6 previously. If desired, the clamping pressure zone may be moved between reference boundaries "d" and "b" (or "n") one or more times to perform multiple purging passes to increase the amount of the fluid that may be delivered to chambers A and more thoroughly empty chambers B and the flow paths between chambers B and chambers D of fluid.

The clamping pressure zone may then be moved to reference boundary "e" and then back to reference boundaries "b" or "n" to push fluid from chambers E, e.g., a wash fluid or buffer, through chambers D and B (and P) to chambers A, thereby washing chambers B and further causing any fluid from chambers O that may remain in chambers B to move to chambers A. One or more repetitions of such clamping pressure zone movement may be performed to further reduce the amount of any of the fluid from chambers O that may remain within the chambers B, if desired.

The clamping pressure zone may then be moved to reference boundary "g" and then back to reference boundaries "b" or "n" to push any fluid from chambers E, e.g., a wash fluid or buffer, that may remain in chambers B-G into chambers A (chambers F may, as discussed with respect to other examples, be a low- or zero-volume chamber, e.g., a T-intersection, and chambers G may act as catch basins for small amounts of fluid that may leak past the various dynamic seals depicted), thereby purging such chambers more thoroughly. One or more repetitions of such clamping pressure zone movement may be performed to further reduce the amount of any of the fluid from chambers E that may remain within the chambers B, if desired.

The clamping pressure zone may then move to reference boundary "h" in order to pressurize the fluids contained within chambers H and I such that a release pressure of the releasable seal(s) that separate chambers H and I is exceeded, thereby causing such a seal or seals to release and allow the fluids in chambers H and I to mix. The clamping pressure zone may then optionally be caused to move back and forth between reference boundaries "h" and "g" so as to more thoroughly mix the fluids from chambers H and I before being caused to move to reference boundary "j," thereby driving the fluid mixture (e.g., luminol) from chambers H and I through chamber J, which may cause additional mixing of the fluid mixture, and into chamber K. The clamping pressure zone may then be caused to move to reference boundary "c" to push the fluid mixture from chamber K into chamber W. The connection of the tenth flow path with chamber K may be unrestricted, as shown, or may be a releasable seal. The fluidic connections between chamber W and chambers Q and Z may be configured such that the fluid flowed from chamber W towards chambers Q and Z first flows into chamber Z, which may act as a bubble trap, before flowing into chambers Q. For example, the flow path to chamber Z may include a releasable seal that has a release pressure that is lower than that of the flow paths to chambers Q. Alternatively, such flow paths may not be sealed, but the flow resistance through the flow paths to chambers Q may be higher than that of the flow path to chamber Z. In particular, if the fluidic structure is oriented as shown, e.g., with reference boundary "j" being below reference boundary "a," then bubbles that are contained within chamber K may naturally tend to be the first fluids that are transported towards chambers Q and Z and will thus be sequestered within chamber Z instead of being passed on to chambers Q.

As the clamping pressure zone continues to move towards reference boundary "c," the fluid that is provided to chambers Q may eventually be forced into chambers B, where it may react with, for example, the antibodies that are immobilized within the chambers B, thereby providing a visual indicator that has an intensity that is indicative of the amount of the antibody that is present (and thus indicate, either directly or indirectly, the amount or concentration of target substance that was present in that part of the fluidic circuit). The intensity of the visual indicator may, for example, be measured using an optical measurement sensor, e.g., an imaging sensor, photocell(s), or other suitable sensing system.

It will be understood that the fluidic circuit of FIG. 126D may be implemented in a number of ways. For example, the fluidic connections of the fifteenth flow paths with chambers X, e.g., at locations 36, may, in some implementations, omit the indicated releasable seals. Similarly, the releasable seals at locations 38 may also, in some implementations, be omitted. In some implementations, the releasable seals at locations 37 may be dynamic seals; if temporary seals are used instead, configuring such temporary seals to have characteristics of a dynamic seal may increase the effectiveness of such a fluidic connection in trapping bubbles that may exist in the fluid flow.

FIG. 126E, in addition to depicting an example of a fluidic circuit such as that shown in FIG. 126D, also includes additional information. For example, as mentioned earlier, each reference boundary may, in effect, constitute a zone of locations-any one of which may serve as the reference boundary in question. Moreover, if the clamping pressure zone is described as being moved to any particular reference boundary more than once for a given fluidic circuit, it is to be understood that such movement may involve moving to one location within such a zone and then later moving the clamping pressure zone to a different location, but one that is still within that zone. Thus, for example, the shaded bands in the locations of the reference boundaries "k," "l," "m," "o," "a," "n," "b," and "g" represent the zones associated with each of those bands. Zones for other reference boundaries in FIG. 126E are not depicted, but may similarly exist.

FIG. 126E also includes dot-dash-dot boundaries that are used to highlight various functional sub-circuits of the depicted fluidic circuit. Each such highlighted sub-circuit is an example of how the referenced circuit may be integrated into a larger fluidic system, thus illustrating the "building block" nature of the various fluidic circuits described herein.

Various variants of the fluidic circuit of FIGS. 126C and 126D are to be understood to be part of this disclosure as well. For example, in some implementations, further flow paths or channels (not shown) may be provided from all chambers having fluid in them initially, e.g., chambers M or L, E, H, and I, to chambers along a common edge (also not shown), e.g., on a side of reference boundary "k" facing away from reference boundary "l." Such edge-located chambers may serve as loading ports that allow the fluid-containing chambers to be loaded with fluids from a chain of chambers/ports along a common edge, thereby facilitating easy fluid loading. Such flow paths may, after loading is complete, be live sealed to seal the fluids within the relevant chambers. In some variants, dynamic seals may be located at locations 24 and/or 26, although in other variants, one or both such locations may be open flow path connections or channels.

Figure 126G:
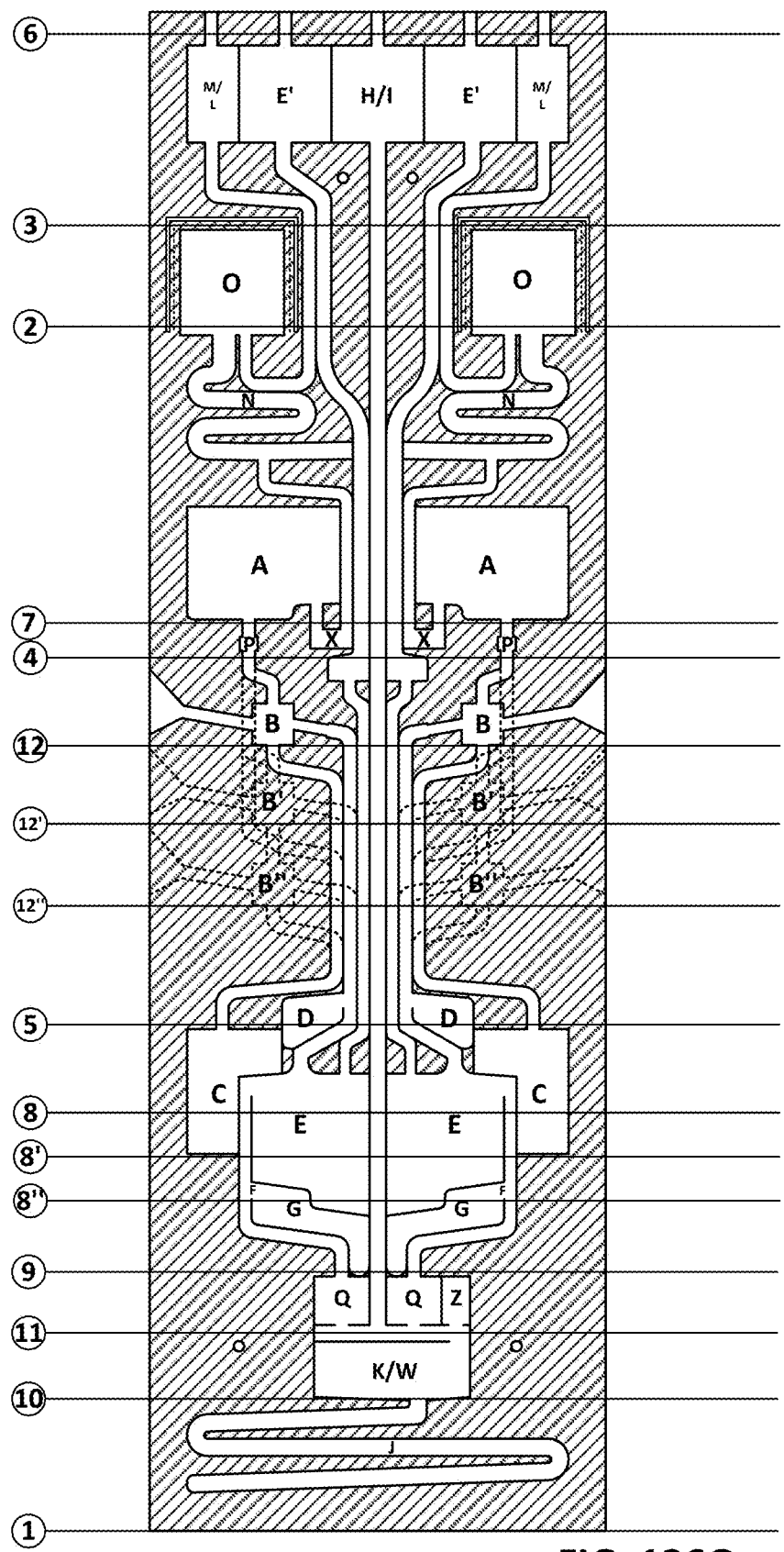

FIG. 126G depicts another example fluidic structure that is similar to the fluidic structure of FIG. 126E. The example fluidic structure of FIG. 126G does, however, differ from that of FIG. 126E in some respects. For example, the fluidic structure of FIG. 126G is designed such that all of the liquids that are to be used during operation of the fluidic structure are located in chambers located along the top edge (with respect to the page orientation) of the fluidic structure, leaving the remainder of the fluidic structure "dry" prior to use. Thus, the chambers marked "M/L" may each contain a mixture of eluent, e.g., a buffer that may provide a liquid carrier, and THC-specific antibody that is conjugated to horseradish peroxidase (HRP), the chambers marked "E'" may each contain a wash liquid, e.g., a buffer, and the chamber marked "H/I" may contain an indicator compound, e.g., luminol. While the chambers marked "M/L" are each shown as a single chamber, it will be understood that each such chamber may also, in some implementations, be separated into two portions, e.g., via a temporary seal, and each portion used to separately store, in isolation from the other portion of that chamber, a different constituent element. For example, one portion may be used to store eluent and the other portion a lyophilized antibody, similar to the arrangement shown in FIG. 126E. When pressure is applied to the two portions, the temporary seal may be caused to rupture, thereby allowing the eluent to flow into the portion with the lyophilized antibody and reconstituting it. The chamber marked "H/I" may also, in some implementations, be similarly constructed so as to have temporary seal dividing the chamber into two portions, each of which may be used to house a separate constituent element or reactant that, when mixed with the other constituent element, react to form the indicator (thereby allowing the indicator to potentially be stored in a shelf-stable format and then mixed when needed).

The arrangement of liquid-containing chambers along the top edge of the fluidic structure of FIG. 126G allows for a clamping pressure zone to be initially applied to the fluidic structure and traversed across nearly all of the fluidic structure without causing any fluidic movement. For example, if a roller is applied to the bottom of the fluidic structure (with respect to the page orientation) and then rolled across the fluidic structure from bottom to the region in between chambers "O" and chambers "M/L," "E'," and "H/I," the clamping pressure from the roller will not apply pressure to any of the liquid contents of chambers "M/L," "E'," and "H/I." This allows the roller to be used to apply clamping pressure to features located in this region without necessarily initiating fluidic flow of the liquid reagents housed in the chambers "M/L," "E'," and "H/I." For example, chambers "O," which may be breath sample collection chambers such as are discussed later with respect to FIGS. 130A-130F, may require that permanent seals be created around part of the perimeter of chambers "O" (thereby forming some of the walls of chambers "O") using a heat sealing technique. A heater element or elements may be located in a platen that is used to support the fluidic structure as the roller moves across the fluidic structure. The heater element(s) may be configured so as to provide localized heating in the shape and location of the portions of the fluidic structure that are to be heat-sealed to form the permanent seals. The roller may then traverse the fluidic structure that is located where the heater element(s) are and press the layers of the fluidic structure material against the heaters, thereby sealing them together to form a desired permanent seal. Due to the configuration of the fluidic structure of FIG. 126G, this may all occur without any pressurization of the chambers having liquids in them (aside from whatever small amount of liquid may be present within the sample chambers "O" as a result of sample collection). This may allow whatever samples that are collected to be sealed within the fluidic structure prior to any liquid flow, thereby reducing the chances of leakage and/or contamination.

Another difference between the fluidic structure of FIG. 126G and that of FIG. 126E is that the mixing chambers "N" have been relocated to be downstream of the chambers "O," as opposed to being between chambers "O" and chambers "M/L." The chambers "Y" that are present in the fluidic structure of FIG. 126E and were used as bubble traps are also omitted in the fluidic structure of FIG. 126G. Instead, bubble removal from the eluted collected samples located in the chambers "O" is accomplished by rapidly moving a clamping pressure zone across the chambers "O" to force the liquid mixtures that are in chambers "O" into the chambers "N." The clamping pressure zone traversal direction is then reversed before the liquids in the chambers "N" are forced out of the chambers "N," allowing the liquid in the chambers "N" to drain back out into the chambers "O." The clamping pressure zone may not move to the very top of the chambers "O" during such reversed movement and may instead only move partway up the chambers "O," thereby permitting only some of the liquid mixture that is in the chambers "N" to move back into the chambers "O." The clamping pressure zone may be caused to perform such back-and-forth movement multiple times, with each such back-and-forth movement causing the fluid mixture in the chambers "O" to move into the chambers "N" (mixing within the serpentine channels thereof as it does) and then at least partially drain back into the chambers "O". It was found that if the clamping pressure zone was moved fast enough across chambers "O" that the fluid speeds within the chambers "N" were relatively high, e.g., on the order of 10 µL/s to 20 µL/s or higher in a serpentine passage that was on the order of 1.6 mm wide (in terms of fluid velocity, this flow rate results in fluid flow velocities of approximately 12 mm/s to 24 mm/s or higher in such a channel), the liquid mixtures that were forced into the chambers "N" (which are serpentine passages) tended to separate into two portions—a first portion that had a high concentration of bubbles and a second portion that was largely or completely bubble-free and positioned behind the first portion with respect to fluid flow from the chambers "O" through the chambers "N." As the fluid mixtures were forced into and through the serpentine channels at the higher speeds discussed above, gas bubbles that were trapped in the liquid mixture tended to move through the serpentine channels faster than the liquid itself. When the clamping pressure zone movement direction was then reversed, thereby removing the driving pressure on the liquid mixture, the liquid mixture in the serpentine channels would reverse flow, with at least a portion thereof draining back into the chambers "O" due to capillary action. However, the reverse flow generally occurred at lower fluid flow speeds, and the bubbles tended not to move in the reverse direction at speeds that were significantly different from the liquid mixture. By performing multiple repeat back-and-forth movements of the clamping pressure zone so as to drive the fluid mixture through the serpentines at higher speed and then allow the fluid mixture to drain back out again into the chambers "O" at lower speed, the bubbles that were trapped in the liquid mixture tended to be caused to congregate near the ends of the serpentine channels that were farthest (or farther) from the chambers "O." In the case of the serpentine channels forming chambers "N," the tail ends of those serpentine channels extend past the passages leading to chambers "A." This allows the gas bubbles that are separated out of the liquid mixtures from chambers "O" through such clamping pressure zone movement to be stored in the dead volumes in the tail ends while the liquid mixtures that have had bubbles removed are caused to flow through the passages leading to chambers "A" when the clamping pressure zone is finally caused to advance across the serpentine channels. Whatever bubbles are located in the tail ends of the serpentine channels will still be driven towards the chambers "A," but this will occur after the liquid mixtures that are generally free of bubbles (or which have been subjected to bubble removal) are introduced to chambers "A." Moreover, such bubbles may also be trapped within chambers "X" as the clamping pressure zone moves across the chambers "A."

Another difference between the fluidic structure of FIG. 126G and that of FIG. 126E is in the layout of chambers "C"-"G"; while the layout of these chambers is somewhat different, they may nonetheless operate in a generally similar manner, and be used in generally the same way, as their counterparts in the fluidic structure of FIG. 126E. One feature that is present in chambers "E" in the fluidic structure of FIG. 126G that is not in the counterpart chambers "E" in the fluidic structure of FIG. 126E is the bottom edge profiles of the chambers "E." In the chambers "E" of the fluidic structure of FIG. 126G, the bottom edges thereof (which are located in between chambers "E" and chambers "G") have two distinct features that may both, either individually or in combination, act to reduce the effort needed to move a clamping pressure zone across the chambers "E" and towards the chambers "G" (or, with respect to the orientation of the page, from top to bottom). As can be seen, the chambers "E" have a large volume of "dead" space-soon after the clamping pressure zone starts moving downward from the top edges of the chambers "E," the clamping pressure zone will seal off the only exits from chambers "E" leading to chambers "G." As a result, the liquid that is trapped within the chambers "E" will have nowhere to escape to as the clamping pressure zone continues to move towards the chambers "G," causing the liquid within the chambers "E" to become trapped and eventually pressurize to the point where the chambers "E" swell or bulge outward into a taut blister. If a spring-loaded or compliant roller is used to apply the clamping pressure zone, the roller must either compress or be displaced upward (out of the page with respect to the Figure orientation) to roll over the bump/blister in order to move past the bump/blister to chambers "G". If the seals or walls of chambers "E" are straight and generally parallel to the roller axis of rotation (e.g., similar to the chambers "E" in the fluidic structure of FIG. 126E), the resulting blister or bump caused by the trapped fluid may, in effect, be generally cylindrical in nature (with a cylinder axis that is parallel to the roller axis of rotation). This may make it difficult for the roller to move over the bumps/blisters, as the entire lengths of the transverse edges in between chambers "E" and "G" will generally serve as speed-bumps that have a constant height and radius along their lengths, thereby producing resistive forces along their lengths that need to be overcome by the roller all at the same time.

If the bottom edges of the chambers "E" are instead sloped at an angle, e.g., sloped at an oblique angle with respect to the roller rotation axis and/or the direction of travel of the clamping pressure zone (as shown in FIG. 126G), then this may act to cause the trapped blisters of liquid to instead be conical (or at least partially conical) instead of cylindrical, thereby causing the blisters to have varying heights and radiuses along their lengths (in the left-right direcitons with respect to the page). This geometric variance causes the resistive forces that need to be overcome to move the clamping pressure zone over the blisters to be gradients that vary in magnitude across the widths of such edges (instead of being generally constant across the widths of the edges). As a result, there will generally be a lower-magnitude resistive force where the clamping pressure zone meets such an edge, allowing the roller that is used to apply the clamping pressure zone to more easily overcome the resistive force at that location and traverse across the edge. As the roller moves towards the chambers "G," the fluid that is trapped within the chambers "E" in between the roller and the chambers "G" may be squeezed past the clamping pressure zone in such locations, thereby reducing the overall volume of liquid that is in the blister in a gradual manner and allowing the maximum blister height to get slowly smaller and smaller as the roller advances. This has the effect of reducing the amount of effort that is needed to cause the roller to move over the trapped fluid in the chambers "E." This, in turn, reduces the amount of power needed to drive the roller, reduces the stresses within the drive mechanism, and reduces the chances of the roller getting stuck.

The presence of a jog in the bottom edge may also act in a similar manner. As can be seen, the edges of the chambers "E" that form the boundaries between the chambers "E" and the chambers "G" have jogs or offsets in them-portions of each such wall are offset some distance from other portions thereof and in directions generally perpendicular to those walls. As a result, the liquid that is trapped in between such a chamber edge and the clamping pressure zone may make a blister that has two distinct heights and radiuses-one associated with one edge portion, and the other with another edge portion (it will be understood that such an edge may also have greater than two offset portions, e.g., three, four, five, etc. offset portions arranged in a generally stair-step manner-such variants will correspondingly have blisters with similar numbers of different height regions). The jogged nature of such an edge wall may produce resistive forces that the roller must overcome that vary as a function of the location, similar to the angled edge wall discussed above. However, while the angled edge wall may produce resistive forces that generally vary smoothly, e.g., a gradient, the jogged edge wall may produce resistive forces that generally vary in a stepwise manner. Both features (angled and jogged edge walls) may be used to reduce the resistive forces that the roller must overcome in traversing a blister of trapped liquid, either separately or, as is shown here, in combination.

The fluidic structure of FIG. 126G also differs from the fluidic structure of FIG. 126E in the configuration of the chambers "H/I" and chambers "K/W" and "J." In the fluidic structure of FIG. 126E, chambers "H" and "I" are located near the bottom of the fluidic structure, e.g., approximately even with chambers "Q," and the binary substrate components that are located therein, e.g., to make an indicator such as luminol, are then forced through the chamber "J" (a serpentine mixing passage) before being emptied into chamber "K" and the mixed indicator then being delivered to the chambers "Q" via the chamber "W."

In the fluidic structure of FIG. 126G, the chambers "H" and "I" are instead located at the very top of the fluidic structure, as discussed earlier, and the contents thereof driven down into chambers "K/W" by the movement of the clamping pressure zone from the top of chamber "H/I" towards the chambers "Q." The indicator that is in the chambers "H/I" is driven down a long, central passage that terminates in a T-junction; each arm of the T-junction may have a dynamic seal that fluidically connects that T-arm to one of the chambers "Q." At least one of the T-junction arms may also have a flow path that leads to the chamber "K/W," such that the indicator that is driven into the arms of the T-junction flows into the chamber "K/W" and then into the chamber "J." The clamping pressure zone may then be moved back-and-forth across the chamber "K/W" to cause the indicator to move into and out of the chamber "J," thereby mixing the indicator further. When the indicator is sufficiently mixed, then the clamping pressure zone may be moved so as to traverse all or most of the chamber "J" and then reverse direction to drive the mixed indicator back into the T-junction. The indicator may then flow into the chambers "Q" (the flow path leading to the central passage back to the chamber "H/I" may be sealed by a dynamic seal at the T-junction intersection point—this dynamic seal may have a higher release pressure than the dynamic seals sealing off the chambers "Q").

The fluidic structure of FIG. 126G may be used to perform an assay, similar to the fluidic structures of FIGS. 126A through 126E. For example, during sample collection a breath sample may be flowed through breath collection areas within chambers O (for example, as discussed later with respect to FIGS. 130A through 130F). The breath sample may be directed through capture media of some sort, e.g., a fibrous filter material, in a direction generally perpendicular to the page of FIG. 126G. Once the desired breath sample has been obtained, flaps of the material layers that form the fluidic structure that had been peeled away to provide access to the capture media may be repositioned on either side of the capture media and the fluidic structure placed in a device that is configured to apply a movable clamping pressure zone to the fluidic structure (see, for example, FIG. 1). The clamping pressure zone may then be applied to the fluidic structure, e.g., by rolling a roller onto the fluidic structure while supporting the opposite side of the fluidic structure with a platen (or with another roller). The clamping pressure zone may be initially applied to the fluidic structure at location 1 (near the bottom of the page) and then moved up to location 2, which may be located at the ends of the chambers "O" that are closest to location 1. At this point, a heater element in the platen (or additional roller) may be activated to locally heat portions of the material layers that are compressed by the clamping pressure zone, thereby fusing those material layers together in that location. The heater elements may be arranged so as to form π-shaped permanent seals around the chambers "O" as the clamping pressure zone moves from location 2 to location 3, effectively sealing the chambers "O" off from the outside world (the newly formed permanent seals resulting from this thermal bonding operation may extend from existing permanent seals, e.g., along the sides of the chambers "O" where the inlet and outlet flow paths are for the chambers "O" all the way around the region where the chambers "O" are eventually located, thereby sealing the chambers "O" such that the only fluid ingress/egress points for the chambers "O" are via the two fluidic passages connecting with each of the chambers "O."

Once the chambers "O" are sealed, the clamping pressure zone may be caused to move from location 3 down to location 4 (or, if desired, another location in between chambers "P" and location 1). Such movement may act to cause air that may be trapped within the fluidic structure through the chambers "O" sealing operations to be urged through the chambers "N" and down towards the chambers "B." If desired, the clamping pressure zone may be moved back and forth between locations 3 and 4 multiple times to more effectively purge the traversed portion of the fluidic structure of air. If desired, the clamping pressure zone may then be moved to location 5 to further purge the portion of the fluidic structure that is "above" location 5 (with respect to the page orientation) of air, thereby driving whatever air may be trapped within that portion of the fluidic structure into the chambers "C."

After purging the above-discussed portion of the fluidic structure of air, the clamping pressure zone may be moved to location 6 and then its direction of travel reversed so as to cause the clamping pressure zone to move to location 2. In doing so, the pressure applied to the chambers "M/L," "E'," and "H/I" by the clamping pressure zone may cause the liquids stored therein to pressurize and cause the dynamic or temporary seals sealing each such chamber to release, thereby causing the liquids contained therein to flow out of those chambers and through the flow paths connected with each such chamber. The liquids in the chambers "M/L" may thus be forced into the chambers "O" and then into the chambers "N," where they may undergo mixing (the exits from the chambers "O" that lead to the chambers "N" may be provided by dynamic or temporary seals that have a lower release pressure than dynamic seals that may be located at the other exit points from the chambers "O." The clamping pressure zone may then optionally be moved between locations 2 and β one or more times, for example, to cause the liquid directed into the chambers "N" to move between the chambers "O" and the chambers "N" one or more times— each such reciprocating liquid movement may result in further mixing (the smaller passage leading from the serpentine passages of chambers "N" to the chambers "X" may be sealed with a dynamic or temporary seal that prevents the reciprocated liquid from exiting the chambers "N" until pressurized to the release pressure of such seals). Moreover, if desired, the speed of the clamping pressure zone movement may be controlled (as discussed earlier) so as to encourage the separation and sequestration of bubbles from the liquid.

The clamping pressure zone may then move from location 2 to location 7, thereby driving the fluid in the chambers "N" through the chambers "X," "A," "P" (which may act as another bubble trap), "B" (which may house, for example, immobilized antigen that may be specific to an antibody that was included in the liquid from chambers "M/L"), and "C" (which may be used to store a portion of the sample/liquid mixture for later laboratory analysis). The clamping pressure zone may be caused to remain at location 7 for some time, e.g., a period of time selected to allow for unbound antibody that remains in the chambers "B" to bind with the antigen therefor that is immobilized in the chambers "B," and may then be caused to move to, for example, location 5. In doing so, the clamping pressure zone may push the liquid that remains in chambers "B" into chambers "C." Another set of heating elements may then be activated to cause the fluid flow paths into the chambers "C" to be permanently sealed, e.g., with a heat seal formed by the heat provided by the heater elements and the pressure applied by the clamping pressure zone.

The clamping pressure zone may then be moved from location 5 to location 8 and then back to location 7 in order to drive whatever liquid may remain in chambers "B" into chambers "A." The clamping pressure zone may then be moved back and forth between location 7 and locations 8, 8', and 8" (each time moving closer to location 1) in order to move portions of a wash liquid from chambers "E" through chambers "B" and into chambers "A," thereby washing out whatever previously delivered liquid may remain in chambers "B" and flushing it into chambers "A." The wash liquid that is in chambers "E" may be delivered to chambers "E" from chambers "E'" by earlier movements of the clamping pressure zone. The flow passages from the chambers "E'" to the chambers "E" may have dynamic seals located at the locations where they join the chambers "E" that have higher release pressures than the flow paths from the chambers "E" to the chambers "B."

After the wash liquid from chambers "E" has been flushed through chambers "B" and into chambers "A," the clamping pressure zone may be caused to move to location 9 and then moved between location 9 and location 7 one or more times in order to drive whatever liquid from chambers "E" may have leaked into chambers "G" into chambers "A" (and to purge whatever other liquid may remain in chambers "E," "D," and "B" into chambers "A"). Such movement may also be performed such that the clamping pressure zone moves to intermediary locations along chambers "G" in between each movement to location 7 before finally moving to location 9, thereby incrementally purging the chambers "G."

After purging of the chambers "G" is complete, the clamping pressure zone may then be moved to location 10, which causes the indicator that was initially stored in chamber "H/I" and that has been pushed into chamber "K/W" to be pushed into chamber "J," which may be a serpentine mixing channel. The clamping pressure zone may then be moved from location 10 to location 11 and back again one or more times in order to cause the indicator liquid to be reciprocated into/out of the chamber "J," thereby causing it to be more thoroughly mixed.

After a desired number of mixing cycles of the indicator has been performed by reciprocating the indicator liquid into/out of the chamber "J," the clamping pressure zone may be caused to move to location 1 and then reverse course to location 12, thereby first driving the indicator liquid (and any bubbles that may be in the initial portion thereof) into chamber Z and then driving the remainder of the indicator liquid into chambers "Q." The entrances to the chambers "Q" from the chamber "K/W" may be dynamic seals that have a lower release pressure than the dynamic seal that is formed at where the longitudinal center passage that leads from the chamber "H/I" exits from between the chambers "Q." Similarly, the chamber "Z" may have a dynamic seal with a lower release pressure than the chambers "Q." Thus, when liquid is pushed from the chamber "K/W" towards the chambers "Q," the liquid will first flow into the chamber "Z," then into the chambers "Q." The exits from the chambers "Q" to the chambers "E" may have dynamic seals that have release pressures that are higher than the dynamic seals that lead into the chambers "Q," such that when the indicator liquid is flowed into the chambers "Q," the chambers "Q" fill up with equal amounts of liquid indicator. Any excess indicator fluid may then flow into the chamber "Z" or, in some cases, into the passage leading back to the chamber "H/I" (the dynamic seal in between the chambers "Q" that leads to this passage may have a release pressure that is less than that of the dynamic seals leading from the chambers "Q" to the chambers "E," for example). When the clamping pressure zone is then moved to location 12 (or 12' or 12", if analyses are being performed in chambers "B" that are located in other positions in the fluidic structure, as indicated by the dotted outlines-see FIG. 126F), the indicator liquid may be driven from the chambers "Q" into the chambers "B," where it may react with the bound antibody that is present with the chambers "B," thereby producing luminescence, the magnitude of which may be measured by an optical measurement system, e.g., a photosensor, and used to determine an amount of whatever target substance, molecule, virus, or microorganism is being measured by the assay.

During the above-discussed operations, the chambers "D" and "G" may act as fluidic diodes. The region where each chamber "D" or "G" fluidically connects with the adjoining passageway may, in effect, form a small mini-chamber with three dynamic seals leading from it-one into the adjacent chamber "D" or "G," and the other two positioned just on either side of the first and spanning across the passage. The dynamic seals leading into the chambers "D" or "G" may be configured to have release pressures that are less than the release pressures of the adjacent dynamic seals across the corresponding passages with respect to fluid that is pressurized within the mini-chamber. Thus, when liquid is flowed into the mini-chamber via the passage (regardless of direction), the mini-chamber will pressurize until the release pressure of the dynamic seal leading to the chamber "D" or the chamber "G" is reached, thereby allowing the pressurized liquid to flow into the chamber "D" or the chamber "G" that is adjacent that dynamic seal. As can be seen, when the clamping pressure zone is caused to move from, for example, location 9 to location 8, the liquid that is trapped in the chambers "G," if any, is caused to flow into the chambers "E." However, when the clamping pressure zone is caused to move from location 8 to location 9, the liquid that is trapped in the chambers "G" is unable to escape due to the fact that the dynamic seals leading thereto are located at positions on the chambers "G" that are closest to location 8, and the portions of the chambers "G" that are closest/closer to location 9 are walled off by permanent seals. The chambers "D" work in a similar fashion, although with smaller volumes. Such fluidic diodes allow liquid to freely flow upwards (with respect to the page orientation) but prevent that fluid from flowing downwards (with respect to the page orientation). Thus, for example, the wash fluid from the chambers "E" is able to flow "upward" towards the chambers "B" and "A," but is unable to flow "downward" towards the chambers "Q" past the chambers "G." This ensures that wash liquid does not mix with the indicator liquid (potentially diluting it or interfering with its luminescent properties). Similarly, liquid from the chambers "B" that may contain sample material and antibodies bound thereto may be prevented from flowing past the chambers "D" and into the chambers "E," although wash liquid from the chambers "E" may be permitted to flow past the chambers "D" and into the chambers "B."

Figure 126H:
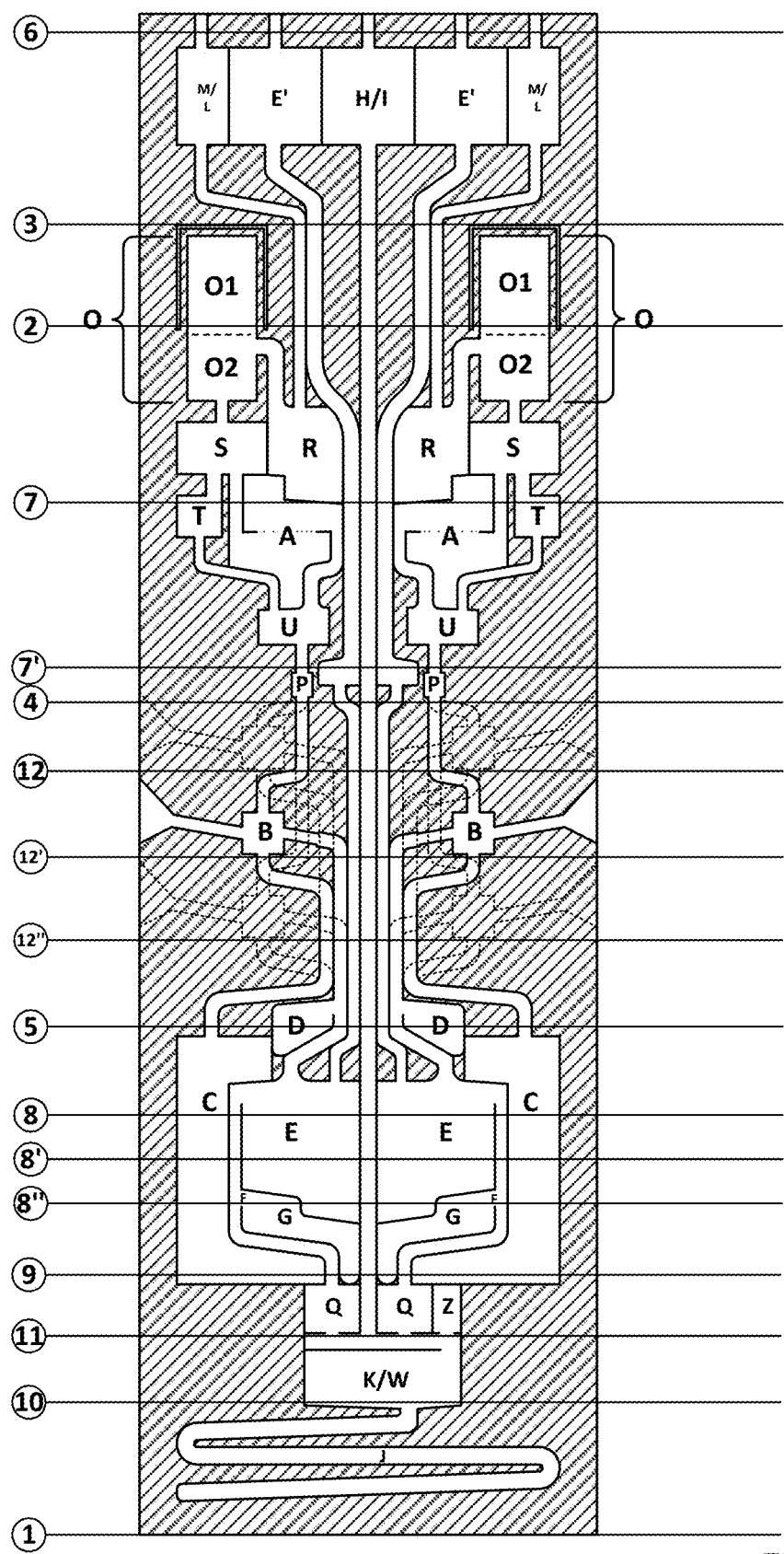

FIG. 126H depicts another example fluidic structure that is similar to that shown in FIG. 126G. The fluidic structure of FIG. 126H differs from the fluidic structure of FIG. 126G in the region in between locations 3 and 4 in several respects. For example, the chambers "O" in the fluidic structure of FIG. 126H are each separated into two portions "$O_1$" and "$O_2$" (the boundaries between the two portions are indicated by a horizontal dashed line). The portions "$O_1$" have capture media located (e.g., an absorbent, fibrous (or foam) pad or filter, therewithin and may generally be coextensive with flaps of the flexible material that is used to make the fluidic structure that may be peeled back to allow access to the capture media. As can be seen in FIG. 126H, the π-shaped cutouts around the portions "$O_1$" allow the layers of flexible defining the tops and bottoms of the portions "$O_2$" to be peeled away from each other to expose whatever capture media is located within the portions "$O_1$."

The portions "$O_2$" of the chambers "O," in contrast, may generally be free of the capture media, although there may, in some cases, be a third portion in between the portions "O1" and "O2" that includes the capture media but is located within a region of the fluidic structure that is unable to be peeled back. Such a configuration may facilitate more thorough purging of liquid from the chambers "O." For example, if the capture media in the chambers "O" are completely coextensive with the chambers "O," e.g., generally each filling the entirety of one of the chambers "O," it may be difficult to use a clamping pressure zone to drive the liquid that may be in the chambers "O" out of such chambers, e.g., towards the chambers P. Such difficulties may arise when the liquids that are located within the chambers "O" are present in large enough volumes that the pressure developed in those liquids as the clamping pressure zone moves across the chambers "O," in combination with the presence of the capture media in the same region, allows the liquid to leak past the clamping pressure zone via the capture media. Thus, for example, as the clamping pressure zone moves from location 3 to location 2 in order to drive the liquid in the chambers "O" (with reference to the fluidic structure of FIG. 126G), at least some of the liquid in the chambers "O" may end up moving in the opposite direction from the clamping pressure zone, effectively squeezing beneath the clamping pressure zone via the capture media rather than being forced into the chambers "N."

By splitting the chambers "O" into two portions "$O_1$" and "$O_2$" and limiting the amount of liquid that may be present in the chambers "O," the purging of liquid from the chambers "O" may occur in two stages. This is discussed further below with respect to the overall operation of the fluidic structure of FIG. 126H.

The fluidic structure of FIG. 126H may be operated in a manner very similar to how the fluidic structure of FIG. 126G. The initial sequence of clamping pressure zone movements between the locations 1-7 may be the same. However, when the clamping pressure zone moves from location 6 to location 7, the liquids in the chambers "M/L" are not driven in the chambers "N" of the fluidic structure of FIG. 126G but are instead driven into the chambers "R" of the fluidic structure of FIG. 126H. When the clamping pressure zone traverses the chambers "R" prior to arriving at location 7, the liquid trapped therein is retained in the chambers "R" as the clamping pressure zone moves over the liquid-filled portions of the chambers "R." The clamping pressure zone is then moved back to location 2. The junctions between the chambers "R" and the passages leading to the chambers "M/L" may have dynamic seals that have higher release pressures than the junctions between the chambers "R" and the passages leading to the chambers "O" (these junctions between the chambers "R" and the passages leading to the chambers "O" may have dynamic or temporary seals, or no seal at all-regardless, pressurized liquid within the chambers "R" will preferentially flow into the chambers "O" than back into the chambers "M/L"). Thus, the liquid that is present in the chambers "R" (which may be an eluent mixed with, for example, an antibody that is specific to the substance for which measurement or detection is sought) is caused by the movement of the clamping pressure zone from location 7 to location 2 (or, in some cases, only to the region in between the chambers "O" and the chambers "R") to move into the chambers "O."

When the liquid is initially introduced into the chambers "O" (the flaps of material between which chambers "O" are defined are heat-sealed together, e.g., as discussed with respect to FIGS. 130A through 130F, in operations performed prior to the movement of liquids into the chambers "R"), capillary action may cause the liquid to preferentially flow into the portions "$O_1$"; alternatively, the clamping pressure zone may be moved from, for example, location 7 to location 2, thereby pressurizing the liquid and forcing it to flow into the portions "$O_1$." The clamping pressure zone may then be moved to location 3 and then back to location 2, thereby driving the liquid that is in the portions "$O_1$" into the portions "$O_2$." The portions "$O_1$" and "$O_2$" may be sized such that each portion is able to separately contain a significant fraction (e.g., 50%, 60%, 70%, 80%, 90% or more), or all, of the liquid that is expected to be contained within the respective chamber "O" during operation. As can be seen, the portions "$O_1$" and "$O_2$" are simply separate regions of the same chamber structure (and thus have the same widths); there is thus effectively no flow restriction between the two portions. However, it will be understood that similar implementations may feature discrete chambers for each of the portions "$O_1$" and "$O_2$," with those discrete chambers being linked by one or more passages—such passages, however, may be selected so as to have a very low flow resistance, e.g., a flow resistance that is incapable of producing a back pressure that would cause the pressurized liquid to leak past the clamping pressure zone during clamping pressure zone movement. Thus, when the clamping pressure zone moves from location 3 to location 2, the liquid that is present in the portions "$O_1$" is forced into the portions "$O_2$" with little or no back pressure developing. This allows the full force provided by the clamping pressure zone to be applied to the capture media (without any of that force being counteracted by pressurized liquid), thereby minimizing the potential for the liquid to flow past the clamping pressure zone and away from the portions "$O_2$." Once the liquid has been forced into the portions "$O_2$," the clamping pressure zone may continue to move towards the chambers "S," thereby causing the liquids contained in the portions "$O_2$" to pressurize to a release pressure of the dynamic seals that lead from the chambers "O" to the chambers "S" and then flow into the chambers "S."

The clamping pressure zone may then be caused to move to location 7', causing the liquids in the chambers "S" to flow into the chambers "T," "A," "U," "P," "B," and "C" in a particular sequence. For example, the fluid passages from the chambers "S" to the chambers "T" and "A" may each be equipped with dynamic or temporary seals where they meet with the chambers "S"; the seals for the passages to the chambers "T" may have a release pressure that is lower than that of the seals of the passages leading to the chambers "A." Similarly, the passages leading from the chambers "T" to the chambers "U" may have dynamic or temporary seals where they meet with the chambers "T" that have release pressures that are higher than the release pressures of the dynamic seals in the chambers "S" that lead to the chambers "T" and "A." Thus, when the clamping pressure zone moves from location 2 to 7', the liquid that is forced into the chambers "S" is caused to then flow first into the chambers "T" until the chambers "T" are full, at which point the pressure in the chambers "S" may increase until the release pressure of the dynamic seals leading to the chambers "A" is released, thereby causing the remaining liquid in the chambers "S" to flow into the chambers "A." The chambers "A" are generally split into at least two portions (with the boundary between the two portions indicated by a grey dashed line in FIG. 126H—the boundary may also be a region that is interposed between the two portions instead of a linear boundary). The two portions may be generally any arbitrary shape, with each portion having one or more flow paths leading from it that are sealed by dynamic seals. The connection between the two portions may be a large, open connection (as shown in FIG. 126H) or may be provided by one or more passages that are sealed, if sealed at all, by dynamic or temporary seals with release pressures that are lower than the release pressures of the dynamic seals of the flow paths leading from the portions. The flow path(s) leading from each portion fluidically connect with chambers on opposing sides of the boundary between the two portions such that each portion is connected with one or more chambers on the opposite side of the boundary from that portion by such a flow path or flow paths. Moreover, each portion is defined by a continuous permanent seal that extends from the boundary, around that portion, and back to the boundary such that when the clamping pressure zone is positioned at the transition from the boundary to either of the portions, the clamping pressure zone seals off that portion, thereby preventing the liquid contained therein from being able to flow through the flow path(s) leading therefrom. Such a chamber arrangement may be used as a bi-directional waste collection system. If each portion is sized large enough to contain a total amount of waste liquid that is to be retained within the chamber, the waste liquid may be introduced into the chamber via the flow paths leading to either or both of the portions, with the introduced waste liquid being retained in the chamber when the clamping pressure zone moves from one end of the chamber to the other regardless of which direction the clamping pressure zone is moving. Thus, in FIG. 126H, each chamber "A" may have a pressurized volume that is equal to or greater than the pressurized volume of the chamber "S" minus the pressurized volume of the chamber "T."

With respect to the various release pressures discussed above, it will be understood that while the release pressures discussed above are discussed with respect to pairs of seals (since the fluidic structures discussed generally exhibit bilateral symmetry across much of the fluidic structure), the relative magnitudes discussed are with respect to the release pressures for seals within the same left or right half of the fluidic structure. For example, if there are pairs of dynamic seals A and B on the left and right halves of the fluidic structure and the dynamic seals A have a higher release pressure than the dynamic seals B, this should be understood to be inclusive of the scenario where the dynamic seal A in the left half has a higher release pressure than the dynamic seal B in the left half, and the dynamic seal A in the right half has a higher release pressure than the dynamic seal B in the right half, but the dynamic seal A in the left half may have a lower release pressure than the dynamic seal B in the right half (or vice versa).

Once the liquid in the chambers "S" is forced into the chambers "T" and "A," the continued movement of the clamping pressure zone towards location 7' causes the liquid that is in the chambers "T" to pressurize and exceed the release pressure of the dynamic seals of the passages leading to the chambers "U." The continued movement of the clamping pressure zone towards location 7' further causes the liquid in the chambers "U" to then flow into and through the chambers "P" (which may act as a bubble-removal feature) and then fill the chambers "B." At this point, the further movements of the clamping pressure zone may be generally as described earlier with respect to the fluidic structure of FIG. 126G (to location 8 onwards).

It will be understood that while the fluidic structures of FIGS. 126G and 126H depict implementations in which the eluent and antibody, as well as the indicator, are provided as pre-mixed solutions in a single chambers, those same implementations may also be provided with one or both such liquid mixtures provided as separate elements, e.g., eluent and lyophilized antibody in separate chambers or two binary components of indicator stored in separate chambers, similar to the implementation of FIG. 126E. In such implementations, for example, the chambers "M/L" may be similar to the chambers "M" and "L" in FIG. 126E. In some such implementations, the serpentine channel "N" of FIG. 126E may be used as part of the flow path leading from the chambers "M/L" to the chambers "O" or "R," as the case may be. Similarly, if a binary indicator composition is used, the chamber "H/I" may instead be provided by two separate chambers "H" and "I" that are both configured to deliver their contents to the chamber "K/W," either by separate flow paths or a common flow path. The two components may then be mixed using the mixing feature provided by the chamber "J," which is a serpentine channel.

It will also be understood that the fluidic structure of FIG. 126H, like that of FIG. 126G, may be overlaid with multiple other similar instances of such a fluidic structure for simultaneous application of the clamping pressure zone across those multiple layers. Such fluidic structures may, for example, have identical fluidic layouts except for the locations of the chambers "B" (in FIG. 126H, the depicted chambers "B" are flanked on either side by chambers "B" locations on other fluidic structures when arranged in a layered configuration).

As discussed above, fluidic circuits such as those discussed herein, e.g., such as those shown in FIGS. 126C and 126D, may include chambers that are configured to receive a breath sample, e.g., that are designed to act as breath capture modules. Various implementations of such chambers may be used in such fluidic circuits.

Figure 127A:
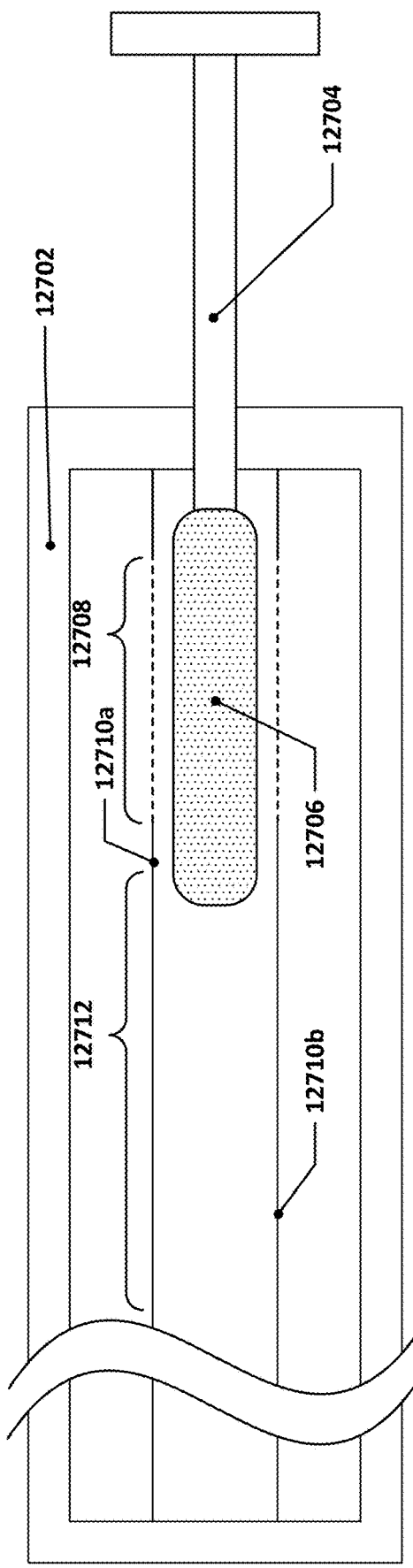
FIGS. 127A and 127B depict example structures that may be used to provide a breath capture module.
Figure 127B:
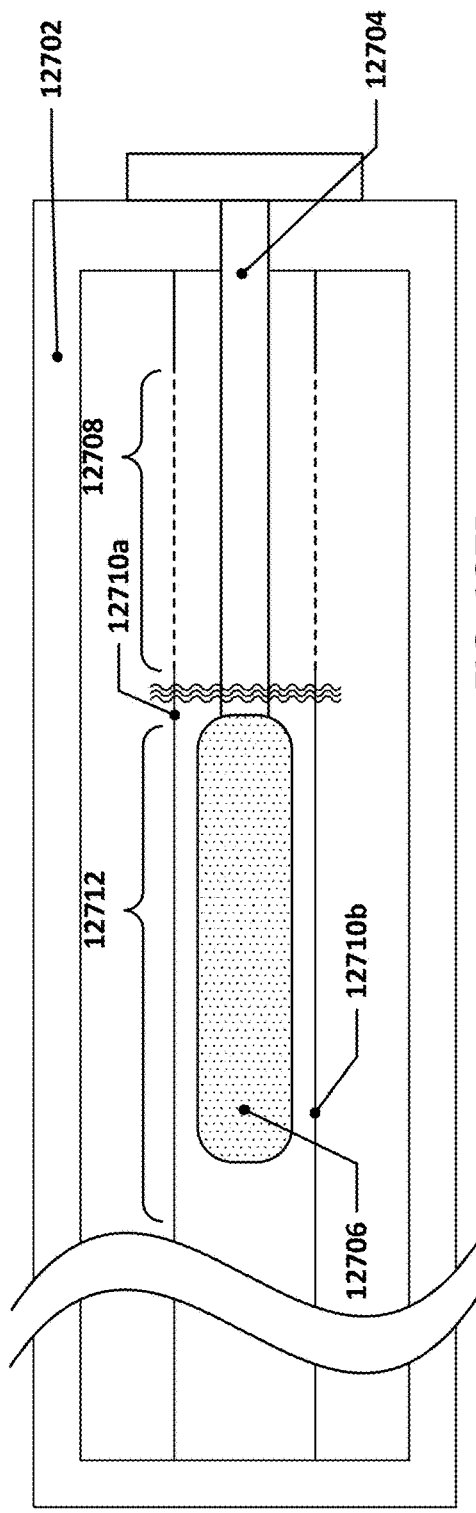

FIGS. 127A and 127B depict an example of one such chamber. In FIGS. 127A, two portions of material 12710a and 12710b are joined together via permanent seals, e.g., as discussed above, to form a fluidic circuit. A part of the fluidic circuit defines a chamber 12712. At least one, if not both, of the portions of material 12710a/b may, as with earlier fluidic circuit elements discussed herein, be of an inelastic, yet flexible, material, e.g., BoPET or other similar material (this applies to other breath capture modules discussed below as well). The fluidic structure formed by the portions of material 12710a and 12710b may be supported by a rigid frame 12702, for example, and a capture medium 12706 may be sandwiched between the portions of material 12710a and 12710b and supported by a rigid (or semi-rigid) support 12704. The support 12704, and the capture medium 12706 supported thereby, may be movable relative to the frame 12702, e.g., by sliding the support 12704 through a hole in the frame 12702, for example, thereby causing the capture medium 12706 to be moved between two positions relative to the portions of material 12710a and 12710b. In the first position (shown in FIG. 127A), the capture medium 12706 may be aligned with a hole or opening 12708 in the portions of material 12710a and 12710b, while in the second position, the capture medium 12706 may be pushed into the chamber 12712. During breath sample capture, the capture medium 12706 and support 12704 may be placed in the first position and a subject's breath may be directed through the opening 12708 and the capture medium 12706. The capture medium 12706 may, for example, be a relatively thin, fibrous or porous material, such as cellulose or other hydrophilic material, that may provide a relatively large amount of wetted surface area yet still have a low enough flow resistance that a breath sample may still flow therethrough without undue effort. While not shown, the fluidic structure around the opening 12708 may optionally be clamped between two rigid or semi-rigid elements, e.g., walls that encircle the opening 12708, that serve to support/immobilize the capture medium 12706 and/or to focus and constrain a breath sample to flow therethrough. After the breath sample is collected, the support 12704 may be moved to the second position, thereby moving the capture medium 12706 into the chamber 12712. Pressure and heat may then be applied to the portions of material 12710a and 12710b at a location, e.g., indicated by the wavy lines, in between the capture medium 12706 and the opening 12708 to thermally seal off the chamber 12712 (and the capture medium 12706) from the opening 12708.

Figure 128A:
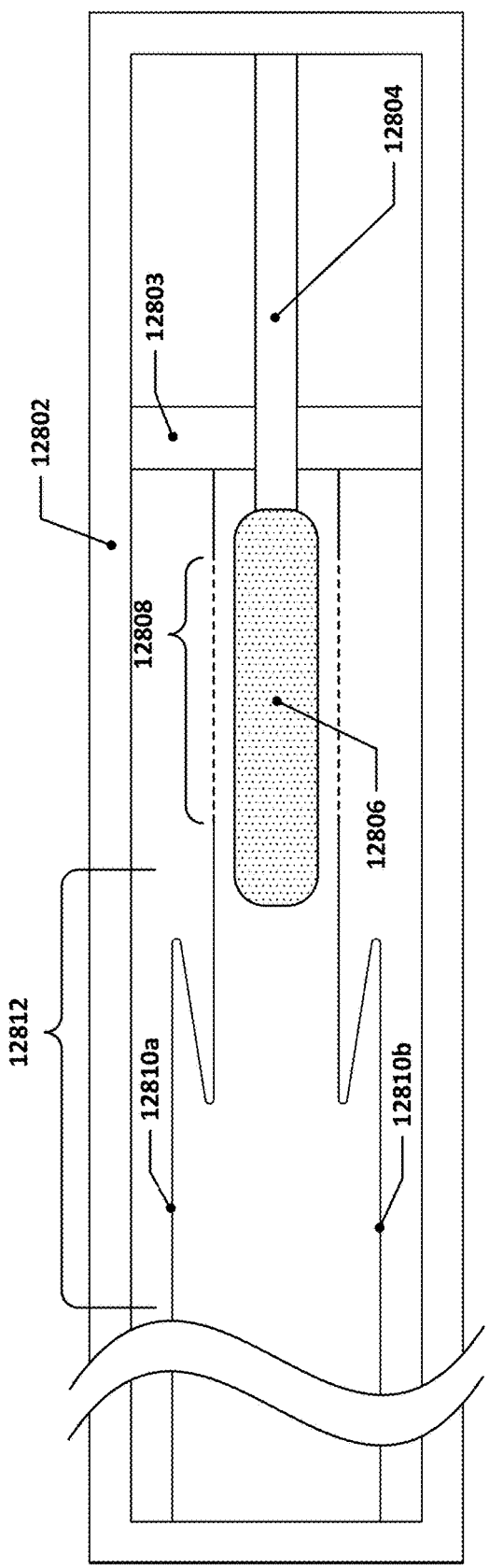
FIGS. 128A and 128B depict example structures that may be used to provide another breath capture module.
Figure 128B:
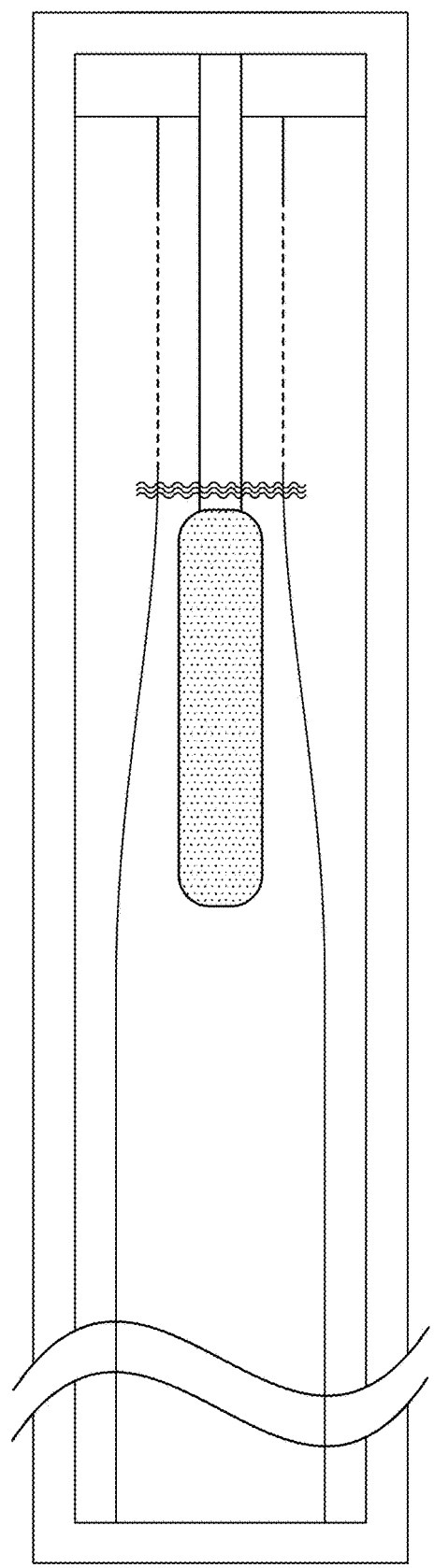

FIGS. 128A and 128B depict another example of such a breath capture module. In FIGS. 128A, two portions of material 12810a and 12810b are joined together via permanent seals, e.g., as discussed above, to form a fluidic circuit. A part of the fluidic circuit defines a chamber 12812. The fluidic structure formed by the portions of material 12810a and 12810b may be supported by a rigid frame 12802 at one end, for example, and a moveable slide 12803 at the other end. A capture medium 12806 may be sandwiched between the portions of material 12810a and 12810b and supported by a rigid (or semi-rigid) support 12804. The support 12804, and the capture medium 12806 supported thereby, may be fixed relative to the frame 12802, but the movable slide may be slidably engaged with the frame 12802 so that it may be moved between a first position and a second position. In the first position (shown in FIG. 128A), the movable slide 12803 may be positioned close to the capture medium 12806, and the portions of material 12810a and 12810b may be partially collapsed, e.g., folded over into an accordion pleat or similar, to shorten the overall length of the fluidic structure. With the moveable slide 12803 in the first position, the capture medium 12806 may be aligned with a hole or opening 12808 in the portions of material 12810a and 12810b. In the second position, the moveable slide 12803 may be positioned away from the capture medium 12806, thereby pulling on the portions of material 12810a and 12810b and causing the collapsed or folded over parts of the portions of material 12810a and 12810b (into which the openings 12808 do not extend) to extend so as to cover the capture medium 12804. The capture medium 12806 is thus, when the moveable slide 12803 is in the second position, offset from the opening 12808 so that, as shown in FIG. 128B, a permanent seal may be formed in the portions of material 12810a and 12810b between the capture medium 12806 and the opening 12808, e.g., by the application of heat and pressure to the location indicated by the wavy lines.

During breath sample capture, the moveable slide 12803 may be placed in the first position and a subject's breath may be directed through the opening 12808 and the capture medium 12806. The capture medium 12806 may, for example, be a relatively thin, fibrous or porous material, such as cellulose or other hydrophilic material, that may provide a relatively large amount of wetted surface area yet still have a low enough flow resistance that a breath sample may still flow therethrough without undue effort. While not shown, the fluidic structure around the opening 12808 may optionally be clamped between two rigid or semi-rigid elements, e.g., walls that encircle the opening 12808, that serve to support/immobilize the capture medium 12806 and/or to focus and constrain a breath sample to flow therethrough. After the breath sample is collected, the moveable slide 12803 may be moved to the second position, thereby extending the portions of material 12810a and 12810b so as to cover the capture medium 12806. Pressure and heat may then be applied to the portions of material 12810a and 12810b at the location indicated by the wavy lines in FIG. 128B to thermally seal off the chamber 12812 (and the capture medium 12806) from the opening 12808.

Figure 129A:
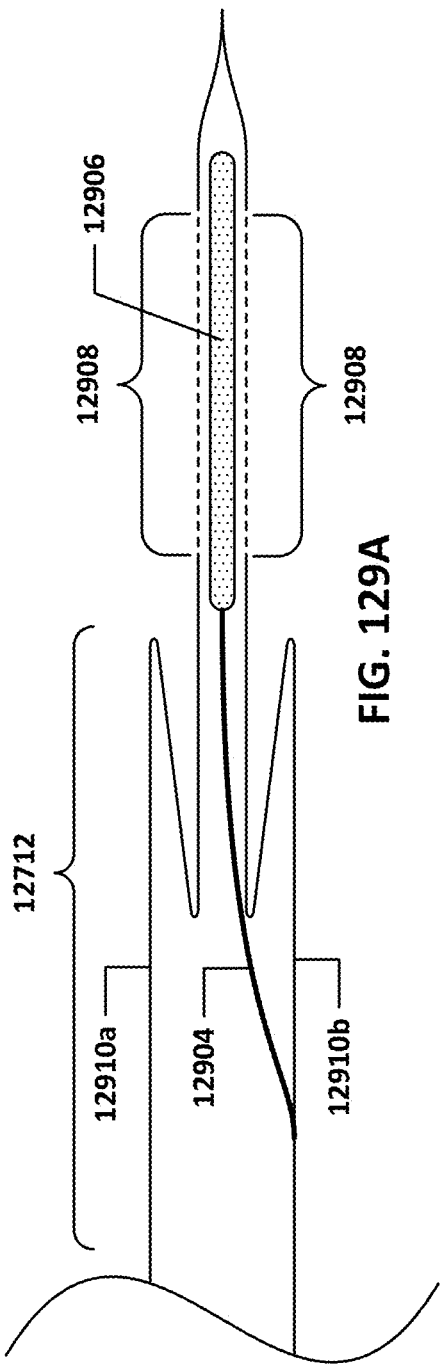

FIGS. 129A through 129E depict various stages of operation of yet another example of a breath capture module. As seen in FIG. 129A, the depicted breath capture module may be implemented as part of a fluidic circuit that is formed between two portions of material, 12910*a* and 12910*b*. The portions of material 12910*a* and 12910*b* may be sealed together so as to form a chamber 12912. A capture medium 12906 may be housed between the portions of material 12910*a* and 12910*b* and attached to a tether 12904 that may, in turn, be attached to one or both of the portions of material 12910*a* and 12910*b*. The portions of material 12910*a* and 12910*b* may, as seen in FIG. 129A, be folded or pleated such that an opening 12908 in the portions of material 12910*a* and 12910*b* is aligned with the capture medium 12906, as shown in FIG. 129A. The capture medium, for example, may be a thin porous material, such as cellulose, tissue paper, a paper towel, cotton, rayon, or other material that is hydrophilic but also has permeability so as to air flow therethrough. Generally speaking, and fibrous, e.g., textile-based (woven or unwoven), material that is hydrophilic in nature may be used. Such material may, in some implementations, have a thickness of 0.1 mm to 1 mm, which may provide sufficient adsorption surface area to collect a usable breath constituent sample from breath flowed therethrough but may also provide a flow resistance that is low enough that it is feasible to flow an exhaled breath sample therethrough (in some instances, with the assistance of a vacuum assist system).

Figure 129B:
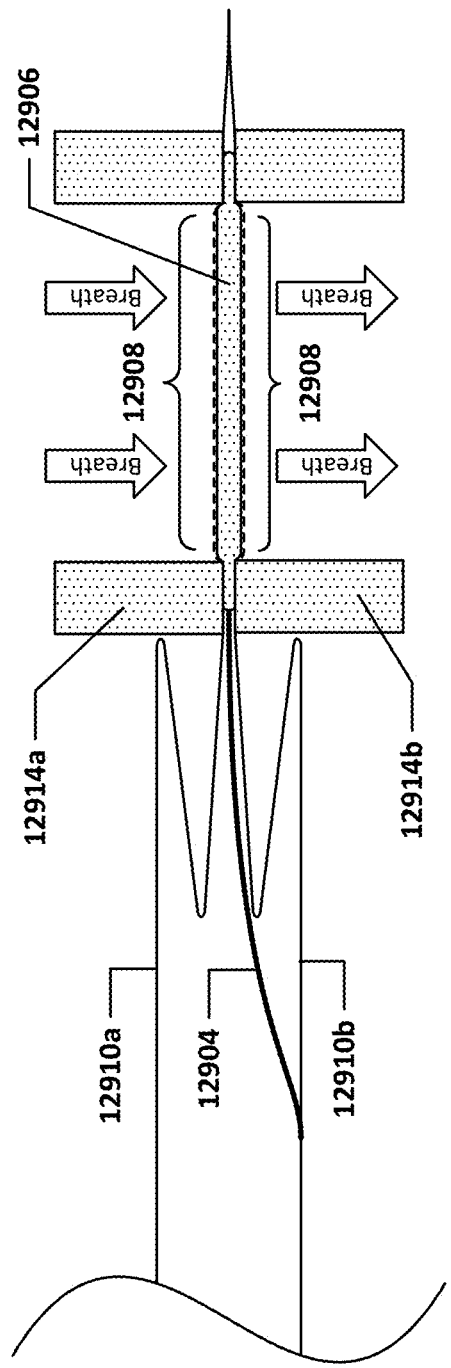

In FIG. 129B, the portion of the portions of material 12910*a* and 12910*b* in which the opening 12908 is located may be clamped between, for example two rigid or semi-rigid wall structures 12914*a* and 12914*b* that may provide a constrained flow path from a mouthpiece or other structure through which a breath sample or fluid may be flowed in order to expose the capture medium 12906 to the exhaled breath. In some implementations, the capture medium 12906 and the wall structures 12914*a/b* may be sized such that the capture medium 12906 is clamped between the wall structures 12914*a/b*, as shown, and in other implementations, the capture medium 12906 and the wall structures 12914*a/b* may be sized such that the wall structures 12914*a/b* clamp the portions of material 12910*a/b* but not the capture medium 12906.

In FIG. 129C, the wall structures 12914*a/b* have been removed after the breath sample has been flowed through the opening 12908 and the capture medium 12906; this configuration is nearly identical to that of FIG. 129A except that the capture medium 12906 now has breath sample constituents adsorbed thereupon.

In FIG. 129D, the portions of material 12910*a/b* that extend beyond the capture medium 12906 may be subjected to a tensile force that pulls the portions of material 12910*a/b* with the openings 12908 away from the capture medium 12906 such that the pleats/folds of the portions of material 12910*a/b* are stretched out/unfolded so as to bracket the capture medium 12906, which may be prevented from following the extended parts of the portions of material 12910*a/b* by the tether 12904. Thus, after the portions of material 12910*a/b* are extended, the capture medium 12906 may be located between the portions of material 12910*a/b* that do not have the openings 12908 therein.

In FIG. 129E, the portions of material 12910*a/b* that are between the capture medium 12906 and the openings 12908 may be subjected to a heat-sealing operation, e.g., by being clamped between two structures and subjected to heat, as suggested by the arrows indicating compression and the wavy lines indicating the supply of heat to the portions of material 12910*a/b* clamped between the two depicted blocks. After the capture medium has been sealed within the chamber 12912, the sample adsorbed thereupon may, for example, be eluted by flowing an eluent into the now-sealed chamber 12912 and then transported to other portions of a fluidic circuit for analysis and/or processing.

Figure 130A:
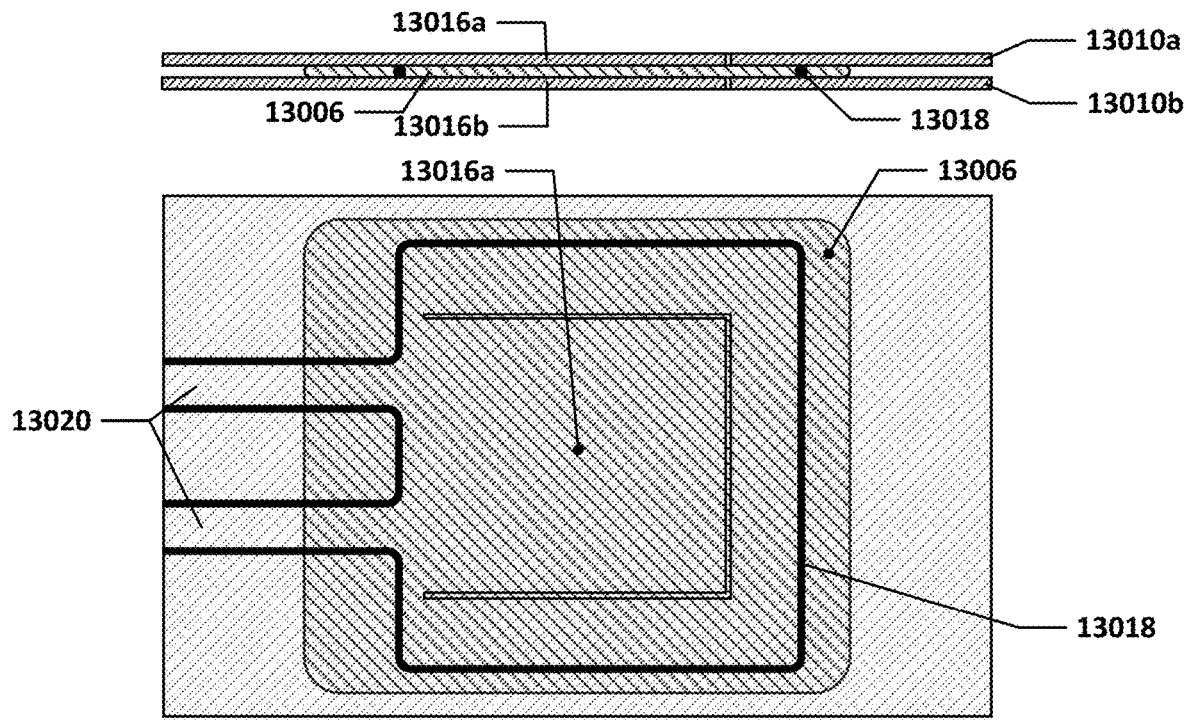
FIGS. 130A through 130F depict example structures that may be used to provide yet another breath capture module.

FIGS. 130A through 130F depict various stages of operation for yet another breath capture module. Each of FIGS. 130A through 130F depicts a side section view of the breath capture module at top as well as a plan view of the breath capture module at bottom. As can be seen in FIG. 130A, two portions of material 13010*a* and 13010*b* have interposed between them a capture medium 13006. The portions of material 13010*a* and 13010*b* may be sealed together by a permanent seal 13018 that may define a chamber in which the breath sample is to be captured. The capture medium 13006 in this example is sized larger than the chamber defined by the permanent seal 13018 and is thus anchored in place by the permanent seal 13018. However, in other implementations, the capture medium 13006 may be sized smaller than the chamber, e.g., such that it is entirely within the permanent seal 13018. In some such implementations, the capture medium 13006 may be affixed to one or the other of the portions of material 13010*a* or 13010*b*. The chamber may be fluidically connected with one or more flow paths 13020 (two are shown, but more or fewer such flow paths may also be provided).

Each portion of material 13010*a/b* may have a flap 13016*a/b*, respectively, that overlaps the capture medium 13006 and which may be peeled back to expose the capture medium 13006 positioned there beneath. The flaps 13016*a/b* may, for example, be formed by cutting a U-shaped or similar cut in the portions of material 13010*a/b*.

Figure 130B:
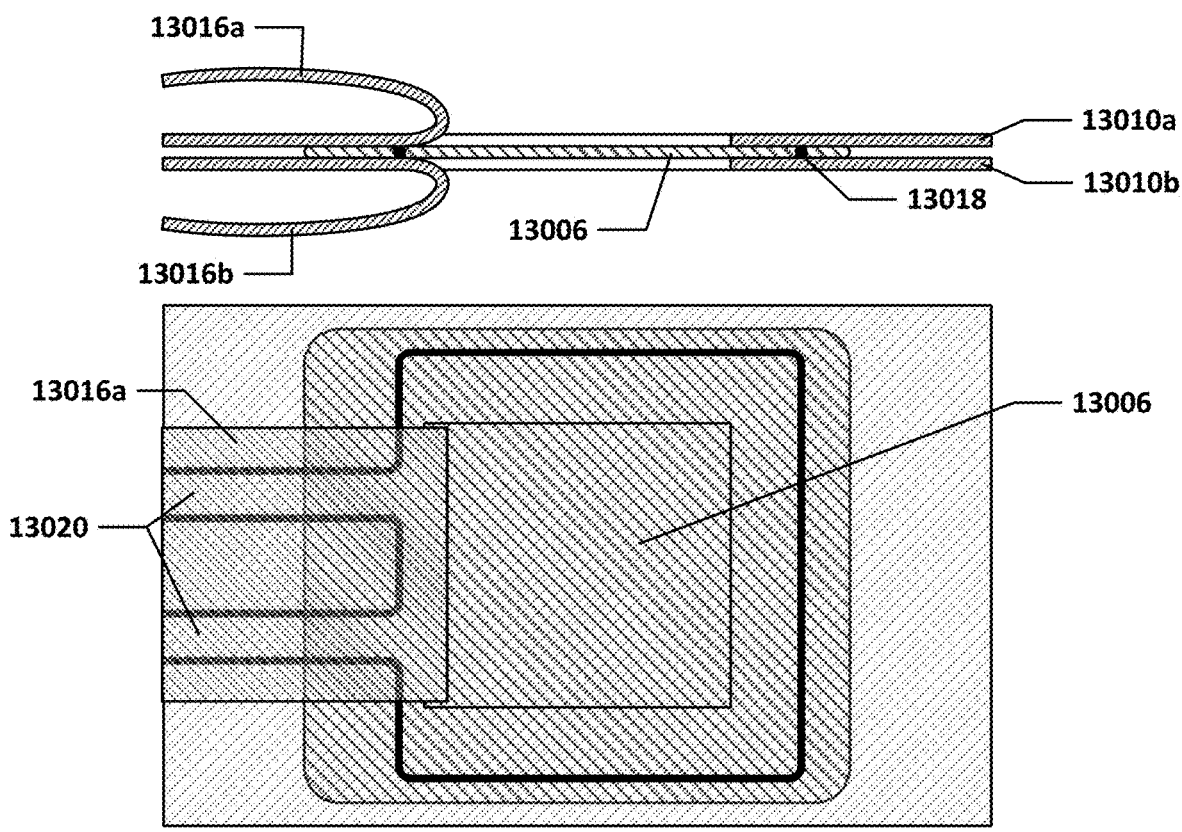

FIG. 130B shows the fluidic structure of FIG. 130A with the flaps 13016*a/b* pulled away and folded back from the capture medium 13006, thereby exposing the capture medium 13006.

Figure 130C:
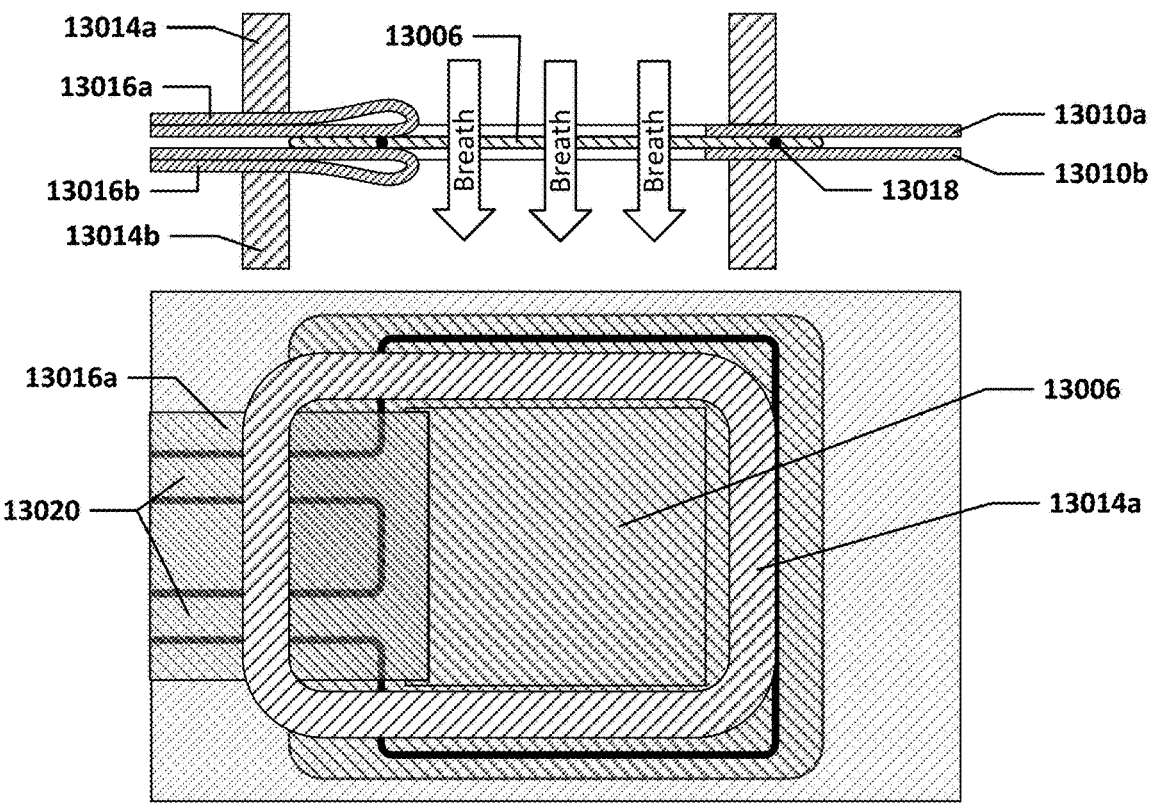

FIG. 130C shows the fluidic structure of FIG. 130B with two sets of wall structures 12914*a/b* that are placed so as to clamp the portions of material GA10*a/b* around the opening in the portions of material 13010*a/b*, thereby providing a plenum through which air, e.g., from a breath sample, may be flowed. Such wall structures may, for example, constrain the air flow such that it must pass through the capture medium 13006.

Figure 130D:
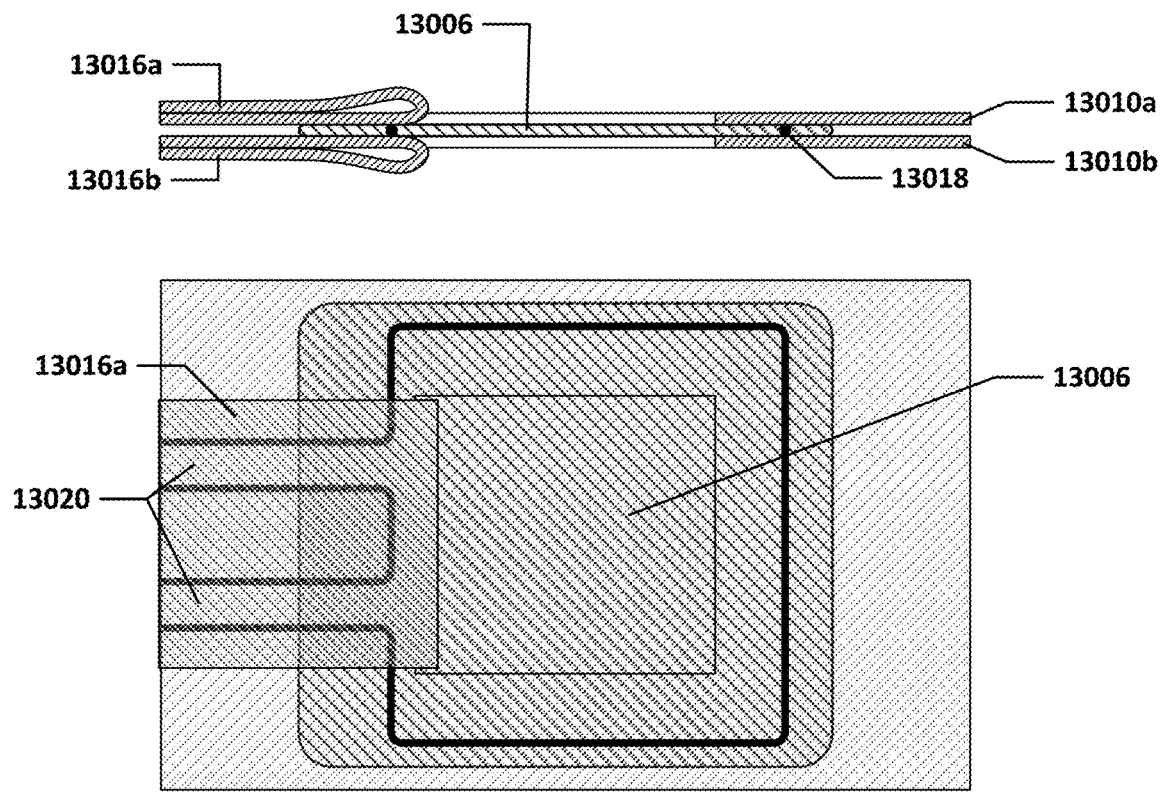
Figure 130E:
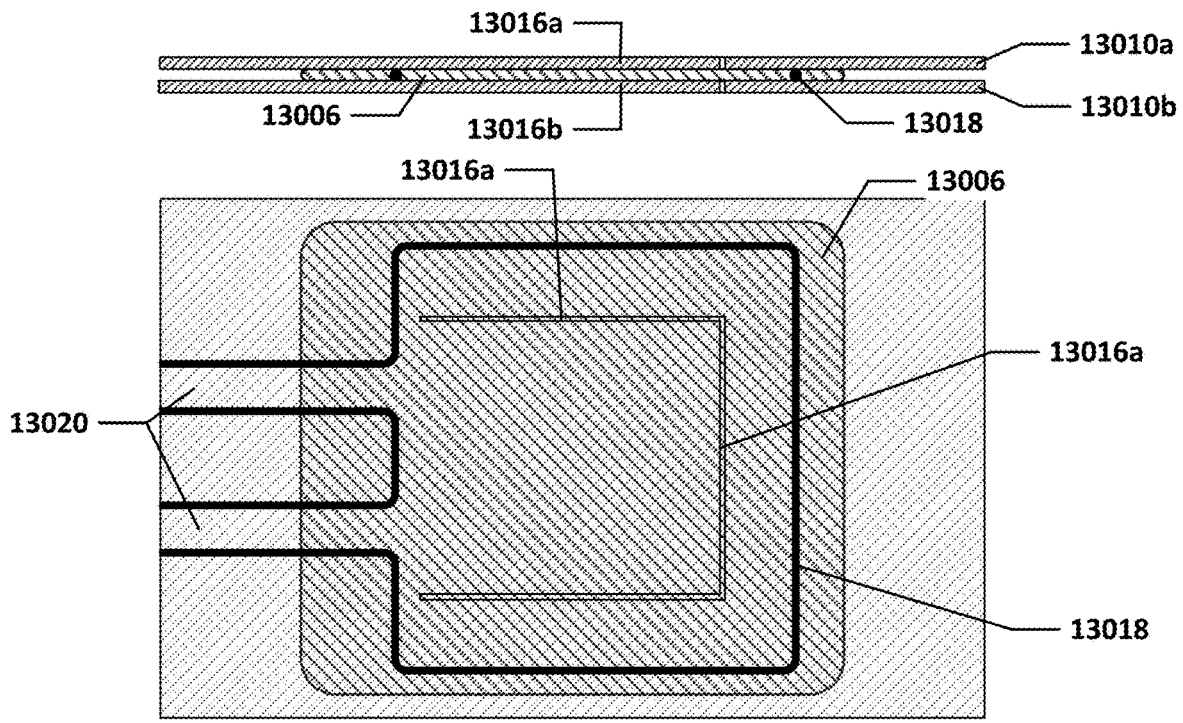

In FIG. 130D, the wall structures have been removed, and in FIG. 130E, the flaps 13016*a/b* have been folded flat against the capture medium 13006.

Figure 130F:
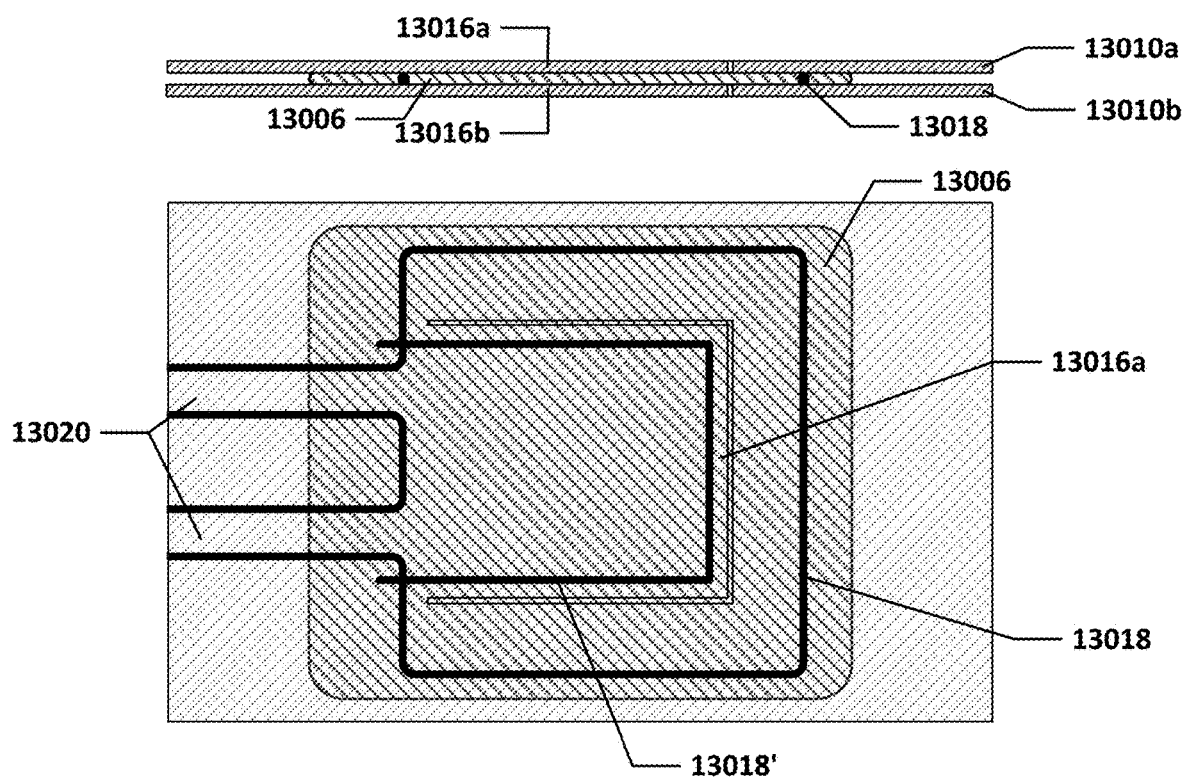

In FIG. 130F, an additional permanent seal 13018' has been applied to the portions of material 13010*a/b*, e.g., by clamping particular portions of the portions of material 13010*a/b* together and applying heat to the clamped-together portions. The additional permanent seal 13018' may extend around the perimeter of the flaps 13016*a/b*, there by sealing the two flaps 13016/*a/b* together with the capture medium 13006 sandwiched therebetween. The additional permanent seal 13018' may also extend so as to cross over the permanent seal 13018, thereby creating a sealed chamber that includes a portion of the capture medium 13006 that was earlier exposed to the flow of breath therethrough.

In other similar such implementations, the capture medium may instead be unsupported by either portion of material 13010*a* or 13010*b*, e.g., it may be attached to one of the flaps 13016*a/b* near where that flap 13016*a* or 13016*b* attaches to the rest of the respective portion 13010*a* or 13010*b*. In such implementations, the wall structures 13014*a/b* may instead clamp directly on the capture medium 13006.

Figure 131:
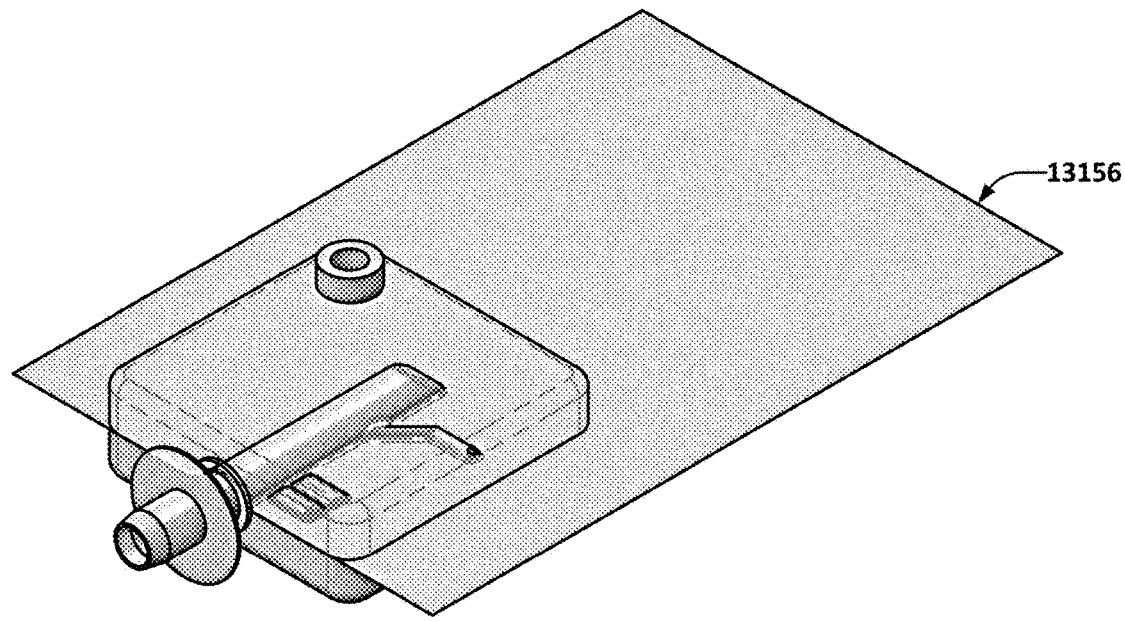
FIGS. 131 and 132 depict an example breath capture fluidic structure.
Figure 132:
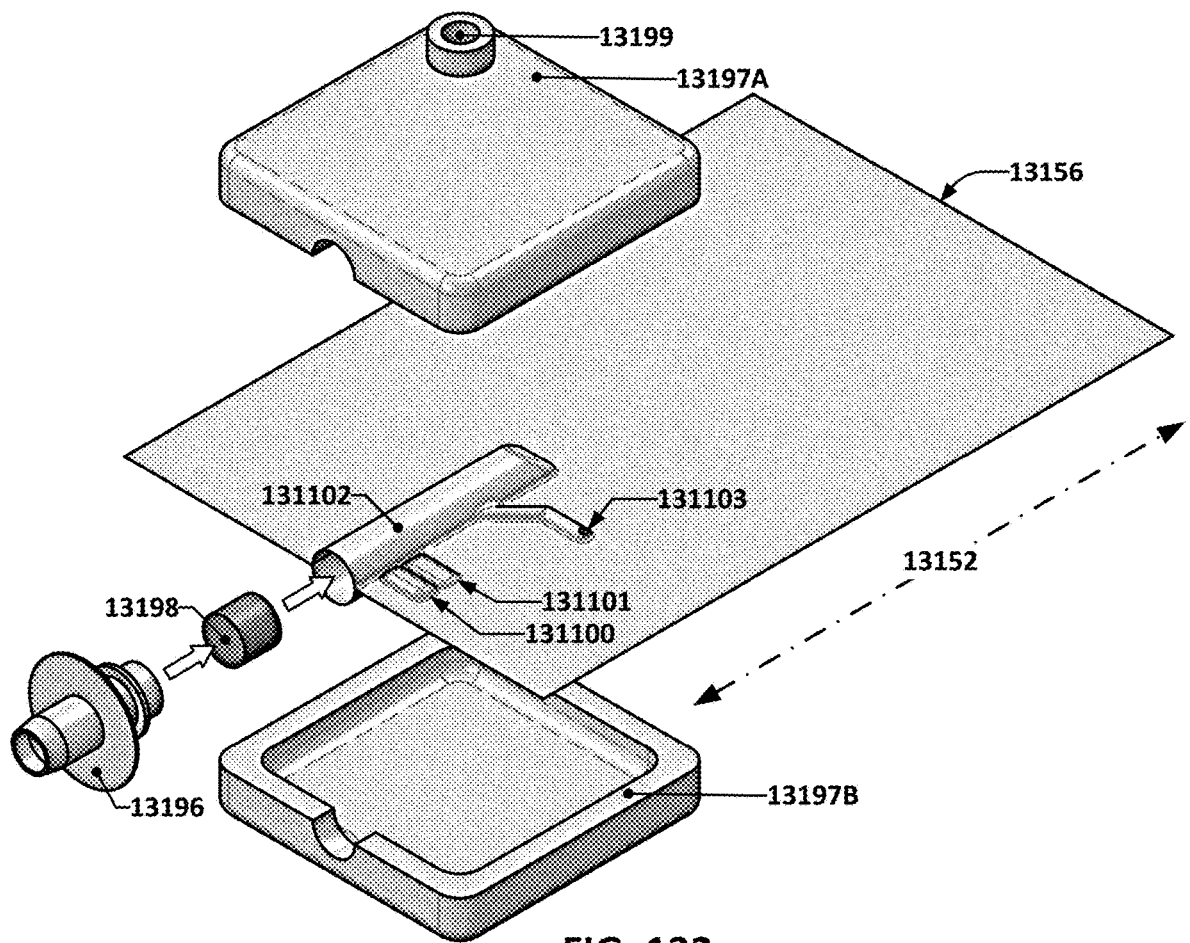

FIGS. 131 and 132 depict two views of another sample collection module, e.g., a breath collection module, that may be used to obtain a breath sample in a fluidic structure such as those discussed herein. In FIGS. 131 and 132, a fluidic structure 13156 is shown—the fluidic structure 13156 may have a plurality of different fluidic structures arranged therewithin, e.g. fluidic structures such as those discussed herein. Such additional fluidic structures are not depicted here since the focus of this example is on the fluidic structures shown in FIGS. 131 and 132.

As seen in FIGS. 131 and 132, the fluidic structure 13156 may include a main passage 131102 that is sized to accept capture media 13198 and a mouthpiece 13196. The main passage 131102 is shown in an "inflated" state, forming a generally circular tunnel, but can also be collapsed flat or nearly flat when the mouthpiece 13196 is removed and the main passage 131102 subjected to a clamping pressure zone. The capture media 13198 may, for example, be made of a porous, compressible material, e.g., foam, fibrous mesh, or other material that is sufficiently porous that a person is able to exhale therethrough but which is also able to provide a high surface-area-to-volume ratio that facilitates adsorption of breath constituents that, e.g., aerosols, molecular components, etc., that may be in breath that is exhaled therethrough.

The main passage 131102 may, at the end opposite the opening in which the mouthpiece 13196 is inserted, be sealed with a temporary seal. The temporary seal may act to seal the main passage off from the remainder of the downstream fluidic structures that may be present (and which are not shown).

In preparation for breath sample collection, the fluidic structure 13156 may be clamped between vacuum manifolds 13197A and 13197B. The vacuum manifolds 13197A and 13197B may, when clamped together with the fluidic structure 13156 clamped therebetween, seal against the fluidic structure 13156. At the same time, the mouthpiece 13196 that is inserted into the fluidic structure 13156 may act to push the portions of the fluidic structure 13156 that surround the mouthpiece 13196 into contact with the vacuum manifolds 13197A and 13197B.

When vacuum is drawn on the vacuum manifolds 13197A and 13197B, e.g., via vacuum port 13199, the pressure within the vacuum manifolds 13197A and 13197B may be reduced to sub-atmospheric levels. As a result, the portions of the fluidic structure 13156 that are subjected to such negative pressure and that are in fluidic communication with the ambient environment, e.g., the main passage 131102, may be caused to inflate due to the higher pressure that is applied by the ambient atmospheric pressure.

The main passage 131102 is fluidically connected with a vacuum assist port 131103, which may provide a source of assistive suction to help with breath sample collection. The main passage 131102 must be fluidically connected with either an outlet to ambient atmospheric pressure or with a sub-atmospheric pressure environment so that a subject is able to actually exhale through the main passage 131102 and the capture media contained therewithin. In implementations featuring a fluidic connection to an atmospheric pressure environment, the main passage 131102 may, for example, be fluidically connected with another passage that extends through the side walls of the vacuum manifolds, e.g., similar to how the main passage 131102 does. In implementations such as the depicted example, however, the main passage may be fluidically connected with a vacuum assist port 131103 that fluidically connects the interior of the main passage 131102 with the sub-atmospheric pressure environment within the clamped-together vacuum manifolds 13197A and 13197B. Thus, when a vacuum is drawn on the vacuum manifolds 13197A and 13197B via the vacuum port 13199, the sub-atmospheric pressure within the vacuum manifolds 13197A and 13197B will act to draw air from within the main passage 131102 into the vacuum manifolds 13197A and 13197B and out through the vacuum port 13199. This suction may assist in helping the subject breath through the capture media 13198.

A subject may, during testing, breath through the mouthpiece 13196 for a specified time period, number of exhalations, or total exhaled breath volume (e.g., as may be measured by a flow meter that may be included in the system), thereby facilitating the collection of a breath sample by the capture media 13198. Once the breath sample is collected, the mouthpiece 13196 may (optionally) be removed and the vacuum manifolds 13197A and 13197B unclamped, thereby releasing the fluidic structure 13156. A clamping pressure zone may then be applied to the fluidic structure 13156 and moved across the fluidic structure 13145 and along the axis 13152, starting at a location near the open end of the main passage 131102 and moving towards the closed end of the main passage 131102.

In doing so the clamping pressure zone may cause a temporary seal for elution blister or chamber 131100 to rupture or release, allowing an eluent contained therewithin to flow into, for example, a lyophilized material blister or chamber 131101 before being directed to flow into the main passage 131102. The elution blister 131100 may be fluidically connected with the lyophilized material blister 131101 via a temporary seal that ruptures when the elution blister is pressurized by the advancement of the clamping pressure zone along the axis 13152. Similarly, the lyophilized material blister 131101 may be fluidically connected with the main passage 131102 by a temporary seal that ruptures when the clamping pressure zone advances further along the axis 13152. The temporary seal that seals the lyophilized material blister 131101 off from the main passage 131102 may be positioned such that is proximate the capture media 13198.

Thus, as the clamping pressure zone moves across the fluidic structure 13156, the clamping pressure zone may first force the eluent into the lyophilized material blister 131101, where it may mix with the lyophilized material contained therewithin, and then force the mixture into the main passage 131102, where it may absorb into the capture media, thereby eluting captured breath sample. If desired, the clamping pressure zone may be moved back and forth across the elution blister 131100 and the lyophilized material blister 131101 to facilitate mixing of the eluent with the lyophilized material and/or dissolution of the lyophilized material in the eluent. After allowing the eluent to elute the collected breath sample, the clamping pressure zone may be caused to move further along the axis 13152, thereby driving the eluent from the capture media 13198 and towards the temporary seal at the end of the main passage 131102. When the clamping pressure zone continues to move towards the temporary seal, the resulting pressure increase in the eluted breath sample solution may cause the temporary seal to rupture, thereby allowing the eluted breath sample solution to be delivered to various downstream fluidic structures, e.g., in order to facilitate analysis.

The fluidic circuits discussed herein may be used in the context of fluidic circuit systems that may be used to perform a variety of fluidic operations, including fluidic operations in support of performing an assay or other type of analysis. It will, however, be understood that the fluidic circuits of FIGS. 126A through 126D, in particular, may be used to perform an assay or assays. In some such assays, the substance that the assay(s) are configured to detect and/or quantify may be THC or an associated compound.

The following discussion provides several examples of different chemical elements or compounds that may be used in such an assay in order to detect or measure a quantity of THC or related compound.

For example, the solution that may be used to elute a collected breath sample from the breath capture module may, generally speaking, include or more detergents to break down or process captured aerosol droplets or particles, thereby releasing the desired analyte (e.g., THC or related compound) into solution. Furthermore, the pH of the extraction solution can be modified to facilitate solubility of the analyte within the solution. For instance, the pH can be optimized to be near the pKa of functional groups that will provide a charged species, thereby increasing solubility of the analyte within an aqueous solution.

In the event that the analyte is THC or a related compound, the elution or extraction solution may include a detergent that releases THC from aerosol droplets or particles. The extraction solution can also possess a pH of about 9 to enhance solubility of THC in the solution. Non-limiting detergents include an anionic detergent, such as a bile acid, a bile salt, or a derivative thereof, as well as other detergents described herein. The extraction solution may, for example, result from mixing the contents of, for example, chambers L and M from FIG. 126C or 126D or may be provided by a single chamber or may be provided by a single chamber, e.g., without mixing.

In some embodiments, the extraction solution allows for a minimal working volume, thereby reducing the risk of further diluting the analyte in the systems, apparatuses, and devices described herein. Furthermore, detection (e.g., by use of an immunoassay) can be performed in the presence of the extraction solution, thus reducing the number of separating and/or rinsing steps that can further dilute the sample.

In use, the extraction solution can facilitate the isolation of the desired analyte from the captured breath sample or the captured ambient air sample. For instance, the extraction solution can be optimized to separate the analyte from surfactant molecules that are present in the breath sample, thereby releasing the analyte to allow the analyte to be flowed downstream for measurement. In another instance, the extraction solution can be optimized to separate the analyte from the surface of particular matter that are present in the ambient air sample, thereby releasing the analyte.

One non-limiting extraction solution includes: (i) a detergent at a concentration of about 0.1 to about 1% by weight (e.g., about 0.1 (w/w) % to about 1 (w/w) %); and (ii) a buffering agent at a concentration to provide a pH from about 8-10 (e.g., about 9.0-9.5). In one embodiment, the same formulation of the extraction solution may be employed to process both the breath sample and an ambient air sample that is collected within the same fluidic circuit or structure. In further embodiments, the same extraction solution is employed with an immunoassay without further diluting the eluted breath sample or the eluted ambient air sample.

In some embodiments, the detergent includes a bile acid, a bile salt, or a derivative thereof, as well as any described herein. In particular embodiments, the detergent includes deoxycholic acid, cholic acid, or a salt thereof. In other embodiments, the detergent includes a structure of formula (I):

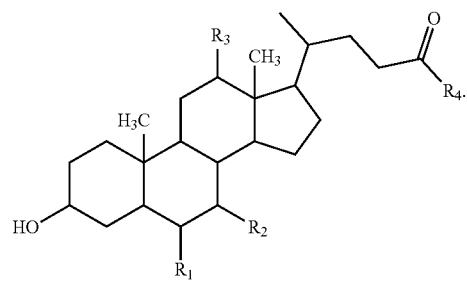

(I) or a salt thereof and/or an isomer thereof, wherein: each of $R_1$, $R_2$, and $R_3$ is, independently, H, hydroxyl, or optionally substituted alkyl; and $R_4$ is H, hydroxyl, optionally substituted alkyl, optionally substituted heteroalkyl, optionally substituted amino, or optionally substituted heterocyclyl. In other embodiments (e.g., for formula (1) or a salt thereof and/or an isomer thereof), $R_4$ includes an anionic moiety. By anionic moiety is meant a monoatomic or polyatomic species having one or more elementary charges of the electron.

In some embodiments, the buffering agent includes a buffering agent, e.g., a zwitterionic buffering agent. Non-limiting zwitterionic agents include 3-(cyclohexylamino)-2-hydroxy-1-propanesulfonic acid (CAPSO), 3-(cyclohexylamino)-1-propanesulfonic acid (CAPS), 3-([1,1-dimethyl-2-hydroxyethyl]amino)-2-hydroxypropane sulfonic acid (AMPSO), a free acid form thereof, or a salt form thereof, as well as any others described herein.

The extraction solution can include one or more other additives. Non-limiting additives can include a non-ionic detergent, an anionic detergent, a cationic detergent, a zwitterionic detergent, an ionic detergent, a buffering agent, a solvent (e.g., an aqueous solvent), a phospholipase, a chelating agent, an antioxidant, a salt, a protein, an amino acid, an enzyme, a denaturant, a protease inhibitor, a reducing agent, a sugar, a polyol, a betaine, and the like, as well as combinations thereof. Further extraction solutions, as well as methods and apparatuses using such solution, are described in U.S. Provisional Application No. 63/201,389, filed Apr. 27, 2021, titled "BREATH ANALYTE DETECTION AND MEASUREMENT," which is incorporated herein by references in its entirety. In some implementations, e.g., in particular types of assays, antibodies that may be specific to the substance of interest may be included as an additive in the extraction solution. For example, as discussed herein, in some assays, antibodies may be included in the extraction solution (eluent) and may bind to the target substance in the sample that is extracted or eluted by the extraction solution.

Various components of an extraction solution for use in isolating and/or evaluating an analyte obtained from a breath sample and/or an ambient air sample. The extraction solution can include one or more detergents, which can assist in releasing the analyte from surfactant molecules present in the breath sample and/or the ambient air sample.

In some instances, the concentration of the detergent can be close to the critical micelle concentration (cmc). The cmc indicates the concentration at which micelles form within a solution. The cmc can depend on the structure of the detergent, as well as various conditions, such as temperature, salt concentration, pH, buffer component, etc. Non-limiting cmc values can include from about 0.01 (w/w) % to 1.0 (w/w) %; or from about 0.5 mM to 25 mM in water at 25°

C. Non-limiting concentrations of one or more detergents in the extraction solution can include, e.g., from about 0.01 (w/w) % to 2.5 (w/w) %; or from about 0.5 mM to 50 mM.

In some implementations, elution solvents may be selection to target and solubilize phospholipid "scabs" that may form due to impaction of breath constituents within a breath capture module, e.g., on a capture medium, so as to release the species of interest into solution. Addition of surfactants such as polysorbate 20 (such as Tween 20) or Triton (offered by Dow Chemical Company) in the range of 0.1-1% by mass can assist in solubilizing phospholipids dried on surfaces of the BCM.

In addition to surfactants, other agents which may be alternatively or additionally used to solubilize phospholipids may also be added to improve elution efficiency. Of particular interest are a class of bile acid salts—sodium salts of cholic acid and deoxycholic acid, which have a biological function of digesting cellular membranes and are hence very effective in solubilizing phospholipids. Typical concentrations of these bile salts range between 0.1-1%. These bile salts can also be used in combination with other surfactants for potentially synergistic effects.

Phospholipases, a class of enzymes which are specific to digesting phospholipids, may also be used to solubilize DPPC and release the analyte of interest into solution. Phospholipases A, B, C, and D act on different regions of the phospholipid molecule. A combination of these enzymes in concentrations of 0.01-0.5 IU/mL may be used in the elution buffer in some implementations.

The pH of the elution buffer may also contribute to solubilization of the analyte of interest. For example, THC has higher solubility at pH>8, in which case the elution buffer used for THC collection may be selected to have a high pH, e.g., >8. Buffers such as MOPS, carbonate, borate, Tris, etc. can be adjusted to a pH between 8-10 and may thus be suitable for such usage. The higher pH may be combined with other strategies described above to maximize solubilization of target analyte.

In various embodiments, in order achieve a desired degree of sensitivity, e.g., picogram sensitivity, that may allow for reliable THC detection and/or quantification, an immunoassay or other highly sensitive detection and measurement technique, such as chemical assays, enzymatic assays, electrochemical detection/sensors, etc., may be used. Suitable immunoassays may include surface-based antibody-down immunoassays, surface-based antigen-down immunoassays, noncompetitive immunoassays, heterogeneous competitive immunoassays, and homogeneous competitive immunoassays. Several suitable immunoassays will now be described with reference to FIGS. 133-137. The operation of these immunoassays and their generalization to other recognition elements and analytes will be well understood, and implementation details for suitable immunoassays will be readily ascertained, by those of ordinary skill in the art.

As described herein, any appropriate assay or sensor, including immunoassays, chemical assays, enzymatic assays, amplification assays, ligation assays, polymerase-based assays, electrochemical detection/sensors, piezoelectrical detection/sensors, nanopore-based detection/sensors, mass spectrometry, Raman spectroscopy, infrared spectroscopy, near infrared spectroscopy, etc., may be used to detect and quantify a wide range of analytes in breath and in ambient air that are captured as described herein. The immunoassays described with specific reference to the example of the analyte THC may be readily adapted to other analytes in breath, such as are further referenced and described below, as will be well understood by those of ordinary skill in the art given the disclosure provided herein.

The assay can include any that can be used to determine an amount of the analyte or to evaluate an analyte level. In particular embodiments, the assay is an immunoassay that employs a capture agent that can directly or indirectly bind the target analyte. Further, multiple capture agents (e.g., optionally employed with one or more linkers and/or detectable labels) can be used to bind the target and provide a detectable signal for such binding. Exemplary linkers include any useful linker, such as polyethylene glycol (e.g., $(CH_2CH_2O)_m$, where $m$ is from 1 to 50), a covalent bond, an alkylene group (e.g., an optionally substituted $C_{1-12}$ alkylene or alkynyl chain), a heteroalkylene group, a carbocyclic ring (e.g., an aromatic ring, such as a phenyl group), and/or a polypeptide (e.g., a dipeptide, tripeptide, etc.). Such linkers can be installed in any useful manner, such as by using aromatic electrophilic substitution reactions, click-chemistry reactions, azo coupling reactions, etc. The capture agent may, for example be mixed with the extraction solution or eluent discussed above.

Non-limiting capture agents include one or more of the following: a protein that binds to or detects one or more targets (e.g., an antibody including monoclonal or polyclonal forms thereof, an affibody, an enzyme, or fragments or recombinant forms of any of these), a globulin protein (e.g., bovine serum albumin), an amino acid, a peptide (e.g., a polypeptide, including modified forms thereof, such as glycosylated polypeptides or multimeric polypeptides), a polysaccharide (e.g., a cyclic polysaccharide), a nucleic acid (e.g., a nucleotide, a single stranded DNA, a single stranded RNA, an oligonucleotide, DNA probes, RNA probes, including modified forms of any of these), an aptamer, a thioaptamer, a lectin, a cell surface receptor, a nanoparticle, a microparticle, a sandwich assay reagent, a label (e.g., one or more fluorescent labels, colorimetric labels, quantum dots, nanoparticles, microparticles, barcodes, radio labels (e.g., RF labels or barcodes), avidin, streptavidin, biotin, tags, dyes, an enzyme that can optionally include one or more linking agents and/or one or more dyes, as well as combinations thereof), a catalyst (e.g., that reacts with one or more targets), a lipid (e.g., a glycosylated lipid), and/or an enzyme (e.g., that reacts with one or more targets, such as any described herein). The capture agent can optionally include one or more labels, e.g., any described herein. In some embodiments, more than one capture agent, optionally with one or more linking agents, can be used to detect a target of interest.

In particular embodiments, the assay is an immunoassay, in which the capture agent is an antibody that specifically binds to the target analyte. For instance, for the target analyte that is THC, the antibody can be an anti-THC antibody.

The assay can be conducted to determine an amount of the analyte. In some embodiments, the assay is conducted in the presence of the extraction solution, thereby forming a complex. In some embodiments, the complex is formed between the target analyte (e.g., an antigen) and the capture agent configured to bind the analyte (e.g., an antibody). The target analyte can include those particular analyte compounds present within the test sample or the control sample, as well as those present as immobilized compounds on any surface within the system, apparatus, or device (e.g., immobilized on surfaces of a channel, a bead, a particle, etc.—for example, in the implementation of FIGS. 126C and 126D, within chamber(s) B). Furthermore, the complex can be formed by binding between an immobilized capture agent and a target analyte; between an immobilized target analyte and the capture agent(s); or between a target analyte and a detectable label, as can be present during various embodiments of sandwich assays, antigen-down assays, competition assays, or other immunoassay formats, as described herein.

A further operation can include forming a labeled complex having a detectable label. The labeled complex can include a target analyte bound directly or indirectly to a detectable label, which can be formed by exposing the analyte to the detectable label. Such labeled complexes can be captured by immobilized capture agents, in a direct binding or competitive binding format. In other embodiments, the labeled complex can include a target analyte, one or more capture agents, and a detectable label (e.g., which can bound directly or indirectly to the target analyte and/or the capture agent(s)). The detectable label, for example, may be provided by mixing fluids from two otherwise separate chambers, e.g., chambers L and M in FIGS. 126C and 126D, for example.

The complex or the labeled complex can be further treated with any useful reagent to conduct a detection assay that can improve the limit of detection. For instance, one such reagent can be a signal amplification reagent, which provides a detectable signal indicative of the formation of the complex. Such a signal amplification reagent can be a tyramide reagent to conduct a tyramide signal amplification reaction, which provides a detectable signal in the presence of an enzyme (e.g., horseradish peroxidase) that can be present within the complex. In another instance, the reagent can be a connector oligonucleotide to conduct a proximity ligation assay, which provides a detectable signal in the presence of the complex having oligonucleotide tags. Other reagents and detection assays are described herein.

The labeled complex can optionally include a bead or a particle, as described herein; and the target analyte(s), capture agent(s), and/or detectable label(s) can be disposed on the bead (e.g., disposed on a surface of a bead by way of one or more optional linkers). Such beads and particles can include nanoparticles, microparticles, and such in any useful format (e.g., solid, core-shell, multilayer particles) and any useful material (e.g., metallic, polymeric, silica, magnetic, and/or fluorescent materials).

Any useful detectable label can be employed. In certain instances, the detectable label can be any that provides a detectable signal indicative of a presence or an absence of the target analyte after conducting the assay. The labels can provide a fluorescent signal, a chemiluminescent signal, an electroluminescent signal, a luminescent signal, a radiation signal, an electric signal, an electrochemical signal, an optical signal, or a colorimetric signal. Such detectable labels can be provided (e.g., by way of flow) to a reaction chamber configured to conduct the assay. In some embodiments, the label is a substrate, which can include a chromogenic substrate, a fluorogenic substrate, a fluorescent substrate, a chemiluminescent substrate, and others. Such a substrate can be configured to provide a detectable signal upon performing a reaction (e.g., a binding reaction, a covalent reaction, an enzymatic reaction, etc.).

Non-limiting detectable labels can include a dye, such as an electroactive detection agent, a fluorescent dye, a luminescent dye, a chemiluminescent dye, a colorimetric dye, a radioactive agent, a particle (e.g., such as a microparticle, a nanoparticle, a latex bead, a colloidal particle, a magnetic particle, a fluorescent particle, a coated particle), a quantum dot, a nanoparticle, a microparticle, a barcode, or a label, such as an electroactive label, an electrocatalytic label, a fluorescent label, a colorimetric label, or a radio label (e.g., an RF label or barcode), an enzyme (including fragments or recombinant forms, as well as enzymes that can optionally include one or more linking agents and/or one or more dyes), a globulin protein (e.g., bovine serum albumin), an amino acid, a peptide (e.g., a polypeptide), a polysaccharide (e.g., a cyclic polysaccharide), a nucleic acid (e.g., a DNA probe, RNA probe, including modified forms of any of these), a sandwich assay reagent, a capture agent (e.g., configured to bind to the target analyte or another capture agent), avidin, streptavidin, biotin, a tag, a catalyst (e.g., that reacts with one or more reagents that can provide a detectable signal), as well as combinations thereof. Non-limiting enzymes include a peroxidase, a phosphatase, an oxidase, a lactase, a caspase, or a caspase, including horse radish peroxidase, alkaline phosphatase, glucose oxidase, beta-galactosidase, and the like.

A detectable label can include direct or indirect binding in the complex (e.g., by way of a linker or another capture agent). Furthermore, the detectable label can be bound in the complex by way of non-covalent or covalent interactions. In one embodiment, the detectable label is provided employing click-chemistry reactions, azo coupling reactions, or other reactions to directly label the analyte or the capture agent.

A click chemistry reaction can be conducted by providing a click-chemistry reaction pair having a first group and a second group. Whereas one group of the pair is provided as part of the detectable label, the other group is provided as part of the analyte or the capture agent. The first and second groups can react to from a bond. Non-limiting click-chemistry reaction pairs include those selected from a Huisgen 1,3-dipolar cycloaddition reaction between an alkynyl group and an azido group to form a triazole-containing linker; a Diels-Alder reaction between a diene having a $4\pi$ electron system (e.g., an optionally substituted 1,3-unsaturated compound, such as optionally substituted 1,3-butadiene, 1-methoxy-3-trimethylsilyloxy-1,3-butadiene, cyclopentadiene, cyclohexadiene, or furan) and a dienophile or heterodienophile having a $2\pi$ electron system (e.g., an optionally substituted alkenyl group or an optionally substituted alkynyl group); a ring opening reaction with a nucleophile and a strained heterocyclyl electrophile; and a splint ligation reaction with a phosphorothioate group and an iodo group; and a reductive amination reaction with an aldehyde group and an amino group. Either of the groups described in the reactions above can constitute the first An azo coupling reaction can be conducted by providing a reaction pair having a first group and a second group, thereby forming an azo compound. Whereas one group of the pair can be provided as part of the detectable label, the other group can be provided as part of the analyte or the capture agent. For instance, the first group can be an amino group extending from an aromatic ring, which can be converted into a diazonium group ($-N_2^+$) in the presence of nitrous acid (HONO), which is typically generated by use of sodium nitrite ($NaNO_2$) and an acid (e.g., HCl, $H_2SO_4$, and the like). The second group can include an aromatic ring, in which functional groups present in the aromatic ring can direct the position in which the azo group ($-N=N-$) is present in the resulting azo compound. For instance, if the second group includes a phenol, then the azo group is typically attached to the ortho- or para-position of the second group. Any of the detectable labels herein can be modified to include an aromatic amine, which in turn can be converted into a diazonium group for participating in an electrophilic aromatic substitution reaction with an aromatic group present in the analyte and/or the capture agent. For instance, THC includes an aromatic phenol group, which can serve as the second group in the azo coupling reaction; and a detectable label can include any having an aromatic amine. For instance, the detectable label can be NH$_2$—Ar-Lk-[D]$_b$, in which Ar is an aromatic; Lk is a multivalent linker (e.g., a bivalent, trivalent, or tetravalent linker); D is an enzyme, biotin, avidin, a dye, a label, a quantum dot, a barcode, and/or a particle; and b is 1, 2, 3, 4, or greater. In particular embodiments, Lk is an optionally substituted alkylene, optionally substituted heteroalkylene, or a polyethylene glycol. The valency of the linker Lk can correspond to the number of D components included in the detectable label. For instance, if Lk is a trivalent linker, then b can be 2 to provide two D components.

Another further operation can include measuring a detectable signal arising from the labeled complex, wherein the detectable signal is indicative of a presence or an absence of the analyte. The measuring operation can include exposing the labeled complex to a source that provides the detectable signal. The source can be configured to produce the detectable signal from the detectable label. In some embodiments, a reaction chamber including the detectable label or labeled complex is exposed to the source. Non-limiting sources can include a source of radiation (e.g., electromagnetic radiation), light, optical energy, a magnetic field, an electric field, and the like.

Yet in other embodiments, a detectable signal is provided in a label-free methodology. For instance, such methodology can include mass spectrometry, Raman spectroscopy, infrared spectroscopy, or near-infrared spectroscopy, in which a label is not required. Rather, the analyte itself provides a chemical signature that indicates the presence of that analyte. For example, mass spectrometry provides one or more a molecular ion signals indicative of the ion fragments formed by a particular compound having a particular chemical structure. Similarly, Raman spectroscopy, infrared spectroscopy, and near-infrared spectroscopy provide corresponding signals indicative of the chemical structure for the analyte. Further examples are provided herein.

Figure 133B:
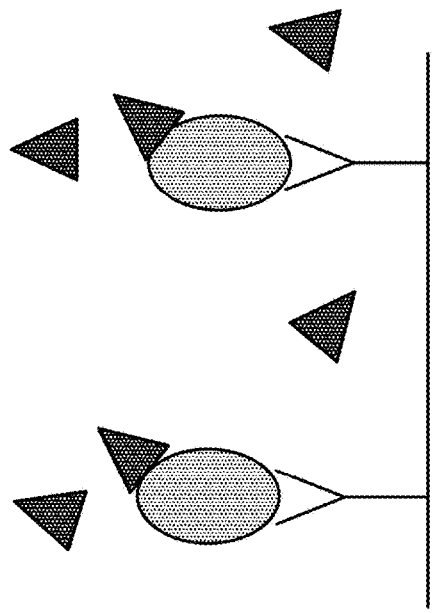
FIGS. 133A-133D depict a surface-based antibody-down immunoassay.

Such detection methodologies can be used with an immunoassay in some instances. FIGS. 133A-133D depict a surface-based antibody-down, direct diazonium reporter immunoassay. According to this immunoassay, a binder for an analyte of interest in breath, in this example THC, such as a monoclonal or polyclonal antibody, peptides, or aptamers, is/are surface-bound to the reaction chamber, e.g., chambers B in the fluidic circuit of FIG. 126C or 126D, walls or beads within such chambers according to well-known techniques. Such beads can include any described herein, including magnetic beads. Surface binding to the reaction chamber walls or beads may be accomplished by passive adsorption, covalent binding, or a combination, for example. THC from the breath sample portion or the ambient air sample portion can be eluted using the extraction solution, which is then drawn into the reaction chamber is captured by binding to the THC antibody, as depicted in FIG. 133A. In particular embodiments, this capture step is performed in the presence of the extraction solution. Suitable reagents and reaction conditions are well or readily ascertained by those of ordinary skill in the art given the description provided herein. For example, in one implementation, mouse monoclonal anti-THC antibody is immobilized on the surface via passive adsorption. In solution, THC from breath sample or the ambient air sample binds to the antibody immobilized on the capture surface.

Determining an amount of THC captured from a breath sample obtained from a subject or from an ambient air sample via this immunoassay can include flowing a detectable label. Here, this operation involves flowing a diazotized label (e.g., a diazotized fluorophore) into the reaction chamber and forming a solution, such that the diazotized label binds to any THC from the breath sample portion or the ambient air sample portion that is captured by binding to the THC antibody to form a diazotized label-THC adduct, as depicted in FIG. 133B. This adduct is a labeled complex, as well as a captured complex, as described herein.

In various embodiments, the diazotized label has the formula:

i. F—N+≡N X⁻·S b. wherein:
i. F is a functionalized fluorophore, enzyme, biotin, avidin, dye, label, capture agent, quantum dot, barcode, and/or particle;
ii. N+≡N is a diazonium functional group;
iii. X⁻ is a negatively charged ion balancing the charge on the diazo functional group; and
iv. S is a diazonium functional group stabilizer.

F can be an amine-functionalized label, such as a primary amine-functionalized label, in which the amine can be converted to form the diazonium functional group. The label can be a fluorophore, which can be any one of: xanthene, cyanine, naphthalene, coumarin, oxadiazole, anthracene, pyrene, oxazine, acridine, arylmethine, tetrapyrrole, green fluorescent protein, red fluorescent protein, yellow fluorescent protein, cadmium selenide quantum dot, cadmium selenide/zinc sulfide alloy quantum dot, cadmium selenide sulfide quantum dot, cadmium selenide sulfide/zinc sulfide alloy quantum dot, cadmium telluride quantum dot, cadmium sulfide quantum dot, lead sulfide quantum dot, or indium phosphide/zinc sulfide alloy quantum dot derivatives, and mixtures thereof. In particular examples, the fluorophore is a xanthene, for example a rhodamine, for example rhodamine 123, for example rhodamine 123 diazotized at a primary amine group. The label can also be a protein, such as an enzyme (e.g., a peroxidase, a phosphatase, an oxidase, a lactase, a caspase, or a protease). In other embodiments, the label can be a substrate configured to provide a detectable signal upon performing a reaction (e.g., a binding reaction, a covalent reaction, an enzymatic reaction, etc.). Non-limiting substrates can include a chromogenic substrate, a fluorogenic substrate, a chemiluminescent substrate, and others.

The F—N+≡N group of a suitable diazotized label is selected to bind to a cannabinoid. In various embodiments, the F—N+≡N binds to the para or ortho position of a phenol ring of tetrahydrocannabinol forming an N═N azo bond, such that an adduct is formed having the following formula:

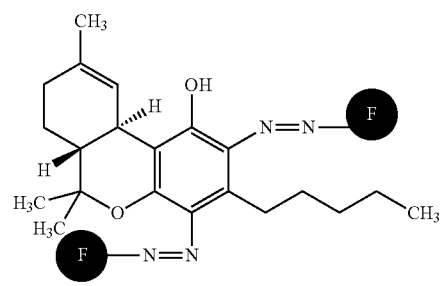

wherein F is the functionalized label, and only one or the other —N═N—F group is present.

The acidic diazotized label solution is formed from constituent materials in an acidic solution. For example, the acidic solution may contain dilute HCl, such as 100 µM HCl. Indicators/labels containing stabilized N+=N diazo functional groups can be been synthesized to rapidly (e.g., <2 min) and selectively bind to THC and/or derivatives thereof at the para or ortho position of the phenol ring forming an N=N azo bond. The binding produces a chemically bonded F-labeled THC adduct. The diazotized label is generally of the form:

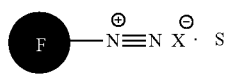

where:

F is a fluorophore, examples of which may include xanthene, cyanine, naphthalene, coumarin, oxadiazole, anthracene, pyrene, oxazine, acridine, arylmethine, tetrapyrrole, green fluorescent protein, red fluorescent protein, yellow fluorescent protein, cadmium selenide quantum dot, cadmium selenide/zinc sulfide alloy quantum dot, cadmium selenide sulfide quantum dot, cadmium seleninde sulfide/ zinc sulfide alloy quantum dot, cadmium telluride quantum dot, cadmium sulfide quantum dot, lead sulfide quantum dot, or indium phosphide/zinc sulfide alloy quantum dot derivatives; an enzyme, examples of which may include a peroxidase, a phosphatase, an oxidase, a lactase, a caspase, or a protease; biotin, avidin, or derivatives thereof; a dye, such as any described herein; a label, such as a radiolabel or any described herein; a capture agent, such as any described herein; a barcode; a particle, such as a nanoparticle or a microparticle, or any combination thereof;

$N^+\equiv N$ is a diazonium-functional group that is chemically attached (e.g., bonded, grafted, functionalized, or conjugated) to F;

$X^-$ is a negatively charged ion that charge balances the positively charged diazo functional group $N^+\equiv N$, examples of which may include a halide, fluoride, sulfide, chloride, nitride, bromide, iodide, arsenate, phosphate, arsenite, hydrogen phosphate, dihydrogen phosphate, borate, sulfate, nitrate, hydrogen sulfate, nitrite, thiosulfate, sulfite, perchlorate, iodate, chlorate, bromate, chlorite, hypochlorite, hypobromite, carbonate, chromate, hydrogen carbonate, dichromate, acetate, formate, cyanide, amide, cyanate, peroxide, thiocyanate, oxalate, hydroxide, or permanganate ion derivatives, or any combination thereof; and S is a $N^+\equiv N$ stabilizer, for prevention of decomposition of the diazo compound, composed of salts and/or polymers, examples of which may include tin chloride, cadmium chloride, manganese chloride, zinc chloride, sodium fluoroborate, aromatic, aliphatic, or heterocyclic sulfonic acids, sulfates, and chlorides, polymers with free terminal halo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, methylenedioxy, orthocarbonate ester, amide, amine, ammonium, imine, imide, azide, azo, diazo, cyanate, nitrate, nitrile, nitro, pyridine, thiol, sulfide, disulfide, sulfoxide, sulfone, sulfinic acid, sulfonic acid (e.g., naphthalene sulfonic acids, such as naphthalene-1,5-disulfonic acid and naphthalene-1,3,6-trisulfonic acid), camphosulphonic acid, thiocyanate, thione, thial, sulfonyl chloride, carbonyl chloride, phosphine, phosphonic acid, phosphate, phosphodiester, borohydrofluoric acid, boronic acid, boronic ester, boronic acid, borinic ester, fluoroborate (e.g., sodium fluoroborate), crown ether (e.g., 18-crown-6 ether), or any combination thereof.

Indicators including stabilized $N^+\equiv N$ diazo functional groups can be synthesized, for example, by a process including the combination of a primary amine (—$NH_2$) functionalized F (listed above), in an acidic solution ($H^+X^-$) with sodium nitrite ($NaNO_2$) and stabilizers, S (listed above):

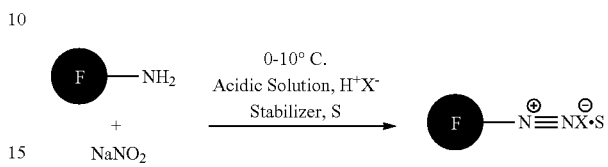

Figure 133D:
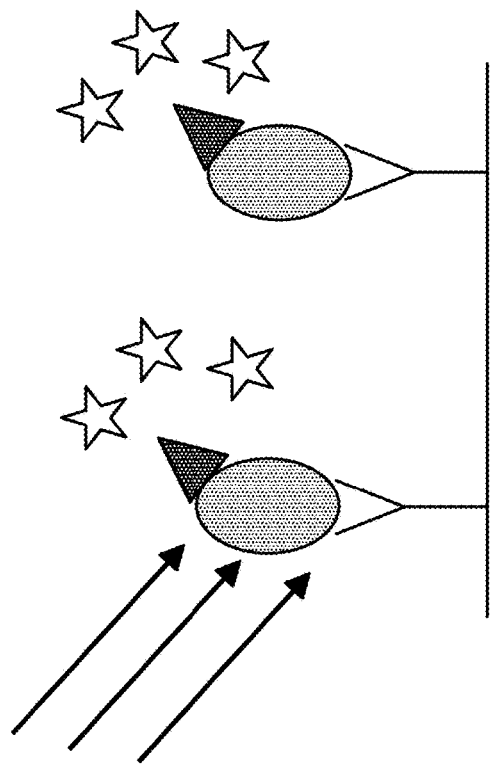
Figure 133A:
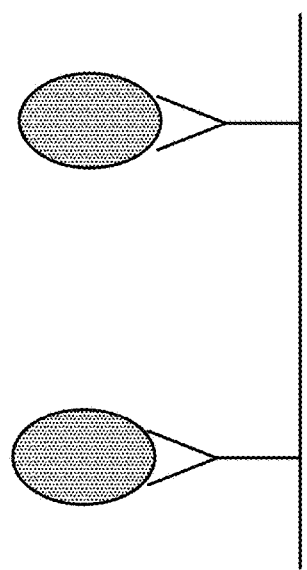

The diazotized label-THC adduct is then exposed to a source (e.g., a light source) in situ in the reaction chamber to produce a detectable signal (e.g., fluorescence), as depicted in FIG. 133D. For example, the diazotized label may be rhodamine 123 diazotized at a primary amine group, the excitation wavelength may be 511 nm and the emission wavelength may be 534 nm. The fluorescence may be measured, the amount of THC captured from the sample (e.g., the breath sample or the ambient air sample) determined based on the measured fluorescence. Depending on the label or dye employed as F, different sources may be used having differing excitation wavelengths for the electromagnetic radiation, as well as differing sources of radiation, magnetic field, or electric field.

In this direct immunoassay, the measured detectable signal (e.g., fluorescence) is directly proportional to the amount of THC captured from the breath sample or the ambient air sample.

Figure 133C:
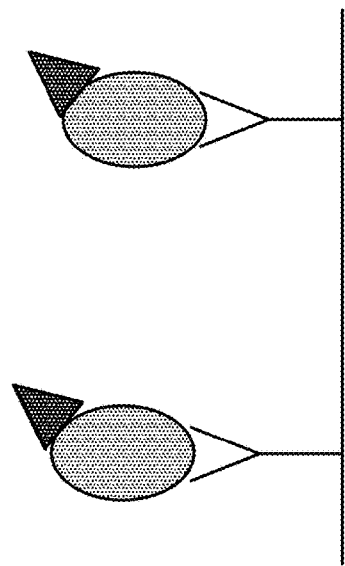

In various embodiments, prior to exposing the diazotized label-THC adduct to the light source to produce the detectable signal (e.g., fluorescence), any unbound breath constituents and unbound diazotized label are washed away from the reaction chamber, as depicted in FIG. 133C. For example, the washing operation may involve flowing a buffer such as Phosphate Buffered Saline (PBS) with a surfactant, e.g., such as 0.01% Tween® 20. Other suitable buffers include tris-buffered saline and similar buffers. Particularly suitable wash buffer is generally derived empirically by the person of ordinary skill. While the detectable signal of the adduct has a spectral difference from unbound diazotized label and so can be likely detected in a homogeneous assay (without a wash step), a wash step is generally used to remove any other breath constituents that could also bind the diazotized label and therefore contaminate the assay. Such wash fluids, e.g., buffers, may, in the context of FIGS. 126C and 126D, be housed within chamber(s) E, for example. Such wash buffers may, for example, be stored in chamber(s) E of the fluidic circuit of FIG. 126C or 126D (this may apply generally to wash buffers discussed herein).

Figure 134B:
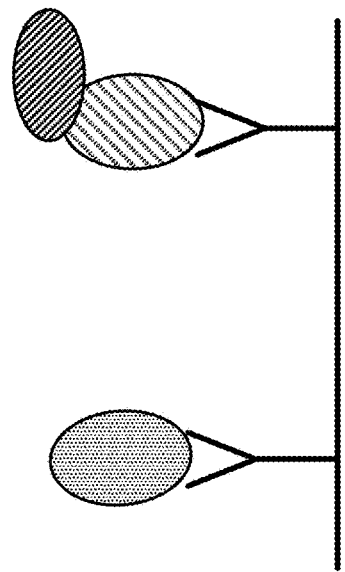
FIGS. 134A-134C depict a surface-based antibody-down, competitive immunoassay.
Figure 134C:
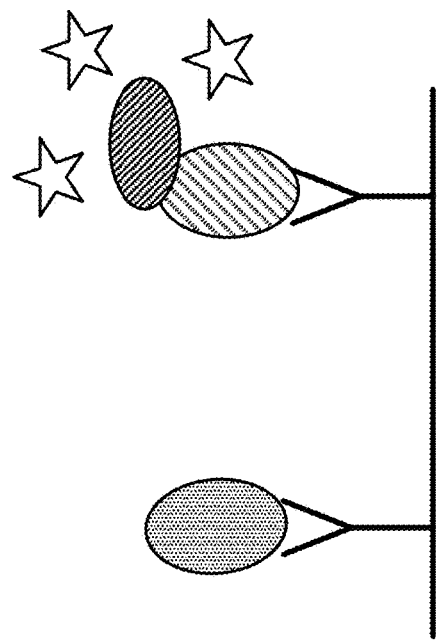
Figure 134A:
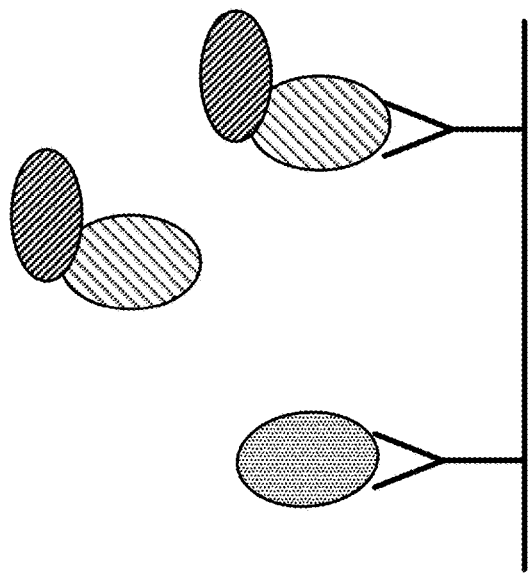

FIGS. 134A-134C depict a surface-based competitive antibody-down, chemiluminescence immunoassay. According to this immunoassay, a THC binder, such as a monoclonal or polyclonal antibody, peptides, or aptamers, is/are surface-bound to the reaction chamber walls or beads according to well-known techniques. Such beads can include any described herein, including magnetic beads. Surface binding to the reaction chamber walls or beads may be accomplished by passive adsorption, covalent binding, or a combination, for example. THC from the sample portion (e.g., the breath sample portion or the ambient air sample portion) can be eluted using the extraction solution, which is then drawn into the reaction chamber is captured by binding to the THC antibody, as depicted in FIG. 134A. In particular embodiments, this capture step is performed in the presence of the extraction solution. Suitable reagents and reaction conditions are well or readily ascertained by those of ordinary skill in the art given the description provided herein, for example, as described above.

Determining an amount of THC captured from a sample (e.g., a breath sample obtained from a subject or an ambient air sample) via this immunoassay involves flowing a known amount of a detectable label. Herein, the detectable label is an enzyme, which is attached to an analyte to form a labeled complex (an enzyme-conjugated synthetic THC antigen). Other detectable labels may be employed, such as any described herein.

This complex can be flowed into the reaction chamber and then form a solution. In use, any (unlabeled) THC from the sample portion (e.g., the breath sample portion or the ambient air sample portion) captured by binding to the THC antibody competes with the enzyme-conjugated synthetic THC antigen to bind to the surface-bound THC antibody, as further depicted in FIG. 134A. Here, the labeled and captured complex includes the THC antibody and the labeled-synthetic target analyte.

Then, as depicted in FIG. 134B, any unbound THC from the sample portion (e.g., the breath sample portion or the ambient air sample portion) and any unbound enzyme-conjugated synthetic THC antigen are washed away from the reaction chamber.

After the wash operation, a substrate (e.g., a chemiluminescent substrate) for the enzyme is flowed into the reaction chamber, and the enzyme is allowed to activate the substrate, as depicted in FIG. 134C. The resultant detectable signal (e.g., chemiluminescence for a chemiluminescent substrate) is measured, and the amount of THC captured from the sample (e.g., the breath sample or the ambient air sample) determined based on the measured chemiluminescence. Instead of chemiluminescence, other labels and dyes may be employed (e.g., fluorescent, luminescent, electroactive, colorimetric, radioactive, electrocatalytic labels or dyes) to provide other detectable signals (e.g., fluorescence, luminescence, electrical signals, color changes, radiation signals, etc.).

In various embodiments, the measuring may be done in situ in the reaction chamber. In various embodiments, the measuring is done ex situ of the reaction chamber in a separate fluidically-connected channel or chamber.

In this competitive immunoassay, the measured detectable signal (e.g., chemiluminescence or fluorescence) is inversely proportional to the amount of THC captured from the breath sample or the ambient air sample.

Figure 135A:
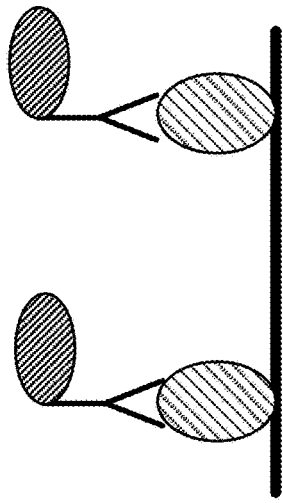
FIGS. 135A-135C depict a surface-based antigen-down, heterogeneous, competitive single-antibody immunoassay.

FIGS. 135A-133C depicts a surface-based antigen-down, heterogeneous, competitive single-antibody immunoassay. According to this immunoassay, a synthetic THC antigen, such as THC-BSA hapten, is surface-bound to the reaction chamber walls or beads. Such beads can include any described herein, including magnetic beads. Surface binding to the reaction chamber walls or beads may be accomplished by passive adsorption, covalent binding, or a combination. Suitable reagents and reaction conditions are well or readily ascertained by those of ordinary skill in the art given the description provided herein.

THC from the sample portion (e.g., the breath sample portion or the ambient air sample portion) can be eluted using the extraction solution, which is then drawn into the reaction chamber to be captured by adsorption on the reaction chamber walls or beads. Determining an amount of THC captured from a sample (e.g., a breath sample obtained from a subject or an ambient air sample) via this immunoassay involves flowing a known amount of a detectable label. Herein, the detectable label is an enzyme, which is attached to a capture agent to form a labeled complex (an enzyme-conjugated THC antibody). Other detectable labels may be employed, such as any described herein.

This complex can be flowed into the reaction chamber to form a solution with any THC from the breath sample portion or the ambient air sample portion. Any THC from the breath sample portion or the ambient air sample portion competes with the surface bound THC antigen for the enzyme-conjugated THC antibody in the solution, as depicted in FIG. 135A. Here, the labeled and captured complex includes the immobilized target analyte and the labeled-THC antibody.

Figure 135B:
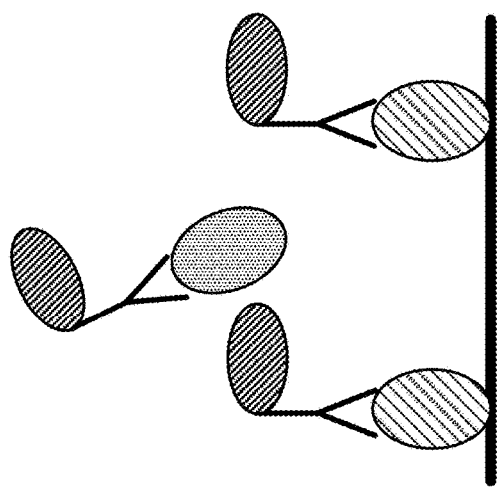

Then, as depicted in FIG. 135B, any unbound THC from the sample portion (e.g., the breath sample portion or the ambient air sample portion) and any unbound enzyme-conjugated THC antibody are washed away from the reaction chamber.

Figure 135C:
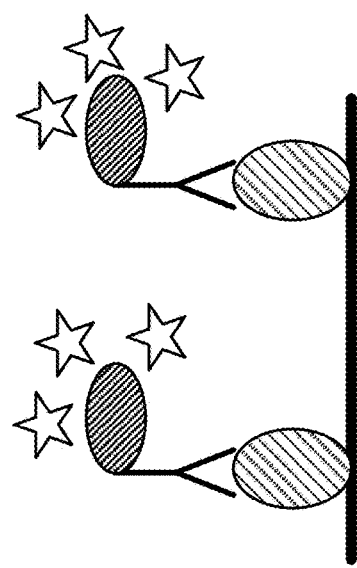

After the wash operation, a chemiluminescent substrate for the enzyme is flowed into the reaction chamber, and the enzyme is allowed to activate the chemiluminescent substrate, as depicted in FIG. 135C. The chemiluminescence is measured, and the amount of THC captured from the sample (e.g., the breath sample or the ambient air sample) determined based on the measured chemiluminescence. Instead of chemiluminescence, other labels and dyes may be employed (e.g., fluorescent, luminescent, electroactive, colorimetric, radioactive, electrocatalytic labels or dyes) to provide other detectable signals (e.g., fluorescence, luminescence, electrical signals, color changes, radiation signals, etc.).

In various embodiments, the measuring may be done in situ in the reaction chamber. In various embodiments, the measuring is done ex situ of the reaction chamber in a separate fluidically-connected channel or chamber.

In this competitive immunoassay, the measured detectable signal (e.g., chemiluminescence or fluorescence) is inversely proportional to the amount of THC captured from the breath sample or the ambient air sample.

Figure 136F:
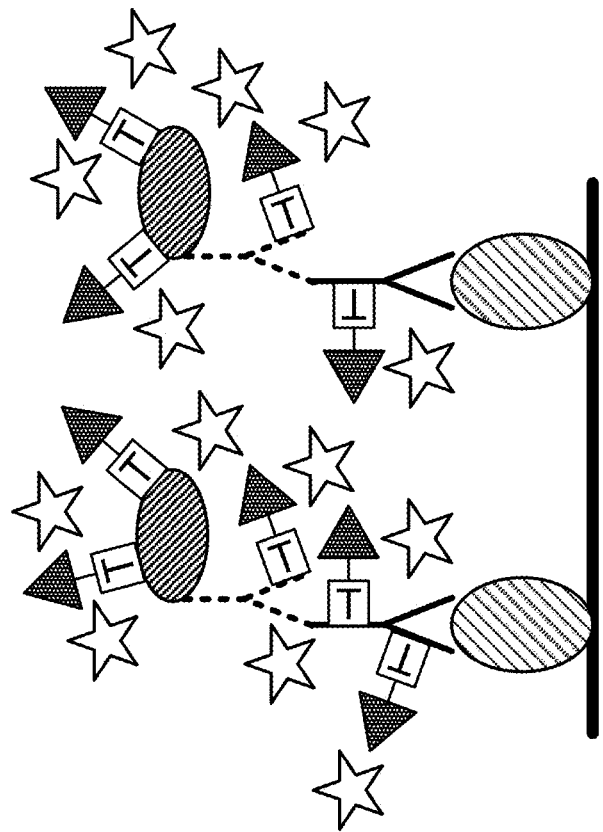
Figure 136E:
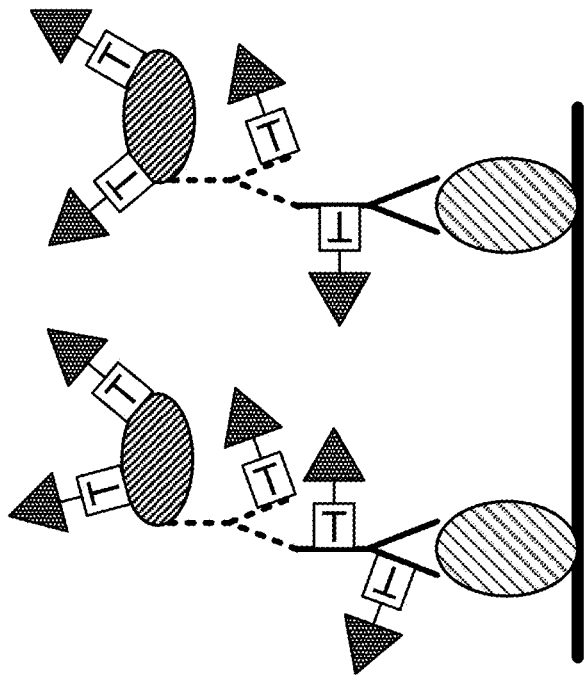

FIGS. 136A-136D depicts a surface-based antigen-down, heterogeneous, competitive two-antibody immunoassay; and FIGS. 136E-136F depicts an optional embodiment including a signal amplification reagent (e.g., a tyramide reagent). According to this immunoassay, a synthetic THC antigen is surface-bound to the reaction chamber walls or beads according to well-known procedures, such as described above. Such beads can include any described herein, including magnetic beads. Suitable reagents and reaction conditions are well or readily ascertained by those of ordinary skill in the art given the description provided herein.

THC from the sample portion (e.g., the breath sample portion or the ambient air sample portion) can be eluted using the extraction solution, which is then drawn into the reaction chamber and captured by adsorption on the reaction chamber walls or beads. Determining an amount of THC captured from the sample (e.g., a breath sample obtained from a subject or an ambient air sample) via this immunoassay involves flowing a known amount of a THC antibody into the reaction chamber and forming a solution with any THC from the breath sample portion or the ambient air sample portion, such that any THC from the sample portion competes with the surface bound THC antigen for the THC antibody in the solution, as depicted in FIG. 136A.

Then, as depicted in FIG. 136B, any unbound THC from the sample portion (e.g., the breath sample portion or the ambient air sample portion) and any unbound THC antibody are washed away from the reaction chamber.

After this wash operation, a detectable label is flowed into the reaction chamber. Here, the detectable label is an enzyme-conjugated second antibody, which is flowed into the reaction chamber forming a solution, such that the enzyme-conjugated second antibody binds to the THC antibody on the surface bound THC antigen, as depicted in FIG. 136C. Here, the labeled and captured complex includes the immobilized THC antigen, the capture agent bound to the antigen, and a secondary capture agent that includes a detectable label (the enzyme-conjugated second antibody).

Then, any unbound THC from the sample portion (e.g., the breath sample portion or the ambient air sample portion) and any unbound THC antibody are washed away from the reaction chamber.

After this second wash operation, a chemiluminescent substrate for the enzyme is flowed into the reaction chamber and the enzyme is allowed to activate the chemiluminescent substrate, as depicted in FIG. 136D. The chemiluminescence is measured, and the amount of THC captured from the sample (e.g., the breath sample or the ambient air sample) determined based on the measured chemiluminescence. Instead of chemiluminescence, other labels and dyes may be employed (e.g., fluorescent, luminescent, electroactive, colorimetric, radioactive, electrocatalytic labels or dyes) to provide other detectable signals (e.g., fluorescence, luminescence, electrical signals, color changes, radiation signals, etc.).

In various embodiments, the measuring may be done in situ in the reaction chamber. In various embodiments, the measuring is done ex situ of the reaction chamber in a separate fluidically-connected channel or chamber.

In this competitive immunoassay, the measured detectable signal (e.g., chemiluminescence or fluorescence) is inversely proportional to the amount of THC captured from the breath sample or the ambient air sample.

Tyramide signal amplification can be employed, in which a tyramine- or tyramide-based reagent (referred herein as a tyramide reagent) is employed in the presence of an enzyme to activate the tyramide reagent. For instance, in the presence of an enzyme, such as HRP, the tyramide reagent becomes activated (e.g., peroxidated), which in turn reacts with electron rich moieties (e.g., tyrosine or tryptophan) and forms covalent bonds. If the enzyme is conjugated to an antibody, then introduction of the tyramide reagent can result in reaction with the enzyme, thereby providing a bound tyramide reagent. In this way, tyramide reagent (as well as any label attached to the tyramide reagent) is deposited.

The tyramide reagent, in turn, can include further detectable labels, thereby amplifying a detectable signal indicative of the presence of the target. Detection systems and signal amplification agents, such as detectably labeled phenols, activated conjugates, are described in U.S. Pat. Nos. 5,731,158, 5,583,001, and 5,196,306, as well as PerkinElmer Inc., "TSA Signal Amplification (TSA) Systems," Document No. 007703_01, 16 pages, accessed at perkinelmer.com/lab-solutions/resources/docs/BRO_tsasignalamplification systems.pdf, each of which is incorporated herein by reference in its entirety.

In one embodiment, the assay can include conducting an immunoassay with HRP-conjugated antibody but adding a tyramide reagent at the end (instead of luminol), as depicted in FIG. 136E in which "T" indicates the tyramide reagent. These reagents can then react with HRP to bind a fluorophore or other molecule nearby, as depicted in FIG. 136F.

Such a tyramide reagent can be employed in cycles to exponentially boost a detectable signal. For instance, a biotin-labeled tyramide reagent and a streptavidin-labeled HRP can be introduced to the chamber or channel in cycles. One non-limiting embodiment can include steps to incubate with the biotin-labeled tyramide reagent, wash, incubate with a streptavidin-labeled HRP (which will bind to all of the new biotin-labeled reagents deposited near the antibodies), wash, incubate with a biotin-labeled tyramide reagent again with all of the just deposited HRPs participating during the biotin deposition reaction, and then repeat as needed.

In various implementations of the chemiluminescent embodiments described above with reference to FIGS. 134, 135, and 136, the enzyme may be horseradish peroxidase (HRP) and the substrate may be, for example, TMB (3,3', 5,5'-tetramethylbenzidine), which gives blue reaction products upon reaction with HRP that have major absorbance peaks at 370 nm and 652 nm; OPD (o-phenylenediamine) which gives a yellow-orange, water-soluble reaction product with an absorbance maximum of 492 nm upon reaction with HRP; or ABTS (2,2'-azinobis [3-ethylbenzothiazoline-6-sulfonic acid]) which gives a green, water-soluble end reaction product upon reaction with HRP that gives two major absorbance peaks at 410 nm and 650 nm. These reagents are available from Sigma-Aldrich.

FIGS. 137A-137C depicts a homogeneous competitive immunoassay. According to this immunoassay, THC from a sample portion (e.g., the breath sample portion or the ambient air sample portion) drawn into the reaction chamber is captured by adsorption on the reaction chamber walls, as depicted in FIG. 137A. Determining an amount of THC captured from a sample (e.g., a breath sample obtained from a subject or an ambient air sample) via this immunoassay involves a luminescent oxygen channeling immunoassay (LOCI™) or AlphaLISA™ immunoassay, such as are described in *Luminescent oxygen channeling assay (LOCI™): sensitive, broadly applicable homogeneous immunoassay method*, E. F. Ullman et al., Clinical Chemistry, 42:9, 1518 (1996); and *AlphaLISA immunoassays: the no-wash alternative to ELISAs for research and drug discovery*, L. Beaudet et al., Perkin Elmer Application Notes, December 2008; incorporated by reference herein for background and details of the two assays. Antibody specific to THC is immobilized on donor beads, either by direct adsorption or via Streptavidin-Biotin linkage. Acceptor beads are prepared by adsorbing a synthetic THC antigen.

In this context, these immunoassays involve flowing donor beads and acceptor beads into the reaction chamber and forming a solution with any THC from the breath sample portion or the ambient air sample portion, such that any THC from the sample portion competes with synthetic THC bound to the acceptor beads to bind to antibody immobilized on the donor beads, as depicted in FIG. 137B. Donor beads bind either to free THC from the sample portion or to the acceptor beads' immobilized THC. The higher the concentration of free THC from breath sample or the ambient air sample, the lower the concentration of donor bead—acceptor bead pairs.

The donor bead-acceptor bead pairs in the solution are then exposed to a light source of a first wavelength in situ in the reaction chamber to produce a fluorescence of a second wavelength different from the first, as depicted in FIG.

137C. This fluorescence signal is only emitted when the donor and acceptor beads are in close proximity to each other. This results in only bound pairs emitting light, while free beads do not emit any light. This reaction, which only occurs between beads which are in close proximity is what allows the homogenous phase immunoassay, without the requirement for washing, which is integral to traditional surface-based immunoassays.

The detectable signal (e.g., fluorescence) may be measured and the amount of THC captured from the breath sample or the ambient air sample determined based on the measured fluorescence.

In this competitive, homogeneous immunoassay, the measured fluorescence is inversely proportional to the amount of THC captured from the breath sample or the ambient air sample.

Following completion of one of the immunoassay formats described above, the determined amount of THC captured the breath sample may be compared to a threshold level for THC in breath, such as described above with reference to FIG. 4, for example, less than 10 picogram/liter (pg/L) of breath, or from 2 to 5 pg/L of breath, or from 2 to 3 pg/L of breath, for example, about 2.4 pg/L of breath. However, as noted above, the threshold may vary depending upon the capture efficiency of the device or system with which the method is conducted. In other embodiments, the determined amount of THC captured the breath sample may be compared to a background level of THC in ambient air.

Then, it may be indicated whether or not the amount of THC captured from the breath sample exceeds the threshold level or the background level. A result wherein the amount of THC in the breath sample exceeds the threshold and/or the background levels may be a positive test result for recent inhalation of THC, which may be correlated to THC impairment. In various embodiments, the indicating may include a visible and/or audible signal and/or readout on a display associated with a device on which the determination and comparison is conducted.

Any useful detection methodology can be employed with an immunoassay. In one embodiment, a proximity ligation assay (PLA) can be employed to detect oligonucleotide-labeled targets. For instance, PLA involves tagging molecules with DNA sequences that can be ligated if they come into close proximity. This ligated DNA (a circular DNA template) can be amplified by rolling circle amplification (RCA) to produce an amplicon, followed by LAMP or PCR, if desired. The amplicon can then be detected by using labeled oligonucleotide probes, which can be designed to hybridize with particular complementary sequences within the amplicon. Alternatively, the amplicon can be detected by using intercalating fluorophores to bind to double stranded regions within the amplicon.

In one embodiment, the assay can include conducting a competitive immunoassay (e.g., as described herein), in which both the synthetic THC antigen and the anti-THC antibody are labeled with oligonucleotide (oligo) probes to provide an oligo-labeled THC and an oligo-labeled anti-THC antibody. In use, the oligo-labeled THC can compete with THC from a sample (e.g., a breath sample or an ambient air sample), thereby resulting in a differential signal.

If both of the oligo-labeled THC and anti-THC antibody are in proximity to each other, then a hybridizing connector oligonucleotide is introduced (after conducting the immunoassay) to join the oligo probes. Then, a ligase is provided to ligate the oligo probes and the connector oligonucleotide, thereby forming a circular template amenable for RCA. The resulting amplicon can be then detected by using intercalating fluorophores or hybridizing fluorophore-labelled oligonucleotides.

In other embodiments, a piezoelectrical analysis system can be employed to detect changes in acoustic frequency based on the presence of a target in proximity to a piezoelectric material. Non-limiting piezoelectric materials include zinc oxide, lead zirconate titanate (PZT), aluminum nitride, indium nitride, and the like, which can be provided as a membrane, a film, or a substrate.

Generally, a current is applied to the piezoelectric material to provide an oscillating circuit that is characterized by a certain frequency. Adsorption of molecules on the piezoelectric material can change the mass of the material, which in turn can result in a detectable frequency change. In particular, this methodology can be optionally employed with a bead-based reagent, which can provide a larger change in mass with a commensurate larger frequency change. Furthermore, magnetic flux or magnetic fields can be employed to provide bead-based reagents to the piezoelectric material in a controlled manner.

In one embodiment, the assay can include conducting a competitive immunoassay in the presence of a piezoelectric material. THC from a sample (e.g., a breath sample or an ambient air sample) could compete with a synthetic THC antigen that is attached to a magnetic bead (e.g., via COOH chemistry) (a THC-bead reagent). The capture antibody can be attached to the piezoelectric material by way of chemisorption, physisorption, etc. The presence of the THC-bead reagent bound to the capture antibody can alter the oscillation frequency of the piezoelectric material when it is actuated (e.g., by applying an AC field to the piezoelectric material). THC from the sample would competitively displace the THC-bead reagent from the capture antibody (which is in turn attached to this membrane), thus resulting in a differential signal.

Non-limiting methods for a bead-based system with a piezoelectric membrane-based approach is described in, e.g., Jokerst J V et al., "A Magnetic Bead-Based Sensor for the Quantification of Multiple Prostate Cancer Biomarkers," *PLoS ONE* 2015; 10(9): e0139484 (15 pages), which is incorporated herein by reference in its entirety.

The principle of Electrochemical Impedance Spectroscopy (EIS) is that large proteins can be detected electrically. For instance, EIS can be employed to detect changes in impendence based on the presence of a target in proximity to an electrode. Such electrodes can be patterned in any useful manner on a substrate, and an anti-THC antibody can be attached to a surface of the electrode (e.g., directly or by way of a linker). Upon applying a current to the electrode, the resultant current response or impedance can be determined.

In one embodiment, the assay can include conducting a competitive immunoassay in the presence of an electrode having an immobilized anti-THC antibody. Here, THC from a sample (e.g., a breath sample or an ambient air sample) could compete with a synthetic THC antigen bound to a protein (e.g., BSA) (a protein-THC reagent) for binding to the anti-THC antibody. The protein can be detected by measuring the impedance at the electrode (the surface on which the antibody is bound) with an AC signal. Since the protein-THC reagent competes with the THC in the sample, the amount of protein on the electrode will be inversely proportional to the amount of THC in the breath sample or the ambient air sample.

Non-limiting methods for an EIS-based biosensor is described in, e.g., Stevenson H et al., "A rapid response electrochemical biosensor for detecting THC in saliva," *Sci. Rep.* 2019; 9:12701 (11 pages), which is incorporated herein by reference in its entirety.

Nanopore-based analysis can be employed to detect transient decreases in ionic conductivity when a target either blocks or translocates through a nanopore. Such transient conductivity events can be measured providing a nanopore within a fluid chamber, applying a voltage across the nanopore, and measuring current as a target from the fluid chamber enters the nanopore. To obtain specificity for the target, the surface of the nanopore can be functionalized, e.g., with an anti-THC antibody. Nanopores can be provided as a single nanopore or as an array (e.g., an m×n array of nanopores, in which each of m and n is 1 or more) within any useful substrate (e.g., a semiconductor substrate). The nanopore can have any useful shape, size, or length (through the substrate).

In one embodiment, the assay can include conducting a competitive immunoassay in the presence of a nanopore having an immobilized anti-THC antibody. Here, THC from a sample (e.g., a breath sample or an ambient air sample) could compete with a synthetic THC antigen bound to a bead (a THC-bead reagent). The extent of blocking provided by THC or a THC-bead reagent can be distinguished and, optionally, the number of such blocking events can be counted over time.

Alternatively, a magnetic bead can be employed, in which such beads can then be magnetically driven through the nanopores in a membrane. Immobilized antibodies that are not bound to free THC from the sample (e.g., the breath sample or the ambient air sample) can then be available to bind the THC-bead reagent. Then, the magnetic field can be reversed to remove unbound beads. The beads remaining on the membrane can then be detected with labelled anti-THC antibodies.

Non-limiting methods for a nanopore-based sensor is described in, e.g., Chuah K et al., "Nanopore blockade sensors for ultrasensitive detection of proteins in complex biological samples," *Nat. Commun.* 2019; 10: 2109 (9 pages), which is incorporated herein by reference in its entirety.

Other label-free spectroscopy methods can be used to detect the analyte. For instance, mass spectrometry (MS) can be employed to obtain a spectrum, and detection can include assessing whether the spectrum includes a chemical signature (e.g., molecular ion signals) indicative of the presence of the analyte. Such methods can be combined with other analytic methods, such as in gas chromatography-mass spectrometry (GC-MS), liquid chromatography-mass spectrometry (LC-MS), and the like.

In another instance, Raman spectroscopy can be employed, including surface-enhanced Raman spectroscopy (SERS) by using a SERS-active substrate that causes excitement of localized surface plasmons upon exposure to a laser light, thereby enhancing Raman signals and allowing for trace detection of THC. Such SERS-active substrates can include a metal, including a metal film or metal particles, including metal nanoparticles. Non-limiting methods and devices relating to SERS detection is described in, e.g., U.S. application Ser. No. 17/302,801, filed May 12, 2021, "Systems and methods using surface-enhanced Raman spectroscopy for detecting tetrahydrocannabinol", which is incorporated herein by reference in its entirety.

In yet another instance, infrared (IR, from 40 to 13,000 $cm^{-1}$) or near IR (from 10,000 to 4000 $cm^{-1}$) spectroscopy can be employed, including Fourier Transform (FT) forms thereof. Any of these spectroscopic analyses can include further data analysis, such as by way of principal component analysis (PCA) or principal component regression (PCR).

Non-limiting methods for spectroscopic analysis of analytes, such as with FTIR, is described in, e.g., Townsend D et al., "Application Note: The Determination of Total THC and CBD Content in Cannabis Flower by Fourier Transform Near Infrared Spectroscopy," 2018; Document No. 014329_01, 5 pages, accessed at perkinelmer.com/lab-solutions/resources/docs/app_determination_of_thc_and_ cbd_cannabisflower.pdf, which is incorporated herein by reference in its entirety.

The above examples have focused on fluidic circuits that may be actuated through movement of a clamping pressure zone across the fluidic circuit and along a reference axis. In such implementations, the clamping pressure zone remains generally pressed against the fluidic circuit during all operation of the fluidic circuit. However, in some implementations, a mechanism may be used that may allow for the clamping pressure zone to be periodically removed from contacting the fluidic circuit, e.g., if a roller is used to apply the clamping pressure zone, the roller may be lifted off of the fluidic circuit so as to no longer compress it before being pushed back against the fluidic circuit in order to compress it again. During the interval(s) in which the clamping pressure zone is not being applied to the fluidic circuit, the clamping pressure zone may, in some implementations, be moved to a different location on the fluidic circuit before being pressed against the fluidic circuit again. In such implementations, the relative locations of the chambers and flow path routing may be different from the examples described above, but the fluidic connections between chambers and the sequence in which fluids are caused to flow between the various chambers used may remain the same. It will also be understood that some implementations, particularly those involving reciprocal motion, such as fluidic circuits for mixing or multi-step wash operations, may derive particular benefit from being implemented in a system in which the clamping pressure zone may be removed from the fluidic circuit, e.g., by lifting the roller off of the fluidic structure. In the case of fluidic circuits for mixing, it may be advantageous to remove the clamping pressure zone near one or both ends of the chamber or flow paths in which the mixing operation is caused to occur so as to reduce the potential for leakage out of that region of the fluidic circuit into another region thereof. It may also or alternatively be advantageous in such mixing fluidic circuits to operate the fluidic circuit with the clamping pressure zone not entirely removed, but having its compressive force reduced. For example, if a roller is used to apply the clamping pressure zone, the roller may be caused to lift slightly off of the fluidic circuit, such that it does not touch or materially compress the portions of the fluidic circuit that are flat (not fluid-filled) but is still close enough thereto that portions of the fluidic circuit that have fluid in them may be caused to contact the roller and thus have the contents thereof pressurized to some extent. This may allow the pressures developed within such fluidic circuits to be kept at a lower level, thereby reducing the possibility of internal leakage from the fluidic circuit and/or premature release of any releasable seals used. In some fluidic circuits that use reciprocal movement of the clamping pressure zone, it may be desirable to have the clamping pressure zone apply pressure in one direction, e.g., to move fluid into a particular chamber, but to avoid having the clamping pressure zone apply pressure when moving in the opposite direction (thus reducing the chance that fluid that was just pushed into a chamber might then be caused to be pushed back out of that same chamber.

It will be understood that while the fluidic circuits discussed above are designed to work with clamping pressure zones that remain in continuous contact with the fluidic circuit during fluidic operations driven by the clamping pressure zone, the above fluidic circuits may also be used with clamping pressure zones that may be periodically withdrawn from pressing against the fluidic circuits. In such implementations, the flow paths, seals, and chambers discussed above may still be used, although the reference boundaries and the relative placement of the chambers and flow path fluidic connections relative to such reference boundaries may be ignored since the flexibility in placement of such clamping pressure zones, and the ability to move such a clamping pressure zone without simultaneously pressing on the fluidic circuit being operated, renders such constraints unnecessary. Accordingly, it is contemplated that any of the fluidic circuits discussed herein may also be implemented without regard for the relative positioning of the various chambers and flow paths discussed herein in order to be used with such clamping pressure zones.

It will be understood that the fluidic circuits discussed herein may, in various implementations, be specifically designed to be interfaced with an analysis system that is configured, for example, to apply a clamping pressure zone, as discussed herein, to such fluidic circuits. The fluidic circuits may thus be equipped with fiducials or other features that allow such fluidic circuits to be aligned properly within such an analysis system, e.g., such that chambers are in various expected locations relative to the analysis system. For example, if the analysis system includes a platen with a cavity or opening in it that is intended to be aligned with a particular chamber and/or flow path of the fluidic circuit, the fiducials or other features may, when the fluidic circuit is interfaced with the analysis system, guide, govern, or constrain the placement of the fluidic circuit such that the fluidic circuit is properly aligned so as to cause the relevant chamber and/or flow path to be aligned with the cavity or opening.

While numerous specific fluidic structures have been described above in conjunction with the implementations depicted in the figures, various other implementations of fluidic structures will also be understood to fall within the scope of this disclosure, including fluidic structures that combine two or more of the fluidic structures discussed herein, or that may blend the features of two fluidic structures together.

Figure 138:
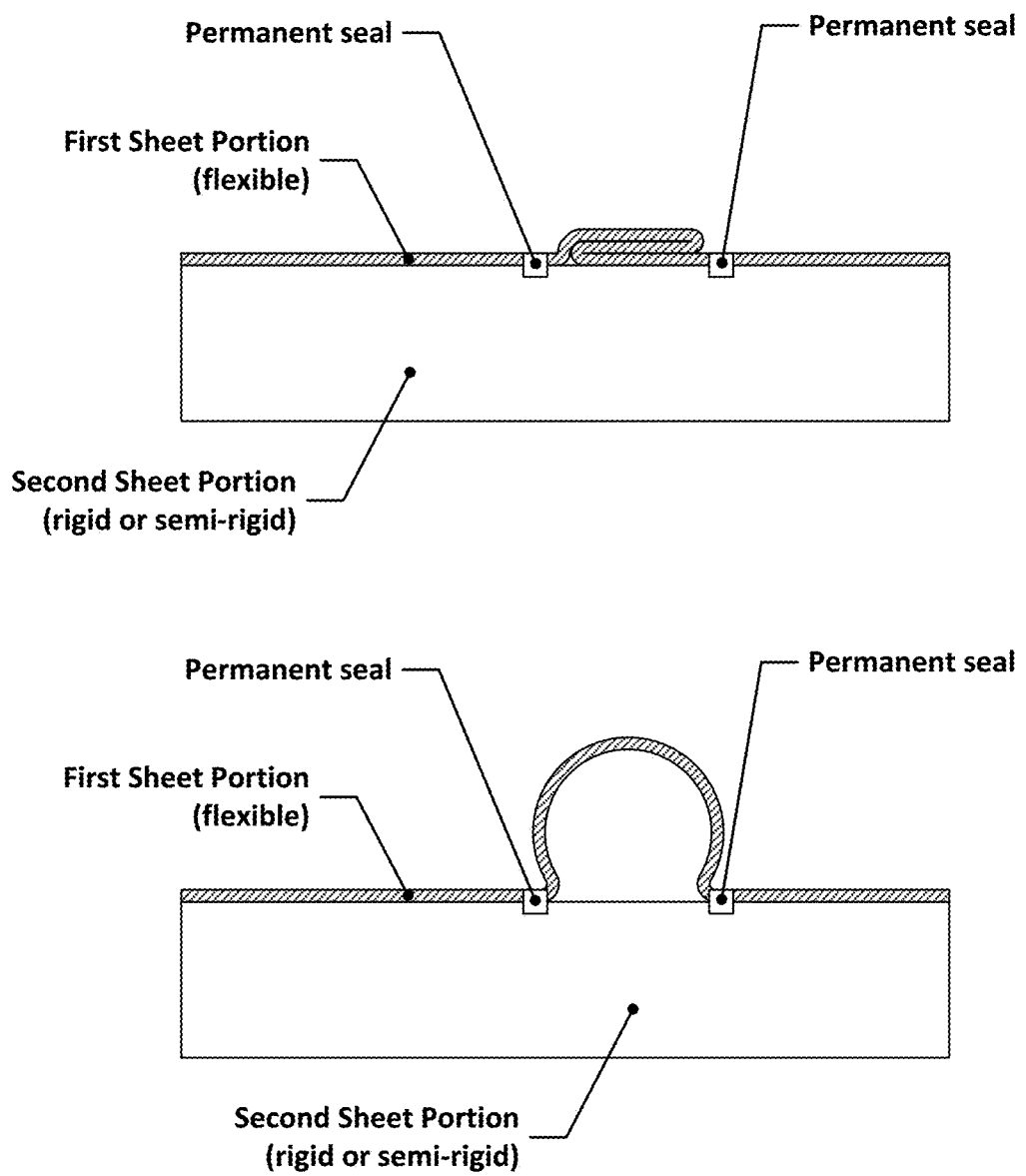
FIG. 138 depicts an example of a flexible portion of material thermally bonded to a rigid or semi-rigid portion of material.

It will also be recognized that the fluidic structures discussed herein may, in some implementations, have more than two portions of material arranged in a layered formation and/or have one layer that is rigid or semi-rigid as opposed to flexible. For example, in some implementations, such as is shown in FIG. 138, a flexible portion of material may be thermally bonded to a rigid or semi-rigid portion of material (or plate portion) by permanent seals such that the flexible portion of material has a greater length of material in between the permanent seals than the rigid or semirigid material does. This extra material, for example, may be collapsed, folded over on itself, or buckled such that it may lie flat, or nearly flat, against the rigid or semi-rigid material/plate when subjected to a vacuum, as shown in the upper part of FIG. 138. When the space between the flexible portion of material and the rigid or semi-rigid portion in between the permanent seals is then pressurized, the flexible portion may inflate-potentially (although not necessarily) to a diameter or width larger than the space between the permanent seals, as shown in the lower portion of FIG. 138. In implementations in which the fluidic structure includes a rigid portion of material, it will be understood that the rigid portion of material may, in some cases, take the place of the platen, i.e., take the majority of the load exerted by the clamping pressure zone. Furthermore, in such implementations it may also be the case that the rigid portion of material may include some or all of the features discussed above, e.g., fluid bypass recesses.

In implementations in which the fluidic structure has more than two layers, the same general principles as outlined and discussed above may be used, although there may also be holes within the fluidic structure that fluidically connect passages between a first set of two adjacent portions of material in the fluidic structure with passages between a second set of two adjacent portions of material in the fluidic structure. In other such implementations, h While various specific details have been discussed above with respect to various example implementations, it will be apparent that some implementations may share certain operational and structural aspects in common. For example, in some implementations, the various elements of a fluidic circuit may be arranged along an axis such that any fluid-containing reservoirs are located at positions along that axis (or an axis or axes parallel thereto) such that when a clamping pressure zone is advanced across the fluidic structure in a direction along that axis or those axes, the contents of the fluid-containing reservoirs are introduced into one or more flow paths of the fluidic circuit of which they are part in a sequence that facilitates a chemical or biological analysis.

In some other or additional such implementations, two or more fluid-containing reservoirs within the fluidic structure may each be fluidically connected with one or more passages within the fluidic structure by a corresponding cross-passage. Each cross-passage may have a first end that is fluidically connected with the corresponding reservoir and a second end that is fluidically connected with one of the one or more passages. For each cross-passage, the second end of the cross-passage may be the same distance from, or closer to, a common reference plane than the first end of that passage, where the common reference plane is positioned such that all of the reservoirs are located on one side of the common reference plane. The reference plane, for example, may also be perpendicular to the direction of travel of the clamping pressure zone when the fluidic structure is in use.

It will be further understood that the systems that utilize the fluidic structures discussed above may also include a controller, e.g., with one or more processors and one or more memory devices, that may be configured to control various aspects of the system. For example, the one or more memory devices may store computer-executable instructions for controlling the one or more processors to control one or more motors, heating elements, and/or other component so as to perform any of the actions discussed above, e.g., move a roller forward and/or backward relative to a fluidic structure, heat a portion of a fluidic structure to cause that portion to thermally bond and form a permanent seal or to heat fluid within the fluidic structure at that location, activate an optical sensor to obtain a light measurement reading, activate one or more light sources to illuminate a sample, activate a vibramotor or solenoid to assist with bubble separation or other fluidic separation, and so forth.

It will also be understood that in some implementations, instructions for performing the functions and techniques described herein, e.g., instructions that cause one or more actuators to move a clamping pressure zone and/or apply heat to create a thermal seal, etc. according to the techniques discussed herein may be implemented in hardware, digital electronic circuitry, computer software, firmware, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular implementations only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example implementations of the present disclosure are described herein with reference to illustrations of idealized implementations (and intermediate structures) of the present disclosure. As such, variations from the shapes of the illustrations as a result, for example, of manufacturing techniques and/or tolerances, are to be expected. Thus, the example implementations of the present disclosure should not be construed as necessarily limited to the particular shapes of regions illustrated herein, but are to include deviations in shapes that result, for example, from manufacturing.

Any and/or all elements, as disclosed herein, can, if suitable therefore, be formed from a same, structurally continuous piece, such as being unitary, and/or be separately manufactured and/or connected, such as being an assembly and/or modules. Any and/or all elements, as disclosed herein, can be manufactured via any suitable manufacturing processes, whether additive manufacturing, subtractive manufacturing and/or other any other types of manufacturing. For example, some suitable manufacturing processes may include three-dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

For the purposes of this disclosure, the term "fluidically connected" is used with respect to volumes, plenums, holes, etc., that may be connected with one another in order to form a fluidic connection, similar to how the term "electrically connected" is used with respect to components that are connected together to form an electric connection. The term "fluidically interposed," if used, may be used to refer to a component, volume, plenum, or hole that is fluidically connected with at least two other components, volumes, plenums, or holes such that fluid flowing from one of those other components, volumes, plenums, or holes to the other or another of those components, volumes, plenums, or holes would first flow through the "fluidically interposed" component before reaching that other or another of those components, volumes, plenums, or holes. For example, if a pump is fluidically interposed between a reservoir and an outlet, fluid that flowed from the reservoir to the outlet would first flow through the pump before reaching the outlet.

It is to be understood that the phrases "for each <item> of the one or more <items>," "each <item> of the one or more <items>," or the like, if used herein, are inclusive of both a single-item group and multiple-item groups, i.e., the phrase "for . . . each" is used in the sense that it is used in programming languages to refer to each item of whatever population of items is referenced. For example, if the population of items referenced is a single item, then "each" would refer to only that single item (despite the fact that dictionary definitions of "each" frequently define the term to refer to "every one of two or more things") and would not imply that there must be at least two of those items.

Similarly, the term "set" or "subset" should not be viewed, in itself, as necessarily encompassing a plurality of items—it will be understood that a set or a subset can encompass only one member or multiple members (unless the context indicates otherwise).

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

The description of the present disclosure has been presented for purposes of illustration and description, but is not intended to be exhaustive or limited to the present disclosure in the form disclosed. Many modifications and variations will be apparent to those of ordinary skill in the art without departing from the scope and spirit of the present disclosure. Exemplary implementations were chosen and described in order to best explain the principles of the present disclosure and its practical application, and to enable others of ordinary skill in the art to understand the present disclosure for various implementations with various modifications as are suited to the particular use contemplated.

While various implementations have been described above, it should be understood that they have been presented by way of example only, and not limitation. The descriptions are not intended to limit the scope of the technology to the particular forms set forth herein. Thus, the breadth and scope of a preferred implementation should not be limited by any of the above-described exemplary implementations. It should be understood that the above description is illustrative and not restrictive. To the contrary, the present descriptions are intended to cover such alternatives, modifications, and equivalents as may be included within the spirit and scope of the technology as defined by the appended claims and otherwise appreciated by one of ordinary skill in the art. The scope of the technology should, therefore, be determined not with reference to the above detailed description, but instead should be determined with reference to the appended claims along with their full scope of equivalents.

What is claimed is:

1. A method, comprising:
   applying a linear pressure front to a portion of a fluidic circuit having a plurality of chambers connected by a network of flow paths that is located between a first portion of material and a second portion of material, wherein the first portion of material is a flexible, inelastic material and wherein one or more portions of the first portion of material and the second portion of material are sealed together so as to provide one or more seals that define a boundary of the fluidic circuit interposed between the first portion of material and the second portion of material;
   causing the linear pressure front to move along a first axis so as to cause a first fluid contained in a second chamber of the fluidic circuit to pressurize to a level that exceeds a release pressure of a first releasable seal on a flow path that fluidically connects the second chamber with a first chamber; and
   causing the linear pressure front to continue moving along the first axis so as to cause the first fluid to flow from the second chamber into the first chamber via the flow path.

2. The method of claim 1, wherein the second portion of material is also a flexible, inelastic material.

3. The method of claim 1, wherein:
   the first releasable seal is a dynamic seal located on the flow path, and
   the dynamic seal has a first release pressure when a side of the dynamic seal fluidically interposed in between the dynamic seal and the first chamber is exposed to a first fluid pressure and a second release pressure when a side of the dynamic seal fluidically interposed in between the dynamic seal and the second chamber is exposed to a second fluid pressure, and
   the first release pressure is greater than the second release pressure.

4. The method of claim 3, wherein the second pressure is substantially no pressure.

5. The method of claim 3, wherein the dynamic seal is formed at a location where the flow path fluidically connects with the first chamber.

6. The method of claim 3, wherein:
   the first chamber and the second chamber are located between a first location and a second location,
   the causing the linear pressure front to move along the first axis so as to cause the first fluid contained in the second chamber of the fluidic circuit to pressurize to the level that exceeds the release pressure of the first releasable seal and to then cause the first fluid to flow into the first chamber via the flow path involves moving the linear pressure front from the first location to the second location, and
   the method further comprises moving the linear pressure front from the second location to the first location after the first fluid is flowed into the first chamber and substantially preventing flow of the first fluid from the first chamber to the second chamber by way of the dynamic seal.

7. The method of claim 1, wherein the first chamber is fluidly connected to the second chamber by a passage that extends generally transversely to the first axis.

* * * * *